US007034132B2

(12) United States Patent
Anderson et al.

(10) Patent No.: US 7,034,132 B2
(45) Date of Patent: Apr. 25, 2006

(54) THERAPEUTIC POLYPEPTIDES, NUCLEIC ACIDS ENCODING SAME, AND METHODS OF USE

(76) Inventors: David W. Anderson, 85 Montoya Dr., Branford, CT (US) 06405; Jason C. Baumgartner, 1697 Quinnipiac Ave., New Haven, CT (US) 06513; Ferenc L. Boldog, 1687 Hartford Turnpike, North Haven, CT (US) 06473; Stacie J. Casman, 17 Peck St., North Haven, CT (US) 06473; Shlomit R. Edinger, 766 Edgewood Ave., New Haven, CT (US) 06515; Esha A. Gangolli, 31 Strawberry Hill Rd., Madison, CT (US) 06443; Valerie Gerlach, 18 Rock Pasteur Rd., Branford, CT (US) 06405; Linda Gorman, 329 Monticello Dr., Branford, CT (US) 06405; Xiaojia Guo, 713 Robert Frost Dr., Branford, CT (US) 06405; Tord Hjalt, 514 Main St., Apt. 30, East Haven, CT (US) 06512; Ramesh Kekuda, 71 Aiken St., Unit R3, Norwalk, CT (US) 06851; Li Li, 56 Jerimoth Dr., Branford, CT (US) 06405; John R. MacDougall, 117 Russell St., Hamden, CT (US) 06517; Uriel M. Malyankar, 229 Branford Rd., #330, Branford, CT (US) 06405; Isabelle Millet, 74 Carrington Ave., Milford, CT (US) 06460; Muralidhara Padigaru, 71 Hampton Park, Branford, CT (US) 06405; Meera Patturajan, 45 Harrison Ave., Apt. 1C, Branford, CT (US) 06405; Carol E. A. Pena, 604 Orange St., #2, New Haven, CT (US) 06511; Luca Rastelli, 52 Pepperbush La., Guilford, CT (US) 06437; Richard A. Shimkets, 5 Indian Meadows Dr., Guilford, CT (US) 06437; David J. Stone, 223 Whitehorn Dr., Guilford, CT (US) 06437; Kimberly A. Spytek, 28 Court St., #1, New Haven, CT (US) 06511; Corine A. M. Vernet, 1739 Foxon Rd., Apartment L6, Branford, CT (US) 06471; Edward Z. Voss, 123 Knollwood Dr., Wallingford, CT (US) 06492; Bryan D. Zerhusen, 337 Monticello Dr., Branford, CT (US) 06405

( * ) Notice: Subject to any disclaimer, the term of this patent is extended or adjusted under 35 U.S.C. 154(b) by 322 days.

(21) Appl. No.: 10/162,335

(22) Filed: Jun. 3, 2002

(65) Prior Publication Data

US 2004/0009480 A1 Jan. 15, 2004

Related U.S. Application Data

(60) Provisional application No. 60/295,607, filed on Jun. 4, 2001, provisional application No. 60/295,661, filed on Jun. 4, 2001, provisional application No. 60/296,404, filed on Jun. 6, 2001, provisional application No. 60/296,418, filed on Jun. 6, 2001, provisional application No. 60/297,414, filed on Jun. 11, 2001, provisional application No. 60/297,567, filed on Jun. 12, 2001, provisional application No. 60/298,285, filed on Jun. 14, 2001, provisional application No. 60/298,556, filed on Jun. 15, 2001, provisional application No. 60/299,949, filed on Jun. 21, 2001, provisional application No. 60/300,883, filed on Jun. 26, 2001, provisional application No. 60/301,550, filed on Jun. 28, 2001, provisional application No. 60/311,972, filed on Aug. 13, 2001, provisional application No. 60/315,069, filed on Aug. 27, 2001, provisional application No. 60/315,071, filed on Aug. 27, 2001, provisional application No. 60/315,660, filed on Aug. 29, 2001, provisional application No. 60/322,293, filed on Sep. 14, 2001, provisional application No. 60/322,706, filed on Sep. 17, 2001, provisional application No. 60/341,186, filed on Dec. 14, 2001, provisional application No. 60/361,189, filed on Feb. 28, 2002, provisional application No. 60/363,673, filed on Mar. 12, 2002, and provisional application No. 60/363,676, filed on Mar. 12, 2002.

(51) Int. Cl.
*C07H 21/02* (2006.01)
*C07H 21/04* (2006.01)

(52) U.S. Cl. .................. 536/23.1; 530/350; 514/12; 435/69.1; 435/6; 435/7.1

(58) Field of Classification Search ................ 536/23.1; 530/514; 514/12; 435/6, 7.1, 69.1
See application file for complete search history.

(56) References Cited

U.S. PATENT DOCUMENTS 4,446,129 A      5/1984   Sawada (Continued)

FOREIGN PATENT DOCUMENTS

EP          0 198 645          10/1986

(Continued)

OTHER PUBLICATIONS

Watanabe et al., BTLA is a lymphocyte inhibitory receptor with similarities to CTLA–4 and PD–1, Jul. 2003, nature immunology, vol. 4, No. 7, pp. 670–679.*

(Continued)

*Primary Examiner*—Robert A. Wax
*Assistant Examiner*—Robert B. Mondesi
(74) *Attorney, Agent, or Firm*—Mintz, Levin, Cohn, Ferris, Glovsky and Popeo; Ivor R. Elrifi, Esq.; Naomi S. Biswas, Esq.

(57) ABSTRACT

Disclosed herein are nucleic acid sequences that encode G-coupled protein-receptor related polypeptides. Also disclosed are polypeptides encoded by these nucleic acid sequences, and antibodies, which immunospecifically-bind to the polypeptide, as well as derivatives, variants, mutants, or fragments of the aforementioned polypeptide, polynucleotide, or antibody. The invention further discloses therapeutic, diagnostic and research methods for diagnosis, treatment, and prevention of disorders involving any one of these novel human nucleic acids and proteins.

13 Claims, No Drawings

U.S. PATENT DOCUMENTS

| | | | |
|---|---|---|---|
| 4,643,991 A | 2/1987 | Digenis et al. | |
| 4,746,729 A | 5/1988 | Kuettner et al. | |
| 4,968,614 A | 11/1990 | Takiguchi et al. | |
| 4,985,361 A | 1/1991 | Takiguchi et al. | |
| 5,212,068 A | 5/1993 | Takiguchi et al. | |
| 5,464,822 A | 11/1995 | Christophers et al. | |
| 5,627,034 A | 5/1997 | Gould et al. | 435/6 |
| 5,716,805 A | 2/1998 | Srinivasan et al. | 435/59.1 |
| 6,057,101 A | 5/2000 | Nandabalan et al. | 435/6 |
| 6,083,693 A | 7/2000 | Nandabalan et al. | 435/6 |
| 6,313,265 B1 | 11/2001 | Phillips et al. | 530/350 |
| 6,316,604 B1 | 11/2001 | Fearon et al. | 530/416 |

FOREIGN PATENT DOCUMENTS

| | | |
|---|---|---|
| EP | 0 869 178 | 10/1998 |
| EP | 1 033 401 | 9/2000 |
| EP | 1 033 405 | 9/2000 |
| EP | 1 067 182 | 1/2001 |
| EP | 1 130 094 | 9/2001 |
| EP | 1 134 286 | 9/2001 |
| EP | 1 149 903 | 10/2001 |
| GB | 2 209 526 | 5/1989 |
| JP | 59125896 | 7/1984 |
| JP | 61192288 | 8/1986 |
| JP | 62000276 | 1/1987 |
| JP | 10099084 | 4/1998 |
| JP | 2000157263 | 6/2000 |
| JP | 2001008687 | 1/2001 |
| JP | 2001327289 | 11/2001 |
| WO | WO 91/11461 | 8/1991 |
| WO | WO 94/05691 | 3/1994 |
| WO | WO 94/10308 | 5/1994 |
| WO | WO 95/22611 | 8/1995 |
| WO | WO 96/37610 | 11/1996 |
| WO | WO 98/00440 | 1/1998 |
| WO | WO 98/05733 | 2/1998 |
| WO | WO 98/13484 | 4/1998 |
| WO | WO 98/24475 | 6/1998 |
| WO | WO 98/30907 | 7/1998 |
| WO | WO 98/36062 | 8/1998 |
| WO | WO 99/06427 | 2/1999 |
| WO | WO 99/14328 | 3/1999 |
| WO | WO 99/20764 | 4/1999 |
| WO | WO 99/25833 | 5/1999 |
| WO | WO 99/31274 | 6/1999 |
| WO | WO 99/46290 | 9/1999 |
| WO | WO 99/55865 | 11/1999 |
| WO | WO 99/58660 | 11/1999 |
| WO | WO 99/59618 | 11/1999 |
| WO | WO 99/60164 | 11/1999 |
| WO | WO 00/07545 | 2/2000 |
| WO | WO 00/09552 | 2/2000 |
| WO | WO 00/31255 | 2/2000 |
| WO | WO 00/31256 | 2/2000 |
| WO | WO 00/12551 | 3/2000 |
| WO | WO 00/21555 | 4/2000 |
| WO | WO 00/29576 | 5/2000 |
| WO | WO 00/39284 | 7/2000 |
| WO | WO 00/39327 | 7/2000 |
| WO | WO 00/40722 | 7/2000 |
| WO | WO 00/53747 | 9/2000 |
| WO | WO 00/53755 | 9/2000 |
| WO | WO 00/53758 | 9/2000 |
| WO | WO 00/55350 | 9/2000 |
| WO | WO 00/58473 | 10/2000 |
| WO | WO 00/61625 | 10/2000 |
| WO | WO 00/63376 | 10/2000 |
| WO | WO 00/69884 | 11/2000 |
| WO | WO 00/70050 | 11/2000 |
| WO | WO 00/73448 | 12/2000 |
| WO | WO 00/73452 | 12/2000 |
| WO | WO 00/73454 | 12/2000 |
| WO | WO 00/75358 | 12/2000 |
| WO | WO 01/00672 | 1/2001 |
| WO | WO 01/04311 | 1/2001 |
| WO | WO 01/11086 | 2/2001 |
| WO | WO 01/12662 | 2/2001 |
| WO | WO 01/12806 | 2/2001 |
| WO | WO 01/19988 | 3/2001 |
| WO | WO 01/21658 | 3/2001 |
| WO | WO 01/22920 | 4/2001 |
| WO | WO 01/23402 | 4/2001 |
| WO | WO 01/23419 | 4/2001 |
| WO | WO 01/27289 | 4/2001 |
| WO | WO 01/38490 | 5/2001 |
| WO | WO 01/38501 | 5/2001 |
| WO | WO 01/40451 | 6/2001 |
| WO | WO 01/40466 | 6/2001 |
| WO | WO 01/44475 | 6/2001 |
| WO | WO 01/48192 | 7/2001 |
| WO | WO 01/49309 | 7/2001 |
| WO | WO 01/51520 | 7/2001 |
| WO | WO 01/53312 | 7/2001 |
| WO | WO 01/53346 | 7/2001 |
| WO | WO 01/53453 | 7/2001 |
| WO | WO 01/54477 | 8/2001 |
| WO | WO 01/55437 | 8/2001 |
| WO | WO 01/57188 | 8/2001 |
| WO | WO 01/57190 | 8/2001 |
| WO | WO 01/57270 | 8/2001 |
| WO | WO 01/57272 | 8/2001 |
| WO | WO 01/57274 | 8/2001 |
| WO | WO 01/57275 | 8/2001 |
| WO | WO 01/57276 | 8/2001 |
| WO | WO 01/57278 | 8/2001 |
| WO | WO 01/60850 | 8/2001 |
| WO | WO 01/61005 | 8/2001 |
| WO | WO 01/62927 | 8/2001 |
| WO | WO 01/66689 | 9/2001 |
| WO | WO 01/66690 | 9/2001 |
| WO | WO 01/68848 | 9/2001 |
| WO | WO 01/71004 | 9/2001 |
| WO | WO 01/71042 | 9/2001 |
| WO | WO 01/73034 | 10/2001 |
| WO | WO 01/75067 | 10/2001 |
| WO | WO 01/77335 | 10/2001 |
| WO | WO 01/81363 | 11/2001 |
| WO | WO 01/83782 | 11/2001 |
| WO | WO 01/88156 | 11/2001 |
| WO | WO 01/88188 | 11/2001 |
| WO | WO 01/90193 | 11/2001 |
| WO | WO 01/90357 | 11/2001 |
| WO | WO 01/98353 | 12/2001 |
| WO | WO 02/02610 | 1/2002 |
| WO | WO 02/06294 | 1/2002 |

OTHER PUBLICATIONS

GenBank Accession No.: A57293 (Mar. 3, 1998).
GenBank Accession No.: AAB01432 (May 30, 1996).
GenBank Accession No.: AAB07456 (Sep. 5, 1996).
GenBank Accession No.: AAB09968 (Oct. 7, 1996).
GenBank Accession No.: AAB12448 (Oct. 7, 1996).
GenBank Accession No.: AAB24089 (Aug. 5, 1999).
GenBank Accession No.: AAB29188 (Mar. 10, 1994).
GenBank Accession No.: AAB30232 (Sep. 23, 1994).
GenBank Accession No.: AAB33462 (Jul. 27, 1995).
GenBank Accession No.: AAB42780 (Feb. 7, 1997).
GenBank Accession No.: AAB43640 (Feb. 7, 1997).
GenBank Accession No.: AAB43668 (Feb. 7, 1997).

GenBank Accession No.: AAB47559 (Feb. 18, 1997).
GenBank Accession No.: AAB47719 (Feb. 19, 1997).
GenBank Accession No.: AAB49891 (Mar. 19, 1997).
GenBank Accession No.: AAB50374 (Mar. 25, 1997).
GenBank Accession No.: AAB50907 (Mar. 28, 1997).
GenBank Accession No.: AAB50908 (Mar. 28, 1997).
GenBank Accession No.: AAB51802 (Apr. 14, 1997).
GenBank Accession No.: AAB56028 (May 14, 1997).
GenBank Accession No.: AAB60935 (Jul. 16, 2001).
GenBank Accession No.: AAB61419 (Mar. 24, 1999).
GenBank Accession No.: AAB61483 (Jun. 24, 1997).
GenBank Accession No.: AAB65181 (May 1, 2002).
GenBank Accession No.: AAB67741 (Aug. 27, 1997).
GenBank Accession No.: AAB67743 (Aug. 27, 1997).
GenBank Accession No.: AAB67744 (Aug. 27, 1997).
GenBank Accession No.: AAB70508 (Sep. 18, 1997).
GenBank Accession No.: AAB74705 (Oct. 8, 1997).
GenBank Accession No.: AAB74945 (Oct. 8, 1997).
GenBank Accession No.: AAB80225 (Oct. 8, 1997).
GenBank Accession No.: AAB80245 (Oct. 8, 1997).
GenBank Accession No.: AAB82313 (Oct. 30, 1997).
GenBank Accession No.: AAB82314 (Oct. 30, 1997).
GenBank Accession No.: AAB82315 (Oct. 30, 1997).
GenBank Accession No.: AAB82316 (Oct. 30, 1997).
GenBank Accession No.: AAB82317 (Oct. 30, 1997).
GenBank Accession No.: AAB83147 (Nov. 6, 1997).
GenBank Accession No.: AAB84203 (Nov. 11, 1997).
GenBank Accession No.: AAB84615 (Jun. 19, 2002).
GenBank Accession No.: AAB85060 (Jun. 19, 2002).
GenBank Accession No.: AAB88478 (Dec. 19, 1997).
GenBank Accession No.: AAB90544 (Dec. 15, 1997).
GenBank Accession No.: AAB90717 (Dec. 15, 1997).
GenBank Accession No.: AAC50484 (Sep. 28, 2001).
GenBank Accession No.: AAD21820 (Mar. 24, 1999).
GenBank Accession No.: AAD50978 (Aug. 23, 1999).
GenBank Accession No.: AAE00692 (Sep. 29, 1999).
GenBank Accession No.: AAE00693 (Sep. 29, 1999).
GenBank Accession No.: AAE05371 (Sep. 29, 1999).
GenBank Accession No.: AAE07514 (Sep. 29, 1999).
GenBank Accession No.: AAE09440 (Sep. 29, 1999).
GenBank Accession No.: AAE10347 (Sep. 29, 1999).
GenBank Accession No.: AAE10348 (Sep. 29, 1999).
GenBank Accession No.: AAE10350 (Sep. 29, 1999).
GenBank Accession No.: AAE15809 (Sep. 29, 1999).
GenBank Accession No.: AAE17494 (Sep. 29, 1999).
GenBank Accession No.: AAG00221 (Aug. 16, 2000).
GenBank Accession No.: AAG00304 (Aug. 17, 2000).
GenBank Accession No.: AAG00573 (Dec. 8, 2000).
GenBank Accession No.: AAG26041 (Oct. 25, 2000).
GenBank Accession No.: AAH22561 (Feb. 4, 2002).
GenBank Accession No.: AAH26867 (Aug. 7, 2002).
GenBank Accession No.: AAH27786 (Aug. 7, 2002).
GenBank Accession No.: AAH26069 (May 1, 2002).
GenBank Accession No.: AAK51233 (Sep. 5, 2001).
GenBank Accession No.: AAL12498 (Nov. 21, 2001).
GenBank Accession No.: AAL78632 (Feb. 18, 2002).
GenBank Accession No.: AAL84788 (Apr. 4, 2002).
GenBank Accession No.: AAL90874 (Mar. 19, 2002).
GenBank Accession No.: AAM00948 (Apr. 2, 2002).
GenBank Accession No.: AAM05438 (Apr. 3, 2002).
GenBank Accession No.: AAM17791 (Apr. 22, 2002).
GenBank Accession No.: AAM20130 (Sep. 18, 2002).
GenBank Accession No.: AAM23933 (May 9, 2002).
GenBank Accession No.: AAM24206 (May 9, 2002).
GenBank Accession No.: AAM24248 (May 9, 2002).
GenBank Accession No.: AAM30301 (May 17, 2002).
GenBank Accession No.: AAM34044 (Aug. 20, 2002).
GenBank Accession No.: AAM38919 (May 29, 2002).
GenBank Accession No.: AAM39059 (May 29, 2002).
GenBank Accession No.: AAM39241 (May 23, 2002).
GenBank Accession No.: AAM39715 (May 23, 2002).
GenBank Accession No.: AAM40705 (May 23, 2002).
GenBank Accession No.: AAM41027 (May 23, 2002).
GenBank Accession No.: AAM41501 (May 23, 2002).
GenBank Accession No.: AAM48977 (Jul. 10, 2002).
GenBank Accession No.: AAM50797 (Jun. 16, 2002).
GenBank Accession No.: AAM61147 (Jun. 21, 2002).
GenBank Accession No.: AAM73861 (Jul. 2, 2002).
GenBank Accession No.: AAM78338 (Jul. 22, 2002).
GenBank Accession No.: AAM78560 (Jul. 23, 2002).
GenBank Accession No.: AAM78649 (Jul. 19, 2002).
GenBank Accession No.: AAM78708 (Jul. 19, 2002).
GenBank Accession No.: AAM78714 (Jul. 19, 2002).
GenBank Accession No.: AAM78715 (Jul. 19, 2002).
GenBank Accession No.: AAM79544 (Jul. 18, 2002).
GenBank Accession No.: AAM79633 (Jul. 19, 2002).
GenBank Accession No.: AAM79854 (Jul. 18, 2002).
GenBank Accession No.: AAM93277 (Aug. 8, 2002).
GenBank Accession No.: BAB47486 (May 10, 2002).
GenBank Accession No.: CAC05323 (Aug. 25, 2000).
GenBank Accession No.: CAC21966 (Jan. 13, 2001).
GenBank Accession No.: CAC21967 (Jan. 13, 2001).
GenBank Accession No.: CAC33327 (Feb. 28, 2001).
GenBank Accession No.: CAC34918 (Mar. 21, 2001).
GenBank Accession No.: CAC37763 (Apr. 30, 2001).
GenBank Accession No.: CAC38714 (May 11, 2001).
GenBank Accession No.: CAC38715 (May 11, 2001).
GenBank Accession No.: CAC42545 (Jun. 22, 2001).
GenBank Accession No.: CAC42682 (Jun. 22, 2001).
GenBank Accession No.: CAC83612 (Mar. 1, 2002).
GenBank Accession No.: CAC84565 (Mar. 1, 2002).
GenBank Accession No.: CAC86014 (Mar. 1, 2002).
GenBank Accession No.: CAC86015 (Mar. 1, 2002).
GenBank Accession No.: CAC86016 (Mar. 1, 2002).
GenBank Accession No.: CAD20434 (Jan. 7, 2002).
GenBank Accession No.: CAD28481 (Mar. 20, 2002).
GenBank Accession No.: O75069 (Jun. 15, 2002).
GenBank Accession No.: O88799 (Oct. 16, 2001).
GenBank Accession No.: O94876 (Jun. 15, 2002).
GenBank Accession No.: O95715 (Jun. 15, 2002).
GenBank Accession No.: P01042 (Oct. 16, 2001).
GenBank Accession No.: P01044 (Jun. 15, 2002).
GenBank Accession No.: P01046 (Jun. 15, 2002).
GenBank Accession No.: P01047 (Jun. 15, 2002).
GenBank Accession No.: P01213 (Jun. 15, 2002).
GenBank Accession No.: P01214 (Jun. 15, 2002).
GenBank Accession No.: P01235 (Oct. 16, 2001).
GenBank Accession No.: P02790 (Jun. 15, 2002).
GenBank Accession No.: P04003 (Jun. 15, 2002).
GenBank Accession No.: P08217 (Jun. 15, 2002).
GenBank Accession No.: P08218 (Jun. 15, 2002).
GenBank Accession No.: P08419 (Jun. 15, 2002).
GenBank Accession No.: P20058 (Jun. 15, 2002).
GenBank Accession No.: P20059 (Jun. 15, 2002).
GenBank Accession No.: P26008 (Jun. 15, 2002).
GenBank Accession No.: S53711 (May 7, 1993).
GenBank Accession No.: T20992 (Feb. 18, 2000).
GenBank Accession No.: T46294 (Jan. 9, 1998).

SWALL (SPTR) Accession No.: O02834 (Jul. 1, 1997).
SWALL (SPTR) Accession No.: O15389 (Jan. 1, 1998).
SWALL (SPTR) Accession No.: O28838 (Oct. 6, 2001).
SWALL (SPTR) Accession No.: O34255 (Oct. 16, 2001).
SWALL (SPTR) Accession No.: O35852 (Jan. 1, 1998).
SWALL (SPTR) Accession No.: O42414 (Jan. 1, 1998).
SWALL (SPTR) Accession No.: O70304 (Aug. 1, 1998).
SWALL (SPTR) Accession No.: O76518 (Nov. 1, 1998).
SWALL (SPTR) Accession No.: O94856 (May 1, 1999).
SWALL (SPTR) Accession No.: P26009 (May 1, 1992).
SWALL (SPTR) Accession No.: P30152 (Apr. 1, 1993).
SWALL (SPTR) Accession No.: P32970 (Oct. 1, 1993).
SWALL (SPTR) Accession No.: P33146 (Oct. 1, 1993).
SWALL (SPTR) Accession No.: P50828 (Oct. 1, 1996).
SWALL (SPTR) Accession No.: P53708 (Oct. 1, 1996).
SWALL (SPTR) Accession No.: P55291 (Oct. 1, 1996).
SWALL (SPTR) Accession No.: P58397 (Jun. 15, 2002).
SWALL (SPTR) Accession No.: P80188 (Apr. 1, 1993).
SWALL (SPTR) Accession No.: Q13308 (May 30, 2000).
SWALL (SPTR) Accession No.: Q28065 (Nov. 1, 1997).
SWALL (SPTR) Accession No.: Q29461 (Nov. 1, 1997).
SWALL (SPTR) Accession No.: Q60478 (Nov. 1, 1997).
SWALL (SPTR) Accession No.: Q60736 (Nov. 1, 1996).
SWALL (SPTR) Accession No.: Q60842 (Nov. 1, 1996).
SWALL (SPTR) Accession No.: Q61810 (Nov. 1, 1996).
SWALL (SPTR) Accession No.: Q62786 (Nov. 1, 1997).
SWALL (SPTR) Accession No.: Q63191 (Nov. 1, 1997).
SWALL (SPTR) Accession No.: Q63514 (Nov. 1, 1997).
SWALL (SPTR) Accession No.: Q8UVQ7 (Mar. 1, 2002).
SWALL (SPTR) Accession No.: Q8VCV9 (Mar. 1, 2002).
SWALL (SPTR) Accession No.: Q8VIP8 (Mar. 1, 2002).
SWALL (SPTR) Accession No.: Q90275 (Nov. 1, 1996).
SWALL (SPTR) Accession No.: Q90924 (Nov. 1, 1996).
SWALL (SPTR) Accession No.: Q90ZK1 (Dec. 1, 2001).
SWALL (SPTR) Accession No.: Q91048 (May 30, 2000).
SWALL (SPTR) Accession No.: Q91641 (Nov. 1, 1997).
SWALL (SPTR) Accession No.: Q91V02 (Dec. 1, 2001).
SWALL (SPTR) Accession No.: Q91Y09 (Dec. 1, 2001).
SWALL (SPTR) Accession No.: Q91Y10 (Dec. 1, 2001).
SWALL (SPTR) Accession No.: Q91Z60 (Dec. 1, 2001).
SWALL (SPTR) Accession No.: Q920S0 (Dec. 1, 2001).
SWALL (SPTR) Accession No.: Q95104 (Nov. 1, 1997).
SWALL (SPTR) Accession No.: Q95JN1 (Dec. 1, 2001).
SWALL (SPTR) Accession No.: Q961X3 (Dec. 1, 2001).
SWALL (SPTR) Accession No.: Q96CW9 (Dec. 1, 2001).
SWALL (SPTR) Accession No.: Q96DU4 (Dec. 1, 2001).
SWALL (SPTR) Accession No.: Q96FE5 (Dec. 1, 2001).
SWALL (SPTR) Accession No.: Q96HB9 (Dec. 1, 2001).
SWALL (SPTR) Accession No.: Q96J57 (Oct. 1, 1993).
SWALL (SPTR) Accession No.: Q96JH0 (Dec. 1, 2001).
SWALL (SPTR) Accession No.: Q96LA4 (Dec. 1, 2001).
SWALL (SPTR) Accession No.: Q96LB8 (Dec. 1, 2001).
SWALL (SPTR) Accession No.: Q96LB9 (Dec. 1, 2001).
SWALL (SPTR) Accession No.: Q96NI6 (Dec. 1, 2001).
SWALL (SPTR) Accession No.: Q96P20 (Jun. 15, 2002).
SWALL (SPTR) Accession No.: Q96P29 (Dec. 1, 2001).
SWALL (SPTR) Accession No.: Q96P30 (Dec. 1, 2001).
SWALL (SPTR) Accession No.: Q96P31 (Dec. 1, 2001).
SWALL (SPTR) Accession No.: Q96PW9 (Dec. 1, 2001).
SWALL (SPTR) Accession No.: Q96QC8 (Dec. 1, 2001).
SWALL (SPTR) Accession No.: Q96QV5 (Dec. 1, 2001).
SWALL (SPTR) Accession No.: Q96RS4 (Dec. 1, 2001).
SWALL (SPTR) Accession No.: Q96RW7 (Dec. 1, 2001).
SWALL (SPTR) Accession No.: Q98849 (Oct. 16, 2001).
SWALL (SPTR) Accession No.: Q98TY3 (Jun. 1, 2001).
SWALL (SPTR) Accession No.: Q99KQ9 (Jun. 1, 2001).
SWALL (SPTR) Accession No.: Q99ND0 (Jun. 1, 2001).
SWALL (SPTR) Accession No.: Q9BE71 (Jun. 1, 2001).
SWALL (SPTR) Accession No.: Q9BGY6 (Jun. 1, 2001).
SWALL (SPTR) Accession No.: Q9BTR1 (May 30, 2000).
SWALL (SPTR) Accession No.: Q9BXJ2 (Jun. 15, 2002).
SWALL (SPTR) Accession No.: Q9BXJ5 (Jun. 15, 2002).
SWALL (SPTR) Accession No.: Q9BYI9 (Jun. 1, 2001).
SWALL (SPTR) Accession No.: Q9BZ20 (Jun. 1, 2001).
SWALL (SPTR) Accession No.: Q9BZ83 (Jun. 1, 2001).
SWALL (SPTR) Accession No.: Q9BZR6 (Jun. 1, 2001).
SWALL (SPTR) Accession No.: Q9CRG1 (Jun. 15, 2002).
SWALL (SPTR) Accession No.: Q9CYK3 (Jun. 1, 2001).
SWALL (SPTR) Accession No.: Q9D1T0 (Jun. 1, 2001).
SWALL (SPTR) Accession No.: Q9D4M0 (Jun. 1, 2001).
SWALL (SPTR) Accession No.: Q9D4Y7 (Jun. 1, 2001).
SWALL (SPTR) Accession No.: Q9D5B9 (Jun. 1, 2001).
SWALL (SPTR) Accession No.: Q9D8I5 (Jun. 1, 2001).
SWALL (SPTR) Accession No.: Q9D8U4 (Jun. 1, 2001).
SWALL (SPTR) Accession No.: Q9ES93 (Mar. 1, 2001).
SWALL (SPTR) Accession No.: Q9GM43 (Mar. 1, 2001).
SWALL (SPTR) Accession No.: Q9H158 (Oct. 18, 2002).
SWALL (SPTR) Accession No.: Q9H324 (Jun. 15, 2002).
SWALL (SPTR) Accession No.: Q9H3U3 (Mar. 1, 2001).
SWALL (SPTR) Accession No.: Q9H796 (Mar. 1, 2001).
SWALL (SPTR) Accession No.: Q9H7K2 (Mar. 1, 2001).
SWALL (SPTR) Accession No.: Q9HD75 (Mar. 1, 2001).
SWALL (SPTR) Accession No.: Q9I997 (Oct. 1, 2000).
SWALL (SPTR) Accession No.: Q9KFY7 (Oct. 1, 2000).
SWALL (SPTR) Accession No.: Q9MZD6 (Oct. 1, 2000).
SWALL (SPTR) Accession No.: Q9N008 (Oct. 1, 2000).
SWALL (SPTR) Accession No.: Q9N0E3 (Oct. 1, 2000).
SWALL (SPTR) Accession No.: Q9NPH6 (Jun. 15, 2002).
SWALL (SPTR) Accession No.: Q9NS15 (Oct. 1, 2000).
SWALL (SPTR) Accession No.: Q9NS21 (Oct. 1, 2000).
SWALL (SPTR) Accession No.: Q9NS93 (Jun. 15, 2002).
SWALL (SPTR) Accession No.: Q9NSQ6 (Oct. 1, 2000).
SWALL (SPTR) Accession No.: Q9NUS4 (Jun. 15, 2002).
SWALL (SPTR) Accession No.: Q9NXU2 (Oct. 1, 2000).
SWALL (SPTR) Accession No.: Q9NY51 (Jun. 15, 2002).
SWALL (SPTR) Accession No.: Q9NY52 (Jun. 15, 2002).
SWALL (SPTR) Accession No.: Q9NY54 (Jun. 15, 2002).
SWALL (SPTR) Accession No.: Q9NYZ4 (Oct. 1, 2000).
SWALL (SPTR) Accession No.: Q9P244 (Oct. 1, 2000).
SWALL (SPTR) Accession No.: Q9P2B2 (Oct. 1, 2000).
SWALL (SPTR) Accession No.: Q9PVY2 (May 1, 2000).
SWALL (SPTR) Accession No.: Q9QVN5 (May 1, 2000).
SWALL (SPTR) Accession No.: Q9QVP7 (May 1, 2000).
SWALL (SPTR) Accession No.: Q9R013 (Oct. 16, 2001).
SWALL (SPTR) Accession No.: Q9RC64 (May 1, 2000).
SWALL (SPTR) Accession No.: Q9UBX1 (Oct. 16, 2001).
SWALL (SPTR) Accession No.: Q9UGM3 (May 1, 2000).
SWALL (SPTR) Accession No.: Q9UKJ4 (May 1, 2000).
SWALL (SPTR) Accession No.: Q9ULH4 (May 1, 2000).
SWALL (SPTR) Accession No.: Q9ULS5 (Oct. 16, 2001).
SWALL (SPTR) Accession No.: Q9UP79 (Oct. 16, 2001).
SWALL (SPTR) Accession No.: Q9VI21 (May 1, 2000).
SWALL (SPTR) Accession No.: Q9VWD2 (May 1, 2000).
SWALL (SPTR) Accession No.: Q9VZ84 (May 1, 2000).
SWALL (SPTR) Accession No.: Q9WUQ1 (Oct. 16, 2001).
SWALL (SPTR) Accession No.: Q9WV91 (Nov. 1, 1999).
SWALL (SPTR) Accession No.: Q9Y211 (Nov. 1, 1999).
SWALL (SPTR) Accession No.: Q9Y286 (Nov. 1, 1999).

SWALL (SPTR) Accession No.: Q9Y4V9 (Nov. 1, 1999).
SWALL (SPTR) Accession No.: Q9Y5H6 (Oct. 16, 2001).
SWALL (SPTR) Accession No.: Q9Y5I4 (Oct. 16, 2001).
Alderborn et al. (2000). "Determination of single–nucleotide polymorphisms by real–time pyrophosphate DNA sequencing." *Genome Res 10*(8): 1249–1258.
Almeida et al. (1998). "GAC1, a new member of the leucine–rich repeat superfamily on chromosome band 1q32.1, is amplified and overexpressed in malignant gliomas." *Oncogene 16*(23): 2997–3002.
Battye et al. (2001). "Repellent signaling by Slit requires the leucine–rich repeats." *J. Neurosci 21*(12): 4290–4298.
Bormann et al. (1999). "zfNLRR, a novel leucine–rich repeat protein is preferentially expressed during regeneration in zebrafish." *Mol Cell Neurosci 13*(3): 167–179.
Bosco et al. (2000). "Importance of cell–matrix interactions in rat islet beta–cell secretion in vitro: role of alpha6beta1 integrin." *Diabetes 49*(2): 233–243.
Braisted et al. (2000). "Netrin–1 promotes thalamic axon growth and is required for proper development of the thalamocortical projection." *J Neurosci 20*(15): 5792–5801.
Colman et al. (2000). "Domain 5 of high molecular weight kininogen (kininostatin) down– regulates endothelial cell proliferation and migration and inhibits angiogenesis." *Blood 95*(2): 543–550.
Darabi et al. (1995). "Differential gene expression in experimental hepatocellular carcinoma induced by woodchuck hepatitis B virus." *Cancer Lett 95*(1–2): 153–159.
Ellezam et al. (2001). "Expression of netrin–1 and its receptors DCC and UNC–5H2 after axotomy and during regeneration of adult rat retinal ganglion cells." *Exp Neurol 168*(1): 105–115.
Guo et al. (2001). "Kininostatin, an angiogenic inhibitor, inhibits proliferation and induces apoptosis of human endothelial cells." *Arterioscler Thromb Vasc Biol 21*(9): 1427–1433.
Hartner et al. (2002). "The alpha8 integrin chain affords mechanical stability to the glomerular capillary tuft in hypertensive glomerular disease." *Am J Pathol 160*(3): 861–867.
Hatzivassiliou et al. (2001). "IRTA1 and IRTA2, novel immunoglobulin superfamily receptors expressed in B cells and involved in chromosome 1q21 abnormalities in B cells malignancy." *Immunity 14*(3): 277–289.
Hilschmann et al. (2001). "The immunoglobulin–like genetic predetermination of the brain: the protocadherins, blueprint of the neuronal network." *Naturwissenschaften 88*(1): 2–12.
Itoh et al. (1998). "Cloning and expressions of three mammalian homologues of Drosophila slit suggest possible roles for Slit in the formation and maintenance of the nervous system." *Brain Res Mol Brain Res 62*(2): 175–186.
Jiang et al. (1995). "Structural predictions for the ligand–binding region of glycoprotein hormone receptors and the nature of hormone–receptor interactions." *Stucture 3*(12): 1341–1353.
Kaufmann et al. (1999). "The M–cadherin catenin complex interacts with microtubules in skeletal muscle cells: implications for the fusion of myoblasts." *J Cell Sci 112*(Pt 1): 55–68.
Kelic et al. (2001). "CD81 regulates neuron–induced astrocyte cell–cycle exit." *Mol Cell Neurosci 17*(3); 551–560.

Kjeldsen et al. (2000). "Human neutrophil gelatinase–associated lipocalin and homologous proteins in rat and mouse." *Biochim Biophys Acta 1482*(1–2): 272–283.
Kuno et al. (1997). "Molecular cloning of a gene encoding a new type of metalloproteinase– disintegrin family protein with thrombospondin motifs as an inflammation associated gene." *J Biol Chem 272*(1): 556–562.
Ledesma et al. (2000). "Brain plasmin enhances APP alpha–cleavage and Abeta degradation and is reduced in Alzheimer's disease brains." *EMBO Rep 1*(6): 530–535.
Leimig et al. (2002). "Functional amelioration of murine galactosialidosis by genetically modified bone marrow hematopoietic progenitor cells." *Blood 99*(9): 3169–3178.
Llambi et al. (2001). "Netrin–1 acts as a survival factor via its receptors UNC5H and DCC." *Embo J 20*(11): 2715–2722.
Martel–Pelletier et al. (2001). "Metalloproteases and inhibitors in arthritic diseases." *Best Pract Res Clin Rheumatol 15*(5): 805–829.
Masui et al. (2001). "Expression of METH–1 and METH–2 in pancreatic cancer." *Clin Cancer Res 7*(11): 3437–3443.
Michi et al. (2001). "Claudin–4: a new target for pancreatic cancer treatment using *Clostridium perfringens* enterotoxin." *Gastroenterology 121*(3): 678–684.
Miwa et al. (2000). "Involvement of claudin–1 in the beta–catenin/Tcf signaling pathway and its frequent upregulation in human colorectal cancers." *Oncol Res 12*(11–12): 469–476.
Morrison et al. (1995). "Mat–8, a novel phospholemman–like protein expressed in human breast tumors, induces a chloride conductance in *Xenopus oocytes.*" *J Biol Chem 270*(5): 2176–2182.
Mossie et al. (1995). "Colon carcinoma kinase–4 defines a new subclass of the receptor tyrosine kinase family." *Oncogene 11*(10): 2179–2184.
Padilla et al. (1998). "Cadherins M, 11, and 6 expression patterns suggest complementary roles in mouse neuromuscular axis development." *Mol Cell Neurosci 11*(4): 217–233.
Pittenger et al. (1999). "Multilineage potential of adult human mesenchymal stem cells." *Science 284*(5411): 143–147.
Ranscht, B. (2000). "Cadherins: molecular codes for axon guidance and synapse formation." *Int J Dev Neurosci 18*(7): 643–651.
Shimkets et al. (1999). "Gene expression analysis by transcript profiling coupled to a gene database query." *Nat Biotechnol 17*(8): 798–803.
Stassar et al. (2001). "Identification of human renal cell carcinoma associated genes by suppression subtractive hybridization." *Br J Cancer 85*(9): 1372–1382.
Stipp et al. (2001). "FPRP, a major, highly stoichiometric, highly specific CD81– and CD9– associated protein." *J Biol Chem 276*(7): 4853–4862.
Taniguchi et al. (2000). "Functional dissection of drosophila capricious: its novel roles in neuronal pathfinding and selective synapse formation." *J Neurobiol 42*(1): 104–116.
Ujhazy et al. (2001). "Familial intrahepatic cholestasis 1: studies of localization and function." *Hepatology 34*(4 Pt 1): 768–775.
International Search Report for PCT/US02/17428. Mailed on Aug. 19, 2003.
Attwood, T. K. (2000). "Genomics. The Babel of bioinformatics." Science 290(5491): 471–3.

Gerhold, D. and C. T. Caskey (1996). "It's the genes! EST access to human genome content." Bioessays 18(12): 973–81.

Wells, T. N. and M. C. Peitsch (1997). "The chemokine information source: identification and characterization of novel chemokines using the WorldWideWeb and expressed sequence tag databases." J Leukoc Biol 61(5): 545–50.

Russell, R. B. and G. J. Barton (1994). "Structural features can be unconserved in proteins with similar folds. An analysis of side–chain to side–chain contacts secondary structure and accessibility." J Mol Biol 244(3): 332–50.

Lopez, P., Herve,P., Myllykallio ,H. and Forterre, P. (1999). "Whole genome sequence information: Going wrong with confidence ." Mol Microbiol (32):881–891.

Written Opinion for PCT/US02/17428, mailed on Oct. 12, 2004.

* cited by examiner

US 7,034,132 B2

THERAPEUTIC POLYPEPTIDES, NUCLEIC ACIDS ENCODING SAME, AND METHODS OF USE

RELATED APPLICATIONS

This application claims priority from Provisional Applications U.S. Ser. No. 60/295,607, filed Jun. 4, 2001; U.S. Ser. No. 60/295,661, filed Jun. 4, 2001; U.S. Ser. No. 60/296,404, filed Jun. 6, 2001; U.S. Ser. No. 60/296,418, filed Jun. 6, 2001; U.S. Ser. No. 60/297,414, filed Jun. 11, 2001; U.S. Ser. No. 60/297,567, filed Jun. 12, 2001; U.S. Ser. No. 60/298,285, filed Jun. 14, 2001; U.S. Ser. No. 60/298,556, filed Jun. 15, 2001; U.S. Ser. No. 60/299,949, filed Jun. 21, 2001; U.S. Ser. No. 60/300,883, filed Jun. 26, 2001; U.S. Ser. No. 60/301,550, filed Jun. 28, 2001; U.S. Ser. No. 60/311,972, filed Aug. 13, 2001; U.S. Ser. No. 60/315,069, filed Aug. 27, 2001; U.S. Ser. No. 60/315,071, filed Aug. 27, 2001; U.S. Ser. No. 60/315,660, filed Aug. 29, 2001; U.S. Ser. No. 60/322,293, filed Sep. 14, 2001; U.S. Ser. No. 60/322,706, filed Sep. 17, 2001; U.S. Ser. No. 60/341,186, filed Dec. 14, 2001; U.S. Ser. No. 60/361,189, filed Feb. 28, 2002; U.S. Ser. No. 60/363,673, filed Mar. 12, 2002, and U.S. Ser. No. 60/363,676, filed Mar. 12, 2002, each of which is incorporated by reference in its entirety.

FIELD OF THE INVENTION

The present invention relates to novel polypeptides, and the nucleic acids encoding them, having properties related to stimulation of biochemical or physiological responses in a cell, a tissue, an organ or an organism. More particularly, the novel polypeptides are gene products of novel genes, or are specified biologically active fragments or derivatives thereof. Methods of use encompass diagnostic and prognostic assay procedures as well as methods of treating diverse pathological conditions.

BACKGROUND OF THE INVENTION

Eukaryotic cells are characterized by biochemical and physiological processes, which under normal conditions are exquisitely balanced to achieve the preservation and propagation of the cells. When such cells are components of multicellular organisms such as vertebrates or, more particularly, organisms such as mammals, the regulation of the biochemical and physiological processes involves intricate signaling pathways. Frequently, such signaling pathways include constituted of extracellular signaling proteins, cellular receptors that bind the signaling proteins and signal transducing components located within the cells.

Signaling proteins may be classified as endocrine effectors, paracrine effectors or autocrine effectors. Endocrine effectors are signaling molecules secreted by a given organ into the circulatory system, which are then transported to a distant target organ or tissue. The target cells include the receptors for the endocrine effector, and when the endocrine effector binds, a signaling cascade is induced. Paracrine effectors involve secreting cells and receptor cells in close proximity to each other, such as two different classes of cells in the same tissue or organ. One class of cells secretes the paracrine effector, which then reaches the second class of cells, for example by diffusion through the extracellular fluid. The second class of cells contains the receptors for the paracrine effector; binding of the effector results in induction of the signaling cascade that elicits the corresponding biochemical or physiological effect. Autocrine effectors are highly analogous to paracrine effectors, except that the same cell type that secretes the autocrine effector also contains the receptor. Thus the autocrine effector binds to receptors on the same cell, or on identical neighboring cells. The binding process then elicits the characteristic biochemical or physiological effect.

Signaling processes may elicit a variety of effects on cells and tissues including, by way of nonlimiting example, induction of cell or tissue proliferation, suppression of growth or proliferation, induction of differentiation or maturation of a cell or tissue, and suppression of differentiation or maturation of a cell or tissue.

Many pathological conditions involve dysregulation of expression of important effector proteins. In certain classes of pathologies the dysregulation is manifested as diminished or suppressed level of synthesis and secretion of protein effectors. In other classes of pathologies the dysregulation is manifested as increased or up-regulated level of synthesis and secretion of protein effectors. In a clinical setting a subject may be suspected of suffering from a condition brought on by altered or mis-regulated levels of a protein effector of interest. Therefore there is a need to assay for the level of the protein effector of interest in a biological sample from such a subject, and to compare the level with that characteristic of a nonpathological condition. There also is a need to provide the protein effector as a product of manufacture. Administration of the effector to a subject in need thereof is useful in treatment of the pathological condition. Accordingly, there is a need for a method of treatment of a pathological condition brought on by a diminished or suppressed levels of the protein effector of interest. In addition, there is a need for a method of treatment of a pathological condition brought on by a increased or up-regulated levels of the protein effector of interest.

SUMMARY OF THE INVENTION

The invention is based in part upon the discovery of isolated polypeptides including amino acid sequences selected from mature forms of the amino acid sequences selected from the group consisting of SEQ ID NO:2n, wherein n is an integer between 1 and 54. The invention also is based in part upon variants of a mature form of the amino acid sequence selected from the group consisting of SEQ ID NO:2n, wherein n is an integer between 1 and 54, wherein any amino acid in the mature form is changed to a different amino acid, provided that no more than 15% of the amino acid residues in the sequence of the mature form are so changed. In another embodiment, the invention includes the amino acid sequences selected from the group consisting of SEQ ID NO:2n, wherein n is an integer between 1 and 54. In another embodiment, the invention also comprises variants of the amino acid sequence selected from the group consisting of SEQ ID NO:2n, wherein n is an integer between 1 and 54 wherein any amino acid specified in the chosen sequence is changed to a different amino acid, provided that no more than 15% of the amino acid residues in the sequence are so changed. The invention also involves fragments of any of the mature forms of the amino acid sequences selected from the group consisting of SEQ ID NO:2n, wherein n is an integer between 1 and 54, or any other amino acid sequence selected from this group. The invention also comprises fragments from these groups in which up to 15% of the residues are changed.

In another embodiment, the invention encompasses polypeptides that are naturally occurring allelic variants of the sequence selected from the group consisting of SEQ ID NO:2n, wherein n is an integer between 1 and 54. These allelic variants include amino acid sequences that are the translations of nucleic acid sequences differing by a single nucleotide from nucleic acid sequences selected from the group consisting of SEQ ID NOS: 2n−1, wherein n is an integer between 1 and 54. The variant polypeptide where any amino acid changed in the chosen sequence is changed to provide a conservative substitution.

In another embodiment, the invention comprises a pharmaceutical composition involving a polypeptide with an amino acid sequence selected from the group consisting of SEQ ID NO:2n, wherein n is an integer between 1 and 54 and a pharmaceutically acceptable carrier. In another embodiment, the invention involves a kit, including, in one or more containers, this pharmaceutical composition.

In another embodiment, the invention includes the use of a therapeutic in the manufacture of a medicament for treating a syndrome associated with a human disease, the disease being selected from a pathology associated with a polypeptide with an amino acid sequence selected from the group consisting of SEQ ID NO:2n, wherein n is an integer between 1 and 54 wherein said therapeutic is the polypeptide selected from this group.

In another embodiment, the invention comprises a method for determining the presence or amount of a polypeptide with an amino acid sequence selected from the group consisting of SEQ ID NO:2n, wherein n is an integer between 1 and 54 in a sample, the method involving providing the sample; introducing the sample to an antibody that binds immunospecifically to the polypeptide; and determining the presence or amount of antibody bound to the polypeptide, thereby determining the presence or amount of polypeptide in the sample.

In another embodiment, the invention includes a method for determining the presence of or predisposition to a disease associated with altered levels of a polypeptide with an amino acid sequence selected from the group consisting of SEQ ID NO:2n, wherein n is an integer between 1 and 54 in a first mammalian subject, the method involving measuring the level of expression of the polypeptide in a sample from the first mammalian subject; and comparing the amount of the polypeptide in this sample to the amount of the polypeptide present in a control sample from a second mammalian subject known not to have, or not to be predisposed to, the disease, wherein an alteration in the expression level of the polypeptide in the first subject as compared to the control sample indicates the presence of or predisposition to the disease.

In another embodiment, the invention involves a method of identifying an agent that binds to a polypeptide with an amino acid sequence selected from the group consisting of SEQ ID NO:2n, wherein n is an integer between 1 and 54, the method including introducing the polypeptide to the agent; and determining whether the agent binds to the polypeptide. The agent could be a cellular receptor or a downstream effector.

In another embodiment, the invention involves a method for identifying a potential therapeutic agent for use in treatment of a pathology, wherein the pathology is related to aberrant expression or aberrant physiological interactions of a polypeptide with an amino acid sequence selected from the group consisting of SEQ ID NO:2n, wherein n is an integer between 1 and 54, the method including providing a cell expressing the polypeptide of the invention and having a property or function ascribable to the polypeptide; contacting the cell with a composition comprising a candidate substance; and determining whether the substance alters the property or function ascribable to the polypeptide; whereby, if an alteration observed in the presence of the substance is not observed when the cell is contacted with a composition devoid of the substance, the substance is identified as a potential therapeutic agent.

In another embodiment, the invention involves a method for screening for a modulator of activity or of latency or predisposition to a pathology associated with a polypeptide having an amino acid sequence selected from the group consisting of SEQ ID NO:2n, wherein n is an integer between 1 and 54, the method including administering a test compound to a test animal at increased risk for a pathology associated with the polypeptide of the invention, wherein the test animal recombinantly expresses the polypeptide of the invention; measuring the activity of the polypeptide in the test animal after administering the test compound; and comparing the activity of the protein in the test animal with the activity of the polypeptide in a control animal not administered the polypeptide, wherein a change in the activity of the polypeptide in the test animal relative to the control animal indicates the test compound is a modulator of latency of, or predisposition to, a pathology associated with the polypeptide of the invention. The recombinant test animal could express a test protein transgene or express the transgene under the control of a promoter at an increased level relative to a wild-type test animal The promoter may or may not b the native gene promoter of the transgene.

In another embodiment, the invention involves a method for modulating the activity of a polypeptide with an amino acid sequence selected from the group consisting of SEQ ID NO:2n, wherein n is an integer between 1 and 54, the method including introducing a cell sample expressing the polypeptide with a compound that binds to the polypeptide in an amount sufficient to modulate the activity of the polypeptide.

In another embodiment, the invention involves a method of treating or preventing a pathology associated with a polypeptide with an amino acid sequence selected from the group consisting of SEQ ID NO:2n, wherein n is an integer between 1 and 54, the method including administering the polypeptide to a subject in which such treatment or prevention is desired in an amount sufficient to treat or prevent the pathology in the subject. The subject could be human.

In another embodiment, the invention involves a method of treating a pathological state in a mammal, the method including administering to the mammal a polypeptide in an amount that is sufficient to alleviate the pathological state, wherein the polypeptide is a polypeptide having an amino acid sequence at least 95% identical to a polypeptide having the amino acid sequence selected from the group consisting of SEQ ID NO:2n, wherein n is an integer between 1 and 54 or a biologically active fragment thereof.

In another embodiment, the invention involves an isolated nucleic acid molecule comprising a nucleic acid sequence encoding a polypeptide having an amino acid sequence selected from the group consisting of a mature form of the amino acid sequence given SEQ ID NO:2n, wherein n is an integer between 1 and 54; a variant of a mature form of the amino acid sequence selected from the group consisting of SEQ ID NO:2n, wherein n is an integer between 1 and 54 wherein any amino acid in the mature form of the chosen sequence is changed to a different amino acid, provided that no more than 15% of the amino acid residues in the sequence of the mature form are so changed; the amino acid sequence selected from the group consisting of SEQ ID NO:2n, wherein n is an integer between 1 and 54; a variant of the amino acid sequence selected from the group consisting of SEQ ID NO:2n, wherein n is an integer between 1 and 54, in which any amino acid specified in the chosen sequence is changed to a different amino acid, provided that no more than 15% of the amino acid residues in the sequence are so changed; a nucleic acid fragment encoding at least a portion of a polypeptide comprising the amino acid sequence selected from the group consisting of SEQ ID NO:2n, wherein n is an integer between 1 and 54 or any variant of the polypeptide wherein any amino acid of the chosen sequence is changed to a different amino acid, provided that no more than 10% of the amino acid residues in the sequence are so changed; and the complement of any of the nucleic acid molecules.

In another embodiment, the invention comprises an isolated nucleic acid molecule having a nucleic acid. sequence encoding a polypeptide comprising an amino acid sequence selected from the group consisting of a mature form of the amino acid sequence given SEQ ID NO:2n, wherein n is an integer between 1 and 54, wherein the nucleic acid molecule comprises the nucleotide sequence of a naturally occurring allelic nucleic acid variant.

In another embodiment, the invention involves an isolated nucleic acid molecule including a nucleic acid sequence encoding a polypeptide having an amino acid sequence selected from the group consisting of a mature form of the amino acid sequence given SEQ ID NO:2n, wherein n is an integer between 1 and 54 that encodes a variant polypeptide, wherein the variant polypeptide has the polypeptide sequence of a naturally occurring polypeptide variant.

In another embodiment, the invention comprises an isolated nucleic acid molecule having a nucleic acid sequence encoding a polypeptide comprising an amino acid sequence selected from the group consisting of a mature form of the amino acid sequence given SEQ ID NO:2n, wherein n is an integer between 1 and 54, wherein the nucleic acid molecule differs by a single nucleotide from a nucleic acid sequence selected from the group consisting of SEQ ID NOS: 2n–1, wherein n is an integer between 1 and 54.

In another embodiment, the invention includes an isolated nucleic acid molecule having a nucleic acid sequence encoding a polypeptide including an amino acid sequence selected from the group consisting of a mature form of the amino acid sequence given SEQ ID NO:2n, wherein n is an integer between 1 and 54, wherein the nucleic acid molecule comprises a nucleotide sequence selected from the group consisting of the nucleotide sequence selected from the group consisting of SEQ ID NO:2n–1, wherein n is an integer between 1 and 54; a nucleotide sequence wherein one or more nucleotides in the nucleotide sequence selected from the group consisting of SEQ ID NO:2n–1, wherein n is an integer between 1 and 54 is changed from that selected from the group consisting of the chosen sequence to a different nucleotide provided that no more than 15% of the nucleotides are so changed; a nucleic acid fragment of the sequence selected from the group consisting of SEQ ID NO:2n–1, wherein n is an integer between 1 and 54; and a nucleic acid fragment wherein one or more nucleotides in the nucleotide sequence selected from the group consisting of SEQ ID NO:2n–1, wherein n is an integer between 1 and 54 is changed from that selected from the group consisting of the chosen sequence to a different nucleotide provided that no more than 15% of the nucleotides are so changed.

In another embodiment, the invention includes an isolated nucleic acid molecule having a nucleic acid sequence encoding a polypeptide including an amino acid sequence selected from the group consisting of a mature form of the amino acid sequence given SEQ ID NO:2n, wherein n is an integer between 1 and 54, wherein the nucleic acid molecule hybridizes under stringent conditions to the nucleotide sequence selected from the group consisting of SEQ ID NO:2n–1, wherein n is an integer between 1 and 54, or a complement of the nucleotide sequence.

In another embodiment, the invention includes an isolated nucleic acid molecule having a nucleic acid sequence encoding a polypeptide including an amino acid sequence selected from the group consisting of a mature form of the amino acid sequence given SEQ ID NO:2n, wherein n is an integer between 1 and 54, wherein the nucleic acid molecule has a nucleotide sequence in which any nucleotide specified in the coding sequence of the chosen nucleotide sequence is changed from that selected from the group consisting of the chosen sequence to a different nucleotide provided that no more than 15% of the nucleotides in the chosen coding sequence are so changed, an isolated second polynucleotide that is a complement of the first polynucleotide, or a fragment of any of them.

In another embodiment, the invention includes a vector involving the nucleic acid molecule having a nucleic acid sequence encoding a polypeptide including an amino acid sequence selected from the group consisting of a mature form of the amino acid sequence given SEQ ID NO:2n, wherein n is an integer between 1 and 54. This vector can have a promoter operably linked to the nucleic acid molecule. This vector can be located within a cell.

In another embodiment, the invention involves a method for determining the presence or amount of a nucleic acid molecule having a nucleic acid sequence encoding a polypeptide including an amino acid sequence selected from the group consisting of a mature form of the amino acid sequence given SEQ ID NO:2n, wherein n is an integer between 1 and 54 in a sample, the method including providing the sample; introducing the sample to a probe that binds to the nucleic acid molecule; and determining the presence or amount of the probe bound to the nucleic acid molecule, thereby determining the presence or amount of the nucleic acid molecule in the sample. The presence or amount of the nucleic acid molecule is used as a marker for cell or tissue type. The cell type can be cancerous.

In another embodiment, the invention involves a method for determining the presence of or predisposition for a disease associated with altered levels of a nucleic acid molecule having a nucleic acid sequence encoding a polypeptide including an amino acid sequence selected from the group consisting of a mature form of the amino acid sequence given SEQ ID NO:2n, wherein n is an integer between 1 and 54 in a first mammalian subject, the method including measuring the amount of the nucleic acid in a sample from the first mammalian subject; and comparing the amount of the nucleic acid in the sample of step (a) to the amount of the nucleic acid present in a control sample from a second mammalian subject known not to have or not be predisposed to, the disease; wherein an alteration in the level of the nucleic acid in the first subject as compared to the control sample indicates the presence of or predisposition to the disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The present invention provides novel nucleotides and polypeptides encoded thereby. Included in the invention are the novel nucleic acid sequences, their encoded polypeptides, antibodies, and other related compounds. The sequences are collectively referred to herein as "NOVX nucleic acids" or "NOVX polynucleotides" and the corresponding encoded polypeptides are referred to as "NOVX polypeptides" or "NOVX proteins." Unless indicated otherwise, "NOVX" is meant to refer to any of the novel sequences disclosed herein. Table 1 provides a summary of the NOVX nucleic acids and their encoded polypeptides.

TABLE 1

Sequences and Corresponding SEQ ID Numbers

| NOVX Assignment | Internal Identification | SEQ ID NO (nucleic acid) | SEQ ID NO (amino acid) | Homology |
| --- | --- | --- | --- | --- |
| Nov1a | CG100488-01 | 1 | 2 | Elastase 2B like *homo sapiens* |
| Nov1b | CG100488-06 | 3 | 4 | Elastase 2B like *homo sapiens* |
| Nov1c | CG100488-07 | 5 | 6 | Elastase 2B like *homo sapiens* |
| Nov1d | CG100488-08 | 7 | 8 | Elastase 2B like *homo sapiens* |
| Nov1e | CG100488-09 | 9 | 10 | Elastase 2B like *homo sapiens* |
| Nov1f | 198353297 | 11 | 12 | Elastase 2B like *homo sapiens* |
| Nov1g | 198353301 | 13 | 14 | Elastase 2B like *homo sapiens* |
| Nov1h | 198353319 | 15 | 16 | Elastase 2B like *homo sapiens* |
| Nov1i | 198362547 | 17 | 18 | Elastase 2B like *homo sapiens* |
| Nov1j | 198362642 | 19 | 20 | Elastase 2B like *homo sapiens* |
| Nov2a | CG100560-01 | 21 | 22 | Leucine Rich Repeat like *homo sapiens* |
| Nov2b | CG100560-02 | 23 | 24 | Leucine Rich Repeat like *homo sapiens* |
| Nov3a | CG101012-01 | 25 | 26 | Gonadotrophin beta-subunit like *homo sapiens* |
| Nov4a | CG101584-01 | 27 | 28 | odorant binding protein like *homo sapiens* |
| Nov5a | CG101707-01 | 29 | 30 | Complement C1q |
| Nov6a | CG101836-01 | 31 | 32 | Cathepsin F like *homo sapiens* |
| Nov6b | CG101836-02 | 33 | 34 | Cathepsin F like *homo sapiens* |
| Nov7a | CG102221-01 | 35 | 36 | netrin G1 like *homo sapiens* |
| Nov8a | CG102325-01 | 37 | 38 | Secreted reprolysin |
| Nov9a | CG102832-01 | 39 | 40 | CAC37763 like *homo sapiens* |
| Nov9b | CG102832-02 | 41 | 42 | Ig domain-containing transmembrane protein like *homo sapiens* |
| Nov9c | 197195425 | 43 | 44 | Ig domain-containing transmembrane protein like *homo sapiens* |
| Nov9d | 197192431 | 45 | 46 | Ig domain-containing transmembrane protein like *homo sapiens* |
| Nov9e | 197192437 | 47 | 48 | Ig domain-containing transmembrane protein like *homo sapiens* |
| Nov9f | 197192443 | 49 | 50 | Ig domain-containing transmembrane protein like *homo sapiens* |
| Nov9g | 197192448 | 51 | 52 | Ig domain-containing transmembrane protein like *homo sapiens* |
| Nov10a | CG102942-01 | 53 | 54 | lipocalin 2 like *homo sapiens* |
| Nov10b | CG102942-03 | 55 | 56 | Neutrophil Gelatinase-Associated lipocalin like *homo sapiens* |
| Nov10c | 237376776 | 57 | 58 | Neutrophil Gelatinase-Associated lipocalin like *homo sapiens* |
| Nov11a | CG104016-01 | 59 | 60 | DENN domain containing protein like *homo sapiens* |
| Nov11b | 197208336 | 61 | 62 | DENN domain containing protein like *homo sapiens* |
| Nov11c | 197306179 | 63 | 64 | DENN domain containing protein like *homo sapiens* |
| Nov11d | 219903686 | 65 | 66 | DENN domain containing protein like *homo sapiens* |
| Nov11e | 219903690 | 67 | 68 | DENN domain containing protein like *homo sapiens* |
| Nov12a | CG104903-01 | 69 | 70 | Kininogen Precursor like *homo sapiens* |
| Nov12b | CG104903-02 | 71 | 73 | Kininogen Precursor like *homo sapiens* |
| Nov12c | CG104903-03 | 73 | 74 | Kininogen Precursor like *homo sapiens* |

TABLE 1-continued

Sequences and Corresponding SEQ ID Numbers

| NOVX Assignment | Internal Identification | SEQ ID NO (nucleic acid) | SEQ ID NO (amino acid) | Homology |
|---|---|---|---|---|
| Nov12d | CG104903-05 | 75 | 76 | Kininogen Precursor like *homo sapiens* |
| Nov12e | CG104903-06 | 77 | 78 | Kininogen Precursor like *homo sapiens* |
| Nov12f | CG104903-07 | 79 | 80 | Kininogen Precursor like *homo sapiens* |
| Nov12g | CG104903-08 | 81 | 82 | Kininogen Precursor like *homo sapiens* |
| Nov12h | CG104903-09 | 83 | 84 | Kininogen Precursor like *homo sapiens* |
| Nov13a | CG105982-01 | 85 | 86 | Serine Protease-CUB Domain Protein like *homo sapiens* |
| Nov14a | CG107614-02 | 87 | 88 | Hemopexin-like |
| Nov15a | CG109445-01 | 89 | 90 | neuronal leucine-rich repeat protein like *homo sapiens* |
| Nov16a | CG109496-01 | 91 | 92 | neuronal leucine-rich repeat protein like *homo sapiens* |
| Nov17a | CG109532-01 | 93 | 94 | Immunoglobulin domains containing protein like *homo sapiens* |
| Nov17b | 207775340 | 95 | 96 | Immunoglobulin domains containing protein like *homo sapiens* |
| Nov17c | 207775361 | 97 | 98 | Immunoglobulin domains containing protein like *homo sapiens* |
| Nov17d | 207775365 | 99 | 100 | Immunoglobulin domains containing protein like *homo sapiens* |
| Nov18a | CG50213-01 | 101 | 102 | small inducible cytokine subfamily B member 14 (BRAK) |
| Nov18b | CG50213-02 | 103 | 104 | small inducible cytokine subfamily B member 14 (BRAK) |
| Nov18c | CG50213-03 | 105 | 106 | small inducible cytokine subfamily B member 14 (BRAK) |
| Nov19a | CG88912-02 | 107 | 108 | BETA-NEOENDORPHIN-DYNORPHIN PRECURSOR like *homo sapiens* |

Table 1 indicates homology of NOVX nucleic acids to known protein families. Thus, the nucleic acids and polypeptides, antibodies and related compounds according to the invention corresponding to a NOVX as identified in column 1 of Table 1 will be useful in therapeutic and diagnostic applications implicated in, for example, pathologies and disorders associated with the known protein families identified in column 5 of Table 1.

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

Consistent with other known members of the family of proteins, identified in column 5 of Table 1, the NOVX polypeptides of the present invention show homology to, and contain domains that are characteristic of, other members of such protein families. Details of the sequence relatedness and domain analysis for each NOVX are presented in Example A.

The NOVX nucleic acids and polypeptides can also be used to screen for molecules, which inhibit or enhance NOVX activity or function. Specifically, the nucleic acids and polypeptides according to the invention may be used as targets for the identification of small molecules that modulate or inhibit diseases associated with the protein families listed in Table 1.

The NOVX nucleic acids and polypeptides are also useful for detecting specific cell types. Details of the expression analysis for each NOVX are presented in Example C. Accordingly, the NOVX nucleic acids, polypeptides, antibodies and related compounds according to the invention will have diagnostic and therapeutic applications in the detection of a variety of diseases with differential expression in normal vs. diseased tissues, e.g. a variety of cancers.

Additional utilities for NOVX nucleic acids and polypeptides according to the invention are disclosed herein.

NOVX Clones

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

The NOVX genes and their corresponding encoded proteins are useful for preventing, treating or ameliorating medical conditions, e.g., by protein or gene therapy. Pathological conditions can be diagnosed by determining the amount of the new protein in a sample or by determining the presence of mutations in the new genes. Specific uses are described for each of the NOVX genes, based on the tissues in which they are most highly expressed. Uses include developing products for the diagnosis or treatment of a variety of diseases and disorders.

The NOVX nucleic acids and proteins of the invention are useful in potential diagnostic and therapeutic applications and as a research tool. These include serving as a specific or selective nucleic acid or protein diagnostic and/or prognostic marker, wherein the presence or amount of the nucleic acid or the protein are to be assessed, as well as potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), and (v) a composition promoting tissue regeneration in vitro and in vivo (vi) biological defense weapon.

In one specific embodiment, the invention includes an isolated polypeptide comprising an amino acid sequence selected from the group consisting of: (a) a mature form of the amino acid sequence selected from the group consisting of SEQ ID NO:2n, wherein n is an integer between 1 and 54; (b) a variant of a mature form of the amino acid sequence selected from the group consisting of SEQ ID NO:2n, wherein n is an integer between 1 and 54, wherein any amino acid in the mature form is changed to a different amino acid, provided that no more than 15% of the amino acid residues in the sequence of the mature form are so changed; (c) an amino acid sequence selected from the group consisting of SEQ ID NO:2n, wherein n is an integer between 1 and 54; (d) a variant of the amino acid sequence selected from the group consisting of SEQ ID NO:2n, wherein n is an integer between 1 and 54 wherein any amino acid specified in the chosen sequence is changed to a different amino acid, provided that no more than 15% of the amino acid residues in the sequence are so changed; and (e) a fragment of any of (a) through (d).

In another specific embodiment, the invention includes an isolated nucleic acid molecule comprising a nucleic acid sequence encoding a polypeptide comprising an amino acid sequence selected from the group consisting of: (a) a mature form of the amino acid sequence given SEQ ID NO:2n, wherein n is an integer between 1 and 54; (b) a variant of a mature form of the amino acid sequence selected from the group consisting of SEQ ID NO:2n, wherein n is an integer between 1 and 54 wherein any amino acid in the mature form of the chosen sequence is changed to a different amino acid, provided that no more than 15% of the amino acid residues in the sequence of the mature form are so changed; (c) the amino acid sequence selected from the group consisting of SEQ ID NO:2n, wherein n is an integer between 1 and 54; (d) a variant of the amino acid sequence selected from the group consisting of SEQ ID NO:2n, wherein n is an integer between 1 and 54, in which any amino acid specified in the chosen sequence is changed to a different amino acid, provided that no more than 15% of the amino acid residues in the sequence are so changed; (e) a nucleic acid fragment encoding at least a portion of a polypeptide comprising the amino acid sequence selected from the group consisting of SEQ ID NO:2n, wherein n is an integer between 1 and 54 or any variant of said polypeptide wherein any amino acid of the chosen sequence is changed to a different amino acid, provided that no more than 10% of the amino acid residues in the sequence are so changed; and (f) the complement of any of said nucleic acid molecules.

In yet another specific embodiment, the invention includes an isolated nucleic acid molecule, wherein said nucleic acid molecule comprises a nucleotide sequence selected from the group consisting of: (a) the nucleotide sequence selected from the group consisting of SEQ ID NO:2n−1, wherein n is an integer between 1 and 54; (b) a nucleotide sequence wherein one or more nucleotides in the nucleotide sequence selected from the group consisting of SEQ ID NO:2n−1, wherein n is an integer between 1 and 54 is changed from that selected from the group consisting of the chosen sequence to a different nucleotide provided that no more than 15% of the nucleotides are so changed; (c) a nucleic acid fragment of the sequence selected from the group consisting of SEQ ID NO:2n−1, wherein n is an integer between 1 and 54; and (d) a nucleic acid fragment wherein one or more nucleotides in the nucleotide sequence selected from the group consisting of SEQ ID NO:2n−1, wherein n is an integer between 1 and 54 is changed from that selected from the group consisting of the chosen sequence to a different nucleotide provided that no more than 15% of the nucleotides are so changed.

NOVX Nucleic Acids and Polypeptides

One aspect of the invention pertains to isolated nucleic acid molecules that encode NOVX polypeptides or biologically active portions thereof. Also included in the invention are nucleic acid fragments sufficient for use as hybridization probes to identify NOVX-encoding nucleic acids (e.g., NOVX mRNAs) and fragments for use as PCR primers for the amplification and/or mutation of NOVX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

A NOVX nucleic acid can encode a mature NOVX polypeptide. As used herein, a "mature" form of a polypeptide or protein disclosed in the present invention is the product of a naturally occurring polypeptide, precursor form, or proprotein. The naturally occurring polypeptide, precursor or proprotein includes, by way of nonlimiting example, the full-length gene product encoded by the corresponding gene. Alternatively, it may be defined as the polypeptide, precursor or proprotein encoded by an ORF described herein. The product "mature" form arises, by way of nonlimiting example, as a result of one or more naturally occurring processing steps that may take place within the cell (host cell) in which the gene product arises. Examples of such processing steps leading to a "mature" form of a polypeptide or protein include the cleavage of the N-terminal methionine residue encoded by the initiation codon of an ORF or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "probe", as utilized herein, refers to nucleic acid sequences of variable length, preferably between at least about 10 nucleotides (nt), and 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies.

The term "isolated" nucleic acid molecule, as used herein, is a nucleic acid which is separated from other nucleic acid molecules which are present in the natural source of the nucleic acid. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated NOVX nucleic acid molecules can contain less than about 5 kb, 4 kb, 3 kb, 2 kb, 1 kb, 0.5 kb, 0.1 kb, or less of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material, culture medium, or of chemical precursors or other chemicals.

A nucleic acid molecule of the invention, e.g., a nucleic acid molecule having the nucleotide sequence SEQ ID NOS: 2n–1, wherein n is an integer between 1 and 54, or a complement of this nucleotide sequence, can be isolated using standard molecular biology techniques and the sequence information provided herein. Using all or a portion of the nucleic acid sequence of SEQ ID NOS:2n–1, wherein n is an integer between 1 and 54, as a hybridization probe, NOVX molecules can be isolated using standard hybridization and cloning techniques (e.g., as described in Sambrook, et al., (eds.), MOLECULAR CLONING: A LABORATORY MANUAL 2$^{nd}$ Ed., Cold Spring Harbor Laboratory Press, Cold Spring Harbor, N.Y., 1989; and Ausubel, et al., (eds.), CURRENT PROTOCOLS IN MOLECULAR BIOLOGY, John Wiley & Sons, New York, N.Y., 1993).

A nucleic acid of the invention can be amplified using cDNA, mRNA or, alternatively, genomic DNA as a template with appropriate oligonucleotide primers according to standard PCR amplification techniques. The nucleic acid so amplified can be cloned into an appropriate vector and characterized by DNA sequence analysis. Furthermore, oligonucleotides corresponding to NOVX nucleotide sequences can be prepared by standard synthetic techniques, e.g., using an automated DNA synthesizer.

As used herein, the term "oligonucleotide" refers to a series of linked nucleotide residues. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides of SEQ ID NOS:2n–1, wherein n is an integer between 1 and 54, or a complement thereof. Oligonucleotides may be chemically synthesized and may also be used as probes.

In another embodiment, an isolated nucleic acid molecule of the invention comprises a nucleic acid molecule that is a complement of the nucleotide sequence shown in SEQ ID NOS:2n–1, wherein n is an integer between 1 and 54, or a portion of this nucleotide sequence (e.g., a fragment that can be used as a probe or primer or a fragment encoding a biologically-active portion of A NOVX polypeptide). A nucleic acid molecule that is complementary to the nucleotide sequence shown SEQ ID NOS:2n–1, wherein n is an integer between 1 and 54, is one that is sufficiently complementary to the nucleotide sequence shown SEQ ID NOS:2n–1, wherein n is an integer between 1 and 54, that it can hydrogen bond with few or no mismatches to the nucleotide sequence shown SEQ ID NOS:2n–1, wherein n is an integer between 1 and 54, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

"Fragments" provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full length sequence. Fragments may be derived from any contiguous portion of a nucleic acid or amino acid sequence of choice.

A full-length NOVX clone is identified as containing an ATG translation start codon and an in-frame stop codon. Any disclosed NOVX nucleotide sequence lacking an ATG start codon therefore encodes a truncated C-terminal fragment of the respective NOVX polypeptide, and requires that the corresponding full-length cDNA extend in the 5' direction of the disclosed sequence. Any disclosed NOVX nucleotide sequence lacking an in-frame stop codon similarly encodes a truncated N-terminal fragment of the respective NOVX polypeptide, and requires that the corresponding full-length cDNA extend in the 3' direction of the disclosed sequence.

"Derivatives" are nucleic acid sequences or amino acid sequences formed from the native compounds either directly, by modification, or by partial substitution. "Analogs" are nucleic acid sequences or amino acid sequences that have a structure similar to, but not identical to, the native compound, e.g. they differ from it in respect to certain components or side chains. Analogs may be synthetic or derived from a different evolutionary origin and may have a similar or opposite metabolic activity compared to wild type. Homologs are nucleic acid sequences or amino acid sequences of a particular gene that are derived from different species.

Derivatives and analogs may be full length or other than full length. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences include those sequences coding for isoforms of NOVX polypeptides. Isoforms can be expressed in different tissues of the same organism as a result of, for example, alternative splicing of RNA. Alternatively, isoforms can be encoded by different genes. In the invention, homologous nucleotide sequences include nucleotide sequences encoding for A NOVX polypeptide of species other than humans, including, but not limited to vertebrates, and thus can include, e.g., frog, mouse, rat, rabbit, dog, cat, cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding a human NOVX protein. Homologous nucleic acid sequences include those nucleic acid sequences that encode conservative amino acid substitutions (see below) in SEQ ID NOS:2n–1, wherein n is an integer between 1 and 54, as well as a polypeptide possessing NOVX biological activity. Various biological activities of the NOVX proteins are described below.

A NOVX polypeptide is encoded by the open reading frame ("ORF") of a NOVX nucleic acid. An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bonafide cellular protein, a minimum size requirement is often set, e.g., a stretch of DNA that would encode a protein of 50 amino acids or more.

The nucleotide sequences determined from the cloning of the human NOVX genes allows for the generation of probes and primers designed for use in identifying and/or cloning NOVX homologues in other cell types, e.g. from other tissues, as well as NOVX homologues from other vertebrates. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NOS:2n–1, wherein n is an integer between 1 and 54; or an anti-sense strand nucleotide sequence of SEQ ID NOS:2n–1, wherein n is an integer between 1 and 54; or of a naturally occurring mutant of SEQ ID NOS:2n–1, wherein n is an integer between 1 and 54.

Probes based on the human NOVX nucleotide sequences can be used to detect transcripts or genomic sequences encoding the same or homologous proteins. In various embodiments, the probe has a detectable label attached, e.g. the label can be a radioisotope, a fluorescent compound, an enzyme, or an enzyme co-factor. Such probes can be used as a part of a diagnostic test kit for identifying cells or tissues which mis-express A NOVX protein, such as by measuring a level of A NOVX-encoding nucleic acid in a sample of cells from a subject e.g., detecting NOVX mRNA levels or determining whether a genomic NOVX gene has been mutated or deleted.

"A polypeptide having a biologically-active portion of A NOVX polypeptide" refers to polypeptides exhibiting activity similar, but not necessarily identical, an activity of a polypeptide of the invention, including mature forms, as measured in a particular biological assay, with or without dose dependency. A nucleic acid fragment encoding a "biologically-active portion of NOVX" can be prepared by isolating a portion SEQ ID NOS:2n–1, wherein n is an integer between 1 and 54, that encodes a polypeptide having A NOVX biological activity (the biological activities of the NOVX proteins are described below), expressing the encoded portion of NOVX protein (e.g., by recombinant expression in vitro) and assessing the activity of the encoded portion of NOVX.

NOVX Nucleic Acid and Polypeptide Variants

The invention further encompasses nucleic acid molecules that differ from the nucleotide sequences shown in SEQ ID NOS:2n–1, wherein n is an integer between 1 and 54, due to degeneracy of the genetic code and thus encode the same NOVX proteins as that encoded by the nucleotide sequences shown in SEQ ID NOS:2n–1, wherein n is an integer between 1 and 54. In another embodiment, an isolated nucleic acid molecule of the invention has a nucleotide sequence encoding a protein having an amino acid sequence shown in SEQ ID NOS:2n, wherein n is an integer between 1 and 54.

In addition to the human NOVX nucleotide sequences shown in SEQ ID NOS:2n–1, wherein n is an integer between 1 and 54, it will be appreciated by those skilled in the art that DNA sequence polymorphisms that lead to changes in the amino acid sequences of the NOVX polypeptides may exist within a population (e.g., the human population). Such genetic polymorphism in the NOVX genes may exist among individuals within a population due to natural allelic variation. As used herein, the terms "gene" and "recombinant gene" refer to nucleic acid molecules comprising an open reading frame (ORF) encoding A NOVX protein, preferably a vertebrate NOVX protein. Such natural allelic variations can typically result in 1–5% variance in the nucleotide sequence of the NOVX genes. Any and all such nucleotide variations and resulting amino acid polymorphisms in the NOVX polypeptides, which are the result of natural allelic variation and that do not alter the functional activity of the NOVX polypeptides, are intended to be within the scope of the invention.

Moreover, nucleic acid molecules encoding NOVX proteins from other species, and thus that have a nucleotide sequence that differs from the human SEQ ID NOS:2n–1, wherein n is an integer between 1 and 54, are intended to be within the scope of the invention. Nucleic acid molecules corresponding to natural allelic variants and homologues of the NOVX cDNAs of the invention can be isolated based on their homology to the human NOVX nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NOS:2n–1, wherein n is an integer between 1 and 54. In another embodiment, the nucleic acid is at least 10, 25, 50, 100, 250, 500, 750, 1000, 1500, 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least about 65% homologous to each other typically remain hybridized to each other.

Homologs (i.e., nucleic acids encoding NOVX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel, et al., (eds.), CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequences SEQ ID NOS:2n–1, wherein n is an integer between 1 and 54, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NOS:2n–1, wherein n is an integer between 1 and 54, or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel, et al. (eds.), 1993, CURRENT PROTOCOLS IN MOLECULAR BIOLOGY, John Wiley & Sons, NY, and Kriegler, 1990; GENE TRANSFER AND EXPRESSION, A LABORATORY MANUAL, Stockton Press, NY.

In a third embodiment, a nucleic acid that is hybridizable to the nucleic acid molecule comprising the nucleotide sequences SEQ ID NOS:2n–1, wherein n is an integer between 1 and 54, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g, as employed for cross-species hybridizations). See, e.g., Ausubel, et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981. *Proc Natl Acad Sci USA* 78: 6789–6792.

Conservative Mutations

In addition to naturally-occurring allelic variants of NOVX sequences that may exist in the population, the skilled artisan will further appreciate that changes can be introduced by mutation into the nucleotide sequences SEQ ID NOS:2n–1, wherein n is an integer between 1 and 54, thereby leading to changes in the amino acid sequences of the encoded NOVX proteins, without altering the functional ability of the NOVX proteins. For example, nucleotide substitutions leading to amino acid substitutions at "non-essential" amino acid residues can be made in the sequence SEQ ID NOS:2n, wherein n is an integer between 1 and 54. A "non-essential" amino acid residue is a residue that can be altered from the wild-type sequences of the NOVX proteins without altering their biological activity, whereas an "essential" amino acid residue is required for such biological activity. For example, amino acid residues that are conserved among the NOVX proteins of the invention are predicted to be particularly non-amenable to alteration. Amino acids for which conservative substitutions can be made are well known within the art.

Another aspect of the invention pertains to nucleic acid molecules encoding NOVX proteins that contain changes in amino acid residues that are not essential for activity. Such NOVX proteins differ in amino acid sequence from SEQ ID NOS:2n–1, wherein n is an integer between 1 and 54, yet retain biological activity. In one embodiment, the isolated nucleic acid molecule comprises a nucleotide sequence encoding a protein, wherein the protein comprises an amino acid sequence at least about 40 homologous to the amino acid sequences SEQ ID NOS:2n, wherein n is an integer between 1 and 54. Preferably, the protein encoded by the nucleic acid molecule is at least about 60% homologous to SEQ ID NOS:2n, wherein n is an integer between 1 and 54; more preferably at least about 70% homologous SEQ ID NOS:2n, wherein n is an integer between 1 and 54; still more preferably at least about 80% homologous to SEQ ID NOS:2n, wherein n is an integer between 1 and 54; even more preferably at least about 90% homologous to SEQ ID NOS:2n, wherein n is an integer between 1 and 54; and most preferably at least about 95% homologous to SEQ ID NOS:2n, wherein n is an integer between 1 and 54.

An isolated nucleic acid molecule encoding A NOVX protein homologous to the protein of SEQ ID NOS:2n, wherein n is an integer between 1 and 54, can be created by introducing one or more nucleotide substitutions, additions or deletions into the nucleotide sequence of SEQ ID NOS:2n–1, wherein n is an integer between 1 and 54, such that one or more amino acid substitutions, additions or deletions are introduced into the encoded protein.

Mutations can be introduced into SEQ ID NOS:2n–1, wherein n is an integer between 1 and 54, by standard techniques, such as site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the NOVX protein is replaced with another amino acid residue from the same side chain family. Alternatively, in another embodiment, mutations can be introduced randomly along all or part of A NOVX coding sequence, such as by saturation mutagenesis, and the resultant mutants can be screened for NOVX biological activity to identify mutants that retain activity. Following mutagenesis SEQ ID NOS:2n–1, wherein n is an integer between 1 and 54, the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, HFY, wherein the letters within each group represent the single letter amino acid code.

In one embodiment, a mutant NOVX protein can be assayed for (i) the ability to form protein:protein interactions with other NOVX proteins, other cell-surface proteins, or biologically-active portions thereof, (ii) complex formation between a mutant NOVX protein and A NOVX ligand; or (iii) the ability of a mutant NOVX protein to bind to an intracellular target protein or biologically-active portion thereof; (e.g. avidin proteins).

In yet another embodiment, a mutant NOVX protein can be assayed for the ability to regulate a specific biological function (e.g., regulation of insulin release).

Antisense Nucleic Acids

Another aspect of the invention pertains to isolated antisense nucleic acid molecules that are hybridizable to or complementary to the nucleic acid molecule comprising the nucleotide sequence of SEQ ID NOS:2n–1, wherein n is an integer between 1 and 54, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire NOVX coding strand, or to only a portion thereof. Nucleic acid molecules encoding fragments, homologs, derivatives and analogs of A NOVX protein of SEQ ID NOS:2n, wherein n is an integer between 1 and 54, or antisense nucleic acids complementary to A NOVX nucleic acid sequence of SEQ ID NOS:2n–1, wherein n is an integer between 1 and 54, are additionally provided.

In one embodiment, an antisense nucleic acid molecule is antisense to a "coding region" of the coding strand of a nucleotide sequence encoding A NOVX protein. The term "coding region" refers to the region of the nucleotide sequence comprising codons, which are translated into amino acid residues. In another embodiment, the antisense nucleic acid molecule is antisense to a "noncoding region" of the coding strand of a nucleotide sequence encoding the NOVX protein. The term "noncoding region" refers to 5' and 3' sequences, which flank the coding region that are not translated into amino acids (i.e., also referred to as 5' and 3' untranslated regions).

Given the coding strand sequences encoding the NOVX protein disclosed herein, antisense nucleic acids of the invention can be designed according to the rules of Watson and Crick or Hoogsteen base pairing. The antisense nucleic acid molecule can be complementary to the entire coding region of NOVX mRNA, but more preferably is an oligonucleotide that is antisense to only a portion of the coding or noncoding region of NOVX mRNA. For example, the antisense oligonucleotide can be complementary to the region surrounding the translation start site of NOVX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, beta-D-mannosylqueosine, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding A NOVX protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. A α-anomeric nucleic acid molecule forms specific double-stranded hybrids with complementary RNA in which, contrary to the usual β-units, the strands run parallel to each other. See, e.g., Gaultier, et al., 1987. *Nucl. Acids Res.* 15: 6625–6641. The antisense nucleic acid molecule can also comprise a 2'-o-methylribonucleotide (See, e.g., Inoue, et al. 1987. *Nucl. Acids Res.* 15: 6131–6148) or a chimeric RNA-DNA analogue (See, e.g., Inoue, et al., 1987. *FEBS Lett.* 215: 327–330.

Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585–591) can be used to catalytically cleave NOVX mRNA transcripts to thereby inhibit translation of NOVX mRNA. A ribozyme having specificity for a NOVX-encoding nucleic acid can be designed based upon the nucleotide sequence of A NOVX cDNA disclosed herein (i.e., SEQ ID NOS:2n−1, wherein n is an integer between 1 and 54). For example, a derivative of a *Tetrahymena* L-19 IVS RNA can be constructed in which the nucleotide sequence of the active site is complementary to the nucleotide sequence to be cleaved in a NOVX-encoding mRNA. See, e.g., U.S. Pat. No. 4,987,071 to Cech, et al. and U.S. Pat. No. 5,116,742 to Cech, et al. NOVX mRNA can also be used to select a catalytic RNA having a specific ribonuclease activity from a pool of RNA molecules. See, e.g., Bartel et al., (1993) *Science* 261:1411–1418.

Alternatively, NOVX gene expression can be inhibited by targeting nucleotide sequences complementary to the regulatory region of the NOVX nucleic acid (e.g., the NOVX promoter and/or enhancers) to form triple helical structures that prevent transcription of the NOVX gene in target cells. See, e.g., Helene, 1991. *Anticancer Drug Des.* 6: 569–84; Helene, et al. 1992. *Ann. N.Y Acad. Sci.* 660: 27–36; Maher, 1992. *Bioassays* 14: 807–15.

In various embodiments, the NOVX nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. *Bioorg Med Chem* 4: 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. *Proc. Natl. Acad. Sci. USA* 93:14670–14675.

PNAs of NOVX can be used in therapeutic and diagnostic applications. For example, PNAs can be used as antisense or antigene agents for sequence-specific modulation of gene expression by, e.g., inducing transcription or translation arrest or inhibiting replication. PNAs of NOVX can also be used, for example, in the analysis of single base pair mutations in a gene (e.g., PNA directed PCR clamping; as artificial restriction enzymes when used in combination with other enzymes, e.g., $S_1$ nucleases (See, Hyrup, et al., 1996. supra); or as probes or primers for DNA sequence and hybridization (See, Hyrup, et al., 1996, supra; Perry-O'Keefe, et al., 1996. supra).

In another embodiment, PNAs of NOVX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NOVX can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. *Nucl Acids Res* 24: 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. *Nucl Acid Res* 17: 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. *Bioorg. Med. Chem. Lett.* 5: 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. *Proc. Nat. Acad. Sci. U.S.A.* 86: 6553–6556; Lemaitre, et al., 1987. *Proc. Natl. Acad. Sci.* 84: 648–652; PCT Publication No. WO88/09810) or the blood-brain barrier (see, e.g., PCT Publication No. WO 89/10134). In addition, oligonucleotides can be modified with hybridization triggered cleavage agents (see, e.g., Krol, et al., 1988. *BioTechniques* 6:958–976) or intercalating agents (see, e.g., Zon, 1988. *Pharm. Res.* 5: 539–549). To this end, the oligonucleotide may be conjugated to another molecule, e.g., a peptide, a hybridization triggered cross-linking agent, a transport agent, a hybridization-triggered cleavage agent, and the like.

NOVX Polypeptides

A polypeptide according to the invention includes a polypeptide including the amino acid sequence of NOVX polypeptides whose sequences are provided in SEQ ID NOS:2n, wherein n is an integer between 1 and 54. The invention also includes a mutant or variant protein any of whose residues may be changed from the corresponding residues shown in SEQ ID NOS:2n, wherein n is an integer between 1 and 54, while still encoding a protein that maintains its NOVX activities and physiological functions, or a functional fragment thereof.

In general, A NOVX variant that preserves NOVX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated NOVX proteins, and biologically-active portions thereof, or derivatives, fragments, analogs or homologs thereof. Also provided are polypeptide fragments suitable for use as immunogens to raise anti-NOVX antibodies. In one embodiment, native NOVX proteins can be isolated from cells or tissue sources by an appropriate purification scheme using standard protein purification techniques. In another embodiment, NOVX proteins are produced by recombinant DNA techniques. Alternative to recombinant expression, A NOVX protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the NOVX protein is derived, or substantially free from chemical precursors or other chemicals when chemically synthesized. The language "substantially free of cellular material" includes preparations of NOVX proteins in which the protein is separated from cellular components of the cells from which it is isolated or recombinantly-produced. In one embodiment, the language "substantially free of cellular material" includes preparations of NOVX proteins having less than about 30% (by dry weight) of non-NOVX proteins (also referred to herein as a "contaminating protein"), more preferably less than about 20% of non-NOVX proteins, still more preferably less than about 10% of non-NOVX proteins, and most preferably less than about 5% of non-NOVX proteins. When the NOVX protein or biologically-active portion thereof is recombinantly-produced, it is also preferably substantially free of culture medium, i.e., culture medium represents less than about 20%, more preferably less than about 10%, and most preferably less than about 5% of the volume of the NOVX protein preparation.

The language "substantially free of chemical precursors or other chemicals" includes preparations of NOVX proteins in which the protein is separated from chemical precursors or other chemicals that are involved in the synthesis of the protein. In one embodiment, the language "substantially free of chemical precursors or other chemicals" includes preparations of NOVX proteins having less than about 30% (by dry weight) of chemical precursors or non-NOVX chemicals, more preferably less than about 20% chemical precursors or non-NOVX chemicals, still more preferably less than about 10% chemical precursors or non-NOVX chemicals, and most preferably less than about 5% chemical precursors or non-NOVX chemicals.

Biologically-active portions of NOVX proteins include peptides comprising amino acid sequences sufficiently homologous to or derived from the amino acid sequences of the NOVX proteins (e.g., the amino acid sequence shown in SEQ ID NOS:2n, wherein n is an integer between 1 and 54) that include fewer amino acids than the full-length NOVX proteins, and exhibit at least one activity of A NOVX protein. Typically, biologically-active portions comprise a domain or motif with at least one activity of the NOVX protein. A biologically-active portion of A NOVX protein can be a polypeptide which is, for example, 10, 25, 50, 100 or more amino acid residues in length.

Moreover, other biologically-active portions, in which other regions of the protein are deleted, can be prepared by recombinant techniques and evaluated for one or more of the functional activities of a native NOVX protein.

In an embodiment, the NOVX protein has an amino acid sequence shown SEQ ID NOS:2n, wherein n is an integer between 1 and 54. In other embodiments, the NOVX protein is substantially homologous to SEQ ID NOS:2n, wherein n is an integer between 1 and 54, and retains the functional activity of the protein of SEQ ID NOS:2n, wherein n is an integer between 1 and 54, yet differs in amino acid sequence due to natural allelic variation or mutagenesis, as described in detail, below. Accordingly, in another embodiment, the NOVX protein is a protein that comprises an amino acid sequence at least about 45% homologous to the amino acid sequence SEQ ID NOS:2n, wherein n is an integer between 1 and 54, and retains the functional activity of the NOVX proteins of SEQ ID NOS:2n, wherein n is an integer between 1 and 54.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (ie., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch, 1970. *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOS:2n–1, wherein n is an integer between 1 and 54.

The term "sequence identity" refers to the degree to which two polynucleotide or polypeptide sequences are identical on a residue-by-residue basis over a particular region of comparison: The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides NOVX chimeric or fusion proteins. As used herein, A NOVX "chimeric protein" or "fusion protein" comprises A NOVX polypeptide operatively-linked to a non-NOVX polypeptide. An "NOVX polypeptide" refers to a polypeptide having an amino acid sequence corresponding to A NOVX protein SEQ ID NOS:2n, wherein n is an integer between 1 and 54, whereas a "non-NOVX polypeptide" refers to a polypeptide having an amino acid sequence corresponding to a protein that is not substantially homologous to the NOVX protein, e.g., a protein that is different from the NOVX protein and that is derived from the same or a different organism. Within A NOVX fusion protein the NOVX polypeptide can correspond to all or a portion of A NOVX protein. In one embodiment, A NOVX fusion protein comprises at least one biologically active portion of A NOVX protein. In another embodiment, A NOVX fusion protein comprises at least two biologically active portions of A NOVX protein. In yet another embodiment, A NOVX fusion protein comprises at least three biologically active portions of A NOVX protein. Within the fusion protein, the term "operatively-linked" is intended to indicate that the NOVX polypeptide and the non-NOVX polypeptide are fused in-frame with one another. The non-NOVX polypeptide can be fused to the N-terminus or C-terminus of the NOVX polypeptide.

In one embodiment, the fusion protein is a GST-NOVX fusion protein in which the NOVX sequences are fused to the C-terminus of the GST (glutathione S-transferase) sequences. Such fusion proteins can facilitate the purification of recombinant NOVX polypeptides.

In another embodiment, the fusion protein is A NOVX protein containing a heterologous signal sequence at its N-terminus. In certain host cells (e.g., mammalian host cells), expression and/or secretion of NOVX can be increased through use of a heterologous signal sequence.

In yet another embodiment, the fusion protein is a NOVX-immunoglobulin fusion protein in which the NOVX sequences are fused to sequences derived from a member of the immunoglobulin protein family. The NOVX-immunoglobulin fusion proteins of the invention can be incorporated into pharmaceutical compositions and administered to a subject to inhibit an interaction between A NOVX ligand and A NOVX protein on the surface of a cell, to thereby suppress NOVX-mediated signal transduction in vivo. The NOVX-immunoglobulin fusion proteins can be used to affect the bioavailability of A NOVX cognate ligand. Inhibition of the NOVX ligand/NOVX interaction may be useful therapeutically for both the treatment of proliferative and differentiative disorders, as well as modulating (e.g. promoting or inhibiting) cell survival. Moreover, the NOVX-immunoglobulin fusion proteins of the invention can be used as immunogens to produce anti-NOVX antibodies in a subject, to purify NOVX ligands, and in screening assays to identify molecules that inhibit the interaction of NOVX with A NOVX ligand.

A NOVX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A NOVX-encoding nucleic acid can be cloned into such an expression vector such that the fusion moiety is linked in-frame to the NOVX protein.

NOVX Agonists and Antagonists

The invention also pertains to variants of the NOVX proteins that function as either NOVX agonists (i.e., mimetics) or as NOVX antagonists. Variants of the NOVX protein can be generated by mutagenesis (e.g., discrete point mutation or truncation of the NOVX protein). An agonist of the NOVX protein can retain substantially the same, or a subset of, the biological activities of the naturally occurring form of the NOVX protein. An antagonist of the NOVX protein can inhibit one or more of the activities of the naturally occurring form of the NOVX protein by, for example, competitively binding to a downstream or upstream member of a cellular signaling cascade, which includes the NOVX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the NOVX proteins.

Variants of the NOVX proteins that function as either NOVX agonists (i.e., mimetics) or as NOVX antagonists can be identified by screening combinatorial libraries of mutants (e.g., truncation mutants) of the NOVX proteins for NOVX protein agonist or antagonist activity. In one embodiment, a variegated library of NOVX variants is generated by combinatorial mutagenesis at the nucleic acid level and is encoded by a variegated gene library. A variegated library of NOVX variants can be produced by, for example, enzymatically ligating a mixture of synthetic oligonucleotides into gene sequences such that a degenerate set of potential NOVX sequences is expressible as individual polypeptides, or alternatively, as a set of larger fusion proteins (e.g., for phage display) containing the set of NOVX sequences therein. There are a variety of methods, which can be used to produce libraries of potential NOVX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NOVX sequences. Methods for synthesizing degenerate oligonucleotides are well known within the art. See, e.g., Narang, 1983. *Tetrahedron* 39: 3; Itakura, et al., 1984. *Annu. Rev. Biochem.* 53: 323; Itakura, et al., 1984. *Science* 198: 1056; Ike, et al., 1983. *Nucl. Acids Res.* 11: 477.

Polypeptide Libraries

In addition, libraries of fragments of the NOVX protein coding sequences can be used to generate a variegated population of NOVX fragments for screening and subsequent selection of variants of A NOVX protein. In one embodiment, a library of coding sequence fragments can be generated by treating a double stranded PCR fragment of A NOVX coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encodes N-terminal and internal fragments of various sizes of the NOVX proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NOVX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify NOVX variants. See, e.g., Arkin and Yourvan, 1992. *Proc. Natl. Acad. Sci. USA* 89: 7811–7815; Delgrave, et al., 1993. *Protein Engineering* 6:327–331.

NOVX Antibodies

The term "antibody" as used herein refers to immunoglobulin molecules and immunologically active portions of immunoglobulin (Ig) molecules, i.e., molecules that contain an antigen-binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NOs: 2n, wherein n is an integer between 1 and 54, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of NOVX that is located on the surface of the protein, e.g., a hydrophilic region. A hydrophobicity analysis of the human NOVX protein sequence will indicate which regions of a NOVX polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each incorporated herein by reference in their entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51–63].

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding, 1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.* 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al,(*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., *J. Exp Med.,* 176: 1191–1195 (1992) and Shopes, *J. Immunol.,* 148: 2918–2922 (1992). Homodimeric antibodies with enhanced anti-tumor activity can also be prepared using heterobifunctional cross-linkers as described in Wolff et al. *Cancer Research,* 53: 2560–2565 (1993). Alternatively, an antibody can be engineered that has dual Fc regions and can thereby have enhanced complement lysis and ADCC capabilities. See Stevenson et al., *Anti-Cancer Drug Design,* 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

Immunoliposomes

The antibodies disclosed herein can also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al ., *J. Biol. Chem.* 257: 286–288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

Diagnostic Applications of Antibodies Directed Against the Proteins of the Invention Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds (see below).

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Therapeutics

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight.-Common dosing frequencies may range, for example, from twice daily to once a week.

Pharmaceutical Compositions of Antibodies

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889–7893 (1993). The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., $F_{ab}$ or $F_{(ab)2}$) can be used. The term "labeled", with regard to the probe or antibody, is intended to encompass direct labeling of the probe or antibody by coupling (i e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Thory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques.

NOVX Recombinant Expression Vectors and Host Cells

Another aspect of the invention pertains to vectors, preferably expression vectors, containing a nucleic acid encoding A NOVX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NOVX proteins, mutant forms of NOVX proteins, fusion proteins, etc.).

The recombinant expression vectors of the invention can be designed for expression of NOVX proteins in prokaryotic or eukaryotic cells. For example, NOVX proteins can be expressed in bacterial cells such as *Escherichia coli,* insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the NOVX expression vector is a yeast expression vector. Examples of vectors for expression in yeast *Saccharomyces cerivisae* include pYepSec (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, NOVX can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufmnan, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. Cell 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to NOVX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews—Trends in Genetics,* Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NOVX protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding NOVX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NOVX protein. Accordingly, the invention further provides methods for producing NOVX protein using the host cells of the invention. In one embodiment, the method comprises culturing the host cell of invention (into which a recombinant expression vector encoding NOVX protein has been introduced) in a suitable medium such that NOVX protein is produced. In another embodiment, the method further comprises isolating NOVX protein from the medium or the host cell.

Transgenic NOVX Animals

The host cells of the invention can also be used to produce non-human transgenic animals. For example, in one embodiment, a host cell of the invention is a fertilized oocyte or an embryonic stem cell into which NOVX protein-coding sequences have been introduced. Such host cells can then be used to create non-human transgenic animals in which exogenous NOVX sequences have been introduced into their genome or homologous recombinant animals in which endogenous NOVX sequences have been altered. Such animals are useful for studying the function and/or activity of NOVX protein and for identifying and/or evaluating modulators of NOVX protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NOVX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NOVX-encoding nucleic acid into the male pronuclei of a fertilized oocyte (e.g., by microinjection, retroviral infection) and allowing the oocyte to develop in a pseudopregnant female foster animal. The human NOVX cDNA sequences SEQ ID NOS:2n−1, wherein n is an integer between 1 and 54, can be introduced as a transgene into the genome of a non-human animal. Alternatively, a non-human homologue of the human NOVX gene, such as a mouse NOVX gene, can be isolated based on hybridization to the human NOVX cDNA (described further supra) and used as a transgene. Intronic sequences and polyadenylation signals can also be included in the transgene to increase the efficiency of expression of the transgene. A tissue-specific regulatory sequence(s) can be operably-linked to the NOVX transgene to direct expression of NOVX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the NOVX transgene in its genome and/or expression of NOVX mRNA in tissues or cells of the animals. A transgenic founder animal can then be used to breed additional animals carrying the transgene. Moreover, transgenic animals carrying a transgene-encoding NOVX protein can further be bred to other transgenic animals carrying other transgenes.

To create a homologous recombinant animal, a vector is prepared which contains at least a portion of A NOVX gene into which a deletion, addition or substitution has been introduced to thereby alter, e.g., functionally disrupt, the NOVX gene. The NOVX gene can be a human gene (e.g., the cDNA of SEQ ID NOS:2n−1, wherein n is an integer between 1 and 54), but more preferably, is a non-human homologue of a human NOVX gene. For example, a mouse homologue of human NOVX gene of SEQ ID NOS:2n−1, wherein n is an integer between 1 and 54, can be used to construct a homologous recombination vector suitable for altering an endogenous NOVX gene in the mouse genome. In one embodiment, the vector is designed such that, upon homologous recombination, the endogenous NOVX gene is functionally disrupted (i.e., no longer encodes a functional protein; also referred to as a "knock out" vector).

Alternatively, the vector can be designed such that, upon homologous recombination, the endogenous NOVX gene is mutated or otherwise altered but still encodes functional protein (e.g., the upstream regulatory region can be altered to thereby alter the expression of the endogenous NOVX protein). In the homologous recombination vector, the altered portion of the NOVX gene is flanked at its 5'- and 3'-termini by additional nucleic acid of the NOVX gene to allow for homologous recombination to occur between the exogenous NOVX gene carried by the vector and an endogenous NOVX gene in an embryonic stem cell. The additional flanking NOVX nucleic acid is of sufficient length for successful homologous recombination with the endogenous gene. Typically, several kilobases of flanking DNA (both at the 5'- and 3'-termini) are included in the vector. See, e.g., Thomas, et al., 1987. *Cell* 51: 503 for a description of homologous recombination vectors. The vector is ten introduced into an embryonic stem cell line (e.g., by electroporation) and cells in which the introduced NOVX gene has homologously-recombined with the endogenous NOVX gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/oxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The NOVX nucleic acid molecules, NOVX proteins, and anti-NOVX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., A NOVX protein or anti-NOVX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The isolated nucleic acid molecules of the invention can be used to express NOVX protein (e.g., via a recombinant expression vector in a host cell in gene therapy applications), to detect NOVX mRNA (e.g., in a biological sample) or a genetic lesion in A NOVX gene, and to modulate NOVX activity, as described further, below. In addition, the NOVX proteins can be used to screen drugs or compounds that modulate the NOVX protein activity or expression as well as to treat disorders characterized by insufficient or excessive production of NOVX protein or production of NOVX protein forms that have decreased or aberrant activity compared to NOVX wild-type protein (e.g.; diabetes (regulates insulin release); obesity (binds and transport lipids); metabolic disturbances associated with obesity, the metabolic syndrome X as well as anorexia and wasting disorders associated with chronic diseases and various cancers, and infectious disease(possesses anti-microbial activity) and the various dyslipidemias. In addition, the anti-NOVX antibodies of the invention can be used to detect and isolate NOVX proteins and modulate NOVX activity. In yet a further aspect, the invention can be used in methods to influence appetite, absorption of nutrients and the disposition of metabolic substrates in both a positive and negative fashion.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to NOVX proteins or have a stimulatory or inhibitory effect on, e.g., NOVX protein expression or NOVX protein activity. The invention also includes compounds identified in the screening assays described herein.

In one embodiment, the invention provides assays for screening candidate or test compounds which bind to or modulate the activity of the membrane-bound form of A NOVX protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. USA*. 90: 6909; Erb, et al., 1994. *Proc. Natl. Acad. Sci. U.S.A.* 91:11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a membrane-bound form of NOVX protein, or a biologically-active portion thereof, on the cell surface is contacted with a test compound and the ability of the test compound to bind to A NOVX protein determined. The cell, for example, can of mammalian origin or a yeast cell. Determining the ability of the test compound to bind to the NOVX protein can be accomplished, for example, by coupling the test compound with a radioisotope or enzymatic label such that binding of the test compound to the NOVX protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of NOVX protein, or a biologically-active portion thereof, on the cell surface with a known compound which binds NOVX to form an assay mixture, contacting the assay mixture with a test compound, and determining the ability of the test compound to interact with A NOVX protein, wherein determining the ability of the test compound to interact with A NOVX protein comprises determining the ability of the test compound to preferentially bind to NOVX protein or a biologically-active portion thereof as compared to the known compound.

In another embodiment, an assay is a cell-based assay comprising contacting a cell expressing a membrane-bound form of NOVX protein, or a biologically-active portion thereof, on the cell surface with a test compound and determining the ability of the test compound to modulate (e.g., stimulate or inhibit) the activity of the NOVX protein or biologically-active portion thereof. Determining the ability of the test compound to modulate the activity of NOVX or a biologically-active portion thereof can be accomplished, for example, by determining the ability of the NOVX protein to bind to or interact with A NOVX target molecule. As used herein, a "target molecule" is a molecule with which A NOVX protein binds or interacts in nature, for example, a molecule on the surface of a cell which expresses A NOVX interacting protein, a molecule on the surface of a second cell, a molecule in the extracellular milieu, a molecule associated with the internal surface of a cell membrane or a cytoplasmic molecule. A NOVX target molecule can be a non-NOVX molecule or A NOVX protein or polypeptide of the invention. In one embodiment, A NOVX target molecule is a component of a signal transduction pathway that facilitates transduction of an extracellular signal (e.g. a signal generated by binding of a compound to a membrane-bound NOVX molecule) through the cell membrane and into the cell. The target, for example, can be a second intercellular protein that has catalytic activity or a protein that facilitates the association of downstream signaling molecules with NOVX.

Determining the ability of the NOVX protein to bind to or interact with A NOVX target molecule can be accomplished by one of the methods described above for determining direct binding. In one embodiment, determining the ability of the NOVX protein to bind to or interact with A NOVX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising A NOVX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting A NOVX protein or biologically-active portion thereof with a test compound and determining the ability of the test compound to bind to the NOVX protein or biologically-active portion thereof. Binding of the test compound to the NOVX protein can be determined either directly or indirectly as described above. In one such embodiment, the assay comprises contacting the NOVX protein or biologically-active portion thereof with a known compound which binds NOVX to form an assay mixture, contacting the assay mixture with a test compound, and determining the ability of the test compound to interact with A NOVX protein, wherein determining the ability of the test compound to interact with A NOVX protein comprises determining the ability of the test compound to preferentially bind to NOVX or biologically-active portion thereof as compared to the known compound.

In still another embodiment, an assay is a cell-free assay comprising contacting NOVX protein or biologically-active portion thereof with a test compound and determining the ability of the test compound to modulate (e.g. stimulate or inhibit) the activity of the NOVX protein or biologically-active portion thereof. Determining the ability of the test compound to modulate the activity of NOVX can be accomplished, for example, by determining the ability of the NOVX protein to bind to A NOVX target molecule by one of the methods described above for determining direct binding. In an alternative embodiment, determining the ability of the test compound to modulate the activity of NOVX protein can be accomplished by determining the ability of the NOVX protein further modulate A NOVX target molecule. For example, the catalytic/enzymatic activity of the target molecule on an appropriate substrate can be determined as described, supra.

In yet another embodiment, the cell-free assay comprises contacting the NOVX protein or biologically-active portion thereof with a known compound which binds NOVX protein to form an assay mixture, contacting the assay mixture with a test compound, and determining the ability of the test compound to interact with A NOVX protein, wherein determining the ability of the test compound to interact with A NOVX protein comprises determining the ability of the NOVX protein to preferentially bind to or modulate the activity of A NOVX target molecule.

The cell-free assays of the invention are amenable to use of both the soluble form or the membrane-bound form of NOVX protein. In the case of cell-free assays comprising the membrane-bound form of NOVX protein, it may be desirable to utilize a solubilizing agent such that the membrane-bound form of NOVX protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl--N,N-dimethyl-3-ammonio-1-propane sulfonate, 3-(3-cholamidopropyl) dimethylamminiol-l-propane sulfonate (CHAPS), or 3-(3-cholamidopropyl) dimethylamminiol-2-hydroxy-1-propane sulfonate (CHAPSO).

In more than one embodiment of the above assay methods of the invention, it may be desirable to immobilize either NOVX protein or its target molecule to facilitate separation of complexed from uncomplexed forms of one or both of the proteins, as well as to accommodate automation of the assay. Binding of a test compound to NOVX protein, or interaction of NOVX protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-NOVX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NOVX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of NOVX protein binding or activity determined using standard techniques.

Other techniques for immobilizing proteins on matrices can also be used in the screening assays of the invention. For example, either the NOVX protein or its target molecule can be immobilized utilizing conjugation of biotin and streptavidin. Biotinylated NOVX protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with NOVX protein or target molecules, but which do not interfere with binding of the NOVX protein to its target molecule, can be derivatized to the wells of the plate, and unbound target or NOVX protein trapped in the wells by antibody conjugation. Methods for detecting such complexes, in addition to those described above for the GST-immobilized complexes, include immunodetection of complexes using antibodies reactive with the NOVX protein or target molecule, as well as enzyme-linked assays that rely on detecting an enzymatic activity associated with the NOVX protein or target molecule.

In another embodiment, modulators of NOVX protein expression are identified in a method wherein a cell is contacted with a candidate compound and the expression of NOVX mRNA or protein in the cell is determined. The level of expression of NOVX mRNA or protein in the presence of the candidate compound is compared to the level of expression of NOVX mRNA or protein in the absence of the candidate compound. The candidate compound can then be identified as a modulator of NOVX mRNA or protein expression based upon this comparison. For example, when expression of NOVX mRNA or protein is greater (i.e., statistically significantly greater) in the presence of the candidate compound than in its absence, the candidate compound is identified as a stimulator of NOVX mRNA or protein expression. Alternatively, when expression of NOVX mRNA or protein is less (statistically significantly less) in the presence of the candidate compound than in its absence, the candidate compound is identified as an inhibitor of NOVX mRNA or protein expression. The level of NOVX mRNA or protein expression in the cells can be determined by methods described herein for detecting NOVX mRNA or protein.

In yet another aspect of the invention, the NOVX proteins can be used as "bait proteins" in a two-hybrid assay or three hybrid assay (see, e.g., U.S. Pat. No. 5,283,317; Zervos, et al., 1993. *Cell* 72: 223–232; Madura, et al., 1993. *J. Biol. Chem.* 268: 12046–12054; Bartel, et al., 1993. *Biotechniques* 14: 920–924; Iwabuchi, et al., 1993. *Oncogene* 8: 1693–1696; and Brent WO 94/10300), to identify other proteins that bind to or interact with NOVX ("NOVX-binding proteins" or "NOVX-bp") and modulate NOVX activity. Such NOVX-binding proteins are also likely to be involved in the propagation of signals by the NOVX proteins as, for example, upstream or downstream elements of the NOVX pathway.

The two-hybrid system is based on the modular nature of most transcription factors, which consist of separable DNA-binding and activation domains. Briefly, the assay utilizes two different DNA constructs. In one construct, the gene that codes for NOVX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming A NOVX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with NOVX.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the NOVX sequences, SEQ ID NOS:2n−1, wherein n is an integer between 1 and 54, or fragments or derivatives thereof, can be used to map the location of the NOVX genes, respectively, on a chromosome. The mapping of the NOVX sequences to chromosomes is an important first step in correlating these sequences with genes associated with disease.

Briefly, NOVX genes can be mapped to chromosomes by preparing PCR primers (preferably 15–25 bp in length) from the NOVX sequences. Computer analysis of the NOVX, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the NOVX sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. *Science* 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NOVX sequences to design oligonucleotide primers, sub-localization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. *Nature*, 325: 783–787.

Moreover, differences in the DNA sequences between individuals affected and unaffected with a disease associated with the NOVX gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The NOVX sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the NOVX sequences described herein can be used to prepare two PCR primers from the 5'- and 340 -termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The NOVX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NOS:2n−1, wherein n is an integer between 1 and 54, are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining NOVX protein and/or nucleic acid expression as well as NOVX activity, in the context of a biological sample (e.g., blood, serum, cells, tissue) to thereby determine whether an individual is afflicted with a disease or disorder, or is at risk of developing a disorder, associated with aberrant NOVX expression or activity. The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers. The invention also provides for prognostic (or predictive) assays for determining whether an individual is at risk of developing a disorder associated with NOVX protein, nucleic acid expression or activity. For example, mutations in A NOVX gene can be assayed in a biological sample. Such assays can be used for prognostic or predictive purpose to thereby prophylactically treat an individual prior to the onset of a disorder characterized by or associated with NOVX protein, nucleic acid expression, or biological activity.

Another aspect of the invention provides methods for determining NOVX protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.) Yet another aspect of the invention pertains to monitoring the influence of agents (e.g., drugs, compounds) on the expression or activity of NOVX in clinical trials.

These and other agents are described in further detail in the following sections.

Diagnostic Assays

An exemplary method for detecting the presence or absence of NOVX in a biological sample involves obtaining a biological sample from a test subject and contacting the biological sample with a compound or an agent capable of detecting NOVX protein or nucleic acid (e.g., mRNA, genomic DNA) that encodes NOVX protein such that the presence of NOVX is detected in the biological sample. An agent for detecting NOVX mRNA or genomic DNA is a labeled nucleic acid probe capable of hybridizing to NOVX mRNA or genomic DNA. The nucleic acid probe can be, for example, a full-length NOVX nucleic acid, such as the nucleic acid of SEQ ID NOS:2n−1, wherein n is an integer between 1 and 54, or a portion thereof, such as an oligonucleotide of at least 15, 30, 50, 100, 250 or 500 nucleotides in length and sufficient to specifically hybridize under stringent conditions to NOVX mRNA or genomic DNA. Other suitable probes for use in the diagnostic assays of the invention are described herein.

An agent for detecting NOVX protein is an antibody capable of binding to NOVX protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect NOVX mRNA, protein, or genomic DNA in a biological sample in vitro as well as in vivo. For example, in vitro techniques for detection of NOVX mRNA include Northern hybridizations and in situ hybridizations. In vitro techniques for detection of NOVX protein include enzyme linked immunosorbent assays (ELISAs), Western blots, immunoprecipitations, and immunofluorescence. In vitro techniques for detection of NOVX genomic DNA include Southern hybridizations. Furthermore, in vivo techniques for detection of NOVX protein include introducing into a subject a labeled anti-NOVX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting NOVX protein, mRNA, or genomic DNA, such that the presence of NOVX protein, mRNA or genomic DNA is detected in the biological sample, and comparing the presence of NOVX protein, mRNA or genomic DNA in the control sample with the presence of NOVX protein, mRNA or genomic DNA in the test sample.

The invention also encompasses kits for detecting the presence of NOVX in a biological sample. For example, the kit can comprise: a labeled compound or agent capable of detecting NOVX protein or mRNA in a biological sample; means for determining the amount of NOVX in the sample; and means for comparing the amount of NOVX in the sample with a standard. The compound or agent can be packaged in a suitable container. The kit can further comprise instructions for using the kit to detect NOVX protein or nucleic acid.

Prognostic Assays

The diagnostic methods described herein can furthermore be utilized to identify subjects having or at risk of developing a disease or disorder associated with aberrant NOVX expression or activity. For example, the assays described herein, such as the preceding diagnostic assays or the following assays, can be utilized to identify a subject having or at risk of developing a disorder associated with NOVX protein, nucleic acid expression or activity. Alternatively, the prognostic assays can be utilized to identify a subject having or at risk for developing a disease or disorder. Thus, the invention provides a method for identifying a disease or disorder associated with aberrant NOVX expression or activity in which a test sample is obtained from a subject and NOVX protein or nucleic acid (e.g., mRNA, genomic DNA) is detected, wherein the presence of NOVX protein or nucleic acid is diagnostic for a subject having or at risk of developing a disease or disorder associated with aberrant NOVX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NOVX expression or activity. For example, such methods can be used to determine whether a subject can be effectively treated with an agent for a disorder. Thus, the invention provides methods for determining whether a subject can be effectively treated with an agent for a disorder associated with aberrant NOVX expression or activity in which a test sample is obtained and NOVX protein or nucleic acid is detected (e.g., wherein the presence of NOVX protein or nucleic acid is diagnostic for a subject that can be administered the agent to treat a disorder associated with aberrant NOVX expression or activity).

The methods of the invention can also be used to detect genetic lesions in A NOVX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding A NOVX-protein, or the misexpression of the NOVX gene. For example, such genetic lesions can be detected by ascertaining the existence of at least one of: (i) a deletion of one or more nucleotides from A NOVX gene; (ii) an addition of one or more nucleotides to A NOVX gene; (iii) a substitution of one or more nucleotides of A NOVX gene, (iv) a chromosomal rearrangement of A NOVX gene; (v) an alteration in the level of a messenger RNA transcript of A NOVX gene, (vi) aberrant modification of A NOVX gene, such as of the methylation pattern of the genomic DNA, (vii) the presence of a non-wild-type splicing pattern of a messenger RNA transcript of A NOVX gene, (viii) a non-wild-type level of A NOVX protein, (ix) allelic loss of A NOVX gene, and (x) inappropriate post-translational modification of A NOVX protein. As described herein, there are a large number of assay techniques known in the art which can be used for detecting lesions in A NOVX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the NOVX-gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to A NOVX gene under conditions such that hybridization and amplification of the NOVX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); Qβ Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in A NOVX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in NOVX can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in NOVX can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NOVX gene and detect mutations by comparing the sequence of the sample NOVX with the corresponding wild-type (control) sequence. Examples of sequencing reactions include those based on techniques developed by Maxim and Gilbert, 1977. *Proc. Natl. Acad. Sci. USA* 74: 560 or Sanger, 1977. *Proc. Natl. Acad. Sci. USA* 74: 5463. It is also contemplated that any of a variety of automated sequencing procedures can be utilized when performing the diagnostic assays (see, e.g., Naeve, et al., 1995. *Biotechniques* 19: 448), including sequencing by mass spectrometry (see, e.g., PCT International Publication No. WO 94/16101; Cohen, et al., 1996. *Adv. Chromatography* 36: 127–162; and Griffin, et al., 1993. *Appl. Biochem. Biotechnol* 38: 147–159).

Other methods for detecting mutations in the NOVX gene include methods in which protection from cleavage agents is used to detect mismatched bases in RNA/RNA or RNA/DNA heteroduplexes. See, e.g., Myers, et al., 1985. *Science* 230: 1242. In general, the art technique of "mismatch cleavage" starts by providing heteroduplexes of formed by hybridizing (labeled) RNA or DNA containing the wild-type NOVX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NOVX cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis* 15: 1657–1662. According to an exemplary embodiment, a probe based on A NOVX sequence, e.g., a wild-type NOVX sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NOVX genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766; Cotton, 1993. *Mutat. Res.* 285: 125–144; Hayashi, 1992. *Genet. Anal. Tech. Appl.* 9: 73–79. Single-stranded DNA fragments of sample and control NOVX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. *Nature* 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving A NOVX gene.

Furthermore, any cell type or tissue, preferably peripheral blood leukocytes, in which NOVX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on NOVX activity (e.g., NOVX gene expression), as identified by a screening assay described herein can be administered to individuals to treat (prophylactically or therapeutically) disorders (The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers.) In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NOVX protein, expression of NOVX nucleic acid, or mutation content of NOVX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.,* 23: 983–985; Linder, 1997. Clin. Chem., 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome Pregnancy Zone Protein Precursor enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of NOVX protein, expression of NOVX nucleic acid, or mutation content of NOVX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with A NOVX modulator, such as a modulator identified by one of the exemplary screening assays described herein.

Monitoring of Effects During Clinical Trials

Monitoring the influence of agents (e.g., drugs, compounds) on the expression or activity of NOVX (e.g., the ability to modulate aberrant cell proliferation and/or differentiation) can be applied not only in basic drug screening, but also in clinical trials. For example, the effectiveness of an agent determined by a screening assay as described herein to increase NOVX gene expression, protein levels, or upregulate NOVX activity, can be monitored in clinical trails of subjects exhibiting decreased NOVX gene expression, protein levels, or downregulated NOVX activity. Alternatively, the effectiveness of an agent determined by a screening assay to decrease NOVX gene expression, protein levels, or downregulate NOVX activity, can be monitored in clinical trails of subjects exhibiting increased NOVX gene expression, protein levels, or upregulated NOVX activity. In such clinical trials, the expression or activity of NOVX and, preferably, other genes that have been implicated in, for example, a cellular proliferation or immune disorder can be used as a "read out" or markers of the immune responsiveness of a particular cell.

By way of example, and not of limitation, genes, including NOVX, that are modulated in cells by treatment with an agent (e.g., compound, drug or small molecule) that modulates NOVX activity (e.g., identified in a screening assay as described herein) can be identified. Thus, to study the effect of agents on cellular proliferation disorders, for example, in a clinical trial, cells can be isolated and RNA prepared and analyzed for the levels of expression of NOVX and other genes implicated in the disorder. The levels of gene expression (ie., a gene expression pattern) can be quantified by Northern blot analysis or RT-PCR, as described herein, or alternatively by measuring the amount of protein produced, by one of the methods as described herein, or by measuring the levels of activity of NOVX or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of A NOVX protein, mRNA, or genomic DNA in the preadministration sample; (iii) obtaining one or more post-administration samples from the subject; (iv) detecting the level of expression or activity of the NOVX protein, mRNA, or genomic DNA in the post-administration samples; (v) comparing the level of expression or activity of the NOVX protein, mRNA, or genomic DNA in the pre-administration sample with the NOVX protein, mRNA, or genomic DNA in the post administration sample or samples; and (vi) altering the administration of the agent to the subject accordingly. For example, increased administration of the agent may be desirable to increase the expression or activity of NOVX to higher levels than detected, i.e., to increase the effectiveness of the agent. Alternatively, decreased administration of the agent may be desirable to decrease expression or activity of NOVX to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant NOVX expression or activity. The disorders include cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation, adrenoleukodystrophy, congenital adrenal hyperplasia, prostate cancer, neoplasm; adenocarcinoma, lymphoma, uterus cancer, fertility, hemophilia, hypercoagulation, idiopathic thrombocytopenic purpura, immunodeficiencies, graft versus host disease, AIDS, bronchial asthma, Crohn's disease; multiple sclerosis, treatment of Albright Hereditary Osteoedystrophy, and other diseases, disorders and conditions of the like.

These methods of treatment will be discussed more fully, below.

Diseases and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (ie., due to a heterologous insertion within the coding sequences of coding sequences to an aforementioned peptide) that are utilized to "knockout" endogenous function of an aforementioned peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant NOVX expression or activity, by administering to the subject an agent that modulates NOVX expression or at least one NOVX activity. Subjects at risk for a disease that is caused or contributed to by aberrant NOVX expression or activity can be identified by, for example, any or a combination of diagnostic or prognostic assays as described herein. Administration of a prophylactic agent can occur prior to the manifestation of symptoms characteristic of the NOVX aberrancy, such that a disease or disorder is prevented or, alternatively, delayed in its progression. Depending upon the type of NOVX aberrancy, for example, A NOVX agonist or NOVX antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating NOVX expression or activity for therapeutic purposes. The modulatory method of the invention involves contacting a cell with an agent that modulates one or more of the activities of NOVX protein activity associated with the cell. An agent that modulates NOVX protein activity can be an agent as described herein, such as a nucleic acid or a protein, a naturally-occurring cognate ligand of A NOVX protein, a peptide, A NOVX peptidomimetic, or other small molecule. In one embodiment, the agent stimulates one or more NOVX protein activity. Examples of such stimulatory agents include active NOVX protein and a nucleic acid molecule encoding NOVX that has been introduced into the cell. In another embodiment, the agent inhibits one or more NOVX protein activity. Examples of such inhibitory agents include antisense NOVX nucleic acid molecules and anti-NOVX antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of A NOVX protein or nucleic acid molecule. In one embodiment, the method involves administering an agent (e.g., an agent identified by a screening assay described herein), or combination of agents that modulates (e.g., up-regulates or down-regulates) NOVX expression or activity. In another embodiment, the method involves administering A NOVX protein or nucleic acid molecule as therapy to compensate for reduced or aberrant NOVX expression or activity.

Stimulation of NOVX activity is desirable in situations in which NOVX is abnormally downregulated and/or in which increased NOVX activity is likely to have a beneficial effect. One example of such a situation is where a subject has a disorder characterized by aberrant cell proliferation and/or differentiation (e.g., cancer or immune associated disorders). Another example of such a situation is where the subject has a gestational disease (e.g., preclampsia).

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Invention

The NOVX nucleic acids and proteins of the invention are useful in potential prophylactic and therapeutic applications implicated in a variety of disorders including, but not limited to: metabolic disorders, diabetes, obesity, infectious disease, anorexia, cancer-associated cancer, neurodegenerative disorders, Alzheimer's Disease, Parkinson's Disorder, immune disorders, hematopoietic disorders, and the various dyslipidemias, metabolic disturbances associated with obesity, the metabolic syndrome X and wasting disorders associated with chronic diseases and various cancers.

As an example, a cDNA encoding the NOVX protein of the invention may be useful in gene therapy, and the protein may be useful when administered to a subject in need thereof. By way of non-limiting example, the compositions of the invention will have efficacy for treatment of patients suffering from: metabolic disorders, diabetes, obesity, infectious disease, anorexia, cancer-associated cachexia, cancer, neurodegenerative disorders, Alzheimer's Disease, Parkinson's Disorder, immune disorders, hematopoietic disorders, and the various dyslipidemias.

Both the novel nucleic acid encoding the NOVX protein, and the NOVX protein of the invention, or fragments thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies, which immunospecifically-bind to the novel substances of the invention for use in therapeutic or diagnostic methods.

The invention will be further described in the following examples, which do not limit the scope of the invention described in the claims.

EXAMPLES

Example A

Polynucleotide and Polypeptide Sequences, and Homology Data

Example 1

The NOV1 clone was analyzed, and the nucleotide and encoded polypeptide sequences are shown in Table 1A.

TABLE 1A

NOV1 Sequence Analysis

| | SEQ ID NO:1 | 239bp |
|---|---|---|
| NOV 1a, CG100488-01 DNA Sequence | AACCAGGGCCTTATCCAGGGCCACGCTTACAGAACTCCCACGGACACACCATGATTAG | |
| | GACCCTGCTGCTGTCCACTTTGGTGGCCCTCAGTTGTGGGGTCTCCACTTACGCGCCT | |
| | GATATGTCTAGGATGCTTGGAGGTGAAGAAGCGAGGCCCAACAGCTGGCCCTGGCAGG | |
| | TGAGTCTGCAGTACAGCTCCAATGGCCAGTCGTACCACACCTGCGGAGCGTCCCTGAT | |
| | AGCCAACAGCTGGGTCCTGACGGCTGCCCACTGCATCAGCTCCTCCGGGATCTACCGC | |
| | GTGATGCTGGGCCAGCATAACCTCTACGTTGCAGAGTCCGGCTCGCTGGCCGTCAGTG | |
| | TCTCTAAGATTGTGGTGCACAAGGACTGGAACTCCGACCAGGTCTCCAAAGGGAACGA | |
| | CATTGCCCTGCTCAAACTGCCTAACCCCGTCTCCCTCACCGACAAGATCCAGCTGGCC | |
| | TGCCTCCCTCCTGCCGGCACCATTCTACCCAACAACTACCCCTGCTACCTCACGGGCT | |
| | GGGGAAGGCTGCAGAGTAACGGGGCTCTCCCTGATGACCTGAAGCAGGCCCAGTTGCT | |
| | GGTTGTGGACTATGCCACCTGCTCCAGCTCTGGCTGGTGGGGCAGCACCGTGAAGACG | |
| | AATATGATCTGTGCTGGGGGTGATGGCGTGATATGCACCTGCAACGGAGACTCCGGTG | |
| | GGCCGCTGAACTGTCAGGCATCTCACGGCCGGTCCGAGGTCCATGGCATCGGCAGCCT | |

TABLE 1A-continued

NOV1 Sequence Analysis

```
CACGTCGGTCCTTGGTTGCAACTACTACTACAAGCCCTCCATCTTCACGCGGGTCTCC

AACTACAACGACTGGATCAATTCGGTAAGAACCGGAGCAGCCCTGAGCCCCAAGGCAC

TGACCTGCTCACCTGGCCTCGGGAGTGCCATGCCCACCTGGCGACTGAGAACCCCCTC

CTTCCTCTTGAGACCTACATGGGAACCCCTTGGACGAGGCTGCAGACCTTGGCAACTG

CTGAGTCCCCATGGGTCCCCAAAATTTCTGTGTGGGTAAAGCTCAGTGAAAAGGAAC

ATGAGAGTATGGCCTTGTCCAAAGACGTTGGACACTCCTCAGGTACGTTAAGAGTGAG

TTCCACAGGAATGATTTTATTTTTGTGTATTTGTGTGTGGCCCAGACTCTACCATCCA

GTGCTATAAATGGGTATATGTCTGCAAAACCCAAAACCTGATACTTTGAGACCCCCAT

AGCATTAATTATTGCAAATTA
```

| | |
|---|---|
| | ORF Start: ATG at 51    ORF Stop: TAA at 1167<br>SEQ ID NO: 2          372 aa MW at 40287.8 kD |
| NOV1a,<br>CG100488-01<br>Protein<br>Sequence | MIRTLLLSTLVALSCGVSTYAPDMSRMLGGEEARPNSWPWQVSLQYSSNGQWYHTCGG<br><br>SLIANSWVLTAAHCISSSGIYRVMLGQHNLYVAESGSLAVSVSKIVVHKDWNSDQVSK<br><br>GNDIALLKLANPVSLTDKIQLACLPPAGTILPNNYPCYVTGWGRLQSNGALPDDLKQG<br><br>QLLVVDYATCSSSGWWGSTVKTNMICAGGDGVICTCNGDSGGPLNCQASDGRWEVHGI<br><br>GSLTSVLGCNYYYKPSIFTRVSNYNDWINSVRTGAALSPKALTCSPGLGSAMPTWRLR<br><br>TPSFLLRARWEPLGGGCRPWQLLSPPWVPKISVWVKLSEKEHESMALSKDVGHSSGTL<br><br>RVSSTGMILFLCICVWPRLYHPVL |
| | SEQ ID NO:3          1188bp |
| NOV1b,<br>CG100488-06<br>DNA<br>Sequence | ATGATTAGGACCCTGCTGCTGTCCACTTTGGTGGCTGGAGCCCTCAGTTGTGGGGTCT<br><br>CCACTTACGCGCCTGATATGTCTAGGATGCTTGGAGGTGAAGAAGCGAGGCCCAACAG<br><br>CTGGCCCTGGCAGGTGAGTCTGCAGTACAGCTCCAATGGCCAGTGGTACCACACCTGC<br><br>GGAGGGTCCCTGATAGCCAACAGCTGGGTCCTGACGGCTGCCCACTGCATCAGCTCCT<br><br>CCGGGATCTACCGCGTGATGCTGGGCCAGCATAACCTCTACGTTCAGAGTCCGGCTC<br><br>GCTGGCCGTCAGTGTCTCTAAGATTGTGGTGCACAAGGACTGGAACTCCGACCAGGTC<br><br>TCCAAAGGGAACGACATTGCCCTGCTCAAACTGGCTAACCCCGTCTCCCTCACCGACA<br><br>AGATCCAGCTGGCCTGCCTCCCTCCTGCCGGCACCATTCTACCCAACAACTACCCCTG<br><br>CTACGTCACGGGCTGGGGAAGGCTGCAGACCAACGGGGCTCTCCCTGATGACCTGAAG<br><br>CAGGGCCAGTTGCTGGTTGTGGACTATGCCACCTGCTCCAGCTCTGGCTGGTGGGGCA<br><br>GCACCGTGAAGACGAATATGATCTGTGCTGGGGGTAATGGCGTGATATGCACCTGCAA<br><br>CGGAGACTCTGGCGGGCCACTGAACTGTCAGGCGTCTGACGGCCGGTGGCAGGTGCAC<br><br>GGCATCGTCAGCTTCGGGTCTCGCCTCGGCTGCAACTACTACCACAAGCCCTCCGTCT<br><br>TCACGCGGGTCTCCAATTACATCGACTGGATCAATTCGGTAAGAACCGGACCAGCCTT<br><br>GAGCCCCAAGGCACTACCCTGCTCACCTGGCCTCGGGAGTGCCATGCCCACCTGGTGA<br><br>CTGAGAATCCCCTCCTTCCTCTTGAGAGCTAGATGGGAACCCCTTGGAGGAGGCTGCA<br><br>GACCTGAGTAACTGCTGGGCCTGCCATGGGTCCCCAAAATTTCTGTGTGGATAAAGCT<br><br>GAGTGAAAAGGAACATAGAGGGTGGCCTTGTCCAAAGAGGTTGGACACTCCTCAGGCA<br><br>TATGAAGAGTGAGTTCCGCTGGGCGCCGTGGCTCATGCCTGTAATCCCAGCTCTTTGG |

TABLE 1A-continued

NOV1 Sequence Analysis

GAGGCCAAGGCGGGCAGATCACGAGGTCAGAAGTTCAAGACCAGCCTGACCAACCTGG

CAAAACCCCATGTCTACTAAAAAAATCC

|  | ORF Start: ATG at 1<br>SEQ ID NO: 4 | ORF Stop: TGA at 868<br>289 aa MW at 30820.8 kD |
|---|---|---|
| NOV1b,<br>CG100488-06<br>Protein<br>Sequence | MIRTLLLSTLVAGALSCGVSTYAPDMSRMLGGEEARPNSWPWQVSLQYSSNGQWYHTC<br>GGSLIANSWVLTAAHCISSSGIYRVMLGQHNLYVAESGSLAVSVSKIVVHKDWNSDQV<br>SKGNDIALLKLANPVSLTDKIQLACLPPAGTILPNNYPCYVTGWGRLQTNGALPDDLK<br>QGQLLVVDYATCSSSGWWGSTVKTNMICAGGNGVICTCNGDSGGPLNCQASDGRWQVH<br>GIVSFGSRLGCNYYHKPSVFTRVSNYIDWINSVRTGPALSPKALPCSPGLGSAMPTW | |
|  | SEQ ID NO: 5 | 889 bp |
| NOV1c,<br>CG100488-07<br>DNA<br>Sequence | ATGATTAGGACCCTGCTGCTGTCCACTTTGGTGGCTGGAGCCCTCAGTTGTGGGGTCT<br>CCACTTACGCGCCTGATATGTCTAGGATGCTTGGAGGTGAAGAAGCGAGGCCCAACAG<br>CTGGCCCTCGCAGGTGAGTCTGCAGTACACCTCCAATGGCCAGTGGTACCACACCTGC<br>GGAGGGTCCCTGATAGCCAACAGCTGGGTCCTCACGGCTGCCCACTGCATCAGCTCCT<br>CCGGGATCTACCGCGTGATGCTGGGCCAGCATAACCTCTACGTTGCAGAGTCCGGCTC<br>GCTGGCCGTCAGTGTCTCTAAGATTGTGGTGCACAAGGACTGGAACTCCGACCAGGTC<br>TCCAAAGGGAACGACATTGCCCTGCTCAAACTGGCTAACCCCGTCTCCCTCACCGACA<br>AGATCCAGCTGGCCTGCCTCCCTCCTGCCGGCACCATTCTACCCAACAACTACCCCTG<br>CTACGTCACGGGCTGGGGAAGGCTGCAGACCAACGGGGCTCTCCCTGATGACCTGAAG<br>CAGGGCCAGTTGCTGGTTGTGGACTATGCCACCTGCTCCAGCTCTGGCTGGTGGGGCA<br>GCACCGTGAAGACGAATATGATCTGTGCTGGGGGTAATGGCGTGATATGCACCTGCAA<br>CGCAGACTCTGGCGGGCCACTGAACTGTCACGCGTCTGACGGCCGGTGGCAGCTGCAC<br>GGCATCGTCACCTTCGGGTCTCGCCTCGGCTGCAACTACTACCACAAGCCCTCCGTCT<br>TCACGCGGGTCTCCAATTACATCGACTGGATGATTGCAAATAACTAACCAAAAGAAGT<br>CCCTGGGACTGTTTCAGACTTGGAAAGGTCACGGAAGGAAAATAATATAATAAAGTGG<br>CAACTATGCAAAAAAAAAA | |
|  | ORF Start: ATG at 1<br>SEQ ID NO: 6 | ORF Stop: TAA at 799<br>266 aa MW at 28573.2 kD |
| NOV1c,<br>CG100488-07<br>Protein<br>Sequence | MIRTLLLSTLVAGALSCGVSTYAPDMSRMLGGEEARPNSWPWQVSLQYSSNGQWYHTC<br>GGSLIANSWVLTAAHCISSSGIYRVMLGQHNLYVAESGSLAVSVSKIVVHKDWNSDQV<br>SKGNDIALLKLANPVSLTDKIQLACLPPAGTILPNNYPCYVTGWGRLQTNGALPDDLK<br>QGQLLVVDYATCSSSGWWCSTVKTNMICAGGNGVICTCNGDSGGPLNCQASDGRWQVH<br>GIVSFGSRLGCNYYHKPSVFTRVSNYIDWMIANN | |
|  | SEQ ID NO:7 | 1188bp |
| NOV1d,<br>CG100488-08<br>DNA<br>Sequence | ATGATTAGGACCCTGCTCCTGTCCACTTTGGTGGCTGGAGCCCTCAGTTGTGGGGACC<br>CCACTTACCCACCTTATGTGACTAGGGTGGTTGGCGGTGAAGAAGCGAGGCCCAACAG<br>CTGGCCCTGGCAGGTGAGTCTGCAGTACAGCTCCAATGGCCAGTGGTACCACACCTGC | |

TABLE 1A-continued

NOV1 Sequence Analysis

GGAGGGTCCCTGATAGCCAACAGCTGGGTCCTGACGGCTGCCCACTGCATCAGCTCCT

CCGGGATCTACCGCGTGATGCTGGGCCAGCATAACCTCTACGTTGCAGAGTCCGGCTC

GCTGGCCGTCAGTGTCTCTAAGATTGTGGTGCACAAGGACTGGAACTCCGACCAGGTC

TCCAAAGGGAACGACATTGCCCTGCTCAAACTGGCTAACCCCGTCTCCCTCACCGACA

AGATCCAGCTGGCCTGCCTCCCTCCTGCCGGCACCATTCTACCCAACAACTACCCCTG

CTACGTCACGGGCTGGGGAAGGCTGCAGGCCAACGGGGCTCTCCCTGATGACCTGAAG

CAGGGCCAGTTGCTGGTTGTGGACTATGCCACCTGCTCCAGCTCTGGCTGGTGGGGCA

GCACCGTGAAGACGAATATGATCTGTGCTGGGGGTAATGGCGTGATATGCACCTGCAA

CGGAGACTCTGGCGGGCCACTGAACTGTCAGGCGTCTGACGGCCGGTGGCAGGTGCAC

GGCATCGTCAGCTTCGGGTCTCGCCTCGGCTGCAACTACTACCACAAGCCCTCCGTCT

TCACGCGGGTCTCCAATTACATCGACTGGATCAATTCGGTAAGAACCGGACCAGCCTT

GAGCCCCAAGGCACTACCCTGCTCACCTGGCCTCGGGAGTGCCATGCCCACCTGGTGA

<u>CTGAGAATCCCCTCCTTCCTCTTGAGAGCTAGATGGGAACCCCTTGGAGGAGGCTGCA</u>

<u>GACCTGAGTAACTGCTGGGCCTGCCATGGGTCCCCCAAATTTCTGTGTGGATAAAGCT</u>

<u>GAGTGAAAAGGAACATAGAGGGTGGCCTTGTCCAAAGAGGTTGGACACTCCTCAGGCA</u>

<u>TATGAAGAGTGAGTTCCGCTGGGCGCCGTGGCTCATGCCTGTAATCCCAGCTCTTTGG</u>

<u>GAGGCCAAGGCGGGCAGATCACGAGGTCAGAAGTTCAAGACCAGCCTGACCAACCTGG</u>

<u>CAAAACCCCATGTCTACTAAAAAATCC</u>

ORF Start: ATG at 1   ORF Stop: TGA at 868
SEQ ID NO: 8           289 aa MW at 30826.8 kD

| NOV1d, CG100488-08 Protein Sequence | MIRTLLLSTLVAGALSCGDPTYPPYVTRVVGGEEARPNSWPWQVSLQYSSNGQWYHTC<br><br>GGSLIANSWVLTAAHCISSSGIYRVMLGQHNLYVAESGSLAVSVSKIVVHKDWNSDQV<br><br>SKGNDIALLKLANPVSLTDKIQLACLPPAGTILPNNYPCYVTGWGRLQANGALPDDLK<br><br>QGQLLVVDYATCSSSGWWGSTVKTNMICAGGNGVICTCNGDSGGPLNCQASDGRWQVH<br><br>GIVSFGSRLGCNYYHKPSVFTRVSNYIDWINSVRTGPALSPKALPCSPGLGSAMPTW |
|---|---|

SEQ ID NO: 9          889 bp

| NOV1e, CG100488-09 DNA Sequence | ATGATTAGGACCCTGCTGCTGTCCACTTTGGTGGCTGGACCCCTCAGTTGTGGGGACC<br><br>CCACTTACCCACCTTATGTGACTAGGGTGGTTGGCGGTGAAGAAGCGAGGCCCAACAG<br><br>CTGGCCCTGGCAGGTGAGTCTGCAGTACAGCTCCAATGGCCAGTGGTACCACACCTGC<br><br>GGAGCGTCCCTGATAGCCAACAGCTGGGTCCTGACGGCTGCCCACTGCATCAGCTCCT<br><br>CCGGGATCTACCCCGTGATGCTGGGCCAGCATAACCTCTACGTTGCAGAGTCCGGCTC<br><br>GCTGGCCGTCAGTGTCTCTAACATTGTGGTGCACAAGGACTGGAACTCCGACCAGGTC<br><br>TCCAAAGGGAACGACATTGCCCTGCTCAAACTGGCTAACCCCGTCTCCCTCACCGACA<br><br>AGATCCAGCTGGCCTGCCTCCCTCCTGCCGGCACCATTCTACCCAACAACTACCCCTG<br><br>CTACGTCACGGGCTGGGGAAGGCTGCAGGCCAACGGGGCTCTCCCTGATGACCTGAAG<br><br>CAGGGCCAGTTGCTGGTTGTGGACTATGCCACCTGCTCCAGCTCTGGCTGGTGGGGCA<br><br>GCACCGTGAAGACGAATATGATCTGTGCTGGGGGTAATGGCGTGATATGCACCTGCAA<br><br>CGGAGACTCTGGCGGGCCACTGAACTGTCAGGCGTCTGACGGCCGGTCGCAGGTGCAC |
|---|---|

TABLE 1A-continued

NOV1 Sequence Analysis

GGCATCGTCAGCTTCGGGTCTCGCCTCGGCTGCAACTACTACCACAAGCCCTCCGTCT
TCACGCGGGTCTCCAATTACATCGACTGGATGATTGCAAATAACTAACCAAAAGAAGT
CCCTGGGACTGTTTCAGACTTGGAAAGGTCACGGAAGGAAAATAATATAATAAAGTGG
CAACTATGCAAAAAAAAAA

ORF Start: ATG at 1  ORF Stop: TAA at 799
SEQ ID NO: 10         266 aa MW at 285 79.2 kD

| | |
|---|---|
| NOV1e, CG100488-09 Protein Sequence | MIRTLLLSTLVAGALSCGDPTYPPYVTRVVGGEEARPNSWPWQVSLQYSSNGQWYHTC GGSLIANSWVLTAAHCISSSGIYRVMLGQHNLYVAESGSLAVSVSKIVVHKDWNSDQV SKGNDIALLKLANPVSLTDKIQLACLPPAGTILPNNYPCYVTGWGRLQANGALPDDLK QGQLLVVDYATCSSSGWWGSTVKTNMICAGGNGVICTCNGDSGGPLNCQASDGRWQVH GIVSFGSRLGCNYYHKPSVFTRVSNYIDWMIANN |

SEQ ID NO: 11    11080 bp

| | |
|---|---|
| NOV1f 198353297 DNA Sequence | GGATCCGTCTCCACTTACGCGCCTGATATGTCTAGGATGCTTGGAGGTGAAGAAGCGA GGCCCAACAGCTGGCCCTGGCAGATCTCCCTGCAGTACAGCTCCAATGGCCAGTGGTA CCACACCTGCGGAGGGTCCCTGATAGCCAACAGCTGGGTCCTGACGGCTGCCCACTGC ATCAGCTCCTCCGGGATCTACCGCGTGATGCTGGGCCAGCATAACCTCTACGTTGCAG AGTCCGGCTCGCTGGCCGTCAGTGTCTCTAAGATTGTGGTGCACAAGGACTGGAACTC CGACCAGGTCTCCAAAGGGAACGACATTGCCCTGCTCAAACTGGCTAACCCCGTCTCC CTCGCCGACAAGATCCAGCTGGCCTGCCTCCCTCCTGCCGGCACCATTCTACCCAACA ACTACCCCTGCTACGTCACGGGCTGGGGAAGGCTGCAGACCAACGGGGCTCTCCCTGA TGACCTGAAGCAGGGCCGGTTGCTGGTTGTGGACTATGCCACCTGCTCCAGCTCTGGC TGGTGGGGCAGCACCGTGAAGACGAATATGATCTGTGCTGGGGGTGATGGCGTGATAT GCACCTGCAACGGAGACTCCGGTGGGCCGCTGAACTGTCAGGCATCTGACGGCCGGTG GGAGGTGCATGGCATCGGCAGCCTCACGTCGGTCCTTGGTTGCAACTACTACTACAAG GGAGGTGCATGGCATCGGCAGCCTCACGTCGGTCCTTGGTTGCAACTACTACTACAAG CCCTCCATCTTCACGCGGGTCTCCAACTACAACGACTGGATCAATTCGGTAAGAACCG GAGCAGCCCTGAGCCCCAAGGCACTGACCTGCTCACCTGGCCTCGGGAGTGCCATGCC CACCTGGCGACTGAGAACCCCCTCCTTCCTCTTGAGAGCTAGATGGGAACCCCTTGGA GGAGGCTGCAGACCTTGGCAACTGCTGAGTCCCCCATGGGTCCCCAAAATTTCTGTGT GGGTAAAGCTGAGTGAAAAGGAACATGAGAGTATGGCCTTGTCCAAAGACGTTGGACA CTCCTCAGGTACGTTAAGAGTGAGTTCCACAGGAATGATTTTATTTTTGTGTATTTGT GTGTGGCCCAGACTCTACCATCCAGTGCTACTCGAG |

ORF Start: at 1  ORF Stop: end of sequence
SEQ ID NO: 12    360 aa MW at 39027.2 kD

| | |
|---|---|
| NOV1f, 198353297 Protein Sequence | GSVSTYAPDMSRMLGGEEARPNSWPWQISLQYSSNGQWYHTCGGSLIANSWVLTAAHC ISSSGIYRVMLGQHNLYVAESGSLAVSVSKIVVHKDWNSDQVSKGNDIALLKLANPVS LADKIQLACLPPAGTILPNNYPCYVTGWGRLQTNGALPDDLKQGRLLVVDYATCSSSG WWGSTVKTNMICAGGDGVICTCNGDSGGPLNCQASDGRWEVHGIGSLTSVLGCNYYYK |

TABLE 1A-continued

NOV1 Sequence Analysis

PSIFTRVSNYNDWINSVRTGAALSPKALTCSPGLGSAMPTWRLRTPSFLLRARWEPLG

GGCRPWQLLSPPWVPKISVWVKLSEKEHESMALSKDVGHSSGTLRVSSTGMILFLCIC

VWPRLYHPVLLE

| | SEQ ID NO:13 | 1080 bp |
|---|---|---|

NOV1g, 198353301 DNA Sequence

GGATCCGTCTCCACTTACGCGCCTGATATGTCTAGGATGCGTGGAGGTGAAGAAGCGA

GGCCCAACAGCTGGCCCTGGCAGGTCTCCCTGCAGTACAGCTCCAATGGCCAGTGGTA

CCACACCTGCGGAGGCTCCCTGATAGCCAACAGCTGGGTCCTGACGGCTGCCCACTGC

ATCAGCTCCTCCGGGATCTACCGCGTGATGCTGGGCCAGCATAACCTCTACGTTGCAG

AGTCCGGCTCGCTGGCCGTCAGTGTCTCTAAGATTGTGGTGCACAAGGACTGGAACTC

CGACCAGGTCTCCAAAGGGAACGACATTGCCCTGCTCAAACTGGCTAACCCCGTCTCC

CTCACCGACAACATCCAGCTGGCCTGCCTCCCTCCTGCCGGCACCATTCTACCCAACA

ACTACCCCTGCTACGTCACGGGCTGGGGAAGGCTGCAGACCAACGGGGCTCTCCCTGA

TGACCTGAAGCAGGGCCGGTTGCTGGTTGTGGACTATGCCACCTGCTCCAGCTCTGGC

TGGTGGGGCAGCACCGTGAAGACGAATATGATCTGTGCTGGGGGTGATGGCGTGATAT

GCACCTGCAACGGAGACTCCGGTGGGCCGCTCAACTGCCAGCCATCTCACGGCCGGTG

GGAGGTGCATGGCATCGGCAGCCTCACGTCGGTCCTTGGTTGCAACTACTACTACAAG

CCCTCCATCTTCACGCGGGTCTCCAACTACAACGACTGGATCAATTCGGTAAGAACCG

GAGCAGCCCTGAGTCCCAAGGCACTGCCCTGCTCACCTGGCCTCGGGAGTGCCATGCC

CACCTGGCGACTGAGAACCCCCTCCTTCCTCTTGAGAGCTAGATGGGAACCCCTTGGA

GGAGGCTGCAGACCTTGCCAACTGCTGAGTCCCCCATGGGTCCCCAAAATTTCTGTGT

GGGTAAAGCTGAGTGAAAAGGAACATGAGAGTATGGCCTTGTCCAAAGACGTTGGACA

CTCCTCAGGTATGTTAAGAGTGAGTTCCACAGGAATGATTTTATTTTTGTGTATTTGT

GAATGGCCCAGACTCTACCATCCAGTGCTACTCGAG

| | ORF Start: at 1 | ORF Stop: end of sequence |
|---|---|---|
| | SEQ ID NO:14 | 360 aa MW at 39142.3 kD |

NOV1g, 198353301 Protein Sequence

GSVSTYAPDMSRMRGGEEARPNSWPWQVSLQYSSNGQWYHTCGGSLIANSWVLTAAHC

ISSSGIYRVMLGQHNLYVAESGSLAVSVSKIVVHKDWNSDQVSKGNDIALLKLANPVS

LTDKIQLACLPPAGTILPNNYPCYVTGWGRLQTNGALPDDLKQGRLLVVDYATCSSSG

WWGSTVKTNNICAGGDGVICTCNGDSGGPLNCQASDGRWEVHGIGSLTSVLGCNYYYK

PSIFTRVSNYNDWINSVRTGAALSPKALPCSPGLGSAMPTWRLRTPSFLLRARWEPLG

GGCRPWQLLSPPWVPKISVWVKLSEKEHESMALSKDVGHSSGMLRVSSTGMILFLCIC

EWPRLYHPVLLE

| | SEQ ID NO: 15 | 1080 bp |
|---|---|---|

NOV1h, 198353319 DNA Sequence

GGATCCGTCTCCACTTACGCGCCTGATATGTCTAGGATGCTTGGAGGTGAAGAAGCGA

GGCCCAACAGCTGGCCCTGGCAGGTCTCCCTGCAGTACAGCTCCAATGGCCAGTGGTA

CCACACCTGCGGAGGGTCCCTGATAGCCAACAGCTGGGTCCTGACGGCTGCCCACTGC

ATCAGCTCCTCCAGGATCTACCGCGTGATGCTGGGCCAGCATAACCTCTACGTTGCAG

AGTCCGGCTCGCTAGCCGTCAGTGTCTCTAAGATTGTGGTGCACAAGGACTGGAACTC

TABLE 1A-continued

NOV1 Sequence Analysis

CAACCAGGTCTCCAAAGGGAACGACATTGCCCTGCTCAAACTGGCTAACCCCGTCTCC

CTCACCGACAAGATCCAGCTGGCCTGCCTCCCTCCTGCCGGCACCATTCTACCCAACA

ACTACCCCTGCTACGTCACAGGCTGGGGAAGGCTGCAGACCAACGGGGCTCTCCCTGA

TGACCTGAAGCAGGGCCGGTTGCTGGTTGTGGACTATGCCACCTGCTCCAGCTCTGGC

TGGTGGGGCAGCACCGTGAAGACGAATATGATTTGTGCTGGGGGTGATGGCGTGATAT

GCACCTGCAACGGAGACTCCGGTGGGCCGCTGAACTGTCAGGCATCTGACGGCCGGTG

GGAGGTGCATGGCATCGGCAGCCTCACGTCGGTCCTTGGTTGCAACTACTACTACAAG

CCCTCCATCTTCACGCGGGTCTCCAACTACAACGACTGGATCAATTCGGTAAGAACCG

GAGCAGCCCTGAGTCCCAAGGCACTGCCCTGCTCACCTGGCCTCGGGAGTGCCATGCC

CACCTGGCGACTGAGAACCCCCTCCTTCCTCTTGAGAGCTAGATGGGAACCCCTTGGA

GGAGGCTGCAGACCTTGGCAACTGCTGAGTCCCCCATGGGTCCCCAAAATTTCTGTGT

GGGTAAAGCTGAGTGAAAAGGAACATGAGAGTATGGCCTTGTCCAAAGACGTTGGACA

CTCCTCAGGTATGTTAAGAGTGAGTTCCACAGGAATGATTTTATTTTTGTGTATTTGT

GAATGGCCCAGACTCTACCATCCAGTGCTACTCGAG

| | |
|---|---|
| | ORF Start: at 1  ORF Stop: end of sequence<br>SEQ ID NO: 14  360 aa MW at 39142.3kD |
| NOV1g,<br>198353301<br>Protein<br>Sequence | GSVSTYAPDMSRMRGGEEARPNSWPWQVSLQYSSNGQWYHTCGGSLIANSWVLTAAHC<br>ISSSGIYRVMLGQHNLYVAESGSLAVSVSKIVVHKDWNSDQVSKGNDIALLKLANPVS<br>LTDKIQLACLPPAGTILPNNYPCYVTGWGRLQTNGALPDDLKQGRLLVVDYATCSSSG<br>WWGSTVKTNMICAGGDGVICTCNGDSGGPLNCQASDGRWEVHGIGSLTSVLGCNYYYK<br>PSIFTRVSNYNDWINSVRTGAALSPKALPCSPGLGSAMPTWRLRTPSFLLRARWEPLG<br>GGCRPWQLLSPPWVPKISVWVKLSEKEHESMALSKDVGHSSGMLRVSSTGMILFLCIC<br>EWPRLYHPVLLE |
| | SEQ ID NO: 15  1080 bp |
| NOV1h,<br>198353319<br>DNA<br>Sequence | GGATCCGTCTCCACTTACGCGCCTGATATGTCTAGGATGCTTGGAGGTGAAGAAGCGA<br>GGCCCAACAGCTGGCCCTGGCAGGTCTCCCTGCAGTACAGCTCCAATGGCCAGTGGTA<br>CCACACCTGCGGAGGGTCCCTGATAGCCAACAGCTGGGTCCTGACGGCTGCCCACTGC<br>ATCAGCTCCTCCAGGATCTACCGCGTGATGCTGGGCCAGCATAACCTCTACGTTGCAG<br>AGTCCGGCTCGCTAGCCGTCAGTGTCTCTAAGATTGTGGTGCACAAGGACTGGAACTC<br>CAACCAGGTCTCCAAAGGGAACGACATTGCCCTGCTCAAACTGGCTAACCCCGTCTCC<br>CTCACCGACAAGATCCAGCTGGCCTGCCTCCCTCCTGCCGGCACCATTCTACCCAACA<br>ACTACCCCTGCTACGTCACAGGCTGGGGAAGGCTGCAGACCAACGGGGCTCTCCCTGA<br>TGACCTGAAGCAGGGCCGGTTGCTGGTTGTGGACTATGCCACCTGCTCCAGCTCTGGC<br>TGGTGGGGCAGCACCGTGAAGACGAATATGATTTGTGCTGGGGGTGATGGCGTGATAT<br>GCACCTGCAACGGAGACTCCGGTGGGCCGCTGAACTGTCAGGCATCTGACGGCCGGTG<br>GGAGGTGCATGGCATCGGCAGCCTCACGTCGGTCCTTGGTTGCAACTACTACTACAAG<br>CCCTCCATCTTCACGCGGGTCTCCAACTACAACGACTGGATCAATTCGGTAAGAACCG |

TABLE 1A-continued

NOV1 Sequence Analysis

|  |
|---|
| GAGCAGCCCTGAGCCCCAAGGCACTGACCTGCTCACCTGGCCTCGGGAGTGCCATGCC<br>CACCTGGCGACTGAGAACCCCCTCCTTCCTCTTGAGAGCTAGATGGGAACCCCTTGGA<br>GGAGGCTGCAGACCTTGGCAACTGCTGAGTCCCCCATGGGTCCCCAAAATTTCTGTGT<br>GGGTAAAGCTGAGTGAAAAGGAACATGAGAGTATGGCCTTGTCCAAAGACGTTGGACA<br>CTCCTCAGGTATGTTAAGAGTGAGTTCCACAGGAATGATTTTATTTTTGTGTATTTGT<br>GTGTGGCCCAGACTCTACCATCCAGTGCTACTCGAG |

| | ORF Start: at 1<br>SEQ ID NO: 16 | ORF Stop: end of sequence<br>360 aa MW at 39171.4 kD |
|---|---|---|
| NOV1h,<br>198353319<br>Protein<br>Sequence | GSVSTYAPDMSRMLGGEEARPNSWPWQVSLQYSSNGQWYHTCGGSLIANSWVLTAAHC<br>ISSSRIYRVMLGQHNLYVAESGSLAVSVSKIVVHKDWNSNQVSKGNDIALLKLANPVS<br>LTDKIQLACLPPAGTILPNNYPCYVTGWRLQTNGALPDDLKQGRLLVVDYATCSSSG<br>WWGSTVKTNMICAGGDGVICTCNGDSGGPLNCQASDGRWEVHGIGSLTSVLGCNYYYK<br>PSIFTRVSNYNDWINSVRTGAALSPKALTCSPGLGSAMPTWRLRTPSFLLRARWEPLG<br>GGCRPWQLLSPPWVPKISVWVKLSEKEHESMALSKDVGHSSGMLRVSSTGMILFLCIC<br>VWPRLYHPVLLE | |

| | SEQ ID NO: 17 | 1080 bp |
|---|---|---|
| NOV1i,<br>198362547<br>DNA<br>Sequence | GGATCCGTCTCCACTTACGCGCCTGATATGTCTAGGATGCTTGGAGGTGAAGAAGCGA<br>GGCCCAACAGCTGGCCCTGGCAGGTCTCCCTGCAGTACAGCTCCAATGGCCAGTGGTA<br>CCACACCTGCGGAGGGTCCCTGATAGCCAACAGCTGGGTCCTGACGGCTGCCCACTGC<br>ATCACCTCCTCCGCGATCTACCGCGTGATGCTGGGCCAGCATAACCTCTACGTTGCAG<br>AGTCCGGCTCGCTGGCCGTCAGTGTCTCTAAGATTGTGGTGCACAAGGACTGGAACTC<br>CGACCAGGTCTCCAAAGGGAACGACATTGCCCTGCTCAAACTGGCTAACCCCGTCTCC<br>CTCACCGACAAGATCCAGCTGGCCTGCCTCCCTCCTGCCGGCACCATTCTACCCAACA<br>ACTACCCCTGCTACGTCACGGGCTGGGGAAGGCTGCAGACCAACGGGGCTCTCCCTGA<br>TGACCTGAAGCAGGGCCGGTTGCTGGTTGTGGACTATGCCACCTGCTCCAGCTCTGGC<br>TGGTGGGGCAGCACCGTGAAGACGAATATGATCTGTGCTGGGGGTGATGGCGTCATAT<br>GCACCTGCAACGGAGACTCCGGTGGGCCGCTGAACTGTCAGGCATCTGACGGCCGGTG<br>GGAGGTGCATGGCATCGGCAGCCTCACGTCGGTCCTTGGTTGCAACTACTACTACAAG<br>CCCTCCATCTTCACGCGGGTCTCCAACTACAACGACTGGATCAATTCGGTAAGAACCG<br>GAGCAGCCCTGAGCCCCAAGCCACTGCCCTGCTCACCTGGCCTCGGGAGTGCCATGCC<br>CACCTGGCGACTGAGAACCCCCTCCTTCCTCTTGACAGCTAGATGGGAACCCCTTGGA<br>GGAGGCTGCAGACCTTGGCAACTGCTGAGTCCCCCATGGGTCCCCAAAATTTCTGTGT<br>GGGTAAAGCTGAGTGAAAAGGAACATGAGAGTATGGCCTTGTCCAAAGACGTTGGACA<br>CTCCTCAGGTATGTTAAGAGTGAGTTCCACAGGAATGATTTTATTTTTGTGTATTTGT<br>GTGTGGCCCAGACTCTACCATCCAGTGCTACTCGAG | |

TABLE 1A-continued

NOV1 Sequence Analysis

| | ORF Start: at 1<br>SEQ ID NO: 18 | ORF Stop: end of sequence<br>360 aa MW at 39069.3 kD |
|---|---|---|
| NOV1i,<br>198362547<br>Protein<br>Sequence | GSVSTYAPDMSRMLGGEEARPNSWPWQVSLQYSSNGQWYHTCGGSLIANSWVLTAAHC<br><br>ISSSGIYRVMLGQHNLYVAESGSLAVSVSKIVVHKDWNSDQVSKGNDIALLKLANPVS<br><br>LTDKIQLACLPPAGTILPNNYPCYVTGWRLQTNGALPDDLKQGRLLVVDYATCSSSG<br><br>WWGSTVKTNMICAGGDGVICTCNGDSGGPLNCQASDGRWEVHGIGSLTSVLGCNYYYK<br><br>PSIFTRVSNYNDWINSVRTGAALSPKALPCSPGLGSAMPTWRLRTPSFLLRARWEPLG<br><br>GGCRPWQLLSPPWVPKISVWVKLSEKEHESMALSKDVGHSSGMLRVSSTGMILFLCIC<br><br>VWPRLYHPVLLE | |
| | SEQ ID NO: 19 | 1023 bp |
| NOV1j,<br>198362642<br>DNA<br>Sequence | GGATCCGTCTCCACTTACGCGCCTGATATGTCTAGGATGCTTGGAGGTGAAGAAGCGA<br><br>GGCCCAACAGCCGGCCCTGGCAGGTCTCCCTGCAGTACAGCTCCAATGGCCAGTGGTA<br><br>CCACACCTGCGGAGGGTCCCTGATAGCCAACAGCTGGGTCCTGACGGCTGCCCACTGC<br><br>ATCAGCTCCTCCGGGATCTACCGCGTGATGCTGGGCCAGCATAACCTCTACGTTGCAG<br><br>AGTCCGGCTCGCTGGCCGTCAGTGTCTCTAAGATTGTGGTGCACAAGGACTGGAACTC<br><br>CGACCAGGTCTCCAAAGGGAACGACATTGCCCTGCTCAAACTGGCTAACCCCGTCTCC<br><br>CTCACCGACAAGATCCAGCTGGCCTGCCTCCCTCCTGCCGGCACCATTCTACCCAACA<br><br>ACTACCCCTGCTACGTCACGGGCTGGGGAAGGCTGCAGACCAACGGGGCTCTCCCTGA<br><br>TGACCTGAAGCAGGGCCGGTTGCTGGTTGTGGACTATGCCACCTGCTCCAACTCTGGC<br><br>TGGTGGGGCAGCACCGTGAAGACGAATATGATCTGTGCTGGGGGTGATGGCGTGATAT<br><br>GCACCTGCAACGGAGACTCCGGTGGCCGCTGAACTGTCAGGCATCTGACGGCCGGTG<br><br>GGAGGTGCATGGCATCGGCAGCCTCACGTCGGTCCTTGGTTGCAACTACTACTACAAG<br><br>CCCTCCATCTTCACGCGGGTCTCCAACTACAACGACTGGATCAATTCGGTAAGAACCG<br><br>GAGCAGCCCTGAGCCCCAAGGCACTGACCTGCTCACCTGGCCTCGGGAGTGCCATGCC<br><br>CACCTGGCGACTGAGAACCCCCTCCTTCCTCTTGAGAACTAGATGGGAACCCCTTGGA<br><br>GGAGGCTGCAGACCTTGGCAACTGCTGAGTCCCCCATGGGTCCCCAAAATTTCTGTGT<br><br>GGGTAAAGCTGAGTGAAAAGGAACATGAGAGTATGGCCTTGTCCAAAGACGTTGGACA<br><br>CTCCTCAGGTACGTTAAGAGTGAGTTCCACACTCGAG | |
| | ORF Start: at 1<br>SEQ ID NO:20 | ORF Stop: end of sequence<br>341 aa MW at 36814.4 kD |
| NOV1j,<br>198362642<br>Protein<br>Sequence | GSVSTYAPDMSRMLGGEEARPNSRPWQVSLQYSSNGQWYHTCGGSLIANSWVLTAAHC<br><br>ISSSGIYRVMLGQHNLYVAESGSLAVSVSKIVVHKDWNSDQVSKGNDIALLKLANPVS<br><br>LTDKIQLACLPPAGTILPNNYPCYVTGWRLQTNGALPDDLKQGRLLVVDYATCSNSG<br><br>WWGSTVKTNMICAGGDGVICTCNGDSGGPLNCQASDGRWEVHGIGSLTSVLGCNYYYK<br><br>PSIFTRVSNYNDWINSVRTGAALSPKALTCSPGLGSAMPTWRLRTPSFLLRTRWEPLG<br><br>GGCRPWQLLSPPWVPKISVWVKLSEKEHESMALSKDVGHSSGTLRVSSTLE | |

Sequence comparison of the above protein sequences yields the following
sequence relationships shown in Table 1B.

TABLE 1B

Comparison of NOV1a against NOV1b through NOV1j.

| Protein Sequence | NOV1a Residues/ Match Residues | Identities/Similarities for the Matched Region |
|---|---|---|
| NOV1b | 1 ... 287 | 275/289 (95%) |
|  | 1 ... 289 | 280/289 (96%) |
| NOV1c | 1 ... 260 | 249/262 (95%) |
|  | 1 ... 262 | 255/262 (97%) |
| NOV1d | 1 ... 287 | 267/289 (92%) |
|  | 1 ... 289 | 276/289 (95%) |
| NOV1e | 1 ... 260 | 241/262 (91%) |
|  | 1 ... 262 | 251/262 (94%) |
| NOV1f | 17 ... 372 | 352/356 (98%) |
|  | 3 ... 358 | 355/356 (98%) |
| NOV1g | 17 ... 372 | 350/356 (98%) |
|  | 3 ... 358 | 352/356 (98%) |
| NOV1h | 17 ... 372 | 351/356 (98%) |
|  | 3 ... 358 | 354/356 (98%) |
| NOV1i | 17 ... 372 | 352/356 (98%) |
|  | 3 ... 358 | 354/356 (98%) |
| NOV1j | 17 ... 353 | 332/337 (98%) |
|  | 3 ... 339 | 335/337 (98%) |

Further analysis of the NOV1a protein yielded the following properties shown in Table 1C.

TABLE 1C

Protein Sequence Properties NOV1a

| | |
|---|---|
| PSort analysis: | 0.5469 probability located in outside; 0.1000 probability located in endoplasmic reticulum (membrane); 0.1000 probability located in endoplasmic reticulum (lumen); 0.1000 probability located in lysosome (lumen) |
| SignalP analysis: | Cleavage site between residues 17 and 18 |

A search of the NOV1a protein against the Geneseq database, a proprietary database that contains sequences published in patents and a patent publication, yielded several homologous proteins shown in Table 1D.

TABLE 1D

Geneseq Results for NOV1a

| Geneseq Identifier | Protein/Organism/Length [Patent #, Date] | NOV1a Residues/ Match Residues | Identities/ Similarities for the Matched Region | Expect Value |
|---|---|---|---|---|
| AAM78338 | Human protein SEQ ID NO 1000 - Homo sapiens, 1052 aa. [WO200157190-A2, 09-AUG-2001] | 1 ... 277<br>1 ... 279 | 261/279 (93%)<br>268/279 (95%) | e-156 |
| AAP70760 | Human pancreas elastase-2 - Sus scrofa, 269 aa. [JP62000276-A, 06-JAN-1987] | 1 ... 263<br>1 ... 265 | 259/265 (97%)<br>262/265 (98%) | e-155 |
| AAP60059 | Sequence of human pancreatic elastase IIB - Homo sapiens, 253 aa. [EP198645-A, 22-OCT-1986] | 15 ... 263<br>1 ... 249 | 245/249 (98%)<br>248/249 (99%) | e-149 |
| AAP60062 | Sequence of human pancreatic elastase IIA encoded on pH2E2 - Homo sapiens, 269 aa. [EP198645-A, 22-OCT-1986] | 1 ... 263<br>1 ... 265 | 230/265 (86%)<br>248/265 (92%) | e-137 |
| AAP61723 | Human elastase II - Homo sapiens, 269 aa. [JP61192288-A, 26-AUG-1986] | 1 ... 263<br>1 ... 265 | 229/265 (86%)<br>246/265 (92%) | e-135 |

In a BLAST search of public sequence database, the NOV1a protein was found to have homology to the proteins shown in the BLASTP data in Table 1E.

TABLE 1E

Public BLASTP Results for NOV1a

| Protein Accession Number | Protein/Organism/Length | NOV1a Residues/ Match Residues | Identities/ Similarities for the Matched Portion | Expect Value |
|---|---|---|---|---|
| Q96QV5 | BA265F14.3 (ELASTASE 2B) - Homo sapiens (Human), 269 aa. | 1 ... 263<br>1 ... 265 | 262/265 (98%)<br>263/265 (98%) | e-157 |
| P08218 | Elastase 2B precursor (EC 3.4.21.71) - Homo sapiens (Human), 269 aa. | 1 ... 263<br>1 ... 265 | 259/265 (97%)<br>262/265 (98%) | e-155 |

TABLE 1E-continued

Public BLASTP Results for NOV1a

| Protein Accession Number | Protein/Organism/Length | NOV1a Residues/ Match Residues | Identities/ Similarities for the Matched Portion | Expect Value |
|---|---|---|---|---|
| P08217 | Elastase 2A precursor (EC 3.4.21.71) - Homo sapiens (Human), 269 aa. | 1 ... 263<br>1 ... 265 | 230/265 (86%)<br>248/265 (92%) | e-137 |
| P08419 | Elastase 2 precursor (EC 3.4.21.71) - Sus scrofa (Pig), 269 aa. | 1 ... 263<br>1 ... 265 | 204/265 (76%)<br>230/265 (85%) | e-122 |
| Q29461 | Elastase 2 precursor (EC 3.4.21.71) - Bos taurus (Bovine), 269 aa. | 1 ... 263<br>1 ... 265 | 202/265 (76%)<br>231/265 (86%) | e-121 |

PFam analysis predicts that the NOV1a protein contains the domains shown in the Table 1F.

TABLE 1F

Domain Analysis of NOV1a

| Pfam Domain | NOV1a Match Region | Identities/ Similarities for the Matched Region | Expect Value |
|---|---|---|---|
| trypsin | 27 ... 260 | 120/261 (46%)<br>192/261 (74%) | 1.3e-87 |

Example 2

The NOV2 clone was analyzed, and the nucleotide and encoded polypeptide sequences are shown in Table 2A.

TABLE 2A

NOV2 Sequence Analysis

SEQ ID NO: 21    1800 bp

NOV2a, CG100560-01 DNA Sequence

GAGCCTCTCTTCACCATGTGCTTCGTCCCCCTGGTGTGCTGGGTGGTGTGTACCTGCC

TCCAGCAGCAGCTGGAGGGTGGGGGCTGTTGAGACAGACGTCCAGGACCACCACTGC

AGTGTACATGCTCTACCTGCTGAGTCTGATGCAACCCAAGCCGGGGCCCCGCGCCTC

CAGCCCCCACCCAACCAGAGAGGGTTGTGCTCCTTGGCGGCAGATGGGCTCTGGAATC

AGAAAATCCTATTTGAGGAGCAGGACCTCCGGAAGCACGGCCTAGACGGGGAAGACGT

CTCTGCCTTCCTCAACATGAACATCTTCCAGAAGGACATCAACTGTGAGAGGTACTAC

AGCTTCATCCACTTGAGTTTCCAGGAATTCTTTGCAGCTATGTACTATATCCTGGACG

AGGGGGAGGGCGGGGCAGGCCCAGACCAGGACGTGACCAGGCTGTTGACCGAGTACGC

GTTTTCTGAAAGGAGCTTCCTGGCACTCACCAGCCGCTTCCTGTTTGGACTCCTGAAC

GAGGAGACCAGGAGCCACCTGGAGAAGAGTCTCTGCTGGAAGGTCTCGCCGCACATCA

AGATGGACCTGTTGCAGTGGATCCAAAGCAAAGCTCAGAGCGACGGCTCCACCCTGCA

GCAGGGCTCCTTGGAGTTCTTCAGCTGCTTGTACGAGATCCAGGAGGAGGAGTTTATC

CAGCAGGCCCTGAGCCACTTCCAGGTGATCGTGGTCAGCAACATTGCCTCCAAGATGG

AGCACATGGTCTCCTCGTTCTGTCTGAAGCGCTGCAGGAGCGCCCAGGTGCTGCACTT

GTATGGCGCCACCTACAGCGCGGACGGGAAGACCGCGCGAGGTGCTCCGCAGGAGCG

CACACGCTGTTGGTGCAGCTGAGACCAGAGAGGACCGTTCTGCTGGACGCCTACAGTG

AACATCTGGCAGCGGCCCTGTGCACCAATCCAAACCTGATAGAGCTGTCTCTGTACCG

AAATGCCCTGGGCAGCCGGGGGGTGAAGCTGCTCTGTCAAGGACTCAGACACCCCAAC

TABLE 2A-continued

NOV2 Sequence Analysis

TGCAAACTTCAGAACCTGAGGAGGCTGAAGAGGTGCCGCATCTCCAGCTCAGCCTGCG

AGGACCTCTCTGCAGCTCTCATAGCCAATAAGAATTTGACAAGGATGGATCTCAGTGG

CAACGGCGTTGGATTCCCAGGCATGATGCTGCTTTGCGAGGGCCTGCGGCATCCCCAG

TGCAGGCTGCAGATGATTCAGTTGAGGAAGTGTCAGCTGGAGTCCGGGGCTTGTCAGG

AGATGGCTTCTGTGCTCGGCACCAACCCACATCTGGTTGAGTTGGACCTGACAGGAAA

ACGAGCTGGCCTCAACTCTCAGTGTGAACCAGAGCCTGAGAGAGCTGGACCTGAGCCT

GAATGAGCTGGGGGACCTCGGGGTGCTGCTGCTGTGTGAGGGCCTCAGGCATCCCACG

TGCAAGCTCCAGACCCTGCGGAGGTTGGGCATCTGCCGGCTGGGCTCTGCCGCCTGTG

AGGGTCTTTCTGTGGTGCTCCAGGCCAACCACAACCTCCGGGAGCTGGACTTGAGTTT

CAACGACCTGGGAGACTGGGGCCTGTGGTTGCTGGCTGAGGGGCTGCAACATCCCGCC

TGCAGACTCCAGAAACTGTGGTGA<u>GCATCGGGGAGTGACGGGGTGGCAGTGGTCACGT</u>

<u>TT</u>

| | |
|---|---|
| | ORF Start: ATG at 16  ORF Stop: TGA at 1762<br>SEQ ID NO: 22      582 aa MW at 65280.8 kD |
| NOV2a,<br>CG100560-01<br>Protein<br>Sequence | MCFVPLVCWVVCTCLQQQLEGGGLLRQTSRTTTAVYMLYLLSLMQPKPGAPRLQPPPN<br><br>QRGLCSLAADGLWNQKILFEEQDLRKHGLDGEDVSAFLNMNIFQKDINCERYYSFIHL<br><br>SFQEFFAAMYYILDEGEGGAGPDQDVTRLLTEYAFSERSFLALTSRFLFGLLNEETRS<br><br>HLEKSLCWKVSPHIKMDLLQWIQSKAQSDGSTLQQGSLEFFSCLYEIQEEEFIQQALS<br><br>HFQVIVVSNIASKMEHMVSSFCLKRCRSAQVLHLYGATYSADGEDRARCSAGAHTLLV<br><br>QLRPERTVLLDAYSEHLAAALCTNPNLIELSLYRNALGSRGVKLLCQGLRHPNCKLQN<br><br>LRRLKRCRISSSACEDLSAALIANKNLTRMDLSGNGVGFPGMMLLCEGLRHPQCRLQM<br><br>IQLRKCQLESGACQEMASVLGTNPHLVELDLTGNALEDLGLRLLCQGLRHPVCRLRTL<br><br>WCRLKICRLTAAACDELASTLSVNQSLRELDLSLNELGDLGVLLLCEGLRHPTCKLQT<br><br>LRRLGICRLGSAACEGLSVVLQANHNLRELDLSFNDLGDWGLWLLAEGLQHPACRLQK<br><br>LW |
| | SEQ ID NO: 23      1683 bp |
| NOV2b,<br>CG100560-02<br>DNA<br>Sequence | <u>GCGCGCCTCTCTTCACC</u>ATGTGCTTCGTCCCCCTGGTGTGCTGGGTGGTGTGTACCTG<br><br>CCTCCAGCAGCAGCTGGAGGGTGGGGGGCTGTTGAGACAGACGTCCAGGACCACCACT<br><br>GCAGTGTACATGCTCTACCTGCTGAGTCTGATGCAACCCAAGCCGGGGCCCCGCGCC<br><br>TCCAGCCCCACCCAACCAGAGAGGGTTGTGCTCCTTGGCGGCAGATGGGCTCTGGAA<br><br>TCAGAAAATCCTATTTGAGGAGCAGGACCTCCGGAAGCACGGCCTAGACGGGGAAGAC<br><br>GTCTCTGCCTTCCTCAACATGAACATCTTCCAGAAGGACATCAACTGTGAGAGGTACT<br><br>ACAGCTTCATCCACTTGAGTTTCCAGGAATTCTTTGCAGCTATGTACTATATCCTGGA<br><br>CGAGGGGAGGCGGGCAGGCCCAGACCAGGACGTGACCAGGCTGTTGACCGAGTAC<br><br>GCGTTTTCTGAAAGGAGCTTCCTGGCACTCACCAGCCGCTTCCTGTTTGGACTCCTGA<br><br>ACGAGGAGACCAGGAGCCACCTGGAGAAGAGTCTCTGCTGGAAGGTCTCGCCGCACAT<br><br>CAAGATGGACCTGTTGCAGTGGATCCAAAGCAAAGCTCAGAGCGACGGCTCCACCCTG<br><br>CAGCAGGGCTCCTTGGAGTTCTTCAGCTGCTTGTACGAGATCCAGGAGGAGGAGTTTA |

TABLE 2A-continued

NOV2 Sequence Analysis

TCCAGCAGGCCCTGAGCCACTTCCAGGTGATCGTGGTCAGCAACATTGCCTCCAAGAT

GGAGCACATGGTCTCCTCGTTCTGTCTGAAGCGCTGCAGGAGCGCCCAGGTGCTGCAC

TTGTATGGCGCCACCTACAGCGCGGACGGGGAAGACCGCGCGAGGTGCTCCGCAGGAG

CGCACACGCTGTTGGTGCAGCTCAGACCAGAGAGGACCGTTCTGCTGGACGCCTACAG

TGAACATCTGGCAGCGGCCCTGTGCACCAATCCAAACCTGATAGAGCTGTCTCTGTAC

CGAAATGCCCTGGGCAGCCGGGGGTGAAGCTGCTCTGTCAAGGACTCAGACACCCCA

ACTGCAAACTTCAGAACCTGAGGCTGAAGAGGTGCCGCATCTCCAGCTCAGCCTGCGA

GGACCTCTCTGCAGCTCTCATAGCCAATAAGAATTTGACAAGGATGGATCTCAGTGGC

AACGGCGTTGGATTCCCAGGCATGATGCTGCTTTGCGAGGGCCTGCGGCATCCCCAAT

GCAGGCTGCAGATGATTCAGCTGAAGATCTGCCGCCTCACTGCTGCTGCCTGTGACGA

GCTGGCCTCAACTCTCAGTGTGAACCAGAGCCTGAGAGAGCTGGACCTGAGCCTGAAT

GAGCTGGGGGACCTCGGGGTGCTGCTGCTGTGTGAGGGCCTCAGGCATCCCACGTGCA

AGCTCCAGACCCTGCGGTTGGGCATCTGCCGGCTGGGCTCTGCCGCCTGTGAGGGTCT

TTCTGTGGTGCTCCAGGCCAACCACAACCTCCGGGAGCTGGACTTGAGTTTCAACGAC

CTGGGAGACTGGGGCCTGTGGTTGCTGGCTGAGGGGCTGCAACATCCCGCCTGCAGAC

TCCAGAAACTGTGGTGAGCATCGGGGAGTGACGGGGTGGCAGTGGTCACGTTTGGACA

GTGGAAGCGCCTTCTCATCCTTCATTTTTCTATTTATGAACTATCCTGCTTCACTACA

A

ORF Start: ATG at 18   ORF Stop: TGA at 1581
SEQ ID NO: 24          521 aa MW at 58384.7 kD NOV2b, CG100560-02 Protein Sequence

MCFVPLVCWVVCTCLQQQLEGGGLLRQTSRTTTAVYMLYLLSLMQPKPGAPRLQPPPN

QRGLCSLAADGLWNQKILFEEQDLRKHGLDGEDVSAFLNMNIFQKDINCERYYSFIHL

SFQEFFAANYYILDEGEGGAGPDQDVTRLLTEYAFSERSFLALTSRFLFGLLNEETRS

HLEKSLCWKVSPHIKMDLLQWIQSKAQSDGSTLQQGSLEFFSCLYEIQEEEFIQQALS

HFQVIVVSNIASKMEHMVSSFCLKRCRSAQVLHLYGATYSADGEDRARCSAGAHTLLV

QLRPERTVLLDAYSEHLAAALCTNPNLIELSLYRNALGSRGVKLLCQGLRHPNCKLQN

LRLKRCRISSSACEDLSAALIANKNLTRMDLSGNGVGFPGMNLLCEGLRHPQCRLQMI

QLKICRLTAAACDELASTLSVNQSLRELDLSLNELGDLGVLLLCEGLRHPTCKLQTLR

LGICRLGSAACEGLSVVLQANHNLRELDLSFNDLGDWGLWLLAECLQHPACRLQKLW

Sequence comparison of the above protein sequences yields the following sequence relationships shown in Table 2B.

TABLE 2B

Comparison of NOV2a against NOV2b.

| Protein Sequence | NOV2a Residues/ Match Residues | Identities/Similarities for the Matched Region |
|---|---|---|
| NOV2b | 1 ... 523 | 450/523 (86%) |
|  | 1 ... 520 | 464/523 (88%) |

Further analysis of the NOV2a protein yielded the following properties shown in Table 2C.

TABLE 2C

Protein Sequence Properties NOV2a

| PSort analysis: | 0.3700 probability located in outside; 0.1900 probability located in lysosome (lumen); 0.1000 probability located in endoplasmic reticulum (membrane); 0.1000 probability located in endoplasmic reticulum (lumen) |
|---|---|
| SignalP analysis: | Cleavage site between residues 50 and 51 |

A search of the NOV2a protein against the Geneseq database, a proprietary database that contains sequences published in patents and patent publication, yielded several homologous proteins shown in Table 2D.

TABLE 2D

Geneseq Results for NOV2a

| Geneseq Identifier | Protein/Organism/Length [Patent #, Date] | NOV2a Residues/ Match Residues | Identities/ Similarities for the Matched Region | Expect Value |
|---|---|---|---|---|
| AAU01067 | Human secreted protein sequence encoded by gene #28 - *Homo sapiens*, 630 aa. [WO200123402-A1, 05-APR-2001] | 1 ... 581<br>1 ... 596 | 275/602 (45%)<br>380/602 (62%) | e−143 |
| AAE07514 | Human PYRIN-1 protein - *Homo sapiens*, 1034 aa. [WO200161005-A2, 23-AUG-2001] | 1 ... 581<br>406 ... 1001 | 275/602 (45%)<br>380/602 (62%) | e−143 |
| AAU01096 | Gene 28 Human secreted protein homologous amino acid sequence - *Homo sapiens*, 484 aa. [WO200123402-A1, 05-APR-2001] | 1 ... 523<br>1 ... 482 | 236/532 (44%)<br>324/532 (60%) | e−123 |
| AAY39778 | CBDAKD01 protein sequence - *Homo sapiens*, 514 aa. [WO9946290-A1, 16-SEP-1999] | 1 ... 464<br>1 ... 481 | 210/487 (43%)<br>298/487 (61%) | e−106 |
| ABG04570 | Novel human diagnostic protein #4561 - *Homo sapiens*, 168 aa. [WO200175067-A2, 11-OCT-2001] | 156 ... 324<br>1 ... 168 | 167/169 (98%)<br>167/169 (98%) | 5e−90 |

In a BLAST search of public sequence datbases, the NOV2a protein was found to have homology to the proteins shown in the BLASTP data in Table 2E.

TABLE 2E

Public BLASTP Results for NOV2a

| Protein Accession Number | Protein/Organism/Length | NOV2a Residues/ Match Residues | Identities/ Similarities for the Matched Portion | Expect Value |
|---|---|---|---|---|
| AAH28069 | HYPOTHETICAL 120.2 KDA PROTEIN - *Homo sapiens* (Human), 1061 aa. | 1 ... 582<br>400 ... 976 | 577/582 (99%)<br>577/582 (99%) | 0.0 |
| Q96P20 | Cold autoinflammatory syndrome 1 protein (Cryopyrin) (NACHT-, LRR- and PYD-containing protein 3) (PYRIN-containing APAF1-like protein 1) (Angiotensin/vasopressin receptor AII/AVP-like) - *Homo sapiens* (Human), 1034 aa. | 1 ... 581<br>406 ... 1001 | 275/602 (45%)<br>380/602 (62%) | e−143 |
| AAL78632 | NALP3 LONG ISOFORM - *Homo sapiens* (Human), 1036 aa. | 1 ... 581<br>408 ... 1003 | 275/602 (45%)<br>379/602 (62%) | e−143 |
| AAL90874 | MAST CELL MATURATION INDUCIBLE PROTEIN 1 - *Mus musculus* (Mouse), 1033 aa. | 1 ... 581<br>404 ... 1000 | 274/603 (45%)<br>372/603 (61%) | e−140 |
| AAL12498 | CRYOPYRIN - *Homo sapiens* (Human), 920 aa. | 1 ... 464<br>406 ... 887 | 220/485 (45%)<br>310/485 (63%) | e−115 |

PFam analysis predicts that the NOV2a protein contains the domains shown in the Table 2F.

TABLE 2F

Domain Analysis of NOV2a

| Pfam Domain | NOV2a Match Region | Identities/Similarities for the Matched Region | Expect Value |
|---|---|---|---|

Example 3

The NOV3 clone was analyzed, and the nucleotide and encoded polypeptide sequences are shown in Table 3A.

TABLE 3A

NOV3 Sequence Analysis

SEQ ID NO: 25  481 bp

| NOV3a, CG101012-01 DNA Sequence | CTTGTCTTGTTCCAGTTCTCAGAGGGAATGCTTTCAATTTTTCTCTATTCAGTATTAT<br>GTTGGCTGTGGGTTTGTCATAGATTGTGTGCCGTGAGGGAGTTTACTTTCCTGGCCAA<br>GAAGCCAGGCTGCAGGGGCCTTCGGATCACCACGGATGCCTGCTGGGGTCGCTGTGAG<br>ACCTTCTATCTATGGGGACAGAAACCCATTCTGGAACCCCCCTATATTGAAGCCCATC<br>ATCGAGTCTGTACCTACAACGAGACCAAACAGGTGACTGTCAAGCTGCCCAACTGTGC<br>CCCGGGAGTCGACCCCTTCTACACCTATCCCGTGGCCATCCGCTGTGACTGCGGAGCC<br>TGCTCCACTGCCACCACGGAGTGTGAGACCATCTGAGGCCGCTAGCTGCTCTCTGCAG<br>ACCCACCTGTGTGAGCAGCACATGCAGTTATACTTCCTGGATGCAAGACTGTTTAATT<br>TCGACCACACCCATGGA |
|---|---|
| | ORF Start: ATG at 28  ORF Stop: TGA at 382<br>SEQ ID NO: 26  118 aa  MW at 13491.6 kDp |
| NOV3a, CG101012-01 Protein Sequence | MLSIFLYSVLCWLWVCHRLCAVREFTFLAKKPGCRGLRITTDACWGRCETFYLWGQKP<br>ILEPPYIEAHHRVCTYNETKQVTVKLPNCAPGVDPFYTYPVAIRCDCGACSTATTECE<br>TI |

Further analysis of the NOV3a protein yielded the following properties shown in Table 3B.

TABLE 3B

Protein Sequence Properties NOV3a

| PSort analysis: | 0.5500 probability located in endoplasmic reticulum (membrane); 0.1900 probability located in lysosome (lumen); 0.1449 probability located in microbody (peroxisome); 0.1000 probability located in endoplasmic reticulum (lumen) |
|---|---|

TABLE 3B-continued

Protein Sequence Properties NOV3a

| SignalP analysis: | Cleavage site between residues 22 and 23 |
|---|---|

A search of the NOV3a protein against the Geneseq database, a proprietary database that contains sequences published in patents and patent publication, yielded several homologous proteins shown in Table 3C.

TABLE 3C

Geneseq Results for NOV3a

| Geneseq Identifier | Protein/Organism/Length [Patent #, Date] | NOV3a Residues/ Match Residues | Identities/ Similarities for the Matched Region | Expect Value |
|---|---|---|---|---|
| AAU10366 | Human beta-like glycoprotein hormone, Beta10 - *Homo sapiens*, 130 aa. [WO200173034-A2, 04-OCT-2001] | 20 . . . 118<br>36 . . . 130 | 93/99 (93%)<br>95/99 (95%) | 7e−53 |
| AAG64065 | Human anterior pituitary hormone-related polypeptide #2 - *Homo sapiens*, 106 aa. [WO200144475-A1, 21-JUN-2001] | 20 . . . 118<br>12 . . . 106 | 93/99 (93%)<br>95/99 (95%) | 7e−53 |
| AAG64064 | Human anterior pituitary hormone-related polypeptide - *Homo sapiens*, 130 aa. [WO200144475-A1, 21-JUN-2001] | 20 . . . 118<br>36 . . . 130 | 93/99 (93%)<br>95/99 (95%) | 7e−53 |
| AAG63211 | Amino acid sequence of a human cystine knot polypeptide - *Homo sapiens*, 130 aa. [WO200153346-A1, 26-JUL-2001] | 20 . . . 118<br>36 . . . 130 | 93/99 (93%)<br>95/99 (95%) | 7e−53 |
| AAE09440 | Human sbghGTa protein - *Homo sapiens*, 130 aa. [WO200160850-A1, 23-AUG-2001] | 20 . . . 118<br>36 . . . 130 | 93/99 (93%)<br>95/99 (95%) | 7e−53 |

In a BLAST search of public sequence datbases, the NOV3a protein was found to have homology to the proteins shown in the BLASTP data in Table 3D.

TABLE 3D

Public BLASTP Results for NOV3a

| Protein Accession Number | Protein/Organism/Length | NOV3a Residues/ Match Residues | Identities/ Similarities for the Matched Portion | Expect Value |
| --- | --- | --- | --- | --- |
| Q9I997 | FOLLICLE-STIMULATING HORMONE PRECURSOR - *Acipenser baerii* (Siberian sturgeon), 128 aa. | 2 . . . 118<br>3 . . . 116 | 49/119 (41%)<br>66/119 (55%) | 8e−20 |
| Q98849 | Gonadotropin beta-II chain precursor (GTH-II-beta) (Luteinizing hormone-like GTH) - *Carassius auratus* (Goldfish), 140 aa. | 4 . . . 115<br>9 . . . 120 | 43/117 (36%)<br>63/117 (53%) | 8e−16 |
| Q90ZK1 | FOLLICLE STIMULATING HORMONE BETA SUBUNIT PRECURSOR - *Rana ridibunda* (Laughing frog) (Marsh frog), 123 aa (fragment). | 5 . . . 115<br>1 . . . 108 | 46/112 (41%)<br>59/112 (52%) | 2e−15 |
| P01235 | Gonadotropin beta-II chain precursor (GTH-II-beta) (Luteinizing hormone-like GTH) - *Cyprinus carpio* (Common carp), 144 aa. | 26 . . . 115<br>39 . . . 124 | 37/91 (40%)<br>54/91 (58%) | 2e−15 |
| Q98TY3 | LUTEINIZING HORMONE BETA SUBUNIT - *Mylopharyngodon piceus*, 140 aa. | 1 . . . 115<br>8 . . . 120 | 44/118 (37%)<br>62/118 (52%) | 2e−15 |

PFam analysis predicts that the NOV3a protein contains the domains shown in the Table 3E.

TABLE 3E

Domain Analysis of NOV3a

| Pfam Domain | NOV3a Match Region | Identities/Similarities for the Matched Region | Expect Value |
| --- | --- | --- | --- |
| Cys_knot | 29 . . . 116 | 36/92 (39%)<br>62/92 (67%) | 2.5e−14 |

Example 4

The NOV4 clone was analyzed, and the nucleotide and encoded polypeptide sequences are shown in Table 4A.

TABLE 4A

NOV4 Sequence Analysis

SEQ ID NO: 27    682 bp

NOV4a, G101584-01 DNA Sequence

ATGAAGACCCTGTTCCTGGGTGTCACGCTCGGCCTGGCCGCTGCCCTGTCCTTCACCC

TGGAGGAGGAGGATGTGCATCCAGAAGAAAATCCTGATGCGGAATGGGGGCAGGAAGC

TCATGTACCTGCAGGAGCTGCCCAGGAGGGACCACTACATCTTTTACTGCAAAGACCA

GCACCATGGGGGCCTGCTCCACATGGGAAAGCTTGTGGGTGCTCCCTGCAGGGCCGTG

CCGCTGTCCCCACGTCGGCTCACCTGGCCACCTCACCTGCAGGTAGGAATTCTGATAC

CAACCGCGAGCCCCTGGAAGAATTTAAGAAATTGGTGCAGCCCAAGGGACTCTCGGAG

GAGGACATTTTCACGCCCCTCCAGACGGGTCACGATGCCTGTGCCCACTCCCCTGTGT

CCCTCTGCTGTGTCTGTCTGCTATCTCCAGTGTCCCATGACCCCCATGTCCTCCCATG

TCCCCCGCATTCCCCATGTGCCCCGAGTCTCCTCGCAGGGGCTCCCGGGCCCTGTTTA

GCGTCCTCCTCATTGGAGGCTCTGTGCTCTGGGCTGCGATGGGGTCTGGGGCTCCGCG

TABLE 4A-continued

NOV4 Sequence Analysis

CTCTGGGCTGCGATGGGGTCTGGGGCTCCGCACTCTGGGCTGCGATGGGGTCTGGGGC

TCCGCGCTCTGGGCTGCGATGGGCTCTGGGGCTCTGAGCTCTGG

| | |
|---|---|
| ORF Start: ATG at 1 | ORF Stop: TGA at 673 |
| SEQ ID NO: 28 | 224 aa MW at 23172.1 kD |

| | |
|---|---|
| NOV4a, CG101584-01 Protein Sequence | MKTLFLGVTLGLAAALSFTLEEEDVHPEENPDAEWGQEAHVPAGAAQEGPLHLLLQRP APWGPAPHGKACGCSLQCRAAVPTSAHLATSPAGRNSDTNREALEEFKKLVQRKGLSE EDIFTPLQTGEDGCAQSPVSLCCVCLLSPVSHDPHVLPCPPHSPCAPSLLAGAPGPCL ASSSLEALCSGLRWGLGLRALGCDGVWGSALWAAMGSGAPRSGLRWALGL |

Further analysis of the NOV4a protein yielded the following properties shown in Table 4B.

TABLE 4B

| | Protein Sequence Properties NOV4a |
|---|---|
| PSort analysis: | 0.7571 probability located in outside; 0.1000 probability located in endoplasmic reticulum (membrane); 0.1000 probability located in endoplasmic reticulum (lumen); 0.1000 probability located in microbody (peroxisome) |
| SignalP analysis: | Cleavage site between residues 16 and 17 |

A search of the NOV4a protein against the Geneseq database, a proprietary database that contains sequences published in patents and patent publication, yielded several homologous proteins shown in Table 4C.

TABLE 4C

Geneseq Results for NOV4a

| Geneseq Identifier | Protein/Organism/Length [Patent #, Date] | NOV4a Residues/ Match Residues | Identities/ Similarities for the Matched Region | Expect Value |
|---|---|---|---|---|
| AAB67741 | Amino acid sequence of odorant binding polypeptide OBPIIa-delta - Homo sapiens, 147 aa. [WO200112806-A2, 22-FEB-2001] | 1 . . . 126 1 . . . 141 | 115/141 (81%) 119/141 (83%) | 1e−56 |
| AAB67744 | Amino acid sequence of odorant binding polypeptide OBPIIb-gamma - Homo sapiens, 85 aa. [WO200112806-A2, 22-FEB-2001] | 1 . . . 71 1 . . . 85 | 70/85 (82%) 71/85 (83%) | 7e−33 |
| AAB67743 | Amino acid sequence of odorant binding polypeptide OBPIIb-beta - Homo sapiens, 179 aa. [WO200112806-A2, 22-FEB-2001] | 31 . . . 71 139 . . . 179 | 38/41 (92%) 38/41 (92%) | 1e−17 |
| ABG11867 | Novel human diagnostic protein #11858 - Homo sapiens, 200 aa. [WO200175067-A2, 11-OCT-2001] | 92 . . . 154 130 . . . 198 | 46/74 (62%) 47/74 (63%) | 3e−13 |
| ABG11867 | Novel human diagnostic protein #11858 - Homo sapiens, 200 aa. [WO200175067-A2, 11-OCT-2001] | 92 . . . 154 130 . . . 198 | 46/74 (62%) 47/74 (63%) | 3e−13 |

In a BLAST search of public sequence datbases, the NOV4a protein was found to have homology to the proteins shown in the BLASTP data in Table 4D.

TABLE 4D

Public BLASTP Results for NOV4a

| Protein Accession Number | Protein/Organism/Length | NOV4a Residues/ Match Residues | Identities/ Similarities for the Matched Portion | Expect Value |
|---|---|---|---|---|
| Q9NY54 | PUTATIVE ODORANT BINDING PROTEIN AD - Homo sapiens (Human), 147 aa. | 1 . . . 126<br>1 . . . 141 | 115/141 (81%)<br>119/141 (83%) | 3e-56 |
| Q9NY51 | PUTATIVE ODORANT BINDING PROTEIN BG - Homo sapiens (Human), 85 aa. | 1 . . . 71<br>1 . . . 85 | 70/85 (82%)<br>71/85 (83%) | 2e-32 |
| CAC33327 | SEQUENCE 11 FROM PATENT WO0112806 - Homo sapiens (Human), 179 aa (fragment). | 31 . . . 71<br>139 . . . 179 | 38/41 (92%)<br>38/41 (92%) | 3e-17 |
| Q9NY52 | PUTATIVE ODORANT- BINDING PROTEIN BB - Homo sapiens (Human), 165 aa. | 31 . . . 71<br>125 . . . 165 | 38/41 (92%)<br>38/41 (92%) | 3e-17 |
| Q9NPH6 | Odorant-binding protein 2b precursor (OBPIIb) - Homo sapiens (Human), 170 aa. | 92 . . . 126<br>130 . . . 164 | 35/35 (100%)<br>35/35 (100%) | 3e-12 |

PFam analysis predicts that the NOV4a protein contains the domains shown in the Table 4E.

TABLE 4E

Domain Analysis of NOV4a

| Pfam Domain | NOV4a Match Region | Identities/Similarities for the Matched Region | Expect Value |
|---|---|---|---|
| lipocalin | 92 . . . 128 | 13/37 (35%)<br>31/37 (84%) | 0.00022 |

Example 5

The NOV5 clone was analyzed, and the nucleotide and encoded polypeptide sequences are shown in Table 5A.

TABLE 5A

NOV5 Sequence Analysis

SEQ ID NO: 29        1178 bp

NOV5a, CG101707-01 DNA Sequence

GGGATGGGAAAACTATGCCTGGGGCCGACGCTCTGCCCGGCTGCTGCCGCTGAGGAAA

GCCGGGACGCGGAGCCCCGCCGAGAGCTTCTTTGCTCCGGACGCCCCTGGACGTGGCG

GGCAGCCGCGAGGGTAACCACCATGATCCCCTGGGTGCTCCTGGCCTGTGCCCTCCCC

TGTGCTGCTGACCCACTGCTTGGCGCCTTTGCTCGCAGGGACTTCCGGAAAGGCTCCC

CTCAACTGGTCTGCAGCCTGCCTGGCCCCCAGGGCCCACCCGGCCCCCAGGAGCCCC

AGGGCCCTCAGGAATGATGGGACGAATGGGCTTTCCTGGCAAAGACGCCCAAGATGGA

CACGACGGCGACCGGGGGACAGCGGAGAGGAAGGTCCACCTGGCCGGACAGGTAACC

GGGGAAAGCCAGGACCAAAGGGCAAAGCCGGGGCCATTGGGCGGGCTGGCCCCCGTGG

CCCCAAGGGGGTCAACGGTACCCCCGGGAAGCATGGCACACCAGGCAAGAAGGGGCCC

AAGGGCAAGAAGGGGGAGCCAGGCCTCCCAGGCCCCTGCAGCTGTGGCAGTGGCCATA

CCAAGTCAGCTTTCTCGGTGGCAGTGACCAAGAGCTACCCACGGGAGCGGCTGCCCAT

CAAGTTTGACAAGATTCTGATGAACGAGGGTGGCCACTACAATGCTTCCAGCGGCAAG

TTCGTCTGCGGCGTGCCTGCGATCTACTACTTCACCTACGACATCACGCTGGCCAACA

TABLE 5A-continued

NOV5 Sequence Analysis

AGCACCTGGCCATCGGCCTCGTGCACAACGGCCAGTACCGCATCCGGACCTTTGATGC

CAACACCGGCAACCACGATGTGGCCTCAGGCTCCACCATCCTGGCTCTCAAGCAGGGT

GACGAAGTTTGGCTGCAGATCTTCTACTCAGAGCAGAACGGGCTCTTCTATGACCCTT

ACTGCACAGACAGCCTCTTTACGGGCTTCCTAATCTATGCCGACCAGGATCACCCCAA

CGAGGTATAGACATGCCACGGCGGTCCTCCAGGCAGGGAACAAGCTTCTGGACTTGGG

CTTACAGAGCAAGACCCCACAACTGTAGGCTGGGGGTGGGGGGTCGAGTGAGCGGTTC

TAGCCTCAGGCTCACCTCCTCCGCCTCTTTTTTTTCCCCTTCATTAAATCCAAACCTT

TTTATTCATCCAAAAAAA

| | | |
|---|---|---|
| | ORF Start: ATG at 4 | ORF Stop: TAG at 994 |
| | SEQ ID NO: 30 | 330 aa MW at 34833.2 kD |

| NOV5a, CG101707-01 Protein Sequence | MGKLCLGPTLCPAAAAEESRDAEPRRELLCSGRPWTWRAAARVTTMIPWVLLACALPC<br><br>AADPLLGAFARRDFRKGSPQLVCSLPGPQGPPGPPGAPGPSGMMGRMGRPGKDGQDGH<br><br>DGDRGDSGEEGPPGRTGNRGKPGPKGKAGAIGRAGPRGPKGVNGTPGKHGTPGKKGPK<br><br>GKKGEPGLPGPCSCGSGHTKSAFSVAVTKSYPRERLPIKFDKILNNEGGHYNASSGKF<br><br>VCGVPGIYYFTYDITLANKHLAIGLVHNGQYRIRTFDANTGNHDVASGSTILALKQGD<br><br>EVWLQIFYSEQNGLFYDPYWTDSLFTGFLIYADQDDPNEV |

Further analysis of the NOV5a protein yielded the following properties shown in Table 5B.

TABLE 5B

Protein Sequence Properties NOV5a

| | |
|---|---|
| PSort analysis: | 0.7900 probability located in plasma membrane; 0.4043 probability located in microbody (peroxisome); 0.3000 probability located in Golgi body; 0.2000 probability located in endoplasmic reticulum (membrane) |
| SignalP analysis: | Cleavage site between residues 61 and 62 |

A search of the NOV5a protein against the Geneseq database, a proprietary database that contains sequences published in patents and patent publication, yielded several homologous proteins shown in Table 5C.

TABLE 5C

Geneseq Results for NOV5a

| Geneseq Identifier | Protein/Organism/Length [Patent #, Date] | NOV5a Residues/ Match Residues | Identities/ Similarities for the Matched Region | Expect Value |
|---|---|---|---|---|
| AAU19557 | Human diagnostic and therapeutic polypeptide (DITHP) #143 - *Homo sapiens*, 331 aa. [WO200162927-A2, 30 Aug. 2001] | 1 . . . 330<br>2 . . . 331 | 329/330 (99%)<br>329/330 (99%) | 0.0 |
| AAB50374 | Human adipocyte complement related protein homologue zacrp2 - *Homo sapiens*, 285 aa. [WO200073448-A1, 7 Dec. 2000 | 46 . . . 330<br>1 . . . 285 | 285/285 (100%)<br>285/285 (100%) | e−177 |
| AAY54321 | A polypeptide designated ACRP30R1L which is a homologue of ACRP30 - *Homo sapiens*, 285 aa. [WO9959618-A1, 15 Nov. 1999] | 46 . . . 330<br>1 . . . 285 | 285/285 (100%)<br>285/285 (100%) | e−177 |
| AAB30232 | Human adipocyte complement related protein homologue zacrp2 - | 46 . . . 330<br>1 . . . 285 | 285/285 (100%) | e−177 |

TABLE 5C-continued

Geneseq Results for NOV5a

| Geneseq Identifier | Protein/Organism/Length [Patent #, Date] | NOV5a Residues/ Match Residues | Identities/ Similarities for the Matched Region | Expect Value |
|---|---|---|---|---|
| ABB72178 | *Homo sapiens*, 285 aa. [WO200063376-A1, 26 Oct. 2000] Rat protein isolated from skin cells SEQ ID NO:294 - *Rattus sp*, 294 aa. [WO200190357-A1, 29 Nov. 2001] | 42 . . . 330 6 . . . 294 | 271/289 (93%) 278/289 (95%) | e-168 |

In a BLAST search of public sequence datbases, the NOV5a protein was found to have homology to the proteins shown in the BLASTP data in Table 5D.

TABLE 5D

Public BLASTP Results for NOV5a

| Protein Accession Number | Protein/Organism/Length | NOV5a Residues/ Match Residues | Identities/ Similarities for the Matched Portion | Expect Value |
|---|---|---|---|---|
| Q9BXJ5 | Complement-c1q tumor necrosis factor-related protein 2 precursor - *Homo sapiens* (Human), 285 aa. | 46 . . . 330 1 . . . 285 | 285/285 (100%) 285/285 (100%) | e-177 |
| Q9D8U4 | 1810033K05RIK PROTEIN - *Mus musculus* (Mouse), 294 aa. | 42 . . . 330 6 . . . 294 | 272/289 (94%) 279/289 (96%) | e-168 |
| CAC21967 | SEQUENCE 14 FROM PATENT WO0073448 - *Mus musculus* (Mouse), 289 aa. | 76 . . . 325 29 . . . 278 | 160/250 (64%) 191/250 (76%) | 1e-96 |
| CAC21966 | SEQUENCE 1 FROM PATENT WO0073448 - *Homo sapiens* (Human), 303 aa. | 76 . . . 325 43 . . . 292 | 159/250 (63%) 192/250 (76%) | 3e-96 |
| Q9BXJ2 | Complement-c1q tumor necrosis factor-related protein 7 precursor - *Homo sapiens* (Human), 289 aa. | 76 . . . 325 29 . . . 278 | 159/250 (63%) 192/250 (76%) | 3e-96 |

PFam analysis predicts that the NOV5a protein contains the domains shown in the Table 5E.

TABLE 5E

Domain Analysis of NOV5a

| Pfam Domain | NOV5a Match Region | Identities/ Similarities for the Matched Region | Expect Value |
|---|---|---|---|
| Collagen | 83 . . . 141 | 32/60 (53%) 40/60 (67%) | 3.3e-05 |
| Collagen | 142 . . . 201 | 23/60 (38%) 37/60 (62%) | 0.0014 |
| C1q | 196 . . . 320 | 45/138 (33%) 93/138 (67%) | 2.3e-38 |

Example 6

The NOV6 clone was analyzed, and the nucleotide and encoded polypeptide sequences are shown in Table 6A.

TABLE 6A

NOV6 Sequence Analysis

SEQ ID NO: 31    1611 bp

NOV6a,
CG101836-01
DNA
Sequence

GGAGCGTCTGTTGGGTCCGGGCCGCCGGCTTCGCCCTCGCCATGGCGCCCTGGCTGCA

GCTCCTGTCGCTGCTGGGGCTGCTCCCGGGCGCAGTGGCCGCCCCGCCCAGCCCCGA

GCCGCCAGCTTTCAGGCCTGGGGGCCGCCGTCCCCGCAGCTGCTGGCGCCCACCCGCT

TABLE 6A-continued

NOV6 Sequence Analysis

TCGCGCTGGAGATGTTCAACCGCGGCCGCGCTCCGGGACGCGGGCCGTGCTGGGCCT

TGTGCGCGACCGTCCGCGCCTCACCTACTCCTCTCTCCAGGCGGGCCAGGGGTCGCTG

TACTCCCTGGAGGCCACCCTGGAGGAGCCACCCTGCAACGACCCCATGGTGTGCCGGC

TCCCCGTGTCCAAGAAAACCCTGGTGACTTTCAAAGTCCTGGATGAGCTCGGGGGCG

CGTGCTGCTGCGGAAGGACTGTGGCCCAGTGGACACCAAGGTTCCAGGTGCTGGGGAG

CCCAAGTCAGCCTTCACTCAGGGCTCAGCCATGATTTCTTCTCTGTCCCAAAACCATC

CAGACAACAGAAACGAGACTTTCAGCTCAGTCATTTCCCTGTTGAATGAGGATCCCCT

GTCCCAGGACTTGCCTGTGAAGATGGCTTCAATCTTCAAGAACTTTGTCATTACCTAT

AACCGGACATATGAGTCAAAGGAAGAAGCCCGGTGGCGCCTGTCCGTCTTTGTCAATA

ACATGGTGCGAGCACAGAAGATCCAGGCCCTGGACCGTGGCACAGCTCAGTATGGAGT

CACCAAGTTCAGTGATCTCACAGAGGAGGAGTTCCGCACTATCTACCTGAATACTCTC

CTGAGAAAAGAGCCTGGCAACAAGATGAAGCAAGCCAAGTCTGTGGGTGACCTCGCCC

CACCTGAATGGGACTGGAGGAGTAAGGGGGCTGTCACAAAAGTCAAAGACCAGGGCAT

CTGTGGCTCCTGCTGGGCCTTCTCAGTCACAGGCAATGTGGAGGGCCAGTGGTTTCTC

AACCAGGGGACCCTGCTCTCCCTCTCTGAACAGGAGCTCTTGGACTGTGACAAGATGG

ACAAGGCCTGCATGGGCGGCTTGCCCTCCAATGCCTACTCCGCCATAAAGAATTTGGG

AGGGCTGGAGACAGAGGATGACTACAGCTACCAGGCTCACATGCAGTCCTGCAACTTC

TCAGCAGAGAAGGCCAAGGTCTACATCAATGACTCCGTGGAGCTGAGCCAGAACGAGC

AGGAGCTCGCAGCCTGGCTGGCCAAGAGAGGCCCAATCTCCGTGGCCATCAATGCCTT

TGGCATGCAGTTTTACCGCCACGGCATCTCCCGCCCTCTCCGGCCCCTCTGCAGCCCT

TGCGTCATTGACCATGCGGTGTTGCTTGTGGGCTACGGAACCGTGAGTTCTGACGTTC

CCTTTTGGGCCATCAAGAACAGCTGGGGCACTGACTGGGGTGAGAAGGGTTACTACTA

CTTGCATCGCGGGTCCGGGGCATGTGGCGTGAACACCATGGCCAGCTCGGCGGTGCTG

GACTGAAGAGGGGCCCCCAGCTCGGGACCTGGTGCTGATCAGAGTGGCTGCTGCCCCA

GCCTGACATGTGTCCAGGCCCCTCCCCGCCAGGTACAGCTCGCAG

| | |
|---|---|
| | ORE Start: ATG at 42    ORF Stop: TGA at 1512<br>SEQ ID NO: 32       490 aa MW at 53794.7 kD |
| NOV6a,<br>CG101836-01<br>Protein<br>Sequence | MAPWLQLLSLLGLLPGAVAAPAQPRAASFQAWGPPSPQLLAPTRFALEMFNRGRAAGT<br><br>RAVLGLVRDRPRLTYSSLQAGQGSLYSLEATLEEPPCNDPMVCRLPVSKKTLVTFKVL<br><br>DELGGRVLLRKDCGPVDTKVPGAGEPKSAFTQGSAMISSLSQNHPDNRNETFSSVISL<br><br>LNEDPLSQDLPVKMASIFKNFVITYNRTYESKEEARWRLSVFVNNMVRAQKIQALDRG<br><br>TAQYGVTKFSDLTEEEFRTIYLNTLLRKEPGNKMKQAKSVGDLAPPEWDWRSKGAVTK<br><br>VKDQGMCGSCWAFSVTGNVEGQWFLNQGTLLSLSEQELLDCDKMDKACMGGLPSNAYS<br><br>AIKNLGGLETEDDYSYQGHNQSCNFSAEKAKVYINDSVELSQNEQELAAWLAKRGPIS<br><br>VAINAFGMQFYRHGISRPLRPLCSPCVIDHAVLLVGYGTVSSDVPFWAIKNSWCTDWC<br><br>EKGYYYLHRGSGACGVNTMASSAVVD |
| | SEQ ID NO: 33      1226 bp |
| NOV6b,<br>CG101836-02<br>DNA | GCTTCGCCCTCGCCATGGCGCCCTGGCTGCAGCTCCTGTCGCTGCTGGGGCTGCTCCC<br><br>GGGCGCAGTGGCCGCCCCCGCCCAGCCCCAAGTCCTGGATGAGCTCGGAAGACACGTG |

TABLE 6A-continued

NOV6 Sequence Analysis

| Sequence | |
|---|---|
| | CTGCTGCGGAAGGACTGTGGCCCAGTGGACACCAAGGTTCCAGGTGCTGGGGAGCCCA |
| | AGTCAGCCTTCACTCAGGGCTCAGCCATGATTTCTTCTCTGTCCCAAAACCATCCAGA |
| | CAACAGAAACGAGACTTTCAGCTCAGTCATTTCCCTGTTGAATGAGGATCCCCTGTCC |
| | CAGGACTTGCCTGTGAAGATGGCTTCAATCTTCAAGAACTTTGTCATTACCTATAACC |
| | GGACATATGAGTCAAAGGAAGAAGCCCGGTGGCGCCTGTCCGTCTTTGTCAATAACAT |
| | GGTGCGAGCACAGAAGATCCAGGCCCTGGACCGTGGCACAGCTCAGTATGGAGTCACC |
| | AAGTTCAGTGATCTCACAGAGGAGGAGTTCCGCACTATCTACCTGAATACTCTCCTGA |
| | GGAAAGAGCCTGGCAACAAGATGAAGCAAGCCAAGTCTGTGGGTGACCTCGCCCCACC |
| | TGAATGGGACTGGAGGAGTAAGGGGGCTGTCACAAAAGTCAAAGACCAGGGCATGTGT |
| | GGCTCCTGCTGGGCCTTCTCAGTCACAGGCAATGTGGAGGGCCAGTGGTTTCTCAACC |
| | AGGGGACCCTGCTCTCCCTCTCTGAACAGGAGCTCTTGGACTGTGACAAGATGGACAA |
| | GGCCTGCATGGGCGGCTTGCCCTCCAATGCCTACTCGGCCATAAAGAATTTGGGAGGG |
| | CTGGAGACAGAGGATGACTACAGCTACCAGGGTCACATGCAGTCCTGTCTTCTCAG |
| | CAGAGAAGGCCAAGGTCTACATCAATGACTCCGTGGAGCTGAGCCAGAACGAGCAGAA |
| | GCTGGCAGCCTGGCTGGCCAAGAGAGGCCCAATCTCCGTGGCCATCAATGCCTTTGGC |
| | ATGCAGTTTTACCGCCACGGATCTCCCGCCCTCTCCGCCCCCTCTGCAGCCCTTGGC |
| | TCATTGACCATGCGGTGTTGCTTGTGGGCTACGGCAACCGCTCTGACGTTCCCTTTTG |
| | GGCCATCAAGAACAGCTGGGGCACTGACTGGGGTGAGAAGGGTTACTACTACTTGCAT |
| | CGCGGGTCCGGGGCCTGTGGCGTGAACACCATGGCCAGCTCGGCGGTGGTGGACTGAA |
| | GAGGGGCC |
| ORF Start: ATG at 15 | ORF Stop: TGA at 1215 |
| SEQ ID NO: 34 | 400 aa MW at 44237.8 kD |
| NOV6b, CG10136-02 Protein Sequence | MAPWLQLLSLLGLLPGAVAAPAQPQVLDELGRHVLLRKDCGPVDTKVPGAGEPKSAFT |
| | QGSAMISSLSQNHPDNRNETFSSVISLLNEDPLSQDLPVKMASIFKNFVITYNRTYES |
| | KEEARWRLSVFVNNMVRAQKIQALDRGTAQYGVTKFSDLTEEEFRTIYLNTLLRKEPG |
| | NKMKQAKSVGDLAPPEWDWRSKGAVTKVKDQGMCGSCWAFSVTGNVEGQWFLNQGTLL |
| | SLSEQELLDCDKMDKACMGGLPSNAYSAIKNLGGLETEDDYSYQGHMQSCNFSAEKAK |
| | VYINDSVELSQNEQKLAAWLAKRGPISVAINAFGMQFYRHGISRPLRPLCSPWLIDHA |
| | VLLVGYGNRSDVPFWAIKNSWGTDWGEKGYYYLHRGSGACGVNTMASSAVVD |

Sequence comparison of the above protein sequences yields the following sequence relationships shown in Table 6B.

TABLE 6B

Comparison of NOV6a against NOV6b.

| Protein Sequence | NOV6a Residues/ Match Residues | Identities/ Similarities for the Matched Region |
|---|---|---|
| NOV6b | 117 . . . 490 | 366/374 (97%) |
| | 28 . . . 400 | 368/374 (97%) |

Further analysis of the NOV6a protein yielded the following properties shown in Table 6C.

TABLE 6C

Protein Sequence Properties NOV6a

| | |
|---|---|
| PSort analysis: | 0.4514 probability located in outside; 0.1900 probability located in lysosome (lumen); 0.1000 probability located in endoplasmic reticulum (membrane); 0.1000 probability located in endoplasmic reticulum (lumen) |
| SignalP analysis: | Cleavage site between residues 20 and 21 |

A search of the NOV6a protein against the Geneseq database, a proprietary database that contains sequences published in patents and patent publication, yielded several homologous proteins shown in Table 6D.

TABLE 6D

Geneseq Results for NOV6a

| Geneseq Identifier | Protein/Organism/Length [Patent #, Date] | NOV6a Residues/ Match Residues | Identities/ Similarities for the Matched Region | Expect Value |
| --- | --- | --- | --- | --- |
| AAB11960 | Human cathepsin Y - *Homo sapiens*, 484 aa. [JP2000157263-A, 13 Jun. 2000] | 1 . . . 490<br>1 . . . 484 | 469/491 (95%)<br>476/491 (96%) | 0.0 |
| AAW53200 | Human spleen-derived cysteine protease - *Homo sapiens*, 392 aa. [JP10099084-A, 21 Apr. 1998] | 99 . . . 490<br>1 . . . 392 | 381/393 (96%)<br>386/393 (97%) | 0.0 |
| AAW37957 | Amino acid sequence of human cathepsin polypeptide-1 - *Homo sapiens*, 392 aa. [WO9813484-A1, 02 Apr. 1998] | 99 . . . 490<br>1 . . . 392 | 378/393 (96%)<br>384/393 (97%) | 0.0 |
| AAY45041 | Human Apop2 protein - *Homo sapiens*, 338 aa. [WO200007545-A2, 17 Feb. 2000] | 152 . . . 490<br>1 . . . 338 | 333/339 (98%)<br>335/339 (98%) | 0.0 |
| AAB51802 | Gene 26 human secreted protein homologous amino acid sequence #131 - *Homo sapiens*, 234 aa. [WO200061625-A1, 19 Oct. 2000] | 256 . . . 490<br>1 . . . 234 | 229/235 (97%)<br>231/235 (97%) | e−35 |

In a BLAST search of public sequence datbases, the NOV6a protein was found to have homology to the proteins shown in the BLASTP data in Table 6E.

TABLE 6E

Public BLASTP Results for NOV6a

| Protien Accession Number | Protein/Organism/Length | NOV6a Residues/ Match Residues | Identities/ Similarities for the Matched Portion | Expect Value |
| --- | --- | --- | --- | --- |
| Q9UBX1 | Cathepsin F precursor (EC 3.4.22.41) (CATSF) - *Homo sapiens* (Human), 484 aa. | 1 . . . 490<br>1 . . . 484 | 469/491 (95%)<br>476/491 (96%) | 0.0 |
| Q9R013 | Cathepsin F precursor (EC 3.4.22.41) - *Mus musculus* (Mouse), 462 aa. | 1 . . . 490<br>1 . . . 462 | 350/493 (70%)<br>401/493 (80%) | 0.0 |
| Q9ES93 | CATHEPSIN F - *Mus musculus* (Mouse), 462 aa. | 1 . . . 490<br>1 . . . 462 | 348/493 (70%)<br>399/493 (80%) | 0.0 |
| T46294 | hypothetical protein DKFZp434F0610.1 - human, 308 aa (fragment). | 166 . . . 444<br>1 . . . 279 | 276/279 (98%)<br>278/279 (98%) | e−161 |
| Q99KQ9 | SIMILAR TO CATHEPSIN F - *Mus musculus* (Mouse), 302 aa. | 188 . . . 490<br>1 . . . 302 | 249/303 (82%)<br>281/303 (92%) | e−153 |

PFam analysis predicts that the NOV6a protein contains the domains shown in the Table 6F.

TABLE 6F

Domain Analysis of NOV6a

| Pfam Domain | NOV6a Match Region | Identities/ Similarities for the Matched Region | Expect Value |
| --- | --- | --- | --- |
| gpdh | 404 . . . 413 | 5/10 (50%)<br>8/10 (80%) | 0.35 |
| Peptidase_C1 | 276 . . . 488 | 102/337 (30%)<br>184/337 (55%) | 1.8e−104 |

Example 7

The NOV7 clone was analyzed, and the nucleotide and encoded polypeptide sequences are shown in Table 7A.

TABLE 7A

NOV7 Sequence Analysis

| | | |
|---|---|---|
| | SEQ ID NO: 35 | 1704 bp |

| | |
|---|---|
| NOV7a, CG102221-01 DNA Sequence | TGGTAGATGTGGCATTTCCATGCTGAGGCCGCGAGTCCCGCCTGACCCCGTCGCTGCC<br><br>TCTCCAGGCTTCTCTGGGCCGCGCCTCTGCAGACTGCGCAGCCATGCTGCATCTGCT<br><br>GGCGCTCTTCCTGCACTGCCTCCCTCTGGCCTCTGGGGACTATGACATCTGCAAATCC<br><br>TGGGTGACCACAGATGAGGGCCCCACCTGGGAGTTCTACGCCTGCCAGCCCAAGGTGA<br><br>TGCGCCTGAAGGACTACGTCAAGGTGAAGGTGGAGCCCTCAGGCATCACATGTGGAGA<br><br>CCCCCCTGAGAGGTTCTGCTCCCATCCCTACCTATGCAGCAACGAGTGTGACGCCTCC<br><br>AACCCGGACCTGGCCCACCCGCCCAGGCTCATGTTCGACAAGGAGGAGGAGGGCCTGG<br><br>CCACCTACTGGCAGAGCATCACCTGGAGCCGCTACCCCAGCCCGCTGGAAGCCAACAT<br><br>CACCCTTTCGTGGAACAAGACCGTGGAGCTGACCGACGACGTGGTGATGACCTTCGAG<br><br>TACGGCCGGCCCACGGTCATGGTCCTGGAGAAGTCCCTGGACAACGGGCGCACCTGGC<br><br>AGCCCTACCAGTTCTACGCCGAGGACTGCATGGAGGCCTTCGGTATGTCCGCCCGCCG<br><br>GGCCCGCGACATGTCATCCTCCAGCGCGCACCGCGTGCTCTGCACCGAGGAGTACTCG<br><br>CGCTGGGCAGGCTCCAAGAAGGAGAAGCACGTGCGCTTCGAGGTGCGGGACCGCTTCG<br><br>CCATCTTTGCCGGCCCCGACCTGCGCAACATGGACAACCTCTACACGCGGCTGGAGAG<br><br>CGCCAAGGGCCTCAAGGAGTTCTTCACCCTCACCGACCTGCGCATGCGGCTGCTGCGC<br><br>CCGGCGCTGGGCGGCACCTATGTGCAGCGGGAGAACCTCTACAAGTACTTCTACGCCA<br><br>TCTCCAACATCGAGGTCATCGGCAGGTGCAAGTGCAACCTGCACGCCAACCTGTGCTC<br><br>CATGCGCGAGGGCAGCCTGCAGTGCGAGTGCGAGCACAACACCACCGGCCCCGACTGC<br><br>GGCAAGTGCAAGAAGAATTTCCGCACCCGGTCCTGGCGGGCCGGCTCCTACCTGCCGC<br><br>TGCCCCATGGCTCTCCCAACGCCTGTGACTGCGAATGCTACGGTCACTCCAACCGCTG<br><br>CAGCTACATTGACTTCCTGAATGTGGTGACCTGCGTCAGCTGCAAGCACAACACGCGA<br><br>GGTCAGCACTGCCAGCACTGCCGGCTGGGCTACTACCGCAACGGCTCGGCAGAGCTGG<br><br>ATGATGAGAACGTCTGCATTGAGTGTAACTGCAACCAGATAGGCTCCGTGCACGACCG<br><br>GTGCAACGAGACCGGCTTCTGCGAGTGCCGCGAGGCCGCGGCGGGCCCCAAGTGCGAC<br><br>GACTGCCTCCCCACGCACTACTGGCGCCAGGGCTGCTACCCCAACGTGTGCGACGACG<br><br>ACCAGCTCCTGTGCCAGAACGCAGGCACCTGCCTGCACAACCAGCGCTGCGCCTGCCC<br><br>GCCCGCCTACACCGGCGTGCCTCCGAGCAGCCCCGCTGCGACCCCCCGACCATGAC<br><br>GGCGGTCTGGACTGCGACCGCGCGCCCGGGGCCGCCCCGCGCCCCGCCACCCTGCTCG<br><br>GCTGCCTGCTGCTGCTGGGGCTGGCCGCCCGCCTGGGCCGCTGACCCCCCCCGGAGG<br><br>ACGCTCCCCGCACCCGGAGGCC |

| | |
|---|---|
| | ORF Start: ATG at 103 ORF Stop: TGA at 1666<br>SEQ ID NO: 36      521 aa  MW at 58964.0 kD |

| | |
|---|---|
| NOV7a, CG102221-01 Protein Sequence | MLHLLALFLHCLPLASGDYDICKSWVTTDEGPTWEFYACQPKVMRLKDYVKVKVEPSG<br><br>ITCGDPPERFCSHPYLCSNECDASNPDLAHPPRLMFDKEEEGLATYWQSITWSRYPSP<br><br>LEANITLSWNKTVELTDDVVMTFEYGRPTVMVLEKSLDNGRTWQPYQFYAEDCMEAFG |

TABLE 7A-continued

NOV7 Sequence Analysis

MSARRARDMSSSSAHRVLCTEEYSRWAGSKKEKHVRFEVRDRFAIFAGPDLRNNDNLY

TRLESAKGLKEFFTLTDLRMRLLRPALGGTYVQRENLYKYFYAISNIEVIGRCKCNLH

ANLCSMREGSLQCECEHNTTGPDCGKCKKNFRTRSWRAGSYLPLPHGSPNACDCECYG

HSNRCSYIDFLNVVTCVSCKHNTRGQHCQHCRLGYYRNGSAELDDENVCIECNCNQIG

SVHDRCNETGFCECREGAAGPKCDDCLPTHYWRQGCYPNVCDDDQLLCQNGGTCLQMQ

RCACPRGYTGVRCEQPRCDPADDDGGLDCDRAPGAAPRPATLLGCLLLLGLAARLGR

TABLE 7B

| Protein Sequence Properties NOV7a | |
|---|---|
| PSort analysis: | 0.7000 probability located in plasma membrane; 0.3000 probability located in microbody (peroxisome); 0.2000 probability located in endoplasmic reticulum (membrane); 0.1000 probability located in mitochondrial inner membrane |
| SignalP analysis: | Cleavage site between residues 18 and 19 |

A search of the NOV7a protein against the Geneseq database, a proprietary database that contains sequences published in patents and patent publication, yielded several homologous proteins shown in Table 7C.

TABLE 7C

Geneseq Results for NOV7a

| Geneseq Identifier | Protein/Organism/Length [Patent #, Date] | NOV7a Residues/ Match Residues | Identities/ Similarities for the Matched Region | Expect Value |
|---|---|---|---|---|
| ABB53284 | Human polypeptide #24 - *Homo sapiens*, 533 aa. [WO200181363-A1, 01 Nov. 2001] | 1 . . . 521<br>1 . . . 533 | 521/533 (97%)<br>521/533 (97%) | 0.0 |
| ABB05418 | Mouse membrane bound type netrin protein SEQ ID NO:8 - *Mus musculus*, 539 aa. [JP2001327289-A, 27 Nov. 2001] | 17 . . . 519<br>28 . . . 537 | 308/515 (59%)<br>379/515 (72%) | 0.0 |
| ABB53283 | Human polypeptide #23 - *Homo sapiens*, 286 aa. [WO200181363-A1, 01 Nov. 2001] | 1 . . . 284<br>1 . . . 286 | 284/286 (99%)<br>284/286 (99%) | e-170 |
| ABB05419 | Mouse membrane bound type netrin protein SEQ ID NO:10 - *Mus musculus*, 483 aa. [JP2001327289-A, 27 Nov. 2001] | 17 . . . 427<br>28 . . . 461 | 220/438 (50%)<br>277/438 (63%) | e-124 |
| AAB65181 | Human PRO1133(UNQ571) protein sequence SEQ ID NO:129 - *Homo sapiens*, 438 aa. [WO200073454-A1, 07 Dec. 2000] | 13 . . . 427<br>24 . . . 416 | 210/419 (50%)<br>274/419 (65%) | e-123 |

In a BLAST search of public sequence datbases, the NOV7a protein was found to have homology to the proteins shown in the BLASTP data in Table 7D.

TABLE 7D

Public BLASTP Results for NOV7a

| Protein Accession Number | Protein/Organism/Length | NOV7a Residues/ Match Residues | Identities/ Similarities for the Matched Portion | Expect Value |
|---|---|---|---|---|
| BAB47486 | KIAA1857 PROTEIN - *Homo sapiens* (Human), 549 aa (fragment). | 1 . . . 521<br>20 . . . 549 | 520/530 (98%)<br>521/530 (98%) | 0.0 |
| Q96CW9 | HYPOTHETICAL 59.8 KDA PROTEIN - *Homo sapiens* (Human), 530 aa. | 1 . . . 521<br>1 . . . 530 | 520/530 (98%)<br>521/530 (98%) | 0.0 |
| Q8VIP8 | NETRIN-G2A - *Mus musculus* (Mouse), 530 aa. | 1 . . . 519<br>1 . . . 528 | 493/529 (93%)<br>505/529 (95%) | 0.0 |
| AAL84788 | LAMINET-2A - *Mus musculus domesticus* (western European house mouse), 530 aa. | 1 . . . 519<br>1 . . . 528 | 492/529 (93%)<br>504/529 (95%) | 0.0 |
| Q96JH0 | KIAA1857 PROTEIN - *Homo sapiens* (Human), 438 aa (fragment). | 1 . . . 342<br>20 . . . 363 | 342/344 (99%)<br>342/344 (99%) | 0.0 |

PFam analysis predicts that the NOV7a protein contains the domains shown in the Table 7E.

TABLE 7E

Domain Analysis of NOV7a

| Pfam Domain | NOV7a Match Region | Identities/ Similarities for the Matched Region | Expect Value |
|---|---|---|---|
| laminin_Nterm | 39 . . . 283 | 79/282 (28%)<br>134/282 (48%) | 5.9e-12 |
| laminin_EGF | 285 . . . 342 | 15/68 (22%)<br>38/68 (56%) | 1.5e-06 |
| laminin_EGF | 344 . . . 397 | 18/63 (29%)<br>39/63 (62%) | 0.00013 |
| laminin_EGF | 400 . . . 442 | 20/59 (34%) | 8.3e-09 |

TABLE 7E-continued

Domain Analysis of NOV7a

| Pfam Domain | NOV7a Match Region | Identities/ Similarities for the Matched Region | Expect Value |
|---|---|---|---|
| EGF | 447 . . . 477 | 35/59 (59%)<br>16/47 (34%)<br>22/47 (47%) | 0.00014 |

Example 8

The NOV8 clone was analyzed, and the nucleotide and encoded polypeptide sequences are shown in Table 8A.

TABLE 8A

NOV8 Sequence Analysis

SEQ ID NO: 37    910 bp

NOV8a, CG102325-01 DNA Sequence

GGTCCGGGGGGCTGCCGGTCCCGGGTACCATGTGTGACGGCGCCCTGCTGCCTCCGC

TCGTCCTGCCCGTGCTGCTGCTGCTGGTTTGGGGACTGGACCCGGGCACAGCTGTCGG

CGACGCGGCGGCCGACGTGGAGGTGGTGCTCCCGTGGCGGGTGCGCCCCGACGACGTG

CACCTGCCGCCGCTGCCCGCAGCCCCCGCGCCCCGACGGCGGCGACGCCCCCGCACGC

CCCCAGCCGCCCCGCGCGCCCGGCCCGGAGAGCGCGCCCTGCTGCTGCACCTGCCGGC

CTTCGGGCGCGACCTGTACCTTCAGCTGCGCCGCGACCTGCGCTTCCTGTCCCGAGGC

TTCGAGGTGGAGGAGGCGGGCGCGGCCCGGCGCCGCGGCCGCCCCGCCGAGCTGTGCT

TCTACTCCGCCCGTGTGCTCGGCCACCCCGGCTCCCTCGTCTCGCTCAGCCCCTGCGG

CGCCGCCGGCGGCCTGCTACTCCCCGCGCCACCTCCGGGTCGGCCCGTCCGGTCTGTT

GCGACGCAGAGTGGTCGCCGTGGAGGGTGGGGTGGGCGCCTCTGCTGGAAGTCCAG

CCTCCAGGGGAACCGGAGGGAACCCCCTGCCTTTCCACCTCTCCCCATCCCCCACCCC

GGCCTTCGGTACCCTCTATAGGCAAAGGGGTGGGAGGCGCAGcATCCCAGTCCAGCG

TABLE 8A-continued

NOV8 Sequence Analysis

CCTCTGCAGCCCGTGGAACCCGCGCGGAGCTGGGGTTGCGTGGGGGTATACGCCGCCC

GCTCTAGGGAGCGCAGATCTGGCACGGATGAAACTGTCAGGGCCCTGGACAGAGGCGC

CTTGGCCCCAATGTAG<u>AGAACACTGCATCTGCACCGCCGTGTCAAAGTGTATGTCACG</u>

<u>GGAGTACCTGTGTACGTGTAGGTGTTATGTTCTTGGACTT</u>

ORF Start: ATG at 31    ORF Stop: TAG at 826
SEQ ID NO: 38           265 aa MW at 28223.0 kD

| NOV8a, CG102325-01 Protein Sequence | MCDGALLPPLVLPVLLLLVWGLDPGTAVGDAAADVEVVLPWRVRPDDVHLPPLPAAPG PRRRRRPRTPPAAPRARPGERALLLNLPAFGRDLYLQLRRDLRFLSRGFEVEEAGAAR RRGRPAELCFYSGRVLGHPGSLVSLSACGAAGGLVLPAPPPGRPVRSVATQSGRRGGW GWGASAGSPASRGTGGNPLPFHLSPSPTPAFGTLYRQRGWEGQHPSPAPLQPVEPARS WGCVGVYAARSRERRSGRDETVRALDRGALAPM |

Further analysis of the NOV8a protein yielded the following properties shown in Table 8B.

TABLE 8B

Protein Sequence Properties NOV8a

| PSort analysis: | 0.8200 probability located in outside; 0.1000 probability located in endoplasmic reticulum (membrane); 0.1000 probability located in endoplasmic reticulum (lumen); 0.1000 probability located in lysosome (lumen) |
| SignalP analysis: | Cleavage site between residues 28 and 29 |

A search of the NOV8a protein against the Geneseq database, a proprietary database that contains sequences published in patents and patent publication, yielded several homologous proteins shown in Table 8C.

TABLE 8C

Geneseq Results for NOV8a

| Geneseq Identifier | Protein/Organism/Length [Patent #, Date] | NOV8a Residues/ Match Residues | Identities/ Similarities for the Matched Region | Expect Value |
|---|---|---|---|---|
| AAE10350 | Human ADAMTS-J1.4 variant protein - *Homo sapiens*, 891 aa. [EP1134286-A2, 19-SEP-2001] | 1 . . . 151<br>1 . . . 151 | 151/151 (100%)<br>151/151 (100%) | 6e−85 |
| AAE10348 | Human ADAMTS-J1.2 variant protein - *Homo sapiens*, 635 aa. [EP1134286-A2, 19-SEP-2001] | 1 . . . 151<br>1 . . . 151 | 151/151 (100%)<br>151/151 (100%) | 6e−85 |
| AAE10347 | Human ADAMTS-J1.1 variant protein - *Homo sapiens*, 745 aa. [EP1134286-A2, 19-SEP-2001] | 1 . . . 151<br>1 . . . 151 | 151/151 (100%)<br>151/151 (100%) | 6e−85 |
| AAU72894 | Human metalloprotease partial protein sequence #6 - *Homo sapiens*, 1428 aa. [WO200183782-A2, 08-NOV-2001] | 27 . . . 151<br>434 . . . 558 | 125/125 (100%)<br>125/125 (100%) | 1e−68 |
| AAU72900 | Human metalloprotease partial protein sequence #12 - *Homo sapiens*, 1094 aa. [WO200183782-A2, 08-NOV-2001] | 51 . . . 151<br>142 . . . 244 | 52/112 (46%)<br>59/112 (52%) | 3e−15 |

In a BLAST search of public sequence datbases, the NOV8a protein was found to have homology to the proteins shown in the BLASTP data in Table 8D.

TABLE 8D

Public BLASTP Results for NOV8a

| Protein Accession Number | Protein/Organism/Length | NOV8a Residues/ Match Residues | Identities/ Similarities for the Matched Portion | Expect Value |
| --- | --- | --- | --- | --- |
| CAC86016 | METALLOPROTEASE DISINTEGRIN 17, WITH THROMBOSPONDIN DOMAINS - Homo sapiens (Human), 1095 aa. | 1 ... 151<br>1 ... 151 | 151/151 (100%)<br>151/151 (100%) | 1e−84 |
| CAC84565 | ADAMTS-19 - Homo sapiens (Human), 1207 aa. | 51 ... 151<br>142 ... 244 | 51/112 (45%)<br>59/112 (52%) | 1e−14 |
| CAC86014 | METALLOPROTEASE DISINTEGRIN 15 WITH THROMBOSPONDIN DOMAINS - Homo sapiens (Human), 950 aa. | 25 ... 259<br>13 ... 218 | 72/248 (29%)<br>100/248 (40%) | 5e−08 |
| Q9WUQ1 | ADAMTS-1 precursor (EC 3.4.24.—) (A disintegrin and metalloproteinase with thrombospondin motifs 1) (ADAM-TS 1) (ADAM-TS1) - Rattus norvegicus (Rat), 967 aa. | 69 ... 149<br>66 ... 153 | 35/90 (38%)<br>46/90 (50%) | 1e−06 |
| Q9UP79 | ADAMTS-8 precursor (EC 3.4.24.—) (A disintegrin and metalloproteinase with thrombospondin motifs 8) (ADAM-TS 8) (ADAM-TS8) (METH-2) (METH-8) - Homo sapiens (Human), 890 aa. | 52 ... 187<br>3 ... 165 | 52/167 (31%)<br>65/167 (38%) | 3e−06 |

PFam analysis predicts that the NOV8a protein contains the domains shown in the Table 8E.

TABLE 8E

Domain Analysis of NOV8a

| Pfam Domain | NOV8a Match Region | Identities/ Similarities for the Matched Region | Expect Value |
| --- | --- | --- | --- |
| Pep_M12B_propep | 95 ... 192 | 26/119 (22%)<br>60/119 (50%) | 0.021 |

Example 9

The NOV9 clone was analyzed, and the nucleotide and encoded polypeptide sequences are shown in Table 9A.

TABLE 9A

NOV9 Sequence Analysis

| | SEQ ID NO: 39 | 958 bp |
| --- | --- | --- |
| NOV9a, CG102832-01 DNA Sequence | GCAGCACCCGCAGCCAGAGCCGCGCTCGGCATGATGCCCGGGGCGCCGCTCCTGCGGC<br><br>TGCTGACCGCGGTCTCTGCGGCAGTGGCAGTGGCAGTGCCCGGGGCGCCCGGGACGGT<br><br>AATGCCCCCCACCACGGGGGACGCCACCCTGGCCTTCGTCTTCGACGTCACCGGCTCC<br><br>ATGTGGGACGAACTGATGCAGGTGATCGATGGCGCCTCGCGCATTCTGGTGCGCAGTC<br><br>TGAGCCGCCGCAGCCAGGCCATCGCCAACTACGCGCTGGTGCCCTTCCACGACCCAGA<br><br>TATTGGCCCAGTGACCCTCACGGCGGACCCCACAGTGTTTCAGAGGGAGCTGAGAGAA<br><br>CTCTACGTGCAGGGAGGTGGTGACTGCCCGGAGATGAGTGTGGGGGCCATTAAGGCTG<br><br>CCGTGGAGGTTGCCAACCCCGGATCCTTCATCTACGTCTTTTCGGATGCCCGCGCCAA | |

TABLE 9A-continued

NOV9 Sequence Analysis

```
AGACTATCACAAGAAGGAAGAGCTGCTGCGGCTCCTGCAGCTCAAGCAATCACAGGTG

GTCTTTGTGCTGACGGGGGACTGTGGCGACCGCACCCATCCTGGCTACCTGGCTTATG

AGGAGATCGCTGCCACCAGCTCTGGGCAGGTGTTCCACCTGGACAAGCAGCAAGTGAC

AGAGGTGCTGAAGTGGGTGGAGTCAGCGATCCAGGCCTCCAAGGTGCACCTGCTGTCC

ACACACCACGAGGAGGAGGGGGAGCACACATGGACACTCCCCTTTGACCCCAGCCTGA

AGGAGGTCACCATCTCATTGAGTGGGCCAGGGCCTGAGATTGAAGTCCAAGATCCGCT

GGGTATGGACCACCCCGGGGCTGGCCTCCTCTTTGGCCCCAAGACTGAGGTGGAAGCC

CAGGATGGGACAAAGAAAGAGACCAAGGGTGACAGGGCTTCAGACATGAGGCTCCAGG

AATAGGGAAATATGGGTGGGGGGGACACG
```

ORF Start: ATG at 31  ORF Stop: TAG at 931
SEQ ID NO: 40           300 aa MW at 32481.5 kD

NOV9a,
CG102832-01
Protein
Sequence

```
MMPGAPLLRLLTAVSAAVAVAVACAPGTVMPPTTGDATLAFVFDVTGSMWDELMQVID

CASRILERSLSRRSQAIANYALVPFHDPDIGPVTLTADPTVFQRELRELYVQGGGDCP

EMSVGAIKAAVEVANPGSFIYVFSDARAKDYHKKEELLRLLQLKQSQVVFVLTGDCGD

RTHPGYLAYEEIAATSSGQVFHLDKQQVTEVLKWVESAIQASKVHLLSTDHEEEGEHT

WRLPFDPSLKEVTISLSGPGPEIEVQDPLGMDHPGAGLLFGPKTEVEAQDGTKKETKG

DRASDMRLQE
```

SEQ ID NO: 41    2916 bp

NOV9b,
CG102832-02
DNA
Sequence

```
GCAGCACCCGCAGCCAGAGCCGCGCTCGGCATGATGCCCGGGGCGCCGCTCCTGCGGC

TGCTGACCGCGGTCTCTGCGGCAGTGGCAGTCGCAGTGGCCGGGGCGCCCGGGACGGT

AATGCCCCCCACCACGGGGGACGCCACCCTGGCCTTCGTCTTCGACGTCACCGGCTCC

ATGTGGGACGAACTGATGCAGGTGATCGATGGCGCCTCGCGCATTCTGGAACGCAGTC

TGAGCCGCCGCAGCCAGGCCATCGCCAACTACGCGCTGGTGCCCTTCCACGACCCAGA

TATTGGCCCAGTGACCCTCACGGCGGACCCCACAGTGTTTCAGAGGCAGCTGAGAGAA

CTCTACGTGCAGGGAGGTGCTGACTGCCCGGAGATGAGTGTGGCGCCCATTAAGGCTG

CCGTGGAGGTTGCCAACCCCGGATCCTTCATCTACGTCTTTTCGGATGCCCGCGCCAA

AGACTATCACAAGAAGGAAGAGCTGCTGCGGCTCCTGCAGCTCAAGCAATCACAGGTG

GTCTTTGTGCTGACGGGGGACTGTGGCGACCGCACCCATCCTGGCTACCTGGCTTATG

AGGAGATCGCTGCCACCAGCTCTGGGCAGGTGTTCCACCTGGACAAGCAGCAAGTGAC

AGAGGCAGGTGCTTCCGTGTTTCCAGGCAAAATTGTGCAGGAGCACAGGATCCTTTCA

GGGGCCAGCTGGGAAATGATGAACAACGCTCTCTCTGGAAAGGACAAGCACACCCATT

TCCGTGGTATAAATGCTCCCACCTCGGCTGATTCCAAGTCAGAGTTGGGAAGTGACGC

TGACACTCAGCTTTCCGGAGCCTACACAAGTGGCTCCCACACACCACTGGATCCCGCA

CAGGCACCTCTCACCGCCAGTTGGGTTAACGAGAGCCCCTACCTGGTGCTGAAGTGGG

TGGAGTCAGCGATCCAGGCCTCCAAGGTGCACCTGCTGTCCACAGACCACGAGGAGGA

GGGGGAGCACACATGGAGACTCCCCTTTGACCCCAGCCTGAAGGAGGTCACCATCTCA

TTGAGTGGGCCAGGGCCTGAGATTGAAGTCCAAGATCCGCTGGGTATGGACCACCCCG

GGGCTGGCCTCCTCTTTGGCCCCAAGACTGAGGTGGAAGCCCAGGATGGGACAAAGAA
```

TABLE 9A-continued

NOV9 Sequence Analysis

```
AGAGACCAAGGGGAGGATCCTGCAGGAGGACGAGGGCCTCAACGTGCTTCTCAACATC

CCTGACTCGGCCAAGGTCGTAGCCTTTAAGCCTGAGCATCCGGGGCTGTGGTCCATCA

AGGTCTATAGCAGTGGCCGCCATTCAGTGAGGATCACAGGCCTCAGCAACATTGACTT

CCGAGCCGGCTTCTCCACTCAGCCCTTGCTGGACCTCAACCACACCCTCGAGTGGCCC

TTGCAAGGAGTCCCCATCTCCCTGGTGATCAATTCCACGGGCCTGAAGGCACCCGGCC

GCCTAGACTCGGTGGAGCTGGCACAAAGCTCAGGGAAGCCCCTCCTGACTCTGCCCAC

GAAGCCCCTCTCCAATGGCTCCACCCATCAGCTGTGGGCGGGCCGCCCTTCCACACC

CCCAAGGAGCGCTTCTACCTCAAGGTGAAGGGCAAGGACCATGAGGGAAACCCCCTCC

TTCGTGTCTCTGGAGTGTCCTACAGTGGGGTGGCCCCAGGCGCTCCCCTCGTCAGCAT

GGCCCCAGGATCCATGGCTACCTGCACCAGCCCCTGCTGGTCTCCTGCTCGGTGCAC

AGTGCCCTTCCCTTCCGGCTGCAGCTGCGGCGAGGTGAAGCCACGCTGGGCGAAGAGA

GGCACTTTCAGGAGTCGGGAAACAGCAGCTGGAGATCCTGCGGGCCTCCAAGGCCGA

GGAGGGCACGTACGAGTGCACAGCCGTCAGCAGGGCTGGGACCGGGCGAGCAAAGGCC

CAGATTGTTGTCACCCTGCACCTCAGGGTGGGGTTCGGGGCAGCACCAGGGCTTGCAC

GAAGACCCCCTCCCTTGCCTCAGCTCCTTGGTTCCTCCTGTGCTCATGTCCCTGCAGA

CCCCCCCCCGCAGCTGGTCCCTGCTCCCAACGTGACCGTGTCCCAGGGGAGACTGCC

GTCCTATCCTGCCGGGTCCTAGGCGAGGCCCCCTACAACCTGACGTGGGTCCGGGACT

GGCGAGTCCTGCCGGCCTCGACGGGCCGAGTTGCCCAGCTGGCTGACCTGTCCCTGGA

GATCAGTGGCATCATCCCCACAGACGGCGGGAGGTACCACTGTGTGGCCAGCAATGCC

AATGGGGTCACAAGGGCATCCGTCTGGCTCCTGGTGCGACAGCCCCCACAGGTCAGCA

TCCACACCAGCTCCCAGCACTTCTCCCAAGGTGTGGAGGTGAAGGTCAGCTGCTCAGC

CTCTGGATACCCCACACCCCACATCTCCTGGAGCCGTGAGAGCCAAGCCCTACAAGAG

GACAGCAGAATCCATGTGGACGCACAGGCAACCCTGATTATTCAGGGGGTAGCCCCAG

AGGATGCTGGGAATTACAGCTGCCAGGCCACTAATGACGTTGGCACTGACCAGGAGAC

GGTCACCCTCTACTACACAGACCCACCGTCGGTCTCTGCTGTAAATGCCGTGGTGCTG

GTGGCCGTTGGGGAGGAGGCTGTGTTGGTGTGAGGCATCTGGGCTTCCCCCCCCCC

GAGTCATCTGGTATCGAGGGGGTCTTGAAATGATCCTGGCCCCTGAGGGCTCCAGCTC

TGGGAAGCTGCGGATCCCGGCGGCTCAGGAGAGGGATCCTGGCACCTACACCTGCCGG

GCTGTCAATGAGTTGGGTGACGCCTCTGCAGAAATCCAGCTGGCGGTTGGACATGCGC

CCCAGCTGACGGAGCTGCCCCGGGATGTCACTGTGGAACTGGGGAGGAGTGCCCAGCT

GCGGCGTGGGACTTAA
```

ORF Start: AIG at 31  ORF Stop: TAA at 2914
SEQ ID NO: 42  961 aa  MW at 102789.2 kD NOV9b, CG102832-02 Protein Sequence

MMPGAPLLRLLTAVSAAVAVAVAGAPGTVMPPTTGDATLAFVFDVTGSMWDELMQVID

GASRILERSLSRRSQAIANYALVPFHDPDIGPVTLTADPTVFQRELRELYVQGGGDCP

EMSVGAIKAAVEVANPGSFIYVFSDARAKDYHKKEELLRLLQLKQSQVVFVLTGDCGD

RTHPGYLAYEEIAATSSGQVFHLDKQQVTEAGASVFPGKIVQEHRILSGASWEMMNNA

LSGKDKHTHFRGINAPTSADSKSELGSDADTQLSGAYTSGSHTPLDPAQAPLTASWVN

TABLE 9A-continued

NOV9 Sequence Analysis

| | |
|---|---|
| | ESPYLVLKWVESAIQASKVHLLSTDHEEEGEHTWRLPFDPSLKEVTISLSGPGPEIEV |
| | QDPLGMDHPGAGLLFGPKTEVEAQDGTKKETKGRILQEDEGLNVLLNIPDSAKVVAFK |
| | PEHPGLWSIKVYSSGRHSVRITGVSNIDFRAGFSTQPLLDLNHTLEWPLQGVPISLVI |
| | NSTGLKAPGRLDSVELAQSSGKPLLTLPTKPLSNGSTHQLWGGPPFHTPKERFYLKVK |
| | GKDHEGNPLLRVSGVSYSGVAPGAPLVSMAPRIHGYLHQPLLVSCSVHSALPFRLQLR |
| | RGEARLGEERHFQESGNSSWEILRASKAEEGTYECTAVSRAGTGRAKAQIVVTLHLRV |
| | GFGAAPGLARRPPPLPQLLGSSCAHVPADPPPQLVPAPNVTVSPGETAVLSCRVLGEA |
| | PYNLTWVRDWRVLPASTGRVAQLADLSLEISGIIPTDGGRYQCVASNANGVTRASVWL |
| | LVREAPQVSIHTSSQHFSQGVEVKVSCSASGYPTPHISWSRESQALQEDSRIHVDAQG |
| | TLIIQGVAPEDAGNYSCQATNEVGTDQETVTLYYTDPPSVSAVNAVVLVAVGEEAVLV |
| | CEASGVPPPRVIWYRGGLEMILAPEGSSSGKLRIPAAQERDAGTYTCRAVNELGDASA |
| | EIQLAVGHAPQLTELPRDVTVELGRSAQLRRGT |

| | SEQ ID NO: 43 | 1023 bp |
|---|---|---|
| NOV9c, 197195425 DNA Sequence | CTCGAGTGTGGAACTCACTCTTAACGTACCTGAGGAGTGTCCAACGTCTTTGGACAAG<br>GCCATACTCTCATGTTCCTTTTCACTCAGCTTTACCCACACAGAAATTTTGGGGACCC<br>ATGGGGGACTCAGCAGTTGCCAAGGTCTGCAGCCTCCTCCAAGGGGTTCCCATCTAGT<br>TCTCAAGAGGAAGGAGGGGGTTCTCAGTCGCCAGGTGGGCATGGCACTCCCGAGGCCA<br>GGTGAGCAGGTCAGTGCCTTGGGGCTCAGGGCTGCTCCGGTTCTTACCGAATTGATCC<br>AGTCGTTGTAGTTGGAGACCCGCGTGAAGATGGAGGGCTTGTAGTAGTAGTTGCAACC<br>AAGGACCGACGTGAGGCTGCCGATGCCATGCACCTCCCACCGGCCGTCAGATGCCTGA<br>CAGTTCAGCGGCCCACCGGAGTCTCCGTTGCAGGTGCATATCACGCCATCACCCCCAG<br>CACAGATCATATTCGTCTTCACGGTGCTGCCCCACCAGCCAGAGTTGGAGCAGGTGGC<br>ATAGTCCACAACCAGCAACCGGCCCTGCTTCAGGTCATCAGGGAGAGCCCCGTTGGTC<br>TGCAGCCTTCCCCAGCCCGTGACGTAGCAGGGGTAGTTGTTGGGTAGAATGGTGCCGG<br>CAGGAGGGAGGCAGGCCAGCTGGATCTTGTCGGTGAGGGAGACGGGGTTAGCCAGTTT<br>GAGCAGGGCAATGTCGTTCCCTTTGGAGACCTGGTCGGAGTTCCAGTCCTTGTGCACC<br>ACAATCTTAGAGACACTGACGGCCAGCGAGCCGGACTCTGCAACGTAGAGGTTATGCT<br>GGCCCAGCATCACGCGGTAGATCCCGGAGGAGCTGATGCAGTGGGCAGCCGTCAGGAC<br>CCAGCTGTTGGCTATCAGGGACCCTCCGCAGGTGTGGTACCACTGGCCATTGGAGCTG<br>TACTGCAGGGAGACCTGCCAGGGCCGGCTGTTGGGCCTCGCTTCTTCACCTCCAAGCA<br>TCCTAGACATATCAGGCGCGTAAGTGGAGACGGATCC |

| | ORF Start: at 628 | ORF Stop: end of sequence |
|---|---|---|
| | SEQ ID NO: 44 | 132 aa MW at 13513.0 kD |

| NOV9C, 197195425 Protein Sequence | NGAGRREAGQLDLVGEGDGVSQFEQGNVVPFGDLVGVPVLVHHNLRDTDGQRAGLCNV<br>EVMLAQHHAVDPGGADAVGSRQDPAVGYQGPSAGVVPLAIGAVLQGDLPGPAVGPRFF<br>TSKHPRHIRRVSGDGS |

TABLE 9A-continued

NOV9 Sequence Analysis

| | SEQ ID NO:45 | 2058 bp |
|---|---|---|

NOV9d,
197192431
DNA
Sequence

AAGCTTGTGGCAGTGGCCGGGGCGCCCGGGACGGTAATGCCCCCCACCACGGGGGACG

CCACCCTGGCCTTCGTCTTCGACGTCACCGGCTCCATGTGGGACGAACTGATGCAGGT

CATCGATCGCGCCTCGCGCATTCTGGAACGCAGTCTGAGCCGCCGCAGCCAGGCCATC

CCCAACTACGCGCTGGTGCCCTTCCACCACCCAGATATTGGCCCAGTGACCCTCACGG

CGGACCCCACAGTGTTTCAGAGGGAGCTGAGAGAACTCTACGTGCAGGGAGGTGGTGA

CTGCCCGGAGATGAGTGTGGGGGCCATTAAGGCTGCCGTGGAGGTTGCCAACCCCGGA

TCCTTCATCTACGTCTTTTCGGATGCCCGCGCCAAAGACTATCACAAGAAGGAAGAGC

TGCTGCGGCTCCTGCAGCTCAAGCAATCACAGGTGGTCTTTGTGCTGACGGGGACTG

TGGCGACCACACCCATCCTGGCTACCTGGCTTATGACCAGATCGCTGCCACCAGCTCT

GGGCAGGTGTTCCACCTGGACAAGCAGCAAGTGACAGAGGTGCTGAAGTGGGTGGAGT

CAGCGATCCAGGCCTCCAAGCTGCACCTGCTGTCCACAGACCACGAGGAGGAGGGGGA

GCACACATGGAGACTCCCCTTTGACCCCAGCCTGAAGGAGGTCACCATCTCATTGAGT

GGGCCAGGGCCTGAGATTGAAGTCCAAGATCCGCTGGGGAGGATCCTGCAGGAGGACG

AGGGCCTCAACGTGCTTCTCAACATCCCTGACTCGGCCAAGGTCGTAGCCTTTAAGCC

TGAGCATCCGGGGCTGTGGTCCATCAAGGTCTATAGCAGTGGCCGCCATTCAGTGAGG

ATCACAGGCGTCAGCAACATTGACTTCCGAGCCGGCTTCTCCACTCAGCCCTTGCTGG

ACCTCAACCACACCCTCGAGTGGCCCTTGCAAGGAGTCCCCATCTCCCTGGTGATCAA

TTCCACGGGCCTGAAGGCACCCGGCCGCCTAGACTCGGTGGAGCTGGCACAAAGCTCA

GGGAAGCCCCTCCTGACTCTGCCCACGAAGCCCCTCTCCAATGGCTCCACCCATCAGC

TGTGGGGCGGGCCACCCTTCCACACCCCCAAGGAGCGCTTCTACCTCAAGGTGAAGGG

CAAGGACCATGAGGGAAACCCCCTCCTTCGTGTCTCTGGAGTGTCCTACAGTGGGGTG

GCCCCAGGCGCTCCCCTCGTCAGCATGGTCCCCAGGATCCATGGCTACCTGCACCAGC

CCCTGCTGGTCTCCTGCTCGCTGCACAGTGCCCTTCCCTTCCGGCTGCAGCTGCGGCG

AGGTGAAGCCAGGCTGGGCGAAGAGAGGCACTTTCAGGAGTCGGGAAACAGTAGCTGG

GAGATCCTGCGGCCCTCCAAGGCCGAGGAGGGCACGTACGAGTGCACAGCCGTCAGCA

GGGCTGGGACCGGGCGAGCAAAGGCCCAGATTGTTGTCACAGACCCCCCGCCGCACCT

GGTCCCTGCTCCCAACGTGACCGTGTCCCCAGGGGAGACTGCCGTCCTATCCTGCCGG

GTCCTAGGCGAGGCCCCCTACAACCTGACGTGGGTCCGGGACTGGCGAGTCCTGCCGG

CCTCGACGGGCCGAGTTGCCCAGCTGGCTGACCTGTCCCTGGAGATCAGTGGCATCAT

CCCCACAGACGGCGGGAGGTACCAGTGTGTGGCCAGCAATGCCAATGGGGTCACAAGG

GCATCCGTCTGGCTCCTGGTGCGAGAGGTCCCACAGGTCAGCATCCACACCAGCTCCC

AGCACTTCTCCCAAGGTGTGGAGGTGAAGGTCAGCTGCTCAGCCTCTGGATACCCCAC

ACCCCACATCTCCTGGAGCCGTGAGAGCCAAGCCCTACAAGAGGACAGCAGAATCCAT

GTGGACGCACAGGGAACCCTGATTATTCAGGGGGTAGCCCCAGAGGATGCTGGGAATT

ACAGCTGCCAGGCGACTAATGAGGTTGGCACTGACCAGGAGACGGTCACCCTCTACTA

CACAGACCCACCGTCGGTCTCTGTCGAC

TABLE 9A-continued

NOV9 Sequence Analysis

ORF Start: at 1  ORF Stop: end of sequence
SEQ ID NO: 46  686 aa MW at 74318.2 kD

| NOV9d, 197192431 Protein Sequence | KLVAVAGAPGTVMPPTTGDATLAFVFDVTGSMWDELMQVIDGASRILERSLSRRSQAI<br>ANYALVPFHDPDIGPVTLTADPTVFQRELRELYVQGGGDCPEMSVGAIKAAVEVANPG<br>SFIYVFSDARAKDYHKKEELLRLLQLKQSQVVFVLTGDCGDHTHPGYLAYEEIAATSS<br>GQVFHLDKQQVTEVLKWVESAIQASKVHLLSTDHEEEGEHTWRLPFDPSLKEVTISLS<br>GPGPEIEVQDPLGRILQEDEGLNVLLNIPDSAKVVAFKPEHPGLWSIKVYSSGRHSVR<br>ITGVSNIDFRAGFSTQPLLDLNHTLEWPLQGVPISLVINSTGLKAPGRLDSVELAQSS<br>GKPLLTLPTKPLSNGSTHQLWGGPPFHTPKERFYLKVKGKDHEGNPLLRVSGVSYSGV<br>APGAPLVSMVPRIHGYLHQPLLVSCSVHSALPFRLQLRRGEARLGEERHFQESGNSSW<br>EILRASKAEEGTYECTAVSRAGTGRAKAQIVVTDPPPQLVPAPNVTVSPGETAVLSCR<br>VLGEAPYNLTWVRDWRVLPASTGRVAQLADLSLEISGIIPTDGGRYQCVASNANGVTR<br>ASVWLLVREVPQVSIHTSSQHFSQGVEVKVSCSASGYPTPHISWSRESQALQEDSRIH<br>VDAQGTLIIQGVAPEDAGNYSCQATNEVGTDQETVTLYYTDPPSVSVD |
|---|---|

SEQ ID NO: 47  2058 bp

| NOV9e, 197192437 DNA Sequence | AAGCTTGTGGCAGTGGCCGGGGCGCCCGGGACGGTAATGCCCCCACCACGGGGACG<br>CCACCCTGGCCTTCGTCTTCGACGTCACCGGCTCCATGTGGGACGAACTGATGCAGGT<br>GATCGATGGCGCCTCGCGCATTCTGGAACGCAGTCTGAGCCGCCGCAGCCAGGCCATC<br>GCCAACTACGCGCTGGTGCCCTTCCACGACCCAGATATTGGCCCAGTGACCCTCACGG<br>CGGACCCCACAGTGTTTCAGAGGGAGCTGACAGAACTCTACGTGCAGGGAGGTGGTGA<br>CTGCCCGGAGATGAGTGTGGGGGCCATTAAGGCTGCCGTGGAGGTTGCCAACCCCGGA<br>TCCTTCATCTACGTCTTTTCGGATGCCCGCGCCAAAGACTATCACAAGAAGGAAGAGC<br>TGCTGCGGCTCCTGCAGCTCAACCAATCACAGGTGGTCTTTGTGCTGACGGGGACTG<br>TCCCGACCACACCCATCCTGGCTACCTGCCTTATCAGGAGATCGCTGCCACCACCTCT<br>GGGCAGGTGTTCCACCTGGACAAGCAGCAAGTGACAGAGGTGCTGAAGTGGGTGGAGT<br>CAGCGATCCAGGCCTCCAAGGTGCACCTGCTGTCCACAGACCACGAGGAGGAGGGGGA<br>GCACACATGGAGACTCCCCTTTGACCCCAGCCTGAAGGAGGTCACCATCTCATTGAGT<br>GGGCCAGGGCCTGAGATTGAAGTCCAAGATCCGCTGGGGAGGATCCTGCACGAGGACG<br>AGGGCCTCAACGTGCTTCTCAACATCCCTGACTCGGCCAAGGTCGTAGCCTTTAAGCC<br>TGAGCATCCGGGGCTGTGGTCCATCAAGGTCTATAGCAGTGGCCGCCATTCAGTGAGG<br>ATCACAGGCGTCAGCAACATTGACTTCCGAGCCGGCTTCTCCACTCAGCCCTTGCTGG<br>ACCTCAACCACCCTCGAGTGGCCCTTGCAAGGAGTCCCCATCTCCCTGGTGATCAA<br>TTCCACGGGCCTGAAGGCACCCGGCCGCCTAGACTCGGTGGAGCTGGCACAAAGCTCA<br>GGGAAGCCCCTCCTGACTCTGCCCACGAAGCCCCTCTCCAATGGCTCCACCCATCAGC<br>TGTGGGGCGGGCCGCCCTTCCACACCCCCAAGGAGCGCTTCTACCTCAAGGTGAAGGG<br>CAAGGACCATGAGGGAAACCCCCTCCTTCGTGTCTCTGGAGTGTCCTACAGTGGGGTG<br>GCCCCAGGCGCTCCCCTCGTCAGCATGGCCCCAGGATCCATGGCTACCTGCACCAGC<br>CCCTGCTGGTCTCCTGCTCGGTGCACAGTGCCCTTCCCTTCCGGCTGCAGCTGCGGCG<br>AGGTGAAGCCAGGCTGGGCGAAGAGAGGCACTTTCAGGAGTCGGGAAACAGCAGCTGG |
|---|---|

TABLE 9A-continued

NOV9 Sequence Analysis

```
GAGATCCTGCGGGCCTCCAAGGCCGAGGAGGGCACGTACGAGTGCACAGCCGTCAGCA
GGGCTGGGACCGGGCGAGCAAAGGCCCAGATTGTTGTCACAGACCCCCCGCCGCAGCT
GGTCCCTGCTCCCAACGTGACCGTGTCCCCAGAAGAGACTGCCGTCCTATCCTGCCGG
GTCCTAGGCGAGGCCCCCTACAACCTGACGTGGGTCCGGGACTGGCGAGTCCTGCCGG
CCTCGACGGGCCGAGTTGCCCAGCTGGCTGACCTGTCCCTGGAGATCAGTGGCATCAT
CCCCACAGACGGCGGGAGGTACCAGTGTGTGGCCAGCAATGCCAATGGGGTCACAAGG
GCATCCGTCTGGCTCCTGGTGCGAGAGGCCCCACAGGTCACCATCCACACCAGCTCCC
AGCACTTCTCCCAAGGTGTGGAGGTGAAGGTCAGCTCCTCAGCCTCTGGATACCCCAC
ACCCCACATCTCCTGGAGCCGTGAGAGCCAAGCCCTACAAGAGGACAGCAGAATCCAT
GTGGACGCACAGGGAACCCTGATTATTCAGGGGGTAGCCCCAGAGGATGCTGGGAATT
ACAGCTGCCAGGCGACTAATGAGGTTGGCACTGACCAGGAGACGGTCACCCTCTACGA
CACAGACCCACCGTCGGTCTCTGTCGAC
```

| | |
|---|---|
| | ORF Start: at 1     ORF Stop: end of sequence<br>SEQ ID NO: 48     686 aa MW at 74214.0 kD |
| NOV9e,<br>197192437<br>Protein<br>Sequence | KLVAVAGAPGTVMPPTTGDATLAFVFDVTGSMWDELMQVIDGASRILERSLSRRSQAI<br>ANYALVPFHDPDIGPVTLTADPTVFQRELRELYVQCGCDCPEMSVGAIKAAVEVANPG<br>SFIYVFSDARAKDYHKKEELLRLLQLKQSQVVFVLTGDCGDHTHPGYLAYEEIAATSS<br>GQVFHLDKQQVTEVLKWVESAIQASKVHLLSTDHEEEGEHTWRLPFDPSLKEVTISLS<br>GPGPEIEVQDPLGRILQEDEGLNVLLNIPDSAKVVAFKPEHPGLWSIKVYSSGRHSVR<br>ITGVSNIDFRAGFSTQPLLDLNHTLEWPLQGVPISLVINSTGLKAPGRLDSVELAQSS<br>GKPLLTLPTKPLSNGSTHQLWGGPPFHTPKERFYLKVKGKDHEGNPLLRVSGVSYSGV<br>APGAPLVSMAPRIHGYLHQPLLVSCSVHSALPFRLQLRRGEARLGEERHFQESGNSSW<br>EILRASKAEEGTYECTAVSRAGTGRAKAQIVVTDPPPQLVPAPNVTVSPGETAVLSCR<br>VLGEAPYNLTWVRDWRVLPASTGRVAQLADLSLEISGIIPTDGGRYQCVASNANGVTR<br>ASVWLLVREAPQVSIHTSSQHFSQGVEVKVSCSASGYPTPHISWSRESQALQEDSRIH<br>VDAQGTLIIQGVAPEDAGNYSCQATNEVGTDQETVTLYDTDPPSVSVD |
| | SEQ ID NO: 49     2058 bp |
| NOV9f,<br>197192443<br>DNA<br>Sequence | AAGCTTGTGGCAGTGGCCGGGGCGCCCGGGACGGTAATGCCCCCCACCACGGGGGACG<br>CCACCCTGGCCTTCGTCTTCGACGTCACCGGCTCCATGTGGGACGAACTGATGCAGGT<br>GATCGATGGCGCCTCGCGCATTCTGGAACGCAGTCTCAGCCGCCGCAGCCAGGCCATC<br>GCCAACTACGCGCTGGTGCCCTTCCACGACCCAGATATTGGCCCAGTGACCCTCACGG<br>CGGACCCCACAGTGTTTCAGAGGGAGCTGAGAGAACTCTACGTGCAGGGAGGTGGTGA<br>CTGCCCGGAGATGAGTGTGGGGGCCATTAAGGCTGCCGTGGAGGTTGCCAACCCCGGA<br>TCCTTCATCTACGTCTTTTCGGATGCCCGCGCCAAAGACTATCACAAGAACGAAGAGC<br>TGCTGCGGCTCCTGCAGCTCAAGCAATCACAGGTGGTCTTTGTGCTGACGGGCGACTG<br>TGGCGACCACACCCATCCTGGCTACCTGGCTTATGAGGAGATCGCTGCCACCAGCTCT<br>GGGCAGGTGTTCCACCTGGACAAGCAGCAAGTGACAGAGGTGCTGAAGTGGGTGGAGT<br>CAGCGATCCAGGCCTCCAAGGTGCACCTGCTGTCCACAGACCACGAGGAGGAGGGGGA |

TABLE 9A-continued

NOV9 Sequence Analysis

```
GCACACATGGAGACTCCCCTTTGACCCCAGCCTGAAGGAGGTCACCATCTCATTGAGT
GGGCCAGGGCCTGAGATTGAAGTCCAAGATCCGCTGGGGAGGATCCTGCAGGAGGACG
AGGGCCTCAACGTCCTTCTCAACATCCCTGACTCGGCCAAGGTCGTAGCCTTTAAGCC
TGAGCATCCGGGGCTGTCGTCCATCAAGGTCTATAGCAGTGGCCGCCATTCAGTGAGG
ATCACAGGCGTCAGCAACATTGACTTCCGAGCCCGCTTCTCCACTCAGCCCTTGCTGG
ACCTCAACCACACCCTCGAGTGGCCCTTGCAAGGAGTCCCCATCTCCCTGGTGATCAA
TTCCACGGGCCTGAAGGCACCCGGCCGCCTAGACTCGGTGGAGCTGGCACAAAGCTCA
GGGAAGCCCCTCCTGACTCTGCCCACCAAGCCCCTCTCCAATGGCTCCACCCATCAGC
TGTGGGGCGGGCCGCCCTTCCACACCCCCAAGGAGCGCTTCTACCTCAAGGTGAAGCG
CAAGGACCATGAGGGAAACCCCCTCCTTCGTGTCTCTGGAGTGTCCTACAGTGGGGTG
GCCCCAGGCGCTCCCCTCGTCAGCATGGCCCCAGGATCCATGGCTACCTCCACCAGC
CCCTGCTGGTCTCCTGCTCGGTGCACAGTGCCCTTCCCTTCCGGCTGCAGCTGCGGCG
AGGTGAAGCCAGGCTGGGCGAAGACAGGCACTTTCAGGAGTCGGGAAACAGCAGCTGG
GAGATCCTGCGGGCCTCCAAGGCCGAGGAGGGCACCTACGAGTGCACAGCCGTCAGCA
GGGCTGGGACCGGGCGAGCAAAGGCCCAGATTGTTGTCACAGACCCCCGCCGCAGCT
GGTCCCTGCTCCCAACGTGACCGTGTCCCCAGGGGAGGCTGCCGTCCTATCCTGCCGG
GTCCTAGGCGAGGCCCCCTACAACCTGACGTGGGTCCGGGACTGGCGAGTCCTGCCGG
CCTCGACGGGCCGAGTTGCCCAGCTGGCTGACCTGTCCCTGGAGATCAGTGGCATCAT
CCCCACAGACGGCGGGAGGTACCAGTGTGTGGCCAGCAATGCCAATGGGGTCACAAGG
GCATCCGTCTGGCTCCTGGTGCGAGAGGCCCCACAGGTCAGCATCCACACCAGCTCCC
AGCACTTCTCCCAAGGTGTGGAGGTGAAGGTCAGCTGCTCAGCCTCTGGATACCCCAC
ACCCCACATCTCCTGGAGCCGTGAGAGCCAAGCCCTACAAGAGGACAGCAGAATCCAT
GTGGACGCACAGGGAACCCTGATTATTCAGGGGGTAGCCCCAGAGGATGCTGGGAATT
ACAGCTGCCAGGCGACTAATGACGTTGGCACTGACCAGGAGACGGTCACCCTCTACTA
CACAGACCCACCGTCGGTCTCTGTCCAC
```

| | |
|---|---|
| ORF Start: at 1 | ORF Stop: end of sequence |
| SEQ ID NO: 50 | 686 aa MW at 74232.0 kD |

| NOV9f, 197192443 Protein Sequence | KLVAVAGAPGTVMPPTTGDATLAFVFDVTGSMWDELMQVIDGASRILERSLSRRSQAE ANYALVPFHDPDIGPVTLTADPTVFQRELRELYVQGGGDCPEMSVGAIKAAVEVANPG SFIYVFSDARAKDYHKKEELLRLLQLKQSQVVFVLTGDCGDHTHPGYLAYEEIAATSS GQVFHLDKQQVTEVLKWVESAIQASKVHLLSTDHEEEGEHTWRLPFDPSLKEVTISLS GPGPEIEVQDPLGRILQEDEGLNVLLNIPDSAKVVAFKPEHPGLWSIKVYSSGRHSVR ITGVSNIDFRAGFSTQPLLDLNHTLEWPLQGVPISLVINSTGLKAPGRLDSVELAQSS GKPLLTLPTKPLSNGSTHQLWGGPPFHTPKERFYLKVKGKDHEGNPLLRVSGVSYSGV APGAPLVSMAPRIHGYLHQPLLVSCSVHSALPFRLQLRRGEARLGEERHFQESGNSSW EILRASKAEEGTYECTAVSRAGTGRAKAQIVVTDPPPQLVPAPNVTVSPGEAAVLSCR VLGEAPYNLTNVRDWRVLPASTGRVAQLADLSLEISGIIPTDGGRYQCVASNANGVTR ASVWLLVREAPQVSIHTSSQHFSQGVEVKVSCSASGYPTPHISWSRESQALQEDSRIH |

TABLE 9A-continued

NOV9 Sequence Analysis

VDAQGTLIIQGVAPEDAGNYSCQATNEVGTDQETVTLYYTDPPSVSVD

SEQ ID NO: 51 2058 bp

| | |
|---|---|
| NOV9g, 197192448 DNA Sequence | AAGCTTGTGGCAGTGGCCGGGGCGCCCGGGACGGTAATGCCCCCCACCACGGGGACG<br>CCACCCTGGCCTTCGTCTTCGACGTCACCGGCTCCATGTGGGACGAACTGATGCAGGT<br>GATCGATGGCGCCTCGCGCATTCTGGAACGCAGTCTGAGCCGCCGCAGCCAGGCCATC<br>GCCAACTACGCGCTGGTGCCCTTCCACGACCCAGATATTGGCCCAGTGACCCTCACGG<br>CGGACCCCACAGTGTTTCAGAGGGAGCTGAGAGAACTCTACGTGCAGGGAGGTGGTGA<br>CTGCCCGGAGATGAGTGTGGGGGCCATTAAGGCTGCCGTGGAGGTTGCCAACCCCGGA<br>TCCTTCATCTACGTCTTTTCGGATGCCCGCGCCAAAGACTATCACAAGAACCAAGAGC<br>TGCTGCGGCTCCTGCAGCTCAAGCAATCACAGGTGGTCTTTGTGCTGACGGCGGACTG<br>TGGCGACCACACCCATCCTGGCTACCTGGCTTATGAGGAGATCGCTGCCACCAGCTCT<br>GGGCAGGTGTTCCACCTGGACAACCACCAAGTGACAGAGGTGCTGAAGTGGGTGGAGT<br>CAGCGATCCAGGCCTCCAAGGTGCACCTGCTGTCCACAGACCACGAGGAGGAGGGGGA<br>GCACACATGGAGACTCCCCTTTGACCCCAGCCTGAAGGAGGTCACCATCTCATTGAGT<br>GGGCCAGGGCCTGAGATTGAAGTCCAAGATCCGCTGGGGAGGATCCTGCAGGAGGACG<br>AGGGCCTCAACGTGCTTCTCAACATCCCTGACTCGGCCAAGGTCGTAGCCTTTAAGCC<br>TGAGCATCCGGGGCTGTGGTCCATCAAGGTCTATAGCAGTGGCCGCCATTCAGTGAGG<br>ATCACAGGCGTCAGCAACATTGACTTCCGAGCCGGCTTCTCCACTCAGCCCTTGCTGG<br>ACCTCAACCACACCCTCGAGTGGCCCTTGCAAGGAGTCCCCATCTCCCTGGTGATCAA<br>TTCCACGGGCCTGAAGGCACCCGGCCGCCTAGACTCGGTGGAGCTGGCACAAAGCTCA<br>GGGAAGCCCCTCCTGACTCTGCCCACGAAGCCCCTCTCCAATGGCTCCACCCATCAGC<br>TGTGGGCGGGCCGCCCTTCCACACCCCCAAGGAGCGCTTCTACCTCAAGGTGAAGGG<br>CAAGGACCATGAGGGAAACCCCCTCCTTCGTGTCTCTGGAGTGTCCTACAGTGGGGTG<br>GCCCCAGGCGCTCCCCTCGTCAGCATGGCCCCAGGATCCATGGCTACCTCCACCAGC<br>CCCTGCTCGTCTCCTGCTCGGTGCACAGTGCCCTTCCCTTCCGGCTGCACCTCCGGCG<br>AGGTGAAGCCAGGCTGGGCGAAGAGAGGCACTTTCACGAGTCGGGAAACAGCAGCTGG<br>GAGATCCTGCGGGCCTCCAAGGCCGAGGAGCGCACGTACCAGTGCACAGCCGTCAGCA<br>GGGCTGGGACCGGGCGAGCAAAGGCCCAGATTGTTGTCACAGACCCCCGCCGCAGCT<br>GGTCCCTGCTCCCAACGTGACCGTGTCCCCAGGGGAGACTGCCGTCCTATCCTGCCGG<br>GTCCTAGGCGAGGCCCCCTACAACCTGACGTGGGTCCGGGACTGGCGAGTCCTGCCGG<br>CCTCGACGGGCCGAGTTGCCCAGCTGGCTGACCTGTCCCTGGAGATCAGTGGCATCAT<br>CCCCACAGACGGCGGGAGGTACCAGTGTGTGGCCAGCAATGCCAATCCGGTCACAAGG<br>ACATCCGTCTGGCTCCTGGTGCGAGAGGCCCCACAGGTCAGCATCCACACCAGCTCCC<br>AGCACTTCTCCCAAGGTGTGGAGGTGAACGTCAGCTGCTCAGCCTCTCGATACCCCAC<br>ACCCCACATCTCCTGGAGCCGTGAGAGCCAAGCCCTACAAGAGGACAGCAGAATCCAT<br>GTGGACGCACAGGGAACCCTGATTATTCAGGGGGTAGCCCCAGAGGATCCTGGGAATT<br>ACAGCTGCCAGGCGACTAATGAGGTTGGCACTGACCAGGAGACGGTCACCCTCTACTA<br>CACAGACCCACCGTCGGTCTCTGTCGAC |

TABLE 9A-continued

NOV9 Sequence Analysis

ORF Start: at 1  ORF Stop: end of sequence
SEQ ID NO: 52    686 aa MW at 74292.1 kD NOV9g, 197192448 Protein Sequence

KLVAVAGAPGTVMPPTTGDATLAFVFDVTGSMWDELMQVIDGASRILERSLSRRSQAI

ANYALVPFHDPDIGPVTLTADPTVFQRELRELYVQGGGDCPEMSVGAIKAAVEVANPG

SFIYVFSDARAKDYHKKEELLRLLQLKQSQVVFVLTGDCGDHTHPGYLAYEEIAATSS

GQVFHLDKQQVTEVLKWVESAIQASKVHLLSTDHEEEGEHTWRLPFDPSLKEVTISLS

GPGPEIEVQDPLGRILQEDEGLNVLLNIPDSAKVVAFKPEHPGLWSIKVYSSGRHSVR

ITGVSNIDFRAGFSTQPLLDLNHTLEWPLQGVPISLVINSTGLKAPGRLDSVELAQSS

GKPLLTLPTKPLSNGSTHQLWGGPPFHTPKERFYLKVKGKDHEGNPLLRVSGVSYSGV

APGAPLVSMAPRIHGYLHQPLLVSCSVHSALPFRLQLRRGEARLGEERHFQESGNSSW

EILRASKAEEGTYECTAVSRAGTGRAKAQIVVTDPPPQLVPAPNVTVSPGETAVLSCR

VLGEAPYNLTWVRDWRVLPASTGRVAQLADLSLEISGIIPTDGGRYQCVASNANGVTR

TSVWLLVREAPQVSIHTSSQHFSQGVEVKVSCSASGYPTPHISWSRESQALQEDSRIH

VDAQGTLIIQGVAPEDAGNYSCQATNEVGTDQETVTLYYTDPPSVSVD

Sequence comparison of the above protein sequences yields the following sequence relationships shown in Table 9B.

TABLE 9B

Comparison of NOV9a against NOV9b through NOV9g.

| Protein Sequence | NOV9a Residues/ Match Residues | Identities/ Similarities for the Matched Region |
|---|---|---|
| NOV9b | 1 . . . 204 | 166/204 (81%) |
|  | 1 . . . 204 | 166/204 (81%) |
| NOV9c | 80 . . . 133 | 15/54 (27%) |
|  | 28 . . . 71 | 21/54 (38%) |
| NOV9d | 20 . . . 262 | 217/243 (89%) |
|  | 3 . . . 245 | 217/243 (89%) |
| NOV9e | 20 . . . 262 | 217/243 (89%) |
|  | 3 . . . 245 | 217/243 (89%) |
| NOV9f | 20 . . . 262 | 217/243 (89%) |
|  | 3 . . . 245 | 217/243 (89%) |
| NOV9g | 20 . . . 262 | 217/243 (89%) |
|  | 3 . . . 245 | 217/243 (89%) |

Further analysis of the NOV9a protein yielded the following properties shown in Table 9C.

TABLE 9C

Protein Sequence Properties NOV9a

| PSort analysis: | 0.8200 probability located in outside; 0.1000 probability located in endoplasmic reticulum (membrane); 0.1000 probability located in endoplasmic reticulum (lumen); 0.1000 probability located in lysosome (lumen) |
|---|---|
| SignalP analysis: | Cleavage site between residues 17 and 18 |

A search of the NOV9a protein against the Geneseq database, a proprietary database that contains sequences published in patents and patent publication, yielded several homologous proteins shown in Table 9D.

TABLE 9D

Geneseq Results for NOV9a

| Geneseq Identifier | Protein/Organism/Length [Patent #, Date] | NOV9a Residues/ Match Residues | Identities/ Similarities for the Matched Region | Expect Value |
|---|---|---|---|---|
| AAB83147 | Rat secreted factor encoded by clone P00210D09 - Rattus sp, 275 aa. [WO200123419-A2, 05-APR-2001] | 1 . . . 271 1 . . . 272 | 231/272 (84%) 241/272 (87%) | e−129 |
| AAY53667 | Sequence gi/3328186 from an alignment with protein 608 - Unidentified, 3117 aa. [WO9960164-A1, 25-NOV-1999] | 34 . . . 262 32 . . . 265 | 119/234 (50%) 168/234 (70%) | 1e−64 |

TABLE 9D-continued

Geneseq Results for NOV9a

| Geneseq Identifier | Protein/Organism/Length [Patent #, Date] | NOV9a Residues/ Match Residues | Identities/ Similarities for the Matched Region | Expect Value |
|---|---|---|---|---|
| AAU75886 | Human adhesion molecule protein AD4/AAD21820.1 - *Homo sapiens*, 852 aa. [WO200208423-A2, 31-JAN-2002] | 311 . . . 547 | 119/239 (49%) | 1e−21 |
| AAU75884 | Human adhesion molecule protein AD2/G7c - *Homo sapiens*, 536 aa. [WO200208423-A2, 31-JAN-2002] | 34 . . . 263<br>13 . . . 249 | 72/239 (30%)<br>119/239 (49%) | 1e−21 |
| AAM79854 | Human protein SEQ ID NO: 3500 - *Homo sapiens*, 836 aa. [WO200157190-A2, 09-AUG-2001] | 34 . . . 263<br>311 . . . 547 | 72/239 (30%)<br>119/239 (49%) | 1e−21 |

In a BLAST search of public sequence datbases, the NOV9a protein was found to have homology to the proteins shown in the BLASTP data in Table 9E.

TABLE 9E

Public BLASTP Results for NOV9a

| Protein Accession Number | Protein/Organism/Length | NOV9a Residues/ Match Residues | Identities/ Similarities for the Matched Portion | Expect Value |
|---|---|---|---|---|
| CAC37763 | SEQUENCE 2 FROM PATENT WO0123419 - *Rattus norvegicus* (Rat), 275 aa. | 1 . . . 271<br>1 . . . 272 | 231/272 (84%)<br>241/272 (87%) | e−128 |
| Q96RW7 | HEMICENTIN - *Homo sapiens* (Human), 5636 aa. | 35 . . . 262<br>38 . . . 265 | 169/228 (74%)<br>199/228 (87%) | 3e−97 |
| T20992 | hypothetical protein F15G9.4a - *Caenorhabditis elegans*, 5175 aa. | 34 . . . 262<br>32 . . . 265 | 119/234 (50%)<br>168/234 (70%) | 3e−64 |
| O76518 | HEMICENTIN PRECURSOR - *Caenorhabditis elegans*, 5198 aa. | 34 . . . 262<br>32 . . . 265 | 119/234 (50%)<br>168/234 (70%) | 3e−64 |
| Q96QC8 | G7C PROTEIN - *Homo sapiens* (Human), 852 aa. | 34 . . . 263<br>311 . . . 547 | 72/239 (30%)<br>119/239 (49%) | 3e−21 |

PFam analysis predicts that the NOV9a protein contains the domains shown in the Table 9F.

TABLE 9F

Domain Analysis of NOV9a

| Pfam Domain | NOV9a Match Region | Identities/ Similarities for the Matched Region | Expect Value |
|---|---|---|---|

Example 10

The NOV10 clone was analyzed, and the nucleotide and encoded polypeptide sequences are shown in Table 10A.

TABLE 10A

NOV10 Sequence Analysis

| | SEQ ID NO: 53 | 621 bp |
|---|---|---|
| NOV10a, CG102942-01 DNA Sequence | <u>ATC</u>ATGCCCCTAGGTCTCCTGTGGCTGGGCCTAGCCCTGTTGGGGGCTCTGCATGCCC<br>AGGCCCAGGACTCCACCTCAGACCTGATCCCAGCCCCACCTCTGAGCAAGGTCCCTCT<br>GCAGCAGAACTTCCAGGACAACCAATTCCAGGGGAAGTGGTATGTGGTAGGCCTGGCA | |

TABLE 10A-continued

NOV10 Sequence Analysis

```
GGGAATGCAATTCTCAGAGAAGACAAAGACCCGCAAAAGATGTATGCCACCATCTATG
AGCTGAAAGAAGACAAGAGCTACAATGTCACCTCCGTCCTGTTTAGGAAAAAGAAGTG
TGACTACTGGATCAGGACTTTTGTTCCAGGTTGCCAGCCCGGCGAGTTCACGCTGGGC
AACATTAAGAGTTACCCTGGATTAACGAGTTACCTCGTCCGAGTGGTGAGCACCAACT
ACAACCAGCATGCTATGGTGTTCTTCAAGAAAGTTTCTCAAAACAGGGAGTACTTCAA
GATCACCCTCTACGGTAGAACCAAGGAGCTGACTTCGGAACTAAAGGAGAACTTCATC
CGCTTCTCCAAATCTCTGGGCCTCCCTGAAAACCACATCGTCTTCCCTGTCCCAATCG
GTAATGGCCAGTCTGGATGAGGGGACGGGGACATGGGACT
```

| | | |
|---|---|---|
| | ORF Start: ATG at 4 | ORF Stop: TGA at 598 |
| | SEQ ID NO: 54 | 198 aa    MW at 22456.7 kD |

| NOV10a, CG102942-01 Protein Sequence | MPLGLLWLGLALLGALHAQAQDSTSDLIPAPPLSKVPLQQNFQDNQFQGKWYVVGLAG<br>NAILREDKDPQKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKELTSELKENFIR<br>FSKSLGLPENHIVFPVPIGNGQSG |

| | SEQ ID NO: 55 | 609 bp |
|---|---|---|

| NOV10b, CG102942-03 DNA Sequence | ATCATGCCCCTAGGTCTCCTGTGGCTGGGCCTAGCCCTGTTGGGGGCTCTGCATGCCC<br>AGGCCCAGGACTCCACCTCAGACCTGATCCCAGCCCCACCTCTGAGCAAGGTCCCTCT<br>GCAGCAGAACTTCCAGGACAACCAATTCCAGGGGAAGTGGTATGTGGTAGGCCTGGCA<br>GGCAATGCAATTCTCAGAGAAGACAAAGACCCGCAAAAGATGTATGCCACCATCTATG<br>AGCTGAAAGAAGACAAGAGCTACAATGTCACCTCCGTCCTGTTTAGGAAAAAGAAGTG<br>TGACTACTGGATCAGGACTTTTGTTCCAGGTTGCCAGCCCGGCGAGTTCACGCTGGGC<br>AACATTAAGAGTTACCCTGGATTAACGAGTTACCTCGTCCGAGTGGTGAGCACCAACT<br>ACAACCAGCATGCTATGGTGTTCTTCAAGAAAGTTTCTCAAAACAGGGAGTACTTCAA<br>GATCACCCTCTACGGAGAACCAAGGAGCTGACTTCGGAACTAAAGGAGAACTTCATC<br>CGCTTCTCCAAATCTCTGGGCCTCCCTGAAAACCACATCGTCTTCCCTGTCCCAATCG<br>GTAATGGCCAGTCTGGATGAGGGGACGGG |

| | ORF Start: ATG at 4 | ORF Stop: TGA at 598 |
|---|---|---|
| | SEQ ID NO: 56 | 198 aa    MW at 22456.7 kD |

| NOV10b, CG102942-03 Protein Sequence | MPLGLLWLGLALLGALHAQAQDSTSDLIPAPPLSKVPLQQNFQDNQFQGKWYVVGLAG<br>NAILREDKDPQKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKELTSELKENFIR<br>FSKSLGLPENHIVFPVPIGNGQSG |

| | SEQ ID NO: 57 | 477 bp |
|---|---|---|

| NOV10c, 237376776 DNA Sequence | CGCGGATCCCAATTCCAGGGGAAGTGGTATGTGGTAGGCCTGGCAGGGAATGCAATTC<br>TCAGAGGAGACAAAGACCCGCAAAAGATGTATGCCACCATCTATGAGCTGAAAGAAGA<br>CAAGAGCTACAATGTCACCTCCGTCCTGTTTAGGAAAAAGAAGTGTGACTACTGGATC<br>AGGACTTTTGTTCCAGGTTGCCAGCCCGGCGAGTTCACGCTGGGCAACATTAAGAGTT |

TABLE 10A-continued

NOV10 Sequence Analysis

ACCCTGGATTAACGAGTTACCTCGTCCGAGTGGTGAGCACCAACTACAACCAGCATGC

TATGGTGTTCTTCAAGAAAGTTTCTCAAAACAGGGAGTACTTCAAGATCACCCTCTAC

GGGAGAACCAAGGAGCTGACTTCGGAACTAAAGGAGAACTTCATCCGCTTCTCCAAAT

CTCTGGGCCTCCCTGAAAACCACATCGTCTTCCCTGTCCCAATCGGTAATGGCCAGTC

TGGACTCGAGGCG

| | | |
|---|---|---|
| | ORF Start: at 1<br>SEQ ID NO: 58 | ORF Stop: end of sequence<br>159 aa    MW at 18222.8 kD |
| NOV10c,<br>237376776<br>Protein<br>Sequence | RGSQFQGKWYVVGLAGNAILRGDKDPQKMYATIYELKEDKSYNVTSVLFRKKKCDYWI<br>RTFVPGCQPGEFTLGNIKSYPGLTSYLVRVVSTNYNQHAMVFFKKVSQNREYFKITLY<br>GRTKELTSELKENFIRFSKSLGLPENHIVFPVPIGNGQSGLEA | |

Sequence comparison of the above protein sequences yields the following sequence relationships shown in Table 10B.

TABLE 10B

Comparison of NOV10a against NOV10b and NOV10c.

| Protein Sequence | NOV10a Residues/<br>Match Residues | Identities/Similarities<br>for the Matched Region |
|---|---|---|
| NOV10b | 19 . . . 198 | 180/180 (100%) |
| | 19 . . . 198 | 180/180 (100%) |
| NOV10c | 45 . . . 198 | 152/154 (98%) |
| | 3 . . . 156 | 153/154 (98%) |

Further analysis of the NOV10a protein yielded the following properties shown in Table 10C.

TABLE 10C

Protein Sequence Properties NOV10a

| | |
|---|---|
| PSort<br>analysis: | 0.4658 probability located in outside; 0.1134 probability located in microbody (peroxisome); 0.1000 probability located in endoplasmic reticulum (membrane); 0.1000 probability located in endoplasmic reticulum (lumen) |
| SignalP<br>analysis: | Cleavage site between residues 21 and 22 |

A search of the NOV10a protein against the Geneseq database, a proprietary database that contains sequences published in patents and patent publication, yielded several homologous proteins shown in Table 10D.

TABLE 10D

Geneseq Results for NOV10a

| Geneseq<br>Identifier | Protein/Organism/Length<br>[Patent #, Date] | NOV10a<br>Residues/<br>Match<br>Residues | Identities/<br>Similarities for<br>the Matched<br>Region | Expect<br>Value |
|---|---|---|---|---|
| AAG74315 | Human colon cancer antigen<br>protein SEQ ID NO: 5079 - *Homo<br>sapiens*, 254 aa. [WO200122920-<br>A2, 05-APR-2001] | 1 . . . 192<br>57 . . . 248 | 192/192 (100%)<br>192/192 (100%) | e−110 |
| AAY71470 | Human neutrophil gelatinase<br>associated protein (NGAL) -<br>*Homo sapiens*, 198 aa.<br>[WO200029576-A1, 25-MAY-2000] | 1 . . . 192<br>1 . . . 192 | 192/192 (100%)<br>192/192 (100%) | e−110 |
| AAB43668 | Human cancer associated protein<br>sequence SEQ ID NO: 1113 -<br>*Homo sapiens*, 254 aa.<br>[WO200055350-A1, 21-SEP-2000] | 1 . . . 192<br>57 . . . 248 | 192/192 (100%)<br>192/192 (100%) | e−110 |
| AAW49088 | Human NGAL protein - *Homo<br>sapiens*, 197 aa. [WO9830907-A1,<br>16-JUL-1998] | 1 . . . 192<br>1 . . . 191 | 189/192 (98%)<br>190/192 (98%) | e−107 |
| AAW18203 | Human NGAL protein - *Homo<br>sapiens*, 197 aa. [US5627034-A,<br>06-MAY-1997] | 1 . . . 192<br>1 . . . 191 | 189/192 (98%)<br>190/192 (98%) | e−107 |

In a BLAST search of public sequence datbases, the NOV10a protein was found to have homology to the proteins shown in the BLASTP data in Table 10E.

TABLE 10E

Public BLASTP Results for NOV10a

| Protein Accession Number | Protein/Organism/Length | NOV10a Residues/ Match Residues | Identities/ Similarities for the Matched Portion | Expect Value |
|---|---|---|---|---|
| P80188 | Neutrophil gelatinase-associated lipocalin precursor (NGAL) (P25) (25 kDa alpha-2-microglobulin-related subunit of MMP-9) (Lipocalin 2) (Oncogene 24p3) - Homo sapiens (Human), 198 aa. | 1 . . . 192<br>1 . . . 192 | 192/192 (100%)<br>192/192 (100%) | e−110 |
| JC2339 | neutrophil gelatinase-associated lipocalin precursor - human, 197 aa. | 1 . . . 192<br>1 . . . 191 | 189/192 (98%)<br>190/192 (98%) | e−107 |
| Q9QVP7 | NEU-RELATED LIPOCALIN- Rattus sp, 198 aa. | 1 . . . 191<br>1 . . . 191 | 121/191 (63%)<br>150/191 (78%) | 1e−66 |
| P30152 | Neutrophil gelatinase-associated lipocalin precursor (NGAL) (P25) (Alpha-2-microglobulin-related protein) (Alpha-2U globulin-related protein) (Lipocalin 2) - Rattus norvegicus (Rat), 198 aa. | 1 . . . 191<br>1 . . . 191 | 120/191 (62%)<br>148/191 (76%) | 1e−65 |
| Q60842 | CHROMOSOME 24P3 - Mus musculus (Mouse), 283 aa (fragment). | 1 . . . 194<br>8 . . . 203 | 119/196 (60%)<br>154/196 (77%) | 3e−64 |

PFam analysis predicts that the NOV10a protein contains the domains shown in the Table 10F.

TABLE 10F

Domain Analysis of NOV10a

| Pfam Domain | NOV10a Match Region | Identities/ Similarities for the Matched Region | Expect Value |
|---|---|---|---|
| lipocalin | 46 . . . 189 | 42/152 (28%)<br>115/152 (76%) | 5.4e−34 |

Example 11

The NOV11 clone was analyzed, and the nucleotide and encoded polypeptide sequences are shown in Table 11A.

TABLE 11A

NOV11 Sequence Analysis

SEQ ID NO: 59    2210 bp

NOV11a, CG104016-01 DNA Sequence

ATGACAATTTTAAGAGTGTTTAACCAAGACTGTTCCTTTAAATGTGTTCTTTTGCTGC

TGTTTAATTATACATGTCAATTATTTACAGATCCTGTGGTATTGTGGAAATTCCCAGA

GGACTTTGGAGACCAGGAAATACTACAGAGTGTGCCAAAGTTCTGTTTTCCCTTTGAC

GTTGAAAGGTACAGTATAAGTCAAGTTGGACAGCACTTTACCTTTGTACTGACAGACA

TTGAAAGTAAACAGAGATTTGGATTCTGCAGACTGACGTCAGGAGGCACAATTTGTTT

ATGCATCCTTAGTTACCTTCCCTGGTTTGAAGTGTATTACAAGCTTCTAAATACTCTT

GCAGATTACTTGGCTAAGCATTCCTACTTCATTGCCCCTGATGTAACTGGACTCCCAA

CAATACCCGAGAGTAGAAATCTTACAGAATATTTTGTTGCCGTGGATGTGAACAACAT

GCTGCAGCTGTATGCCAGTATGCTGCATGAAAGGCGCATCGTGATTATCTCGAGCAAA

TTAAGCACTTTAACTGCCTGTATCCATGGATCAGCTGCTCTTCTATACCCAATGTATT

GGCAACACATATACATCCCAGTGCTTCCTCCACACCTGCTGGACTACTGCAGTGCCCC

TABLE 11A-continued

NOV11 Sequence Analysis

AATGCCATACCTGATTGGAATACACTCCAGCCTCATAGAGAGTGAAAAACAAATCA
TTGGAAGATGTTGTTATGTTAAATGTTGATACAAACACATTAGAATCACCATTTAGTG
ACTTGAACAACCTACCAAGTGATGTGGTAAGTGCCTTGAAAAATAAACTGAAGAAGCA
GTCTACAGCTACGGGTGATGGAGTAGCTAGGGCCTTTCTTAGAGCACAGGCTGCTTTG
TTTGGATCCTACAGAGATGCACTGAGATACAAACCTGGTGAGCCCATCACTTTCTGTG
AGGAGAGTTTTGTAAAGCACCGCTCAAGCGTGATGAAACAGTTCCTGGAAACTGCCAT
TAACCTCCAGCTTTTTAAGCAGGTATTTATCGATGGTCGACTGGCAAAACTAAATGCA
GGAAGGGGTTTCTCTGATGTATTTGAAGAAGAGATCACTTCAGGTGGCTTTTGTGGAG
GTAAAGACAAGTTACAATATAAATATGTTTCTGTTTTTCTTTTGCAGAAAGGAGGTGC
ACTGTTCAACACAGCAATGACCAAAGCAACCCCTGCTGTACGGACAGCATATAAATTT
GCAAAAAATCATGCAAAGCTGGGACTAAAGGAAGTGAAGAGTAAACTAAAACACAAGG
AAAATGAAGAAGATTATGGGACCTGTTCTAGTTCTGTACAATATACACCAGTTTACAA
ATTACACAATGAAAAGGGAGGAAACTCAGAAAAGCGTAAGCTTGCTCAGGCACGCTTA
AAAAGGCCTCTTAAGAGCCTTGATGGTGCTCTATATGATGATGAAGATGATGATGACA
TTGAAAGAGCAAGCAAGTTATCTTCTGAAGATGGTGAAGAAGCTTCTGCTTATCTCTA
TGAGAGTGATGACTCTGTTGAAACAAGAGTGAAGACTCCTTACTCAGGTGAAATGGAC
TTACTAGGAGAGATTCTTGATACATTGAGCACACACAGCTCAGATCAGGGGAAGCTGG
CAGCTGCAAAGAGCTTGGATTTCTTTAGATCAATGGATGACATTGATTACAAACCTAC
GAATAAATCTAATGCTCCTAGTGAGAATAACCTGGCTTTCCTCTGTGGTGGTTCTGGT
GACCAAGCACAGTGGAATCTTGGGCAAGACGATAGTGCCCTCCATGGCAAACACCTCC
CTCCATCTCCTAGGAAGCGGGTTTCCTCTAGTGGTTTGACAGATTCTCTGTTTATCCT
GAGAGAGGAAAACAGTAACAAGCACCTCGGTGCTGACAATGTGAGTGACCCTACTTCA
GGACTGGATTTCCAACTCACTTCCCCTGAAGTTTCCCAGACTGATAAAGGAAAAACAG
AAAAGAGGGAAACACTAAGCCAGATTTCAGATGATCTGCTTATACCCGGTCTTGGGCG
GCATTCATCGACTTTTGTTCCTTGGGAGAAAGAAGGGAAAGAAGCCAAAGAGACTTCA
GAAGATATTGGACTGCTCCATGAAGTAGTGTCATTATGTCATATGACATCTGACTTCC
AACAAAGCTTGAACATTTCAGACAAAAACACAAATGGAAACCAAACTTAA<ins>ATCTTGCA</ins>
<ins>TCCAAG</ins>

| | |
|---|---|
| | ORF Start: ATG at 1     ORF Stop: TAA at 2194 <br> SEQ ID NO: 60     731 aa    MW at 81769.5 kD |
| NOV11a, CG104016-01 Protein Sequence | MTILRVFNQDCSFKCVLLLLFNYTCQLFTDPVVLWKFPEDFGDQEILQSVPKFCFPFD <br> VERYSISQVGQHFTFVLTDIESKQRFGFCRLTSGGTICLCILSYLPWFEVYYKLLNTL <br> ADYLAKHSYFIAPDVTGLPTIPESRNLTEYFVAVDVNNMLQLYASMLHERRIVIISSK <br> LSTLTACIHGSAALLYPMYWQHIYIPVLPPHLLDYCSAPMPYLIGIHSSLIERVKNKS <br> LEDVVMLNVDTNTLESPFSDLNNLPSDVVSALKNKLKKQSTATGDVARAFLRAQAAL <br> FGSYRDALRYKPGEPITFCEESFVKHRSSVMKQFLETAINLQLFKQVFIDGRLAKLNA <br> GRGFSDVFEEEITSGGFCGGKDKLQYKYVSVFLLQKGGALFNTAMTKATPAVRTAYKF <br> AKNHAKLGLKEVKSKLKHKENEEDYGTCSSSVQYTPVYKLHNEKGGNSEKRKLAQARL |

TABLE 11A-continued

NOV11 Sequence Analysis

KRPLKSLDGALYDDEDDDDIERASKLSSEDGEEASAYLYESDDSVETRVKTPYSGEMD

LLGEILDTLSTHSSDQGKLAAAKSLDFFRSMDDIDYKPTNKSNAPSENNLAFLCGGSG

DQAEWNLGQDDSALHGKHLPPSPRKRVSSSGLTDSLFILREENSNKHLGADNVSDPTS

GLDFQLTSPEVSQTDKGKTEKRETLSQISDDLLIPGLGRHSSTFVPWEKEGKEAKETS

EDIGLLHEVVSLCHMTSDFQQSLNISDKNTNGNQT

| | SEQ ID NO: 61 | 2256 bp |
|---|---|---|
| NOV11b, 197208336 DNA Sequence | AGATCTGATCCTGTGGTATTGTGGAAATTCCCAGAGGACTTTGGAGACCAGGAAATAC TACAGAGTGTGCCAAAGTTCTGTTTTCCCTTTGACGTTGAAAGGGTGTCTCAGAATCA AGTTGGACAGCACTTTACCTTTGTACTGACAGACATTGAAAGTAAACAGAGATTTGGA TTCTGCAGACTGACGTCAGGAGGCACAATTTGTTTATGCATCCTTAGTTACCTTCCCT GGTTTGAAGTGTATTACAAGCTTCTAAATACTCTTGCAGATTACTTGGCTAAGGAACT GGAAAATGATTTGAATGAAACTCTCAGATCACTGTATAACCACCCAGTACCAAAGGCA AATACTCCTGTAAATTTGAGTGTGAACCAAGAGATATTTATTACCTGTGAGCAAGTTC TGAAAGATCAGCCTGCTCTACTACCGCATTCCTACTTCATTGCCCCTGATGTAACTGG ACTCCCAACAATACCCGAGAGTAGAAATCTTACAGAATATTTTGTTGCCGTGGATGTG AACAACATGCTGCAGCTGTATGCCAGTATGCTGCATGAAAGGCGCATCGTGATTATCT CGAGCAAATTAAGCACTTTAACTGCCTGTATCCATGGATCAGCTGCTCTTCTATACCC AATGTATTGGCAACACATATACATCCCAGTGCTTCCTCCACACCTGCTGGACTACTGC TGTGCCCCAATGCCATACCTGATTGGAATACACTCCAGCCTCATAGAGAGAGTGAAAA ACAAATCATTGGAAGATGTTGTTATGTTAAATGTTGATACAAACACATTAGAATCACC ATTTAGTGACTTGAACAACCTACCAAGTGATGTGGTCTCGGCCTTGAAAAATAAACTG AAGAAGCAGTCTACAGCTACGGGTGATGGAGTAGCTAGGGCCTTTCTTAGAGCACAGG CTGCTTTGTTTGGATCCTACAGAGATGCACTGAGATACAAACCTGGTGAGCCCATCAC TTTCTGTGAGGAGAGTTTTGTAAAGCACCGCTCAAGCGTGATGAAACAGTTCCTGGAA ACTGCCATTAACCTCCAGCTTTTTAAGCAGTTTATCGATGGTCGACTGGCAAAACTAA ATGCAGGAAGGGGTTTCTCTGATGTATTTGAAGAAGAGATCACTTCAGGTGGCTTTTG TGGAGGGAACCCGAGGTCATATCAACAATGGGTGCATACAGTCAAGAAAGGAGGTGCA CTGTTCAACACAGCAATGACCAAAGCAACCCCTGCTGTACGGACAGCATATAAATTTG CAAAAAATCATGCAAAGCTGGGACTAAAGGAAGTGAAGAGTAAACTAAAACACAAGGA AAATGAAGAAGATTATGGGACCTGTTCTAGTTCTGTACAATATACACCAGTTTACAAA TTACACAATGAAAAGGGAGGAAACTCAGAAAAGCGTAAGCTTGCTCAGGCACGCTTAA AAAGGCCTCTTAAGAGCCTTGATGGTGCTCTATATGATGATGAAGATGATGATGACAT TGAAAGAGCAAGCAAGTTATCTTCTGAAGATGGTGAAGAAGCTTCTGCTTATCTCTAT GAGAGTGATGACTCTGTTGAAACAAGAGTGAAGACTCCTTACTCAGGTGAAATGGACT TACTAGGAGAGATTCTTGATACATTGAGCACACACAGCTCAGATCAGGGGAGGCTGGC AGCTGCAAAGAGCTTGGATTTCTTTAGATCAATGGACGACATTGATTACAAACCTACG AATAAATCTAATGCTCCAGTGAGAATAACCTGGCTTTCCTCTGTGGTGGTTCTGGTG ACCAAGCAGAGTGGAATCTTGGGCAAGACGATAGTGCCCTCCATGGCAAACACCTCCC |

TABLE 11A-continued

NOV11 Sequence Analysis

|  |  |
|---|---|
|  | TCCATCTCCTAGGAAGCGGGTTTCCTCTAGTGGTTTGACAGATTCTCTGTTTATCCTG |
|  | AAAGAGGAAAACAGTAACAAGCACCTCGGTGCTGACAATGTGAGTGACCCTACTTCAG |
|  | GACTGGATTTCCAACTCACTTCCCCTGAAGTTTCCCAGACTGATAAAGGAAAAACAGA |
|  | AAAGAGGGAAACACTAAGCCAGATTTCAGATGATCTGCTTATACCCGGTCTTGGGCGG |
|  | CATTCATCGACTTTTGTTCCTTGGGAGAAAGAAGGGAAAGAAGCCAAAGAGACTTCAG |
|  | AAGATATTGGACTGCTCCATGAACTAGTGTCATTATGTCATATGACATCTGACTTCCA |
|  | ACAAAGCTTGAACATTTCAGACAAAAACACAAATGGAAACCAAACTAGATCT |

|  | ORF Start: at 1 | ORF Stop: end of sequence |
|---|---|---|
|  | SEQ ID NO: 62 | 752 aa    MW at 84005.6 kD |

| NOV11b, 197208336 Protein Sequence | RSDPVVLWKFPEDFGDQEILQSVPKFCFPFDVERVSQNQVGQHFTFVLTDIESKQRFG |
|---|---|
|  | FCRLTSGGTICLCILSYLPWFEVYYKLLNTLADYLAKELENDLNETLRSLYNHPVPKA |
|  | NTPVNLSVNQEIFITCEQVLKDQPALLPHSYFIAPDVTGLPTIPESRNLTEYFVAVDV |
|  | NNMLQLYASMLHERRIVIISSKLSTLTACIHGSAALLYPMYWQHIYIPVLPPHLLDYC |
|  | CAPMPYLIGIHSSLIERVKNKSLEDVVMLNVDTNTLESPFSDLNNLPSDVVSALKNKL |
|  | KKQSTATGDGVARAFLRAQAALFGSYRDALRYKPGEPITFCEESFVKHRSSVMKQFLE |
|  | TAINLQLFKQFIDGRLAKLNAGRGFSDVFEEEITSGGFCGGNPRSYQQWVHTVKKGGA |
|  | LFNTAMTKATPAVRTAYKFAKNHAKLGLKEVKSKLKHKENEEDYGTCSSSVQYTPVYK |
|  | LHNEKGGNSEKRKLAQARLKRPLKSLDGALYDDEDDDDIERASKLSSEDGEEASAYLY |
|  | ESDDSVETRVKTPYSGEMDLLGEILDTLSTHSSDQGRLAAAKSLDFFRSMDDIDYKPT |
|  | NKSNAPSENNLAFLCGGSGDQAEWNLGQDDSALHGKHLPPSPRKRVSSSGLTDSLFIL |
|  | KEENSNKHLGADNVSDPTSGLDFQLTSPEVSQTDKGKTEKRETLSQISDDLLIPGLGR |
|  | HSSTFVPWEKEGKEAKETSEDIGLLHEVVSLCHMTSDFQQSLNISDKNTNGNQTRS |

|  | SEQ ID NO: 63 | 2256 bp |
|---|---|---|

| NOV11c, 197306179 DNA Sequence | AGATCTGATCCTGTGGTATTGTGGAAATTCCCAGAGGACTTTGGAGACCAGGAAATAC |
|---|---|
|  | TACAGAGTGTGCCAAAGTTCTGTTTTCCCTTTGACGTTGAAAGGGTGTCTCAGAATCA |
|  | AGTTGGACAGCACTTTACCTTTGTACTGACAGACATTGAAAGTAAACAGAGATTTGGA |
|  | TTCTGCAGACTGACGTCAGGAGGCACAATTTGTTTATGCATCCTTAGTTACCTTCCCT |
|  | GGTTTGAAGTGTATTACAAGCTTCTAAATACTCTTGCAGATTACTTGGCTAAGGAACT |
|  | GGAAAATGATTTGAATGAAACTCTCAGATCACTGTATAACCACCCAGTACCAAAGGCA |
|  | AATACTCCTGTAAATTTGAGTGTGAACCAAGAGATATTTATTACCTGTGAGCAAGTTC |
|  | TGAAAGATCAGCCTGCTCTACTACCGCATTCCTACTTCATTGCCCCTGATGTAACTGG |
|  | ACTCCCAACAATACCCGAGAGTAGAAATCTTACAGAATATTTTGTTGCCGTGGATGTG |
|  | AACAACATGCTGCAGCTGTATGCCAGTATGCTGCATGAAAGGCGCATCGTGATTATCT |
|  | CGAGCAAATTAAGCACTTTAACTGCCTGTATCCATGGATCAGCTGCTCTTCTATACCC |
|  | AATGTATTGGCAACACATATACATCCCAGTGCTTCCTCCACACCTGCTGGACTACTGC |
|  | TGTGCCCCAATGCCATACCTGATTGGAATACACTCCAGCCTCATAGAGAGAGTGAAAA |
|  | ACAAATCATTGGAAGATGTTGTTATGTTAAATGTTGATACAAACACATTAGAATCACC |
|  | ATTTAGTGACTTGAACAACCTACCAAGTGATGTGGTCTCGGCCTTGAAAAATAAACTG |

TABLE 11A-continued

NOV11 Sequence Analysis

AAGAAGCAGTCTACAGCTACGGGTGATGGAGTAGCTAGGGCCTTTCTTAGAGCACAGG
CTGCTTTGTTTGGATCCTACAGAGATGCACTGAGATACAAACCTGGTGAGCCCATCAC
TTTCTGTGAGGAGAGTTTTGTAAAGCACCGCTCAAGCGTGATGAAACAGTTCCTGGAA
ACTGCCATTAACCTCCAGCTTTTTAAGCAGTTTATCGATGGTCGACTGGCAAAACTAA
ATGCAGGAAGGGGTTTCTCTGATGTATTTGAAGAAGAGATCACTTCAGGTGGCTTTTG
TGGAGGGAACCCGAGGTCATATCAACAATGGGTGCATACAGTCAAGAAAGGAGGTGCA
CTGTTCAACACAGCAATGACCAAAGCAACCCCTGCTGTACGGACAGCATATAAATTTG
CAAAAAATCATGCAAAGCTGGGACTAAAGGAAGTGAAGAGTAAACTAAAACACAAGGA
AAATGAAGAAGATTATGGGACCTGTTCTAGTTCTGTACAATATACACCAGTTTACAAA
TTACACAATGAAAAGGGAGGAAACTCAGAAAAGCGTAAGCTTGCTCAGGCACGCTTAA
AAAGGCCTCTTAAGAGCCTTGATGGTGCTCTATATGATGATGAAGATGATGATGACAT
TGAAAGAGCAAGCAAGTTATCTTCTGAAGATGGTGAAGAAGCTTCTGCTTATCTCTAT
GAGAGTGATGACTCTGTTGAAACAAGAGTGAAGACTCCTTACTCAGGTGAAATGGACT
TACTAGGAGAGATTCTTGATACATTGAGCACACACAGCTCAGATCAGGGGAGGCTGGC
AGCTGCAAAGAGCTTGGATTTCTTTAGATCAATGGACGACATTGATTACAAACCTACG
AATAAATCTAATGCTCCTAGTGAGAATAACCTGGCTTTCCTCTGTGGTGGTTCTGGTG
ACCAAGCAGAGTGGAATCTTGGGCAAGACGATAGTGCCCTCCATGGCAAACACCTCCC
TCCATCTCCTAGGAAGCGGGTTTCCTCTAGTGGTTTGACAGATTCTCTGTTTATCCTG
AAAGAGGAAAACAGTAACAAGCACCTCGGTGCTGACAATGTGAGTGACCCTACTTCAG
GACTGGATTTCCAACTCACTTCCCCTGAAGTTTCCCAGACTGATAAAGGAAAAACAGA
AAAGAGGGAAACACTAAGCCAGATTTCAGATGATCTGCTTATACCCGGTCTTGGGCGG
CATTCATCGACTTTTGTTCCTTGGGAGAAAGAAGGGAAAGAAGCCAAAGAGACTTCAG
AAGATATTGGACTGCTCCATGAAGTAGTGTCATTATGTCTATGACATCTGACTTCCA
ACAAAGCTTGAACATTTCAGACAAAAACACAAATGGAAACCAAACTAGATCT

ORF Start: at 1                ORF Stop: end of sequence
SEQ ID NO: 64                  752 aa    MW at 84005.6 kD NOV11c, 197306179 Protein Sequence RSDPVVLWKFPEDFGDQEILQSVPKFCFPFDVERVSQNQVGQHFTFVLTDIESKQRFG
FCRLTSGGTICLCILSYLPWFEVYYKLLNTLADYLAKELENDLNETLRSLYNHPVPKA
NTPVNLSVNQEIFITCEQVLKDQPALLPHSYFIAPDVTGLPTIPESRNLTEYFVAVDV
NNMLQLYASMLHERRIVIISSKLSTLTACIHGSAALLYPMYWQHIYIPVLPPHLLDYC
CAPMPYLIGIHSSLIERVKNKSLEDVVMLNVDTNTLESPFSDLNNLPSDVVSALKNKL
KKQSTATGDGVARAFLRAQAALFGSYRDALRYKPGEPITFCEESFVKHRSSVMKQFLE
TAINLQLFKQFIDGRLAKLNAGRGFSDVFEEEITSGGFCGGNPRSYQQWVHTVKKGGA
LFNTANTKATPAVRTAYKFAKNHAKLGLKEVKSKLKHKENEEDYGTCSSSVQYTPVYK
LHNEKGGNSEKRKLAQARLKRPLKSLDGALYDDEDDDDIERASKLSSEDGEEASAYLY
ESDDSVETRVKTPYSGEMDLLGEILDTLSTHSSDQGRLAAAKSLDFFRSMDDIDYKPT
NKSNAPSENNLAFLCGGSGDQAEWNLGQDDSALHGKHLPPSPRKRVSSSGLTDSLFIL

TABLE 11A-continued

NOV11 Sequence Analysis

KEENSNKHLGADNVSDPTSGLDFQLTSPEVSQTDKGKTEKRETLSQISDDLLIPGLGR

HSSTFVPWEKEGKEAKETSEDIGLLHEVVSLCHMTSDFQQSLNISDKNTNGNQTRS

| | SEQ ID NO: 65 | 2259 bp |
|---|---|---|

NOV11d, 219903686 DNA Sequence

AGATCTGATCCTGTGGTATTGTGGAAATTCCCAGAGGACTTTGGAGACCAGGAAATAC

TACAGAGTGTGCCAAAGTTCTGTTTTCCCTTTGACGTTGAAAGGGTGTCTCAGAATCA

AGTTGGACAGCACTTTACCTTTGTACTGACAGACATTGAAAGTAAACAGAGATTTGGA

TTCTGCAGACTGACGTCAGGAGGCACAATTTGTTTATGCATCCTTAGTTACCTTCCCT

GGTTTGAAGTGTATTACAAGCTTCTAAATACTCTTGCAGATTACTTGGCTAAGGAACT

GGAAAATGATTTGAATGAAACTCTCAGATCACTGTATAACCACCCAGTACCAAAGGCA

AATACTCCTGTAAATTTGAGTGTGAACCAAGAGATATTTATTGCCTGTGAGCAAGTTC

TGAAAGATCAGCCTGCTCTAGTACCGCATTCCTACTTCATTGCCCCTGATGTAACTGG

ACTCCCAACAATACCCGAGAGTAGAAATCTTACAGAATATTTTGTTGCCGTGGATGTG

AACAACATGCTGCAGCTGTATGCCAGTATGCTGCATGAAAGGCGCATCGTGATTATCT

CGAGCAAATTAAGCACTTTAACTGCCTGTATCCATGGATCAGCTGCTCTTCTATACCC

AATGTATTGGCAACACATATACATCCCAGTGCTTCCTCCACACCTGCTGGACTACTGC

TGTGCCCCAATGCCATACCTGATTGGAATACACTCCAGCCTCATAGAGAGAGTGAAAA

ACAAATCATTGGAAGATGTTGTTATGTTAAATGTTGATACAAACACATTAGAATCACC

ATTTAGTGACTTGAACAACCTACCAAGTGATGTGGTCTCGGCCTTGAAAAATAAACTG

AAGAAGCAGTCTACAGCTACGGGTGATGGAGTAGCTAGGGCCTTTCTTAGAGCACAGG

CTGCTTTGTTTGGATCCTACAGAGATGCACTGAGATACAAACCTGGTGAGCCCATCAC

TTTTCTGTGAGGAGAGTTTTGTAAAGCACCGCTCAAGCGTGATGAAACAGTTCCTGGAA

ACTGCCATTAACCTCCAGCTTTTTAAGCAGTTTATCGATGGTCGACTGGCAAAACTAA

ATGCAGGAAGGGTTTCTCTGATGTATTTGAAGAAGAGATCACTTCAGGTGGCTTTTG

TGGAGGGAACCCGAGGTCATATCAACAATGGGTGCATACAGTCAAGAAAGGAGGTGCA

CTGTTCAACACAGCAATGACCAAAGCAACCCCTGCTGTACGGACAGCATATAAATTTG

CAAAAAATCATGCAAAGCTGGGACTAAAGGAAGTGAAGAGTAAACTAAAACACAAGGA

AAATGAAGAAGATTATGGGACCTGTTCTAGTTCTGTACAATATACACCAGTTTACAAA

TTACACAATGAAAAGGGAGGAAACTCAGAAAAGCGTAAGCTTGCTCAGGCACGCTTAA

AAAGGCCTCTTAAGAGCCTTGATGGTGCTCTATATGATGATGAAGATGATGATGACAT

TGAAAGAGCAAGCAAGTTATCTTCTGAAGATGGTGAAGAAGCTTCTGCTTATCTCTAT

GAGAGTGATGACTCTGTTGAAACAAGAGTGAAGACTCCTTACTCAGGTGAAATGGACT

TACTAGGAGAGATTCTTGATACATTGAGCACACACAGCTCAGATCAGGGGAAGCTGGC

AGCTGCAAAGAGCTTGGATTTCTTTAGATCAATGGATGACATTGATTACAAACCTACG

AATAAATCTAATGCTCCTAGTGAGAATAACCTGGCTTTCCTCTGTAGTGGTTCTGGTG

ACCAAGCAGAGTGGAATCTTGGGCAAGACGATAGTGCCCTCCATGGCAAACACCTCCC

TCCATCTCCTAGGAAGCGGGTTTCCTCTAGTGGTTTGACAGATTCTCTGTCTATCCTG

AAAGAGGAAAACAGTAACAAGCACCTCGGTGCTGACAATGTGAGTGACCCTACTTCAG

GACTGGATTTCCAACTCACTTCCCCTGAAGTTTCCCAGACTGATAAAGGAAAAACAGA

TABLE 11A-continued

NOV11 Sequence Analysis

|  |  |
|---|---|
|  | AAAGAGGGAAACACTAAGCCAGATTTCAGATGATCTGCTTATACCCGGTCTTGGGCGG<br>CATTCATCGACTTTTGTTCCTTGGGAGAAAGAAGGGAAAGAAGCCAAAGAGACTTCAG<br>AAGATATTGGACTGCTCCATGAAGTAGTGTCATTATGTCATATGACATCTGACTTCCA<br>AGCTAAAGCTTGGAACATTTCAGACAAAAACACAAATGGAAACCAAACTAGATCT |
|  | ORF Start: at 1      ORF Stop: end of sequence<br>SEQ ID NO: 66      753 aa    MW at 84031.7 kD |
| NOV11d,<br>219903686<br>Protein<br>Sequence | RSDPVVLWKFPEDFGDQEILQSVPKFCFPFDVERVSQNQVGQHFTFVLTDIESKQRFG<br>FCRLTSGGTICLCILSYLPWFEVYYKLLNTLADYLAKELENDLNETLRSLYNHPVPKA<br>NTPVNLSVNQEIFIACEQVLKDQPALVPHSYFIAPDVTGLPTIPESRNLTEYFVAVDV<br>NNMLQLYASMLHERRIVIISSKLSTLTACIHGSAALLYPMYWQHIYIPVLPPHLLDYC<br>CAPMPYLIGIHSSLIERVKNKSLEDVVMLNVDTNTLESPFSDLNNLPSDVVSALKNKL<br>KKQSTATGDGVARAFLRAQAALFGSYRDALRYKPGEPITFCEESFVKHRSSVMKQFLE<br>TAINLQLFKQFIDGRLAKLNAGRGFSDVFEEEITSGGFCGGNPRSYQQWVHTVKKGGA<br>LFNTAMTKATPAVRTAYKFAKNHAKLGLKEVKSKLKHKENEEDYGTCSSSVQYTPVYK<br>LHNEKGGNSEKRKLAQARLKRPLKSLDGALYDDEDDDDIERASKLSSEDGEEASAYLY<br>ESDDSVETRVKTPYSGEMDLLGEILDTLSTHSSDQGKLAAAKSLDFFRSMDDIDYKPT<br>NKSNAPSENNLAFLCSGSGDQAEWNLGQDDSALHGKHLPPSPRKRVSSSGLTDSLSIL<br>KEENSNKHLGADNVSDPTSGLDFQLTSPEVSQTDKGKTEKRETLSQISDDLLIPGLGR<br>HSSTFVPWEKEGKEAKETSEDIGLLHEVVSLCHMTSDFQAKAWNISDKNTNGNQTRS |
|  | SEQ ID NO: 67      2256 bp |
| NOV11e,<br>219903690<br>DNA<br>Sequence | AGATCTGATCCTGTGGTATTGTGGAAATTCCCAGAGGACTTTGGAGACCAGGAAATAC<br>TACAGAGTGTGCCAAAGTTCTGTTTTCCCTTTGACGTTGAAAGGGTGTCTCAGAATCA<br>AGTTGGACAGCACTTTACCTTTGTACTGACAGACATTGAAAGTAAACAGAGATTTGGA<br>TTCTGCAGACTGACGTCAGGAGGCACAATTTGTTTATGCATCCTTAGTTACCTTCCCT<br>GGTTTGAAGTGTATTACAAGCTTCTAAATACTCTTGCAGATTACTTGGCTAAGGAACT<br>GGAAAATGATTTGAATGAAACTCTCAGATCACTGTATAACCACCCAGTACCAAAGGCA<br>AATACTCCTGTAAATTTGAGTGTGAACCAAGAGATATTTATTGCCTGTGAGCAAGTTC<br>TGAAAGATCAGCCTGCTCTAGTACCGCATTCCTACTTCATTGCCCCTGATGTAACTGG<br>ACTCCCAACAATACCCGAGAGTAGAAATCTTACAGAATATTTTGTTGCCGTGGATGTG<br>AACAACATGCTGCAGCTGTATGCCAGTATGCTGCATGAAAGGCGCATCGTGATTATCT<br>CGAGCAAATTAAGCACTTTAACTGCCTGTATCCATGGATCAGCTGCTCTTCTATACCC<br>AATGTATTGGCAACACATATACATCCCAGTGCTTCCTCCACACCTGCTGGACTACTGC<br>TGTGCCCCAATGCCATACCTGATTGGAATACACTCCAGCCTCATAGAGAGTGAAAA<br>ACAAATCATTGGAAGATGTTGTTATGTTAAATGTTGATACAAACACATTAGAATCACC<br>ATTTAGTGACTTGAACAACCTACCAAGTGATGTGGTCTCGGCCTTGAAAAATAAACTG<br>AAGAAGCAGTCTACAGCTACGGGTGATGGAGTAGCTAGGGCCTTTCTTAGAGCACAGG<br>CTGCTTTGTTTGGATCCTACAGAGATGCACTGAGATACAAACCTGGTGAGCCCATCAC<br>TTTCTGTGAGGAGAGTTTTGTAAAGCACCGCTCAAGCGTGATGAAACAGTTCCTGGAA |

TABLE 11A-continued

NOV11 Sequence Analysis

ACTGCCATTAACCTCCAGCTTTTTAAGCAGTTTATCGATGGTCGACTGGCAAAACTAA
ATGCAGGAAGGGGTTTCTCTGATGTATTTGAAGAAGAGATCACTTCAGGTGGCTTTTG
TGGAGGGAACCCGAGGTCATATCAACAATGGGTGCATACAGTCAAGAAAGGAGGTGCA
CTGTTCAACACAGCAATGACCAAAGCAACCCCTGCTGTACGGACAGCATATAAATTTG
CAAAAAATCATGCAAAGCTGGGACTAAAGGAAGTGAAGAGTAAACTAAAACACAAGGA
AAATGAAGAAGATTATGGGACCTGTTCTAGTTCTGTACAATATACACCAGTTTACAAA
TTACACAATGAAAAGGGAGGAAACTCAGAAAAGCGTAAGCTTGCTCAGGCACGCTTAA
AAAGGCCTCTTAAGAGCCTTGATGGTGCTCTATATGATGATGAAGATGATGATGACAT
TGAAAGAGCAAGCAAGTTATCTTCTGAAGATGGTGAAGAAGCTTCTGCTTATCTCTAT
GAGAGTGATGACTCTGTTGAAACAAGAGTGAAGACTCCTTACTCAGGTGAAATGGACT
TACTAGGAGAGATTCTTGATACATTGAGCACACACAGCTCAGATCAGGGGAAGCTGGC
AGCTGCAAAGAGCTTGGATTTCTTTAGATCAATGGATGACATTGATTACAAACCTACG
AATAAATCTAATGCTCCTAGTGAGAATAACCTGGCTTTCCTCTGTGGTGGTTCTGGTG
ACCAAGCAGAGTGGAATCTTGGGCAAGACGATAGTGCCCTCCATGGCAAACACCTCCC
TCCATCTCCTAGGAAGCGGGTTTCCTCTAGTGGTTTGACAGATTCTCTGTTTATCCTG
AAAGAGGAAAACAGTAACAAGCACCTCGGTGCTGACAATGTGAGTGACCCTACTTCAG
GACTGGATTTCCAACTCACTTCCCCTGAAGTTTCCCAGACTGATAAAGGAAAAACAGA
AAAGAGGGAAACACTAAGCCAGATTTCAGATGATCTGCTTATACCCGGTCTTGGGCGG
CATTCATCGACTTTTGTTCCTTGGGAGAAAGAAGGGAAAGAAGCCAAAGAGACTTCAG
AAGATATTGGACTGCTCCATGAAGTAGTGTCATTATGTCATATGACATCTGACTTCCA
ACAAAGCTTGAACATTTCAGACAAAAACACAAATGGAAACCAAACTAGATCT

| ORF Start: at 1 | ORF Stop: end of sequence |
|---|---|
| SEQ ID NO: 68 | 752 aa    MW at 83933.6 kD |

| NOV11e,<br>219903690<br>Protein<br>Sequence | RSDPVVLWKFPEDFGDQEILQSVPKFCFPFDVERVSQNQVGQHFTFVLTDIESKQRFG<br>FCRLTSGGTICLCILSYLPWFEVYYKLLNTLADYLAKELENDLNETLRSLYNHPVPKA<br>NTPVNLSVNQEIFIACEQVLKDQPALVPHSYFIAPDVTGLPTIPESRNLTEYFVAVDV<br>NNMLQLYASMLHERRIVIISSKLSTLTACIHGSAALLYPMYWQHIYIPVLPPHLLDYC<br>CAPMPYLIGIHSSLIERVKNKSLEDVVMLNVDTNTLESPFSDLNNLPSDVVSALKNKL<br>KKQSTATGDGVARAFLRAQAALFGSYRDALRYKPGEPITFCEESFVKHRSSVMKQFLE<br>TAINLQLFKQFIDGRLAKLNAGRGFSDVFEEEITSGGFCGGNPRSYQQWVHTVKKGGA<br>LFNTAMTKATPAVRTAYKFAKNHAKLGLKEVKSKLKHKENEEDYGTCSSSVQYTPVYK<br>LHNEKGGNSEKRKLAQARLKRPLKSLDGALYDDEDDDDIERASKLSSEDGEEASAYLY<br>ESDDSVETRVKTPYSGEMDLLGEILDTLSTHSSDQGKLAAAKSLDFFRSMDDIDYKPT<br>NKSNAPSENNLAFLCGGSGDQAEWNLGQDDSALHGKHLPPSPRKRVSSSGLTDSLFIL<br>KEENSNKHLGADNVSDPTSGLDFQLTSPEVSQTDKGKTEKRETLSQISDDLLIPGLGR<br>HSSTFVPWEKEGKEAKETSEDIGLLHEVVSLCHMTSDFQQSLNISDKNTNGNQTRS |

Sequence comparison of the above protein sequences yields the following sequence relationships shown in Table 11B.

TABLE 11B

Comparison of NOV11a against NOV11b through NOV11e.

| Protein Sequence | NOV11a Residues/ Match Residues | Identities/Similarities for the Matched Region |
|---|---|---|
| NOV11b | 29 ... 731 | 662/752 (88%) |
|  | 2 ... 750 | 671/752 (89%) |
| NOV11c | 29 ... 731 | 662/752 (88%) |
|  | 2 ... 750 | 671/752 (89%) |
| NOV11d | 29 ... 731 | 658/753 (87%) |
|  | 2 ... 751 | 668/753 (88%) |
| NOV11e | 29 ... 731 | 663/752 (88%) |
|  | 2 ... 750 | 671/752 (89%) |

Further analysis of the NOV11a protein yielded the following properties shown in Table 11C.

TABLE 11C

Protein Sequence Properties NOV11a

| PSort analysis: | 0.3700 probability located in outside; 0.1900 probability located in lysosome (lumen); 0.1304 probability located in microbody (peroxisome); 0.1000 probability located in endoplasmic reticulum (membrane) |
|---|---|
| SignalP analysis: | Cleavage site between residues 30 and 31 |

A search of the NOV11a protein against the Geneseq database, a proprietary database that contains sequences published in patents and patent publication, yielded several homologous proteins shown in Table 11D.

TABLE 11D

Geneseq Results for NOV11a

| Geneseq Identifier | Protein/Organism/Length [Patent #, Date] | NOV11a Residues/ Match Residues | Identities/ Similarities for the Matched Region | Expect Value |
|---|---|---|---|---|
| AAU82007 | Human secreted protein SECP33 - Homo sapiens, 559 aa. [WO200198353-A2, 27-DEC-2001] | 8 ... 430<br>8 ... 457 | 289/454 (63%)<br>351/454 (76%) | e−163 |
| AAM39715 | Human polypeptide SEQ ID NO: 2860 - Homo sapiens, 559 aa. [WO200153312-A1, 26-JUL-2001] | 8 ... 430<br>8 ... 457 | 289/454 (63%)<br>351/454 (76%) | e−163 |
| AAM41501 | Human polypeptide SEQ ID NO: 6432 - Homo sapiens, 545 aa. [WO200153312-A1, 26-JUL-2001] | 8 ... 406<br>13 ... 438 | 275/430 (63%)<br>330/430 (75%) | e−154 |
| ABG03235 | Novel human diagnostic protein #3226 - Homo sapiens, 196 aa. [WO200175067-A2, 11-OCT-2001] | 188 ... 378<br>1 ... 190 | 137/192 (71%)<br>164/192 (85%) | 4e−75 |
| ABG03235 | Novel human diagnostic protein #3226 - Homo sapiens, 196 aa. [WO200175067-A2, 11-OCT-2001] | 188 ... 378<br>1 ... 190 | 137/192 (71%)<br>164/192 (85%) | 4e−75 |

In a BLAST search of public sequence datbases, the NOV11a protein was found to have homology to the proteins shown in the BLASTP data in Table 11E.

TABLE 11E

Public BLASTP Results for NOV11a

| Protein Accession Number | Protein/Organism/Length | NOV11a Residues/ Match Residues | Identities/ Similarities for the Matched Portion | Expect Value |
|---|---|---|---|---|
| Q9NXU2 | CDNA FLJ20054 FIS, CLONE COL00849 - Homo sapiens (Human), 339 aa. | 393 ... 731<br>1 ... 339 | 339/339 (100%)<br>339/339 (100%) | 0.0 |
| AAH22561 | HYPOTHETICAL 45.0 KDA PROTEIN - Homo sapiens (Human), 396 aa. | 27 ... 376<br>15 ... 392 | 340/379 (89%)<br>344/379 (90%) | 0.0 |
| Q9D5B9 | 4930571B16RIK PROTEIN - Mus musculus (Mouse), 499 aa. | 337 ... 731<br>96 ... 499 | 298/407 (73%)<br>337/407 (82%) | e−167 |
| AAH27786 | SIMILAR TO KIAA1608 PROTEIN - Mus musculus (Mouse), 1016 aa. | 8 ... 623<br>8 ... 676 | 342/680 (50%)<br>439/680 (64%) | e−166 |
| Q9H796 | CDNA: FLJ21129 FIS, CLONE CAS06266 - Homo sapiens (Human), 559 aa. | 8 ... 426<br>8 ... 453 | 288/450 (64%)<br>349/450 (77%) | e−162 |

PFam analysis predicts that the NOV11a protein contains the domains shown in the Table 11F.

TABLE 11F

Domain Analysis of NOV11a

| Pfam Domain | NOV11a Match Region | Identities/ Similarities for the Matched Region | Expect Value |
|---|---|---|---|
| DENN | 129 . . . 244 | 48/120 (40%) 84/120 (70%) | 6.4e−35 |

Example 12

The NOV12 clone was analyzed, and the nucleotide and encoded polypeptide sequences are shown in Table 12A.

TABLE 12A

NOV12 Sequence Analysis

SEQ ID NO: 69    1357 bp

NOV12a, CGI04903-01 DNA Sequence

ATGAAACTAATTACCATCCTTTTCCTCTGCTCCAGGCTACTACTAAGTTTAACCCAGG
AATCACAGTCCGAGGAAATTGATGACTGCAATGACAAGGATTTATTTAAAGCTGTGGA
TGCTGCTCTGAAGAAATATAACAGTCAAAACCAAAGTAACAACCAGTTTGTATTGTAC
CGCAAAACCTGGCAGGACTGTGAGTACAAGGATGCTGCAAAAGCAGCCACTGGAGAAT
GCACAGCAACCGTGGGGAAGAGGAGCAGTACGAAATTCTCCGTGGCTACCCAGACCTG
CCAGATTACTCCAGCCGAGGGCCCTGTGGTGACAGCCCAGTACGACTGCCTCGGCTGT
GTGCATCCTATATCAACGCAGAGCCCAGACCTGGAGCCCATTCTGAGACACGGCATTC
AGTACTTTAACAACAACACTCAACATTCCTCCCTCTTCACGCTTAATGAAGTAAAACG
GGCCCAAAGACAGGTGGTGGCTGGATTGAACTTTCGAATTACCTACTCAATTGTGCAA
ACGAATTGTTCCAAAGAGAATTTTCTGTTCTTAACTCCAGACTGCAAGTCCCTTTGGA
ATGGTGATACCGGTGAATGTACAGATAATGCATACATCGATATTCAGCTACGAATTGC
TTCCTTCTCACAGAACTGTGACATTTATCCAGGGAAGGATTTTGTACAACCACCTACC
AAGATTTGCGTGGGCTGCCCCAGAGATATACCCACCAACAGCCCAGAGCTGGAGGAGA
CACTGACTCACACCATCACAAAGCTTAATGCAGAGAATAACGCAACTTTCTATTTCAA
GATTGACAATGTGAAAAAAGCAAGAGTACAGGTGGTGGCTGGCAAGAAATATTTTATT
GACTTCGTGGCCAGGGAAACCACATGTTCCAAGGAAAGTAATGAAGAGTTGACCGAAA
GCTGTGAGACCAAAAAACTTGGCCAAAGCCTAGATTGCAACGCTGAAGTTTATGTGGT
ACCCTGGGAGAAAAAATTTACCCTACTGTCAACTGTCAACCACTGGGAATGATCTCA
CTGATGAAAAGGCCTCCAGGTTTTTCACCTTTCCGATCATCACGAATAGGGGAAATAA
AAGAAGAAACAACTAGTCACCTAAGGTCCTGCGAGTACAAGGGTCGACCCCCAAAGGC
AGGGGCAGAGCCAGCATCTGAGAGGGAGGTCTTGACCAATGGGCAGAATCTTCACT
CCAGGCACATAGCCCCAACCACCTCTGCCAGCAACCTTGAGAGGAAGGACAAGAAGAA
AGATGGGATAGAATTTAAATAGAGAAGAATGCCATTTTATCACTCTGCCTCTGGGTGA
AATAAAGATCAGTCTTGATGTTC

ORF Start: ATG at 1   ORF Stop: TGA at 1195
SEQ ID NO: 70         398 aa    MW at 44684.1 kD NOV12a, CG104903-01 Protein MKLITILFLCSRLLLSLTQESQSEEIDDCNDKDLFKAVDAALKKYNSQNQSNNQFVLY
RKTWQDCEYKDAAKAATGECTATVGKRSSTKFSVATQTCQITPAEGPVVTAQYDCLGC

TABLE 12A-continued

NOV12 Sequence Analysis

| Sequence | |
|---|---|
| | VHPISTQSPDLEPILRHGIQYFNNNTQHSSLFTLNEVKRAQRQVVAGLNFRITYSIVQ |
| | TNCSKENFLFLTPDCKSLWNGDTGECTDNAYIDIQLRIASFSQNCDIYPGKDFVQPPT |
| | KICVGCPRDIPTNSPELEETLTHTITKLNAENNATFYFKIDNVKKARVQVVAGKKYFI |
| | DFVARETTCSKESNEELTESCETKKLGQSLDCNAEVYVVPWEKKIYPTVNCQPLGMIS |
| | LMKRPPGFSPFRSSRIGEIKEETTSHLRSCEYKGRPPKAGAEPASEREVS |

| | SEQ ID NO: 71 | 1848 bp |
|---|---|---|
| NOV12b, CG104903-02 DNA Sequence | ATGAAACTAATTACCATCCTTTTCCTCTGCTCCAGGCTACTACTAAGTTTAACCCAGG | |
| | AATCACAGTCCGAGGAAATTGATGACTGCAATGACAAGGATTTATTTAAAGCTGTGGA | |
| | TGCTGCTCTGAAGAAATATAACAGTCAAAACCAAAGTAACAACCAGTTTGTATTGTAC | |
| | CGCAAAACCTGGCAGGACTGTGAGTACAAGGATGCTGCAAAAGCAGCCACTGGAGAAT | |
| | GCACAGCAACCGTGGGAAGAGGAGCAGTACGAAATTCTCCGTGGCTACCCAGACCTG | |
| | CCAGATTACTCCAGCCGAGGGCCCTGTGGTGACAGCCCAGTACGACTGCCTCGGCTGT | |
| | GTGCATCCTATATCAACGCAGAGCCCAGACCTGGAGCCCATTCTGAGACACGGCATTC | |
| | AGTACTTTAACAACAACACTCAACATTCCTCCCTCTTCACGCTTAATGAAGTAAAACG | |
| | GGCCCAAAGACAGGTGGTGGCTGGATTGAACTTTCGAATTACCTACTCAATTGTGCAA | |
| | ACGAATTGTTCCAAAGAGAATTTTCTGTTCTTAACTCCAGACTGCAAGTCCCTTTGGA | |
| | ATGGTGATACCGGTGAATGTACAGATAATGCATACATCGATATTCAGCTACGAATTGC | |
| | TTCCTTCTCACAGAACTGTGACATTTATCCAGGGAAGGATTTTGTACAACCACCTACC | |
| | AAGATTTGCGTGGGCTGCCCCAGAGATATACCCACCAACAGCCCAGAGCTGGAGGAGA | |
| | CACTGACTCACACCATCACAAAGCTTAATGCAGAGAATAACGCAACTTTCTATTTCAA | |
| | GATTGACAATGTGAAAAAAGCAAGAGTACAGGTGGTGGCTGGCAAGAAATATTTTATT | |
| | GACTTCGTGGCCAGGGAAACCACATGTTCCAAGGAAAGTAATGAAGAGTTGACCGAAA | |
| | GCTGTGAGACCAAAAAAACTTGGCCAAAGCCTAGATTGCAACGCTGAAGTTTATGTGGT | |
| | ACCCTGGGAGAAAAAAATTTACCCTACTGTCAACTGTCAACCACTGGGAATGATCTCA | |
| | CTGATGAAAAGGCCTCCAGGTTTTTCACCTTTCCGATCATCACGAATAGGGGAAATAA | |
| | AAGAAGAAACAACTGTAAGTCCACCCCACACTTCCATGGCACCTGCACAAGATGAAGA | |
| | GCGGGATTCAGGAAAAGAACAAGGGCATACTCGTAGACATGACTGGGGCCATGAAAAA | |
| | CAAAGAAAACATAATCTTGGCCATGGCCATAAACATGAACGTGACCAAGGGCATGGGC | |
| | ACCAAAGAGGACATGGCCTTGGCCATGGACACGAACAACAGCATGGTCTTGGTCATGG | |
| | ACATAAGTTCAAACTTGATGATGATCTTGAACACCAAGGGGGCCATGTCCTTGACCAT | |
| | GGACATAAGCATAAGCATGGTCATGGCCACGGAAAACATAAAAATAAAGGCAAAAAGA | |
| | ATGGAAAGCACAATGGTTGGAAAACAGAGCATTTGGCAAGCTCTTCTGAAGACAGTAC | |
| | TACACCTTCTGCACAGACACAAGAGAAGACAGAAGGGCCAACACCCATCCCTTCCCTA | |
| | GCCAAGCCAGGTGTAACAGTTACCTTTTCTGACTTTCAGGACTCTGATCTCATTGCAA | |
| | CTATGATGCCTCCTATATCACCAGCTCCCATACAGAGTGATGACGATTGGATCCCTGA | |
| | TATCCAGACAGACCCCAAATGGCCTTTCATTTAACCCAATATCAGATTTTCCAGACACG | |

TABLE 12A-continued

NOV12 Sequence Analysis

ACCTCCCCAAAATGTCCTGGACGCCCCTGGAAGTCAGTTAGTGAAATTAATCCAACCA

CACAAATGAAAGAATCTTATTATTTCGATCTCACTGATGGCCTTTCTTAA

| ORF Start: ATG at 1 | ORF Stop: TAA at 1846 |
|---|---|
| SEQ ID NO: 72 | 615 aa   MW at 68746.1 kD |

NOV12b, CG104903-02 Protein Sequence

MKLITILFLCSRLLLSLTQESQSEEIDDCNDKDLFKAVDAALKKYNSQNQSNNQFVLY

RKTWQDCEYKDAAKAATGECTATVGKRSSTKFSVATQTCQITPAEGPVVTAQYDCLGC

VHPISTQSPDLEPILRHGIQYFNNNTQHSSLFTLNEVKRAQRQVVAGLNFRITYSIVQ

TNCSKENFLFLTPDCKSLWNGDTGECTDNAYIDIQLRIASFSQNCDIYPGKDFVQPPT

KICVGCPRDIPTNSPELEETLTHTITKLNAENNATFYFKIDNVKKARVQVVAGKKYFI

DFVARETTCSKESNEELTESCETKKLGQSLDCNAEVYVVPWEKKIYPTVNCQPLGMIS

LMKRPPGFSPFRSSRIGEIKEETTVSPPHTSMAPAQDEERDSGKEQGHTRRHDWGHEK

QRKHNLGHGHKHERDQGHGHQRGHGLGHGHEQQHGLGHGHKFKLDDDLEHQGGHVLDH

GHKHKHGHGHGKHKNKGKKNGKHNGWKTEHLASSSEDSTTPSAQTQEKTEGPTPIPSL

AKPGVTVTFSDFQDSDLIATMMPPISPAPIQSDDDWIPDIQTDPNGLSFNPISDFPDT

TSPKCPGRPWKSVSEINPTTQMKESYYFDLTDGLS

| SEQ ID NO: 73 | 1981 bp |
|---|---|

NOV12c, CG104903-03 DNA Sequence

AATTCCGGTTGAAACCATCCCTCAGCTCCTAGAGGGAGATTGTTAGATCATGAAACTA

ATTACCATCCTTTTCCTCTGCTCCAGGCTACTACTAAGTTTAACCCAGGAATCACAGT

CCGAGGAAATTGACTGCAATGACAAGGATTTATTTAAAGCTGTGGATGCTGCTCTGAA

GAAATATAACAGTCAAAACCAAAGTAACAACCAGTTTGTATTGTACCGCATAACTGAA

GCCACTAAGACGGTTGGCTCTGACACGTTTTATTCCTTCAAGTACGAAATCAAGGAGG

GGGATTGTCCTGTTCAAAGTGGCAAAACCTGGCAGGACTGTGAGTACAAGGATGCTGC

AAAAGCAGCCACTGGAGAATGCACGGCAACCGTGGGGAAGAGGAGCAGTACGAAATTC

TCCGTGGCTACCCAGACCTGCCAGATTACTCCAGCCGAGGGCCCTGTGGTGACAGCCC

AGTACGACTGCCTCGGCTGTGTGCATCCTATATCAACGCAGAGCCCAGACCTGGAGCC

CATTCTGAGACACGGCATTCAGTACTTTAACAACAACACTCAACATTCCTCCCTCTTC

ATGCTTAATGAAGTAAAACGGGCCCAAAGACAGGTGGTGGCTGGATTGAACTTTCGAA

TTACCTACTCAATTGTGCAAACGAATTGTTCCAAAGAGAATTTTCTGTTCTTAACTCC

AGACTGCAAGTCCCTTTGGAATGGTGATACCGGTGAATGTACAGATAATGCATACATC

GATATTCAGCTACGAATTGCTTCCTTCTCACAGAACTGTGACATTTATCCAGGGAAGG

ATTTTGTACAACCACCTACCAAGATTTGCGTGGGCTGCCCCAGAGATATACCCACCAA

CAGCCCAGAGCTGGAGGAGACACTGACTCACACCATCACAAAGCTTAATGCAGAGAAT

AACGCAACTTTCTATTTCAAGATTGACAATGTGAAAAAAGCAAGAGTACAGGTGGTGG

CTGGCAAGAAATATTTTATTGACTTCGTGGCCACGGAAACCACATGTTCCAAGGAAAG

TAATGAAGAGTTGACCGAAAGCTGTGAGACCAAAAAACTTGGCCAAAGCCTAGATTGC

AACGCTGAAGTTTATGTGGTACCCTGGGAGAAAAAATTTACCCTACTGTCAACTGTC

AACCACTGGGAATGATCTCACTGATGAAAAGGCCTCCAGGTTTTTCACCTTTCCGATC

ATCACGAATAGGGGAAATAAAAGAAGAAACAACTGTAAGTCCACCCCACACTTCCATG

TABLE 12A-continued

NOV12 Sequence Analysis

GCACCTGCACAAGATGAAGAGCGGGATTCAGGAAAAGAACAAGGGCATACTCGTAGAC

ATGACTGGGGCCATGAAAAACAAAGAAAACATAATCTTGGCCATGGCCATAAACATGA

ACGTGACCAAGGGCATGGGCACCAAAGAGGACATGGCCTTGGCCATGGACACGAACAA

CAGCATGGTCTTGGTCATGGACATAAGTTCAAACTTGATCATGATCTTGAACACCAAG

GGGGCCATGTCCTTGACCATGGACATAAGCATAAGCATGGTCATGGCCACGGAAAACA

TAAAAATAAAGGCAAAAAGAATGGAAAGCACAATGGTTCGAAAACAGAGCATTTGGCA

AGCTCTTCTGAAGACAGTACTACACCTTCTGCACAGACACAAGAGAAGACAGAAGGGC

CAACACCCATCCCTTCCCTAGCCAAGCCAGGTGTAACAGTTACCTTTTCTGACTTTCA

GGACTCTGATCTCATTGCAACTATGATGCCTCCTATATCACCAGCTCCCATACAGAGT

GATGACGATTGGATCCCTGATATCCAGATAGACCCAAATGGCCTTTCATTTAACCCAA

TATCAGATTTTCCAGACACGACCTCCCCAAAATGTCCTGGACGCCCCTGGAAGTCAGT

TAGTGAAATTAATCCAACCACACAAATGAAAGAATCTTATTATTTCGATCTCACTGAT

GGCCTTTCT

| | ORF Start: ATG at 50<br>SEQ ID NO: 74 | ORF Stop: end of sequence<br>644 aa    MW at 71956.8 kD |
|---|---|---|
| NOV12c,<br>CG104903-03<br>Protein<br>Sequence | MKLITILFLCSRLLLSLTQESQSEEIDCNDKDLFKAVDAALKKYNSQNQSNNQFVLYR<br><br>ITEATKTVGSDTFYSFKYEIKEGDCPVQSGKTWQDCEYKDAAKAATGECTATVGKRSS<br><br>TKFSVATQTCQITPAEGPVVTAQYDCLGCVHPISTQSPDLEPILRHGIQYFNNNTQHS<br><br>SLFMLNEVKRAQRQVVAGLNFRITYSIVQTNCSKENFLFLTPDCKSLWNGDTGECTDN<br><br>AYIDIQLRIASFSQNCDIYPGKDFVQPPTKICVGCPRDIPTNSPELEETLTHTITKLN<br><br>AENNATFYFKIDNVKKARVQVVAGKKYFIDFVARETTCSKESNEELTESCETKKLGQS<br><br>LDCNAEVYVVPWEKKIYPTVNCQPLGMISLMKRPPGFSPFRSSRIGEIKEETTVSPPH<br><br>TSMAPAQDEERDSGKEQGHTRRHDWGHEKQRKHNLGHGHKHERDQGHGHQRGHGLGHG<br><br>HEQQHGLGHGHKFKLDDDLEHQGGHVLDHGHKHKHGHGHGKHKNKGKKNGKHNGWKTE<br><br>HLASSSEDSTTPSAQTQEKTEGPTPIPSLAKPGVTVTFSDFQDSDLIATMMPPISPAP<br><br>IQSDDDWIPDIQIDPNGLSFNPISDFPDTTSPKCPGRPWKSVSEINPTTQMKESYYFD<br><br>LTDGLS |
| | SEQ ID NO: 75 | 1297 bp |
| NOV12d,<br>CG104903-05<br>DNA<br>Sequence | AATTCCGGTTGAAACCATCCCTCAGCTCCTAGAGGGAGATTGTTAGATCATGAAACTA<br><br>ATTACCATCCTTTTCCTCTGCTCCAGGCTACTACTAAGTTTAACCCAGGAATCACAGT<br><br>CCGAGGAAATTGACTGCAATGACAAGGATTTATTTAAAGCTGTGGATCCTGCTCTGAA<br><br>GAAATATAACAGTCAAAACCAAAGTAACAACCAGTTTGTATTGTACCGCATAACTGAA<br><br>GCCACTAAGACGGTTGGCTCTGACACGTTTTATTCCTTCAAGTACGAAATCAAGGAGG<br><br>GGGATTGTCCTGTTCAAAGTGGCAAAACCTGGCAGGACTGTGAGTACAAGGATGCTGC<br><br>AAAAGCAGCCACTGGAGAATGCACAGCAACCGTGGGGAAGAGGAGCAGTACGAAATTC<br><br>TCCGTGGCTACCCAGACCTGCCAGATTACTCCAGCCGAGGGCCCTGTGGTGACAGCCC<br><br>AGTACGACTGCCTCGGCTGTGTGCATCCTATATCAACGCAGAGCCCAGGTTTTTCACC<br><br>TTTCCGATCATCACGAATAGGGGAAATAAAAGAAGAAACAACTGTAAGTCCACCCCAC | |

TABLE 12A-continued

NOV12 Sequence Analysis

ACTTCCATGGCACCTGCACAAGATGAAGAGCGGGATTCAGGAAAAGAACAAGGGCATA

CTCGTAGACATGACTGGGGCCATGAAAAACAAAGAAAACATAATCTTGGCCATGGCCA

TAAACATGAACGTGACCAAGGGCATGGGCACCAAAGAGGACATGGCCTTGGCCATGGA

CACGAACAACAGCATGGTCTTGGTCATGGACATAAGTTCAAACTTGATGATGATCTTG

AACACCAAGGGGGCCATGTCCTTGACCATGGACATAAGCATAAGCATGGTCATGGCCA

CGGAAAACATAAAAATAAAGGCAAAAGAATGGAAAGCACAATGGTTGGAAAACAGAG

CATTTGGCAAGCTCTTCTGAAGACAGTACTACACCTTCTGCACAGACACAAGAGAAGA

CAGAAGGGCCAACACCCATCCCTTCCCTAGCCAAGCCAGGTGTAACAGTTACCTTTTC

TGACTTTCAGGACTCTGATCTCATTGCAACTATGATGCCTCCTATATCACCAGCTCCC

ATACAGAGTGATGACGATTGGATCCCTGATATCCAGATAGACCCAAATGGCCTTTCAT

TTAACCCAATATCAGATTTTCCAGACACGACCTCCCCAAAATGTCCTGGACGCCCCTG

GAAGTCAGTTAGTGAAATTAATCCAACCACACAAATGAAAGAATCTTATTATTTCGAT

CTCACTGATGGCCTTTCTTAA

| | ORF Start: ATG at 50 | ORF Stop: TAA at 1295 |
|---|---|---|
| | SEQ ID NO: 76 | 415 aa    MW at 45897.3 kD |

NOV12d, CG104903-05 Protein Sequence

MKLITILFLCSRLLLSLTQESQSEEIDCNDKDLFKAVDAALKKYNSQNQSNNQFVLYR

ITEATKTVGSDTFYSFKYEIKEGDCPVQSGKTWQDCEYKDAAKAATGECTATVGKRSS

TKFSVATQTCQITPAEGPVVTAQYDCLGCVHPISTQSPGFSPFRSSRIGEIKEETTVS

PPHTSMAPAQDEERDSGKEQGHTRRHDWGHEKQRKHNLGHGHKHERDQGHGHQRGHGL

GHGHEQQHGLGHGHKFKLDDDLEHQGGHVLDHGHKHKHGHGHGKHKNKGKKNGKHNGW

KTEHLASSSEDSTTPSAQTQEKTEGPTPIPSLAKPGVTVTFSDFQDSDLIATMMPPIS

PAPIQSDDDWIPDIQIDPNCLSFNPISDFPDTTSPKCPGRPWKSVSEINPTTQMKESY

YFDLTDGLS

| | SEQ ID NO: 77 | 1892 bp |
|---|---|---|

NOV12e, CG104903-06 DNA Sequence

<u>AATTCCGGTTGAAACCATCCCTCAGCTCCTAGAGGGAGATTGTTAGATCATGAAACTA</u>

<u>ATTACCATCCTTTTCCTCTGCTCCAGGCTACTACTAAGTTTAACCCAGGAATCACAGT</u>

<u>CCGAGGAAATTGACTGCAATGACAAGGATTTATTTAAAGCTGTGGATGCTGCTCTGAA</u>

<u>GAAATATAACAGTCAAAACCAAAGTAACAACCAGTTTGTATTGTACCGCATAACTGAA</u>

<u>GCCACTAAGACGGTTGGCTCTGACACGTTTTATTCCTTCAAGTACGAAATCAAGGAGG</u>

<u>GGGATTGTCCTGTTCAAAGTGGCAAAACCTGGCAGGACTGTGAGTACAAGGATGCTGC</u>

<u>AAAAGCAGCCACTGGAGAATGCACAGCAACCGTGGGAAGAGGAGCAGTACGAAATTCT</u>

<u>CCGTGGCTACCCAGACCTGGAGCCCATTCTGAGACACGGCATTCAGTACTTTTAA</u>CAAC

AACACTCAACATTCCTCCCTCTTCACGCTTAATGAAGTAAAACGGGCCCAAAGACAGG

TGGTGGCTGGATTGAACTTTCGAATTACCTACTCAATTGTGCAAACGAATTGTTCCAA

AGAGAATTTTCTGTTCTTAACTCCAGACTGCAAGTCCCTTTGGAATGGTGATACCGGT

GAATGTACAGATAATGCATACATCGATATTCAGCTACGAATTGCTTCCTTCTCACAGA

ACTGTGACATTTATCCAGGGAAGGATTTTGTACAACCACCTACCAAGATTTGCGTGGG

CTGCCCCAGAGATATACCCACCAACAGCCCAGAGCTGGAGGAGACACTGACTCACACC

TABLE 12A-continued

NOV12 Sequence Analysis

ATCACAAAGCTTAATGCAGAGAATAACGCAACTTTCTATTTCAAGATTGACAATGTGA

AAAAAGCAAGAGTACAGGTGGTGGCTGGCAAGAAATATTTTATTGACTTCGTGGCCAG

GGAAACCACATGTTCCAAGGAAAGTAATCAAGAGTTGACCGAAAGCTGTGAGACCAAA

AAACTTGGCCAAAGCCTAGATTGCAACGCTGAAGTTTATGTGGTACCCTGGGAGAAAA

AAATTTACCCTACTGTCAACTGTCAACCACTGGGAATGATCTCACTGATGAAAAGGCC

TCCAGGTTTTTCACCTTTCCGATCATCACGAATAGGGGAAATAAAAGAAGAAACAACT

GTAAGTCCACCCCACACTTCCATGGCACCTGCACAAGATGAAGAGCGGGATTCAGGAA

AAGAACAAGGGCATACTCGTAGACATGACTGGGGCCATGAAAAACAAAGAAAACATAA

TCTTGGCCATGGCCATAAACATGAACGTGACCAAGGGCATGGGCACCAAAGAGGACAT

GGCCTTGGCCATGGACACGAACAACAGCATGGTCTTGGTCATGGACATAAGTTCAAAC

TTGATGATGATCTTGAACACCAAGGGGCCATGTCCTTGACCATGGACATAAGCATAA

GCATGGTCATGGCCACGGAAAACATAAAAATAAAGGCAAAAAGAATGGAAAGCACAAT

GGTTGGAAAACAGAGCATTTGGCAAGCTCTTCTGAAGACAGTACTACACCTTCTGCAC

AGACACAAGAGAAGACAGAAGGGCCAACACCCATCCCTTCCCTAGCCAAGCCAGGTGT

AACAGTTACCTTTTCTGACTTTCAGGACTCTGATCTCATTGCAACTATGATGCCTCCT

ATATCACCAGCTCCCATACAGAGTGATGACGATTGGATCCCTGATATCCAGATAGACC

CAAATGGCCTTTCATTTAACCCAATATCAGATTTTCCAGACACGACCTCCCCAAAATG

TCCTGGACGCCCCTGGAAGTCAGTTAGTGAAATTAATCCAACCACACAAATGAAAGAA

TCTTATTATTTCGATCTCACTGATGGCCTTTCTTAA

| | ORF Start: ATG at 50 | ORF Stop: TAA at 458 |
| | SEQ ID NO: 78 | 136 aa MW at 15218.9 kD |

| NOV12e, CG104903-06 Protein Sequence | MKLITILFLCSRLLLSLTQESQSEEIDCNDKDLFKAVDAALKKYNSQNQSNNQFVLYR ITEATKTVGSDTFYSFKYEIKEGDCPVQSGKTWQDCEYKDAAKAATGECTATVGRGAV RNSPWLPRPGAHSETRHSVL |

| | SEQ ID NO: 79 | 670 bp |

| NOV12f, CG104903-07 DNA Sequence | ATGAAACTAATTACCATCCTTTTCCTCTGCTCCAGGCTACTACTAAGTTTAACCCAGG AATCACAGTCCGAGGAAATTGATGACTGCAATGACAAGGATTTATTTAAAGCTGTGGA TGCTGCTCTGAAGAAATATAACAGTCAAAACCAAAGTAACAACCAGTTTGTATTGTAC CGCAAAACCTGGCAGGACTGTGAGTACAAGGATGCTGCAAAAGCAGCCACTGGAGAAT GCACAGCAACCGTGGGGAAGAGGAGCAGTACCAAATTCTCCGTGGCTACCCAGACCTG CCAGATTACTCCAGCCGAGGGCCCTGTGGTGACAGCCCAGTACGACTGCCTCGGCTGT GTGCATCCTATATCAACGCAGAGCCCAGGTTTTTCACCTTTCCGATCATCACGAATAG GGGAAATAAAAGAAGAAACAACTAGTCACCTAAGGTCCTGCGAGTACAAGGGTCGACC CCCAAAGGCAGGGGCAGAGCCAGCATCTGAGAGGGAGGTCTCTTGACCAATGGGCAGA ATCTTCACTCCAGGCACATAGCCCCAACCACCTCTGCCAGCAACCTTGAGAGGAAGGA CAAGAAGAAAGATGGGATAGAATTTAAATAGAGAAGAATGCCATTTTATCACTCTGCC TCTGGGTGAAATAAAGATCAGTCTTGATGTTC |

TABLE 12A-continued

NOV12 Sequence Analysis

| | ORF Start: ATG at 1<br>SEQ ID NO: 80 | ORF Stop: TGA at 508<br>169 aa    MW at 18654.7 kD |
|---|---|---|
| NOV12f,<br>CG104903-07<br>Protein<br>Sequence | MKLITILFLCSRLLLSLTQESQSEEIDDCNDKDLFKAVDAALKKYNSQNQSNNQFVLY<br>RKTWQDCEYKDAAKAATGECTATVGKRSSTKFSVATQTCQITPAEGPVVTAQYDCLGC<br>VHPISTQSPGFSPFRSSRIGEIKEETTSHLRSCEYKGRPPKAGAEPASEREVS | |

| | SEQ ID NO: 81 | 1193 bp |
|---|---|---|
| NOV12g,<br>CC104903-08<br>DNA<br>Sequence | ATGAAACTAATTACCATCCTTTTCCTCTGCTCCAGGCTACTACTAAGTTTAACCCAGG<br>AATCACAGTCCGAGGAAATTGACTGCAATGACAAGGATTTATTTAAAGCTGTGGATGC<br>TGCTCTGAAGAAATATAACAGTCAAAACCAAAGTAACAACCAGTTTGTATTGTACCGC<br>ATAACTGAAGCCACTAAGACGGCCACTGGAGAATGCACGGCAACCGTGGGAAGAGGA<br>GCAGTACGAAATTCTCCGTGGCTACCCAGACCTGCCAGATTACTCCAGCCGAGGGCCC<br>TGTGGTGACAGCCCAGTACGACTGCCTCGGCTGTGTGCATCCTATATCAACGCAGAGC<br>CCAGACCTGGAGCCCATTCTGAGACACGGCATTCAGTACTTTAACAACAACACTCAAC<br>ATTCCTCCCTCTTCACGCTTAATGAAGTAAAACGGGCCCAAAGACAGGTGGTGGCTGG<br>ATTGAACTTTCGAATTACCTACTCAATTGTGCAAACGAATTGTTCCAAAGAGAATTTT<br>CTGTTCTTAACTCCAGACTGCGAGTCCCTTTGGAATGGTGATACCGGTGAATGTACAG<br>ATAATGCATACATCGATATTCAGCTACGAATTGCTTCCTTCTCACAGAACTGTGACAT<br>TTATCCAGGGAAGGATTTTGTACAACCACCTACCAAGATTTGCGTGGGCTGCCCCAGA<br>GATATACCCACCAACAGCCCAGAGCTGGAGGAGACACTGACTCACACCATCACAAAGC<br>TTAATGCAGAGAATAACGCAACTTTCTATTTCAAGATTGACAATGTGAAAAAAGCAAG<br>AGTACAGGTGGTGGCTGGCAAGAAATATTTTATTGACTTCGTGGCCAGGGAAACCACA<br>TGTTCCAAGGAAAGTAATGAAGAGTTGACCGAAAGCTGTGAGACCAAAAAACTTGGCC<br>AAAGCCTAGATTGCAACGCTGAAGTTTATGTGGTACCCTGGGAGAAAAAAATTTACCC<br>TACTGTCAACTGTCAACCACTGGGAATGATCTCACTGATGAAAAGGCCTCCAGGTTTT<br>TCACCTTTCCGATCATCACGAATAGGGGAAATAAAAGAAGAAACAACTAGTCACCTAA<br>GGTCCTGCGAGTACAAGGGTCGACCCCCAAAGGCAGGGCAGAGCCAGTATCTGAGAG<br>GGAGGTCTCTTGACCAATGGGCAGAATCTTCAC | |

| | ORF Start: ATG at 1<br>SEQ ID NO: 82 | ORF Stop: TGA at 1171<br>390 aa    MW at 43704.0 kD |
|---|---|---|
| NOV12g,<br>CG104903-08<br>Protein<br>Sequence | MKLITILFLCSRLLLSLTQESQSEEIDCNDKDLFKAVDAALKKYNSQNQSNNQFVLYR<br>ITEATKTATGECTATVGKRSSTKFSVATQTCQITPAEGPVVTAQYDCLGCVHPISTQS<br>PDLEPILRHGIQYFNNNTQHSSLFTLNEVKRAQRQVVAGLNFRITYSIVQTNCSKENF<br>LFLTPDCESLWNGDTGECTDNAYIDIQLRIASFSQNCDIYPGKDFVQPPTKICVGCPR<br>DIPTNSPELEETLTHTITKLNAENNATFYFKIDNVKKARVQVVAGKKYFIDFVARETT<br>CSKESNEELTESCETKKLGQSLDCNAEVYVVPWEKKIYPTVNCQPLGMISLMKRPPGF<br>SPFRSSRICEIKEETTSHLRSCEYKGRPPKAGAEPVSEREVS | |

TABLE 12A-continued

NOV12 Sequence Analysis

| | SEQ ID NO: 83 | 1984 bp |
|---|---|---|

NOV12h,
CG104903-09
DNA
Sequence

AATTCCGGTTGAAACCATCCCTCAGCTCCTAGAGGGAGATTGTTAGATCATGAAACTA
ATTACCATCCTTTTCCTCTGCTCCAGGCTACTACTAAGTTTAACCCAGGAATCACAGT
CCGAGGAAATTGACTCCAATGACAAGGATTTATTTAAAGCTGTGGATGCTGCTCTGAA
GAAATATAACAGTCAAAACCAAAGTAACAACCAGTTTGTATTGTACCGCATAACTGAA
GCCACTAAGACGGTTGGCTCTGACACGTTTTATTCCTTCAAGTACGAAATCAAGGAGG
GGGATTGTCCTGTTCAAAGTGGCAAAACCTGGCAGGACTGTGAGTACAAGGATGCTGC
AAAAGCAGCCACTGGAGAATGCACGGCAACCGTGGGGAAGAGGAGCAGTACGAAATTC
TCCGTGGCTACCCAGACCTGCCAGATTACTCCAGCCGAGGGCCCTGTGGTGACAGCCC
AGTACGACTGCCTCGGCTGTGTGCATCCTATATCAACGCAGAGCCCAGACCTGGAGCC
CATTCTGAGACACGGCATTCAGTACTTTAACAACAACACTCAACATTCCTCCCTCTTC
ATGCTTAATGAAGTAAAACGGGCCCAAAGACAGGTGGTGGCTGGATTGAACTTTCGAA
TTACCTACTCAATTGTGCAAACGAATTGTTCCAAAGAGAATTTTCTGTTCTTAACTCC
AGACTGCAAGTCCCTTTGGAATGGTGATACCGGTGAATGTACAGATAATGCATACATC
GATATTCAGCTACGAATTGCTTCCTTCTCACAGAACTGTGACATTTATCCAGGGAAGG
ATTTTGTACAACCACCTACCAAGATTTGCGTGGGCTGCCCCAGAGATATACCCACCAA
CAGCCCAGAGCTGGAGGAGACACTGACTCACACCATCACAAAGCTTAATGCAGAGAAT
AACGCAACTTTCTATTTCAAGATTGACAATGTGAAAAAAGCAAGAGTACAGGTGGTGG
CTGGCAAGAAATATTTTATTGACTTCGTGGCCAGGGAAACCACATGTTCCAAGGAAAG
TAATGAAGAGTTGACCGAAAGCTGTGAGACCAAAAAAACTTGGCCAAAGCCTAGATTGC
AACGCTGAAGTTTATGTGGTACCCTGGGAGAAAAAAATTTACCCTACTGTCAACTGTC
AACCACTGGGAATGATCTCACTGATGAAAAGGCCTCCAGGTTTTTCACCTTTCCGATC
ATCACGAATAGGGGAAATAAAAGAAGAAACAACTGTAAGTCCACCCCACACTTCCATG
GCACCTGCACAAGATGAAGAGCGGGATTCAGGAAAAGAACAAGGGCATACTCGTAGAC
ATGACTGGGGCCATGAAAAACAAAGAAAACATAATCTTGGCCATGGCCATAAACATGA
ACGTGACCAAGGGCATGGGCACCAAAGAGGACATGGCCTTGGCCATGGACACGAACAA
CAGCATGGTCTTGGTCATGGACATAAGTTCAAACTTGATGATGATCTTGAACACCAAG
GGGGCCATGTCCTTGACCATGGACATAAGCATAAGCATGGTCATGGCCACGCAAAACA
TAAAAATAAAGGCAAAAAGAATGGAAAGCACAATGGTTGGAAAACAGAGCATTTGGCA
AGCTCTTCTGAAGACAGTACTACACCTTCTGCACAGACACAAGAGAAGACAGAAGGGC
CAACACCCATCCCTTCCCTAGCCAAGCCAGGTGTAACAGTTACCTTTTCTGACTTTCA
GGACTCTGATCTCATTGCAACTATGATGCCTCCTATATCACCAGCTCCCATACAGAGT
GATGACGATTGGATCCCTGATATCCAGATAGACCCAAATGGCCTTTCATTTAACCCAA
TATCAGATTTTCCAGACACGACCTCCCCAAAATGTCCTGGACGCCCCTGGAAGTCAGT
TAGTGAAATTAATCCAACCACACAAATGAAAGAATCTTATTATTTCGATCTCACTGAT
GGCCTTTCTTAA

TABLE 12A-continued

NOV12 Sequence Analysis

ORF Start: ATG at 50　　　ORF Stop: TAA at 1982
SEQ ID NO: 84　　　　　　　644 aa　　MW at 71956.8 kD

| | |
|---|---|
| NOV12h, CG104903-09 Protein Sequence | MKLITILFLCSRLLLSLTQESQSEEIDCNDKDLFKAVDAALKKYNSQNQSNNQFVLYR<br>ITEATKTVGSDTFYSFKYEIKEGDCPVQSGKTWQDCEYKDAAKAATGECTATVGKRSS<br>TKFSVATQTCQITPAEGPVVTAQYDCLGCVHPISTQSPDLEPILRHGIQYFNNNTQHS<br>SLFMLNEVKRAQRQVVAGLNFRITYSIVQTNCSKENFLFLTPDCKSLWNGDTGECTDN<br>AYIDIQLRIASFSQNCDIYPGKDFVQPPTKICVGCPRDIPTNSPELEETLTHTITKLN<br>AENNATFYFKIDNVKKARVQVVAGKKYFIDFVARETTCSKESNEELTESCETKKLGQS<br>LDCNAEVYVVPWEKKIYPTVNCQPLGMISLMKRPPGFSPFRSSRIGEIKEETTVSPPH<br>TSMAPAQDEERDSGKEQGHTRRHDWGHEKQRKHNLGHGHKHERDQGHGHQRGHGLGHG<br>HEQQHGLGHGHKFKLDDDLEHQGGHVLDHGHKHKHGHGHGKHKNKGKKNGKHNGWKTE<br>HLASSSEDSTTPSAQTQEKTEGPTPIPSLAKPGVTVTFSDFQDSDLIATMMPPISPAP<br>IQSDDDWIPDIQIDPNGLSFNPISDFPDTTSPKCPGRPWKSVSEINPTTQMKESYYFD<br>LTDGLS |

Sequence comparison of the above protein sequences yields the following sequence relationships shown in Table 12B.

TABLE 12B

Comparison of NOV12a against NOV12b through NOV12h.

| Protein Sequence | NOV12a Residues/ Match Residues | Identities/ Similarities for the Matched Region |
|---|---|---|
| NOV12b | 26 ... 396 | 343/371 (92%) |
| | 26 ... 387 | 344/371 (92%) |
| NOV12c | 28 ... 396 | 340/399 (85%) |
| | 27 ... 416 | 341/399 (85%) |
| NOV12d | 28 ... 129 | 90/132 (68%) |
| | 27 ... 158 | 90/132 (68%) |
| NOV12e | 28 ... 84 | 47/87 (54%) |
| | 27 ... 113 | 48/87 (55%) |
| NOV12f | 26 ... 129 | 92/104 (88%) |
| | 26 ... 129 | 92/104 (88%) |
| NOV12g | 28 ... 398 | 349/371 (94%) |
| | 27 ... 390 | 351/371 (94%) |
| NOV12h | 28 ... 396 | 340/399 (85%) |
| | 27 ... 416 | 341/399 (85%) |

Further analysis of the NOV12a protein yielded the following properties shown in Table 12C.

TABLE 12C

Protein Sequence Properties NOV12a

| | |
|---|---|
| PSort analysis: | 0.5135 probability located in outside; 0.1900 probability located in lysosome (lumen); 0.1000 probability located in endoplasmic reticulum (membrane); 0.1000 probability located in endoplasmic reticulum (lumen) |
| SignalP analysis: | Cleavage site between residues 24 and 25 |

A search of the NOV12a protein against the Geneseq database, a proprietary database that contains sequences published in patents and patent publication, yielded several homologous proteins shown in Table 12D.

TABLE 12D

Geneseq Results for NOV12a

| Geneseq Identifier | Protein/Organism/Length [Patent #, Date] | NOV12a Residues/ Match Residues | Identities/ Similarities for the Matched Region | Expect Value |
|---|---|---|---|---|
| ABG21101 | Novel human diagnostic protein #21092 - *Homo sapiens*, 644 aa. [WO200175067-A2, 11-OCT-2001] | 1 ... 396<br>1 ... 416 | 375/426 (88%)<br>376/426 (88%) | 0.0 |
| ABG21101 | Novel human diagnostic protein #21092 - *Homo sapiens*, 644 aa. [WO200175067-A2, 11-OCT-2001] | 1 ... 396<br>1 ... 416 | 375/426 (88%)<br>376/426 (88%) | 0.0 |

TABLE 12D-continued

Geneseq Results for NOV12a

| Geneseq Identifier | Protein/Organism/Length [Patent #, Date] | NOV12a Residues/ Match Residues | Identities/ Similarities for the Matched Region | Expect Value |
|---|---|---|---|---|
| ABG21105 | Novel human diagnostic protein #21096 - *Homo sapiens*, 435 aa. [WO200175067-A2, 11-OCT-2001] | 1 . . . 398<br>2 . . . 435 | 377/435 (86%)<br>380/435 (86%) | 0.0 |
| ABG21105 | Novel human diagnostic protein #21096 - *Homo sapiens*, 435 aa. [WO200175067-A2, 11-OCT-2001] | 1 . . . 398<br>2 . . . 435 | 377/435 (86%)<br>380/435 (86%) | 0.0 |
| AAP40257 | Bradykinin protein precursor: type I (pKG13, pKG59), 436 aa. [JP59125896-A, 20-JUL-1984] | 1 . . . 398<br>1 . . . 426 | 297/428 (69%)<br>343/428 (79%) | e−174 |

In a BLAST search of public sequence datbases, the NOV12a protein was found to have homology to the proteins shown in the BLASTP data in Table 12E.

TABLE 12E

Public BLASTP Results for NOV12a

| Protein Accession Number | Protein/Organism/Length | NOV12a Residues/ Match Residues | Identities/ Similarities for the Matched Portion | Expect Value |
|---|---|---|---|---|
| KGHUL1 | kininogen, LMW precursor [validated] - human, 427 aa. | 1 . . . 398<br>1 . . . 427 | 396/428 (92%)<br>396/428 (92%) | 0.0 |
| P01042 | Kininogen precursor (Alpha-2-thiol proteinase inhibitor) [Contains: Bradykinin] - *Homo sapiens* (Human), 644 aa. | 1 . . . 396<br>1 . . . 416 | 375/426 (88%)<br>376/426 (88%) | 0.0 |
| P01046 | Kininogen, LMW I precursor (Thiol proteinase inhibitor) [Contains: Bradykinin] - *Bos taurus* (Bovine), 436 aa. | 1 . . . 398<br>1 . . . 426 | 297/428 (69%)<br>343/428 (79%) | e−173 |
| P01047 | Kininogen, LMW II precursor (Thiol proteinase inhibitor) [Contains: Bradykinin] - *Bos taurus* (Bovine), 434 aa. | 1 . . . 398<br>1 . . . 424 | 292/428 (68%)<br>340/428 (79%) | e−170 |
| P01044 | Kininogen, HMW I precursor (Thiol proteinase inhibitor) [Contains: Bradykinin] - *Bos taurus* (Bovine), 621 aa. | 1 . . . 375<br>1 . . . 403 | 280/405 (69%)<br>321/405 (79%) | e−161 |

PFam analysis predicts that the NOV12a protein contains the domains shown in the Table 12F.

TABLE 12F

Domain Analysis of NOV12a

| Pfam Domain | NOV12a Match Region | Identities/ Similarities for the Matched Region | Expect Value |
|---|---|---|---|
| cystatin | 21 . . . 59 | 11/40 (28%)<br>35/40 (88%) | 1.9e−06 |
| cystatin | 60 . . . 97 | 14/40 (35%)<br>30/40 (75%) | 4e−07 |
| cystatin | 115 . . . 219 | 28/113 (25%)<br>92/113 (81%) | 5e−35 |
| cystatin | 237 . . . 341 | 32/113 (28%)<br>94/113 (83%) | 3.4e−39 |

Example 13

The NOV13 clone was analyzed, and the nucleotide and encoded polypeptide sequences are shown in Table 13A.

TABLE 13A

NOV13 Sequence Analysis

| SEQ ID NO: 85 | 1272 bp |
|---|---|

| | |
|---|---|
| NOV13a, CG105982-01 DNA Sequence | <u>CTTCCCCAGGACTCCAGGAGACATAAAACTTGAAACGGGAGACTTCGTGCAAATCCTG</u><br><br><u>CTCCGGACGCTGCTGAAGCTCAGATTTCTCCCACTGCCTGCACAGGGTGCTGCCTGCT</u><br><br><u>GGCGAATGTGACTCTCCTCCTGTTCACCCACAAGGCTGATTTTTCCGTGTTCCTCCTC</u><br><br><u>TGGAAAGAGCATTGCTTTCTCTCTTCCAGCACTTTACCTACATTCATGTCTTTCAGGT</u><br><br>GGCTGCTTCTCTATTATGCTCTGTGCT-<br>TCTCCCTGTCAAAGGCTTCAGCCCACACCGT<br><br>GGAGCTAAACAATATGTTTGGCCAGATC-<br>CAGTCGCCTGGTTATCCAGACTCCTATCCC<br><br>AGTGATTCACAGGTGACTTGGAATAT-<br>CACTGTCCCAGATGGGTTTCGGATCAAGCTTT<br><br>ACTTCATGCACTTCAACTTGGAATCCTC-<br>CTACCTTTGTGAATATGACTATGTGAAGGT<br><br>AGAAACTGAGGACACTTCGAGAGTGC-<br>CAAATGACAAGTGGTTTGGGAGTGGGGCCCTG<br><br>CTCTCTGCGTCCTGGATCCTCACAG-<br>CAGCTCATGTGCTGCGCTCCCAGCGTAGAGACA<br><br>CCACGGTGATACCAGTCTCCAAGGAG-<br>CATGTCACCGTCTACCTGGGCTTGCATGATGT<br><br>GCGAGACAAATCCGGGGCAGTCAA-<br>CAGCTCAGCTGCCCGAGTGGTGCTCCACCCAGAC<br><br>TTCAACATCCAAAACTACAACCAC-<br>GATATAGCTCTGGTGCAGCTGCAGGAGCCTGTGC<br><br>CCCTGGGACCCCACGTTATGCCTGTCT-<br>GCCTGCCAAGGCTTGAGCCTGAAGGCCCGGC<br><br>CCCCCACATGCTGGGCCTGGTGGCCG-<br>GCTGGGGCATCTCCAATCCCAATGTGACAGTG<br><br>GATGAGATCATCAGCAGTGGCACACG-<br>GACCTTGTCAGATGTCCTGCAGTATGTCAAGT<br><br>TACCCGTGGTGCCTCACGCTCAGTG-<br>CAAAACTAGCTATGAGTCCCGCTCGGGCAATTA<br><br>CAGCGTCACGGAGAACATGTTCTGT-<br>GCTGGCTACTACGAGGGCGGCAAAGACACGTGC<br><br>CTTGGAGATAGCGGTGGGGCCTTTGT-<br>CATCTTTGATGACTTGAGCCAGCGCTGGGTGG<br><br>TGCAAGGCCTGGTGTCCTGGGGGGGAC-<br>CTGAAGAATGCGGCAGCAAGCAGGTCTATGG<br><br>AGTCTACACAAAGGTCTCCAATTACGTG-<br>GACTGGGTGTGGGAGCAGATGGGCTTACCA<br><br>CAAAGTGTTGTGGAGCCCCAGGTGGAACGGTGA<br>GCTGACTTACTTCCTCGCGGG |
| | ORF Start: ATG at 220     ORF Stop: TGA at 1249<br>SEQ ID NO: 86     343 aa     MW at 38275.9 kD |
| NOV13a, CG105982-01 Protein Sequence | MSFRWLLLYYALCFSLSKASAHTVELN-<br>NMFGQIQSPGYPDSYPSDSEVTWNITVPDGF<br><br>RIKLYFMHFNLESSYLCEYDYVKVET-<br>EDTSRVPNDKWFGSGALLSASWILTAAHVLRS<br><br>QRRDTTVIPVSKEHVTVYLGLHDVRDKS-<br>GAVNSSAARVVLHPDFNIQNYNHDIALVQL<br><br>QEPVPLGPNVMPVCLPRLEPEGPAPHM-<br>LGLVAGWGISNPNVTVDEIISSGTRTLSDVL |

TABLE 13A-continued

NOV13 Sequence Analysis

QYVKLPVVPHAECKTSYESRSGNYS-
VTENMFCAGYYEGGKDTCLGDSGGAFVIFDDLS

QRWVVQGLVSWGGPEECGSKQVYGVYT-
KVSNYVDWVWEQMGLPQSVVEPQVER

Further analysis of the NOV13a protein yielded the following properties shown in Table 13B.

TABLE 13B

Protein Sequence Properties NOV13a

| | |
|---|---|
| PSort analysis: | 0.3700 probability located in outside; 0.1900 probability located in lysosome (lumen); 0.1000 probability located in endoplasmic reticulum (membrane); 0.1000 probability located in endoplasmic reticulum (lumen) |
| SignalP analysis: | Cleavage site between residues 22 and 23 |

A search of the NOV13a protein against the Geneseq database, a proprietary database that contains sequences published in patents and patent publication, yielded several homologous proteins shown in Table 13C.

TABLE 13C

Geneseq Results for NOV13a

| Geneseq Identifier | Protein/Organism/Length [Patent #, Date] | NOV13a Residues/ Match Residues | Identities/ Similarities for the Matched Region | Expect Value |
|---|---|---|---|---|
| AAB85060 | Human serine protease MASP-3 polypeptide - *Homo sapiens*, 728 aa. [WO200140451-A2, 07-JUN-2001] | 82 . . . 343<br>467 . . . 728 | 259/262 (98%)<br>260/262 (98%) | e-154 |
| AAB47559 | Protease PRTS-1 - *Homo sapiens*, 728 aa. [WO200171004-A2, 27-SEP-2001] | 82 . . . 343<br>467 . . . 728 | 258/262 (98%)<br>259/262 (98%) | e-153 |
| AAB84203 | Amino acid sequence of a human serine protease designated Zfaix1 - *Homo sapiens*, 269 aa. [WO200138501-A2, 31-MAY-2001] | 82 . . . 332<br>19 . . . 269 | 248/251 (98%)<br>249/251 (98%) | e-148 |
| AAG00221 | Human secreted protein, SEQ ID NO: 4302 - *Homo sapiens*, 97 aa. [EP1033401-A2, 06-SEP-2000] | 4 . . . 82<br>2 . . . 80 | 79/79 (100%)<br>79/79 (100%) | 3e-42 |
| AAB60935 | Horseshoe crab recombinant Factor C #2 - *Carcinoscorpius rotundicauda*, 1019 aa. [WO200127289-A2, 19-APR-2001] | 92 . . . 326<br>787 . . . 1015 | 90/244 (36%)<br>127/244 (51%) | 2e-37 |

In a BLAST search of public sequence datbases, the NOV13a protein was found to have homology to the proteins shown in the BLASTP data in Table 13D.

TABLE 13D

Public BLASTP Results for NOV13a

| Protein Accession Number | Protein/Organism/Length | NOV13a Residues/ Match Residues | Identities/ Similarities for the Matched Portion | Expect Value |
|---|---|---|---|---|
| CAC42682 | SEQUENCE 1 FROM PATENT WO0140451 - *Homo sapiens* (Human), 728 aa. | 82 . . . 343<br>467 . . . 728 | 259/262 (98%)<br>260/262 (98%) | e-154 |

TABLE 13D-continued

Public BLASTP Results for NOV13a

| Protein Accession Number | Protein/Organism/Length | NOV13a Residues/ Match Residues | Identities/ Similarities for the Matched Portion | Expect Value |
| --- | --- | --- | --- | --- |
| Q96RS4 | COMPLEMENT FACTOR MASP-3 - *Homo sapiens* (Human), 728 aa. | 82 . . . 343 467 . . . 728 | 259/262 (98%) 260/262 (98%) | e-154 |
| CAC42545 | SEQUENCE 1 FROM PATENT WO0138501 - *Homo sapiens* (Human), 269 aa (fragment). | 82 . . . 332 19 . . . 269 | 248/251 (98%) 249/251 (98%) | e-147 |
| Q920S0 | MBL-ASSOCIATED SERINE PROTEASE-3 - *Mus musculus* (Mouse), 733 aa. | 82 . . . 343 472 . . . 733 | 236/262 (90%) 247/262 (94%) | e-141 |
| Q9PVY2 | MANNOSE-BINDING LECTIN-ASSOCIATED SERINE PROTEASE - *Triakis scyllium* (Leopard shark) (Triakis scyllia), 719 aa. | 82 . . . 330 465 . . . 714 | 158/251 (62%) 198/251 (77%) | 9e-93 |

PFam analysis predicts that the NOV13a protein contains the domains shown in the Table 13E.

TABLE 13E

Domain Analysis of NOV13a

| Pfam Domain | NOV13a Match Region | Identities/ Similarities for the Matched Region | Expect Value |
| --- | --- | --- | --- |
| CUB | 22 . . . 134 | 37/127 (29%) 75/127 (59%) | 1.5e-05 |
| Trypsin | 94 . . . 326 | 86/258 (33%) 192/258 (74%) | 2.2e-66 |

Example 14

The NOV14 clone was analyzed, and the nucleotide and encoded polypeptide sequences are shown in Table 14A.

TABLE 14A

NOV14 Sequence Analysis

SEQ ID NO: 87      861 bp

NOV14a, CG107614-02 DNA Sequence

```
CAGCTCAGCATGGCTAGGGTACTGGGAGCACCCGTTGCACTGGGGTTGTGGAGCCTAT
GCTGGTCTCTGGCCATTGCCACCCCTCTTCCTCCGACTAGTGCCCATGGGAATGTTGC
TGAAGGCGAGACCAAGCCAGACCCAGACGTGACTGAACGCTGCTCAGATGGCTGGAGC
TTTGATGCTACCACCCTGGATGACAATGGAACCATGCTGTTTTTTAAAGGGACCCACT
ACTGGCGTCTGGACACCAGCCGGGATGGCTGGCATAGCTGGCCCATTGCTCATCAGTG
GCCCCAGGGTCCTTCAGCAGTGGATGCTGCCTTTTCCTGGGAAGAAAAACTCTATCTG
GTCCAGGGCACCCAGGTATATGTCTTCCTGACAAAGGGAGGCTATACCCTAGTAAGCG
GTTATCCGAAGCGGCTGGAGAAGGAAGTCGGGACCCCTCATGGGATTATCCTGGACTC
TGTGGATGCGGCCTTTATCTGCCCTGGGTCTTCTCGGCTCCATATCATGGCAGGACGG
CGGCTGTGGTGGCTGGACCTGAAGTCAGGAGCCCAAGCCACGTGGACAGAGCTTCCTT
GGCCCCATGAGAAGGTAGACGGAGCCTTGTGTATGGAAAAGTCCCTTGGCCCTAACTC
ATGTTCCGCCAATGGTCCCGGCTTGTACCTCATCCATGGTCCCAATTTGTACTGCTAC
AGTGATGTGGAGAAACTGAATGCAGCCAAGGCCCTTCCGCAACCCCAGAATGTGACCA
GTCTCCTGGGCTGCACTCACTGAGGGCCTTCTGACATGAGTCTGGCCTGGCCCCACC
TCCTAGTTCCTCATAATAAAGACAGATTGCTTCTTCGCTTCTCACTGAG
```

TABLE 14A-continued

NOV14 Sequence Analysis

| | |
|---|---|
| ORF Start: ATG at 10 | ORF Stop: TGA at 775 |
| SEQ ID NO: 88 | 255 aa  MW at 27921.4 kD |

| | |
|---|---|
| NOV14a, CG107614-02 Protein Sequence | MARVLGAPVALGLWSLCWSLAIATPLPPTSAHGNVAEGETKPDPDVTERCSDGWSFDA<br><br>TTLDDNGTMLFFKGTHYWRLDTSRDGWHSWPIAHQWPQGPSAVDAAFSWEEKLYLVQG<br><br>TQVYVFLTKGGYTLVSGYPKRLEKEVGTPHGIILDSVDAAFICPGSSRLHIMAGRRLW<br><br>WLDLKSGAQATWTELPWPHEKVDGALCMEKSLGPNSCSANGPGLYLIHGPNLYCYSDV<br><br>EKLNAAKALPQPQNVTSLLGCTH |

Further analysis of the NOV14a protein yielded the following properties shown in Table 14B.

TABLE 14B

| Protein Sequence Properties NOV14a | |
|---|---|
| PSort analysis: | 0.4586 probability located in lysosome (lumen); 0.4323 probability located in outside; 0.3077 probability located in microbody (peroxisome); 0.1000 probability located in endoplasmic reticulum (membrane) |
| SignalP analysis: | Cleavage site between residues 32 and 33 |

A search of the NOV14a protein against the Geneseq database, a proprietary database that contains sequences published in patents and patent publication, yielded several homologous proteins shown in Table 14C.

TABLE 14C

Geneseq Results for NOV14a

| Geneseq Identifier | Protein/Organism/Length [Patent #, Date] | NOV14a Residues/ Match Residues | Identities/ Similarities for the Matched Region | Expect Value |
|---|---|---|---|---|
| AAM23933 | Human EST encoded protein SEQ ID NO: 1458 - *Homo sapiens*, 462 aa. [WO200154477-A2, 02-AUG-2001] | 30 ... 255<br>242 ... 462 | 197/226 (87%)<br>201/226 (88%) | e-116 |
| AAG00304 | Human secreted protein, SEQ ID NO: 4385 - *Homo sapiens*, 83 aa. [EP1033401-A2, 06-SEP-2000] | 1 ... 77<br>1 ... 77 | 73/77 (94%)<br>74/77 (95%) | 5e-39 |
| AAP93630 | Sequence of rat transin - *Rattus rattus*, 463 aa. [GB2209526-A, 17-MAY-1989] | 43 ... 179<br>270 ... 401 | 45/142 (31%)<br>68/142 (47%) | 2e-08 |
| AAM48977 | Human matrix metalloproteinase 13 (collagenase 3) - *Homo sapiens*, 471 aa. [WO200206294-A2, 24-JAN-2002] | 30 ... 177<br>264 ... 406 | 38/150 (25%)<br>68/150 (45%) | 4e-07 |
| AAB84615 | Amino acid sequence of matrix metalloproteinase-13 - *Homo sapiens*, 471 aa. [WO200149309-A2, 12-JUL-2001] | 30 ... 177<br>264 ... 406 | 38/150 (25%)<br>68/150 (45%) | 4e-07 |

In a BLAST search of public sequence datbases, the NOV14a protein was found to have homology to the proteins shown in the BLASTP data in Table 14D.

TABLE 14D

Public BLASTP Results for NOV14a

| Protein Accession Number | Protein/Organism/Length | NOV14a Residues/ Match Residues | Identities/ Similarities for the Matched Portion | Expect Value |
|---|---|---|---|---|
| P02790 | Hemopexin precursor (Beta-1B-glycoprotein) - *Homo sapiens* (Human), 462 aa. | 30 . . . 255<br>242 . . . 462 | 197/226 (87%)<br>201/226 (88%) | e−116 |
| OQRB | hemopexin precursor - rabbit, 459 aa. | 28 . . . 255<br>233 . . . 459 | 167/228 (73%)<br>186/228 (81%) | e−100 |
| P20058 | Hemopexin precursor - *Oryctolagus cuniculus* (Rabbit), 460 aa. | 28 . . . 255<br>234 . . . 460 | 167/228 (73%)<br>186/228 (81%) | e−100 |
| P20059 | Hemopexin precursor - *Rattus norvegicus* (Rat), 460 aa. | 30 . . . 254<br>242 . . . 459 | 159/225 (70%)<br>183/225 (80%) | 7e−96 |
| P50828 | Hemopexin precursor (Hyaluronidase) (EC 3.2.1.35) - *Sus scrofa* (Pig), 459 aa. | 48 . . . 253<br>248 . . . 453 | 152/206 (73%)<br>175/206 (84%) | 2e−95 |

PFam analysis predicts that the NOV14a protein contains the domains shown in the Table 14E.

TABLE 14E

Domain Analysis of NOV14a

| Pfam Domain | NOV14a Match Region | Identities/ Similarities for the Matched Region | Expect Value |
|---|---|---|---|
| hemopexin | 56 . . . 99 | 17/50 (34%)<br>31/50 (62%) | 1.4e−09 |
| hemopexin | 101 . . . 146 | 14/50 (28%)<br>37/50 (74%) | 4.5e−07 |

Example 15

The NOV15 clone was analyzed, and the nucleotide and encoded polypeptide sequences are shown in Table 15A.

TABLE 15A

NOV15 Sequence Analysis

SEQ ID NO: 89          2671 bp

NOV15a,
CG109445-01
DNA
Sequence

CCCGCCGGGCGAGCATGGGGCGCCTGGCCTCGAGGCCGCTGCTGCTGGCGCTCCTGTC

GTTGGCTCTTTGCCGAGGGCGTGTGGTGAGAGTCCCCACAGCGACCCTGGTTCGAGTG

GTGGGCACTGAGCTGGTCATCCCCTGCAACGTCAGTGACTATGATGGCCCCAGCGAGC

AAAACTTTGACTGGAGCTTCTCATCTTTGGGGAGCAGCTTTGTGGAGCTTGCAAGCAC

CTGGGAGGTGGGGTTCCCAGCCCAACTGTACCAGGAGCGGCTGCAGAGGGGCGAGATC

CTGTTAAGGCGGACTGCCAACGACGCCGTGGAGCTCCACATAAACAACGTCCAGCCTT

CAGACCAAGGCCACTACAAATGTTCAACCCCCAGCACAGATGCCACTGTCCAGGGAAA

CTATGAGGACACAGTGCAGGTTAAAGTGCTGGCCGACTCCCTGCACGTGGGCCCCAGC

GCGCGGCCCCGCCGAGCCTGAGCCTGCGGGAGGGGGAGCCCTTCGAGCTGCGCTGCA

CCGCCGCCTCCGCCTCGCCGCTGCACACGCACCTGGCGCTGCTGTGGGAGGTGCACCG

CGGCCCGGCCAGGCGGAGCGTCCTCGCCCTGACCCACGAGGGCAGGTTCCACCCGGGC

TABLE 15A-continued

NOV15 Sequence Analysis

CTGGGGTACGAGCAGCGCTACCACAGTGGGGACGTGCGCCTCGACACCGTGGGCAGCG

ACGCCTACCGCCTCTCAGTGTCCCGGGCTCTGTCTGCCGACCAGGGCTCCTACAGGTG

TATCGTCAGCGAGTGGATCGCCGAGCAGGGCAACTGGCAGGAAATCCAAGAAAAGGCC

GTGGAAGTTGCCACCGTGGTGATCCAGCCGACAGTTCTGCGAGCAGCCGTGCCCAAGA

ATGTGTCTGTGGCTGAAGGAAAGGAACTGGACCTGACCTGTAACATCACAACAGACCG

AGCCGATGACGTCCGGCCCGAGGTGACGTGGTCCTTCAGCAGGATGCCTGACAGCACC

CTACCTGGCTCCCGCGTGTTGGCGCGGCTTGACCGTGATTCCCTGGTGCACAGCTCGC

CTCATGTTGCTTTGAGTCATGTGGATGCACGCTCCTACCATTTACTGGTTCGGGATGT

TAGCAAAGAAAACTCTGGCTACTATTACTGCCACGTGTCCCTGTGGGCACCCGGACAC

AACAGGAGCTGGCACAAAGTGGCAGAGGCCGTGTCTTCCCAGCTGGTGTGGGTGTGA

CCTGGCTAGAACCAGACTACCAGGTGTACCTGAATGCTTCCAAGGTCCCCGGGTTTGC

GGATGACCCCACAGAGCTGGCATGCCGGGTGGTGGACACGAAGAGTGGGGAGGCGAAT

GTCCGATTCACGGTTTCGTGGTACTACAGGATGAACCGGCGCAGCGACAATGTGGTGA

CCAGCGAGCTGCTTGCAGTCATGGACGGGGACTGGACGCTAAAATATGGAGAGAGGAG

CAAGCAGCGGGCCCAGGATGGAGACTTTATTTTTTCTAAGGAACATACAGACACGTTC

AATTTCCGGATCCAAAGGACTACAGAGGAAGACAGAGGCAATTATTACTGTGTTGTGT

CTGCCTGGACCAAACAGCGGAACAACAGCTGGGTGAAAAGCAAGGATGTCTTCTCCAA

GCCTGTTAACATATTTTGGGCATTAGAAGATTCCGTGCTTGTGGTGAAGGCGAGGCAG

CCAAAGCCTTTCTTTGCTGCCGGAAATACATTTGAGATGACTTGCAAAGTATCTTCCA

AGAATATTAAGTCGCCACGCTACTCTGTTCTCATCATGGCTGAGAAGCCTGTCGGCGA

CCTCTCCAGTCCCAATGAAACGAAGTACATCATCTCTCTGGACCAGGATTCTGTGGTG

AAGCTGGAGAATTGGACAGATGCATCACGGGTGGATGGCGTTGTTTTAGAAAAAGTGC

AGGAGGATGAGTTCCGCTATCGAATGTACCAGACTCAGGTCTCAGACGCAGGGCTGTA

CCGCTGCATGGTGACAGCCTGGTCTCCTGTCAGGGGCAGCCTTTGGCGAGAAGCAGCA

ACCAGTCTCTCCAATCCTATTGAGATAGACTTCCAAACCTCAGGTCCTATATTTAATG

CTTCTGTGCATTCAGACACACCATCAGTAATTCGGGGAGATCTGATCAAATTGTTCTG

TATCATCACTGTCGAGGGAGCAGCACTGGATCCAGATGACATGGCCTTTGATGTGTCC

TGGTTTGCGGTGCACTCTTTTGGCCTGGACAAGGCTCCTGTGCTCCTGTCTTCCCTGG

ATCGGAAGGGCATCGTGACCACCTCCCGGAGGGACTGGAAGAGCGACCTCAGCCTGGA

GCGCGTGAGTGTGCTGGAATTCTTGCTGCAAGTGCATGGCTCCGAGGACCAGGACTTT

GGCAACTACTACTGTTCCGTGACTCCATGGGTGAAGTCACCAACAGGTTCCTGGCAGA

AGGAGGCAGAGATCCACTCCAAGCCCGTTTTTATAACTGTGAAGATGGATGTGCTGAA

CGCCTTCAAGTATCCCTTGCTGATCGGCGTCGGTCTGTCCACGGTCATCGGGCTCCTG

TCCTGTCTCATCGGGTACTGCAGCTCCCACTGGTGTTGTAAGAAGGAGGTTCAGGAGA

CACGGCGCGAGCGCCGCAGGCTCATGTCGATGGAGATGGACTAG<u>GCTGGCCCGGGAGG</u>

<u>GGA</u>

TABLE 15A-continued

NOV15 Sequence Analysis

|  | ORF Start: ATG at 15 | ORF Stop: TAG at 2652 |
|---|---|---|
|  | SEQ ID NO: 90 | 879 aa    MW at 98569.4 kD |

NOV15a, CG109445-01 Protein Sequence

MGRLASRPLLLALLSLALCRGRVVRVPTATLVRVVGTELVIPCNVSDYDGPSEQNFDW

SFSSLGSSFVELASTWEVGFPAQLYQERLQRGEILLRRTANDAVELHIKNVQPSDQGH

YKCSTPSTDATVQGNYEDTVQVKVLADSLHVGPSARPPPSLSLREGEPFELRCTAASA

SPLHTHLALLWEVHRGPARRSVLALTHEGRFHPGLGYEQRYHSGDVRLDTVGSDAYRL

SVSRALSADQGSYRCIVSEWIAEQGNWQEIQEKAVEVATVVIQPTVLRAAVPKNVSVA

EGKELDLTCNITTDRADDVRPEVTWSFSRMPDSTLPGSRVLARLDRDSLVHSSPHVAL

SHVDARSYHLLVRDVSKENSGYYYCHVSLWAPGHNRSWHKVAEAVSSPAGVGVTWLEP

DYQVYLNASKVPGFADDPTELACRVVDTKSGEANVRFTVSWYYRMNRRSDNVVTSELL

AVMDGDWTLKYGERSKQRAQDGDFIFSKEHTDTFNFRIQRTTEEDRGNYYCVVSAWTK

QRNNSWVKSKDVFSKPVNIFWALEDSVLVVKARQPKPFFAAGNTFEMTCKVSSKNIKS

PRYSVLIMAEKPVGDLSSPNETKYIISLDQDSVVKLENWTDASRVDGVVLEKVQEDEF

RYRMYQTQVSDAGLYRCMVTAWSPVRGSLWREAATSLSNPIEIDFQTSGPIFNASVHS

DTPSVIRGDLIKLFCIITVEGAALDPDDMAFDVSWFAVHSFGLDKAPVLLSSLDRKGI

VTTSRRDWKSDLSLERVSVLEFLLQVHGSEDQDFGNYYCSVTPWVKSPTGSWQKEAEI

HSKPVFITVKMDVLNAFKYPLLIGVGLSTVIGLLSCLIGYCSSHWCCKKEVQETRRER

RRLMSMEMD

Further analysis of the NOV15a protein yielded the following properties shown in Table 15B.

TABLE 15B

| Protein Sequence Properties NOV15a | |
|---|---|
| PSort analysis: | 0.6800 probability located in lysosome (membrane); 0.5140 probability located in plasma membrane; 0.1760 probability located in microbody (peroxisome); 0.1000 probability located in endoplasmic reticulum (membrane) |
| SignalP analysis: | Cleavage site between residues 26 and 27 |

A search of the NOV15a protein against the Geneseq database, a proprietary database that contains sequences published in patents and patent publication, yielded several homologous proteins shown in Table 15C.

TABLE 15C

Geneseq Results for NOV15a

| Geneseq Identifier | Protein/Organism/Length [Patent #, Date] | NOV15a Residues/ Match Residues | Identities/ Similarities for the Matched Region | Expect Value |
|---|---|---|---|---|
| AAM93277 | Human polypeptide, SEQ ID NO: 2751 - Homo sapiens, 863 aa. [EP1130094-A2, 05-SEP-2001] | 1 ... 863<br>1 ... 863 | 862/863 (99%)<br>862/863 (99%) | 0.0 |
| ABB11196 | Human PG F2a receptor regulator homologue, SEQ ID NO: 1566 - Homo sapiens, 138 aa. [WO200157188-A2, 09-AUG-2001] | 236 ... 372<br>2 ... 138 | 131/137 (95%)<br>132/137 (95%) | 7e-70 |
| ABB10996 | Human prostaglandin receptor regulator homologue, SEQ ID NO: 1366 - Homo sapiens, 126 aa. [WO200157188-A2, 09-AUG-2001] | 500 ... 625<br>1 ... 126 | 117/126 (92%)<br>118/126 (92%) | 3e-60 |

TABLE 15C-continued

Geneseq Results for NOV15a

| Geneseq Identifier | Protein/Organism/Length [Patent #, Date] | NOV15a Residues/ Match Residues | Identities/ Similarities for the Matched Region | Expect Value |
|---|---|---|---|---|
| AAB90544 | Human secreted protein, SEQ ID NO: 82 - *Homo sapiens*, 613 aa. [WO200121658-A1, 29-MAR-2001] | 6 . . . 542<br>12 . . . 571 | 163/565 (28%)<br>260/565 (45%) | 2e−59 |
| AAM24248 | Human EST encoded protein SEQ ID NO: 1773 - *Homo sapiens*, 613 aa. [WO200154477-A2, 02-AUG-2001] | 12 . . . 571 | 260/565 (45%) | 2e−59 |

In a BLAST search of public sequence datbases, the NOV15a protein was found to have homology to the proteins shown in the BLASTP data in Table 15D.

TABLE 15D

Public BLASTP Results for NOV15a

| Protein Accession Number | Protein/Organism/Length | NOV15a Residues/ Match Residues | Identities/ Similarities for the Matched Portion | Expect Value |
|---|---|---|---|---|
| Q9P2B2 | KIAA1436 PROTEIN - *Homo sapiens* (Human), 924 aa (fragment). | 1 . . . 879<br>46 . . . 924 | 878/879 (99%)<br>879/879 (99%) | 0.0 |
| Q9WV91 | F2 ALPHA PROSTOGLANDIN REGULATORY PROTEIN - *Mus musculus* (Mouse), 879 aa. | 1 . . . 879<br>1 . . . 879 | 786/879 (89%)<br>830/879 (94%) | 0.0 |
| Q62786 | Prostaglandin F2-alpha receptor regulatory protein precursor (Prostaglandin F2-alpha receptor associated protein) - *Rattus norvegicus* (Rat), 879 aa. | 1 . . . 879<br>1 . . . 879 | 784/879 (89%)<br>834/879 (94%) | 0.0 |
| Q9H3U3 | SMAP-6 - *Homo sapiens* (Human), 186 aa (fragment). | 694 . . . 879<br>1 . . . 186 | 186/186 (100%)<br>186/186 (100%) | e−106 |
| O02834 | ADIPOCYTE MEMBRANE PROTEIN - *Sus scrofa* (Pig), 190 aa (fragment). | 690 . . . 879<br>1 . . . 190 | 184/190 (96%)<br>186/190 (97%) | e−105 |

PFam analysis predicts that the NOV15a protein contains the domains shown in the Table 15E.

TABLE 15E

Domain Analysis of NOV15a

| Pfam Domain | NOV15a Match Region | Identities/ Similarities for the Matched Region | Expect Value |
|---|---|---|---|
| ig | 36 . . . 121 | 15/87 (17%)<br>52/87 (60%) | 0.0013 |
| ig | 162 . . . 249 | 13/89 (15%)<br>60/89 (67%) | 0.00048 |
| ig | 292 . . . 375 | 16/85 (19%)<br>58/85 (68%) | 5.8e−07 |
| ig | 422 . . . 517 | 16/97 (16%)<br>72/97 (74%) | 2.3e−06 |
| ig | 564 . . . 657 | 12/97 (12%)<br>64/97 (66%) | 1.2e−05 |
| ig | 704 . . . 795 | 11/93 (12%)<br>55/93 (59%) | 0.19 |

Example 16

The NOV16 clone was analyzed, and the nucleotide and encoded polypeptide sequences are shown in Table 16A.

TABLE 16A

NOV16 Sequence Analysis

| | SEQ ID NO: 91 | 1565 bp |
|---|---|---|
| NOV16a, CG109496-01 DNA Sequence | <u>GGAATG</u>CTCTCCCGCCTGAGCCTGCTCCAGGAATTGGACCTCAGCTACAACCAGCTCT CAACCCTTGAGCCTGGGGCCTTCCATGGCCTACAAAGCCTACTCACCCTGAGGCTGCA GGGCAATCGGCTCAGAATCATGGGGCCTGGGGTCTTCTCAGGCCTCTCTGCTCTGACC CTGCTGGACCTCCGCCTCAACCAGATTGTTCTCTTCCTAGATGGAGCTTTTGGGGAGC TAGGCAGCCTCCAGAAGCTGGAGGTTGGGGACAACCACCTGGTATTTGTGGCTCCGGG GGCCTTTGCAGGGCTAGCCAAGTTGAGCACCCTCACCCTGGAGCGCTGCAACCTCAGC ACAGTGCCTGGCCTAGCCCTTGCCCGTCTCCCGGCACTAGTGGCCCTAAGGCTTAGAG AACTGGATATTGGGAGGCTGCCAGCTGGGGCCCTGCGGGGGCTGGGGCAGCTCAAGGA GCTGGAGATCCACCTCTGGCCATCTCTGGAGGCTCTGGACCCTGGGAGCCTGGTTGGG CTCAATCTCAGCAGCCTGGCCATCACTCGCTGCAATCTGAGCTCGGTGCCCTTCCAAG CACTGTACCACCTCAGCTTCCTCAGGGTCCTGGATCTGTCCCAGAATCCCATCTCAGC CATCCCAGCCCGAAGGCTCAGCCCCCTGGTGCGGCTCCAGGAGCTACGCCTGTCAGGG GCATGCCTCACCTCCATTGCTGCCCATGCCTTCCATGGCTTGACTGCCTTCCACCTCC TGGATGTGGCAGATAACGCCCTTCAGACACTAGAGGAAACAGCTTTCCCTTCTCCAGA CAAACTGGTCACCTTGAGGCTGTCTGGCAACCCCCTAACCTGTGACTGCCGCCTCCTC TGGCTGCTCCGCCTCCGCCGCCACCTGGACTTTGGCATGTCCCCCCCTGCCTGTGCTG GCCCCCATCATGTCCAGGGGAAGAGCCTGAAGGAGTTTTCAGACATCCTGCCTCCAGG GCACTTCACCTGCAAACCAGCCCTGATCCGAAAGTCGGGGCCTCGATGGGTCATTGCA GAGGAGGGCGGGCATGCGGTTTTCTCCTGCTCTGGAGATGGAGACCCAGCCCCCACTG TCTCCTGGATGAGGCCTCATGGGGCTTGGCTGGGCAGGGCTGGGAGAGTAAGGGTCCT AGAGGATGGGACACTGGAGATCCGCTCAGTGCAGCTACGGGACAGAGGGGCCTATGTC TGTGTGGTTAGCAATGTCGCTGGGAATGACTCCCTGAGGACCTGGCTGGAAGTCATCC AGGTGGAACCACCAAACGGCACACTTTCTGACCCCAACATCACCGTGCCAGGGATCCC AGGGCCTTTTTTTCTGGATAGCAGAGGTGTGGCCATGGTGCTGGCAGTCGGCTTCCTC CCCTTCCTCACCTCAGTGACCCTCTGCTTTGCCCTGATTGCCCTTTGGAGCAAGGGCA AAGGTCGGGTCAAACATCACATGACCTTTGACTTTGTGGCACCTCGGCCCTCTGGGGA TAAAAACTCTGGGGGTAACCGGGTCACTGCCAAGCTCTTCTGA<u>CCTTTCCTTCCCCA</u> |

| | ORF Start: ATG at 4 | ORF Stop: TGA at 1549 |
|---|---|---|
| | SEQ ID NO: 92 | 515 aa    MW at 55659.0 kD |
| NOV16a, CG109496-01 Protein Sequence | MLSRLSLLQELDLSYNQLSTLEPGAFHGLQSLLTLRLQGNRLRIMGPGVFSGLSALTL LDLRLNQIVLFLDGAFGELGSLQKLEVGDNHLVFVAPGAFAGLAKLSTLTLERCNLST VPGLALARLPALVALRLRELDIGRLPAGALRGLGQLKELEIHLWPSLEALDPGSLVGL NLSSLAITRCNLSSVPFQALYHLSFLRVLDLSQNPISAIPARRLSPLVRLQELRLSGA CLTSIAAHAFHGLTAFHLLDVADNALQTLEETAFPSPDKLVTLRLSGNPLTCDCRLLW LLRLRRHLDFGMSPPACAGPHHVQGKSLKEFSDILPPGHFTCKPALIRKSGPRWVIAE EGGHAVFSCSGDGDPAPTVSWMRPHGAWLGRAGRVRVLEDGTLEIRSVQLRDRGAYVC VVSNVAGNDSLRTWLEVIQVEPPNGTLSDPNITVPGIPGPFFLDSRGVAMVLAVGFLP FLTSVTLCFGLIALWSKGKGRVKHHMTFDFVAPRPSGDKNSGGNRVTAKLF |

Further analysis of the NOV16a protein yielded the following properties shown in Table 16B.

TABLE 16B

| Protein Sequence Properties NOV16a | |
|---|---|
| PSort analysis: | 0.7000 probability located in plasma membrane; 0.5204 probability located in mitochondrial inner membrane; 0.4430 probability located in microbody (peroxisome); 0.2217 probability located in mitochondrial intermembrane space |
| SignalP analysis: | No Known Signal Sequence Predicted |

A search of the NOV16a protein against the Geneseq database, a proprietary database that contains sequences published in patents and patent publication, yielded several homologous proteins shown in Table 16C.

TABLE 16C

Geneseq Results for NOV16a

| Geneseq Identifier | Protein/Organism/Length [Patent #, Date] | NOV16a Residues/ Match Residues | Identities/ Similarities for the Matched Region | Expect Value |
|---|---|---|---|---|
| AAW84596 | Amino acid sequence of the human Tango-79 protein - *Homo sapiens*, 614 aa. [WO9906427-A1, 11-FEB-1999] | 8 . . . 500 91 . . . 596 | 229/509 (44%) 312/509 (60%) | e−116 |
| AAB74705 | Human membrane associated protein MEMAP-11 - *Homo sapiens*, 620 aa. [WO200112662-A2, 22-FEB-2001] | 8 . . . 500 97 . . . 602 | 228/509 (44%) 312/509 (60%) | e−116 |
| AAB80225 | Human PRO227 protein - *Homo sapiens*, 620 aa. [WO200104311-A1, 18-JAN-2001] | 8 . . . 500 97 . . . 602 | 227/509 (44%) 311/509 (60%) | e−115 |
| AAU12333 | Human PRO227 polypeptide sequence - *Homo sapiens*, 620 aa. [WO200140466-A2, 07-JUN-2001] | 8 . . . 500 97 . . . 602 | 227/509 (44%) 311/509 (60%) | e−115 |
| AAY13357 | Amino acid sequence of protein PRO227 - *Homo sapiens*, 620 aa. [WO9914328-A2, 25-MAR-1999] | 8 . . . 500 97 . . . 602 | 227/509 (44%) 311/509 (60%) | e−115 |

In a BLAST search of public sequence datbases, the NOV16a protein was found to have homology to the proteins shown in the BLASTP data in Table 16D.

TABLE 16D

Public BLASTP Results for NOV16a

| Protein Accession Number | Protein/Organism/Length | NOV16a Residues/ Match Residues | Identities/ Similarities for the Matched Portion | Expect Value |
|---|---|---|---|---|
| Q9N008 | HYPOTHETICAL 69.2 KDA PROTEIN - *Macaca fascicularis* (Crab eating macaque) (Cynomolgus monkey), 614 aa. | 8 . . . 500 91 . . . 596 | 228/509 (44%) 312/509 (60%) | e−115 |
| Q96FE5 | UNKNOWN (PROTEIN FOR MGC: 17422) - *Homo sapiens* (Human), 614 aa. | 8 . . . 500 91 . . . 596 | 228/509 (44%) 312/509 (60%) | e−115 |
| Q9D1T0 | ADULT MALE TESTIS CDNA, RIKEN FULL-LENGTH ENRICHED LIBRARY, CLONE: 4930471K13, FULL INSERT SEQUENCE - *Mus musculus* (Mouse), 614 aa. | 8 . . . 500 91 . . . 596 | 228/509 (44%) 312/509 (60%) | e−115 |
| Q9BZ20 | BA438B23.1 (NEURONAL LEUCINE-RICH REPEAT PROTEIN) (CDNA FLJ31810 FIS, CLONE NT2RI2009289, WEAKLY SIMILAR TO | 7 . . . 501 82 . . . 588 | 224/507 (44%) 311/507 (61%) | e−113 |

TABLE 16D-continued

Public BLASTP Results for NOV16a

| Protein Accession Number | Protein/Organism/Length | NOV16a Residues/ Match Residues | Identities/ Similarities for the Matched Portion | Expect Value |
|---|---|---|---|---|
| CAC34918 | CARBOXYPEPTIDASE N 83 KDA CHAIN) - *Homo sapiens* (Human), 606 aa. | | | |
| | SEQUENCE 1 FROM PATENT WO0075358 - *Homo sapiens* (Human), 548 aa. | 7 ... 501<br>82 ... 530 | 197/505 (39%)<br>278/505 (55%) | 3e-89 |

PFam analysis predicts that the NOV16a protein contains the domains shown in the Table 16E.

TABLE 16E

Domain Analysis of NOV16a

| Pfam Domain | NOV16a Match Region | Identities/ Similarities for the Matched Region | Expect Value |
|---|---|---|---|
| LRR | 7 ... 30 | 13/25 (52%)<br>22/25 (88%) | 3.8e-05 |
| LRR | 31 ... 54 | 8/25 (32%)<br>19/25 (76%) | 0.64 |
| LRR | 199 ... 222 | 9/25 (36%)<br>16/25 (64%) | 0.27 |
| LRR | 223 ... 246 | 9/25 (36%)<br>19/25 (76%) | 0.32 |

TABLE 16E-continued

Domain Analysis of NOV16a

| Pfam Domain | NOV16a Match Region | Identities/ Similarities for the Matched Region | Expect Value |
|---|---|---|---|
| LRRCT | 280 ... 333 | 19/58 (33%)<br>42/58 (72%) | 3.1e-07 |
| ig | 350 ... 408 | 19/62 (31%)<br>41/62 (66%) | 9.1e-09 |

Example 17

The NOV17 clone was analyzed, and the nucleotide and encoded polypeptide sequences are shown in Table 17A.

TABLE 17A

NOV17 Sequence Analysis

SEQ ID NO: 93    1780 bp

NOV17a, CG109532-01 DNA Sequence

<u>CCAACCCTCTGCCCGGCCGGTGCCC</u>ATGCTTCTGTGGCTGCTGCTGCTGATCCTGACT

CCTGGAAGAGAACAATCAGGGGTGGCCCCAAAAGCTGTACTTCTCCTCAATCCTCCAT

GGTCCACAGCCTTCAAAGGAGAAAAAGTGGCTCTCATATGCAGCAGCATATCACATTC

CCTAGCCCAGGGAGACACATATTGGTATCACGATGAGAAGTTGTTGAAAATAAAACAT

GACAAGATCCAAATTACAGAGCCTGGAAATTACCAATGTAAGACCCGAGGATCCTCCC

TCAGTGATGCCGTGCATGTGGAATTTTCACCTGACTGGCTGATCCTGCAGGCTTTACA

TCCTGTCTTTGAAGGAGACAATGTCATTCTGAGATGTCAGGGGAAAGACAACAAAAAC

ACTCATCAAAAGGTTTACTACAAGGATGGAAAACAGCTTCCTAATAGTTATAATTTAG

AGAAGATCACAGTGAATTCAGTCTCCAGGGATAATAGCAAATATCATTGTACTGCTTA

TAGGAAGTTTTACATACTTGACATTGAAGTAACTTCAAAACCCCTAAATATCCAAGTT

CAAGAGCTGTTTCTACATCCTGTGCTGAGAGCCAGCTCTTCCACGCCCATAGAGGGGA

GTCCCATGACCCTGACCTGTGAGACCCAGCTCTCTCCACAGAGGCCAGATGTCCAGCT

GCAATTCTCCCTCTTCAGAGATAGCCAGACCCTCGGATTGGGCTGGAGCAGGTCCCCC

AGACTCCAGATCCCTGCCATGTGGACTGAAGACTCAGGGTCTTACTGGTGTGAGGTGG

AGACAGTGACTCACAGCATCAAAAAAAGGAGCCTGAGATCTCAGATACGTGTACAGAG

TABLE 17A-continued

NOV17 Sequence Analysis

AGTCCCTGTGTCTAATGTGAATCTAGAGATCCGGCCCACCGGAGGGCAGCTGATTGAA

GGAGAAAATATGGTCCTTATTTGCTCAGTAGCCCAGGGTTCAGGGACTGTCACATTCT

CCTGGCACAAAGAAGGAAGAGTAAGAAGCCTGGGTAGAAAGACCCAGCGTTCCCTGTT

GGCAGAGCTGCATGTTCTCACCGTGAAGGAGAGTGATGCAGGGAGATACTACTGTGCA

GCTGATAACGTTCACAGCCCCATCCTCAGCACGTGGATTCGAGTCACCGTGAGAATTC

CGGTATCTCACCCTGTCCTCACCTTCAGGGCTCCCAGGGCCCACACTGTGGTGGGGGA

CCTGCTGGAGCTTCACTGTGAGTCCCTGAGAGGCTCTCCCCCGATCCTGTACCGATTT

TATCATGAGGATGTCACCCTGGGGAACAGCTCAGCCCCCTCTGGAGGAGGAGCCTCCT

TCAACCTCTCTCTGACTGCAGAACATTCTGGAAACTACTCCTGTGATGCAGACAATGG

CCTGGGGGCCCAGCACAGTCATGGAGTGAGTCTCAGGGTCACAGTTCCGGTGTCTCGC

CCCGTCCTCACCCTCAGGGCTCCCGGGGCCCAGGCTGTGGTGGGGGACCTGCTGGAGC

TTCACTGTGAGTCCCTGAGAGGCTCCTTCCCGATCCTGTACTGGTTTTATCACGAGGA

TGACACCTTGGGGAACATCTCGGCCCACTCTGGAGGAGGGCATCCTTCAACCTCTCT

CTGACTACAGAACATTCTGGAAACTACTCATGTGAGGCTGACAATGGCCTGGGGGCCC

AGCACAGTAAAGTGGTGACACTCAATGTTACAGGTGTGTTAATAGTACCTGGGCTAGA

GGTCACAGTTATGGTAAATAAAATAGTTATCTGACAGATT

| | ORF Start: ATG at 26 | ORF Stop: TGA at 1772 |
| --- | --- | --- |
| | SEQ ID NO: 94 | 582 aa    MW at 64270.5 kD |

| NOV17a,<br>CG109532-01<br>Protein<br>Sequence | MLLWLLLLILTPGREQSGVAPKAVLLLNPPWSTAFKGEKVALICSSISHSLAQGDTYW<br><br>YHDEKLLKIKHDKIQITEPGNYQCKTRGSSLSDAVHVEFSPDWLILQALHPVFEGDNV<br><br>ILRCQGKDNKNTHQKVYYKDGKQLPNSYNLEKITVNSVRDNSKYHCTAYRKFYILDI<br><br>EVTSKPLNIQVQELFLHPVLRASSSTPIEGSPMTLTCETQLSPQRPDVQLQFSLFRDS<br><br>QTLGLGWSRSPRLQIPAMWTEDSGSYWCEVETVTHSIKKRSLRSQIRVQRVPVSNVNL<br><br>EIRPTGGQLIEGENMVLICSVAQGSGTVTFSWHKEGRVRSLGRKTQRSLLAELHVLTV<br><br>KESDAGRYYCAADNVHSPILSTWIRVTVRIPVSHPVLTFRAPRAHTVVGDLLELHCES<br><br>LRGSPPILYRFYHEDVTLGNSSAPSGGGASFNLSLTAEHSGNYSCDADNGLGAQHSHG<br><br>VSLRVTVPVSRPVLTLRAPGAQAVVGDLLELHCESLRGSFPILYWFYHEDDTLGNISA<br><br>HSGGGASFNLSLTTEHSGNYSCEADNGLGAQHSKVVTLNVTGVLIVPGLEVTVMVNKI<br><br>VI |
| --- | --- |

| | SEQ ID NO: 95 | 1263 bp |
| --- | --- | --- |

| NOV17b,<br>207775340<br>DNA<br>Sequence | AAGCTTGGAGAAAAAGTGGCTCTCATATGCAGCAGCATATCACATTCCCTAGCCCAGG<br><br>GAGACACATATTGGTATCACGATGAGAAGTTGTTGAAAATAAAACATGACAAGATCCA<br><br>AATTACAGAGCCTGGAAATTACCAATGTAAGACCCGAGGATCCTCCCTCAGTGATGCC<br><br>GTGCATGTGGAATTTTCACCTGACTGGCTGATCCTGCAGGCTTTACATCCTGTCTTTG<br><br>AAGGAGACAATGTCATTCTGAGATGTCAGGGGAAAGACAACAAAAACACTCATCAAAA<br><br>GGTTTACTACAAGGATGGAAAACAGCTTCCTAATAGTTATAATTTAGAGAAGATCACA<br><br>GTGAATTCAGTCTCCAGGGATAATAGCAAATATCATTGTACTGCTTATAGGAAGTTTT<br><br>ACATACTTGACATTGAAGTAACTTCAAAACCCCTAAATATCCAAGTTCAAGAGCTGTT |
| --- | --- |

TABLE 17A-continued

NOV17 Sequence Analysis

|  |  |
|---|---|
|  | TCTACATCCTGTGCTGAGAGCCAGCTCTTCCACGCCCATAGAGGGGAGTCCCATGACC<br>CTGACCTGTGAGACCCAGCTCTCTCCACAGAGGCCAGATGTCCAGCTGCAATTCTCCC<br>TCTTCAGAGATAGCCAGACCCTCGGATTGGGCTGGAGTAGGTCCCCCAGACTCCAGAT<br>CCCTGCCATGTGGACTGAAGACTCAGGGTCTTACTGGTGTGAGGTGGAGACAGTGACT<br>CACAGCATCAAAAAAAGGAGCCTGAGATCTCAGATACGTGTACAGAGAGTCCCTGTGT<br>CTAATGTGAATCTAGAGATCCGGCCCACCGGAGGGCAGCTGATTGAAGGAGAAAATAT<br>GGTCCTTATTTGCTCAGTAGCCCAGGGTTCAGGGACTGTCACATTCTCCTGGCACAAA<br>GAAGGAAGAGTAAGAAGCCTGGGTAGAAAGACCCAGCGTTCCCTGTTGGCAGAGCTGC<br>ATGTTCTCACCGTGAAGGAGAGTGATGCAGGGAGATACTACTGTGCAGCTGATAACGT<br>TCACAGCCCCATCCTCAGCACGTGGATTCGAGTCACCGTGAGAATTCCGGTATCTCAC<br>CCTGTCCTCACCTTCAGGGCTCCCAGGGCCCACACTGTGGTGGGGACCTGCTGGAGC<br>TTCACTGTGAGTCCCTGAGAGGCTCTCCCCCGATCCTGTACCGATTTTATCATGAGGA<br>TGTCACCCTGGGGAACAGCTCAGCCCCTCTGGAGGAGGAGCCTCCTTCAACCTCTCT<br>CTGACTGCAGAACATTCTGGAAACTACTCATGTGAGGCTCTCGAG |
|  | ORF Start: at 1          ORF Stop: end of sequence<br>SEQ ID NO: 96          421 aa    MW at 47243.1 kD |
| NOV17b,<br>207775340<br>Protein<br>Sequence | KLGEKVALICSSISHSLAQGDTYWYHDEKLLKIKHDKIQITEPGNYQCKTRGSSLSDA<br>VHVEFSPDWLILQALHPVFEGDNVILRCQGKDNKNTHQKVYYKDGKQLPNSYNLEKIT<br>VNSVSRDNSKYHCTAYRKFYILDIEVTSKPLNIQVQELFLHPVLRASSSTPIEGSPMT<br>LTCETQLSPQRPDVQLQFSLFRDSQTLGLGWSRSPRLQIPAMWTEDSGSYWCEVETVT<br>HSIKKRSLRSQIRVQRVPVSNVNLEIRPTGGQLIEGENMVLICSVAQGSGTVTFSWHK<br>EGRVRSLGRKTQRSLLAELHVLTVKESDAGRYYCAADNVHSPILSTWIRVTVRIPVSH<br>PVLTFRAPRAHTVVGDLLELHCESLRGSPPILYRFYHEDVTLGNSSAPSGGGASFNLS<br>LTAEHSGNYSCEALE |
|  | SEQ ID NO: 97          1263 bp |
| NOV17c,<br>207775361<br>DNA<br>Sequence | AAGCTTGGAGAAAAAGTGGCTCTCATATGCAGCAGCATATCACATTCCCTAGCCCAGG<br>GAGACACATATTGGTATCACGATGAGAAGTTGTTGAAAATAAAACATGACAAGATCCA<br>AATTACAGAGCCTGGAAATTACCAATGTAAGACCCGAGGATCCTCCCTCAGTGATGCC<br>GTGCATGTGGAATTTTCACCTGACTGGCTGATCCTGCAGGCTTTACATCCTGTCTTTG<br>AAGGAGACAATGTCATTCTGAGATGTCAGGGGAAAGACAACAAAAACACTCATCAAAA<br>GGTTTACTACAAGGATGGAAAACAGCTTCCTAATAGTTATAATTTAGAGAAGATCACA<br>GTGAATTCAGTCTCCAGGGATAATAGCAAATATCATTGTACTGCTTATAGGAAGTTTT<br>ACATACTTGACATTGAAGTAACTTCAAAACCCCTAAATATCCAAGTTCAAGAGCTGTT<br>TCTACATCCTGTGCTGAGAGCCAGCTCTTCCACGCCCATAGAGGGGAGTCCCATGACC<br>CTGACCTGTGAGACCCAGCTCTCTCCACAGAGGCCAGATGTCCAGCTGCAATTCTCCC<br>TCTTCAGAGATAGCCAGACCCTCGGATTGGGCTGGAGCAGGTCCCCCAGACTCCAGAT<br>CCCTGCCATGTGGACTGAAGACTCAGGGTCTTACTGGTGTGAGGTGGAGACAGTGACT<br>CACAGCATCAAAAAAAGGAGCCTGAGATCTCAGATACGTGTACAGAGAGTCCCTGTGT |

TABLE 17A-continued

NOV17 Sequence Analysis

|  |  |
|---|---|
|  | CTAATGTGAATCTAGAGATCCGGCCCACCGGAGGGCAGCTGATTGAAGGAGAAAATAT |
|  | GGTCCTTATTTGCTCAGTAGCCCAGGGTTCAGGGACTGTCACATTCTCCTGGCACAAA |
|  | GAAGGAAGAGTAAGAAGCCTGGGTAGAAAGACCCAGCGTTCCCTGTTGGCAGAGCTGC |
|  | ATGTTCTCACCGTGAAGGAGAGTGATGCAGGGAGATACTACTGTGCAGCTGATAACGT |
|  | TCACAGCCCCATCCTCAGCACGTGGATTCGAGTCACCGTGAGAATTCCGGTATCTCAC |
|  | CCTGTCCTCACCTTCAGGGCTCCCAGGGCCCACACTGTGGTGGGGGACCTGCTGGAGC |
|  | TTCACTGTGAGTCCCTGAGAGGCTCTCCCCCGATCCTGTACCCATTTTATCATGAGGA |
|  | TGTCACCCTGGGGAACAGCTCAGCCCCCTCTGGAGGAGGAGCCTCCTTCAACCTCTCT |
|  | CTGACTGCAGAACATTCTGGAAACTACTCATGTGAGGCTCTCGAG |

|  |  |  |
|---|---|---|
|  | ORF Start: at 1<br>SEQ ID NO: 98 | ORF Stop: end of sequence<br>421 aa    MW at 47243.1 kD |
| NOV17c,<br>207775361<br>Protein<br>Sequence | KLGEKVALICSSISHSLAQGDTYWYHDEKLLKIKHDKIQITEPGNYQCKTRGSSLSDA<br>VHVEFSPDWLILQALHPVFEGDNVILRCQGKDNKNTHQKVYYKDGKQLPNSYNLEKIT<br>VNSVSRDNSKYHCTAYRKFYILDIEVTSKPLNIQVQELFLHPVLRASSSTPIEGSPMT<br>LTCETQLSPQRPDVQLQFSLFRDSQTLGLGWSRSPRLQIPAMWTEDSGSYWCEVETVT<br>HSIKKRSLRSQIRVQRVPVSNVNLEIRPTGGQLIEGENMVLICSVAQGSGTVTFSWHK<br>EGRVRSLGRKTQRSLLAELHVLTVKESDAGRYYCAADNVHSPILSTWIRVTVRIPVSH<br>PVLTFRAPRAHTVVGDLLELHCESLRGSPPILYRFYHEDVTLGNSSAPSGGGASFNLS<br>LTAEHSGNYSCEALE |

|  |  |  |
|---|---|---|
|  | SEQ ID NO: 99 | 1263 bp |
| NOV17d,<br>207775365<br>DNA<br>Sequence | AAGCTTGGAGAAAAAGTGGCTCTCATATGCAGCAGCATATCACATTCCCTAGCCCAGG |  |
|  | GAGACACATATTGGTATCACGATGAGAAGTTGTTGAAAATAAAACATGACAAGATCCA |  |
|  | AATTACAGAGCCTGGAAATTACCAATGTAAGACCCGAGGATCCTCCCTCAGTGATGCC |  |
|  | GTGCATGTGGAATTTTCACCTGACTGGCTGATCCTGCAGGCTTTACATCCTGTCTTTG |  |
|  | AAGGAGACAATGTCATTCTGAGATGTCAGGGGAAAGACAACAAAAACACTCATCAAAA |  |
|  | GGTTTACTACAAGGATGGAAAACAGCTTCCTAATAGTTATAATTTAGAGAAGATCACA |  |
|  | GTGAATTCAGTCTCCAGGGATAATAGCAAATATCATTGTACTGCTTATAGGAAGTTTT |  |
|  | ACATACTTGACATTGAAGTAACTTCAAAACCCCTAAATATCCAAGTTCAGGAGCTGTT |  |
|  | TCTACATCCTGTGCTGAGAGCCAGCTCTTCCACGCCCATAGAGGGGAGTCCCCTGACC |  |
|  | CTGACCTGTGAGACCCAGCTCTCTCCACAGAGGCCAGATGTCCAGCTGCAATTCTCCC |  |
|  | TCTTCAGAGATAGCCAGACCCCCGGATTGGGCTGGAGCAGGTCCCCCAGACTCCAGAT |  |
|  | CCCTGCCATGTGGACTGAAGACTCAGGGTCTTACTGGTGTGAGGTGGAGACAGTGACT |  |
|  | CACAGCATCAAAAAAGGAGCCTGAGATCTCAGATACGTGTACAGAGAGTCCCTGTGT |  |
|  | CTAATGTGAATCTAGAGATCCGGCCCACCGGAGGGCAGCTGATTGAAGGAGAAAATAT |  |
|  | GGTCCTTATTTGCTCAGTAGCCCAGGGTTCAGGGACTGTCACATTCTCCTGGCACAAA |  |
|  | GAAGGAAGAGTAAGAAGCCTGGGTAGAAAGACCCAGCGTTCCCTGTTGGCAGAGCTGC |  |
|  | ATGTTCTCACCGTGAAGGAGAGTGATGCAGGGAGATACTACTGTGCAGCTGATAACGT |  |
|  | TCACAGCCCCATCCTCAGCACGTGGATTCGAGTCACCGTGAGAATTCCGGTATCTCAC |  |

TABLE 17A-continued

NOV17 Sequence Analysis

```
CCTGTCCCCACCTTCAGGGCTCCCAGGGCCCACACTGTGGTGGGGGACCTGCTGGAGC

TTCACTGTGAGTCCCTGAGAGGCTCTCCCCCGATCCTGTACCGATTTTATCATGAGGA

TGTCACCCTGGGGAACAGCTCAGCCCCCTCTGGAGGAGGAGACTCCTTCAACCTCTCT

CTGACTGCAGAACATTCTGGAAACTACTCATGTGAGGCTCTCGAG
```

| | ORF Start: at 1<br>SEQ ID NO: 100 | ORF Stop: end of sequence<br>421 aa  MW at 47255.0 kD |
|---|---|---|
| NOV17d,<br>207775365<br>Protein<br>Sequence | KLGEKVALICSSISHSLAQGDTYWYHDEKLLKIKHDKIQITEPGNYQCKTRGSSLSDA<br>VHVEFSPDWLILQALHPVFEGDNVILRCQGKDNKNTHQKVYYKDGKQLPNSYNLEKIT<br>VNSVSRDNSKYHCTAYRKFYILDIEVTSKPLNIQVQELFLHPVLRASSSTPIEGSPMT<br>LTCETQLSPQRPDVQLQFSLFRDSQTPGLGWSRSPRLQIPAMWTEDSGSYWCEVETVT<br>HSIKKRSLRSQIRVQRVPVSNVNLEIRPTGGQLIEGENMVLICSVAQGSGTVTFSWHK<br>EGRVRSLGRKTQRSLLAELHVLTVKESDAGRYYCAADNVHSPILSTWIRVTVRIPVSH<br>PVPTFRAPRAHTVVGDLLELHCESLRGSPPILYRFYHEDVTLGNSSAPSGGGDSFNLS<br>LTAEHSGNYSCEALE | |

Sequence comparison of the above protein sequences yields the following sequence relationships shown in Table 17B.

TABLE 17B

Comparison of NOV17a against NOV17b through NOV17d.

| Protein Sequence | NOV17a Residues/<br>Match Residues | Identities/Similarities<br>for the Matched Region |
|---|---|---|
| NOV17b | 37 ... 453<br>3 ... 419 | 404/417 (96%)<br>405/417 (96%) |
| NOV17c | 37 ... 453<br>3 ... 419 | 404/417 (96%)<br>405/417 (96%) |
| NOV17d | 37 ... 453<br>3 ... 419 | 413/417 (99%)<br>414/417 (99%) |

Further analysis of the NOV17a protein yielded the following properties shown in Table 17C.

TABLE 17C

Protein Sequence Properties NOV17a

| PSort<br>analysis: | 0.5374 probability located in outside;<br>0.1900 probability located in lysosome (lumen);<br>0.1000 probability located in endoplasmic<br>reticulum (membrane);<br>0.1000 probability located in endoplasmic reticulum (lumen) |
|---|---|
| SignalP<br>analysis: | Cleavage site between residues 18 and 19 |

A search of the NOV17a protein against the Geneseq database, a proprietary database that contains sequences published in patents and patent publication, yielded several homologous proteins shown in Table 17D.

TABLE 17D

Geneseq Results for NOV17a

| Geneseq<br>Identifier | Protein/Organism/Length<br>[Patent #, Date] | NOV17a<br>Residues/<br>Match<br>Residues | Identities/<br>Similarities for<br>the Matched<br>Region | Expect<br>Value |
|---|---|---|---|---|
| AAB82316 | Human immunoglobulin receptor<br>IRTA3 protein - *Homo sapiens*,<br>734 aa. [WO200138490-A2, 31-MAY-2001] | 1 ... 564<br>1 ... 564 | 564/564 (100%)<br>564/564 (100%) | 0.0 |
| AAB82314 | Human immunoglobulin receptor<br>isoform IRTA2b - *Homo sapiens*,<br>592 aa. [WO200138490-A2, 31-MAY-2001] | 1 ... 564<br>1 ... 561 | 259/568 (45%)<br>334/568 (58%) | e-130 |
| AAB82315 | Human immunoglobulin receptor<br>isoform IRTA2c - *Homo sapiens*,<br>977 aa. [WO200138490-A2, 31-MAY-2001] | 1 ... 575<br>1 ... 572 | 261/579 (45%)<br>338/579 (58%) | e-129 |
| AAB82313 | Human immunoglobulin receptor<br>isoform IRTA2a - *Homo sapiens*,<br>759 aa. [WO200138490-A2, 31-MAY-2001] | 1 ... 575<br>1 ... 572 | 261/579 (45%)<br>338/579 (58%) | e-129 |

TABLE 17D-continued

Geneseq Results for NOV17a

| Geneseq Identifier | Protein/Organism/Length [Patent #, Date] | NOV17a Residues/ Match Residues | Identities/ Similarities for the Matched Region | Expect Value |
|---|---|---|---|---|
| AAB82317 | Human immunoglobulin receptor IRTA4 protein - *Homo sapiens*, 508 aa. [WO200138490-A2, 31-MAY-2001] | 100 . . . 472<br>18 . . . 389 | 227/374 (60%)<br>280/374 (74%) | e-129 |

In a BLAST search of public sequence datbases, the NOV17a protein was found to have homology to the proteins shown in the BLASTP data in Table 17E.

TABLE 17E

Public BLASTP Results for NOV17a

| Protein Accession Number | Protein/Organism/Length | NOV17a Residues/ Match Residues | Identities/ Similarities for the Matched Portion | Expect Value |
|---|---|---|---|---|
| Q96LA4 | FC RECEPTOR-LIKE PROTEIN 3 - *Homo sapiens* (Human), 734 aa. | 1 . . . 564<br>1 . . . 564 | 564/564 (100%)<br>564/564 (100%) | 0.0 |
| Q96P31 | SH2 DOMAIN-CONTAINING PHOSPHATASE ANCHOR PROTEIN 2A - *Homo sapiens* (Human), 734 aa. | 1 . . . 564<br>1 . . . 564 | 564/564 (100%)<br>564/564 (100%) | 0.0 |
| Q96P29 | SH2 DOMAIN-CONTAINING PHOSPHATASE ANCHOR PROTEIN 2C - *Homo sapiens* (Human), 740 aa. | 1 . . . 564<br>1 . . . 570 | 563/570 (98%)<br>564/570 (98%) | 0.0 |
| CAC05323 | BA367J7.2.1 (NOVEL IMMUNOGLOBULIN DOMAINS CONTAINING PROTEIN (ISOFORM 1)) - *Homo sapiens* (Human), 548 aa (fragment). | 1 . . . 548<br>1 . . . 548 | 548/548 (100%)<br>548/548 (100%) | 0.0 |
| Q96P30 | SH2 DOMAIN-CONTAINING PHOSPHATASE ANCHOR PROTEIN 2B - *Homo sapiens* (Human), 639 aa. | 111 . . . 564<br>35 . . . 469 | 318/457 (69%)<br>347/457 (75%) | e-167 |

PFam analysis predicts that the NOV17a protein contains the domains shown in the Table 17F.

TABLE 17F

Domain Analysis of NOV17a

| Pfam Domain | NOV17a Match Region | Identities/ Similarities for the Matched Region | Expect Value |
|---|---|---|---|
| ig | 37 . . . 84 | 12/52 (23%)<br>29/52 (56%) | 0.84 |
| ig | 113 . . . 165 | 12/57 (21%)<br>38/57 (67%) | 0.52 |
| ig | 204 . . . 262 | 18/61 (30%)<br>43/61 (70%) | 2.3e-08 |
| ig | 302 . . . 360 | 15/61 (25%)<br>46/61 (75%) | 8.2e-10 |
| ig | 397 . . . 453 | 13/59 (22%)<br>45/59 (76%) | 0.0004 |
| ig | 490 . . . 546 | 13/60 (22%)<br>43/60 (72%) | 1.7e-05 |

Example 18

The NOV18 clone was analyzed, and the nucleotide and encoded polypeptide sequences are shown in Table 18A.

TABLE 18A

NOV18 Sequence Analysis

| | SEQ ID NO: 101 | 360 bp |
|---|---|---|

| NOV18a CG50213-01 DNA Sequence | CGCTGCTCCTGCTGCTGCTGGCGCTGTACACCGCGCGTGTGGACGGGTCCAAATGCAA GTGCTCCCGGAAGGGACCCAAGATCCGCTACAGCGACGTGAAGAAGCTGGAAATGAAG CCAAAGTACCCGCACTGCGAGGAGAAGATGGTTATCATCACCACCAAGAGCGTGTCCA GGTACCGAGGTCAGGAGCACTGCCTGCACCCCAAGCTGCAGAGCACCAAGCGCTTCAT CAAGTGGTACAACGCCTGGAACGAGAAGCGCAGGGTCTACGAAGAATAGGGTGAAAAA CCTCAGAAGGGAAAACTCCAAACCAGTTGGGAGACTTGTGCAAAGGACTTTGCAGATT AAAAAAAAAAAA |
|---|---|

| | ORF Start: at 3 | ORF Stop: TAG at 279 |
|---|---|---|
| | SEQ ID NO: 10 | 292 aa MW at 11045.0 kD |

| NOV18a, CG50213-01 Protein Sequence | LLLLLLALYTARVDGSKCKCSRKGPKIRYSDVKKLEMKPKYPHCEEKMVIITTKSVSR YRGQEHCLHPKLQSTKRFIKWYNAWNEKRRVYEE |
|---|---|

| | SEQ ID NO: 103 | 228 bp |
|---|---|---|

| NOV18b, CG50213-02 DNA Sequence | AAATGCAAGTGCTCCCGGAAGGGACCCAAGATCCGCTACAGCGACGTGAAGAAGCTGG AAATGAAGCCAAAGTACCCGCACTGCGAGGAGAAGATGGTTATCATCACCACCAAGAG CGTGTCCAGGTACCGAGGTCAGGAGCACTGCCTGCACCCCAAGCTGCAGAGCACCAAG CGCTTCATCAAGTGGTACAACGCCTGGAACGAGAAGCGCAGGGTCTACGAAGAA |
|---|---|

| | ORF Start: at 1 | ORF Stop: end of sequence |
|---|---|---|
| | SEQ ID NO: 104 | 76 aa MW at 9331.9 kD |

| NOV18b, CG50213-02 Protein Sequence | KCKCSRKGPKIRYSDVKKLEMKPKYPHCEEKMVIITTKSVSRYRGQEHCLHPKLQSTK RFIKWYNAWNEKRRVYEE |
|---|---|

| | SEQ ID NO: 105 | 228 bp |
|---|---|---|

| NOV18c, CG50213-03 DNA Sequence | AAATGCAAGTGCTCCCGGAAGGGACCCAAGATCCGCTACAGCGACGTGAAGAAGCTGG AAATGAAGCCAAAGTACCCGCACTGCGAGGAGAAGATGGTTATCATCACCACCAAGAG CGTGTCCAGGTACCGAGGTCAGGAGCACTGCCTGCACCCCAAGCTGCAGAGCACCAAG CGCTTCATCCAGTGGTACAACGCCTGGAACGAGAAGCGCAGGGTCTACGAAGAA |
|---|---|

| | ORF Start: at 1 | ORF Stop: end of sequence |
|---|---|---|
| | SEQ ID NO: 10 | 676 aa MW at 9331.9 kD |

| NOV18c, CG50213-03 Protein Sequence | KCKCSRKGPKIRYSDVKKLEMKPKYPHCEEKMVIITTKSVSRYRGQEHCLHPKLQSTK RFIKWYNAWNEKRRVYEE |
|---|---|

Sequence comparison of the above protein sequences yields the following sequence relationships shown in Table 18B.

TABLE 18B

Comparison of NOV18a against NOV18b and NOV18c.

| Protein Sequence | NOV18a Residues/ Match Residues | Identities/Similarities for the Matched Region |
|---|---|---|
| NOV18b | 17 . . . 92 | 76/76 (100%) |
|  | 1 . . . 76 | 76/76 (100%) |
| NOV18c | 17 . . . 92 | 76/76 (100%) |
|  | 1 . . . 76 | 76/76 (100%) |

Further analysis of the NOV18a protein yielded the following properties shown in Table 18C.

TABLE 18C

Protein Sequence Properties NOV18a

| PSort analysis: | 0.3700 probability located in outside; 0.1800 probability located in nucleus; 0.1000 probability located in endoplasmic reticulum (membrane); 0.1000 probability located in endoplasmic reticulum (lumen) |
|---|---|
| SignalP analysis: | Cleavage site between residues 16 and 17 |

A search of the NOV18a protein against the Geneseq database, a proprietary database that contains sequences published in patents and patent publication, yielded several homologous proteins shown in Table 18D.

TABLE 18D

Geneseq Results for NOV18a

| Geneseq Identifier | Protein/Organism/Length [Patent #, Date] | NOV18a Residues/ Match Residues | Identities/ Similarities for the Matched Region | Expect Value |
|---|---|---|---|---|
| ABB72228 | Human protein isolated from skin cells SEQ ID NO: 344 - *Homo sapiens*, 95 aa. [WO200190357-A1, 29-NOV-2001] | 1 . . . 92<br>4 . . . 95 | 92/92 (100%)<br>92/92 (100%) | 1e−50 |
| AAB56028 | Skin cell protein, SEQ ID NO: 344 - *Homo sapiens*, 95 aa. [WO200069884-A2, 23-NOV-2000] | 1 . . . 92<br>4 . . . 95 | 92/92 (100%)<br>92/92 (100%) | 1e−50 |
| AAB88478 | Human membrane or secretory protein clone PSEC0212 - *Homo sapiens*, 111 aa. [EP1067182-A2, 10-JAN-2001] | 1 . . . 92<br>20 . . . 111 | 92/92 (100%)<br>92/92 (100%) | 1e−50 |
| AAE05371 | Human huKS1 protein - *Homo sapiens*, 95 aa. [WO200148192-A1, 05-JUL-2001] | 1 . . . 92<br>4 . . . 95 | 92/92 (100%)<br>92/92 (100%) | 1e−50 |
| AAY76089 | Human CXC chemokine homologue huKS1, SEQ ID NO: 344 - *Homo sapiens*, 95 aa. [WO9955865-A1, 04-NOV-1999] | 1 . . . 92<br>4 . . . 95 | 92/92 (100%)<br>92/92 (100%) | 1e−50 |

In a BLAST search of public sequence datbases, the NOV18a protein was found to have homology to the proteins shown in the BLASTP data in Table 18E.

TABLE 18E

Public BLASTP Results for NOV18a

| Protein Accession Number | Protein/Organism/Length | NOV18a Residues/ Match Residues | Identities/ Similarities for the Matched Portion | Expect Value |
|---|---|---|---|---|
| JG0182 | chemokine BRAK - human, 99 aa. | 1 . . . 92<br>8 . . . 99 | 92/92 (100%)<br>92/92 (100%) | 2e−50 |
| Q9BTR1 | SMALL INDUCIBLE CYTOKINE SUBFAMILY B (CYS-X-CYS), MEMBER 14 (BRAK) - *Homo sapiens* (Human), 111 aa. | 1 . . . 92<br>20 . . . 111 | 92/92 (100%)<br>92/92 (100%) | 2e−50 |
| O95715 | Small inducible cytokine B14 precursor (Chemokine BRAK) - *Homo sapiens* (Human), 99 aa. | 1 . . . 92<br>8 . . . 99 | 92/92 (100%)<br>92/92 (100%) | 2e−50 |
| Q9NS21 | CHEMOKINE MIP-2 GAMMA - *Homo sapiens* (Human), 111 aa. | 1 . . . 92<br>20 . . . 111 | 91/92 (98%)<br>91/92 (98%) | 9e−50 |
| Q91V02 | MIP2GAMMA - *Mus musculus* (Mouse), 95 aa (fragment). | 1 . . . 92<br>4 . . . 95 | 87/92 (94%)<br>90/92 (97%) | 7e−48 |

PFam analysis predicts that the NOV18a protein contains the domains shown in the Table 18F.

TABLE 18F

| Domain Analysis of NOV18a | | | |
|---|---|---|---|
| Pfam Domain | NOV18a Match Region | Identities/Similarities for the Matched Region | Expect Value |

Example 19

The NOV19 clone was analyzed, and the nucleotide and encoded polypeptide sequences are shown in Table 19A.

TABLE 19A

| NOV19 Sequence Analysis | |
|---|---|
| SEQ ID NO: 107 | 619 bp |
| NOV19a, CG88912-02 DNA Sequence | GCTGCCTGCCTCCTCATGTTCCCCTCCACCACAGCGGACTGCCTGTCGCGGTGCTCCT TGTGTGCTGTAAAGACCCAGGATGGTCCCAAACCTATCAATCCCCTGATTTGCTCCCT GCAATGCCAGGCTGCCCTGCTGCCCTCTGAGGAATGGGAGAGATGCCAGAGCTTTCTG TCTTTTTTCACCCCCTCCACCCTTGGGCTCAATGACAAGGAGGACTTGGGGAGCAAGT CGGTTGGGGAAGGGCCCTACAGTGAGCTGGCCAAGCTCTCTGGGTCATTCCTGAAGGA GCTGAACGATGGTGCCATGGAGACTGGCACACTCTATCTCGCTGAGGAGGACCCCAAG GAGCAGGTCAAACGCTATGGGGGCTTTTTGCGCAAATACCCCAAGAGGAGCTCAGAGG TGGCTGGGGAGGGGACGGGGATAGCATGGGCCATGAGGACCTGTACAAACGCTATGG GGGCTTCTTGCGGCGCATTCGTCCCAAGCTCAAGTGGGACAACCAGAAGCGCTATGGC GGTTTTCTCCGGCGCCAGTTCAAGGTGGTGACTCGGTCTCAGGAAGATCCGAATGCTT ACTCTGGAGAGCTTTTTGATGCATAAGCACTTCTTTTCA |
| ORF Start: at 1 SEQ ID NO: 108 | ORF Stop: TAA at 604 201 aa MW at 22447.1 kD |
| NOV19a, CG88912-02 Protein Sequence | AACLLMFPSTTADCLSRCSLCAVKTQDGPKPINPLICSLQCQAALLPSEEWERCQSFL SFFTPSTLGLNDKEDLGSKSVGEGPYSELAKLSGSFLKELNDGAMETGTLYLAEEDPK EQVKRYGGFLRKYPKRSSEVAGEGDGDSMGHEDLYKRYGGFLRRIRPKLKWDNQKRYG GFLRRQFKVVTRSQEDPNAYSGELFDA |

A search of the NOV19a protein against the Geneseq database, a proprietary database that contains sequences published in patents and patent publication, yielded several homologous proteins shown in Table 19C.

Further analysis of the NOV19a protein yielded the following properties shown in Table 19B.

TABLE 19B

| Protein Sequence Properties NOV19a | |
|---|---|
| PSort analysis: | 0.7562 probability located in mitochondrial matrix space; 0.4352 probability located in mitochondrial inner membrane; 0.4352 probability located in mitochondrial intermembrane space; 0.4352 probability located in mitochondrial outer membrane |
| SignalP analysis: | Cleavage site between residues 13 and 14 |

TABLE 19C

Geneseq Results for NOV19a

| Geneseq Identifier | Protein/Organism/Length [Patent #, Date] | NOV19a Residues/ Match Residues | Identities/ Similarities for the Matched Region | Expect Value |
|---|---|---|---|---|
| AAM79544 | Human protein SEQ ID NO: 3190 - Homo sapiens, 256 aa. [WO200157190-A2, 09-AUG-2001] | 1 . . . 201<br>11 . . . 256 | 201/246 (81%)<br>201/246 (81%) | e−110 |
| AAM78560 | Human protein SEQ ID NO: 1222 - Homo sapiens, 254 aa. [WO200157190-A2, 09-AUG-2001] | 1 . . . 201<br>9 . . . 254 | 201/246 (81%)<br>201/246 (81%) | e−110 |
| AAM05438 | Peptide #4120 encoded by probe for measuring breast gene expression - Homo sapiens, 67 aa. [WO200157270-A2, 09-AUG-2001] | 135 . . . 201<br>1 . . . 67 | 67/67 (100%)<br>67/67 (100%) | 2e−34 |
| AAM30301 | Peptide #4338 encoded by probe for measuring placental gene expression - Homo sapiens, 67 aa. [WO200157272-A2, 09-AUG-2001] | 135 . . . 201<br>1 . . . 67 | 67/67 (100%)<br>67/67 (100%) | 2e−34 |
| AAM17791 | Peptide #4225 encoded by probe for measuring cervical gene expression - Homo sapiens, 67 aa. [WO200157278-A2, 09-AUG-2001] | 135 . . . 201<br>1 . . . 67 | 67/67 (100%)<br>67/67 (100%) | 2e−34 |

In a BLAST search of public sequence datbases, the NOV19a protein was found to have homology to the proteins shown in the BLASTP data in Table 19D.

TABLE 19D

Public BLASTP Results for NOV19a

| Protein Accession Number | Protein/Organism/Length | NOV19a Residues/ Match Residues | Identities/ Similarities for the Matched Portion | Expect Value |
|---|---|---|---|---|
| P01213 | Beta-neoendorphin-dynorphin precursor (Proenkephalin B) (Preprodynorphin) [Contains: Beta-neoendorphin; Dynorphin; Leu-Enkephalin; Rimorphin; Leumorphin] - Homo sapiens (Human), 254 aa. | 1 . . . 201<br>9 . . . 254 | 201/246 (81%)<br>201/246 (81%) | e−110 |
| P01214 | Beta-neoendorphin-dynorphin precursor (Proenkephalin B) (Preprodynorphin) [Contains: Beta-neoendorphin; Dynorphin; Leu-Enkephalin; Rimorphin; Leumorphin] - Sus scrofa (Pig), 256 aa. | 1 . . . 200<br>9 . . . 255 | 164/247 (66%)<br>171/247 (68%) | 2e−84 |
| Q95104 | Beta-neoendorphin-dynorphin precursor (Proenkephalin B) (Preprodynorphin) [Contains: Beta-neoendorphin; Dynorphin; Leu-Enkephalin; Rimorphin; Leumorphin] - Bos taurus (Bovine), 258 aa. | 1 . . . 200<br>9 . . . 257 | 155/249 (62%)<br>170/249 (68%) | 7e−79 |
| Q60478 | Beta-neoendorphin-dynorphin precursor (Proenkephalin B) (Preprodynorphin) [Contains: Beta-neoendorphin; Dynorphin; Leu-Enkephalin; Rimorphin; Leumorphin] - Cavia porcellus (Guinea pig), 245 aa. | 1 . . . 200<br>9 . . . 244 | 153/238 (64%)<br>165/238 (69%) | 3e−77 |
| O35852 | PREPRODYNORPHIN - Mus musculus (Mouse), 248 aa (fragment). | 1 . . . 198<br>9 . . . 246 | 140/238 (58%)<br>157/238 (65%) | 4e−69 |

PFam analysis predicts that the NOV19a protein contains the domains shown in the Table 19E.

TABLE 19E

Domain Analysis of NOV19a

| Pfam Domain | NOV19a Match Region | Identities/Similarities for the Matched Region | Expect Value |
|---|---|---|---|
| Opiods_neuropep | 1 . . . 201 | 145/267 (54%) 197/267 (74%) | 1.3e–115 |

Example B

Sequencing Methodology and Identification of NOVX Clones

1. GeneCalling™ Technology: This is a proprietary method of performing differential gene expression profiling between two or more samples developed at CuraGen and described by Shimkets, et al., "Gene expression analysis by transcript profiling coupled to a gene database query" Nature Biotechnology 17:198–803 (1999). cDNA was derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then digested with up to as many as 120 pairs of restriction enzymes and pairs of linker-adaptors specific for each pair of restriction enzymes were ligated to the appropriate end. The restriction digestion generates a mixture of unique cDNA gene fragments. Limited PCR amplification is performed with primers homologous to the linker adapter sequence where one primer is biotinylated and the other is fluorescently labeled. The doubly labeled material is isolated and the fluorescently labeled single strand is resolved by capillary gel electrophoresis. A computer algorithm compares the electropherograms from an experimental and control group for each of the restriction digestions. This and additional sequence-derived information is used to predict the identity of each differentially expressed gene fragment using a variety of genetic databases. The identity of the gene fragment is confirmed by additional, gene-specific competitive PCR or by isolation and sequencing of the gene fragment.

2. SeqCalling™ Technology: cDNA was derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then sequenced using CuraGen's proprietary SeqCalling technology. Sequence traces were evaluated manually and edited for corrections if appropriate. cDNA sequences from all samples were assembled together, sometimes including public human sequences, using bioinformatic programs to produce a consensus sequence for each assembly. Each assembly is included in CuraGen Corporation's database. Sequences were included as components for assembly when the extent of identity with another component was at least 95% over 50 bp. Each assembly represents a gene or portion thereof and includes information on variants, such as splice forms single nucleotide polymorphisms (SNPs), insertions, deletions and other sequence variations.

3. PathCalling™ Technology:

The NOVX nucleic acid sequences are derived by laboratory screening of cDNA library by the two-hybrid approach. cDNA fragments covering either the full length of the DNA sequence, or part of the sequence, or both, are sequenced. In silico prediction was based on sequences available in CuraGen Corporation's proprietary sequence databases or in the public human sequence databases, and provided either the full length DNA sequence, or some portion thereof.

The laboratory screening was performed using the methods summarized below:

cDNA libraries were derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then directionally cloned into the appropriate two-hybrid vector (Gal4-activation domain (Gal4-AD) fusion). Such cDNA libraries as well as commercially available cDNA libraries from Clontech (Palo Alto, Calif.) were then transferred from E.coli into a CuraGen Corporation proprietary yeast strain (disclosed in U.S. Pat. Nos. 6,057, 101 and 6,083,693, incorporated herein by reference in their entireties).

Gal4-binding domain (Gal4-BD) fusions of a CuraGen Corportion proprietary library of human sequences was used to screen multiple Gal4-AD fusion cDNA libraries resulting in the selection of yeast hybrid diploids in each of which the Gal4-AD fusion contains an individual cDNA. Each sample was amplified using the polymerase chain reaction (PCR) using non-specific primers at the cDNA insert boundaries. Such PCR product was sequenced; sequence traces were evaluated manually and edited for corrections if appropriate. cDNA sequences from all samples were assembled together, sometimes including public human sequences, using bioinformatic programs to produce a consensus sequence for each assembly. Each assembly is included in CuraGen Corporation's database. Sequences were included as components for assembly when the extent of identity with another component was at least 95% over 50 bp. Each assembly represents a gene or portion thereof and includes information on variants, such as splice forms single nucleotide polymorphisms (SNPs), insertions, deletions and other sequence variations.

Physical clone: the cDNA fragment derived by the screening procedure, covering the entire open reading frame is, as a recombinant DNA, cloned into pACT2 plasmid (Clontech) used to make the cDNA library. The recombinant plasmid is inserted into the host and selected by the yeast hybrid diploid generated during the screening procedure by the mating of both CuraGen Corporation proprietary yeast strains N106' and YULH (U.S. Pat. Nos. 6,057,101 and 6,083,693).

4. RACE: Techniques based on the polymerase chain reaction such as rapid amplification of cDNA ends (RACE), were used to isolate or complete the predicted sequence of the cDNA of the invention. Usually multiple clones were sequenced from one or more human samples to derive the sequences for fragments. Various human tissue samples from different donors were used for the RACE reaction. The sequences derived from these procedures were included in the SeqCalling Assembly process described in preceding paragraphs.

5. Exon Linking: The NOVX target sequences identified in the present invention were subjected to the exon linking process to confirm the sequence. PCR primers were designed by starting at the most upstream sequence available, for the forward primer, and at the most downstream sequence available for the reverse primer. In each case, the sequence was examined, walking inward from the respective termini toward the coding sequence, until a suitable sequence that is either unique or highly selective was encountered, or, in the case of the reverse primer, until the stop codon was reached. Such primers were designed based on in silico predictions for the full length cDNA, part (one or more exons) of the DNA or protein sequence of the target sequence, or by translated homology of the predicted exons to closely related human sequences from other species. These primers were then employed in PCR amplification based on the following pool of human cDNAs: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea, uterus. Usually the resulting amplicons were gel purified, cloned and sequenced to high redundancy. The PCR product derived from exon linking was cloned into the pCR2.1 vector from Invitrogen. The resulting bacterial clone has an insert covering the entire open reading frame cloned into the pCR2.1 vector. The resulting sequences from all clones were assembled with themselves, with other fragments in CuraGen Corporation's database and with public ESTs. Fragments and ESTs were included as components for an assembly when the extent of their identity with another component of the assembly was at least 95% over 50 bp. In addition, sequence traces were evaluated manually and edited for corrections if appropriate. These procedures provide the sequence reported herein.

6. Physical Clone: Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein.

The PCR product derived by exon linking, covering the entire open reading frame, was cloned into the pCR2.1 vector from Invitrogen to provide clones used for expression and screening purposes.

Example C

Quantitative Expression Analysis of Clones in Various Cells and Tissues

The quantitative expression of various clones was assessed using microtiter plates containing RNA samples from a variety of normal and pathology-derived cells, cell lines and tissues using real time quantitative PCR (RTQ PCR). RTQ PCR was performed on an Applied Biosystems ABI PRISM® 7700 or an ABI PRISM® 7900 HT Sequence Detection System. Various collections of samples are assembled on the plates, and referred to as Panel 1 (containing normal tissues and cancer cell lines), Panel 2 (containing samples derived from tissues from normal and cancer sources), Panel 3 (containing cancer cell lines), Panel 4 (containing cells and cell lines from normal tissues and cells related to inflammatory conditions), Panel 5D/5I (containing human tissues and cell lines with an emphasis on metabolic diseases), A1_comprehensive_panel (containing normal tissue and samples from autoinflammatory diseases), Panel CNSD.01 (containing samples from normal and diseased brains) and CNS_neurodegeneration_panel (containing samples from normal and Alzheimer's diseased brains).

RNA integrity from all samples is controlled for quality by visual assessment of agarose gel electropherograms using 28S and 18S ribosomal RNA staining intensity ratio as a guide (2:1 to 2.5:1 28s:18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

First, the RNA samples were normalized to reference nucleic acids such as constitutively expressed genes (for example, β-actin and GAPDH). Normalized RNA (5 ul) was converted to cDNA and analyzed by RTQ-PCR using One Step RT-PCR Master Mix Reagents (Applied Biosystems; Catalog No. 4309169) and gene-specific primers according to the manufacturer's instructions.

In other cases, non-normalized RNA samples were converted to single strand cDNA (sscDNA) using Superscript II (Invitrogen Corporation; Catalog No. 18064-147) and random hexamers according to the manufacturer's instructions. Reactions containing up to 10 µg of total RNA were performed in a volume of 20 µl and incubated for 60 minutes at 42° C. This reaction can be scaled up to 50 µg of total RNA in a final volume of 100 µl. sscDNA samples are then normalized to reference nucleic acids as described previously, using 1×TaqMan® Universal Master mix (Applied Biosystems; catalog No. 4324020), following the manufacturer's instructions.

Probes and primers were designed for each assay according to Applied Biosystems Primer Express Software package (version I for Apple Computer's Macintosh Power PC) or a similar algorithm using the target sequence as input. Default settings were used for reaction conditions and the following parameters were set before selecting primers: primer concentration=250 nM, primer melting temperature (Tm) range=58°–60° C., primer optimal Tm=59° C., maximum primer difference=2° C., probe does not have 5'G, probe Tm must be 10° C. greater than primer Tm, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

PCR conditions: When working with RNA samples, normalized RNA from each tissue and each cell line was spotted in each well of either a 96 well or a 384-well PCR plate (Applied Biosystems). PCR cocktails included either a single gene specific probe and primers set, or two multiplexed probe and primers sets (a set specific for the target clone and another gene-specific set multiplexed with the target probe). PCR reactions were set up using TaqMan® One-Step RT-PCR Master Mix (Applied Biosystems, Catalog No. 4313803) following manufacturer's instructions. Reverse transcription was performed at 48° C. for 30 minutes followed by amplification/PCR cycles as follows: 95° C. 10 min, then 40 cycles of 95° C. for 15 seconds, 60° C.

for 1 minute. Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100.

When working with sscDNA samples, normalized sscDNA was used as described previously for RNA samples. PCR reactions containing one or two sets of probe and primers were set up as described previously, using 1×TaqMan® Universal Master mix (Applied Biosystems; catalog No. 4324020), following the manufacturer's instructions. PCR amplification was performed as follows: 95° C. 10 min, then 40 cycles of 95° C. for 15 seconds, 60° C. for 1 minute. Results were analyzed and processed as described previously.

Panels 1, 1.1, 1.2, and 1.3D

The plates for Panels 1, 1.1, 1.2 and 1.3D include 2 control wells (genomic DNA control and chemistry control) and 94 wells containing cDNA from various samples. The samples in these panels are broken into 2 classes: samples derived from cultured cell lines and samples derived from primary normal tissues. The cell lines are derived from cancers of the following types: lung cancer, breast cancer, melanoma, colon cancer, prostate cancer, CNS cancer, squamous cell carcinoma, ovarian cancer, liver cancer, renal cancer, gastric cancer and pancreatic cancer. Cell lines used in these panels are widely available through the American Type Culture Collection (ATCC), a repository for cultured cell lines, and were cultured using the conditions recommended by the ATCC. The normal tissues found on these panels are comprised of samples derived from all major organ systems from single adult individuals or fetuses. These samples are derived from the following organs: adult skeletal muscle, fetal skeletal muscle, adult heart, fetal heart, adult kidney, fetal kidney, adult liver, fetal liver, adult lung, fetal lung, various regions of the brain, the spleen, bone marrow, lymph node, pancreas, salivary gland, pituitary gland, adrenal gland, spinal cord, thymus, stomach, small intestine, colon, bladder, trachea, breast, ovary, uterus, placenta, prostate, testis and adipose.

In the results for Panels 1, 1.1, 1.2 and 1.3D, the following abbreviations are used:

ca.=carcinoma,
*=established from metastasis,
met=metastasis,
s cell var=small cell variant,
non-s=non-sm=non-small,
squam=squamous,
pl. eff=pl effusion=pleural effusion,
glio=glioma,
astro=astrocytoma, and
neuro=neuroblastoma.

General_screening_panel_v1.4, v1.5 and v1.6

The plates for Panels 1.4, 1.5, and 1.6 include 2 control wells (genomic DNA control and chemistry control) and 94 wells containing cDNA from various samples. The samples in Panels 1.4, 1.5, and 1.6 are broken into 2 classes: samples derived from cultured cell lines and samples derived from primary normal tissues. The cell lines are derived from cancers of the following types: lung cancer, breast cancer, melanoma, colon cancer, prostate cancer, CNS cancer, squamous cell carcinoma, ovarian cancer, liver cancer, renal cancer, gastric cancer and pancreatic cancer. Cell lines used in Panels 1.4, 1.5, and 1.6 are widely available through the American Type Culture Collection (ATCC), a repository for cultured cell lines, and were cultured using the conditions recommended by the ATCC. The normal tissues found on Panels 1.4, 1.5, and 1.6 are comprised of pools of samples derived from all major organ systems from 2 to 5 different adult individuals or fetuses. These samples are derived from the following organs: adult skeletal muscle, fetal skeletal muscle, adult heart, fetal heart, adult kidney, fetal kidney, adult liver, fetal liver, adult lung, fetal lung, various regions of the brain, the spleen, bone marrow, lymph node, pancreas, salivary gland, pituitary gland, adrenal gland, spinal cord, thymus, stomach, small intestine, colon, bladder, trachea, breast, ovary, uterus, placenta, prostate, testis and adipose. Abbreviations are as described for Panels 1, 1.1, 1.2, and 1.3D.

Panels 2D, 2.2, 2.3 and 2.4

The plates for Panels 2D, 2.2, 2.3 and 2.4 generally include 2 control wells and 94 test samples composed of RNA or cDNA isolated from human tissue procured by surgeons working in close cooperation with the National Cancer Institute's Cooperative Human Tissue Network (CHTN) or the National Disease Research Initiative (NDRI) or from Ardais or Clinomics). The tissues are derived from human malignancies and in cases where indicated many malignant tissues have "matched margins" obtained from noncancerous tissue just adjacent to the tumor. These are termed normal adjacent tissues and are denoted "NAT" in the results below. The tumor tissue and the "matched margins" are evaluated by two independent pathologists (the surgical pathologists and again by a pathologist at NDRI/CHTN/Ardais/Clinomics). Unmatched RNA samples from tissues without malignancy (normal tissues) were also obtained from Ardais or Clinomics. This analysis provides a gross histopathological assessment of tumor differentiation grade. Moreover, most samples include the original surgical pathology report that provides information regarding the clinical stage of the patient. These matched margins are taken from the tissue surrounding (i.e. immediately proximal) to the zone of surgery (designated "NAT", for normal adjacent tissue, in Table RR). In addition, RNA and cDNA samples were obtained from various human tissues derived from autopsies performed on elderly people or sudden death victims (accidents, etc.). These tissues were ascertained to be free of disease and were purchased from various commercial sources such as Clontech (Palo Alto, Calif.), Research Genetics, and Invitrogen.

HASS Panel v 1.0

The HASS panel v 1.0 plates are comprised of 93 cDNA samples and two controls. Specifically, 81 of these samples are derived from cultured human cancer cell lines that had been subjected to serum starvation, acidosis and anoxia for different time periods as well as controls for these treatments, 3 samples of human primary cells, 9 samples of malignant brain cancer (4 medulloblastomas and 5 glioblastomas) and 2 controls. The human cancer cell lines are obtained from ATCC (American Type Culture Collection) and fall into the following tissue groups: breast cancer, prostate cancer, bladder carcinomas, pancreatic cancers and CNS cancer cell lines. These cancer cells are all cultured under standard recommended conditions. The treatments used (serum starvation, acidosis and anoxia) have been previously published in the scientific literature. The primary human cells were obtained from Clonetics (Walkersville, Md.) and were grown in the media and conditions recommended by Clonetics. The malignant brain cancer samples are obtained as part of a collaboration (Henry Ford Cancer Center) and are evaluated by a pathologist prior to CuraGen receiving the samples. RNA was prepared from these samples using the standard procedures. The genomic and chemistry control wells have been described previously.

Panel 3D and 3.1

The plates of Panel 3D and 3.1 are comprised of 94 cDNA samples and two control samples. Specifically, 92 of these samples are derived from cultured human cancer cell lines, 2 samples of human primary cerebellar tissue and 2 controls. The human cell lines are generally obtained from ATCC (American Type Culture Collection), NCI or the German tumor cell bank and fall into the following tissue groups: Squamous cell carcinoma of the tongue, breast cancer, prostate cancer, melanoma, epidermoid carcinoma, sarcomas, bladder carcinomas, pancreatic cancers, kidney cancers, leukemias/lymphomas, ovarian/uterine/cervical, gastric, colon, lung and CNS cancer cell lines. In addition, there are two independent samples of cerebellum. These cells are all cultured under standard recommended conditions and RNA extracted using the standard procedures. The cell lines in panel 3D, 3.1 and 1.3D are of the most common cell lines used in the scientific literature.

Panels 4D, 4R, and 4.1D

Panel 4 includes samples on a 96 well plate (2 control wells, 94 test samples) composed of RNA (Panel 4R) or cDNA (Panels 4D/4.1D) isolated from various human cell lines or tissues related to inflammatory conditions. Total RNA from control normal tissues such as colon and lung (Stratagene, La Jolla, Calif.) and thymus and kidney (Clontech) was employed. Total RNA from liver tissue from cirrhosis patients and kidney from lupus patients was obtained from BioChain (Biochain Institute, Inc., Hayward, Calif.). Intestinal tissue for RNA preparation from patients diagnosed as having Crohn's disease and ulcerative colitis was obtained from the National Disease Research Interchange (NDRI) (Philadelphia, Pa.).

Astrocytes, lung fibroblasts, dermal fibroblasts, coronary artery smooth muscle cells, small airway epithelium, bronchial epithelium, microvascular dermal endothelial cells, microvascular lung endothelial cells, human pulmonary aortic endothelial cells, human umbilical vein endothelial cells were all purchased from Clonetics (Walkersville, Md.) and grown in the media supplied for these cell types by Clonetics. These primary cell types were activated with various cytokines or combinations of cytokines for 6 and/or 12–14 hours, as indicated. The following cytokines were used; IL-1 beta at approximately 1–5 ng/ml, TNF alpha at approximately 5–10 ng/ml, IFN gamma at approximately 20–50 ng/ml, IL-4 at approximately 5–10 ng/ml, IL-9 at approximately 5–10 ng/ml, IL-13 at approximately 5–10 ng/ml. Endothelial cells were sometimes starved for various times by culture in the basal media from Clonetics with 0.1% serum.

Mononuclear cells were prepared from blood of employees at CuraGen Corporation, using Ficoll. LAK cells were prepared from these cells by culture in DMEM 5% FCS (Hyclone), 100 µM non essential amino acids (Gibco/Life Technologies, Rockville, Md.), 1 mM sodium pyruvate (Gibco), mercaptoethanol $5.5\times10^{-5}$M (Gibco), and 10 mM Hepes (Gibco) and Interleukin 2 for 4–6 days. Cells were then either activated with 10–20 ng/ml PMA and 1–2 µg/ml ionomycin, IL-12 at 5–10 ng/ml, IFN gamma at 20–50 ng/ml and IL-18 at 5–10 ng/ml for 6 hours. In some cases, mononuclear cells were cultured for 4–5 days in DMEM 5% FCS (Hyclone), 100 µM non essential amino acids (Gibco), 1 mM sodium pyruvate (Gibco), mercaptoethanol $5.5\times10^{-5}$M (Gibco), and 10 mM Hepes (Gibco) with PHA (phytohemagglutinin) or PWM (pokeweed mitogen) at approximately 5 µg/ml. Samples were taken at 24, 48 and 72 hours for RNA preparation. MLR (mixed lymphocyte reaction) samples were obtained by taking blood from two donors, isolating the mononuclear cells using Ficoll and mixing the isolated mononuclear cells 1:1 at a final concentration of approximately $2\times10^6$cells/ml in DMEM 5% FCS (Hyclone), 100 µM non essential amino acids (Gibco), 1 mM sodium pyruvate (Gibco), mercaptoethanol ($5.5\times10^{-5}$M) (Gibco), and 10 mM Hepes (Gibco). The MLR was cultured and samples taken at various time points ranging from 1–7 days for RNA preparation.

Monocytes were isolated from mononuclear cells using CD14 Miltenyi Beads, +ve VS selection columns and a Vario Magnet according to the manufacturer's instructions. Monocytes were differentiated into dendritic cells by culture in DMEM 5% fetal calf serum (FCS) (Hyclone, Logan, Utah), 100 µM non essential amino acids (Gibco), 1 mM sodium pyruvate (Gibco), mercaptoethanol $5.5\times10^{-5}$M (Gibco), and 10 mM Hepes (Gibco), 50 ng/ml GMCSF and 5 ng/ml IL4 for 5–7 days. Macrophages were prepared by culture of monocytes for 5–7 days in DMEM 5% FCS (Hyclone), 100 µM non essential amino acids (Gibco), 1 mM sodium pyruvate (Gibco), mercaptoethanol $5.5\times10^{-5}$M (Gibco), 10 mM Hepes (Gibco) and 10% AB Human Serum or MCSF at approximately 50 ng/ml. Monocytes, macrophages and dendritic cells were stimulated for 6 and 12–14 hours with lipopolysaccharide (LPS) at 100 ng/ml. Dendritic cells were also stimulated with anti-CD40 monoclonal antibody (Pharmingen) at 10 µg/ml for 6 and 12–14 hours.

CD4 lymphocytes, CD8 lymphocytes and NK cells were also isolated from mononuclear cells using CD4, CD8 and CD56 Miltenyi beads, positive VS selection columns and a Vario Magnet according to the manufacturer's instructions. CD45RA and CD45RO CD4 lymphocytes were isolated by depleting mononuclear cells of CD8, CD56, CD14 and CD19 cells using CD8, CD56, CD14 and CD19 Miltenyi beads and positive selection. CD45RO beads were then used to isolate the CD45RO CD4 lymphocytes with the remaining cells being CD45RA CD4 lymphocytes. CD45RA CD4, CD45RO CD4 and CD8 lymphocytes were placed in DMEM 5% FCS (Hyclone), 100 µM non essential amino acids (Gibco), 1 mM sodium pyruvate (Gibco), mercaptoethanol $5.5\times10^{-5}$M (Gibco), and 10 mM Hepes (Gibco) and plated at $10^6$ cells/ml onto Falcon 6 well tissue culture plates that had been coated overnight with 0.5 µg/ml anti-CD28 (Pharmingen) and 3 ug/ml anti-CD3 (OKT3, ATCC) in PBS. After 6 and 24 hours, the cells were harvested for RNA preparation. To prepare chronically activated CD8 lymphocytes, we activated the isolated CD8 lymphocytes for 4 days on anti-CD28 and anti-CD3 coated plates and then harvested the cells and expanded them in DMEM 5% FCS (Hyclone), 100 µM non essential amino acids (Gibco), 1 mM sodium pyruvate (Gibco), mercaptoethanol $5.5\times10^{-5}$M (Gibco), and 10 mM Hepes (Gibco) and IL-2. The expanded CD8 cells were then activated again with plate bound anti-CD3 and anti-CD28 for 4 days and expanded as before. RNA was isolated 6 and 24 hours after the second activation and after 4 days of the second expansion culture. The isolated NK cells were cultured in DMEM 5% FCS (Hyclone), 100 µM non essential amino acids (Gibco), 1 mM sodium pyruvate (Gibco), mercaptoethanol $5.5\times10^{-5}$M (Gibco), and 10 mM Hepes (Gibco) and IL-2 for 4–6 days before RNA was prepared.

To obtain B cells, tonsils were procured from NDRI. The tonsil was cut up with sterile dissecting scissors and then passed through a sieve. Tonsil cells were then spun down and resuspended at $10^6$ cells/ml in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco). To activate the cells, we used PWM at 5 µg/ml or anti-CD40 (Pharmingen) at approximately 10 µg/ml and IL4 at 5–10 ng/ml. Cells were harvested for RNA preparation at 24,48 and 72 hours.

To prepare the primary and secondary Th1/Th2 and Tr1 cells, six-well Falcon plates were coated overnight with 10 µg/ml anti-CD28 (Pharmingen) and 2 µg/ml OKT3 (ATCC), and then washed twice with PBS. Umbilical cord blood CD4 lymphocytes (Poietic Systems, German Town, Md.) were cultured at $10^{5-106}$ cells/ml in DMEM 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco) and IL-2 (4 ng/ml). IL-12 (5 ng/ml) and anti-IL4 (1 µg/ml) were used to direct to Th1, while IL-4 (5 ng/ml) and anti-IFN gamma (1 µg/ml) were used to direct to Th2 and IL-10 at 5 ng/ml was used to direct to Tr1. After 4–5 days, the activated Th1, Th2 and Tr1 lymphocytes were washed once in DMEM and expanded for 4–7 days in DMEM 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco) and IL-2 (1 ng/ml). Following this, the activated Th1, Th2 and Tr1 lymphocytes were re-stimulated for 5 days with anti-CD28/OKT3 and cytokines as described above, but with the addition of anti-CD95L (1 µg/ml) to prevent apoptosis. After 4–5 days, the Th1, Th2 and Tr1 lymphocytes were washed and then expanded again with IL-2 for 4–7 days. Activated Th1 and Th2 lymphocytes were maintained in this way for a maximum of three cycles. RNA was prepared from primary and secondary Th1, Th2 and Tr1 after 6 and 24 hours following the second and third activations with plate bound anti-CD3 and anti-CD28 mAbs and 4 days into the second and third expansion cultures in Interleukin 2.

The following leukocyte cells lines were obtained from the ATCC: Ramos, EOL-1, KU-812. EOL cells were further differentiated by culture in 0.1 mM dbcAMP at $5 \times 10^5$ cells/ml for 8 days, changing the media every 3 days and adjusting the cell concentration to $5 \times 10^5$ cells/ml. For the culture of these cells, we used DMEM or RPMI (as recommended by the ATCC), with the addition of 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco). RNA was either prepared from resting cells or cells activated with PMA at 10 ng/ml and ionomycin at 1 µg/ml for 6 and 14 hours. Keratinocyte line CCD106 and an airway epithelial tumor line NCI-H292 were also obtained from the ATCC. Both were cultured in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco). CCD1106 cells were activated for 6 and 14 hours with approximately 5 ng/ml TNF alpha and 1 ng/ml IL-1 beta, while NCI-H292 cells were activated for 6 and 14 hours with the following cytokines: 5 ng/ml IL-4, 5 ng/ml IL-9, 5 ng/ml IL-13 and 25 ng/ml IFN gamma.

For these cell lines and blood cells, RNA was prepared by lysing approximately $10^7$ cells/ml using Trizol (Gibco BRL). Briefly, 1/10 volume of bromochloropropane (Molecular Research Corporation) was added to the RNA sample, vortexed and after 10 minutes at room temperature, the tubes were spun at 14,000 rpm in a Sorvall SS34 rotor. The aqueous phase was removed and placed in a 15 ml Falcon Tube. An equal volume of isopropanol was added and left at −20° C. overnight. The precipitated RNA was spun down at 9,000 rpm for 15 min in a Sorvall SS34 rotor and washed in 70% ethanol. The pellet was redissolved in 300 µl of RNAse-free water and 35 µl buffer (Promega) 5 µl DTT, 7 µl RNAsin and 8 µl DNAse were added. The tube was incubated at 37° C. for 30 minutes to remove contaminating genomic DNA, extracted once with phenol chloroform and re-precipitated with 1/10 volume of 3M sodium acetate and 2 volumes of 100% ethanol. The RNA was spun down and placed in RNAse free water. RNA was stored at −80° C.

AI_comprehensive panel_v1.0

The plates for AI_comprehensive panel_v1.0 include two control wells and 89 test samples comprised of cDNA isolated from surgical and postmortem human tissues obtained from the Backus Hospital and Clinomics (Frederick, Md). Total RNA was extracted from tissue samples from the Backus Hospital in the Facility at CuraGen. Total RNA from other tissues was obtained from Clinomics.

Joint tissues including synovial fluid, synovium, bone and cartilage were obtained from patients undergoing total knee or hip replacement surgery at the Backus Hospital. Tissue samples were immediately snap frozen in liquid nitrogen to ensure that isolated RNA was of optimal quality and not degraded. Additional samples of osteoarthritis and rheumatoid arthritis joint tissues were obtained from Clinomics. Normal control tissues were supplied by Clinomics and were obtained during autopsy of trauma victims.

Surgical specimens of psoriatic tissues and adjacent matched tissues were provided as total RNA by Clinomics. Two male and two female patients were selected between the ages of 25 and 47. None of the patients were taking prescription drugs at the time samples were isolated.

Surgical specimens of diseased colon from patients with ulcerative colitis and Crohns disease and adjacent matched tissues were obtained from Clinomics. Bowel tissue from three female and three male Crohn's patients between the ages of 41–69 were used. Two patients were not on prescription medication while the others were taking dexamethasone, phenobarbital, or tylenol. Ulcerative colitis tissue was from three male and four female patients. Four of the patients were taking lebvid and two were on phenobarbital.

Total RNA from post mortem lung tissue from trauma victims with no disease or with emphysema, asthma or COPD was purchased from Clinomics. Emphysema patients ranged in age from 40–70 and all were smokers, this age range was chosen to focus on patients with cigarette-linked emphysema and to avoid those patients with alpha-lantitrypsin deficiencies. Asthma patients ranged in age from 36–75, and excluded smokers to prevent those patients that could also have COPD. COPD patients ranged in age from 35–80 and included both smokers and non-smokers. Most patients were taking corticosteroids, and bronchodilators.

In the labels employed to identify tissues in the AI_comprehensive panel_v1.0 panel, the following abbreviations are used:

AI=Autoimmunity
Syn=Synovial
Normal=No apparent disease
Rep22/Rep20=individual patients
RA=Rheumatoid arthritis
Backus=From Backus Hospital
OA=Osteoarthritis
(SS) (BA) (MF)=Individual patients
Adj=Adjacent tissue Match control=adjacent tissues
-M=Male
-F=Female
COPD=Chronic obstructive pulmonary disease
Panels 5D and 5I The plates for Panel 5D and 5I include two control wells and a variety of cDNAs isolated from human tissues and cell lines with an emphasis on metabolic diseases. Metabolic tissues were obtained from patients enrolled in the Gestational Diabetes study. Cells were obtained during different stages in the differentiation of adipocytes from human mesenchymal stem cells. Human pancreatic islets were also obtained.

In the Gestational Diabetes study subjects are young (18–40 years), otherwise healthy women with and without gestational diabetes undergoing routine (elective) Caesarean section. After delivery of the infant, when the surgical incisions were being repaired/closed, the obstetrician removed a small sample (<1 cc) of the exposed metabolic tissues during the closure of each surgical level. The biopsy material was rinsed in sterile saline, blotted and fast frozen within 5 minutes from the time of removal. The tissue was then flash frozen in liquid nitrogen and stored, individually, in sterile screw-top tubes and kept on dry ice for shipment to or to be picked up by CuraGen. The metabolic tissues of interest include uterine wall (smooth muscle), visceral adipose, skeletal muscle (rectus) and subcutaneous adipose. Patient descriptions are as follows:

Patient 2: Diabetic Hispanic, overweight, not on insulin

Patient 7–9: Nondiabetic Caucasian and obese (BMI>30)

Patient 10: Diabetic Hispanic, overweight, on insulin

Patient 11: Nondiabetic African American and overweight

Patient 12: Diabetic Hispanic on insulin

Adiocyte differentiation was induced in donor progenitor cells obtained from Osirus (a division of Clonetics/BioWhittaker) in triplicate, except for Donor 3U which had only two replicates. Scientists at Clonetics isolated, grew and differentiated human mesenchymal stem cells (HuMSCs) for CuraGen based on the published protocol found in Mark F. Pittenger, et al., Multilineage Potential of Adult Human Mesenchymal Stem Cells Science Apr. 2, 1999: 143–147. Clonetics provided Trizol lysates or frozen pellets suitable for mRNA isolation and ds cDNA production. A general description of each donor is as follows:

Donor 2 and 3 U: Mesenchymal Stem cells, Undifferentiated Adipose

Donor 2 and 3 AM: Adipose, AdiposeMidway Differentiated

Donor 2 and 3 AD: Adipose, Adipose Differentiated

Human cell lines were generally obtained from ATCC (American Type Culture Collection), NCI or the German tumor cell bank and fall into the following tissue groups: kidney proximal convoluted tubule, uterine smooth muscle cells, small intestine, liver HepG2 cancer cells, heart primary stromal cells, and adrenal cortical adenoma cells. These cells are all cultured under standard recommended conditions and RNA extracted using the standard procedures. All samples were processed at CuraGen to produce single stranded cDNA.

Panel 5I contains all samples previously described with the addition of pancreatic islets from a 58 year old female patient obtained from the Diabetes Research Institute at the University of Miami School of Medicine. Islet tissue was processed to total RNA at an outside source and delivered to CuraGen for addition to panel 5I.

In the labels employed to identify tissues in the 5D and 5I panels, the following abbreviations are used:
GO Adipose=Greater Omentum Adipose
SK=Skeletal Muscle
UT=Uterus
PL=Placenta
AD=Adipose Differentiated
AM=Adipose Midway Differentiated
U=Undifferentiated Stem Cells
Panel CNSD.01

The plates for Panel CNSD.0.1 include two control wells and 94 test samples comprised of cDNA isolated from postmortem human brain tissue obtained from the Harvard Brain Tissue Resource Center. Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains two brains from each of the following diagnoses: Alzheimer's disease, Parkinson's disease, Huntington's disease, Progressive Supernuclear Palsy, Depression, and "Normal controls". Within each of these brains, the following regions are represented: cingulate gyrus, temporal pole, globus palladus, substantia nigra, Brodman Area 4 (primary motor strip), Brodman Area 7 (parietal cortex), Brodman Area 9 (prefrontal cortex), and Brodman area 17 (occipital cortex). Not all brain regions are represented in all cases; e.g., Huntington's disease is characterized in part by neurodegeneration in the globus palladus, thus this region is impossible to obtain from confirmed Huntington's cases. Likewise Parkinson's disease is characterized by degeneration of the substantia nigra making this region more difficult to obtain. Normal control brains were examined for neuropathology and found to be free of any pathology consistent with neurodegeneration.

In the labels employed to identify tissues in the CNS panel, the following abbreviations are used:
PSP=Progressive supranuclear palsy
Sub Nigra=Substantia nigra
Glob Palladus=Globus palladus
Temp Pole=Temporal pole
Cing Gyr=Cingulate gyrus
BA 4=Brodman Area 4
Panel CNS_Neurodegeneration_V1.0

The plates for Panel CNS_Neurodegeneration_V1.0 include two control wells and 47 test samples comprised of cDNA isolated from postmortem human brain tissue obtained from the Harvard Brain Tissue Resource Center (McLean Hospital) and the Human Brain and Spinal Fluid Resource Center (VA Greater Los Angeles Healthcare System). Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains six brains from Alzheimer's disease (AD) patients, and eight brains from "Normal controls" who showed no evidence of dementia prior to death. The eight normal control brains are divided into two categories: Controls with no dementia and no Alzheimer's like pathology (Controls) and controls with no dementia but evidence of severe Alzheimer's like pathology, (specifically senile plaque load rated as level 3 on a scale of 0–3; 0=no evidence of plaques, 3=severe AD senile plaque load). Within each of these brains, the following regions are represented: hippocampus, temporal cortex (Brodman Area 21), parietal cortex (Brodman area 7), and occipital cortex (Brodman area 17). These regions were chosen to encompass all levels of neurodegeneration in AD. The hippocampus is a region of early and severe neuronal loss in AD; the temporal cortex is known to show neurodegeneration in AD after the hippocampus; the parietal cortex shows moderate neuronal death in the late stages of the disease; the occipital cortex is spared in AD and therefore acts as a "control" region within AD patients. Not all brain regions are represented in all cases.

In the labels employed to identify tissues in the CNS_Neurodegeneration_V1.0 panel, the following abbreviations are used:

AD=Alzheimer's disease brain; patient was demented and showed AD-like pathology upon autopsy Control=Control brains; patient not demented, showing no neuropathology Control (Path)=Control brains; patient not demented but showing sever AD-like pathology SupTemporal Ctx=Superior Temporal Cortex Inf Temporal Ctx=Inferior Temporal Cortex A. NOV2A and NOV2B: LRR Protein Expression of gene NOV2A and full length physical clone NOV2B was assessed using the primer-probe sets Ag4180, Ag6318, Ag6602, Ag6659 and Ag6702, described in Tables AA, AB, AC, AD and AE. Please note that NOV2A is recognized by primer-probe set Ag4180 only. Results of the RTQ-PCR runs are shown in Tables AF, AG, AH, AI, AJ and AK.

TABLE AA

Probe Name Ag4180

| Primers | Sequences | Length | Start Position | SEQ ID No |
|---|---|---|---|---|
| Forward | 5'-tcttccagaaggacatcaactg-3' | 22 | 1347 | 109 |
| Probe | TET-5'-cagcttcatccacttgagtttccagg-3'-TAMRA | 26 | 1309 | 110 |
| Reverse | 5'-cccctcgtccaggatatagtac-3' | 22 | 1271 | 111 |

TABLE AB

Probe Name Ag6318

| Primers | Sequences | Length | Start Position | SEQ ID No |
|---|---|---|---|---|
| Forward | 5'-gtagtgaagcaggatagttcataaatagaa-3' | 30 | 3 | 112 |
| Probe | TET-5'-agtggaagcgccttctcatccttcat-3'-TAMRA | 26 | 35 | 113 |
| Reverse | 5'-gcagtggtcacgtttgga-3' | 18 | 62 | 114 |

TABLE AC

Probe Name Ag6602

| Primers | Sequences | Length | Start Position | SEQ ID No |
|---|---|---|---|---|
| Forward | 5'-gtgaggcggcagatcttc-3' | 18 | 426 | 115 |
| Probe | TET-5'-agctgaatcatctgcagcctgcatt-3'-TAMRA | 25 | 444 | 116 |
| Reverse | 5'-attcccaggcatgatgct-3' | 18 | 495 | 117 |

TABLE AD

Probe Name Ag6659

| Primers | Sequences | Length | Start Position | SEQ ID No |
|---|---|---|---|---|
| Forward | 5'-gtgaggcggcagatcttc-3' | 18 | 426 | 118 |
| Probe | TET-5'-agctgaatcatctgcagcctgcatt-3'-TAMRA | 25 | 444 | 119 |
| Reverse | 5'-attcccaggcatgatgct-3' | 18 | 495 | 120 |

TABLE AE

Probe Name Ag6702

| Primers | Sequences | Length | Start Position | SEQ ID No |
|---|---|---|---|---|
| Forward | 5'-gtgaggcggcagatzcttc-3' | 18 | 426 | 121 |
| Probe | TET-5'agctgaatcatctgcagcctgcatt-3'-TAMRA | 25 | 444 | 122 |
| Reverse | 5'-attcccaggcatgatgct-3' | 18 | 495 | 123 |

TABLE AF

AI_comprehensive_panel_v1.0

| Tissue Name | Rel. Exp. (%) Ag6318, Run 275481201 | Rel. Exp. (%) Ag6659, Run 275481281 | Tissue Name | Rel. Exp. (%) Ag6318, Run 275481201 | Rel. Exp. (%) Ag6659, Run 275481281 |
|---|---|---|---|---|---|
| 110967 COPD-F | 5.2 | 0.0 | 112427 Match Control Psoriasis-F | 10.5 | 0.0 |
| 110980 COPD-F | 0.5 | 0.0 | 112418 Psoriasis-M | 11.7 | 0.0 |
| 110968 COPD-M | 2.5 | 1.6 | 112723 Match Control Psoriasis-M | 0.0 | 0.0 |
| 110977 COPD-M | 4.5 | 4.9 | 112419 Psoriasis-M | 10.7 | 5.1 |
| 110989 Emphysema-F | 5.4 | 2.1 | 112424 Match Control Psoriasis-M | 5.2 | 0.0 |
| 110992 Emphysema-F | 1.4 | 0.0 | 112420 Psoriasis-M | 8.4 | 0.0 |
| 110993 Emphysema-F | 2.9 | 0.0 | 112425 Match Control Psoriasis-M | 2.0 | 0.0 |
| 110994 Emphysema-F | 6.1 | 0.0 | 104689 (MF) OA Bone-Backus | 3.9 | 18.4 |
| 110995 Emphysema-F | 2.3 | 0.0 | 104690 (MF) Adj "Normal" Bone-Backus | 5.5 | 5.4 |
| 110996 Emphysema-F | 4.2 | 0.0 | 104691 (MF) OA Synovium-Backus | 8.9 | 19.3 |
| 110997 Asthma-M | 2.2 | 0.0 | 104692 (BA) OA Cartilage-Backus | 1.3 | 0.0 |
| 111001 Asthma-F | 4.7 | 2.1 | 104694 (BA) OA Bone-Backus | 6.7 | 4.5 |
| 111002 Asthma-F | 6.3 | 0.0 | 104695 (BA) Adj "Normal" Bone-Backus | 7.1 | 10.8 |
| 111003 Atopic Asthma-F | 4.5 | 0.0 | 104696 (BA) OA Synovium-Backus | 5.0 | 15.5 |
| 111004 Atopic Asthma-F | 5.4 | 0.0 | 104700 (SS) OA Bone-Backus | 100.0 | 100.0 |
| 111005 Atopic Asthma-F | 1.3 | 0.0 | 104701 (SS) Adj "Normal" Bone-Backus | 8.5 | 0.0 |
| 111006 Atopic Asthma-F | 0.0 | 0.0 | 104702 (SS) OA Synovium-Backus | 7.0 | 3.0 |
| 111417 Allergy-M | 1.5 | 0.0 | 117093 OA Cartilage Rep7 | 0.8 | 0.0 |
| 112347 Allergy-M | 0.5 | 0.0 | 112672 OA Bone5 | 8.1 | 7.6 |
| 112349 | 0.3 | 0.0 | 112673 OA | 9.7 | 2.3 |

TABLE AF-continued

AI_comprehensive_panel_v1.0

| Tissue Name | Rel. Exp. (%) Ag6318, Run 275481201 | Rel. Exp. (%) Ag6659, Run 275481281 | Tissue Name | Rel. Exp. (%) Ag6318, Run 275481201 | Rel. Exp. (%) Ag6659, Run 275481281 |
|---|---|---|---|---|---|
| Normal Lung- F 112357 Normal Lung-F | 6.7 | 10.4 | Synovium5 112674 OA Synovial Fluid cells5 | 8.2 | 1.9 |
| 112354 Normal Lung-M | 2.9 | 0.0 | 117100 OA Cartilage Rep14 | 1.8 | 0.0 |
| 112374 Crohns-F | 9.4 | 3.8 | 112756 OA Bone9 | 0.2 | 0.0 |
| 112389 Match Control Crohns-F | 1.2 | 0.0 | 112757 OA Synovium9 | 6.3 | 0.0 |
| 112375 Crohns-F | 2.1 | 2.6 | 112758 OA Synovial Fluid Cells9 | 6.1 | 6.5 |
| 112732 Match Control Crohns-F | 1.3 | 0.0 | 117125 RA Cartilage Rep2 | 2.9 | 0.0 |
| 112725 Crohns-M | 3.5 | 0.0 | 113492 Bone2 RA | 18.7 | 5.1 |
| 112387 Match Control Crohns-M | 0.7 | 0.0 | 113493 Synovium2 RA | 9.0 | 2.2 |
| 112378 Crohns-M | 1.3 | 0.0 | 113494 Syn Fluid Cells RA | 15.5 | 0.0 |
| 112390 Match Control Crohns-M | 5.1 | 0.0 | 113499 Cartilage4 RA | 14.6 | 1.6 |
| 112726 Crohns-M | 0.6 | 0.0 | 113500 Bone4 RA | 16.4 | 0.0 |
| 112731 Match Control Crohns-M | 6.2 | 0.0 | 113501 Synovium4 RA | 14.0 | 0.0 |
| 112380 Ulcer Col-F | 0.0 | 0.0 | 113502 Syn Fluid Cells4 RA | 6.2 | 0.0 |
| 112734 Match Control Ulcer Col-F | 17.2 | 22.8 | 113495 Cartilage3 RA | 16.2 | 2.5 |
| 112384 Ulcer Col-F | 7.2 | 0.0 | 113496 Bone3 RA | 20.0 | 4.3 |
| 112737 Match Control Ulcer Col-F | 3.0 | 0.0 | 113497 Synovium3 RA | 10.4 | 1.6 |
| 112386 Ulcer Col-F | 5.3 | 0.0 | 113498 Syn Fluid Cells3 RA | 13.9 | 8.3 |
| 112738 Match Control Ulcer Col-F | 0.7 | 0.0 | 117106 Normal Cartilage Rep20 | 1.1 | 0.0 |
| 112381 Ulcer Col-M | 0.0 | 0.0 | 113663 Bone3 Normal | 0.0 | 0.0 |
| 112735 Match Control Ulcer Col-M | 0.5 | 0.0 | 113664 Synovium3 Normal | 0.0 | 0.0 |
| 112382 Ulcer Col-M | 2.6 | 0.0 | 113665 Syn Fluid Cells3 Normal | 0.9 | 0.0 |
| 112394 Match Control Ulcer Col-M | 2.2 | 0.0 | 117107 Normal Cartilage Rep22 | 0.8 | 0.0 |
| 112383 Ulcer Col-M | 0.7 | 0.0 | 113667 Bone4 Normal | 1.4 | 0.0 |
| 112736 Match Control Ulcer Col-M | 1.6 | 0.0 | 113668 Synovium4 Normal | 4.4 | 0.0 |
| 112423 Psoriasis-F | 16.7 | 1.9 | 113669 Syn Fluid Cells4 Normal | 2.0 | 0.0 |

TABLE AG

CNS_neurodegeneration_v1.0

| Tissue Name | Rel. Exp. (%) Ag4180, Run 215539679 | Tissue Name | Rel. Exp. (%) Ag4180, Run 215539679 |
|---|---|---|---|
| AD 1 Hippo | 7.1 | Control (Path) 3 Temporal Ctx | 0.0 |
| AD 2 Hippo | 0.0 | Control (Path) 4 Temporal Ctx | 45.4 |
| AD 3 Hippo | 0.0 | AD 1 Occipital Ctx | 0.0 |
| AD 4 Hippo | 0.0 | AD 2 Occipital Ctx (Missing) | 0.0 |
| AD 5 hippo | 52.1 | AD 3 Occipital Ctx | 13.3 |
| AD 6 Hippo | 57.0 | AD 4 Occipital Ctx | 15.4 |
| Control 2 Hippo | 17.4 | AD 5 Occipital Ctx | 33.0 |
| Control 4 Hippo | 14.3 | AD 6 Occipital Ctx | 40.9 |
| Control (Path) 3 Hippo | 14.8 | Control 1 Occipital Ctx | 55.5 |
| AD 1 Temporal Ctx | 16.7 | Control 2 Occipital Ctx | 0.0 |
| AD 2 Temporal Ctx | 0.0 | Control 3 Occipital Ctx | 19.3 |
| AD 3 Temporal Ctx | 0.0 | Control 4 Occipital Ctx | 19.1 |
| AD 4 Temporal Ctx | 0.0 | Control (Path) 1 Occipital Ctx | 38.4 |
| AD 5 Inf Temporal Ctx | 25.0 | Control (Path) 2 Occipital Ctx | 0.0 |
| AD 5 SupTemporal Ctx | 51.4 | Control (Path) 3 Occipital Ctx | 0.0 |
| AD 6 Inf Temporal Ctx | 0.0 | Control (Path) 4 Occipital Ctx | 0.0 |
| AD 6 Sup Temporal Ctx | 58.6 | Control 1 Parietal Ctx | 0.0 |
| Control 1 Temporal Ctx | 77.9 | Control 2 Parietal Ctx | 0.0 |
| Control 2 Temporal Ctx | 0.0 | Control 3 Parietal Ctx | 0.0 |
| Control 3 Temporal Ctx | 12.7 | Control (Path) 1 Parietal Ctx | 19.3 |
| Control 4 Temporal Ctx | 0.0 | Control (Path) 2 Parietal Ctx | 0.0 |
| Control (Path) 1 Temporal Ctx | 16.2 | Control (Path) 3 Parietal Ctx | 16.7 |
| Control (Path) 2 Temporal Ctx | 0.0 | Control (Path) 4 Parietal Ctx | 100.0 |

TABLE AH

General_screening_panel_v1.4

| Tissue Name | Rel. Exp. (%) Ag4180, Run 221118503 | Tissue Name | Rel. Exp. (%) Ag4180, Run 221118503 |
|---|---|---|---|
| Adipose | 5.1 | Renal ca. TK-10 | 0.9 |
| Melanoma* Hs688(A).T | 0.0 | Bladder | 0.0 |
| Melanoma* Hs688(B).T | 0.4 | Gastric ca. (liver met.) NCI-N87 | 0.0 |
| Melanoma* M14 | 0.0 | Gastric ca. KATO III | 0.3 |
| Melanoma* LOXIMVI | 0.0 | Colon ca. SW-948 | 1.2 |
| Melanoma* SK-MEL-5 | 0.0 | Colon ca. SW480 | 3.3 |
| Squamous cell carcinoma SCC-4 | 0.0 | Colon ca.* (SW480 met) SW620 | 0.0 |
| Testis Pool | 8.0 | Colon ca. HT29 | 0.0 |
| Prostate ca.* (bone met) PC-3 | 1.0 | Colon ca. HCT-116 | 1.1 |
| Prostate Pool | 0.9 | Colon ca. CaCo-2 | 36.3 |
| Placenta | 6.2 | Colon cancer tissue | 6.3 |
| Uterus Pool | 0.0 | Colon ca. SW1116 | 0.0 |
| Ovarian ca. OVCAR-3 | 5.0 | Colon ca. Colo-205 | 0.0 |
| Ovarian ca. SK-OV-3 | 1.1 | Colon ca. SW-48 | 0.0 |
| Ovarian ca. OVCAR-4 | 2.4 | Colon Pool | 3.3 |
| Ovarian ca. OVCAR-5 | 1.0 | Small Intestine Pool | 0.0 |
| Ovarian ca. IGROV-1 | 1.1 | Stomach Pool | 2.0 |
| Ovarian ca. OVCAR-8 | 1.1 | Bone Marrow Pool | 0.8 |
| Ovary | 2.1 | Fetal Heart | 3.9 |
| Breast ca. MCF-7 | 0.0 | Heart Pool | 0.0 |
| Breast ca. MDA-MB-231 | 0.0 | Lymph Node Pool | 1.8 |
| Breast ca. BT 549 | 0.9 | Fetal Skeletal Muscle | 0.5 |
| Breast ca. T47D | 1.3 | Skeletal Muscle Pool | 0.0 |
| Breast ca. MDA-N | 1.2 | Spleen Pool | 18.4 |
| Breast Pool | 1.7 | Thymus Pool | 3.5 |
| Trachea | 0.0 | CNS cancer (glio/astro) U87-MG | 100.0 |
| Lung | 0.0 | CNS cancer (glio/astro) U-118-MG | 0.0 |
| Fetal Lung | 12.9 | CNS cancer (neuro; met) SK-N-AS | 0.0 |
| Lung ca. NCI-N417 | 0.0 | CNS cancer (astro) SF-539 | 0.0 |
| Lung ca. LX-1 | 0.0 | CNS cancer (astro) SNB-75 | 0.5 |
| Lung ca. NCI-H146 | 0.0 | CNS cancer (glio) SNB-19 | 0.5 |
| Lung ca. SHP-77 | 0.0 | CNS cancer (glio) SF-295 | 7.0 |
| Lung ca. A549 | 1.0 | Brain (Amygdala) Pool | 0.0 |
| Lung ca. NCI-H526 | 0.0 | Brain (cerebellum) | 0.0 |
| Lung ca. NCI-H23 | 0.7 | Brain (fetal) | 4.5 |
| Lung ca. NCI-H460 | 0.0 | Brain (Hippocampus) Pool | 0.0 |
| Lung ca. HOP-62 | 0.0 | Cerebral Cortex Pool | 0.0 |
| Lung ca. NCI-H522 | 2.2 | Brain (Substantia nigra) Pool | 1.0 |
| Liver | 3.0 | Brain (Thalamus) Pool | 0.0 |
| Fetal Liver | 3.1 | Brain (whole) | 0.0 |
| Liver ca. HepG2 | 0.0 | Spinal Cord Pool | 0.0 |
| Kidney Pool | 5.7 | Adrenal Gland | 4.1 |
| Fetal Kidney | 2.8 | Pituitary gland Pool | 0.0 |
| Renal ca. 786-0 | 0.0 | Salivary Gland | 0.6 |
| Renal ca. A498 | 0.9 | Thyroid (female) | 7.5 |
| Renal ca. ACHN | 0.0 | Pancreatic ca. CAPAN2 | 0.0 |
| Renal ca. UO-31 | 0.8 | Pancreas Pool | 3.0 |

TABLE AI

General_screening_panel_v1.5

| Tissue Name | Rel. Exp. (%) Ag6318, Run 259139880 | Tissue Name | Rel. Exp. (%) Ag6318, Run 259139880 |
|---|---|---|---|
| Adipose | 0.0 | Renal ca. TK-10 | 0.0 |
| Melanoma* Hs688(A).T | 0.0 | Bladder | 3.1 |
| Melanoma* Hs688(B).T | 0.0 | Gastric ca. (liver met.) NCI-N87 | 0.0 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 2.8 |
| Squamous cell carcinoma SCC-4 | 0.0 | Colon ca.* (SW480 met) SW620 | 0.0 |
| Testis Pool | 1.0 | Colon ca. HT29 | 0.0 |
| Prostate ca.* (bone met) PC-3 | 0.0 | Colon ca. HCT-116 | 0.0 |
| Prostate Pool | 0.5 | Colon ca. CaCo-2 | 77.9 |
| Placenta | 1.7 | Colon cancer tissue | 0.4 |
| Uterus Pool | 0.7 | Colon ca. SW1116 | 100.0 |
| Ovarian ca. OVCAR-3 | 0.0 | Colon ca. Colo-205 | 0.0 |
| Ovarian ca. SK-OV-3 | 1.1 | Colon ca. SW-48 | 0.0 |
| Ovarian ca. OVCAR-4 | 0.0 | Colon Pool | 1.2 |
| Ovarian ca. OVCAR-5 | 0.0 | Small Intestine Pool | 0.0 |
| Ovarian ca. IGROV-1 | 0.0 | Stomach Pool | 0.0 |
| Ovarian ca. OVCAR-8 | 0.0 | Bone Marrow Pool | 0.0 |
| Ovary | 0.0 | Fetal Heart | 0.0 |
| Breast ca. MCF-7 | 0.0 | Heart Pool | 0.0 |
| Breast ca. MDA-MB-231 | 0.0 | Lymph Node Pool | 0.0 |
| Breast ca. BT 549 | 0.0 | Fetal Skeletal Muscle | 0.4 |
| Breast ca. T47D | 0.0 | Skeletal Muscle Pool | 0.0 |
| Breast ca. MDA-N | 0.0 | Spleen Pool | 0.0 |
| Breast Pool | 0.0 | Thymus Pool | 0.5 |
| Trachea | 0.0 | CNS cancer (glio/astro) U87-MG | 2.9 |
| Lung | 0.0 | CNS cancer (glio/astro) U-118-MG | 0.0 |
| Fetal Lung | 1.4 | CNS cancer (neuro; met) SK-N-AS | 0.0 |
| Lung ca. NCI-N417 | 0.0 | CNS cancer (astro) SF-539 | 0.0 |
| Lung ca. LX-1 | 0.0 | CNS cancer (astro) SNB-75 | 0.0 |
| Lung ca. NCI-H146 | 0.0 | CNS cancer (glio) SNB-19 | 0.0 |
| Lung ca. SHP-77 | 0.0 | CNS cancer (glio) SF-295 | 0.0 |
| Lung ca. A549 | 0.0 | Brain (Amygdala) Pool | 0.0 |
| Lung ca. NCI-H526 | 0.0 | Brain (cerebellum) | 0.0 |
| Lung ca. NCI-H23 | 0.0 | Brain (fetal) | 0.5 |
| Lung ca. NCI-H460 | 0.0 | Brain (Hippocampus) Pool | 0.0 |
| Lung ca. HOP-62 | 0.0 | Cerebral Cortex Pool | 1.0 |
| Lung ca. NCI-H522 | 0.0 | Brain (Substantia nigra) Pool | 0.0 |
| Liver | 0.0 | Brain (Thalamus) Pool | 0.0 |
| Fetal Liver | 0.5 | Brain (whole) | 0.0 |
| Liver ca. HepG2 | 0.0 | Spinal Cord Pool | 0.4 |
| Kidney Pool | 0.5 | Adrenal Gland | 0.0 |
| Fetal Kidney | 1.0 | Pituitary gland Pool | 0.0 |
| Renal ca. 786-0 | 0.0 | Salivary Gland | 0.0 |
| Renal ca. A498 | 0.0 | Thyroid (female) | 0.0 |
| Renal ca. ACHN | 0.0 | Pancreatic ca. CAPAN2 | 0.9 |
| Renal ca. UO-31 | 0.0 | Pancreas Pool | 0.0 |

TABLE AJ

Panel 4.1D

| Tissue Name | Rel. Exp. (%) Ag4180, Run 173607813 | Rel. Exp. (%) Ag6318, Run 259196823 | Rel. Exp. (%) Ag6602, Run 274219626 |
|---|---|---|---|
| Secondary Th1 act | 0.0 | 0.0 | 0.0 |
| Secondary Th2 act | 0.0 | 0.0 | 0.0 |
| Secondary Tr1 act | 0.0 | 0.0 | 0.0 |
| Secondary Th1 rest | 0.0 | 0.0 | 0.0 |
| Secondary Th2 rest | 0.0 | 0.0 | 0.0 |
| Secondary Tr1 rest | 0.0 | 0.0 | 0.0 |
| Primary Th1 act | 0.0 | 0.0 | 0.0 |
| Primary Th2 act | 0.0 | 0.0 | 0.0 |
| Primary Tr1 act | 0.0 | 1.7 | 0.0 |
| Primary Th1 rest | 0.0 | 0.0 | 0.0 |
| Primary Th2 rest | 0.0 | 0.0 | 0.0 |
| Primary Tr1 rest | 0.2 | 0.0 | 0.0 |
| CD45RA CD4 lymphocyte act | 0.3 | 0.0 | 0.0 |
| CD45RO CD4 lymphocyte act | 0.0 | 0.0 | 0.0 |
| CD8 lymphocyte act | 0.0 | 0.0 | 0.0 |
| Secondary CD8 lymphocyte rest | 0.0 | 0.0 | 0.0 |
| Secondary CD8 lymphocyte act | 0.0 | 0.0 | 0.0 |
| CD4 lymphocyte none | 0.0 | 0.0 | 0.0 |
| 2ry Th1/Th2/Tr1_anti-CD95 CH11 | 0.0 | 0.0 | 0.0 |
| LAK cells rest | 4.8 | 3.1 | 0.6 |
| LAK cells IL-2 | 0.0 | 0.0 | 0.0 |
| LAK cells IL-2 + IL-12 | 0.0 | 0.0 | 0.0 |
| LAK cells IL-2 + IFN gamma | 0.1 | 0.0 | 0.0 |
| LAK cells IL-2 + IL-18 | 0.0 | 0.0 | 0.0 |
| LAK cells PMA/ionomycin | 1.1 | 1.0 | 0.0 |
| NK Cells IL-2 rest | 0.3 | 0.0 | 0.0 |
| Two Way MLR 3 day | 0.4 | 1.4 | 0.0 |
| Two Way MLR 5 day | 0.0 | 0.0 | 0.0 |
| Two Way MLR 7 day | 0.0 | 0.0 | 0.0 |
| PBMC rest | 23.7 | 3.1 | 3.3 |
| PBMC PWM | 0.0 | 0.0 | 0.0 |
| PBMC PHA-L | 0.2 | 0.0 | 0.0 |
| Ramos (B cell) none | 0.0 | 0.0 | 0.0 |
| Ramos (B cell) ionomycin | 0.0 | 0.0 | 0.0 |
| B lymphocytes PWM | 0.0 | 0.0 | 0.0 |
| B lymphocytes CD40L and IL-4 | 0.0 | 0.0 | 0.0 |
| EOL-1 dbcAMP | 5.7 | 2.8 | 0.4 |

TABLE AJ-continued

Panel 4.1D

| Tissue Name | Rel. Exp. (%) Ag4180, Run 173607813 | Rel. Exp. (%) Ag6318, Run 259196823 | Rel. Exp. (%) Ag6602, Run 274219626 |
|---|---|---|---|
| EOL-1 dbcAMP PMA/ionomycin | 0.0 | 1.3 | 0.0 |
| Dendritic cells none | 4.1 | 0.6 | 2.3 |
| Dendritic cells LPS | 0.3 | 0.0 | 0.0 |
| Dendritic cells anti-CD40 | 2.4 | 0.0 | 0.3 |
| Monocytes rest | 100.0 | 11.0 | 7.4 |
| Monocytes LPS | 6.4 | 0.0 | 1.4 |
| Macrophages rest | 0.9 | 0.0 | 0.0 |
| Macrophages LPS | 0.0 | 0.0 | 0.0 |
| HUVEC none | 0.0 | 0.0 | 0.0 |
| HUVEC starved | 0.0 | 0.0 | 0.0 |
| HUVEC IL-1beta | 0.0 | 0.0 | 0.0 |
| HUVEC IFN gamma | 0.0 | 0.0 | 0.7 |
| HUVEC TNF alpha + IFN gamma | 0.0 | 0.0 | 0.0 |
| HUVEC TNF alpha + IL4 | 0.0 | 0.0 | 0.0 |
| HUVEC IL-11 | 0.0 | 0.0 | 0.0 |
| Lung Microvascular EC none | 0.0 | 0.0 | 0.0 |
| Lung Microvascular EC TNF alpha + IL-1beta | 0.0 | 0.0 | 0.0 |
| Microvascular Dermal EC none | 0.0 | 0.0 | 0.0 |
| Microvasular Dermal EC TNF alpha + IL-1beta | 0.0 | 0.0 | 0.0 |
| Bronchial epithelium TNF alpha + IL1beta | 0.0 | 0.0 | 0.0 |
| Small airway epithelium none | 0.0 | 0.0 | 0.0 |
| Small airway epithelium TNF alpha + IL-1beta | 0.0 | 0.0 | 0.0 |
| Coronery artery SMC rest | 0.0 | 0.0 | 0.0 |
| Coronery artery SMC TNF alpha + IL-1beta | 0.3 | 0.0 | 0.0 |
| Astrocytes rest | 0.0 | 0.0 | 0.0 |
| Astrocytes TNF alpha + IL-1beta | 0.0 | 1.9 | 0.0 |
| KU-812 (Basophil) rest | 0.0 | 0.0 | 0.0 |
| KU-812 (Basophil) PMA/ionomycin | 0.0 | 2.1 | 0.0 |
| CCD1106 (Keratinocytes) none | 0.0 | 0.0 | 0.0 |
| CCD1106 (Keratinocytes) TNF alpha + IL-1beta | 0.0 | 0.0 | 0.0 |
| Liver cirrhosis | 0.2 | 1.0 | 0.0 |
| NCI-H292 none | 0.0 | 0.0 | 0.0 |
| NCI-H292 IL-4 | 0.0 | 0.0 | 0.0 |
| NCI-H292 IL-9 | 0.0 | 2.7 | 0.0 |
| NCI-H292 IL-13 | 0.2 | 0.0 | 0.0 |
| NCI-H292 IFN gamma | 0.0 | 0.0 | 0.0 |
| HPAEC none | 0.0 | 0.0 | 0.0 |
| HPAEC TNF alpha + IL-1beta | 0.0 | 1.4 | 0.0 |
| Lung fibroblast none | 0.0 | 0.0 | 0.0 |
| Lung fibroblast TNF alpha + IL-1 beta | 0.1 | 0.0 | 0.0 |
| Lung fibroblast IL-4 | 0.0 | 0.0 | 0.0 |
| Lung fibroblast IL-9 | 0.0 | 0.0 | 0.0 |
| Lung fibroblast IL-13 | 0.0 | 0.0 | 0.0 |
| Lung fibroblast IFN gamma | 0.0 | 0.0 | 0.0 |
| Dermal fibroblast CCD1070 rest | 0.6 | 0.0 | 0.0 |
| Dermal fibroblast CCD1070 TNF alpha | 0.0 | 0.0 | 0.0 |
| Dermal fibroblast CCD1070 IL-1beta | 0.2 | 0.0 | 0.0 |
| Dermal fibroblast IFN gamma | 1.9 | 0.0 | 0.0 |
| Dermal fibroblast IL-4 | 4.5 | 0.0 | 0.0 |
| Dermal Fibroblasts rest | 1.2 | 0.0 | 0.0 |
| Neutrophils TNFa + LPS | 23.8 | 11.6 | 17.8 |
| Neutrophils rest | 68.8 | 100.0 | 100.0 |
| Colon | 1.0 | 0.0 | 0.0 |
| Lung | 1.0 | 1.4 | 0.0 |
| Thymus | 1.9 | 0.0 | 0.0 |
| Kidney | 17.6 | 1.2 | 0.0 |

TABLE AK

General oncology screening panel_v_2.4

| Tissue Name | Rel. Exp. (%) Ag4180, Run 268695204 | Tissue Name | Rel. Exp. (%) Ag4180, Run 268695204 |
|---|---|---|---|
| Colon cancer 1 | 46.0 | Bladder cancer NAT 2 | 0.0 |
| Colon cancer NAT 1 | 9.1 | Bladder cancer NAT 3 | 0.0 |
| Colon cancer 2 | 55.9 | Bladder cancer NAT 4 | 0.0 |
| Colon cancer NAT 2 | 11.9 | Adenocarcinoma of the prostate 1 | 0.0 |
| Colon cancer 3 | 22.4 | Adenocarcinoma of the prostate 2 | 4.1 |
| Colon cancer NAT 3 | 6.7 | Adenocarcinoma of the prostate 3 | 0.0 |
| Colon malignant cancer 4 | 49.7 | Adenocarcinoma of the prostate 4 | 1.7 |
| Colon normal adjacent tissue 4 | 0.0 | Prostate cancer NAT 5 | 0.0 |
| Lung cancer 1 | 100.0 | Adenocarcinoma of the prostate 6 | 0.0 |
| Lung NAT 1 | 13.8 | Adenocarcinoma of the prostate 7 | 3.5 |
| Lung cancer 2 | 11.9 | Adenocarcinoma of the prostate 8 | 0.0 |
| Lung NAT 2 | 5.7 | Adenocarcinoma of the prostate 9 | 16.0 |
| Squamous cell carcinoma 3 | 10.3 | Prostate cancer NAT 10 | 0.0 |
| Lung NAT 3 | 6.3 | Kidney cancer 1 | 44.1 |
| metastatic melanoma 1 | 32.8 | KidneyNAT 1 | 3.9 |
| Melanoma 2 | 4.1 | Kidney cancer 2 | 65.1 |

TABLE AK-continued

General oncology screening panel_v_2.4

| Tissue Name | Rel. Exp. (%) Ag4180, Run 268695204 | Tissue Name | Rel. Exp. (%) Ag4180, Run 268695204 |
|---|---|---|---|
| Melanoma 3 | 2.7 | Kidney NAT 2 | 2.1 |
| metastatic melanoma 4 | 48.3 | Kidney cancer 3 | 0.0 |
| metastatic melanoma 5 | 51.8 | Kidney NAT 3 | 0.0 |
| Bladder cancer 1 | 9.2 | Kidney cancer 4 | 47.6 |
| Bladder cancer NAT 1 | 0.0 | Kidney NAT 4 | 33.0 |
| Bladder cancer 2 | 0.0 | | |

AI_comprehensive panel_v.1.0 Summary: Ag6318/Ag6659 Two experiments with two different probe and primer sets that are specific to the NOV2B variant produce results that are in reasonable agreement. Highest expression of this gene is seen in bone from an OA patient (CTs=30–34). Expression levels in the other samples in the Ag6659 experiment are below the threshold of reliable detection. In the experiment using probe and primer set Ag6318, low but significant levels of expression are seen in many of the samples on this panel, including bone, synovium, synovial fluid and cartilage from OA and RA patients. These results confirm expression of this gene in samples related to the autoimmune response. Thus, therapeutic modulation of the expression or function of this gene or gene product may be useful in the treatment of OA.

CNS_neurodegeneration_v1.0 Summary: Ag4180 This panel does not show differential expression of this gene in Alzheimer's disease. However, this expression profile confirms the presence of this gene in the brain. This gene encodes a leucine-rich repeat protein. Leucine rich repeats (LRR) mediate reversible protein-protein interactions and have diverse cellular functions, including cellular adhesion and signaling. Several of these proteins, such as connectin, slit, chaoptin, and Toll have pivotal roles in neuronal development in *Drosophila* and may play significant but distinct roles in neural development and in the adult nervous system of humans (Battye R. (2001) J. Neurosci. 21: 4290–4298. Itoh A. (1998) Brain Res. Mol. Brain Res. 62: 175–186). In *Drosophilia*, the LRR region of axon guidance proteins has been shown to be critical for their function (especially in axon repulsion). Since the leucine-rich-repeat protein encoded by this gene shows high expression in the cerebral cortex, it is an excellent candidate neuronal guidance protein for axons, dendrites and/or growth cones in general. Therefore, therapeutic modulation of the levels of this protein, or possible signaling via this protein, may be of utility in enhancing/directing compensatory synaptogenesis and fiber growth in the CNS in response to neuronal death (stroke, head trauma), axon lesion (spinal cord injury), or neurodegeneration (Alzheimer's, Parkinson's, Huntington's, vascular dementia or any neurodegenerative disease). A second experiment with Ag6318 shows low/undetectable levels of expression in all samples on this panel. (CTS>35). (Data not shown.)

General_screening_panel_v1.4 Summary: Ag4180 Highest expression of this gene is seen in a brain cancer cell line (CT=30.8). Low but significant expression is also seen in colon cancer. Thus, expression of this gene could be used to differentiate between these samples and other samples on this panel and as a marker to detect the presence of these cancers. Members of the leucine rich superfamily have been shown to be upregulated in some brain cancers (Almeida A, Oncogene Jun. 11, 1998 16(23):2997–3002) Therefore, therapeutic modulation of the expression or function of this gene may be effective in the treatment of brain and colon cancer.

Low but significant expression is also seen in the thyroid. The extracellular domains of receptors for glycoprotein hormones that influence the development and function of the thyroid are members of the leucine-rich repeat (LRR) protein superfamily and are responsible for the high-affinity binding. (Jiang X. (1995) Structure 3: 1341–1353.) Thus, therapeutic modulation of this gene product may aid in the treatment of metabolic and neuroendocrine disorders.

General_screening_panel_v1.5 Summary: Ag6318 This probe and primer set is specific for the NOV2B variant only and produces a different expression profile than in Panel 1.4. In this panel, expression is exclusive to colon cancer cell lines (CTs=32). Thus, expression of this gene could be used to differentiate between this sample and other samples on this panel and as a marker to detect the presence of colon cancer. Furthermore, therapeutic modulation of the expression or function of this gene may be effective in the treatment of colon cancer.

General_screening_panel_v1.6 Summary: Ag6702 Expression is low/undetectable in all samples on this panel. (CTs>35). (Data not shown.)

Panel 4.1D Summary: Ag4180 Expression of this gene is highest in resting monocytes (CT=28.7). Moderate levels of expression are seen in resting PBMCs, resting neutrophils (CT=29.2), TNF-a and LPS treated neutrophils (CT=30.7), and normal kidney. Low but significant levels of expression are seen in activated dermal fibroblasts, resting LAK cells, LPS treated monocytes, eosinophils and treated dendritic cells.

Two experiments with the probe and primer sets Ag6318 and Ag6602, both specific to NOV2B, show expression in resting neutrophils only (CTs=31–32).

The expression of this transcript in LPS treated monocytes, cells that play a crucial role in linking innate immunity to adaptive immunity, suggests a role for this gene product in initiating inflammatory reactions. Therefore, modulation of the expression or activity of the NOV2A gene may reduce or prevent early stages of inflammation and reduce the severity of inflammatory diseases such as psoriasis, asthma, inflammatory bowel disease, rheumatoid arthritis, osteoarthritis and other lung inflammatory diseases.

General oncology screening panel_v_2.4 Summary: Ag4180 Highest expression of this gene is seen in lung cancer (CT=33.5). In addition, expression is higher in lung, colon and kidney cancers when compared to expression in the corresponding normal adjacent tissue. Thus, expression of this gene could be as a marker to detect the presence of these cancers. Furthermore, therapeutic modulation of the expression or function of this gene may be effective in the treatment of lung, colon and kidney cancer.

B. NOV3A: Gonadotrophin Beta-subunit

Expression of gene NOV3A was assessed using the primer-probe sets Ag338 and Ag74, described in Tables BA and BB. Results of the RTQ-PCR runs are shown in Table BC.

TABLE BA

Probe Name Ag338

| Primers | Sequences | Length | Start Position | SEQ ID No |
|---------|-----------|--------|----------------|-----------|
| Forward | 5'-acaacgagaccaaacaggtgact-3' | 23 | 248 | 124 |
| Probe | TET-5'-tcaagctgcccaactgtgcccc-3'-TAMRA | 22 | 272 | 125 |
| Reverse | 5'-ggccacgggataggtgtaga-3' | 20 | 308 | 126 |

TABLE BB

Probe Name Ag74

| Primers | Sequences | Length | Start Position | SEQ ID No |
|---------|-----------|--------|----------------|-----------|
| Forward | 5'-acaacgagaccaaacaggtgact-3' | 23 | 248 | 127 |
| Probe | TET-5'-caactgtgccccgggagtcgac-3'TAMRA | 22 | 282 | 128 |
| Reverse | 5'-ggccacgggataggtgtaga-3' | 20 | 308 | 129 |

TABLE BC

Panel 1

| Tissue Name | Rel. Exp. (%) Ag338, Run 97805375 | Rel. Exp. (%) Ag74, Run 87354633 |
|-------------|------------------------------------|-----------------------------------|
| Endothelial cells | 0.0 | 0.0 |
| Endothelial cells (treated) | 0.0 | 0.0 |
| Pancreas | 0.0 | 0.0 |
| Pancreatic ca. CAPAN 2 | 0.0 | 0.0 |
| Adrenal gland | 0.0 | 0.0 |
| Thyroid | 0.0 | 0.0 |
| Salivary gland | 0.0 | 0.0 |
| Pituitary gland | 0.0 | 0.0 |
| Brain (fetal) | 0.0 | 0.0 |
| Brain (whole) | 0.5 | 0.0 |
| Brain (amygdala) | 0.6 | 0.0 |
| Brain (cerebellum) | 0.3 | 24.8 |
| Brain (hippocampus) | 0.0 | 0.0 |
| Brain (substantia nigra) | 0.0 | 0.0 |
| Brain (thalamus) | 0.1 | 0.0 |
| Brain (hypothalamus) | 0.0 | 0.0 |
| Spinal cord | 0.0 | 0.0 |
| glio/astro U87-MG | 0.0 | 0.0 |
| glio/astro U-118-MG | 0.0 | 0.0 |
| astrocytoma SW1783 | 0.0 | 0.0 |
| neuro*; met SK-N-AS | 0.0 | 0.0 |
| astrocytoma SF-539 | 0.0 | 0.0 |
| astrocytoma SNB-75 | 0.0 | 0.0 |
| glioma SNB-19 | 0.0 | 0.0 |
| glioma U251 | 0.0 | 0.0 |
| glioma SF-295 | 0.0 | 0.0 |
| Heart | 0.0 | 0.0 |
| Skeletal muscle | 0.0 | 0.0 |
| Bone marrow | 0.0 | 0.0 |
| Thymus | 0.0 | 0.0 |
| Spleen | 0.0 | 0.0 |
| Lymph node | 0.0 | 0.0 |
| Colon (ascending) | 23.2 | 40.3 |
| Stomach | 0.0 | 0.0 |
| Small intestine | 0.0 | 0.0 |
| Colon ca. SW480 | 0.0 | 0.0 |
| Colon ca.* SW620 (SW480 met) | 0.0 | 0.0 |
| Colon ca. HT29 | 0.0 | 0.0 |
| Colon ca. HCT-116 | 0.0 | 0.0 |
| Colon ca. CaCo-2 | 0.0 | 0.0 |
| Colon ca. HCT-15 | 1.7 | 0.0 |
| Colon ca. HCC-2998 | 0.0 | 0.0 |
| Gastric ca. * (liver met) NCI-N87 | 0.0 | 0.0 |
| Bladder | 0.0 | 0.0 |
| Trachea | 0.0 | 0.0 |
| Kidney | 0.0 | 0.0 |
| Kidney (fetal) | 0.0 | 0.0 |
| Renal ca. 786-0 | 0.0 | 0.0 |
| Renal ca. A498 | 0.0 | 0.0 |
| Renal ca. RXF 393 | 0.0 | 0.0 |
| Renal ca. ACHN | 0.0 | 0.0 |
| Renal ca. UO-31 | 0.0 | 0.0 |
| Renal ca. TK-10 | 0.0 | 0.0 |
| Liver | 0.0 | 0.0 |
| Liver (fetal) | 0.0 | 0.0 |
| Liver ca. (hepatoblast) HepG2 | 0.0 | 0.0 |
| Lung | 0.0 | 0.0 |
| Lung (fetal) | 0.0 | 0.0 |
| Lung ca. (small cell) LX-1 | 0.0 | 0.0 |
| Lung ca. (small cell) NCI-H69 | 8.4 | 4.6 |
| Lung ca. (s.cell var.) SHP-77 | 0.0 | 0.0 |
| Lung ca. (large cell)NCI-H460 | 0.0 | 0.0 |
| Lung ca. (non-sm. cell) A549 | 0.4 | 0.0 |
| Lung ca (non-s.cell) NCI-H23 | 0.0 | 0.0 |
| Lung ca. (non-s.cell) HOP-62 | 0.0 | 0.0 |
| Lung ca. (non-s.cl) NCI-H522 | 0.0 | 0.0 |
| Lung ca. (squam.) SW 900 | 0.0 | 0.0 |
| Lung ca. (squam.) NCI-H596 | 1.8 | 0.0 |
| Mammary gland | 0.0 | 0.0 |
| Breast ca.* (pl.ef) MCF-7 | 0.0 | 0.0 |
| Breast ca.* (pl.ef) MDA-MB-231 | 0.0 | 0.0 |
| Breast ca.* (pl. ef) T47D | 1.1 | 18.6 |
| Breast ca. BT-549 | 0.0 | 0.0 |
| Breast ca. MDA-N | 0.0 | 0.0 |
| Ovary | 0.0 | 0.0 |
| Ovarian ca. OVCAR-3 | 0.0 | 0.0 |
| Ovarian ca. OVCAR-4 | 0.0 | 0.0 |
| Ovarian ca. OVCAR-5 | 10.3 | 4.8 |
| Ovarian ca. OVCAR-8 | 0.0 | 0.0 |
| Ovarian ca. IGROV-1 | 1.5 | 0.0 |
| Ovarian ca. (ascites) SK-OV-3 | 0.0 | 0.0 |
| Uterus | 0.0 | 0.0 |
| Placenta | 0.0 | 0.0 |
| Prostate | 0.0 | 0.0 |
| Prostate ca.* (bone met) PC-3 | 0.5 | 0.0 |
| Testis | 5.8 | 100.0 |
| Melanoma Hs688(A).T | 0.0 | 0.0 |
| Melanoma* (met) Hs688(B).T | 0.0 | 0.0 |

TABLE BC-continued

Panel 1

| Tissue Name | Rel. Exp. (%) Ag338, Run 97805375 | Rel. Exp. (%) Ag74, Run 87354633 |
|---|---|---|
| Melanoma UACC-62 | 0.0 | 0.0 |
| Melanoma M14 | 0.0 | 1.0 |
| Melanoma LOX IMVI | 0.0 | 0.0 |
| Melanoma* (met) SK-MEL-5 | 0.0 | 0.0 |
| Melanoma SK-MEL-28 | 100.0 | 0.0 |

CNS_neurodegeneration_v1.0 Summary: Ag338 Results from one experiment with the NOV3A gene are not included. The amp plot indicates that there were experimental difficulties with this run.

Panel 1 Summary: Ag338 Highest expression of the NOV3A gene is detected in a melanoma SK-MEL-28 cell line (CT=27.8). Thus, expression of this gene may be used to distinguish this sample from other samples used in this panel. In addition, low to moderate expression of this gene is also seen in lung cancer, breast cancer and ovarian cancer cell lines. Therefore, therapeutic modulation of this gene product may be useful in the treatment of these cancers.

Low expression of this gene is also seen in testis and colon. Therefore, therapeutic modulation of this gene product may be useful in the treatment of diseases associated testis and colon such as fertility, hypogonadism, inflammatory bowel diseases, cancers.

Ag74 Highest expression of the NOV3A gene is detected in testis (CT=31.4). Thus, expression of this gene can be used to distinguish this sample from other samples in this panel. In addition, moderate expression of this gene is also seen in colon and brain (cerebellum). Therefore, therapeutic modulation of this gene product may be useful in the treatment of neurological disorders and diseases associated with testis and colon.

Panel 4D Summary: Ag338 Expression of the NOV3A gene is low/undetectable (CTs>35) across all of the samples on this panel (data not shown).

General oncology screening panel_v_2.4 Summary: Ag338 Expression of the NOV3A gene is low/undetectable (CTs>35) across all of the samples on this panel (data not shown).

C. NOV4A: Odorant Binding Protein

Expression of gene NOV4A was assessed using the primer-probe sets Ag4218 and Ag4261, described in Tables CA and CB. Results of the RTQ-PCR runs are shown in Tables CC and CD.

TABLE CA

Probe Name Ag4218

| Primers | Sequences | Length | Start Position | SEQ ID No |
|---|---|---|---|---|
| Forwards | 5'-actctcggaggaggacatttt-3' | 21 | 339 | 130 |
| Probe | TET-5'-cagtccctgtgtccctctgctg-3'-TAMRA | 23 | 394 | 131 |
| Reverse | 5'-cactggagatagcagacagaca-3' | 22 | 417 | 132 |

TABLE CB

Probe Name Ag4261

| Primers | Sequences | Length | Start Position | SEQ ID No |
|---|---|---|---|---|
| Forward | 5'-actctcggaggaggacatttt-3' | 21 | 339 | 133 |
| Probe | TET-5'-cagtccctgtgtccctctgctg-3'-TAMRA | 23 | 394 | 134 |
| Reverse | 5'-cactggagatagcagacagaca-3' | 22 | 417 | 135 |

TABLE CC

General_screening_panel_v1.4

| Tissue Name | Rel. Exp. (%) Ag4261, Run 222523498 | Tissue Name | Rel. Exp. (%) Ag4261, Run 222523498 |
|---|---|---|---|
| Adipose | 0.0 | Renal ca. TK-10 | 0.0 |
| Melanoma* Hs688(A).T | 0.0 | Bladder | 0.0 |
| Melanoma* Hs688(B).T | 0.0 | Gastric ca. (liver met.) NCI-N87 | 2.5 |
| Melanoma* M14 | 0.0 | Gastric ca. KATO III | 100.0 |
| Melanoma* LOXIMVI | 0.0 | Colon ca. SW-948 | 1.5 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 0.0 | Colon ca. HT29 | 0.0 |
| Prostate ca.* (bone met) PC-3 | 0.0 | Colon ca. HCT-116 | 0.0 |
| Prostate Pool | 0.0 | Colon ca. CaCo-2 | 0.0 |
| Placenta | 0.0 | Colon cancer tissue | 0.0 |
| Uterus Pool | 0.0 | Colon ca. SW1116 | 0.0 |

TABLE CC-continued

General_screening_panel_v1.4

| Tissue Name | Rel. Exp. (%) Ag4261, Run 222523498 | Tissue Name | Rel. Exp. (%) Ag4261, Run 222523498 |
|---|---|---|---|
| Ovarian ca. OVCAR-3 | 0.0 | Colon ca. Colo-205 | 0.0 |
| Ovarian ca. SK-OV-3 | 13.4 | Colon ca. SW-48 | 0.0 |
| Ovarian ca. OVCAR-4 | 0.0 | Colon Pool | 7.0 |
| Ovarian ca. OVCAR-5 | 0.0 | Small Intestine Pool | 5.7 |
| Ovarian ca. IGROV-1 | 0.0 | Stomach Pool | 0.9 |
| Ovarian ca. OVCAR-8 | 0.0 | Bone Marrow Pool | 8.4 |
| Ovary | 0.0 | Fetal Heart | 0.4 |
| Breast ca. MCF-7 | 0.0 | Heart Pool | 0.0 |
| Breast ca. MDA-MB-231 | 0.0 | Lymph Node Pool | 0.0 |
| Breast ca. BT 549 | 0.0 | Fetal Skeletal Muscle | 0.0 |
| Breast ca. T47D | 0.0 | Skeletal Muscle Pool | 0.0 |
| Breast ca. MDA-N | 0.0 | Spleen Pool | 0.0 |
| Breast Pool | 0.0 | Thymus Pool | 0.0 |
| Trachea | 0.0 | CNS cancer (glio/astro) U87-MG | 0.0 |
| Lung | 0.0 | CNS cancer (glio/astro) U-118-MG | 0.0 |
| Fetal Lung | 2.6 | CNS cancer (neuro; met) SK-N-AS | 0.0 |
| Lung ca. NCI-N417 | 0.0 | CNS cancer (astro) SF-539 | 0.0 |
| Lung ca. LX-1 | 4.2 | CNS cancer (astro) SNB-75 | 0.0 |
| Lung ca. NCI-H146 | 0.0 | CNS cancer (glio) SNB-19 | 0.0 |
| Lung ca. SHP-77 | 0.0 | CNS cancer (glio) SF-295 | 0.0 |
| Lung ca. A549 | 0.0 | Brain (Amygdala) Pool | 0.0 |
| Lung ca. NCI-H526 | 0.0 | Brain (cerebellum) | 0.0 |
| Lung ca. NCI-H23 | 0.0 | Brain (fetal) | 0.0 |
| Lung ca. NCI-H460 | 0.0 | Brain (Hippocampus) Pool | 0.0 |
| Lung ca. HOP-62 | 0.0 | Cerebral Cortex Pool | 0.0 |
| Lung ca. NCI-H522 | 0.0 | Brain (Substantia nigra) Pool | 0.0 |
| Liver | 0.0 | Brain (Thalamus) Pool | 0.0 |
| Fetal Liver | 0.0 | Brain (whole) | 0.0 |
| Liver ca. HepG2 | 0.0 | Spinal Cord Pool | 0.0 |
| Kidney Pool | 0.0 | Adrenal Gland | 0.0 |
| Fetal Kidney | 1.9 | Pituitary gland Pool | 0.0 |
| Renal ca. 786-0 | 0.0 | Salivary Gland | 0.0 |
| Renal ca. A498 | 0.0 | Thyroid (female) | 0.0 |
| Renal ca. ACHN | 0.0 | Pancreatic ca. CAPAN2 | 0.0 |
| Renal ca. UO-31 | 0.0 | Pancreas Pool | 0.0 |

TABLE CD

Panel 4.1D

| Tissue Name | Rel. Exp. (%) Ag4218, Run 174261203 | Tissue Name | Rel. Exp. (%) Ag4218, Run 174261203 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 1.4 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 2.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microvasular Dermal EC TNF alpha + IL-1beta | 0.0 |
| Primary Th1 rest | 0.0 | Bronchial epithelium TNF alpha + IL1beta | 2.3 |
| Primary Th2 rest | 0.0 | Small airway epithelium none | 0.0 |
| Primary Tr1 rest | 0.9 | Small airway epithelium TNF alpha + IL-1beta | 0.0 |

TABLE CD-continued

Panel 4.1D

| Tissue Name | Rel. Exp. (%) Ag4218, Run 174261203 | Tissue Name | Rel. Exp. (%) Ag4218, Run 174261203 |
|---|---|---|---|
| CD45RA CD4 lymphocyte act | 0.0 | Coronery artery SMC rest | 0.0 |
| CD45RO CD4 lymphocyte act | 0.9 | Coronery artery SMC TNF alpha + IL-1beta | 0.0 |
| CD8 lymphocyte act | 0.0 | Astrocytes rest | 0.0 |
| Secondary CD8 lymphocyte rest | 1.0 | Astrocytes TNF alpha + IL-1beta | 0.0 |
| Secondary CD8 lymphocyte act | 0.0 | KU-812 (Basophil) rest | 1.3 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 0.0 |
| LAK cells IL-2 + IL-12 | 0.0 | NCI-H292 none | 2.4 |
| LAK cells IL-2 + IFN gamma | 0.0 | NCI-H292 IL-4 | 0.0 |
| LAK cells IL-2 + IL-18 | 0.0 | NCI-H292 IL-9 | 0.0 |
| LAK cells PMA/ionomycin | 0.0 | NCI-H292 IL-13 | 0.0 |
| NK Cells IL-2 rest | 0.0 | NCI-H292 IFN gamma | 0.0 |
| Two Way MLR 3 day | 0.0 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 0.0 |
| PBMC rest | 0.0 | Lung fibroblast TNF alpha + IL-1beta | 0.0 |
| PBMC PWM | 0.0 | Lung fibroblast IL-4 | 0.0 |
| PBMC PHA-L | 0.0 | Lung fibroblast IL-9 | 0.0 |
| Ramos (B cell) none | 0.0 | Lung fibroblast IL-13 | 2.5 |
| Ramos (B cell) ionomycin | 0.0 | Lung fibroblast IFN gamma | 0.0 |
| B lymphocytes PWM | 0.0 | Dermal fibroblast CCD1070 rest | 0.0 |
| B lymphocytes CD40L and IL-4 | 0.0 | Dermal fibroblast CCD1070 TNF alpha | 0.0 |
| EOL-1 dbcAMP | 0.0 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 1.4 |
| Dendritic cells LPS | 0.0 | Dermal Fibroblasts rest | 1.3 |
| Dendritic cells anti-CD40 | 3.4 | Neutrophils TNFa + LPS | 0.0 |
| Monocytes rest | 0.0 | Neutrophils rest | 0.0 |
| Monocytes LPS | 0.0 | Colon | 0.0 |
| Macrophages rest | 0.0 | Lung | 3.1 |
| Macrophages LPS | 0.0 | Thymus | 14.9 |
| HUVEC none | 0.0 | Kidney | 100.0 |
| HUVEC starved | 0.0 | | |

CNS_neurodegeneration_v1.0 Summary: Ag4218 Expression of the NOV4A gene is low/undetectable in all samples on this panel (CTs>35). (Data not shown.)

General_screening_panel_v1.4 Summary: Ag4218 Expression of the NOV4A gene is restricted to a sample derived from a gastric cancer cell line (CT=32). Thus, expression of this gene could be used to differentiate between this sample and other samples on this panel and as a marker to detect the presence of gastric cancer. Furthermore, therapeutic modulation of the expression or function of this gene may be effective in the treatment of gastric cancer.

Panel 4.1D Summary: Ag4218 Expression of the NOV4A gene is limited to the kidney and thymus (CTs=30–33). Therefore, therapeutic modulation of the expression or function of this gene may modulate kidney and thymus function and be important in the treatment of inflammatory or autoimmune diseases that affect these organs, including lupus and glomerulonephritis.

General oncology screening panel_v_2.4 Summary: Ag4218 Expression of the NOV4A gene is low/undetectable in all samples on this panel (CTs>35). (Data not shown.)

D. NOV6B: Cathepsin F Precursor

Expression of gene NOV6B, representing a full-length physical clone, was assessed using the primer-probe set Ag6946, described in Table DA. Results of the RTQ-PCR runs are shown in Table DB.

TABLE DA

Probe Name Ag6946

| Primers | Sequences | Length | Start Position | SEQ ID No |
|---|---|---|---|---|
| Forward | 5'-ccagcccaagtcctggat-3' | 19 | 80 | 136 |
| Probe | TET-5'-aaccttggtgtccactgggccaca-3'-TAMRA | 24 | 132 | 137 |
| Reverse | 5'-atcatggctgagccctgagt-3' | 20 | 186 | 138 |

TABLE DB

General_screening_panel_v1.6

| Tissue Name | Rel. Exp. (%) Ag6946, Run 278388882 | Tissue Name | Rel. Exp. (%) Ag6946, Run 278388882 |
|---|---|---|---|
| Adipose | 11.4 | Renal ca. TK-10 | 0.0 |
| Melanoma* Hs688(A).T | 21.0 | Bladder | 10.2 |
| Melanoma* Hs688(B).T | 13.4 | Gastric ca. (liver met.) NCI-N87 | 5.2 |
| Melanoma* M14 | 26.1 | Gastric ca. KATO III | 0.0 |
| Melanoma* LOXIMVI | 1.4 | Colon ca. SW-948 | 1.4 |
| Melanoma* SK-MEL-5 | 18.7 | Colon ca. SW480 | 0.0 |
| Squamous cell carcinoma SCC-4 | 3.4 | Colon ca.* (SW480 met) SW620 | 0.0 |
| Testis Pool | 29.7 | Colon ca. HT29 | 0.0 |
| Prostate ca.* (bone met) PC-3 | 17.0 | Colon ca. HCT-116 | 0.0 |
| Prostate Pool | 12.4 | Colon ca. CaCo-2 | 0.0 |
| Placenta | 12.3 | Colon cancer tissue | 3.3 |
| Uterus Pool | 7.2 | Colon ca. SW1116 | 0.0 |
| Ovarian ca. OVCAR-3 | 36.6 | Colon ca. Colo-205 | 0.0 |
| Ovarian ca. SK-OV-3 | 18.8 | Colon ca. SW-48 | 0.1 |
| Ovarian ca. OVCAR-4 | 2.2 | Colon Pool | 23.8 |
| Ovarian ca. OVCAR-5 | 7.9 | Small Intestine Pool | 23.0 |
| Ovarian ca. IGROV-1 | 10.8 | Stomach Pool | 13.4 |
| Ovarian ca. OVCAR-8 | 20.7 | Bone Marrow Pool | 6.8 |
| Ovary | 32.8 | Fetal Heart | 3.5 |
| Breast ca. MCF-7 | 1.5 | Heart Pool | 11.1 |
| Breast ca. MDA-MB-231 | 22.2 | Lymph Node Pool | 19.1 |
| Breast ca. BT 549 | 53.2 | Fetal Skeletal Muscle | 2.8 |
| Breast ca. T47D | 15.3 | Skeletal Muscle Pool | 4.5 |
| Breast ca. MDA-N | 26.8 | Spleen Pool | 6.2 |
| Breast Pool | 22.8 | Thymus Pool | 11.1 |
| Trachea | 14.9 | CNS cancer (glio/astro) U87-MG | 7.0 |
| Lung | 5.1 | CNS cancer (glio/astro) U-118-MG | 1.2 |
| Fetal Lung | 10.5 | CNS cancer (neuro; met) SK-N-AS | 7.4 |
| Lung ca. NCI-N417 | 1.1 | CNS cancer (astro) SF-539 | 1.8 |
| Lung ca. LX-1 | 0.2 | CNS cancer (astro) SNB-75 | 36.9 |
| Lung ca. NCI-H146 | 1.4 | CNS cancer (glio) SNB-19 | 11.0 |
| Lung ca. SHP-77 | 11.4 | CNS cancer (glio) SF-295 | 62.4 |
| Lung ca. A549 | 15.0 | Brain (Amygdala) Pool | 20.9 |
| Lung ca. NCI-H526 | 4.8 | Brain (cerebellum) | 100.0 |
| Lung ca. NCI-H23 | 35.4 | Brain (fetal) | 17.9 |
| Lung ca. NCI-H460 | 10.7 | Brain (Hippocampus) Pool | 24.1 |
| Lung ca. HOP-62 | 30.6 | Cerebral Cortex Pool | 35.4 |
| Lung ca. NCI-H522 | 0.0 | Brain (Substantia nigra) Pool | 25.0 |
| Liver | 13.6 | Brain (Thalamus) Pool | 33.2 |
| Fetal Liver | 4.9 | Brain (whole) | 26.1 |
| Liver ca. HepG2 | 0.0 | Spinal Cord Pool | 28.1 |
| Kidney Pool | 50.0 | Adrenal Gland | 25.7 |
| Fetal Kidney | 11.2 | Pituitary gland Pool | 6.2 |
| Renal ca. 786-0 | 0.0 | Salivary Gland | 18.4 |
| Renal ca. A498 | 8.9 | Thyroid (female) | 12.2 |
| Renal ca. ACHN | 0.0 | Pancreatic ca. CAPAN2 | 6.0 |
| Renal ca. UO-31 | 10.7 | Pancreas Pool | 4.8 |

General_screening_pane_v1.6 Summary: Ag6946 Highest expression of the NOV6B gene is seen in the cerebellum (CT=28.3). In addition, moderate levels of expression are also seen in all regions of the CNS examined. This gene encodes a homolog of cathepsin that has been shown to be deficient in neurodegenerative lysosomal disorder galactosialidosis, which produces nephropathy, ataxia, and premature death. Expression of cathepsin in the brain has been shown to delay the onset of the neuronal degeneration and to correct the ataxia associated with this disease. (Leimig T. Blood 2000 May 1; 99(9):3169–78). Thus, based on the expression of this gene in the CNS and the homology that this gene shows to cathepsin, modulation of this gene could be used in the treatment of this disorder, diseases that affect the cerebellum such as autism and the ataxias, Alzheimer's disease, Parkinson's disease, schizophrenia, multiple sclerosis, stroke and epilepsy.

Moderate levels of expression are also seen in cell lines derived from ovarian cancer, lung cancer and breast cancer. Thus, , therapeutic modulation of the expression or function of this gene may be effective in the treatment of these cancers.

Among tissues with metabolic function, this gene is expressed at moderate to low levels in pituitary, adipose, adrenal gland, pancreas, thyroid, and adult and fetal skeletal muscle, heart, and liver. This widespread expression among these tissues suggests that this gene product may play a role in normal neuroendocrine and metabolic function and that disregulated expression of this gene may contribute to neuroendocrine disorders or metabolic diseases, such as obesity and diabetes.

E. NOV7A: Netrin G1

Expression of gene NOV7A was assessed using the primer-probe set Ag4235, described in Table EA. Results of the RTQ-PCR runs are shown in Tables EB, EC, ED, EE and EF.

TABLE EA

Probe Name Ag4235

| Primers | Sequences | Length | Start Position | SEQ ID No |
|---|---|---|---|---|
| Forward | 5'-ggtcatggtcctggagaagt-3' | 20 | 537 | 139 |
| Probe | TET-5'-acctggcagccctaccagttctacg-3'-TAMRA | 25 | 574 | 140 |
| Reverse | 5'-acataccgaaggcctccat-3' | 19 | 610 | 141 |

TABLE EB

CNS_neurodegeneration_v1.0

| Tissue Name | Rel. Exp. (%) Ag4235, Run 224078156 | Rel. Exp. (%) Ag4235, Run 230510266 |
|---|---|---|
| AD 1 Hippo | 11.7 | 30.1 |
| AD 2 Hippo | 26.8 | 47.0 |
| AD 3 Hippo | 5.0 | 16.8 |
| AD 4 Hippo | 4.6 | 17.0 |
| AD 5 Hippo | 27.5 | 77.9 |
| AD 6 Hippo | 16.3 | 68.8 |
| Control 2 Hippo | 14.3 | 37.6 |
| Control 4 Hippo | 14.2 | 51.4 |
| Control (Path) 3 Hippo | 4.5 | 0.0 |
| AD 1 Temporal Ctx | 7.5 | 9.1 |
| AD 2 Temporal Ctx | 15.0 | 39.2 |
| AD 3 Temporal Ctx | 4.8 | 12.9 |
| AD 4 Temporal Ctx | 9.2 | 10.8 |
| AD 5 Inf Temporal Ctx | 31.6 | 100.0 |
| AD 5 Sup Temporal Ctx | 22.4 | 89.5 |
| AD 6 Inf Temporal Ctx | 18.0 | 58.2 |
| AD 6 Sup Temporal Ctx | 17.7 | 55.1 |
| Control 1 Temporal Ctx | 7.2 | 13.5 |
| Control 2 Temporal Ctx | 18.6 | 55.5 |
| Control 3 Temporal Ctx | 8.4 | 29.9 |
| Control 3 Temporal Ctx | 12.7 | 38.2 |
| Control (Path) 1 Temporal Ctx | 49.0 | 67.4 |
| Control (Path) 2 Temporal Ctx | 14.8 | 50.0 |
| Control (Path) 3 Temporal Ctx | 9.5 | 14.5 |
| Control (Path) 4 Temporal Ctx | 26.4 | 59.9 |
| AD 1 Occipital Ctx | 6.1 | 15.2 |
| AD 2 Occipital Ctx (Missing) | 0.0 | 0.0 |
| AD 3 Occipital Ctx | 5.6 | 11.0 |
| AD 4 Occipital Ctx | 6.7 | 20.7 |
| AD 5 Occipital Ctx | 14.7 | 39.8 |
| AD 6 Occipital Ctx | 4.0 | 4.8 |
| Control 1 Occipital Ctx | 3.2 | 13.3 |
| Control 2 Occipital Ctx | 15.0 | 50.0 |
| Control 3 Occipital Ctx | 7.4 | 24.8 |
| Control 4 Occipital Ctx | 4.9 | 16.4 |
| Control (Path) 1 Occipital Ctx | 33.9 | 81.2 |
| Control (Path) 2 Occipital Ctx | 7.1 | 0.5 |
| Control (Path) 3 Occipital Ctx | 3.2 | 6.6 |
| Control (Path) 4 Occipital Ctx | 15.3 | 41.5 |
| Control 1 Parietal Ctx | 6.9 | 21.9 |
| Control 2 Parietal Ctx | 26.4 | 79.6 |
| Control 3 Parietal Ctx | 8.7 | 7.3 |
| Control (Path) 1 Parietal Ctx | 100.0 | 75.8 |
| Control (Path) 2 Parietal Ctx | 9.3 | 35.6 |
| Control (Path) 3 Parietal Ctx | 3.2 | 9.0 |
| Control (Path) 4 Parietal Ctx | 31.2 | 41.8 |

TABLE EC

General_screening_panel_v1.4

| Tissue Name | Rel. Exp. (%) Ag4235, Run 221994384 | Tissue Name | Rel. Exp. (%) Ag4235, Run 221994384 |
|---|---|---|---|
| Adipose | 0.6 | Renal ca. TK-10 | 0.8 |
| Melanoma* Hs688(A).T | 3.4 | Bladder | 2.7 |
| Melanoma* Hs688(B).T | 3.6 | Gastric ca. (liver met.) NCI-N87 | 0.0 |
| Melanoma* M14 | 0.2 | Gastric ca. KATO III | 0.0 |
| Melanoma* LOXIMVI | 0.0 | Colon ca. SW-948 | 0.0 |
| Melanoma* SK-MEL-5 | 0.2 | Colon ca. SW480 | 0.9 |
| Squamous cell carcinoma SCC-4 | 0.2 | Colon ca.* (SW480 met) SW620 | 0.0 |
| Testis Pool | 1.1 | Colon ca. HT29 | 0.0 |
| Prostate ca.* (bone met) PC-3 | 1.5 | Colon ca. HCT-116 | 0.1 |
| Prostate Pool | 6.2 | Colon ca. CaCo-2 | 0.0 |
| Placenta | 0.4 | Colon cancer tissue | 3.4 |
| Uterus Pool | 0.0 | Colon ca. SW1116 | 100.0 |
| Ovarian ca. OVCAR-3 | 0.1 | Colon ca. Colo-205 | 0.0 |
| Ovarian ca. SK-OV-3 | 0.1 | Colon ca. SW-48 | 0.0 |
| Ovarian ca. OVCAR-4 | 0.0 | Colon Pool | 0.4 |
| Ovarian ca. OVCAR-5 | 0.9 | Small Intestine Pool | 0.6 |

TABLE EC-continued

General_screening_panel_v1.4

| Tissue Name | Rel. Exp. (%) Ag4235, Run 221994384 | Tissue Name | Rel. Exp. (%) Ag4235, Run 221994384 |
|---|---|---|---|
| Ovarian ca. IGROV-1 | 3.4 | Stomach Pool | 0.3 |
| Ovarian ca. OVCAR-8 | 5.1 | Bone Marrow Pool | 0.0 |
| Ovary | 0.2 | Fetal Heart | 0.0 |
| Breast ca. MCF-7 | 0.0 | Heart Pool | 0.3 |
| Breast ca. MDA-MB-231 | 6.1 | Lymph Node Pool | 0.6 |
| Breast ca. BT 549 | 0.0 | Fetal Skeletal Muscle | 0.2 |
| Breast ca. T47D | 1.7 | Skeletal Muscle Pool | 0.4 |
| Breast ca. MDA-N | 0.0 | Spleen Pool | 2.7 |
| Breast Pool | 0.2 | Thymus Pool | 0.7 |
| Trachea | 1.1 | CNS cancer (glio/astro) U87-MG | 6.4 |
| Lung | 0.2 | CNS cancer (glio/astro) U-118-MG | 2.1 |
| Fetal Lung | 0.6 | CNS cancer (neuro; met) SK-N-AS | 0.2 |
| Lung ca. NCI-N417 | 1.3 | CNS cancer (astro) SF-539 | 2.4 |
| Lung ca. LX-1 | 0.0 | CNS cancer (astro) SNB-75 | 2.9 |
| Lung ca. NCI-H146 | 0.4 | CNS cancer (glio) SNB-19 | 4.1 |
| Lung ca. SHP-77 | 2.7 | CNS cancer (glio) SF-295 | 14.2 |
| Lung ca. A549 | 1.4 | Brain (Amygdala) Pool | 55.5 |
| Lung ca. NCI-H526 | 3.2 | Brain (cerebellum) | 10.6 |
| Lung ca. NCI-H23 | 3.3 | Brain (fetal) | 21.2 |
| Lung ca. NCI-H460 | 17.4 | Brain (Hippocampus) Pool | 20.7 |
| Lung ca. HOP-62 | 5.1 | Cerebral Cortex Pool | 14.4 |
| Lung ca. NCI-H522 | 3.2 | Brain (Substantia nigra) Pool | 47.0 |
| Liver | 0.0 | Brain (Thalamus) Pool | 36.1 |
| Fetal Liver | 0.0 | Brain (whole) | 18.9 |
| Liver ca. HepG2 | 0.0 | Spinal Cord Pool | 18.8 |
| Kidney Pool | 0.2 | Adrenal Gland | 0.8 |
| Fetal Kidney | 0.5 | Pituitary gland Pool | 0.0 |
| Renal ca. 786-0 | 2.0 | Salivary Gland | 0.2 |
| Renal ca. A498 | 0.4 | Thyroid (female) | 0.0 |
| Renal ca. ACHN | 0.3 | Pancreatic ca. CAPAN2 | 0.0 |
| Renal ca. UO-31 | 0.0 | Pancreas Pool | 0.5 |

TABLE ED

Panel 4.1D

| Tissue Name | Rel. Exp. (%) Ag4235, Run 175226633 | Tissue Name | Rel. Exp. (%) Ag4235, Run 175226633 |
|---|---|---|---|
| Secondary Th1 act | 3.0 | HUVEC IL-1beta | 0.0 |
| Secondary Th2 act | 9.9 | HUVEC IFN gamma | 0.0 |
| Secondary Tr1 act | 3.8 | HUVEC TNF alpha + IFN gamma | 0.0 |
| SecondaryTh1 rest | 16.0 | HUVEC TNF alpha + IL4 | 0.0 |
| Secondary Th2 rest | 21.3 | HUVEC IL-11 | 0.0 |
| Secondary Tr1 rest | 18.2 | Lung Microvascular EC none | 0.0 |
| Primary Th1 act | 0.0 | Lung Microvascular EC TNF alpha + IL-1beta | 0.0 |
| Primary Th2 act | 5.4 | Microvascular Dermal EC none | 0.0 |
| Primary Tr1 act | 0.0 | Microvasular Dermal EC TNF alpha + IL-1beta | 6.0 |
| Primary Th1 rest | 1.9 | Bronchial epithelium TNF alpha + IL1beta | 0.0 |
| Primary Th2 rest | 1.6 | Small airway epithelium none | 2.9 |
| Primary Tr1 rest | 5.5 | Small airway epithelium TNF alpha + IL-1beta | 0.0 |
| CD45RA CD4 lymphocyte act | 1.2 | Coronery artery SMC rest | 0.0 |

TABLE ED-continued

Panel 4.1D

| Tissue Name | Rel. Exp. (%) Ag4235, Run 175226633 | Tissue Name | Rel. Exp. (%) Ag4235, Run 175226633 |
|---|---|---|---|
| CD45RO CD4 lymphocyte act | 0.0 | Coronery artery SMC TNF alpha + IL-1beta | 2.1 |
| CD8 lymphocyte act | 5.8 | Astrocytes rest | 5.5 |
| Secondary CD8 lymphocyte rest | 3.0 | Astrocytes TNF alpha + IL-1beta | 13.6 |
| Secondary CD8 lymphocyte act | 26.2 | KU-812 (Basophil) rest | 0.0 |
| CD4 lymphocyte none | 3.8 | KU-812 (Basophil) PMA/ionomycin | 0.0 |
| 2ry Th1/Th2/Tr1_anti-CD95 CH11 | 24.1 | CCD1106 (Keratinocytes) none | 0.0 |
| LAK cells rest | 0.0 | CCD1106 (Keratinocytes) TNF alpha + IL-1beta | 1.3 |
| LAK cells IL-2 | 19.8 | Liver cirrhosis | 0.0 |
| LAK cells IL-2 + IL-12 | 0.0 | NCI-H292 none | 1.2 |
| LAK cells IL-2 + IFN gamma | 10.2 | NCI-H292 IL-4 | 0.0 |
| LAK cells IL-2 + IL-18 | 1.5 | NCI-H292 IL-9 | 0.8 |
| LAK cells PMA/ionomycin | 1.3 | NCI-H292 IL-13 | 0.0 |
| NK Cells IL-2 rest | 13.3 | NCI-H292 IFN gamma | 0.0 |
| Two Way MLR 3 day | 3.5 | HPAEC none | 0.0 |
| Two Way MLR 5 day | 2.0 | HPAEC TNF alpha + IL-1beta | 0.0 |
| Two Way MLR 7 day | 3.3 | Lung fibroblast none | 1.9 |
| PBMC rest | 18.8 | Lung fibroblast TNF alpha + IL-1beta | 17.7 |
| PBMC PWM | 4.9 | Lung fibroblast IL-4 | 3.3 |
| PBMC PHA-L | 1.4 | Lung fibroblast IL-9 | 3.9 |
| Ramos (B cell) none | 0.0 | Lung fibroblast IL-13 | 4.8 |
| Ramos (B cell) ionomycin | 0.0 | Lung fibroblast IFN gamma | 2.6 |
| B lymphocytes PWM | 0.0 | Dermal fibroblast CCD1070 rest | 1.3 |
| B lymphocytes CD40L and IL-4 | 1.9 | Dermal fibroblast CCD1070 TNF alpha | 2.7 |
| EOL-1 dbcAMP | 15.4 | Dermal fibroblast CCD1070 IL-1beta | 0.0 |
| EOL-1 dbcAMP PMA/ionomycin | 18.8 | Dermal fibroblast IFN gamma | 0.5 |
| Dendritic cells none | 0.0 | Dermal fibroblast IL-4 | 3.8 |
| Dendritic cells LPS | 0.0 | Dermal fibroblast rest | 0.0 |
| Dendritic cells anti-CD40 | 0.0 | Neutrophils TNFa + LPS | 28.9 |
| Monocytes rest | 12.9 | Neutrophils rest | 56.3 |
| Monocytes LPS | 0.0 | Colon | 5.4 |
| Macropages rest | 5.1 | Lung | 10.9 |
| Macrophages LPS | 1.6 | Thymus | 27.0 |
| HUVEC none | 0.0 | Kidney | 100.0 |
| HUVEC starved | 0.0 | | |

TABLE EE

Panel CNS_1

| Tissue Name | Rel. Exp. (%) Ag4235, Run 181012601 | Tissue Name | Rel. Exp. (%) Ag4235, Run 181012601 |
|---|---|---|---|
| BA4 Control | 7.1 | BA17 PSP | 10.3 |
| BA4 Control2 | 17.3 | BA17 PSP2 | 3.6 |
| BA4 Alzheimer's2 | 7.0 | Sub Nigra Control | 11.7 |
| BA4 Parkinson's | 16.3 | Sub Nigra Control2 | 7.5 |
| BA4 Parkinson's2 | 64.2 | Sub Nigra Alzheimer's2 | 4.3 |
| BA4 Huntington's | 13.2 | Sub Nigra Parkinson's2 | 22.7 |
| BA4 Huntington's2 | 8.2 | Sub Nigra Huntington's | 43.5 |

TABLE EE-continued

Panel CNS_1

| Tissue Name | Rel. Exp. (%) Ag4235, Run 181012601 | Tissue Name | Rel. Exp. (%) Ag4235, Run 181012601 |
|---|---|---|---|
| BA4 PSP | 7.1 | SubNigra Huntington's2 | 6.5 |
| BA4 PSP2 | 9.0 | Sub Nigra PSP2 | 5.6 |
| BA4 Depression | 100.0 | Sub Nigra Depression | 2.7 |
| BA4 Depression2 | 5.8 | Sub Nigra Depression2 | 0.8 |
| BA7 Control | 12.2 | Glob Palladus Control | 7.6 |
| BA7 Control2 | 22.8 | Glob Palladus Control2 | 6.9 |
| BA7 Alzheimer's2 | 3.5 | Glob Palladus Alzheimer's | 4.5 |
| BA7 Parkinson's | 17.7 | Glob Palladus Alzheimer's2 | 7.8 |
| BA7 Parkinson's2 | 27.7 | Glob Palladus Parkinson's | 54.0 |
| BA7 Huntington's | 21.6 | Glob Palladus Parkinson's2 | 5.5 |
| BA7 Huntington's2 | 22.2 | Glob Palladus PSP | 5.4 |
| BA7 PSP | 9.2 | Glob Palladus PSP2 | 3.4 |
| BA7 PSP2 | 6.7 | Glob Palladus Depression | 0.5 |
| BA7 Depression | 5.2 | Temp Pole Control | 8.5 |
| BA9 Control | 7.6 | Temp Pole Control2 | 27.0 |
| BA9 Control2 | 29.1 | Temp Pole Alzheimer's | 4.6 |
| BA9 Alzheimer's | 9.4 | Temp Pole Alzheimer's2 | 5.6 |
| BA9 Alzheimer's2 | 4.5 | Temp Pole Parkinson's | 15.4 |
| BA9 Parkinson's | 21.5 | Temp Pole Parkinson's2 | 24.0 |
| BA9 Parkinson's2 | 17.1 | Temp Pole Huntington's | 21.5 |
| BA9 Huntington's | 14.1 | Temp Pole PSP | 4.0 |
| BA9 Huntington's2 | 15.9 | Temp Pole PSP2 | 3.9 |
| BA9 PSP | 7.3 | Temp Pole Depression2 | 13.8 |
| BA9 PSP2 | 2.2 | Cing Gyr Control | 15.6 |
| BA9 Depression | 5.5 | Cing Gyr Control2 | 14.9 |
| BA9 Depression2 | 4.7 | Cing Gyr Alzheimer's | 5.6 |
| BA17 Control | 15.7 | Cing Gyr Alzheimer's2 | 6.6 |
| BA17 Control2 | 18.0 | Cing Gyr Parkinson's | 18.7 |
| BA17 Alzheimer's2 | 5.9 | Cing Gyr Parkinson's2 | 20.9 |
| BA17 Parkinson's | 25.9 | Cing Gyr Huntington's | 30.4 |
| BA17 Parkinson's2 | 24.0 | Cing Gyr Huntington's2 | 8.0 |
| BA17 Huntington's | 17.4 | Cing Gyr PSP | 6.3 |
| BA17 Huntington's2 | 14.6 | Cing Gyr PSP2 | 0.4 |
| BA17 Depression | 8.9 | Cing Gyr Depression | 5.8 |
| BA17 Depression2 | 15.8 | Cing Gyr Depression2 | 10.1 |

TABLE EF general oncology screening panel_v_2.4

| Tissue Name | Rel. Exp. (%) Ag4235, Run 268624980 | Tissue Name | Rel. Exp. (%) Ag4235, Run 268624980 |
|---|---|---|---|
| Colon cancer 1 | 13.6 | Bladder cancer NAT 2 | 0.0 |
| Colon NAT 1 | 4.0 | Bladder cancer NAT 3 | 0.0 |
| Colon cancer 2 | 5.7 | Bladder cancer NAT 4 | 12.1 |
| Colon cancer NAT 2 | 0.0 | Adenocarcinoma of the prostate 1 | 13.4 |
| Colon cancer 3 | 4.1 | Adenocarcinoma of the prostate 2 | 29.7 |
| Colon cancer NAT 3 | 4.5 | Adenocarcinoma of the prostate 3 | 96.6 |
| Colon malignant cancer 4 | 9.0 | Adenocarcinoma of the prostate 4 | 5.8 |
| Colon normal adjacent tissue 4 | 0.0 | Prostate cancer NAT 5 | 5.2 |
| Lung cancer 1 | 12.4 | Adenocarcinoma of the prostate 6 | 13.2 |
| Lung NAT 1 | 7.5 | Adenocarcinoma of the prostate 7 | 41.8 |
| Lung cancer 2 | 3.3 | Adenocarcinoma of the prostate 8 | 12.2 |
| Lung NAT 2 | 18.6 | Adenocarcinoma of the prostate 9 | 27.9 |
| Squamous cell carcinoma 3 | 9.1 | Prostate cancer NAT 10 | 5.6 |
| Lung NAT 3 | 0.0 | Kidney cancer 1 | 13.8 |
| metastatic melanoma 1 | 2.3 | KidneyNAT 1 | 7.3 |
| Melanoma 2 | 0.0 | Kidney cancer 2 | 100.0 |
| Melanoma 3 | 0.0 | Kidney NAT 2 | 9.0 |
| metastatic melanoma 4 | 10.7 | Kidney cancer 3 | 18.6 |
| metastatic melanoma 5 | 8.1 | Kidney NAT 3 | 0.0 |
| Bladder cancer 1 | 0.0 | Kidney cancer 4 | 52.9 |
| Bladder cancer NAT 1 | 0.0 | Kidney NAT 4 | 0.0 |
| Bladder cancer 2 | 9.5 | | |

CNS_neurodegeneration_v1.0 Summary: Ag4235 Two experiments with same probe and primer sets are in excellent agreements. These results confirm the expression of the NOV7A gene at moderate to low levels in the brain in an independent group of individuals. This gene is downregulated in the temporal cortex of Alzheimer's disease patients when compared with non-demented controls (p=0.0024; p=0.01 when analyzed by Ancova, estimate of total cDNA loaded per well used as a covariate). Thus, therapeutic modulation of this gene or its protein product, may be of use in reversing the dementia, memory loss, and neuronal death associated with this disease.

General_screening_panel_v1.4 Summary: Ag4235 Highest expression of the NOV7A gene is seen in a colon cancer cell line (CT=28.6). Moderate levels of expression are also seen in cell lines derived from brain cancer, lung cancer, ovarian cancer, breast cancer, and melanoma. Thus, expression of this gene could be used to differentiate between this sample and other samples on this panel and as a marker to detect the presence of colon cancer. Furthermore, therapeutic modulation of the expression or function of this gene may be effective in the treatment of colon, brain, lung, ovarian, breast and melanoma cancers.

This gene is prominently expressed at high to moderate levels in all regions of the CNS examined, including the hippocampus, thalamus, substantia nigra, amygdala, cerebellum and cerebral cortex. This gene encodes a protein with homology to netrins, a family of soluble chemotropic factors that have been implicated in axon guidance and neuron survival during development. (Llambi F. EMBO J. 20(11):2715–22; Braisted J E, J Neurosci. 20:5792–801) Netrin may be involved in the regenerative capacity of adult retinal ganglion cells (Ellezam B. Exp Neurol 168(1): 105–15) Therefore, therapeutic modulation of the expression or function of this gene product may be of use in enhancing or directing compensatory synatogenesis and axon/dendritic outgrowth in response to neuronal death (stroke, head trauma) neurodegeneration (Alzheiemr's, Parkinson's, Huntington's, spinocerebellar ataxia, progressive supranuclear palsy) or spinal cord injury.

Among tissues with metabolic function, this gene is expressed at low but significant levels in adipose, adrenal gland, pancreas, and skeletal muscle. This expression suggests that this gene product may play a role in normal neuroendocrine and metabolic function and that disregulated expression of this gene may contribute to neuroendocrine disorders or metabolic diseases, such as obesity and diabetes.

Panel 4.1D Summary: Ag4235 Highest expression of the NOV7A gene is seen in the kidney (CT=31.3). Low but significant levels of expression of this gene are also seen in other samples, including resting and activated neutrophils and eosinophils, TNF-alpha and IL-1 beta activated lung fibroblasts and astrocytes, resting PBMCs, monocytes, and chronically stimulated T cells, and normal thymus and lung. This expression profile suggests that this gene product may be involved in kidney function and in the treatment of inflammatory or autoimmune diseases that affect the kidney, including lupus and glomerulonephritis.

Panel CNS_1 Summary: Ag4235 This panel confirms the presence of the CG102221-021 gene in the brain, with highest expression in Brodman Area 4 of a patient with depression (CT=30.4). Please see Panel 1.4 for discussion of utility of this gene in the central nervous system.

general oncology screening panel_v_2.4 Summary: Ag4235 Highest expression of the NOV7A gene is seen in kidney cancer (CT=33.8). Thus, expression of this gene could be used to differentiate between this sample and other samples on this panel and as a marker to detect the presence of kidney cancer. This gene is also expressed at a low level in prostate cancer compared to normal prostate.

It may be used as a diagnostic marker of kidney and prostate cancer and therapeutic modulation of the activity of the protein may be useful in the treatment of these cancers.

F. NOV8A: Secreted Reprolysin

Expression of gene NOV8A was assessed using the primer-probe set Ag4236, described in Table FA. Results of the RTQ-PCR runs are shown in Tables FB, FC, FD and FE.

TABLE FA

Probe Name Ag4236

| Primers | Sequences | Length | Start Position | SEQ ID No |
|---|---|---|---|---|
| Forward | 5'-ggcagggatgaaactgtca-3' | 19 | 775 | 142 |
| Probe | TET-5'-ccttggcccaatgtagagaacactg-3'-TAMRA | 26 | 812 | 143 |
| Reverse | 5'-ctcccgtgacatacactttgac-3' | 22 | 853 | 144 |

TABLE FB

General_screening_panel_v1.4

| Tissue Name | Rel. Exp. (%) Ag4236, Run 222100995 | Tissue Name | Rel. Exp. (%) Ag4236, Run 222100995 |
|---|---|---|---|
| Adipose | 13.7 | Renal ca. TK-10 | 0.0 |
| Melanoma* Hs688(A).T | 0.0 | Bladder | 21.2 |
| Melanoma* Hs688(B).T | 0.0 | Gastric ca. (liver met.) NCI-N87 | 0.0 |
| Melanoma* M14 | 43.8 | Gastric ca. KATO III | 44.1 |
| Melanoma* LOXIMVI | 0.0 | Colon ca. SW-948 | 12.8 |
| Melanoma* SK-MEL-5 | 0.0 | Colon ca. SW480 | 100.0 |
| Squamous cell carcinoma SCC-4 | 0.0 | Colon ca.* (SW480 met) SW620 | 11.9 |
| Testis Pool | 0.0 | Colon ca. HT29 | 0.0 |
| Prostate ca.* (bone met) PC-3 | 19.2 | Colon ca. HCT-116 | 18.2 |
| Prostate Pool | 0.0 | Colon ca. CaCo-2 | 0.0 |
| Placenta | 0.0 | Colon cancer tissue | 0.0 |
| Uterus Pool | 0.0 | Colon ca. SW1116 | 0.0 |
| Ovarian ca. OVCAR-3 | 0.0 | Colon ca. Colo-205 | 37.4 |
| Ovarian ca. SK-OV-3 | 40.3 | Colon ca. SW-48 | 3.3 |
| Ovarian ca. OVCAR-4 | 4.3 | Colon Pool | 0.0 |
| Ovarian ca. OVCAR-5 | 12.2 | Small Intestine Pool | 11.6 |
| Ovarian ca. IGROV-1 | 0.0 | Stomach Pool | 0.0 |
| Ovarian ca. OVCAR-8 | 0.0 | Bone Marrow Pool | 7.8 |
| Ovary | 5.6 | Fetal Heart | 0.0 |
| Breast ca. MCF-7 | 12.7 | Heart Pool | 0.0 |
| Breast ca. MDA-MB-231 | 0.0 | Lymph Node Pool | 11.3 |
| Breast ca. BT 549 | 3.8 | Fetal Skeletal Muscle | 5.1 |
| Breast ca. T47D | 12.9 | Skeletal Muscle Pool | 29.3 |
| Breast ca. MDA-N | 0.0 | Spleen Pool | 0.0 |
| Breast Pool | 9.2 | Thymus Pool | 20.6 |
| Trachea | 11.3 | CNS cancer (glio/astro) U87-MG | 0.0 |
| Lung | 0.0 | CNS cancer (glio/astro) U-118-MG | 0.0 |
| Fetal Lung | 15.3 | CNS cancer (neuro; met) SK-N-AS | 7.9 |
| Lung ca. NCI-N417 | 0.0 | CNS cancer (astro) SF-539 | 0.0 |
| Lung ca. LX-1 | 13.3 | CNS cancer (astro) SNB-75 | 0.0 |
| Lung ca. NCI-H146 | 42.6 | CNS cancer (glio) SNB-19 | 0.0 |
| Lung ca. SHP-77 | 0.0 | CNS cancer (glio) SF-295 | 0.0 |
| Lung ca. A549 | 0.0 | Brain (Amygdala) Pool | 0.0 |
| Lung ca. NCI-H526 | 0.0 | Brain (cerebellum) | 0.0 |
| Lung ca. NCI-H23 | 0.0 | Brain (fetal) | 7.3 |
| Lung ca. NCI-H460 | 0.0 | Brain (Hippocampus) Pool | 0.0 |
| Lung ca. HOP-62 | 0.0 | Cerebral Cortex Pool | 0.0 |
| Lung ca. NCI-H522 | 0.0 | Brain (Substantia nigra) Pool | 5.4 |
| Liver | 0.0 | Brain (Thalamus) Pool | 9.5 |
| Fetal Liver | 0.0 | Brain (whole) | 0.0 |
| Liver ca. HepG2 | 0.0 | Spinal Cord Pool | 11.1 |
| Kidney Pool | 22.2 | Adrenal Gland | 5.8 |
| Fetal Kidney | 0.0 | Pituitary gland Pool | 0.0 |
| Renal ca. 786-0 | 0.0 | Salivary Gland | 12.2 |
| Renal ca. A498 | 0.0 | Thyroid (female) | 0.0 |
| Renal ca. ACHN | 2.1 | Pancreatic ca. CAPAN2 | 0.0 |
| Renal ca. UO-31 | 0.0 | Pancreas Pool | 12.3 |

TABLE FC

General_screening_panel_v1.6

| Tissue Name | Rel. Exp. (%) Ag4236, Run 277231326 | Tissue Name | Rel. Exp. (%) Ag4236, Run 277231326 |
|---|---|---|---|
| Adipose | 11.5 | Renal ca. TK-10 | 0.0 |
| Melanoma* Hs688(A).T | 0.0 | Bladder | 10.1 |
| Melanoma* Hs688(B).T | 0.0 | Gastric ca. (liver met.) NCI-N87 | 0.0 |
| Melanoma* M14 | 30.8 | Gastric ca. KATO III | 50.0 |
| Melanoma* LOXIMVI | 0.0 | Colon ca. SW-948 | 0.0 |
| Melanoma* SK-MEL-5 | 39.0 | Colon ca. SW480 | 100.0 |
| Squamous cell carcinoma SCC-4 | 0.0 | Colon ca.* (SW480 met) SW620 | 18.6 |
| Testis Pool | 0.0 | Colon ca. HT29 | 10.3 |
| Prostate ca.* (bone met) PC-3 | 45.4 | Colon ca. HCT-116 | 27.0 |
| Prostate Pool | 5.5 | Colon ca. CaCo-2 | 0.0 |
| Placenta | 0.0 | Colon cancer tissue | 3.0 |
| Uterus Pool | 0.0 | Colon ca. SW1116 | 0.0 |
| Ovarian ca. OVCAR-3 | 0.0 | Colon ca. Colo-205 | 20.9 |
| Ovarian ca. SK-OV-3 | 41.8 | Colon ca. SW-48 | 0.0 |
| Ovarian ca. OVCAR-4 | 5.9 | Colon Pool | 6.0 |

TABLE FC-continued

General_screening_panel_v1.6

| Tissue Name | Rel. Exp. (%) Ag4236, Run 277231326 | Tissue Name | Rel. Exp. (%) Ag4236, Run 277231326 |
|---|---|---|---|
| Ovarian ca. OVCAR-5 | 26.8 | Small Intestine Pool | 9.6 |
| Ovarian ca. IGROV-1 | 0.0 | Stomach Pool | 24.7 |
| Ovarian ca. OVCAR-8 | 0.0 | Bone Marrow Pool | 5.5 |
| Ovary | 21.6 | Fetal Heart | 0.0 |
| Breast ca. MCF-7 | 5.8 | Heart Pool | 8.6 |
| Breast ca. MDA-MB-231 | 10.1 | Lymph Node Pool | 7.2 |
| Breast ca. BT 549 | 0.0 | Fetal Skeletal Muscle | 0.0 |
| Breast ca. T47D | 0.0 | Skeletal Muscle Pool | 20.9 |
| Breast ca. MDA-N | 0.0 | Spleen Pool | 12.4 |
| Breast Pool | 9.0 | Thymus Pool | 21.0 |
| Trachea | 2.9 | CNS cancer (glio/astro) U87-MG | 0.0 |
| Lung | 0.0 | CNS cancer (glio/astro) U-118-MG | 0.0 |
| Fetal Lung | 17.2 | CNS cancer (neuro; met) SK-N-AS | 5.9 |
| Lung ca. NCI-N417 | 0.0 | CNS cancer (astro) SF-539 | 0.0 |
| Lung ca. LX-1 | 17.3 | CNS cancer (astro) SNB-75 | 0.0 |
| Lung ca. NCI-H146 | 14.7 | CNS cancer (glio) SNB-19 | 3.9 |
| Lung ca. SHP-77 | 0.0 | CNS cancer (glio) SF-295 | 0.0 |
| Lung ca. A549 | 10.7 | Brain (Amygdala) Pool | 0.0 |
| Lung ca. NCI-H526 | 4.4 | Brain (cerebellum) | 9.9 |
| Lung ca. NCI-H23 | 0.0 | Brain (fetal) | 7.0 |
| Lung ca. NCI-H460 | 7.2 | Brain (Hippocampus) Pool | 0.0 |
| Lung ca. HOP-62 | 0.0 | Cerebral Cortex Pool | 0.0 |
| Lung ca. NCI-H522 | 0.0 | Brain (Substantia nigra) Pool | 6.2 |
| Liver | 0.0 | Brain (Thalamus) Pool | 4.6 |
| Fetal Liver | 0.0 | Brain (whole) | 9.7 |
| Liver ca. HepG2 | 0.0 | Spinal Cord Pool | 3.9 |
| Kidney Pool | 6.2 | Adrenal Gland | 5.4 |
| Fetal Kidney | 5.6 | Pituitary gland Pool | 0.0 |
| Renal ca. 786-0 | 0.0 | Salivary Gland | 5.3 |
| Renal ca. A498 | 0.0 | Thyroid (female) | 0.0 |
| Renal ca. ACHN | 0.0 | Pancreatic ca. CAPAN2 | 0.0 |
| Renal ca. UO-31 | 0.0 | Pancreas Pool | 18.6 |

TABLE FD

Panel 4.1D

| Tissue Name | Rel. Exp. (%) Ag4236, Run 175226753 | Tissue Name | Rel. Exp. (%) Ag4236, Run 175226753 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 5.3 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 1.0 | Lung Microvascular EC TNF alpha + IL-1beta | 0.0 |
| Primary Th2 act | 2.8 | Microvascular Dermal EC none | 0.0 |
| Primary Tr1 act | 1.2 | Microsvascular Dermal EC TNF alpha + IL-1beta | 0.9 |
| Primary Th1 rest | 1.4 | Bronchial epithelium TNF alpha + IL1beta | 0.0 |
| Primary Th2 rest | 4.0 | Small airway epithelium none | 0.0 |
| Primary Tr1 rest | 12.5 | Small airway epithelium TNF alpha + IL-1beta | 0.0 |

TABLE FD-continued

Panel 4.1D

| Tissue Name | Rel. Exp. (%) Ag4236, Run 175226753 | Tissue Name | Rel. Exp. (%) Ag4236, Run 175226753 |
|---|---|---|---|
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 0.0 |
| Secondary CD8 lymphocyte rest | 1.9 | Astrocytes TNF alpha + IL-1beta | 0.0 |
| Secondary CD8 lymphocyte act | 0.0 | KU-812 (Basophil) rest | 0.0 |
| CD4 lymphocyte none | 5.1 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 1.5 |
| LAK cells IL-2 + IL-12 | 0.0 | NCI-H292 none | 0.0 |
| LAK cells IL-2 + IFN gamma | 1.8 | NCI-H292 IL-4 | 0.0 |
| LAK cells IL-2 + IL-18 | 9.2 | NCI-H292 IL-9 | 0.0 |
| LAK cells PMA/ionomycin | 0.0 | NCI-H292 IL-13 | 0.0 |
| NK Cells IL-2 rest | 2.5 | NCI-H292 IFN gamma | 3.3 |
| Two Way MLR 3 day | 1.9 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 0.0 |
| PBMC rest | 4.3 | Lung fibroblast TNF alpha + IL-1beta | 0.0 |
| PBMC PWM | 2.3 | Lung fibroblast IL-4 | 0.0 |
| PBMC PHA-L | 0.0 | Lung fibroblast IL-9 | 0.0 |
| Ramos (B cell) none | 0.0 | Lung fibroblast IL-13 | 3.4 |
| Ramos (B cell) ionomycin | 0.0 | Lung fibroblast IFN gamma | 2.1 |
| B lymphocytes PWM | 0.0 | Dermal fibroblast CCD1070 rest | 0.0 |
| B lymphocytes CD40L and IL-4 | 0.0 | Dermal fibroblast CCD1070 TNF alpha | 0.0 |
| EOL-1 dbcAMP | 0.0 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 0.0 | Dermal Fibroblasts rest | 0.0 |
| Dendritic cells anti-CD40 | 0.0 | Neutrophils TNFa + LPS | 0.0 |
| Monocytes rest | 0.0 | Neutrophils rest | 3.0 |
| Monocytes LPS | 0.0 | Colon | 0.8 |
| Macrophages rest | 0.0 | Lung | 1.1 |
| Macrophages LPS | 0.0 | Thymus | 20.9 |
| HUVEC none | 0.0 | Kidney | 100.0 |
| HUVEC starved | 0.0 | | |

TABLE FE general oncology screening panel_v_2.4

| Tissue Name | Rel. Exp. (%) Ag4236, Run 268664312 | Tissue Name | Rel. Exp. (%) Ag4236, Run 268664312 | Tissue Name | Rel. Exp. (%) Ag4236, Run 268664312 | Tissue Name | Rel. Exp. (%) Ag4236, Run 268664312 |
|---|---|---|---|---|---|---|---|
| Colon cancer 1 | 44.4 | Bladder cancer NAT 2 | 0.0 | NAT 2 | | prostate 1 | |
| Colon cancer NAT 1 | 0.0 | Bladder cancer NAT 3 | 0.0 | Colon cancer 3 | 0.0 | Adenocarcinoma of the prostate 2 | 0.0 |
| Colon cancer 2 | 0.0 | Bladder cancer NAT 4 | 0.0 | Colon cancer NAT 3 | 0.0 | Adenocarcinoma of the prostate 3 | 0.0 |
| Colon cancer | 0.0 | Adenocarcinoma of the | 34.6 | | | | |

TABLE FE-continued general oncology screening panel_v_2.4

| Tissue Name | Rel. Exp. (%) Ag4236, Run 268664312 | Tissue Name | Rel. Exp. (%) Ag4236, Run 268664312 |
|---|---|---|---|
| Colon malignant cancer 4 | 0.0 | Adenocarcinoma of the prostate 4 | 0.0 |
| Colon normal adjacent tissue 4 | 0.0 | Prostate cancer NAT 5 | 20.6 |
| Lung cancer 1 | 9.0 | Adenocarcinoma of the prostate 6 | 0.0 |
| Lung NAT 1 | 0.0 | Adenocarcinoma of the prostate 7 | 0.0 |
| Lung cancer 2 | 39.0 | Adenocarcinoma of the prostate 8 | 0.0 |
| Lung NAT 2 | 19.2 | Adenocarcinoma of the prostate 9 | 0.0 |
| Squamous cell carcinoma 3 | 0.0 | Prostate cancer NAT 10 | 0.0 |
| Lung NAT 3 | 17.2 | Kidney cancer 1 | 0.0 |
| metastatic melanoma 1 | 0.0 | KidneyNAT 1 | 0.0 |
| Melanoma 2 | 30.8 | Kidney cancer 2 | 100.0 |
| Melanoma 3 | 24.5 | Kidney NAT 2 | 61.1 |
| metastatic melanoma 4 | 17.3 | Kidney cancer 3 | 0.0 |
| metastatic melanoma 5 | 48.0 | Kidney NAT 3 | 0.0 |
| Bladder cancer 1 | 0.0 | Kidney cancer 4 | 0.0 |
| Bladder cancer NAT 1 | 0.0 | Kidney NAT 4 | 9.9 |
| Bladder cancer 2 | 0.0 | | |

CNS_neurodegeneration_v1.0 Summary: Ag4236 Expression of the NOV8A gene is low/undetectable (CTs>35) across all of the samples on this panel (data not shown).

General_screening_panel_v1.4 Summary: Ag4236 Highest expression of the NOV8A gene is detected in a colon cancer SW480 cell line (CT=33). In addition, low expression of this gene is also seen in a number of cancer cell lines including colon, gastric, lung, ovarian and melanoma cancer cell lines. Therefore, expression of this gene can be used as diagnostic markers for these cancers and also, therapeutic modulation of this gene product may be beneficial in the treatment of these cancers.

Low expression of this gene is also seen in skeletal muscle. Therefore, therapeutic modulation of this gene may be useful in the treatment of muscle related diseases.

General_screening_panel_v1.6 Summary: Ag4236 Highest expression of the NOV8A gene is detected in a colon cancer cell line (CT=33), in agreement with results in Panel 1.4. In addition, low but significant levels of expression are seen in melanoma, prostate, ovarian and gastric cancer cell lines. Therefore, expression of this gene may be useful as diagnostic marker for colon cancer and therapeutic modulation of this gene product may be beneficial in the treatment of these cancers.

Panel 4.1D Summary: Ag4236 Highest expression of the NOV8A gene is detected in kidney. Therefore, expression of this gene can be used to distinguish kidney sample from other samples used in this panel. In addition, low expression of this gene is also seen in thymus and resting primary Tr1 cells. Therefore, therapeutic modulation of this gene product may be useful in the treatment of autoimmune and inflammatory diseases that affect kidney including lupus and glomerulonephritis. Expression of this gene in a second experiment (run 268719696)is low/undetectable (CTs>35) across all of the samples on this panel (data not shown).

General oncology screening panel_v_2.4 Summary: Ag4236 Highest expression of the NOV8A gene is detected in kidney cancer sample (CT=34.7). Therefore, expression of this gene may be useful as diagnostic marker and therapeutic modulation of this gene product may be beneficial in the treatment of kidney cancer.

G. NOV9A and NOV9B: Ig-domain Containing Transmembrane Protein

Expression of gene NOV9A and variant NOV9B was assessed using the primer-probe sets Ag4244 and Ag4324, described in Tables GA and GB. Please note that NOV9A is recognized by primer-probe set Ag4244 only. Results of the RTQ-PCR runs are shown in Tables GC and GD.

TABLE GA

Probe Name Ag4244

| Primers | Sequences | Length | Start Position | SEQ ID No |
|---|---|---|---|---|
| Forward | 5'-catggagactcccctttgac-3' | 20 | 998 | 145 |
| Probe | TET-5'-cctgaaggaggtcaccatctcattga-3'-TAMRA | 26 | 1023 | 146 |
| Reverse | 5'-cggatcttggacttcaatctc-3' | 21 | 1063 | 147 |

TABLE GB

Probe Name Ag4324

| Primers | Sequences | Length | Start Position | SEQ ID No |
|---|---|---|---|---|
| Forward | 5'-tgggacaaagaaagagaccaa-3' | 21 | 1149 | 148 |
| Probe | TET-5'-ttgctgacgcctgtgatcctcact-3'-TAMRA | 24 | 1302 | 149 |
| Reverse | 5'-caagggctgagtggagaag-3' | 19 | 1344 | 150 |

TABLE GC

General screening panel v1.4

| Tissue Name | Rel. Exp. (%) Ag4244, Run 222018688 | Tissue Name | Rel. Exp. (%) Ag4244, Run 222018688 |
|---|---|---|---|
| Adipose | 3.2 | Renal ca. TK-10 | 0.2 |
| Melanoma* Hs688(A).T | 0.0 | Bladder | 3.2 |
| Melanoma* Hs688(B).T | 0.0 | Gastric ca. (liver met.) NCI-N87 | 0.0 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 10.2 | Colon ca. HT29 | 0.0 |
| Prostate ca.* (bone met) PC-3 | 0.0 | Colon ca. HCT-116 | 0.0 |
| Prostate Pool | 7.5 | Colon ca. CaCo-2 | 0.0 |
| Placenta | 1.5 | Colon cancer tissue | 3.4 |
| Uterus Pool | 10.8 | Colon ca. SW1116 | 0.0 |
| Ovarian ca. OVCAR-3 | 0.0 | Colon ca. Colo-205 | 0.0 |
| Ovarian ca. SK-OV-3 | 0.1 | Colon ca. SW-48 | 0.0 |
| Ovarian ca. OVCAR-4 | 0.0 | Colon Pool | 39.8 |
| Ovarian ca. OVCAR-5 | 0.0 | Small Intestine Pool | 38.7 |
| Ovarian ca. IGROV-1 | 0.2 | Stomach Pool | 18.2 |
| Ovarian ca. OVCAR-8 | 0.6 | Bone Marrow Pool | 22.8 |
| Ovary | 2.1 | Fetal Heart | 6.9 |
| Breast ca. MCF-7 | 0.1 | Heart Pool | 22.4 |
| Breast ca. MDA-MB-231 | 0.0 | Lymph Node Pool | 55.5 |
| Breast ca. BT 549 | 0.0 | Fetal Skeletal Muscle | 29.1 |
| Breast ca. T47D | 0.0 | Skeletal Muscle Pool | 44.8 |
| Breast ca. MDA-N | 0.0 | Spleen Pool | 0.7 |
| Breast Pool | 29.5 | Thymus Pool | 18.6 |
| Trachea | 7.3 | CNS cancer (glio/astro) U87-MG | 0.0 |
| Lung | 6.5 | CNS cancer (glio/astro) U-118-MG | 0.8 |
| Fetal Lung | 26.2 | CNS cancer (neuro; met) SK-N-AS | 10.7 |
| Lung ca. NCI-N417 | 0.0 | CNS cancer (astro) SF-539 | 0.0 |
| Lung ca. LX-1 | 0.0 | CNS cancer (astro) SNB-75 | 0.7 |
| Lung ca. NCI-H146 | 0.9 | CNS cancer (glio) SNB-19 | 0.0 |
| Lung ca. SHP-77 | 0.6 | CNS cancer (glio) SF-295 | 0.0 |
| Lung ca. A549 | 0.0 | Brain (Amygdala) Pool | 0.2 |
| Lung ca. NCI-H526 | 0.0 | Brain (cerebellum) | 0.4 |
| Lung ca. NCI-H23 | 0.0 | Brain (fetal) | 1.0 |
| Lung ca. NCI-H460 | 0.0 | Brain (Hippocampus) Pool | 0.3 |
| Lung ca. HOP-62 | 0.0 | Cerebral Cortex Pool | 0.1 |
| Lung ca. NCI-H522 | 0.0 | Brain (Substantia nigra) Pool | 0.2 |
| Liver | 0.3 | Brain (Thalamus) Pool | 0.4 |
| Fetal Liver | 2.6 | Brain (whole) | 0.7 |
| Liver ca. HepG2 | 0.0 | Spinal Cord Pool | 0.6 |
| Kidney Pool | 100.0 | Adrenal Gland | 2.3 |
| Fetal Kidney | 2.5 | Pituitary gland Pool | 0.7 |
| Renal ca. 786-0 | 0.1 | Salivary Gland | 0.9 |
| Renal ca. A498 | 0.2 | Thyroid (female) | 3.1 |
| Renal ca. ACHN | 0.2 | Pancreatic ca. CAPAN2 | 0.0 |
| Renal ca. UO-31 | 0.0 | Pancreas Pool | 58.6 |

TABLE GD

General oncology screening panel_v_2.4

| Tissue Name | Rel. Exp. (%) Ag4244, Run 268664319 | Tissue Name | Rel. Exp. (%) Ag4244, Run 268664319 |
|---|---|---|---|
| Colon cancer 1 | 1.0 | Bladder cancer NAT 2 | 0.0 |
| Colon NAT 1 | 3.8 | Bladder cancer NAT 3 | 0.0 |
| Colon cancer 2 | 0.4 | Bladder cancer NAT 4 | 1.0 |
| Colon cancer NAT 2 | 1.5 | Adenocarcinoma of the prostate 1 | 0.1 |
| Colon cancer 3 | 0.6 | Adenocarcinoma of the prostate 2 | 0.2 |
| Colon cancer NAT 3 | 8.0 | Adenocarcinoma of the prostate 3 | 0.5 |
| Colon malignant cancer 4 | 0.2 | Adenocarcinoma of the prostate 4 | 0.3 |
| Colon normal adjacent tissue 4 | 0.5 | Prostate cancer NAT 5 | 1.2 |
| Lung cancer 1 | 0.1 | Adenocarcinoma of the prostate 6 | 0.1 |
| Lung NAT 1 | 0.1 | Adenocarcinoma of the prostate 7 | 0.0 |
| Lung cancer 2 | 1.8 | Adenocarcinoma of the prostate 8 | 0.1 |
| Lung NAT 2 | 1.1 | Adenocarcinoma of the prostate 9 | 2.8 |
| Squamous cell carcinoma 3 | 0.9 | Prostate cancer NAT 10 | 0.1 |
| Lung NAT 3 | 0.0 | Kidney cancer 1 | 1.4 |
| metastatic melanoma 1 | 0.8 | KidneyNAT 1 | 0.5 |
| Melanoma 2 | 0.4 | Kidney cancer 2 | 2.0 |
| Melanoma 3 | 0.3 | Kidney NAT 2 | 100.0 |
| metastatic melanoma 4 | 2.4 | Kidney cancer 3 | 0.4 |
| metastatic melanoma 5 | 1.1 | Kidney NAT 3 | 0.6 |
| Bladder cancer 1 | 0.1 | Kidney cancer 4 | 0.7 |
| Bladder cancer NAT 1 | 0.0 | Kidney NAT 4 | 0.3 |
| Bladder cancer 2 | 0.1 | | |

CNS_neurodegeneration_v1.0 Summary: Ag4244/Ag4324 Expression of this gene is low/undetectable in all samples on this panel (CTs>35). (Data not shown.)

General_screening_panel_v1.4 Summary: Ag4244 Highest expression of the NOV9A gene is seen in the kidney (CT=28.3). Expression in fetal kidney is significantly lower (CT=33). Thus, expression of this gene could be used to differentiate between fetal and adult kidney. Overall, this gene appears to be expressed in normal tissues and may be involved in the normal function of the kidney.

Among tissues with metabolic function, this gene is expressed at moderate to low levels in adipose, adrenal gland, pancreas, thyroid, fetal liver and adult and fetal skeletal muscle and heart. This expression among these tissues suggests that this gene product may play a role in normal neuroendocrine and metabolic function and that disregulated expression of this gene may contribute to neuroendocrine disorders or metabolic diseases, such as obesity and diabetes.

A second experiment with the probe and primer set Ag4324, which is specific to NOV9B, shows low/undetectable levels of expression (CTs>35). (Data not shown.)

General oncology screening panel_v_2.4 Summary: Ag4244 Highest expression of the NOV9A gene is seen in the kidney (CT=26.7). This expression is consistent with expression seen in the previous panels. Thus, expression of this gene could be used as a marker of kidney tissue.

H. NOV10A and NOV10B: Novel Lipocalin 2

Expression of gene NOV10A and variant NOV10B was assessed using the primer-probe sets Ag4254 and Ag6132, described in Tables HA and HB. Results of the RTQ-PCR runs are shown in Tables HC, HD and HE. Please note that NOV10B represents a full-length physical clone, validating the prediction of the gene sequence.

TABLE HA

Probe Name Ag4254

| Primers | Sequences | Length | Start Position | SEQ ID No |
|---|---|---|---|---|
| Forward | 5'-cttcatccgcttctccaaat-3' | 20 | 516 | 151 |
| Probe | TET-5'-cctgaaaaccacatcgtcttccctgt-3'-TAMRA | 26 | 547 | 152 |
| Reverse | 5'-ctcatccagactggccattac-3' | 21 | 581 | 153 |

TABLE HB

Probe Name Ag6132

| Primers | Sequences | Length | Start Position | SEQ ID No |
|---|---|---|---|---|
| Forward | 5'-ggagaacttcatccgcttct-3' | 20 | 510 | 154 |
| Probe | TET-5'-cctgaaaaccacatcgtcttccctgt-3'-TAMRA | 26 | 547 | 155 |
| Reverse | 5'-ctcatccagactggccattac-3' | 21 | 581 | 156 |

TABLE HC

AI_comprehensive panel_v1.0

| Tissue Name | Rel. Exp. (%) Ag6132, Run 255326117 | Tissue Name | Rel. Exp. (%) Ag6132, Run 255326117 |
|---|---|---|---|
| 110967 COPD-F | 1.0 | 112427 Match Control Psoriasis-F | 0.5 |
| 110980 COPD-F | 0.0 | 112418 Psoriasis-M | 0.0 |
| 110968 COPD-M | 0.0 | 112723 Match Control Psoriasis-M | 0.0 |
| 110977 COPD-M | 1.9 | 112419 Psoriasis-M | 0.4 |
| 110989 Emphysema-F | 0.0 | 112424 Match Control Psoriasis-M | 0.0 |
| 110992 Emphysema-F | 0.9 | 112420 Psoriasis-M | 1.4 |
| 110993 Emphysema-F | 0.0 | 112425 Match Control Psoriasis-M | 0.8 |
| 110994 Emphysema-F | 0.0 | 104689 (MF) OA Bone-Backus | 0.0 |
| 110995 Emphysema-F | 2.8 | 104690 (MF) Adj "Normal" Bone-Backus | 0.0 |
| 110996 Emphysema-F | 0.0 | 104691 (MF) OA Synovium-Backus | 0.0 |
| 110997 Asthma-M | 4.1 | 104692 (BA) OA Cartilage-Backus | 0.0 |
| 111001 Asthma-F | 0.0 | 104694 (BA) OA Bone-Backus | 1.8 |
| 111002 Asthma-F | 0.8 | 104695 (BA) Adj "Normal" Bone-Backus | 0.0 |
| 111003 Atopic Asthma-F | 0.0 | 104696 (BA) OA Synovium-Backus | 0.0 |
| 111004 Atopic Asthma-F | 1.6 | 104700 (SS) OA Bone-Backus | 27.4 |
| 111005 Atopic Asthma-F | 0.0 | 104701 (SS) Adj "Normal" Bone-Backus | 1.2 |
| 111006 Atopic Asthma-F | 0.0 | 104702 (SS) OA Synovium-Backus | 1.0 |
| 111417 Allergy-M | 0.0 | 117093 OA Cartilage Rep7 | 0.9 |

TABLE HC-continued

AI_comprehensive panel_v1.0

| Tissue Name | Rel. Exp. (%) Ag6132, Run 255326117 | Tissue Name | Rel. Exp. (%) Ag6132, Run 255326117 |
|---|---|---|---|
| 112347 Allergy-M | 0.3 | 112672 OA Bone5 | 0.0 |
| 112349 Normal Lung-F | 0.3 | 112673 OA Synovium5 | 0.0 |
| 112357 Normal Lung-F | 0.0 | 112674 OA Synovial Fluid cells5 | 0.0 |
| 112354 Normal Lung-M | 0.0 | 117100 OA Cartilage Rep14 | 0.0 |
| 112374 Crohns-F | 0.0 | 112756 OA Bone9 | 0.0 |
| 112389 Match Control Crohns-F | 100.0 | 112757 OA Synovium9 | 0.0 |
| 112375 Crohns-F | 0.0 | 112758 OA Synovial Fluid Cells9 | 0.0 |
| 112732 Match Control Crohns-F | 28.3 | 117125 RA Cartilage Rep2 | 0.8 |
| 112725 Crohns-M | 0.9 | 113492 Bone2 RA | 9.6 |
| 112387 Match Control Crohns-M | 0.0 | 113493 Synovium2 RA | 1.5 |
| 112378 Crohns-M | 0.4 | 113494 Syn Fluid Cells RA | 2.4 |
| 112390 Match Control Crohns-M | 0.0 | 113499 Cartilage4 RA | 0.0 |
| 112726 Crohns-M | 0.0 | 113500 Bone4 RA | 0.9 |
| 112731 Match Control Crohns-M | 9.0 | 113501 Synovium4 RA | 0.0 |
| 112380 Ulcer Col-F | 0.0 | 113502 Syn Fluid Cells4 RA | 1.0 |
| 112734 Match Control Ulcer Col-F | 98.6 | 113495 Cartilage3 RA | 0.9 |
| 112384 Ulcer Col-F | 0.5 | 113496 Bone3 RA | 1.4 |
| 112737 Match Control Ulcer Col-F | 0.0 | 113497 Synovium3 RA | 2.3 |
| 112386 Ulcer Col-F | 0.0 | 113498 Syn Fluid Cells3 RA | 2.9 |
| 112738 Match Control Ulcer Col-F | 16.3 | 117106 Normal Cartilage Rep20 | 0.0 |
| 112381 Ulcer Col-M | 0.0 | 113663 Bone3 Normal | 1.1 |
| 112735 Match Control Ulcer Col-M | 0.0 | 113664 Synovium3 Normal | 0.0 |
| 112382 Ulcer Col-M | 16.4 | 113665 Syn Fluid Cells3 Normal | 0.0 |
| 112394 Match Control Ulcer Col-M | 0.0 | 117107 Normal Cartilage Rep22 | 0.0 |
| 112383 Ulcer Col-M | 5.1 | 113667 Bone4 Normal | 0.3 |
| 112736 Match Control Ulcer Col-M | 30.4 | 113668 Synovium4 Normal | 1.2 |
| 112423 Psoriasis-F | 0.0 | 113669 Syn Fluid Cells4 Normal | 5.8 |

TABLE HD

General_screening_panel_v1.6

| Tissue Name | Rel. Exp. (%) Ag6132, Run 277231849 | Tissue Name | Rel. Exp. (%) Ag6132, Run 277231849 |
|---|---|---|---|
| Adipose | 0.0 | Renal ca. TK-10 | 3.7 |
| Melanoma* Hs688(A).T | 0.0 | Bladder | 6.1 |
| Melanoma* Hs688(B).T | 0.0 | Gastric ca. (liver met.) NCI-N87 | 100.0 |
| Melanoma* M14 | 0.0 | Gastric ca. KATO III | 4.4 |
| Melanoma* LOXIMVI | 0.0 | Colon ca. SW-948 | 0.2 |
| Melanoma* SK-MEL-5 | 0.0 | Colon ca. SW480 | 1.0 |
| Squamous cell carcinoma SCC-4 | 3.3 | Colon ca.* (SW480 met) SW620 | 0.1 |
| Testis Pool | 0.1 | Colon ca. HT29 | 1.7 |
| Prostate ca.* (bone met) PC-3 | 0.0 | Colon ca. HCT-116 | 0.1 |
| Prostate Pool | 0.1 | Colon ca. CaCo-2 | 0.0 |
| Placenta | 0.0 | Colon cancer tissue | 30.6 |
| Uterus Pool | 0.2 | Colon ca. SW1116 | 0.0 |
| Ovarian ca. OVCAR-3 | 0.2 | Colon ca. Colo-205 | 0.1 |
| Ovarian ca. SK-OV-3 | 0.1 | Colon ca. SW-48 | 0.0 |
| Ovarian ca. OVCAR-4 | 0.0 | Colon Pool | 0.0 |
| Ovarian ca. OVCAR-5 | 21.9 | Small Intestine Pool | 0.2 |
| Ovarian ca. IGROV-1 | 0.6 | Stomach Pool | 3.2 |
| Ovarian ca. OVCAR-8 | 0.3 | Bone Marrow Pool | 0.9 |
| Ovary | 2.4 | Fetal Heart | 0.0 |
| Breast ca. MCF-7 | 0.0 | Heart Pool | 0.1 |
| Breast ca. MDA-MB-231 | 0.0 | Lymph Node Pool | 0.0 |
| Breast ca. BT 549 | 0.0 | Fetal Skeletal Muscle | 0.0 |
| Breast ca. T47D | 0.0 | Skeletal Muscle Pool | 0.0 |
| Breast ca. MDA-N | 0.0 | Spleen Pool | 0.1 |
| Breast Pool | 0.0 | Thymus Pool | 0.0 |
| Trachea | 5.8 | CNS cancer (glio/astro) U87-MG | 0.0 |
| Lung | 0.1 | CNS cancer (glio/astro) U-118-MG | 0.0 |
| Fetal Lung | 1.8 | CNS cancer (neuro; met) SK-N-AS | 0.0 |
| Lung ca. NCI-N417 | 0.0 | CNS cancer (astro) SF-539 | 0.0 |
| Lung ca. LX-1 | 0.2 | CNS cancer (astro) SNB-75 | 0.0 |
| Lung ca. NCI-H146 | 0.0 | CNS cancer (glio) SNB-19 | 0.2 |
| Lung ca. SHP-77 | 0.0 | CNS cancer (glio) SF-295 | 0.5 |
| Lung ca. A549 | 0.1 | Brain (Amygdala) Pool | 0.0 |
| Lung ca. NCI-H526 | 0.0 | Brain (cerebellum) | 0.0 |
| Lung ca. NCI-H23 | 0.0 | Brain (fetal) | 0.0 |
| Lung ca. NCI-H460 | 0.0 | Brain (Hippocampus) Pool | 0.0 |
| Lung ca. HOP-62 | 0.1 | Cerebral Cortex Pool | 0.0 |
| Lung ca. NCI-H522 | 0.0 | Brain (Substantia nigra) Pool | 0.0 |
| Liver | 0.0 | Brain (Thalamus) Pool | 0.0 |
| Fetal Liver | 0.0 | Brain (whole) | 0.0 |
| Liver ca. HepG2 | 0.0 | Spinal Cord Pool | 0.1 |
| Kidney Pool | 0.0 | Adrenal Gland | 0.0 |
| Fetal Kidney | 0.0 | Pituitary gland Pool | 0.0 |
| Renal ca. 786-0 | 0.0 | Salivary Gland | 0.3 |
| Renal ca. A498 | 0.0 | Thyroid (female) | 0.0 |
| Renal ca. ACHN | 0.0 | Pancreatic ca. CAPAN2 | 14.9 |
| Renal ca. UO-31 | 1.7 | Pancreas Pool | 1.5 |

TABLE HE

Panel 4.1D

| Tissue Name | Rel. Exp. (%) Ag6132, Run 254398390 | Tissue Name | Rel. Exp. (%) Ag6132, Run 254398390 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvascular Dermal EC TNF alpha + IL-1beta | 0.0 |
| Primary Th1 rest | 0.0 | Bronchial epithelium TNF alpha + IL1beta | 5.8 |
| Primary Th2 rest | 0.0 | Small airway epithelium none | 14.2 |
| Primary Tr1 rest | 0.0 | Small airway epithelium TNF alpha + IL-1beta | 100.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 0.0 |
| Secondary CD8 lymphocyte rest | 0.0 | Astrocytes TNF alpha + IL-1beta | 1.9 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.5 |
| LAK cells rest | 0.0 | CCD1106 (Keratinocytes) TNF alpha + IL-1beta | 0.0 |
| LAK cells IL-2 | 0.0 | Liver cirrhosis | 3.5 |
| LAK cells IL-2 + IL-12 | 0.0 | NCI-H292 none | 23.2 |
| LAK cells IL-2 + IFN gamma | 0.0 | NCI-H292 IL-4 | 15.2 |
| LAK cells IL-2 + IL-18 | 0.0 | NCI-H292 IL-9 | 29.1 |
| LAK cells PMA/ionomycin | 0.0 | NCI-H292 IL-13 | 26.4 |
| NK Cells IL-2 rest | 0.0 | NCI-H292 IFN gamma | 2.9 |
| Two Way MLR 3 day | 0.0 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 0.0 |
| PBMC rest | 0.0 | Lung fibroblast TNF alpha + IL-1beta | 0.0 |
| PBMC PWM | 0.0 | Lung fibroblast IL-4 | 0.0 |
| PBMC PHA-L | 0.0 | Lung fibroblast IL-9 | 0.0 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 0.0 | Dermal fibroblast CCD1070 rest | 0.0 |
| B lymphocytes CD40L and IL-4 | 0.0 | Dermal fibroblast CCD1070 TNF alpha | 0.0 |
| EOL-1 dbcAMP | 0.8 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 0.0 | Dermal Fibroblasts rest | 0.0 |
| Dendritic cells anti-CD40 | 0.0 | Neutrophils TNFa + LPS | 0.0 |
| Monocytes rest | 0.0 | Neutrophils rest | 0.0 |
| Monocytes LPS | 0.0 | Colon | 0.0 |

TABLE HE-continued

Panel 4.1D

| Tissue Name | Rel. Exp. (%) Ag6132, Run 254398390 | Tissue Name | Rel. Exp. (%) Ag6132, Run 254398390 |
|---|---|---|---|
| Macrophages rest | 0.0 | Lung | 0.0 |
| Macrophages LPS | 0.0 | Thymus | 0.0 |
| HUVEC none | 0.0 | Kidney | 0.4 |
| HUVEC starved | 0.0 | | |

AI_comprehensive panel_v1.0 Summary: Ag6132 Highest expression of the NOV10A gene is detected in match Crohns and ulcerative colitis control samples (CTs=30.4). Interestingly, expression of this gene is higher in the matched control colon samples as compared to diseased (Crohns and ulcerative colitis) samples. Low expression of this gene is also seen in synovial fluid, bone sample from orthoarthritis and rheumatide arthritis patients. Therefore, therapeutic modulation of this gene may be beneficial in the treatment of inflammatory bowel diseases and arthritis.

The NOV10A gene codes for a variant of neutrophil gelatinase-associated lipocalin precursor (NGAL). NGAL is a 25-kDa lipocalin originally purified from human neutrophils. Besides neutrophils, NGAL is expressed in most tissues normally exposed to microorganisms, and its synthesis is induced in epithelial cells during inflammation (Kjeldsen et al., 2000, Biochim Biophys Acta 1482(1–2) :272–83, PMID: 11058768). Thus, NGAL may serve an important anti-inflammatory function as a scavenger of bacterial products.

CNS_neurodegeneration_v1.0 Summary: Ag4254 Expression of the NOV10A gene is low/undetectable (CTs>35) across all of the samples on this panel (data not shown).

General_screening_panel_v1.4 Summary: Ag4254 Expression of the NOV10A gene is low/undetectable (CTs>35) across all of the samples on this panel (data not shown).

General_screening_panel_v1.6 Summary: Ag6132 Expression of this gene appears to be associated with cancer cell lines in this panel, with highest expression in a gastric cancer cell line (CT=26.3). Moderate levels of expression are also seen in cell lines derived from pancreatic, colon, ovarian and squamous cell cancers. Thus, expression of this gene could be used to differentiate between the gastric cancer cell line and other samples on this panel and as a marker of gastric cancer. Furthermore, therapeutic modulation of the expression or function of this protein may be effective in the treatment of gastric, pancreatic, colon, ovarian and squamous cell cancers.

Panel 4.1D Summary: Ag6132 Highest expression of the NOV10A gene is detected in TNFalpha+IL-1 beta treated small airway epithelium (CTs=30.4). In addition, significant expression of this gene is also seen in resting and cytokine treated NCI-H292 cells, a human airway epithelial cell line that produces mucins and TNFalpha+IL1 beta treated bronchial epithelium. Mucus overproduction is an important feature of bronchial asthma and chronic obstructive pulmonary disease samples. Therefore, therapeutics designed with the protein encoded by the gene may reduce or eliminate symptoms caused by inflammation in lung epithelia in chronic obstructive pulmonary disease, asthma, allergy, and emphysema. Please see AI_comprehensive panel_v1.0 for further discussion of the potential utility of this gene.

Ag4254 Expression of this gene is low/undetectable (CTs>35) across all of the samples on this panel (data not shown).

General oncology screening panel_V_2.4 Summary: Ag4254 Expression of the NOV10A gene is low/undetectable (CTs>35) across all of the samples on this panel (data not shown).

I. NOV11A: DENN Domain Containing Protein

Expression of gene NOV11A was assessed using the primer-probe set Ag4266, described in Table IA. Results of the RTQ-PCR runs are shown in Table IB.

TABLE IA

Probe Name Ag4266

| Primers | Sequences | Length | Start Position | SEQ ID No |
|---|---|---|---|---|
| Forward | 5'-cctttgacgttgaaaggtacag-3' | 22 | 167 | 157 |
| Probe | TET-5'-tcaagttggacagcactttacctttg-3'-TAMRA | 26 | 195 | 158 |
| Reverse | 5'-tctgcagaatccaaatctctgt-3' | 22 | 243 | 159 |

TABLE IB

CNS_neurodegeneration_v1.0

| Tissue Name | Rel. Exp. (%) Ag4266, Run 224076199 | Tissue Name | Rel. Exp. (%) Ag4266, Run 224076199 |
|---|---|---|---|
| AD 1 Hippo | 0.0 | Control (Path) 3 Temporal Ctx | 13.6 |
| AD 2 Hippo | 17.2 | Control (Path) 4 Temporal Ctx | 25.7 |
| AD 3 Hippo | 7.8 | AD 1 Occipital Ctx | 9.5 |
| AD 4 Hippo | 5.8 | AD 2 Occipital Ctx (Missing) | 0.0 |
| AD 5 hippo | 23.2 | AD 3 Occipital Ctx | 12.6 |
| AD 6 Hippo | 100.0 | AD 4 Occipital Ctx | 13.0 |
| Control 2 Hippo | 2.3 | AD 5 Occipital Ctx | 33.2 |
| Control 4 Hippo | 12.2 | AD 6 Occipital Ctx | 6.3 |
| Control (Path) 3 Hippo | 4.0 | Control 1 Occipital Ctx | 0.0 |
| AD 1 Temporal Ctx | 10.3 | Control 2 Occipital Ctx | 19.2 |
| AD 2 Temporal Ctx | 8.7 | Control 3 Occipital Ctx | 7.9 |
| AD 3 Temporal Ctx | 3.9 | Control 4 Occipital Ctx | 3.9 |
| AD 4 Temporal Ctx | 12.0 | Control (Path) 1 Occipital Ctx | 9.2 |
| AD 5 Inf Temporal Ctx | 47.6 | Control (Path) 2 Occipital Ctx | 5.8 |
| AD 5 SupTemporal Ctx | 21.9 | Control (Path) 3 Occipital Ctx | 0.0 |
| AD 6 Inf Temporal Ctx | 60.7 | Control (Path) 4 Occipital Ctx | 2.6 |
| AD 6 Sup Temporal Ctx | 60.7 | Control 1 Parietal Ctx | 13.1 |
| Control 1 Temporal Ctx | 0.0 | Control 2 Parietal Ctx | 24.3 |
| Control 2 Temporal Ctx | 2.6 | Control 3 Parietal Ctx | 11.0 |
| Control 3 Temporal Ctx | 15.8 | Control (Path) 1 Parietal Ctx | 7.7 |
| Control 4 Temporal Ctx | 0.0 | Control (Path) 2 Parietal Ctx | 18.7 |
| Control (Path) 1 Temporal Ctx | 13.8 | Control (Path) 3 Parietal Ctx | 5.0 |
| Control (Path) 2 Temporal Ctx | 18.7 | Control (Path) 4 Parietal Ctx | 23.0 |

CNS_neurodegeneration_v1.0 Summary: Ag4266 This panel confirms the expression of the NOV11A gene at low levels in the brains of an independent group of individuals. However, no differential expression of this gene was detected between Alzheimer's diseased postmortem brains and those of non-demented controls in this experiment. Low expression of this gene in the brain suggests that this gene may play a role in central nervous system and therapeutic modulation of this gene product may be useful in the treatment of CNS disorders such as Alzheimer's disease, Parkinson's disease, epilepsy, multiple sclerosis, schizophrenia and depression.

General_screening_panel_v1.4 Summary: Ag4266 Expression of the NOV11A gene is low/undetectable (CTs>35) across all of the samples on this panel (data not shown).

Panel 4.1D Summary: Ag4266 Expression of the NOV11A gene is low/undetectable (CTs>35) across all of the samples on this panel (data not shown).

J. NOV12A and NOV12F: Kininogen Precursor

Expression of gene NOV12A and variant NOV12F was assessed using the primer-probe sets Ag3374, Ag4279 and Ag5114, described in Tables JA, JB and JC. The NOV12A gene is recognized by primer-probe sets Ag3374 and Ag4279, whereas variant NOV12F is recognized by primer-probe sets Ag3374 and Ag5114. Results of the RTQ-PCR runs are shown in Tables JD, JE, JF, and JG.

TABLE JA

Probe Name Ag3374

| Primers | Sequences | Length | Start Position | SEQ ID No |
|---|---|---|---|---|
| Forward | 5'-gattgcaacgctgaagtttatg-3' | 22 | 961 | 160 |
| Probe | TET-5'-ctgtcaactgtcaaccactgggaatg-3'-TAMRA | 26 | 1013 | 161 |
| Reverse | 5'-gaggccttttcatcagtgagat-3' | 22 | 1039 | 162 |

TABLE JB

Probe Name Ag4279

| Primers | Sequences | Length | Start Position | SEQ ID No |
|---|---|---|---|---|
| Forward | 5'-aatcttcactccaggcacatag-3' | 22 | 1209 | 163 |
| Probe | TET-5'-acctctgccagcaaccttgagagg-3'-TAMRA | 24 | 1239 | 164 |
| Reverse | 5'-tcccatctttcttcttgtcctt-3' | 22 | 1263 | 165 |

TABLE JC

Probe Name Ag5114

| Primers | Sequences | Length | Start Position | SEQ ID No |
|---|---|---|---|---|
| Forward | 5'-acgcagagcccaggtttt-3' | 18 | 364 | 166 |
| Probe | TET-5'-tcacctttccgatcatcacgaatagg-3'-TAMRA | 27 | 382 | 167 |
| Reverse | 5'-cgcaggaccttaggtgactagt-3' | 22 | 427 | 168 |

TABLE JD

Panel 1.3D

| Tissue Name | Rel. Exp. (%) Ag3374, Run 165678152 | Tissue Name | Rel. Exp. (%) Ag3374, Run 165678152 |
|---|---|---|---|
| Liver adenocarcinoma | 0.0 | Kidney (fetal) | 6.0 |
| Pancreas | 0.0 | Renal ca. 786-0 | 0.0 |
| Pancreatic ca. CAPAN 2 | 0.0 | Renal ca. A498 | 0.0 |
| Adrenal gland | 0.0 | Renal ca. RXF 393 | 0.0 |
| Thyroid | 0.0 | Renal ca. ACHN | 0.0 |
| Salivary gland | 0.0 | Renal ca. UO-31 | 0.0 |
| Pituitary gland | 0.0 | Renal ca. TK-10 | 0.0 |
| Brain (fetal) | 0.0 | Liver | 100.0 |
| Brain (whole) | 0.1 | Liver (fetal) | 32.1 |
| Brain (amygdala) | 0.0 | Liver ca. (hepatoblast) HepG2 | 0.0 |
| Brain (cerebellum) | 0.0 | Lung | 0.0 |
| Brain (hippocampus) | 0.0 | Lung (fetal) | 0.0 |
| Brain (substantia nigra) | 0.0 | Lung ca. (small cell) LX-1 | 0.0 |
| Brain (thalamus) | 0.0 | Lung ca. (small cell) NCI-H69 | 0.0 |
| Cerebral Cortex | 0.0 | Lung ca. (s.cell var.) SHP-77 | 0.0 |
| Spinal cord | 0.0 | Lung ca. (large cell)NCI-H460 | 0.0 |
| glio/astro U87-MG | 0.0 | Lung ca. (non-sm. cell) A549 | 0.0 |
| glio/astro U-118-MG | 0.0 | Lung ca. (non-s.cell) NCI-H23 | 0.0 |

TABLE JD-continued

Panel 1.3D

| Tissue Name | Rel. Exp. (%) Ag3374, Run 165678152 | Tissue Name | Rel. Exp. (%) Ag3374, Run 165678152 |
|---|---|---|---|
| astrocytoma SW1783 | 0.0 | Lung ca. (non-s.cell) HOP-62 | 0.0 |
| neuro*; met SK-N-AS | 0.0 | Lung ca. (non-s.cl) NCI-H522 | 0.0 |
| astrocytoma SF-539 | 0.0 | Lung ca. (squam.) SW 900 | 0.0 |
| astrocytoma SNB-75 | 0.0 | Lung ca. (squam.) NCI-H596 | 0.0 |
| glioma SNB-19 | 0.0 | Mammary gland | 0.0 |
| glioma U251 | 0.0 | Breast ca.* (pl.ef) MCF-7 | 0.0 |
| glioma SF-295 | 0.0 | Breast ca.* (pl.ef) MDA-MB-231 | 0.0 |
| Heart (fetal) | 0.0 | Breast ca.* (pl.ef) T47D | 0.0 |
| Heart | 0.0 | Breast ca. BT-549 | 0.0 |
| Skeletal muscle (fetal) | 0.0 | Breast ca. MDA-N | 0.0 |
| Skeletal muscle | 0.0 | Ovary | 0.0 |
| Bone marrow | 0.0 | Ovarian ca. OVCAR-3 | 0.0 |
| Thymus | 0.0 | Ovarian ca. OVCAR-4 | 0.0 |
| Spleen | 0.0 | Ovarian ca. OVCAR-5 | 0.0 |
| Lymph node | 0.0 | Ovarian ca. OVCAR-8 | 0.0 |
| Colorectal | 0.0 | Ovarian ca. IGROV-1 | 0.0 |
| Stomach | 0.0 | Ovarian ca.* (ascites) SK-OV-3 | 0.0 |
| Small intestine | 0.0 | Uterus | 0.0 |
| Colon ca. SW480 | 0.0 | Placenta | 0.0 |
| Colon ca.* SW620(SW480 met) | 0.0 | Prostate | 0.0 |
| Colon ca. HT29 | 0.0 | Prostate ca.* (bone met)PC-3 | 0.0 |
| Colon ca. HCT-116 | 0.0 | Testis | 0.0 |
| Colon ca. CaCo-2 | 1.4 | Melanoma Hs688(A).T | 0.0 |
| Colon ca. tissue(ODO3866) | 0.0 | Melanoma* (met) Hs688(B).T | 0.0 |
| Colon ca. HCC-2998 | 0.0 | Melanoma UACC-62 | 0.0 |
| Gastric ca.* (liver met) NCI-N87 | 0.0 | Melanoma M14 | 0.0 |
| Bladder | 0.0 | Melanoma LOX IMVI | 0.0 |
| Trachea | 0.0 | Melanoma* (met) SK-MEL-5 | 0.0 |
| Kidney | 32.3 | Adipose | 0.0 |

TABLE JE

Panel 2D

| Tissue Name | Rel. Exp. (%) Ag3374, Run 170858346 | Tissue Name | Rel. Exp. (%) Ag3374, Run 170858346 |
|---|---|---|---|
| Normal Colon | 0.7 | Kidney Margin 8120608 | 4.2 |
| CC Well to Mod Diff (ODO3866) | 0.0 | Kidney Cancer 8120613 | 0.1 |
| CC Margin (ODO3866) | 0.0 | Kidney Margin 8120614 | 3.1 |
| CC Gr.2 rectosigmoid (ODO3868) | 0.0 | Kidney Cancer 9010320 | 0.0 |
| CC Margin (ODO3868) | 0.0 | Kidney Margin 9010321 | 4.4 |
| CC Mod Diff (ODO3920) | 0.0 | Normal Uterus | 0.0 |

TABLE JE-continued

Panel 2D

| Tissue Name | Rel. Exp. (%) Ag3374, Run 170858346 | Tissue Name | Rel. Exp. (%) Ag3374, Run 170858346 |
|---|---|---|---|
| CC Margin (ODO3920) | 0.0 | Uterus Cancer 064011 | 0.1 |
| CC Gr.2 ascend colon (ODO3921) | 0.0 | Normal Thyroid | 0.0 |
| CC Margin (ODO3921) | 0.0 | Thyroid Cancer 064010 | 0.0 |
| CC from Partial Hepatectomy (ODO4309) Mets | 6.8 | Thyroid Cancer A302152 | 0.0 |
| Liver Margin (ODO4309) | 100.0 | Thyroid Margin A302153 | 0.0 |
| Colon mets to lung (OD04451-01) | 0.0 | Normal Breast | 0.0 |
| Lung Margin (OD04451-02) | 0.0 | Breast Cancer (OD04566) | 0.0 |
| Normal Prostate 6546-1 | 0.0 | Breast Cancer (OD04590-01) | 0.0 |
| Prostate Cancer (OD04410) | 0.0 | Breast Cancer Mets (OD04590-03) | 0.0 |
| Prostate Margin (OD04410) | 0.0 | Breast Cancer Metastasis (OD04655-05) | 0.0 |
| Prostate Cancer (OD04720-01) | 0.0 | Breast Cancer 064006 | 0.3 |
| Prostate Margin (OD04720-02) | 0.0 | Breast Cancer 1024 | 0.0 |
| Normal Lung 061010 | 0.1 | Breast Cancer 9100266 | 0.0 |
| Lung Met to Muscle (ODO4286) | 0.0 | Breast Margin 9100265 | 0.0 |
| Muscle Margin (ODO4286) | 0.0 | Breast Cancer A209073 | 0.0 |
| Lung Malignant Cancer (OD03126) | 0.0 | Breast Margin A209073 | 0.0 |
| Lung Margin (OD03126) | 0.0 | Normal Liver | 60.7 |
| Lung Cancer (OD04404) | 0.0 | Liver Cancer 064003 | 78.5 |
| Lung Margin (OD04404) | 0.0 | Liver Cancer 1025 | 42.6 |
| Lung Cancer (OD04565) | 0.0 | Liver Cancer 1026 | 19.2 |
| Lung Margin (OD04565) | 0.0 | Liver Cancer 6004-T | 36.9 |
| Lung Cancer (OD04237-01) | 0.0 | Liver Tissue 6004-N | 3.6 |
| Lung Margin (OD04237-02) | 0.0 | Liver Cancer 6005-T | 17.1 |
| Ocular Mel Met to Liver (ODO4310) | 0.0 | Liver Tissue 6005-N | 8.6 |
| Liver Margin (ODO4310) | 76.3 | Normal Bladder | 0.0 |
| Melanoma Mets to Lung (OD04321) | 0.0 | Bladder Cancer 1023 | 0.0 |
| Lung Margin (OD04321) | 0.0 | Bladder Cancer A302173 | 0.0 |
| Normal Kidney | 48.6 | Bladder Cancer (OD04718-01) | 0.0 |
| Kidney Ca, Nuclear grade 2 (OD04338) | 1.6 | Bladder Normal Adjacent (OD04718-03) | 0.0 |
| Kidney Margin (OD04338) | 24.3 | Normal Ovary | 0.0 |
| Kidney Ca Nuclear grade 1/2 (OD04339) | 0.0 | Ovarian Cancer 064008 | 0.0 |
| Kidney Margin (OD04339) | 28.3 | Ovarian Cancer (OD04768-07) | 0.0 |
| Kidney Ca, Clear cell type (OD04340) | 0.0 | Ovary Margin (OD04768-08) | 0.0 |
| Kidney Margin (OD04340) | 26.8 | Normal Stomach | 0.0 |
| Kidney Ca, Nuclear grade 3 (OD04348) | 0.0 | Gastric Cancer 9060358 | 0.0 |
| Kidney Margin (OD04348) | 17.2 | Stomach Margin 9060359 | 0.0 |

TABLE JE-continued

Panel 2D

| Tissue Name | Rel. Exp. (%) Ag3374, Run 170858346 | Tissue Name | Rel. Exp. (%) Ag3374, Run 170858346 |
|---|---|---|---|
| Kidney Cancer (OD04622-01) | 0.0 | Gastric Cancer 9060395 | 0.0 |
| Kidney Margin (OD04622-03) | 2.6 | Stomach Margin 9060394 | 0.0 |
| Kidney Cancer (OD04450-01) | 0.0 | Gastric Cancer 9060397 | 0.0 |
| Kidney Margin (OD04450-03) | 32.1 | Stomach Margin 9060396 | 0.0 |
| Kidney Cancer 8120607 | 0.0 | Gastric Cancer 064005 | 0.0 |

TABLE JF

Panel 3D

| Tissue Name | Rel. Exp. (%) Ag3374, Run 165039071 | Tissue Name | Rel. Exp. (%) Ag3374, Run 165039071 |
|---|---|---|---|
| Daoy-Medulloblastoma | 0.0 | Ca Ski-Cervical epidermoid carcinoma (metastasis) | 0.0 |
| TE671-Medulloblastoma | 0.0 | ES-2-Ovarian clear cell carcinoma | 0.0 |
| D283 Med-Medulloblastoma | 0.0 | Ramos-Stimulated with PMA/ionomycin 6h | 2.3 |
| PFSK-1-Primitive Neuroectodermal | 0.0 | Ramos-Stimulated with PMA/ionomycin 14h | 0.0 |
| XF-498-CNS | 0.0 | MEG-01-Chronic myelogenous leukemia (megokaryoblast) | 0.0 |
| SNB-78-Glioma | 0.0 | Raji-Burkitt's lymphoma | 0.0 |
| SF-268-Glioblastoma | 0.0 | Daudi-Burkitt's lymphoma | 0.0 |
| T98G-Glioblastoma | 0.0 | U266-B-cell plasmacytoma | 0.0 |
| SK-N-SH-Neuroblastoma (metastasis) | 0.0 | CA46-Burkitt's lymphoma | 0.0 |
| SF-295-Glioblastoma | 0.0 | RL-non-Hodgkin's B-cell lymphoma | 0.0 |
| Cerebellum | 0.0 | JM1-pre-B-cell lymphoma | 0.0 |
| Cerebellum | 0.0 | Jurkat-T cell leukemia | 0.0 |
| NCI-H292-Mucoepidermoid lung carcinoma | 0.0 | TF-1-Erythroleukemia | 0.0 |
| DMS-114-Small cell lung cancer | 0.0 | HUT 78-T-cell lymphoma | 0.0 |
| DMS-79-Small cell lung cancer | 0.0 | U937-Histiocytic lymphoma | 0.0 |
| NCI-H146-Small cell lung cancer | 0.0 | KU-812-Myelogenous leukemia | 0.0 |
| NCI-H526-Small cell lung cancer | 0.0 | 769-P-Clear cell renal carcinoma | 0.0 |
| NCI-N417-Small cell lung cancer | 0.0 | Caki-2-Clear cell renal carcinoma | 0.0 |
| NCI-H82-Small cell lung cancer | 0.0 | SW 839-Clear cell renal carcinoma | 0.0 |
| NCI-H157-Squamous cell lung cancer (metastasis) | 0.0 | G401-Wilms' tumor | 0.0 |
| NCI-H1155-Large cell lung cancer | 0.0 | Hs766T-Pancreatic carcinoma (LN metastasis) | 0.0 |
| NCI-H1299-Large cell lung cancer | 0.0 | CAPAN-1-Pancreatic adenocarcinoma (liver metastasis) | 0.0 |
| NCI-H727-Lung carcinoid | 0.0 | SU86.86-Pancreatic carcinoma (liver metastasis) | 0.0 |
| NCI-UMC-11-Lung carcinoid | 0.0 | BxPC-3-Pancreatic adenocarcinoma | 0.0 |
| LX-1-Small cell lung cancer | 0.0 | HPAC-Pancreatic adenocarcinoma | 0.0 |

TABLE JF-continued

Panel 3D

| Tissue Name | Rel. Exp. (%) Ag3374, Run 165039071 | Tissue Name | Rel. Exp. (%) Ag3374, Run 165039071 |
|---|---|---|---|
| Colo-205-Colon cancer | 0.0 | MIA PaCa-2-Pancreatic carcinoma | 0.0 |
| KM12-Colon cancer | 0.0 | CFPAC-1-Pancreatic ductal adenocarcinoma | 0.0 |
| KM20L2-Colon cancer | 0.0 | PANC-1-Pancreatic epithelioid ductal carcinoma | 0.0 |
| NCI-H716-Colon cancer | 0.0 | T24-Bladder carcinma (transitional cell) | 0.0 |
| SW-48-Colon adenocarcinoma | 100.0 | 5637-Bladder carcinoma | 0.0 |
| SW1116-Colon adenocarcinoma | 0.0 | HT-1197-Bladder carcinoma | 0.0 |
| LS 174T-Colon adenocarcinoma | 79.6 | UM-UC-3-Bladder carcinma (transitional cell) | 0.0 |
| SW-948-Colon adenocarcinoma | 0.0 | A204-Rhabdomyosarcoma | 0.0 |
| SW-480-Colon adenocarcinoma | 0.0 | HT-1080-Fibrosarcoma | 0.0 |
| NCI-SNU-5-Gastric carcinoma | 0.0 | MG-63-Osteosarcoma | 0.0 |
| KATO III-Gastric carcinoma | 4.2 | SK-LMS-1-Leiomyosarcoma (vulva) | 0.0 |
| NCI-SNU-16-Gastric carcinoma | 0.0 | SJRH30-Rhabdomyosarcoma (met to bone marrow) | 0.0 |
| NCI-SNU-1-Gastric carcinoma | 0.0 | A431-Epidermoid carcinoma | 0.0 |
| RF-1-Gastric adenocarcinoma | 0.0 | WM266-4-Melanoma | 0.0 |
| RF-48-Gastric adenocarcinoma | 0.0 | DU 145-Prostate carcinoma (brain metastasis) | 0.0 |
| MKN-45-Gastric carcinoma | 0.0 | MDA-MB-468-Breast adenocarcinoma | 0.0 |
| NCI-N87-Gastric carcinoma | 0.0 | SCC-4-Squamous cell carcinoma of tongue | 0.0 |
| OVCAR-5-Ovarian carcinoma | 0.0 | SCC-9-Squamous cell carcinoma of tongue | 0.0 |
| RL95-2-Uterine carcinoma | 0.0 | SCC-15-Squamous cell carcinoma of tongue | 0.0 |
| HelaS3-Cervical adenocarcinoma | 0.0 | CAL 27-Squamous cell carcinoma of tongue | 0.0 |

TABLE JG

Panel 4D

| Tissue Name | Rel. Exp. (%) Ag3374, Run 165296618 | Tissue Name | Rel. Exp. (%) Ag3374, Run 165296618 |
|---|---|---|---|
| Secondary Th1 act | 0.0 | HUVEC IL-1 beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1 beta | 0.0 |
| Primary Th2 act | 0.0 | Microvascular Dermal EC none | 0.0 |
| Primary Tr1 act | 0.0 | Microvasular Dermal EC TNF alpha + IL-1 beta | 0.0 |
| Primary Th1 rest | 0.0 | Bronchial epithelium TNF alpha + IL1 beta | 0.0 |
| Primary Th2 rest | 0.0 | Small airway epithelium none | 0.0 |

| | | | |
|---|---|---|---|
| Primary Tr1 rest | 0.0 | Small airway epithelium TNF alpha + IL-1 beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1 beta | 0.0 |
| CD8 lymphocyte act | 0.0 | Astrocytes rest | 0.0 |
| Secondary CD8 lymphocyte rest | 0.0 | Astrocytes TNF alpha + IL-1 beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1 beta | 0.0 |
| LAK cells IL-2 | 0.0 | Liver cirrhosis | 11.6 |
| LAK cells IL-2 + IL-12 | 0.0 | Lupus kidney | 0.7 |
| LAK cells IL-2 + IFN gamma | 0.0 | NCI-H292 none | 0.0 |
| LAK cells IL-2 + IL-18 | 0.0 | NCI-H292 IL-4 | 0.0 |
| LAK cells PMA/ionomycin | 0.0 | NCI-H292 IL-9 | 0.0 |
| NK Cells IL-2 rest | 0.0 | NCI-H292 IL-13 | 0.0 |
| Two Way MLR 3 day | 0.0 | NCI-H292 IFN gamma | 0.0 |
| Two Way MLR 5 day | 0.0 | HPAEC none | 0.0 |
| Two Way MLR 7 day | 0.0 | HPAEC TNF alpha + IL-1 beta | 0.0 |
| PBMC rest | 0.0 | Lung fibroblast none | 0.0 |
| PBMC PWM | 0.0 | Lung fibroblast TNF alpha + IL-1 beta | 0.0 |
| PBMC PHA-L | 0.0 | Lung fibroblast IL-4 | 0.0 |
| Ramos (B cell) none | 0.0 | Lung fibroblast IL-9 | 0.0 |
| Ramos (B cell) ionomycin | 0.0 | Lung fibroblast IL-13 | 0.0 |
| B lymphocytes PWM | 0.0 | Lung fibroblast IFN gamma | 0.0 |
| B lymphocytes CD40L and IL-4 | 0.0 | Dermal fibroblast CCD1070 rest | 0.0 |
| EOL-1 dbcAMP | 0.0 | Dermal fibroblast CCD1070 TNF alpha | 0.0 |
| EOL-1 dbcAMP PMA/ionomycin | 0.0 | Dermal fibroblast CCD1070 IL-1 beta | 0.0 |
| Dendritic cells none | 0.0 | Dermal fibroblast IFN gamma | 0.0 |
| Dendritic cells LPS | 0.0 | Dermal fibroblast IL-4 | 0.0 |
| Dendritic cells anti-CD40 | 0.0 | IBD Colitis 2 | 0.0 |
| Monocytes rest | 0.0 | IBD Crohn's | 0.0 |
| Monocytes LPS | 0.0 | Colon | 0.0 |
| Macrophages rest | 0.0 | Lung | 0.0 |
| Macrophages LPS | 0.0 | Thymus | 100.0 |
| HUVEC none | 0.0 | Kidney | 0.0 |
| HUVEC starved | 0.0 | | |

CNS_neurodegeneration_v1.0 Summary: Ag5114 Expression of the NOV12F gene is low/undetectable (CTs>35) in all samples on this panel (data not shown).

General_screening panel_v1.5 Summary: Ag5114 Expression of the NOV12F gene is low/undetectable (CTs>35) in all samples on this panel (data not shown).

Panel 1.3D Summary: Ag3374 Expression of this gene is restricted to a few samples, with highest expression in liver (CT=24.1), fetal liver, and kidney. Moderate expression is seen in fetal kidney and low levels of expression are seen in a colon cancer cell line. This expression profile suggests that this gene could be used to differentiate between liver and other samples on this panel and as a marker of liver and kidney tissue.

Panel 2D Summary: Ag3374 Highest expression of this gene is seen in liver derived tissue (CT=23.9), with expression in this panel restricted to liver and kidney derived tissue. This expression is in agreement with expression seen in Panel 1.3D. In addition, this gene is more highly expressed in kidney tissue when compared to normal adjacent tissue. This gene encodes a putative kininogen, which has been shown to inhibit angiogenesis (Colman R. Blood. 95:543; Guo Y. Arterioscler Thromb Vasc Biol. September 2001, pg. 1427). The expressed protein can also be used in the treatment of kidney cancers as it is not expressed in kidney cancers compared to the adjacent normal tissues and inhibition of its activity using antibodies or small molecule drugs may be useful in treating liver cancer. Thus, therapeutic modulation of the expression or function of this gene could be effective in the treatment of liver and kidney cancers.

Panel 3D Summary: Ag3374 Expression in this panel is restricted to samples derived from colon cancer cell lines (CTs=34–35). Thus, expression of this gene could be used to differentiate between this sample and other samples on this panel and as a marker to detect the presence of colon cancer. Furthermore, therapeutic modulation of the expression or function of this gene may be effective in the treatment of colon cancer. A second experiment with probe and primer set Ag4269 shows low/undetectable levels of expression (CTs>35). (Data not shown.)

Panel 4D Summary: Ag3374 This transcript is most highly expressed in the thymus (CT=24.3). The protien encoded by this gene could therefore play an important role in T cell development. Thus, therapeutic modulation of the expression or function of this gene may modulate immune function (T cell development) and be important for organ transplant, AIDS treatment or post chemotherapy immune reconstitution.

In addition, moderate levels of expression are seen in liver cirrhosis and lupus kidney, in agreement with previous panels that showed expression in liver and kidney derived tissues.

Panel 4.1D Summary: Ag5114 Expression of the NOV12F gene is low/undetectable (CTs>35) in all samples on this panel (data not shown).

General oncology screening panel_v_2.4 Summary: Ag5114 Expression of the NOV12F gene is low/undetectable (CTs>35) in all samples on this panel (data not shown).

K. NOV12B, NOV12C, NOV12D, NOV12E, NOV12G and CG104903-09: Kininogen Precursor

Expression of gene NOV12B and variants NOV12C, NOV12D, NOV12E, NOV12G and NOV12H was assessed using the primer-probe sets Ag3374, Ag4269, Ag5115 and Ag5116, described in Tables KA, KB, KC and KD. The correspondence of primer-probe sets to the various variants is described in Table KE. These sequences are variants of NOV12A described in the previous section (section J). Results of the RTQ-PCR runs are shown in Tables KE, KF, KG, KH, KI, KJ, KK, KL, KM, KN and KO. Please note that NOV12G represents a full-length physical clone. In addition, NOV12H represents a full-length physical clone that validates the prediction of the NOV12C sequence.

TABLE KA

Probe Name Ag3374

| Primers | Sequences | Length | Start Position | SEQ ID No |
|---|---|---|---|---|
| Forward | 5'-gattgcaacgctgaagtttatg-3' | 22 | 1005 | 169 |
| Probe | TET-5'-ctgtcaactgtcaaccactgggaatg-3'-TAMRA | 26 | 1057 | 170 |
| Reverse | 5'-gaggccttttcatcagtgagat-3' | 22 | 1083 | 171 |

TABLE KB

Probe Name Ag4269

| Primers | Sequences | Length | Start Position | SEQ ID No |
|---|---|---|---|---|
| Forward | 5'-acagagcatttggcaagct-3' | 19 | 1518 | 172 |
| Probe | TET-5'-cagtactacaccttctgcacagacaca-3'-TAMRA | 27 | 1547 | 173 |
| Reverse | 5'-gttggcccttctgtcttctc-3' | 20 | 1575 | 174 |

TABLE KC

Probe Name Ag5115

| Primers | Sequences | Length | Start Position | SEQ ID No |
|---|---|---|---|---|
| Forward | 5'-cagccactggagaatgca-3' | 18 | 354 | 175 |
| Probe | TET-5'-agcagtacgaaattctccgtggctacc-3'-TAMRA | 27 | 391 | 176 |
| Reverse | 5'-gaatgggctccaggtctg-3' | 18 | 418 | 177 |

TABLE KD

Probe Name Ag5116

| Primers | Sequences | Length | Start Position | SEQ ID No |
|---|---|---|---|---|
| Forward | 5'-acgcagagcccaggtttt-3' | 18 | 500 | 178 |
| Probe | TET-5'-cacctttccgatcatcacgaatagggg-3'-TAMRA | 27 | 519 | 179 |
| Reverse | 5'-gggtggacttacagttgtttcttct-3' | 25 | 553 | 180 |

TABLE KE

| | Probe Name Ag3374 | | | | | |
|---|---|---|---|---|---|---|
| | NOV12B | NOV12C | NOV12D | NOV12E | NOV 12G | NOV 12H |
| Ag3374 | X | X | | X | X | X |
| Ag4269 | X | X | X | | | X |
| Ag5115 | | | | X | | |
| Ag5116 | | | X | | | |

TABLE KF

| CNS_neurodegeneration_v1.0 | | | | | |
|---|---|---|---|---|---|
| Tissue Name | Rel. Exp. (%) Ag4269, Run 217215423 | Rel. Exp. (%) Ag5115, Run 226443863 | Tissue Name | Rel. Exp. (%) Ag4269, Run 217215423 | Rel. Exp. (%) Ag5115, Run 226443863 |
| AD 1 Hippo | 0.0 | 0.0 | Control (Path) 3 Temporal Ctx | 0.0 | 0.0 |
| AD 2 Hippo | 0.0 | 3.1 | Control (Path) 4 Temporal Ctx | 13.9 | 11.5 |
| AD 3 Hippo | 0.0 | 0.0 | AD 1 Occipital Ctx | 26.8 | 4.9 |
| AD 4 Hippo | 39.5 | 0.0 | AD 2 Occipital Ctx (Missing) | 0.0 | 0.0 |
| AD 5 Hippo | 100.0 | 100.0 | AD 3 Occipital Ctx | 0.0 | 0.0 |
| AD 6 Hippo | 0.0 | 0.0 | AD 4 Occipital Ctx | 8.1 | 9.2 |
| Control 2 Hippo | 0.0 | 0.0 | AD 5 Occipital Ctx | 24.8 | 3.6 |
| Control 4 Hippo | 0.0 | 0.0 | AD 6 Occipital Ctx | 0.0 | 98.6 |
| Control (Path) 3 Hippo | 0.0 | 0.0 | Control 1 Occipital Ctx | 0.0 | 0.0 |
| AD 1 Temporal Ctx | 0.0 | 0.0 | Control 2 Occipital Ctx | 57.8 | 85.9 |
| AD 2 Temporal Ctx | 12.9 | 7.9 | Control 3 Occipital Ctx | 24.0 | 4.0 |
| AD 3 Temporal Ctx | 0.0 | 0.0 | Control 4 Occipital Ctx | 0.0 | 0.0 |
| AD 4 Temporal Ctx | 30.4 | 2.9 | Control (Path) 1 Occipital Ctx | 79.0 | 54.0 |
| AD 5 Inf Temporal Ctx | 28.9 | 12.8 | Control (Path) 2 Occipital Ctx | 42.0 | 5.3 |
| AD 5 Sup Temporal Ctx | 0.0 | 0.0 | Control (Path) 3 Occipital Ctx | 0.0 | 0.0 |
| AD 6 Inf Temporal Ctx | 0.0 | 2.3 | Control (Path) 4 Occipital Ctx | 34.6 | 12.4 |

TABLE KF-continued

CNS_neurodegeneration_v1.0

| Tissue Name | Rel. Exp. (%) Ag4269, Run 217215423 | Rel. Exp. (%) Ag5115, Run 226443863 | Tissue Name | Rel. Exp. (%) Ag4269, Run 217215423 | Rel. Exp. (%) Ag5115, Run 226443863 |
|---|---|---|---|---|---|
| AD 6 Sup Temporal Ctx | 35.1 | 3.8 | Control 1 Parietal Ctx | 0.0 | 0.0 |
| Control 1 Temporal Ctx | 0.0 | 0.0 | Control 2 Parietal Ctx | 0.0 | 6.7 |
| Control 2 Temporal Ctx | 17.6 | 4.0 | Control 3 Parietal Ctx | 7.2 | 6.4 |
| Control 3 Temporal Ctx | 14.2 | 0.0 | Control (Path) 1 Parietal Ctx | 16.4 | 63.3 |
| Control 3 Temporal Ctx | 0.0 | 0.0 | Control (Path) 2 Parietal Ctx | 32.8 | 20.0 |
| Control (Path) 1 Temporal Ctx | 27.2 | 13.1 | Control (Path) 3 Parietal Ctx | 1.1 | 0.0 |
| Control (Path) 2 Temporal Ctx | 26.4 | 12.9 | Control (Path) 4 Parietal Ctx | 86.5 | 35.4 |

TABLE KG

General_screening_panel_v1.4

| Tissue Name | Rel. Exp. (%) Ag4269, Run 217044119 | Tissue Name | Rel. Exp. (%) Ag4269, Run 217044119 | Tissue Name | Rel. Exp. (%) Ag4269, Run 217044119 | Tissue Name | Rel. Exp. (%) Ag4269, Run 217044119 |
|---|---|---|---|---|---|---|---|
| Adipose | 0.0 | Renal ca. TK-10 | 0.0 | Breast ca. T47D | 0.0 | Skeletal Muscle Pool | 0.0 |
| Melanoma* Hs688(A).T | 0.0 | Bladder | 0.1 | Breast ca. MDA-N | 0.0 | Spleen Pool | 0.0 |
| Melanoma* Hs688(B).T | 0.0 | Gastric ca. (liver met.) NCI-N87 | 0.0 | Breast Pool | 0.1 | Thymus Pool | 0.0 |
| Melanoma* M14 | 0.0 | Gastric ca. KATO III | 0.0 | Trachea | 0.0 | CNS cancer (glio/astro) U87-MG | 0.0 |
| Melanoma* LOXIMVI | 0.0 | Colon ca. SW-948 | 0.0 | Lung | 0.0 | CNS cancer (glio/astro) U-118-MG | 0.0 |
| Melanoma* SK-MEL-5 | 0.1 | Colon ca. SW480 | 0.0 | Fetal Lung | 0.8 | CNS cancer (neuro;met) SK-N-AS | 0.0 |
| Squamous cell carcinoma SCC-4 | 0.0 | Colon ca.* (SW480 met) SW620 | 0.0 | Lung ca. NCI-N417 | 0.0 | CNS cancer (astro) SF-539 | 0.0 |
| Testis Pool | 0.0 | Colon ca. HT29 | 0.0 | Lung ca. LX-1 | 0.1 | CNS cancer (astro) SNB-75 | 0.0 |
| Prostate ca.* (bone met) PC-3 | 0.0 | Colon ca. HCT-116 | 0.0 | Lung ca. NCI-H146 | 0.0 | CNS cancer (glio) SNB-19 | 0.0 |
| Prostate Pool | 0.0 | Colon ca. CaCo-2 | 5.8 | Lung ca. SHP-77 | 0.0 | CNS cancer (glio) SF-295 | 0.0 |
| Placenta | 0.0 | Colon cancer tissue | 0.2 | Lung ca. A549 | 0.1 | Brain (Amygdala) Pool | 0.0 |
| Uterus Pool | 0.0 | Colon ca. SW1116 | 0.0 | Lung ca. NCI-H526 | 0.0 | Brain (cerebellum) | 0.0 |
| Ovarian ca. OVCAR-3 | 0.0 | Colon ca. Colo-205 | 0.0 | Lung ca. NCI-H23 | 0.0 | Brain (fetal) | 0.0 |
| Ovarian ca. SK-OV-3 | 0.0 | Colon ca. SW-48 | 0.0 | Lung ca. NCI-H460 | 0.0 | Brain (Hippocampus) Pool | 0.0 |
| Ovarian ca. OVCAR-4 | 0.0 | Colon Pool | 0.1 | Lung ca. HOP-62 | 0.0 | Cerebral Cortex Pool | 0.1 |
| Ovarian ca. OVCAR-5 | 0.1 | Small Intestine Pool | 0.0 | Lung ca. NCI-H522 | 0.0 | Brain (Substantia nigra) Pool | 0.0 |
| Ovarian ca. IGROV-1 | 0.0 | Stomach Pool | 0.1 | Liver | 20.0 | Brain (Thalamus) Pool | 0.0 |
| Ovarian ca. OVCAR-8 | 0.0 | Bone Marrow Pool | 0.0 | Fetal Liver | 100.0 | Brain (whole) | 1.3 |
| Ovary | 0.0 | Fetal Heart | 0.0 | Liver ca. HepG2 | 0.2 | Spinal Cord Pool | 0.0 |
| Breast ca. MCF-7 | 0.0 | Heart Pool | 0.0 | | | | |
| Breast ca. MDA-MB-231 | 0.0 | Lymph Node Pool | 0.0 | | | | |
| Breast ca. BT 549 | 0.0 | Fetal Skeletal Muscle | 0.0 | | | | |

TABLE KG-continued

| General_screening_panel_v1.4 | | | |
|---|---|---|---|
| Tissue Name | Rel. Exp. (%) Ag4269, Run 217044119 | Tissue Name | Rel. Exp. (%) Ag4269, Run 217044119 |
| Kidney Pool | 0.0 | Adrenal Gland | 0.1 |
| Fetal Kidney | 12.0 | Pituitary gland Pool | 0.0 |
| Renal ca. 786-0 | 0.0 | Salivary Gland | 0.0 |
| Renal ca. A498 | 0.0 | Thyroid (female) | 0.0 |
| Renal ca. ACHN | 0.0 | Pancreatic ca. CAPAN2 | 0.0 |
| Renal ca. UO-31 | 0.0 | Pancreas Pool | 0.1 |

TABLE KH

| General_screening_panel_v1.5 | | | |
|---|---|---|---|
| Tissue Name | Rel. Exp. (%) Ag5115, Run 228738881 | Tissue Name | Rel. Exp. (%) Ag5115, Run 228738881 |
| Adipose | 0.0 | Renal ca. TK-10 | 0.0 |
| Melanoma* Hs688(A).T | 0.0 | Bladder | 0.1 |
| Melanoma* Hs688(B).T | 0.0 | Gastric ca. (liver met.) NCI-N87 | 0.0 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 0.0 | Colon ca. HT29 | 0.0 |
| Prostate ca.* (bone met) PC-3 | 0.0 | Colon ca. HCT-116 | 0.0 |
| Prostate Pool | 0.0 | Colon ca. CaCo-2 | 5.4 |
| Placenta | 0.0 | Colon cancer tissue | 0.0 |
| Uterus Pool | 0.0 | Colon ca. SW1116 | 0.0 |
| Ovarian ca. OVCAR-3 | 0.0 | Colon ca. Colo-205 | 0.0 |
| Ovarian ca. SK-OV-3 | 0.0 | Colon ca. SW-48 | 0.0 |
| Ovarian ca. OVCAR-4 | 0.0 | Colon Pool | 0.0 |
| Ovarian ca. OVCAR-5 | 0.0 | Small Intestine Pool | 0.0 |
| Ovarian ca. IGROV-1 | 0.0 | Stomach Pool | 0.0 |
| Ovarian ca. OVCAR-8 | 0.0 | Bone Marrow Pool | 0.0 |
| Ovary | 0.0 | Fetal Heart | 0.0 |
| Breast ca. MCF-7 | 0.0 | Heart Pool | 0.0 |
| Breast ca. MDA-MB-231 | 0.0 | Lymph Node Pool | 0.0 |
| Breast ca. BT 549 | 0.0 | Fetal Skeletal Muscle | 0.0 |
| Breast ca. T47D | 0.0 | Skeletal Muscle Pool | 0.0 |
| Breast ca. MDA-N | 0.0 | Spleen Pool | 0.0 |
| Breast Pool | 0.1 | Thymus Pool | 0.0 |
| Trachea | 0.0 | CNS cancer (glio/astro) U87-MG | 0.0 |
| Lung | 0.0 | CNS cancer (glio/astro) U-118-MG | 0.0 |
| Fetal Lung | 0.8 | CNS cancer (neuro; met) SK-N-AS | 0.0 |
| Lung ca. NCI-N417 | 0.0 | CNS cancer (astro) SF-539 | 0.0 |
| Lung ca. LX-1 | 0.0 | CNS cancer (astro) SNB-75 | 0.0 |

TABLE KH-continued

General_screening_panel_v1.5

| Tissue Name | Rel. Exp. (%) Ag5115, Run 228738881 | Tissue Name | Rel. Exp. (%) Ag5115, Run 228738881 |
| --- | --- | --- | --- |
| Lung ca. NCI-H146 | 0.0 | CNS cancer (glio) SNB-19 | 0.0 |
| Lung ca. SHP-77 | 0.0 | CNS cancer (glio) SF-295 | 0.0 |
| Lung ca. A549 | 0.0 | Brain (Amygdala) Pool | 0.0 |
| Lung ca. NCI-H526 | 0.0 | Brain (cerebellum) | 0.0 |
| Lung ca. NCI-H23 | 0.0 | Brain (fetal) | 0.0 |
| Lung ca. NCI-H460 | 0.0 | Brain (Hippocampus) Pool | 0.2 |
| Lung ca. HOP-62 | 0.0 | Cerebral Cortex Pool | 0.1 |
| Lung ca. NCI-H522 | 0.0 | Brain (Substantia nigra) Pool | 0.0 |
| Liver | 27.7 | Brain (Thalamus) Pool | 0.1 |
| Fetal Liver | 100.0 | Brain (whole) | 1.3 |
| Liver ca. HepG2 | 0.0 | Spinal Cord Pool | 0.0 |
| Kidney Pool | 0.0 | Adrenal Gland | 0.0 |
| Fetal Kidney | 13.8 | Pituitary gland Pool | 0.0 |
| Renal ca. 786-0 | 0.0 | Salivary Gland | 0.0 |
| Renal ca. A498 | 0.0 | Thyroid (female) | 0.0 |
| Renal ca. ACHN | 0.0 | Pancreatic ca. CAPAN2 | 0.0 |
| Renal ca. UO-31 | 0.0 | Pancreas Pool | 0.0 |

TABLE KI

Panel 1.3D

| Tissue Name | Rel. Exp. (%) Ag3374, Run 165678152 | Tissue Name | Rel. Exp. (%) Ag3374, Run 165678152 |
| --- | --- | --- | --- |
| Liver adenocarcinoma | 0.0 | Kidney (fetal) | 6.0 |
| Pancreas | 0.0 | Renal ca. 786-0 | 0.0 |
| Pancreatic ca. CAPAN 2 | 0.0 | Renal ca. A498 | 0.0 |
| Adrenal gland | 0.0 | Renal ca. RXF 393 | 0.0 |
| Thyroid | 0.0 | Renal ca. ACHN | 0.0 |
| Salivary gland | 0.0 | Renal ca. UO-31 | 0.0 |
| Pituitary gland | 0.0 | Renal ca. TK-10 | 0.0 |
| Brain (fetal) | 0.0 | Liver | 100.0 |
| Brain (whole) | 0.1 | Liver (fetal) | 32.1 |
| Brain (amygdala) | 0.0 | Liver ca. (hepatoblast) HepG2 | 0.0 |
| Brain (cerebellum) | 0.0 | Lung | 0.0 |
| Brain (hippocampus) | 0.0 | Lung (fetal) | 0.0 |
| Brain (substantia nigra) | 0.0 | Lung ca. (small cell) LX-1 | 0.0 |
| Brain (thalamus) | 0.0 | Lung ca. (small cell) NCI-H69 | 0.0 |
| Cerebral Cortex | 0.0 | Lung ca. (s.cell var.) SHP-77 | 0.0 |
| Spinal cord | 0.0 | Lung ca. (large cell)NCI-H460 | 0.0 |
| glio/astro U87-MG | 0.0 | Lung ca. (non-sm. cell) A549 | 0.0 |
| glio/astro U-118-MG | 0.0 | Lung ca. (non-s.cell) NCI-H23 | 0.0 |
| astrocytoma SW1783 | 0.0 | Lung ca. (non-s.cell) HOP-62 | 0.0 |
| neuro*; met SK-N-AS | 0.0 | Lung ca. (non-s.cl) NCI-H522 | 0.0 |
| astrocytoma SF-539 | 0.0 | Lung ca. (squam.) SW 900 | 0.0 |
| astrocytoma SNB-75 | 0.0 | Lung ca. (squam.) NCI-H596 | 0.0 |
| glioma SNB-19 | 0.0 | Mammary gland | 0.0 |
| glioma U251 | 0.0 | Breast ca.* (pl.ef) MCF-7 | 0.0 |
| glioma SF-295 | 0.0 | Breast ca.* (pl.ef) MDA-MB-231 | 0.0 |

TABLE KI-continued

Panel 1.3D

| Tissue Name | Rel. Exp. (%) Ag3374, Run 165678152 | Tissue Name | Rel. Exp. (%) Ag3374, Run 165678152 |
|---|---|---|---|
| Heart (fetal) | 0.0 | Breast ca.* (pl.ef) T47D | 0.0 |
| Heart | 0.0 | Breast ca. BT-549 | 0.0 |
| Skeletal muscle (fetal) | 0.0 | Breast ca. MDA-N | 0.0 |
| Skeletal muscle | 0.0 | Ovary | 0.0 |
| Bone marrow | 0.0 | Ovarian ca. OVCAR-3 | 0.0 |
| Thymus | 0.0 | Ovarian ca. OVCAR-4 | 0.0 |
| Spleen | 0.0 | Ovarian ca. OVCAR-5 | 0.0 |
| Lymph node | 0.0 | Ovarian ca. OVCAR-8 | 0.0 |
| Colorectal | 0.0 | Ovarian ca. IGROV-1 | 0.0 |
| Stomach | 0.0 | Ovarian ca.* (ascites) SK-OV-3 | 0.0 |
| Small intestine | 0.0 | Uterus | 0.0 |
| Colon ca. SW480 | 0.0 | Placenta | 0.0 |
| Colon ca.* SW620(SW480 met) | 0.0 | Prostate | 0.0 |
| Colon ca. HT29 | 0.0 | Prostate ca.* (bone met)PC-3 | 0.0 |
| Colon ca. HCT-116 | 0.0 | Testis | 0.0 |
| Colon ca. CaCo-2 | 1.4 | Melanoma Hs688(A).T | 0.0 |
| Colon ca. tissue(ODO3866) | 0.0 | Melanoma* (met) Hs688(B).T | 0.0 |
| Colon ca. HCC-2998 | 0.0 | Melanoma UACC-62 | 0.0 |
| Gastric ca.* (liver met) NCI-N87 | 0.0 | Melanoma M14 | 0.0 |
| Bladder | 0.0 | Melanoma LOX IMVI | 0.0 |
| Trachea | 0.0 | Melanoma* (met) SK-MEL-5 | 0.0 |
| Kidney | 32.3 | Adipose | 0.0 |

TABLE KJ

Panel 2.2

| Tissue Name | Rel. Exp. (%) Ag3374, Run 176283594 | Rel. Exp. (%) Ag3374, Run 184372611 | Tissue Name | Rel. Exp. (%) Ag3374, Run 176283594 | Rel. Exp. (%) Ag3374, Run 184372611 |
|---|---|---|---|---|---|
| Normal Colon | 0.2 | 0.3 | Kidney Margin (OD04348) | 38.4 | 14.2 |
| Colon cancer (OD06064) | 0.0 | 0.0 | Kidney malignant cancer (OD06204B) | 0.0 | 0.0 |
| Colon Margin (OD06064) | 0.0 | 0.0 | Kidney normal adjacent tissue (OD06204E) | 4.5 | 4.7 |
| Colon cancer (OD06159) | 0.0 | 0.0 | Kidney Cancer (OD04450-01) | 0.0 | 0.0 |
| Colon Margin (OD06159) | 0.0 | 0.0 | Kidney Margin (OD04450-03) | 17.9 | 41.2 |
| Colon cancer (OD06297-04) | 0.0 | 0.0 | Kidney Cancer 8120613 | 0.0 | 0.0 |
| Colon Margin (OD06297-05) | 0.1 | 0.0 | Kidney Margin 8120614 | 2.9 | 1.8 |
| CC Gr.2 ascend colon (ODO3921) | 0.0 | 0.0 | Kidney Cancer 9010320 | 2.4 | 0.0 |
| CC Margin (ODO3921) | 0.0 | 0.0 | Kidney Margin 9010321 | 1.3 | 1.8 |
| Colon cancer | 0.0 | 0.0 | Kidney Cancer | 0.0 | 0.0 |

TABLE KJ-continued

Panel 2.2

| Tissue Name | Rel. Exp. (%) Ag3374, Run 176283594 | Rel. Exp. (%) Ag3374, Run 184372611 | Tissue Name | Rel. Exp. (%) Ag3374, Run 176283594 | Rel. Exp. (%) Ag3374, Run 184372611 |
|---|---|---|---|---|---|
| metastasis (OD06104) | | | 8120607 | | |
| Lung Margin (OD06104) | 0.0 | 0.0 | Kidney Margin 8120608 | 2.1 | 2.6 |
| Colon mets to lung (OD04451-01) | 0.0 | 0.0 | Normal Uterus | 0.0 | 0.0 |
| Lung Margin (OD04451-02) | 0.1 | 0.0 | Uterine Cancer 064011 | 0.0 | 0.0 |
| Normal Prostate | 0.0 | 0.0 | Normal Thyroid | 0.0 | 0.0 |
| Prostate Cancer (OD04410) | 0.0 | 0.0 | Thyroid Cancer 064010 | 0.0 | 0.0 |
| Prostate Margin (OD04410) | 0.0 | 0.0 | Thyroid Cancer A302152 | 0.0 | 0.0 |
| Normal Ovary | 0.0 | 0.0 | Thyroid Margin A302153 | 0.0 | 0.0 |
| Ovarian cancer (OD06283-03) | 0.0 | 0.0 | Normal Breast | 0.0 | 0.0 |
| Ovarian Margin (OD06283-07) | 0.0 | 0.0 | Breast Cancer (OD04566) | 1.3 | 0.0 |
| Ovarian Cancer 064008 | 1.5 | 0.0 | Breast Cancer 1024 | 1.6 | 0.0 |
| Ovarian cancer (OD06145) | 5.8 | 0.0 | Breast Cancer (OD04590-01) | 0.1 | 0.0 |
| Ovarian Margin (OD06145) | 1.4 | 0.0 | Breast Cancer Mets (OD04590-03) | 0.0 | 0.0 |
| Ovarian cancer (OD06455-03) | 0.2 | 0.0 | Breast Cancer Metastasis (OD04655-05) | 0.0 | 0.0 |
| Ovarian Margin (OD06455-07) | 0.0 | 0.0 | Breast Cancer 064006 | 0.1 | 0.3 |
| Normal Lung | 0.0 | 0.0 | Breast Cancer 9100266 | 0.0 | 0.0 |
| Invasive poor diff. lung adeno (ODO4945-01) | 0.0 | 0.0 | Breast Margin 9100265 | 0.0 | 0.0 |
| Lung Margin (ODO4945-03) | 0.0 | 0.0 | Breast Cancer A209073 | 0.0 | 0.0 |
| Lung Malignant Cancer (OD03126) | 0.0 | 0.0 | Breast Margin A2090734 | 0.0 | 0.0 |
| Lung Margin (OD03126) | 0.0 | 0.0 | Breast cancer (OD06083) | 0.0 | 0.0 |
| Lung Cancer (OD05014A) | 0.0 | 0.0 | Breast cancer node metastasis (OD06083) | 0.0 | 0.0 |
| Lung Margin (OD05014B) | 0.1 | 0.0 | Normal Liver | 57.8 | 94.6 |
| Lung cancer (OD06081) | 0.0 | 0.0 | Liver Cancer 1026 | 8.1 | 15.1 |
| Lung Margin (OD06081) | 0.0 | 0.0 | Liver Cancer 1025 | 47.0 | 60.3 |
| Lung Cancer (OD04237-01) | 0.0 | 0.0 | Liver Cancer 6004-T | 23.3 | 44.8 |
| Lung Margin (OD04237-02) | 0.0 | 0.0 | Liver Tissue 6004-N | 1.8 | 1.1 |
| Ocular Melanoma Metastasis | 0.0 | 0.0 | Liver Cancer 6005-T | 21.8 | 20.7 |
| Ocular Melanoma Margin (Liver) | 49.7 | 100.0 | Liver Tissue 6005-N | 31.6 | 27.0 |
| Melanoma Metastasis | 0.0 | 0.0 | Liver Cancer 064003 | 100.0 | 92.7 |
| Melanoma Margin (Lung) | 0.0 | 0.0 | Normal Bladder | 0.0 | 0.0 |
| Normal Kidney | 8.8 | 13.6 | Bladder Cancer 1023 | 0.0 | 0.0 |

TABLE KJ-continued

Panel 2.2

| Tissue Name | Rel. Exp. (%) Ag3374, Run 176283594 | Rel. Exp. (%) Ag3374, Run 184372611 | Tissue Name | Rel. Exp. (%) Ag3374, Run 176283594 | Rel. Exp. (%) Ag3374, Run 184372611 |
|---|---|---|---|---|---|
| Kidney Ca, Nuclear grade 2 (OD04338) | 27.9 | 26.1 | Bladder Cancer A302173 | 0.0 | 0.0 |
| Kidney Margin (OD04338) | 0.2 | 1.4 | Normal Stomach | 0.2 | 0.0 |
| Kidney Ca Nuclear grade 1/2 (OD04339) | 0.4 | 0.0 | Gastric Cancer 9060397 | 0.0 | 0.0 |
| Kidney Margin (OD04339) | 12.5 | 15.1 | Stomach Margin 9060396 | 0.0 | 0.0 |
| Kidney Ca, Clear cell type (OD04340) | 0.0 | 0.0 | Gastric Cancer 9060395 | 0.0 | 0.0 |
| Kidney Margin (OD04340) | 17.8 | 12.4 | Stomach Margin 9060394 | 0.0 | 0.0 |
| Kidney Ca, Nuclear grade 3 (OD04348) | 0.0 | 0.0 | Gastric Cancer 064005 | 0.0 | 0.0 |

TABLE KK

Panel 2D

| Tissue Name | Rel. Exp. (%) Ag3374, Run 170858346 | Tissue Name | Rel. Exp. (%) Ag3374, Run 170858346 |
|---|---|---|---|
| Normal Colon | 0.7 | Kidney Margin 8120608 | 4.2 |
| CC Well to Mod Diff (ODO3866) | 0.0 | Kidney Cancer 8120613 | 0.1 |
| CC Margin (ODO3866) | 0.0 | Kidney Margin 8120614 | 3.1 |
| CC Gr.2 rectosigmoid (ODO3868) | 0.0 | Kidney Cancer 9010320 | 0.0 |
| CC Margin (ODO3868) | 0.0 | Kidney Margin 9010321 | 4.4 |
| CC Mod Diff (ODO3920) | 0.0 | Normal Uterus | 0.0 |
| CC Margin (ODO3920) | 0.0 | Uterus Cancer 064011 | 0.1 |
| CC Gr.2 ascend colon (ODO3921) | 0.0 | Normal Thyroid | 0.0 |
| CC Margin (ODO3921) | 0.0 | Thyroid Cancer 064010 | 0.0 |
| CC from Partial Hepatectomy (ODO4309) Mets | 6.8 | Thyroid Cancer A302152 | 0.0 |
| Liver Margin (ODO4309) | 100.0 | Thyroid Margin A302153 | 0.0 |
| Colon mets to lung (OD04451-01) | 0.0 | Normal Breast | 0.0 |
| Lung Margin (OD04451-02) | 0.0 | Breast Cancer (OD04566) | 0.0 |
| Normal Prostate 6546-1 | 0.0 | Breast Cancer (OD04590-01) | 0.0 |
| Prostate Cancer (OD04410) | 0.0 | Breast Cancer Mets (OD04590-03) | 0.0 |
| Prostate Margin (OD04410) | 0.0 | Breast Cancer Metastasis (OD04655-05) | 0.0 |
| Prostate Cancer (OD04720-01) | 0.0 | Breast Cancer 064006 | 0.3 |
| Prostate Margin (OD04720-02) | 0.0 | Breast Cancer 1024 | 0.0 |
| Normal Lung 061010 | 0.1 | Breast Cancer 9100266 | 0.0 |

TABLE KK-continued

Panel 2D

| Tissue Name | Rel. Exp. (%) Ag3374, Run 170858346 | Tissue Name | Rel. Exp. (%) Ag3374, Run 170858346 |
|---|---|---|---|
| Lung Met to Muscle (OD04286) | 0.0 | Breast Margin 9100265 | 0.0 |
| Muscle Margin (OD04286) | 0.0 | Breast Cancer A209073 | 0.0 |
| Lung Malignant Cancer (OD03126) | 0.0 | Breast Margin A209073 | 0.0 |
| Lung Margin (OD03126) | 0.0 | Normal Liver | 60.7 |
| Lung Cancer (OD04404) | 0.0 | Liver Cancer 064003 | 78.5 |
| Lung Margin (OD04404) | 0.0 | Liver Cancer 1025 | 42.6 |
| Lung Cancer (OD04565) | 0.0 | Liver Cancer 1026 | 19.2 |
| Lung Margin (OD04565) | 0.0 | Liver Cancer 6004-T | 36.9 |
| Lung Cancer (OD04237-01) | 0.0 | Liver Tissue 6004-N | 3.6 |
| Lung Margin (OD04237-02) | 0.0 | Liver Cancer 6005-T | 17.1 |
| Ocular Mel Met to Liver (OD04310) | 0.0 | Liver Tissue 6005-N | 8.6 |
| Liver Margin (OD04310) | 76.3 | Normal Bladder | 0.0 |
| Melanoma Mets to Lung (OD04321) | 0.0 | Bladder Cancer 1023 | 0.0 |
| Lung Margin (OD04321) | 0.0 | Bladder Cancer A302173 | 0.0 |
| Normal Kidney | 48.6 | Bladder Cancer (OD04718-01) | 0.0 |
| Kidney Ca, Nuclear grade 2 (OD04338) | 1.6 | Bladder Normal Adjacent (OD04718-03) | 0.0 |
| Kidney Margin (OD04338) | 24.3 | Normal Ovary | 0.0 |
| Kidney Ca Nuclear grade 1/2 (OD04339) | 0.0 | Ovarian Cancer 064008 | 0.0 |
| Kidney Margin (OD04339) | 28.3 | Ovarian Cancer (OD04768-07) | 0.0 |
| Kidney Ca, Clear cell type (OD04340) | 0.0 | Ovary Margin (OD04768-08) | 0.0 |
| Kidney Margin (OD04340) | 26.8 | Normal Stomach | 0.0 |
| Kidney Ca, Nuclear grade 3 (OD04348) | 0.0 | Gastric Cancer 9060358 | 0.0 |
| Kidney Margin (OD04348) | 17.2 | Stomach Margin 9060359 | 0.0 |
| Kidney Cancer (OD04622-01) | 0.0 | Gastric Cancer 9060395 | 0.0 |
| Kidney Margin (OD04622-03) | 2.6 | Stomach Margin 9060394 | 0.0 |
| Kidney Cancer (OD04450-01) | 0.0 | Gastric Cancer 9060397 | 0.0 |
| Kidney Margin (OD04450-03) | 32.1 | Stomach Margin 9060396 | 0.0 |
| Kidney Cancer 8120607 | 0.0 | Gastric Cancer 064005 | 0.0 |

TABLE KL

Panel 3D

| Tissue Name | Rel. Exp. (%) Ag3374, Run 165039071 | Tissue Name | Rel. Exp. (%) Ag3374, Run 165039071 |
|---|---|---|---|
| Daoy-Medulloblastoma | 0.0 | Ca Ski-Cervical epidermoid carcinoma (metastasis) | 0.0 |
| TE671-Medulloblastoma | 0.0 | ES-2-Ovarian clear cell carcinoma | 0.0 |
| D283 Med-Medulloblastoma | 0.0 | Ramos-Stimulated with PMA/ionomycin 6 h | 2.3 |

TABLE KL-continued

Panel 3D

| Tissue Name | Rel. Exp. (%) Ag3374, Run 165039071 | Tissue Name | Rel. Exp. (%) Ag3374, Run 165039071 |
|---|---|---|---|
| PFSK-1-Primitive Neuroectodermal | 0.0 | Ramos-Stimulated with PMA/ionomycin 14 h | 0.0 |
| XF-498-CNS | 0.0 | MEG-01-Chronic myelogenous leukemia (megokaryoblast) | 0.0 |
| SNB-78-Glioma | 0.0 | Raji-Burkitt's lymphoma | 0.0 |
| SF-268-Glioblastoma | 0.0 | Daudi-Burkitt's lymphoma | 0.0 |
| T98G-Glioblastoma | 0.0 | U266-B-cell plasmacytoma | 0.0 |
| SK-N-SH-Neuroblastoma (metastasis) | 0.0 | CA46-Burkitt's lymphoma | 0.0 |
| SF-295-Glioblastoma | 0.0 | RL-non-Hodgkin's B-cell lymphoma | 0.0 |
| Cerebellum | 0.0 | JM1-pre-B-cell lymphoma | 0.0 |
| Cerebellum | 0.0 | Jurkat-T cell leukemia | 0.0 |
| NCI-H292-Mucoepidermoid lung carcinoma | 0.0 | TF-1-Erythroleukemia | 0.0 |
| DMS-114-Small cell lung cancer | 0.0 | HUT 78-T-cell lymphoma | 0.0 |
| DMS-79-Small cell Lung cancer | 0.0 | U937-Histiocytic lymphoma | 0.0 |
| NCI-H146-Small cell lung cancer | 0.0 | KU-812-Myelogenous leukemia | 0.0 |
| NCI-H526-Small cell lung cancer | 0.0 | 769-P-Clear cell renal carcinoma | 0.0 |
| NCI-N417-Small cell lung cancer | 0.0 | Caki-2-Clear cell renal carcinoma | 0.0 |
| NCI-H82-Small cell lung cancer | 0.0 | SW 839-Clear cell renal carcinoma | 0.0 |
| NCI-H157-Squamous cell lung cancer (metastasis) | 0.0 | G401-Wilms' tumor | 0.0 |
| NCI-H1155-Large cell lung cancer | 0.0 | Hs766T-Pancreatic carcinoma (LN metastasis) | 0.0 |
| NCI-H1299-Large cell lung cancer | 0.0 | CAPAN-1-Pancreatic adenocarcinoma (liver metastasis) | 0.0 |
| NCI-H727-Lung carcinoid | 0.0 | SU86.86-Pancreatic carcinoma (liver metastasis) | 0.0 |
| NCI-UMC-11-Lung carcinoid | 0.0 | BxPC-3-Pancreatic adenocarcinoma | 0.0 |
| LX-1-Small cell lung cancer | 0.0 | HPAC-Pancreatic adenocarcinoma | 0.0 |
| Colo-205-Colon cancer | 0.0 | MIA PaCa-2-Pancreatic carcinoma | 0.0 |
| KM12-Colon cancer | 0.0 | CFPAC-1-Pancreatic ductal adenocarcinoma | 0.0 |
| KM20L2-Colon cancer | 0.0 | PANC-1-Pancreatic epithelioid ductal carcinoma | 0.0 |
| NCI-H716-Colon cancer | 0.0 | T24-Bladder carcinma (transitional cell) | 0.0 |
| SW-48-Colon adenocarcinoma | 100.0 | 5637-Bladder carcinoma | 0.0 |
| SW1116-Colon adenocarcinoma | 0.0 | HT-1197-Bladder carcinoma | 0.0 |
| LS 174T-Colon adenocarcinoma | 79.6 | UM-UC-3-Bladder carcinma (transitional cell) | 0.0 |
| SW-948-Colon adenocarcinoma | 0.0 | A204-Rhabdomyosarcoma | 0.0 |
| SW-480-Colon adenocarcinoma | 0.0 | HT-1080-Fibrosarcoma | 0.0 |
| NCI-SNU-5-Gastric carcinoma | 0.0 | MG-63-Osteosarcoma | 0.0 |
| KATO III-Gastric carcinoma | 4.2 | SK-LMS-1-Leiomyosarcoma (vulva) | 0.0 |
| NCI-SNU-16-Gastric carcinoma | 0.0 | SJRH30-Rhabdomyosarcoma (met to bone marrow) | 0.0 |
| NCI-SNU-1-Gastric carcinoma | 0.0 | A431-Epidermoid carcinoma | 0.0 |
| RF-1-Gastric adenocarcinoma | 0.0 | WM266-4-Melanoma | 0.0 |

TABLE KL-continued

Panel 3D

| Tissue Name | Rel. Exp. (%) Ag3374, Run 165039071 | Tissue Name | Rel. Exp. (%) Ag3374, Run 165039071 |
|---|---|---|---|
| RF-48-Gastric adenocarcinoma | 0.0 | DU 145-Prostate carcinoma (brain metastasis) | 0.0 |
| MKN-45-Gastric carcinoma | 0.0 | MDA-MB-468-Breast adenocarcinoma | 0.0 |
| NCI-N87-Gastric carcinoma | 0.0 | SCC-4-Squamous cell carcinoma of tongue | 0.0 |
| OVCAR-5-Ovarian carcinoma | 0.0 | SCC-9-Squamous cell carcinoma of tongue | 0.0 |
| RL95-2-Uterine carcinoma | 0.0 | SCC-15-Squamous cell carcinoma of tongue | 0.0 |
| HelaS3-Cervical adenocarcinoma | 0.0 | CAL 27-Squamous cell carcinoma of tongue | 0.0 |

TABLE KM

Panel 4.1D

| Tissue Name | Rel. Exp. (%) Ag4269, Run 182243380 | Rel. Exp. (%) Ag5115, Run 226444771 | Tissue Name | Rel. Exp. (%) Ag4269, Run 182243380 | Rel. Exp. (%) Ag5115, Run 226444771 |
|---|---|---|---|---|---|
| Secondary Th1 act | 0.4 | 0.0 | HUVEC IL-1beta | 0.0 | 0.0 |
| Secondary Th2 act | 0.4 | 0.0 | HUVEC IFN gamma | 0.1 | 0.0 |
| Secondary Tr1 act | 0.0 | 0.0 | HUVEC TNF alpha + IFN gamma | 0.0 | 0.0 |
| Secondary Th1 rest | 0.0 | 0.0 | HUVEC TNF alpha + IL4 | 0.0 | 0.0 |
| Secondary Th2 rest | 0.1 | 0.0 | HUVEC IL-11 | 0.2 | 0.0 |
| Secondary Tr1 rest | 0.2 | 0.0 | Lung Microvascular EC none | 0.2 | 0.0 |
| Primary Th1 act | 0.3 | 0.0 | Lung Microvascular EC TNF alpha + IL-1beta | 0.0 | 0.0 |
| Primary Th2 act | 0.3 | 0.0 | Microvascular Dermal EC none | 0.1 | 0.0 |
| Primary Tr1 act | 0.1 | 0.0 | Microsvasular Dermal EC TNF alpha + IL-1beta | 0.0 | 0.0 |
| Primary Th1 rest | 0.1 | 0.0 | Bronchial epithelium TNF alpha + IL1beta | 0.0 | 0.0 |
| Primary Th2 rest | 0.1 | 0.0 | Small airway epithelium none | 0.0 | 0.0 |
| Primary Tr1 rest | 0.2 | 0.0 | Small airway epithelium TNF alpha + IL-1beta | 0.0 | 0.0 |
| CD45RA CD4 lymphocyte act | 0.0 | 0.0 | Coronery artery SMC rest | 0.1 | 0.0 |
| CD45RO CD4 lymphocyte act | 0.5 | 0.0 | Coronery artery SMC TNF alpha + IL-1beta | 0.0 | 0.0 |
| CD8 lymphocyte act | 0.4 | 0.0 | Astrocytes rest | 0.0 | 0.0 |
| Secondary CD8 lymphocyte rest | 0.5 | 0.0 | Astrocytes TNF alpha + IL-1beta | 0.0 | 0.0 |
| Secondary CD8 lymphocyte act | 1.1 | 0.0 | KU-812 (Basophil) rest | 0.0 | 0.0 |
| CD4 lymphocyte none | 0.1 | 0.0 | KU-812 (Basophil) PMA/ionomycin | 0.0 | 0.0 |

TABLE KM-continued

Panel 4.1D

| Tissue Name | Rel. Exp. (%) Ag4269, Run 182243380 | Rel. Exp. (%) Ag5115, Run 226444771 | Tissue Name | Rel. Exp. (%) Ag4269, Run 182243380 | Rel. Exp. (%) Ag5115, Run 226444771 |
|---|---|---|---|---|---|
| 2ry Th1/Th2/Tr1__anti-CD95 CH11 | 0.0 | 0.0 | CCD1106 (Keratinocytes) none | 0.0 | 0.0 |
| LAK cells rest | 0.1 | 0.0 | CCD1106 (Keratinocytes) TNF alpha + IL-1beta | 0.0 | 0.0 |
| LAK cells IL-2 | 0.4 | 0.0 | Liver cirrhosis | 26.4 | 20.3 |
| LAK cells IL-2 + IL-12 | 0.2 | 0.0 | NCI-H292 none | 0.0 | 0.0 |
| LAK cells IL-2 + IFN gamma | 0.3 | 0.0 | NCI-H292 IL-4 | 0.0 | 0.0 |
| LAK cells IL-2 + IL-18 | 0.4 | 0.0 | NCI-H292 IL-9 | 0.1 | 0.0 |
| LAK cells PMA/ionomycin | 0.5 | 0.0 | NCI-H292 IL-13 | 0.0 | 0.0 |
| NK Cells IL-2 rest | 0.4 | 0.0 | NCI-H292 IFN gamma | 0.0 | 0.0 |
| Two Way MLR 3 day | 0.0 | 0.0 | HPAEC none | 0.0 | 0.0 |
| Two Way MLR 5 day | 0.1 | 0.0 | HPAEC TNF alpha + IL-1beta | 0.0 | 0.0 |
| Two Way MLR 7 day | 0.1 | 0.0 | Lung fibroblast none | 0.1 | 0.0 |
| PBMC rest | 0.0 | 0.0 | Lung fibroblast TNF alpha + IL-1beta | 0.3 | 0.1 |
| PBMC PWM | 0.5 | 0.0 | Lung fibroblast IL-4 | 0.0 | 0.0 |
| PBMC PHA-L | 0.4 | 0.0 | Lung fibroblast IL-9 | 0.1 | 0.1 |
| Ramos (B cell) none | 0.3 | 0.0 | Lung fibroblast IL-13 | 0.1 | 0.1 |
| Ramos (B cell) ionomycin | 0.0 | 0.0 | Lung fibroblast IFN gamma | 0.1 | 0.0 |
| B lymphocytes PWM | 0.5 | 0.0 | Dermal fibroblast CCD1070 rest | 0.0 | 0.0 |
| B lymphocytes CD40L and IL-4 | 0.0 | 0.0 | Dermal fibroblast CCD1070 TNF alpha | 0.3 | 0.0 |
| EOL-1 dbcAMP | 0.1 | 0.0 | Dermal fibroblast CCD1070 IL-1beta | 0.0 | 0.0 |
| EOL-1 dbcAMP PMA/ionomycin | 0.0 | 0.0 | Dermal fibroblast IFN gamma | 0.6 | 0.2 |
| Dendritic cells none | 0.0 | 0.0 | Dermal fibroblast IL-4 | 0.1 | 0.1 |
| Dendritic cells LPS | 0.0 | 0.0 | Dermal Fibroblasts rest | 0.9 | 0.4 |
| Dendritic cells anti-CD40 | 0.0 | 0.0 | Neutrophils TNFa + LPS | 0.5 | 0.1 |
| Monocytes rest | 0.0 | 0.0 | Neutrophils rest | 0.3 | 0.4 |
| Monocytes LPS | 0.0 | 0.0 | Colon | 0.8 | 0.5 |
| Macrophages rest | 0.0 | 0.0 | Lung | 1.8 | 1.1 |
| Macrophages LPS | 0.0 | 0.0 | Thymus | 8.8 | 8.1 |
| HUVEC none | 0.0 | 0.0 | Kidney | 100.0 | 100.0 |
| HUVEC starved | 0.0 | 0.0 | | | |

TABLE KN

Panel 4D

| Tissue Name | Rel. Exp. (%) Ag3374, Run 165296618 | Tissue Name | Rel. Exp. (%) Ag3374, Run 165296618 |
|---|---|---|---|
| Secondary Th1 act | 0.0 | HUVEC IL-1 beta | 0.0 |
| Secondary Th2 act | 0.0 | HUVEC IFN gamma | 0.0 |
| Secondary Tr1 act | 0.0 | HUVEC TNF alpha + | 0.0 |

TABLE KN-continued

Panel 4D

| Tissue Name | Rel. Exp. (%) Ag3374, Run 165296618 | Tissue Name | Rel. Exp. (%) Ag3374, Run 165296618 |
|---|---|---|---|
| Secondary Th1 rest | 0.0 | IFN gamma HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1 beta | 0.0 |
| Primary Th2 act | 0.0 | Microvascular Dermal EC none | 0.0 |
| Primary Tr1 act | 0.0 | Microsvasular Dermal EC TNF alpha + IL-1 beta | 0.0 |
| Primary Th1 rest | 0.0 | Bronchial epithelium TNF alpha + IL1 beta | 0.0 |
| Primary Th2 rest | 0.0 | Small airway epithelium none | 0.0 |
| Primary Tr1 rest | 0.0 | Small airway epithelium TNF alpha + IL-1 beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1 beta | 0.0 |
| CD8 lymphocyte act | 0.0 | Astrocytes rest | 0.0 |
| Secondary CD8 lymphocyte rest | 0.0 | Astrocytes TNF alpha + IL-1 beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1 beta | 0.0 |
| LAK cells IL-2 | 0.0 | Liver cirrhosis | 11.6 |
| LAK cells IL-2 + IL-12 | 0.0 | Lupus kidney | 0.7 |
| LAK cells IL-2 + IFN gamma | 0.0 | NCI-H292 none | 0.0 |
| LAK cells IL-2 + IL-18 | 0.0 | NCI-H292 IL-4 | 0.0 |
| LAK cells PMA/ionomycin | 0.0 | NCI-H292 IL-9 | 0.0 |
| NK Cells IL-2 rest | 0.0 | NCI-H292 IL-13 | 0.0 |
| Two Way MLR 3 day | 0.0 | NCI-H292 IFN gamma | 0.0 |
| Two Way MLR 5 day | 0.0 | HPAEC none | 0.0 |
| Two Way MLR 7 day | 0.0 | HPAEC TNF alpha + IL-1 beta | 0.0 |
| PBMC rest | 0.0 | Lung fibroblast none | 0.0 |
| PBMC PWM | 0.0 | Lung fibroblast TNF alpha + IL-1 beta | 0.0 |
| PBMC PHA-L | 0.0 | Lung fibroblast IL-4 | 0.0 |
| Ramos (B cell) none | 0.0 | Lung fibroblast IL-9 | 0.0 |
| Ramos (B cell) ionomycin | 0.0 | Lung fibroblast IL-13 | 0.0 |
| B lymphocytes PWM | 0.0 | Lung fibroblast IFN gamma | 0.0 |
| B lymphocytes CD40L and IL-4 | 0.0 | Dermal fibroblast CCD1070 rest | 0.0 |
| EOL-1 dbcAMP | 0.0 | Dermal fibroblast CCD1070 TNF alpha | 0.0 |
| EOL-1 dbcAMP PMA/ionomycin | 0.0 | Dermal fibroblast CCD1070 IL-1 beta | 0.0 |
| Dendritic cells none | 0.0 | Dermal fibroblast IFN gamma | 0.0 |
| Dendritic cells LPS | 0.0 | Dermal fibroblast IL-4 | 0.0 |
| Dendritic cells anti-CD40 | 0.0 | IBD Colitis 2 | 0.0 |
| Monocytes rest | 0.0 | IBD Crohn's | 0.0 |
| Monocytes LPS | 0.0 | Colon | 0.0 |
| Macrophages rest | 0.0 | Lung | 0.0 |
| Macrophages LPS | 0.0 | Thymus | 100.0 |
| HUVEC none | 0.0 | Kidney | 0.0 |
| HUVEC starved | 0.0 | | |

TABLE KO

General oncology screening panel_v_2.4

| Tissue Name | Rel. Exp. (%) Ag5115, Run 260280407 | Tissue Name | Rel. Exp. (%) Ag5115, Run 260280407 |
|---|---|---|---|
| Colon cancer 1 | 0.0 | Bladder cancer NAT 2 | 0.0 |
| Colon cancer NAT 1 | 0.0 | Bladder cancer NAT 3 | 0.0 |
| Colon cancer 2 | 0.0 | Bladder cancer NAT 4 | 0.0 |
| Colon cancer NAT 2 | 0.0 | Adenocarcinoma of the prostate 1 | 0.0 |
| Colon cancer 3 | 0.1 | Adenocarcinoma of the prostate 2 | 0.0 |
| Colon cancer NAT 3 | 0.1 | Adenocarcinoma of the prostate 3 | 0.0 |
| Colon malignant cancer 4 | 0.0 | Adenocarcinoma of the prostate 4 | 0.0 |
| Colon normal adjacent tissue 4 | 0.0 | Prostate cancer NAT 5 | 0.0 |
| Lung cancer 1 | 0.0 | Adenocarcinoma of the prostate 6 | 0.0 |
| Lung NAT 1 | 0.0 | Adenocarcinoma of the prostate 7 | 0.0 |
| Lung cancer 2 | 0.0 | Adenocarcinoma of the prostate 8 | 0.0 |
| Lung NAT 2 | 0.0 | Adenocarcinoma of the prostate 9 | 0.0 |
| Squamous cell carcinoma 3 | 0.0 | Prostate cancer NAT 10 | 0.0 |
| Lung NAT 3 | 0.0 | Kidney cancer 1 | 0.0 |
| metastatic melanoma 1 | 0.0 | KidneyNAT 1 | 4.4 |
| Melanoma 2 | 0.0 | Kidney cancer 2 | 2.0 |
| Melanoma 3 | 0.0 | Kidney NAT 2 | 100.0 |
| metastatic melanoma 4 | 0.0 | Kidney cancer 3 | 0.0 |
| metastatic melanoma 5 | 0.0 | Kidney NAT 3 | 24.3 |
| Bladder cancer 1 | 0.0 | Kidney cancer 4 | 0.0 |
| Bladder cancer NAT 1 | 0.0 | Kidney NAT 4 | 12.9 |
| Bladder cancer 2 | 0.0 | | |

CNS_neurodegeneration_v1.0 Summary: Ag4269/Ag5115 These panels do not show differential expression of this gene in Alzheimer's disease. However, this expression profile shows that this gene is expressed at low levels in the CNS, including the hippocampus and cortex. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

General_screening_panel_v1.4 Summary: Ag4269 Highest expression is seen in fetal liver (CT=25). Moderate to low levels of expression are seen in liver, fetal kidney, and cell lines derived from colon and liver cancer. This expression is in agreement with expression in Panel 1.3D, where expression is seen in kidney and liver derived tissues. Thus, expression of this gene could be used as a marker of these tissues.

General_screening_panel_v1.5 Summary: Ag5115 Highest expression of the NOV12E gene is seen in fetal liver (CT=25.2) and liver. Moderate levels of expression are seen in the whole brain, a colon cancer cell line and fetal kidney. Low but significant levels of expression are seen in the hippocampus and fetal lung. This expression is in agreement with expression seen in other panels. However, the NOV12E gene is also detected in fetal lung. Ag5116 This experiment shows low/undetectable levels (CTs>35) of expression in all samples on this panel (data not shown).

Panel 1.3D Summary: Ag3374 Expression of this gene is restricted to a few samples, with highest expression in liver (CT=24.1), fetal liver, and kidney. Moderate expression is seen in fetal kidney and low levels of expression are seen in a colon cancer cell line. This expression profile suggests that this gene could be used to differentiate between liver and other samples on this panel and as a marker of liver and kidney tissue.

Panel 2.2 Summary: See Panel 2D for discussion. Panel 2.2 confirms the results in 2D.

Panel 2D Summary: Ag3374 Highest expression of this gene is seen in liver derived tissue (CT=23.9), with expression in this panel restricted to liver and kidney derived tissue. This expression is in agreement with expression seen in Panel 1.3D. In addition, this gene is more highly expressed in kidney tissue when compared to normal adjacent tissue. This gene encodes a putative kininogen, which has been shown to inhibit angiogenesis (Colman R. Blood. 95:543; Guo Y. Arterioscler Thromb Vase Biol. September 2001, pg. 1427). The expressed protein can also be used in the treatment of kidney cancers as it is not expressed in kidney cancers compared to the adjacent normal tissues and inhibition of its activity using antibodies or small molecule drugs may be useful in treating liver cancer. Thus, therapeutic modulation of the expression or function of this gene could be effective in the treatment of liver and kidney cancers.

Panel 3D Summary: Ag3374 Expression in this panel is restricted to samples derived from colon cancer cell lines (CTs=34–35). Thus, expression of this gene could be used to differentiate between this sample and other samples on this panel and as a marker to detect the presence of colon cancer. Furthermore, therapeutic modulation of the expression or function of this gene may be effective in the treatment of colon cancer. A second experiment with probe and primer set Ag4269 shows low/undetectable levels of expression (CTs>35). (Data not shown.)

Panel 4.1D Summary: Ag5115/Ag4269 Two experiments with two different probe and primer sets are in good agreement with highest expression of the NOV12E in the kidney (CTs=27). In addition, moderate levels of expression of this gene are also seen in thymus, lung and colon. The probe and primer sets for Ag5115 are specific to NOV12E. In a second experiment with Ag4269 low levels of expression of this gene is also seen in selected samples, including T cells, neutrophils, and activated dermal fibroblasts.

Panel 4D Summary: Ag3374 This transcript is most highly expressed in the thymus (CT=24.3). The protein encoded by this gene could therefore play an important role in T cell development. Thus, therapeutic modulation of the expression or function of this gene may modulate immune function (T cell development) and be important for organ transplant, AIDS treatment or post chemotherapy immune reconstitution.

In addition, moderate levels of expression are seen in liver cirrhosis and lupus kidney, in agreement with previous panels that showed expression in liver and kidney derived tissues.

General oncology screening panel_v_2.4 Summary: Ag5115 Expression of the NOV12E is restricted to kidney-derived tissue (highest CT=26). In addition, expression is higher in normal tissue than in adjacent tumor. Thus, expression of this gene could be used as a marker of kidney tissue. Furthermore, therapeutic modulation of this putative kininogen may be effective in the treatment of kidney cancer as a protein therapeutic. Ag5116 This experiment shows low/undetectable levels (CTs>35) of expression in all samples on this panel (data not shown).

L. NOV13A: Serine Protease-CUB Domain Protein
Expression of gene NOV13A, representing a full-length physical clone, was assessed using the primer-probe set Ag6855, described in Table LA. Results of the RTQ-PCR runs are shown in Table LB.

TABLE LA

Probe Name Ag6855

| Primers | Sequences | Length | Start Position | SEQ ID No |
|---|---|---|---|---|
| Forward | 5'-ctttacttcatgcacttcaacttg-3' | 24 | 403 | 181 |
| Probe | TET-5'-cctcctacctttgtgaatatgactatgtga-3'-TAMRA | 30 | 431 | 182 |
| Reverse | 5'-actctcgaagtgtcctcagtttc-3' | 23 | 466 | 183 |

TABLE LB

General_screening_panel_v1.6

| Tissue Name | Rel. Exp. (%) Ag6855, Run 278020605 | Tissue Name | Rel. Exp. (%) Ag6855, Run 278020605 |
|---|---|---|---|
| Adipose | 0.0 | Renal ca. TK-10 | 10.6 |
| Melanoma* Hs688(A).T | 23.3 | Bladder | 0.0 |
| Melanoma* Hs688(B).T | 22.7 | Gastric ca. (liver met.) NCI-N87 | 0.0 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 0.0 | Colon ca. HT29 | 0.0 |
| Prostate ca.* (bone met) PC-3 | 0.0 | Colon ca. HCT-116 | 0.0 |
| Prostate Pool | 7.0 | Colon ca. CaCo-2 | 0.0 |
| Placenta | 0.0 | Colon cancer tissue | 0.0 |
| Uterus Pool | 27.4 | Colon ca. SW1116 | 0.0 |
| Ovarian ca. OVCAR-3 | 0.0 | Colon ca. Colo-205 | 0.0 |
| Ovarian ca. SK-OV-3 | 0.0 | Colon ca. SW-48 | 0.0 |
| Ovarian ca. OVCAR-4 | 0.0 | Colon Pool | 37.1 |
| Ovarian ca. OVCAR-5 | 0.0 | Small Intestine Pool | 77.9 |
| Ovarian ca. IGROV-1 | 0.0 | Stomach Pool | 16.0 |
| Ovarian ca. OVCAR-8 | 0.0 | Bone Marrow Pool | 23.0 |
| Ovary | 5.8 | Fetal Heart | 73.2 |
| Breast ca. MCF-7 | 0.0 | Heart Pool | 43.8 |
| Breast ca. MDA-MB-231 | 0.0 | Lymph Node Pool | 41.5 |
| Breast ca. BT 549 | 0.0 | Fetal Skeletal Muscle | 11.5 |
| Breast ca. T47D | 0.0 | Skeletal Muscle Pool | 9.5 |
| Breast ca. MDA-N | 0.0 | Spleen Pool | 0.0 |
| Breast Pool | 27.5 | Thymus Pool | 22.7 |
| Trachea | 9.9 | CNS cancer (glio/astro) U87-MG | 0.0 |
| Lung | 0.0 | CNS cancer (glio/astro) U-118-MG | 47.3 |
| Fetal Lung | 8.8 | CNS cancer (neuro;met) SK-N-AS | 0.0 |
| Lung ca. NCI-N417 | 0.0 | CNS cancer (astro) SF-539 | 0.0 |
| Lung ca. LX-1 | 0.0 | CNS cancer (astro) SNB-75 | 0.0 |
| Lung ca. NCI-H146 | 0.0 | CNS cancer (glio) SNB-19 | 0.0 |
| Lung ca. SHP-77 | 0.0 | CNS cancer (glio) SF-295 | 32.1 |
| Lung ca. A549 | 0.0 | Brain (Amygdala) Pool | 0.0 |

TABLE LB-continued

General_screening_panel_v1.6

| Tissue Name | Rel. Exp. (%) Ag6855, Run 278020605 | Tissue Name | Rel. Exp. (%) Ag6855, Run 278020605 |
|---|---|---|---|
| Lung ca. NCI-H526 | 0.0 | Brain (cerebellum) | 21.3 |
| Lung ca. NCI-H23 | 0.0 | Brain (fetal) | 46.0 |
| Lung ca. NCI-H460 | 0.0 | Brain (Hippocampus) Pool | 14.0 |
| Lung ca. HOP-62 | 0.0 | Cerebral Cortex Pool | 4.9 |
| Lung ca. NCI-H522 | 0.0 | Brain (Substantia nigra) Pool | 6.3 |
| Liver | 94.0 | Brain (Thalamus) Pool | 7.2 |
| Fetal Liver | 100.0 | Brain (whole) | 9.9 |
| Liver ca. HepG2 | 25.7 | Spinal Cord Pool | 46.7 |
| Kidney Pool | 86.5 | Adrenal Gland | 10.9 |
| Fetal Kidney | 0.0 | Pituitary gland Pool | 0.0 |
| Renal ca. 786-0 | 0.0 | Salivary Gland | 0.0 |
| Renal ca. A498 | 0.0 | Thyroid (female) | 0.0 |
| Renal ca. ACHN | 0.0 | Pancreatic ca. CAPAN2 | 0.0 |
| Renal ca. UO-31 | 0.0 | Pancreas Pool | 0.0 |

General_screening_panel v1.6 Summary: Ag6855 Expression of the NOV13A gene is limited to the fetal liver (CT=34.9). Thus, expression of this gene may be used as a marker of this tissue.

M. NOV14A: Hemopexin

Expression of gene NOV14A, representing a full-length physical clone, was assessed using the primer-probe set Ag6949, described in Table MA. Results of the RTQ-PCR runs are shown in Table MB.

TABLE MA

Probe Name Ag6949

| Primers | Sequences | Length | Start Position | SEQ ID No |
|---|---|---|---|---|
| Forward | 5'-tttaaagggacccactactgg-3' | 22 | 625 | 184 |
| Probe | TET-5'-ctggcatagctggcccattgctcat-3'-TAMRA | 25 | 577 | 185 |
| Reverse | 5'-gaaaaggcagcatccactg-3' | 19 | 536 | 186 |

TABLE MB

General_screening_panel_v1.6

| Tissue Name | Rel. Exp. (%) Ag6949, Run 279032765 | Tissue Name | Rel. Exp. (%) Ag6949, Run 279032765 |
|---|---|---|---|
| Adipose | 0.0 | Renal ca. TK-10 | 0.2 |
| Melanoma* Hs688(A).T | 0.0 | Bladder | 0.2 |
| Melanoma* Hs688(B).T | 0.1 | Gastric ca. (liver met.) NCI-N87 | 0.1 |
| Melanoma* M14 | 0.1 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.1 |
| Testis Pool | 0.1 | Colon ca. HT29 | 0.0 |
| Prostate ca.* (bone met) PC-3 | 0.1 | Colon ca. HCT-116 | 0.2 |
| Prostate Pool | 0.1 | Colon ca. CaCo-2 | 3.3 |
| Placenta | 0.0 | Colon cancer tissue | 0.1 |
| Uterus Pool | 0.0 | Colon ca. SW1116 | 0.0 |
| Ovarian ca. OVCAR-3 | 0.1 | Colon ca. Colo-205 | 0.0 |
| Ovarian ca. SK-OV-3 | 0.1 | Colon ca. SW-48 | 0.0 |

TABLE MB-continued

General_screening_panel_v1.6

| Tissue Name | Rel. Exp. (%) Ag6949, Run 279032765 | Tissue Name | Rel. Exp. (%) Ag6949, Run 279032765 |
|---|---|---|---|
| Ovarian ca. OVCAR-4 | 0.0 | Colon Pool | 0.1 |
| Ovarian ca. OVCAR-5 | 0.5 | Small Intestine Pool | 0.1 |
| Ovarian ca. IGROV-1 | 0.0 | Stomach Pool | 0.1 |
| Ovarian ca. OVCAR-8 | 0.0 | Bone Marrow Pool | 0.0 |
| Ovary | 0.1 | Fetal Heart | 0.1 |
| Breast ca. MCF-7 | 0.3 | Heart Pool | 0.0 |
| Breast ca. MDA-MB-231 | 0.0 | Lymph Node Pool | 0.1 |
| Breast ca. BT 549 | 0.1 | Fetal Skeletal Muscle | 0.0 |
| Breast ca. T47D | 0.2 | Skeletal Muscle Pool | 0.0 |
| Breast ca. MDA-N | 0.0 | Spleen Pool | 0.0 |
| Breast Pool | 0.1 | Thymus Pool | 0.1 |
| Trachea | 0.1 | CNS cancer (glio/astro) U87-MG | 0.0 |
| Lung | 0.1 | CNS cancer (glio/astro) U-118-MG | 0.1 |
| Fetal Lung | 0.4 | CNS cancer (neuro;met) SK-N-AS | 0.1 |
| Lung ca. NCI-N417 | 0.0 | CNS cancer (astro) SF-539 | 0.0 |
| Lung ca. LX-1 | 0.0 | CNS cancer (astro) SNB-75 | 0.2 |
| Lung ca. NCI-H146 | 0.0 | CNS cancer (glio) SNB-19 | 0.0 |
| Lung ca. SHP-77 | 0.0 | CNS cancer (glio) SF-295 | 0.2 |
| Lung ca. A549 | 0.1 | Brain (Amygdala) Pool | 0.0 |
| Lung ca. NCI-H526 | 0.0 | Brain (cerebellum) | 0.4 |
| Lung ca. NCI-H23 | 0.1 | Brain (fetal) | 0.4 |
| Lung ca. NCI-H460 | 0.0 | Brain (Hippocampus) Pool | 0.0 |
| Lung ca. HOP-62 | 0.1 | Cerebral Cortex Pool | 0.0 |
| Lung ca. NCI-H522 | 0.0 | Brain (Substantia nigra) Pool | 0.0 |
| Liver | 100.0 | Brain (Thalamus) Pool | 0.0 |
| Fetal Liver | 87.7 | Brain (whole) | 1.7 |
| Liver ca. HepG2 | 0.2 | Spinal Cord Pool | 0.0 |
| Kidney Pool | 0.2 | Adrenal Gland | 0.0 |
| Fetal Kidney | 0.1 | Pituitary gland Pool | 0.0 |
| Renal ca. 786-0 | 0.0 | Salivary Gland | 0.0 |
| Renal ca. A498 | 0.0 | Thyroid (female) | 0.0 |
| Renal ca. ACHN | 0.0 | Pancreatic ca. CAPAN2 | 0.0 |
| Renal ca. UO-31 | 0.1 | Pancreas Pool | 0.0 |

General_screening_panel_v1.6 Summary: Ag6949 Highest expression of the NOV14A gene is seen in the liver (CT=23). This gene encodes a homolog of hemopexin, a heme binding glycoprotein synthesized in the liver that has been implicated in the transport of heme into liver cells. Thus, expression of this gene could be used as a marker of liver tissue and to differentiate these liver derived samples from other samples on this panel.

Orthologues of hemopexin appear to be upregulated in hepatocellular carcinoma cells infected with woodchuck hepatitis B (Darabi A. Cancer Lett 1995 August 16;95(1–2): 153–9). Thus, based on the preferential expression of this gene in liver and the homology of this gene to hemopexin, therapeutic modulation of the expression or function of this gene may be effective in the treatment of liver cancer.

N. NOV15A: F2 Alpha Prostoglandin Regulatory Protein

Expression of gene NOV15A was assessed using the primer-probe set Ag4383, described in Table NA. Results of the RTQ-PCR runs are shown in Tables NB, NC, ND and NE.

TABLE NA

Probe Name Ag4383

| Primers | Sequences | Length | Start Position | SEQ ID No |
|---|---|---|---|---|
| Forward | 5'-agaccaaggccactacaaatgt-3' | 22 | 350 | 187 |
| Probe | TET-5'-cacagatgccactgtccagggaa-3'-TAMRA | 23 | 383 | 188 |
| Reverse | 5'-acctgcactgtgtcctcatagt-3' | 22 | 406 | 189 |

TABLE NB

CNS_neurodegeneration_v1.0

| Tissue Name | Rel. Exp. (%) Ag4383, Run 224502235 | Tissue Name | Rel. Exp. (%) Ag4383, Run 224502235 |
|---|---|---|---|
| AD 1 Hippo | 12.9 | Control (Path) 3 Temporal Ctx | 7.0 |
| AD 2 Hippo | 23.8 | Control (Path) 4 Temporal Ctx | 34.9 |
| AD 3 Hippo | 3.4 | AD 1 Occipital Ctx | 7.4 |
| AD 4 Hippo | 6.1 | AD 2 Occipital Ctx (Missing) | 0.0 |
| AD 5 Hippo | 67.4 | AD 3 Occipital Ctx | 2.7 |
| AD 6 Hippo | 41.8 | AD 4 Occipital Ctx | 19.5 |
| Control 2 Hippo | 22.8 | AD 5 Occipital Ctx | 46.7 |
| Control 4 Hippo | 16.5 | AD 6 Occipital Ctx | 9.7 |
| Control (Path) 3 Hippo | 6.7 | Control 1 Occipital Ctx | 3.7 |
| AD 1 Temporal Ctx | 16.0 | Control 2 Occipital Ctx | 46.3 |
| AD 2 Temporal Ctx | 17.0 | Control 3 Occipital Ctx | 12.8 |
| AD 3 Temporal Ctx | 5.8 | Control 4 Occipital Ctx | 8.2 |
| AD 4 Temporal Ctx | 19.5 | Control (Path) 1 Occipital Ctx | 83.5 |
| AD 5 Inf Temporal Ctx | 72.7 | Control (Path) 2 Occipital Ctx | 7.1 |
| AD 5 Sup Temporal Ctx | 31.2 | Control (Path) 3 Occipital Ctx | 1.6 |
| AD 6 Inf Temporal Ctx | 38.2 | Control (Path) 4 Occipital Ctx | 10.8 |
| AD 6 Sup Temporal Ctx | 47.6 | Control 1 Parietal Ctx | 8.7 |
| Control 1 Temporal Ctx | 9.8 | Control 2 Parietal Ctx | 36.9 |
| Control 2 Temporal Ctx | 59.5 | Control 3 Parietal Ctx | 15.8 |
| Control 3 Temporal Ctx | 9.7 | Control (Path) 1 Parietal Ctx | 100.0 |
| Control 3 Temporal Ctx | 16.3 | Control (Path) 2 Parietal Ctx | 18.3 |
| Control (Path) 1 Temporal Ctx | 67.8 | Control (Path) 3 Parietal Ctx | 5.5 |
| Control (Path) 2 Temporal Ctx | 44.1 | Control (Path) 4 Parietal Ctx | 45.1 |

TABLE NC

General_screening_panel_v1.4

| Tissue name | Rel. Exp. (%) Ag4383, Run 222567780 | Tissue name | Rel. Exp. (%) Ag4383, Run 222567780 |
|---|---|---|---|
| Adipose | 1.0 | Renal ca. TK-10 | 12.2 |
| Melanoma* Hs688(A).T | 10.4 | Bladder | 4.8 |
| Melanoma* Hs688(B).T | 11.9 | Gastric ca. (liver met.) NCI-N87 | 7.3 |
| Melanoma* M14 | 31.6 | Gastric ca. KATO III | 24.8 |

TABLE NC-continued

General_screening_panel_v1.4

| Tissue name | Rel. Exp. (%) Ag4383, Run 222567780 | Tissue name | Rel. Exp. (%) Ag4383, Run 222567780 |
|---|---|---|---|
| Melanoma* LOXIMVI | 0.0 | Colon ca. SW-948 | 5.5 |
| Melanoma* SK-MEL-5 | 4.1 | Colon ca. SW480 | 11.3 |
| Squamous cell carcinoma SCC-4 | 16.4 | Colon ca.* (SW480 met) SW620 | 3.9 |
| Testis Pool | 2.0 | Colon ca. HT29 | 3.4 |
| Prostate ca.* (bone met) PC-3 | 1.3 | Colon ca. HCT-116 | 16.4 |
| Prostate Pool | 1.7 | Colon ca. CaCo-2 | 2.8 |
| Placenta | 5.3 | Colon cancer tissue | 8.2 |
| Uterus Pool | 1.7 | Colon ca. SW1116 | 3.7 |
| Ovarian ca. OVCAR-3 | 10.2 | Colon ca. Colo-205 | 3.0 |
| Ovarian ca. SK-OV-3 | 9.0 | Colon ca. SW-48 | 6.9 |
| Ovarian ca. OVCAR-4 | 3.4 | Colon Pool | 8.0 |
| Ovarian ca. OVCAR-5 | 15.8 | Small Intestine Pool | 7.5 |
| Ovarian ca. IGROV-1 | 10.2 | Stomach Pool | 4.1 |
| Ovarian ca. OVCAR-8 | 10.0 | Bone Marrow Pool | 2.5 |
| Ovary | 5.1 | Fetal Heart | 3.7 |
| Breast ca. MCF-7 | 3.7 | Heart Pool | 5.0 |
| Breast ca. MDA-MB-231 | 0.4 | Lymph Node Pool | 11.3 |
| Breast ca. BT 549 | 0.3 | Fetal Skeletal Muscle | 2.8 |
| Breast ca. T47D | 30.8 | Skeletal Muscle Pool | 0.7 |
| Breast ca. MDA-N | 6.0 | Spleen Pool | 0.9 |
| Breast Pool | 9.0 | Thymus Pool | 3.5 |
| Trachea | 5.4 | CNS cancer (glio/astro) U87-MG | 20.7 |
| Lung | 0.2 | CNS cancer (glio/astro) U-118-MG | 12.9 |
| Fetal Lung | 5.3 | CNS cancer (neuro; met) SK-N-AS | 6.8 |
| Lung ca. NCI-N417 | 4.7 | CNS cancer (astro) SF-539 | 17.1 |
| Lung ca. LX-1 | 7.3 | CNS cancer (astro) SNB-75 | 100.0 |
| Lung ca. NCI-H146 | 2.4 | CNS cancer (glio) SNB-19 | 8.7 |
| Lung ca. SHP-77 | 6.9 | CNS cancer (glio) SF-295 | 13.9 |
| Lung ca. A549 | 9.3 | Brain (Amygdala) Pool | 0.9 |
| Lung ca. NCI-H526 | 6.3 | Brain (cerebellum) | 0.9 |
| Lung ca. NCI-H23 | 1.9 | Brain (fetal) | 6.7 |
| Lung ca. NCI-H460 | 6.3 | Brain (Hippocampus) Pool | 1.0 |
| Lung ca. HOP-62 | 1.7 | Cerebral Cortex Pool | 1.6 |
| Lung ca. NCI-H522 | 0.6 | Brain (Substantia nigra) Pool | 1.6 |
| Liver | 0.3 | Brain (Thalamus) Pool | 2.0 |
| Fetal Liver | 1.8 | Brain (whole) | 1.9 |
| Liver ca. HepG2 | 3.4 | Spinal Cord Pool | 0.8 |
| Kidney Pool | 15.3 | Adrenal Gland | 6.2 |
| Fetal Kidney | 1.5 | Pituitary gland Pool | 0.4 |
| Renal ca. 786-0 | 34.4 | Salivary Gland | 3.3 |
| Renal ca. A498 | 7.7 | Thyroid (female) | 1.4 |
| Renal ca. ACHN | 3.2 | Pancreatic ca. CAPAN2 | 1.5 |
| Renal ca. UO-31 | 15.6 | Pancreas Pool | 10.1 |

TABLE ND

Panel CNS_1

| Tissue Name | Rel. Exp. (%) Ag4383, Run 190323005 | Tissue Name | Rel. Exp. (%) Ag4383, Run 190323005 |
|---|---|---|---|
| BA4 Control | 34.2 | BA17 PSP | 4.4 |
| BA4 Control2 | 28.9 | BA17 PSP2 | 10.9 |
| BA4 Alzheimer's2 | 0.0 | Sub Nigra Control | 21.5 |
| BA4 Parkinson's | 22.7 | Sub Nigra Control2 | 24.5 |
| BA4 Parkinson's2 | 50.0 | Sub Nigra Alzheimer's2 | 6.8 |
| BA4 Huntington's | 11.9 | Sub Nigra Parkinson's2 | 29.7 |
| BA4 Huntington's2 | 12.4 | Sub Nigra Huntington's | 42.3 |
| BA4 PSP | 3.3 | Sub Nigra Huntington's2 | 23.3 |
| BA4 PSP2 | 18.6 | Sub Nigra PSP2 | 3.1 |
| BA4 Depression | 12.3 | Sub Nigra Depression | 0.0 |
| BA4 Depression2 | 3.4 | Sub Nigra Depression2 | 10.6 |
| BA7 Control | 33.4 | Glob Palladus Control | 9.2 |
| BA7 Control2 | 45.4 | Glob Palladus Control2 | 3.4 |
| BA7 Alzheimer's2 | 3.1 | Glob Palladus Alzheimer's | 20.7 |
| BA7 Parkinson's | 14.8 | Glob Palladus Alzheimer's2 | 3.0 |
| BA7 Parkinson's2 | 33.2 | Glob Palladus Parkinson's | 40.1 |
| BA7 Huntington's | 30.8 | Glob Palladus Parkinson's2 | 11.6 |
| BA7 Huntington's2 | 73.2 | Glob Palladus PSP | 1.5 |
| BA7 PSP | 12.0 | Glob Palladus PSP2 | 6.5 |
| BA7 PSP2 | 20.6 | Glob Palladus Depression | 0.0 |
| BA7 Depression | 0.0 | Temp Pole Control | 17.9 |
| BA9 Control | 20.0 | Temp Pole Control2 | 48.0 |
| BA9 Control2 | 43.2 | Temp Pole Alzheimer's | 0.0 |
| BA9 Alzheimer's | 3.1 | Temp Pole Alzheimer's2 | 2.7 |
| BA9 Alzheimer's2 | 9.2 | Temp Pole Parkinson's | 13.6 |
| BA9 Parkinson's | 3.8 | Temp Pole Parkinson's2 | 36.9 |
| BA9 Parkinson's2 | 41.2 | Temp Pole Huntington's | 33.4 |
| BA9 Huntington's | 36.6 | Temp Pole PSP | 0.0 |
| BA9 Huntington's2 | 11.2 | Temp Pole PSP2 | 0.0 |
| BA9 PSP | 10.7 | Temp Pole Depression2 | 3.2 |
| BA9 PSP2 | 8.0 | Cing Gyr Control | 100.0 |
| BA9 Depression | 2.2 | Cing Gyr Control2 | 31.0 |
| BA9 Depression2 | 9.6 | Cing Gyr Alzheimer's | 31.2 |
| BA17 Control | 32.5 | Cing Gyr Alzheimer's2 | 3.5 |
| BA17 Control2 | 41.5 | Cing Gyr Parkinson's | 40.3 |
| BA17 Alzheimer's2 | 10.8 | Cing Gyr Parkinson's2 | 24.8 |
| BA17 Parkinson's | 8.7 | Cing Gyr Huntington's | 47.6 |
| BA17 Parkinson's2 | 25.9 | Cing Gyr Huntington's2 | 22.2 |
| BA17 Huntington's | 37.4 | Cing Gyr PSP | 0.0 |
| BA17 Huntington's2 | 16.7 | Cing Gyr PSP2 | 0.0 |
| BA17 | 5.2 | Cing Gyr | 6.8 |

TABLE ND-continued

Panel CNS_1

| Tissue Name | Rel. Exp. (%) Ag4383, Run 190323005 | Tissue Name | Rel. Exp. (%) Ag4383, Run 190323005 |
|---|---|---|---|
| Depression BA17 Depression2 | 12.1 | Depression Cing Gyr Depression2 | 6.4 |

TABLE NE

Panel_CNS_1.1

| Tissue Name | Rel. Exp. (%) Ag4383, Run 190028010 | Tissue Name | Rel. Exp. (%) Ag4383, Run 190028010 |
|---|---|---|---|
| Cing Gyr Depression2 | 7.8 | BA17 PSP2 | 4.2 |
| Cing Gyr Depression | 0.0 | BA17 PSP | 15.8 |
| Cing Gyr PSP2 | 3.9 | BA17 Huntington's2 | 2.3 |
| Cing Gyr PSP | 16.8 | BA17 Huntington's | 30.8 |
| Cing Gyr Huntington's2 | 14.6 | BA17 Parkinson's2 | 43.5 |
| Cing Gyr Huntington's | 46.7 | BA17 Parkinson's | 11.4 |
| Cing Gyr Parkinson's2 | 26.1 | BA17 Alzheimer's2 | 8.3 |
| Cing Gyr Parkinson's | 26.4 | BA17 Control2 | 60.7 |
| Cing Gyr Alzheimer's2 | 29.9 | BA17 Control | 35.1 |
| Cing Gyr Alzheimer's | 12.2 | BA9 Depression2 | 0.0 |
| Cing Gyr Control2 | 20.0 | BA9 Depression | 15.5 |
| Cing Gyr Control | 92.0 | BA9 PSP2 | 3.5 |
| Temp Pole Depression2 | 14.3 | BA9 PSP | 7.9 |
| Temp Pole PSP2 | 6.0 | BA9 Huntington's2 | 52.1 |
| Temp Pole PSP | 2.3 | BA9 Huntington's | 65.1 |
| Temp Pole Huntington's | 57.8 | BA9 Parkinson's2 | 100.0 |
| Temp Pole Parkinson's2 | 50.3 | BA9 Parkinson's | 51.4 |
| Temp Pole Parkinson's | 44.8 | BA9 Alzheimer's2 | 12.0 |
| Temp Pole Alzheimer's2 | 7.5 | BA9 Alzheimer's | 3.8 |
| Temp Pole Alzheimer's | 3.8 | BA9 Control2 | 91.4 |
| Temp Pole Control2 | 48.6 | BA9 Control | 7.7 |
| Temp Pole Control | 22.8 | BA7 Depression | 4.1 |
| Glob Palladus Depression | 0.0 | BA7 PSP2 | 24.0 |
| Glob Palladus PSP2 | 0.0 | BA7 PSP | 21.5 |
| Glob Palladus PSP | 0.0 | BA7 Huntington's2 | 54.3 |
| Glob Palladus Parkinson's2 | 3.5 | BA7 Huntington's | 82.9 |
| Glob Palladus Parkinson's | 83.5 | BA7 Parkinson's2 | 42.6 |
| Glob Palladus Alzheimer's2 | 6.5 | BA7 Parkinson's | 31.0 |
| Glob Palladus Alzheimer's | 8.5 | BA7 Alzheimer's2 | 4.1 |
| Glob Palladus Control2 | 4.0 | BA7 Control2 | 46.3 |
| Glob Palladus Control | 3.5 | BA7 Control | 48.3 |
| Sub Nigra Depression2 | 3.6 | BA4 Depression2 | 0.0 |
| Sub Nigra Depression | 0.0 | BA4 Depression | 0.0 |

TABLE NE-continued

Panel_CNS_1.1

| Tissue Name | Rel. Exp. (%) Ag4383, Run 190028010 | Tissue Name | Rel. Exp. (%) Ag4383, Run 190028010 |
|---|---|---|---|
| Sub Nigra PSP2 | 6.1 | BA4 PSP2 | 32.8 |
| Sub Nigra Huntington's2 | 30.4 | BA4 PSP | 7.4 |
| Sub Nigra Huntington's | 59.5 | BA4 Huntington's2 | 1.6 |
| Sub Nigra Parkinson's2 | 36.9 | BA4 Huntington's | 30.6 |
| SubNigra Alzheimer's2 | 0.0 | BA4 Parkinson's2 | 59.5 |
| Sub Nigra Control2 | 10.4 | BA4 Parkinson's | 62.0 |
| Sub Nigra Control | 40.6 | BA4 Alzheimer's2 | 11.0 |
| BA17 Depression2 | 6.0 | BA4 Control2 | 32.5 |
| BA17 Depression | 12.1 | BA4 Control | 28.9 |

CNS_neurodegeneration_v1.0 Summary: Ag4383 This panel confirms the expression of the NOV15A gene at low levels in the brains of an independent group of individuals. This gene is found to be slightly down-regulated in the temporal cortex of Alzheimer's disease patients when analyzed by ANCOVA (p=0.0087). Therefore, treatment with antagonists or agonists may prevent or delay the onset of AD.

General_screening_panel_v1.4 Summary: Ag4383 Highest expression of the NOV15A gene is detected in a CNS cancer cell line (CT=24.5). In addition, significant expression of this gene is seen in cluster of cancer cell lines including CNS, pancreatic, colon, gastric, renal, lung, breast, ovarian, squamous cell carcinoma and melanoma cancer cell lines. Therefore, therapeutic modulation of this gene product may be beneficial in the treatment of these cancers.

Among tissues with metabolic or endocrine function, this gene is expressed at high to moderate levels in pancreas, adipose, adrenal gland, thyroid, pituitary gland, skeletal muscle, heart, liver and the gastrointestinal tract. Therefore, therapeutic modulation of the activity of this gene may prove useful in the treatment of endocrine/metabolically related diseases, such as obesity and diabetes.

In addition, this gene is expressed at moderate levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression.

The NOV15A gene codes for a homologue of mouse F2 alpha prostaglandin regulatory protein (FPRP). FPRP, a cell-surface Ig superfamily protein, associates specifically with CD81 or with CD81 and CD9, but not with integrins or other TM4SF proteins (Stipp et al., 2001, J Biol Chem 276(7):4853–62, PMID: 11087758). CD81 is a critical regulator of neuron-induced astrocytic differentiation (Kelic et al., 2001, Mol Cell Neurosci 17(3):551–60, PMID: 11273649). Therefore, FPRP encoded by this gene may play a role in astrocyte differentiation and brain development.

Panel 4.1D Summary: Ag4383 Results from one experiment with the NOV15A gene are not included. The amp plot indicates that there were experimental difficulties with this run (data not shown).

Panel CNS_1 Summary: Ag4383 This panel confirms the expression of the NOV15A gene at low levels in the brains of an independent group of individuals. Please see Panel 1.4 for a discussion of the potential utility of this gene in treatment of central nervous system disorders.

Panel CNS_1.1 Summary: Ag4383 This panel confirms the expression of the NOV15A gene at low levels in the brains of an independent group of individuals. Please see Panel 1.4 for a discussion of the potential utility of this gene in treatment of central nervous system disorders.

O. NOV16A: Neuronal Leucine-Rich Repeat Protein

Expression of gene NOV16A was assessed using the primer-probe sets Ag4386 and Ag6885, described in Tables OA and OB. Results of the RTQ-PCR runs are shown in Tables OC, OD, OE and OF.

TABLE OA

Probe Name Ag4386

| Primers | Sequences | Length | Start Position | SEQ ID No |
|---|---|---|---|---|
| Forward | 5'-tcacatgacctttgactttgtg-3' | 22 | 1467 | 190 |
| Probe | TET-5'-acctcggccctctggggataaaa-3'-TAMRA | 23 | 1491 | 191 |
| Reverse | 5'-gaaggaaaggtcagaagagctt-3' | 22 | 1540 | 192 |

TABLE OB

Probe Name Ag6885

| Primers | Sequences | Length | Start Position | SEQ ID No |
|---|---|---|---|---|
| Forward | 5'-cctcaaggtgaccagtttgtc-3' | 21 | 811 | 193 |
| Probe | TET-5'-cgcccttcagacactagaggaaacag-3'-TAMRA | 26 | 771 | 194 |
| Reverse | 5'-ctcctggatgtggcagataa-3' | 20 | 751 | 195 |

TABLE OC

CNS_neurodegeneration_v1.0

| Tissue Name | Rel. Exp. (%) Ag4386, Run 224502238 | Tissue Name | Rel. Exp. (%) Ag4386, Run 224502238 |
|---|---|---|---|
| AD 1 Hippo | 6.8 | Control (Path) 3 Temporal Ctx | 0.0 |
| AD 2 Hippo | 11.4 | Control (Path) 4 Temporal Ctx | 11.7 |
| AD 3 Hippo | 6.3 | AD 1 Occipital Ctx | 11.3 |
| AD 4 Hippo | 0.0 | AD 2 Occipital Ctx (Missing) | 0.0 |
| AD 5 hippo | 100.0 | AD 3 Occipital Ctx | 3.0 |
| AD 6 Hippo | 24.5 | AD4 Occipital Ctx | 7.7 |
| Control 2 Hippo | 10.8 | AD 5 Occipital Ctx | 7.2 |
| Control 4 Hippo | 0.0 | AD 6 Occipital Ctx | 7.8 |
| Control (Path) 3 Hippo | 0.0 | Control 1 Occipital Ctx | 0.0 |
| AD 1 Temporal Ctx | 12.3 | Control 2 Occipital Ctx | 33.4 |
| AD 2 Temporal Ctx | 6.3 | Control 3 Occipital Ctx | 13.6 |
| AD 3 Temporal Ctx | 0.0 | Control 4 Occipital Ctx | 0.0 |
| AD 4 Temporal Ctx | 5.8 | Control (Path) 1 Occipital Ctx | 21.3 |
| AD 5 Inf Temporal Ctx | 37.9 | Control (Path) 2 Occipital Ctx | 3.8 |
| AD 5 SupTemporal Ctx | 25.9 | Control (Path) 3 Occipital Ctx | 0.0 |
| AD 6 Inf Temporal Ctx | 19.9 | Control (Path) 4 Occipital Ctx | 4.4 |
| AD 6 Sup Temporal Ctx | 18.0 | Control 1 Parietal Ctx | 8.1 |
| Control 1 Temporal Ctx | 0.0 | Control 2 Parietal Ctx | 8.7 |
| Control 2 Temporal Ctx | 5.9 | Control 3 Parietal Ctx | 5.6 |
| Control 3 Temporal Ctx | 0.0 | Control (Path) 1 Parietal Ctx | 8.9 |
| Control 4 Temporal Ctx | 0.0 | Control (Path) 2 Parietal Ctx | 0.0 |
| Control (Path) 1 Temporal Ctx | 7.9 | Control (Path) 3 Parietal Ctx | 0.0 |
| Control (Path) 2 Temporal Ctx | 12.4 | Control (Path) 4 Parietal Ctx | 11.3 |

TABLE OD

General_screening_panel_v1.4

| Tissue Name | Rel. Exp. (%) Ag4386, Run 222567010 | Tissue Name | Rel. Exp. (%) Ag4386, Run 222567010 |
|---|---|---|---|
| Adipose | 0.1 | Renal ca. TK-10 | 0.2 |
| Melanoma* Hs688(A).T | 0.0 | Bladder | 1.0 |

TABLE OD-continued

General_screening_panel_v1.4

| Tissue Name | Rel. Exp. (%) Ag4386, Run 222567010 | Tissue Name | Rel. Exp. (%) Ag4386, Run 222567010 |
|---|---|---|---|
| Melanoma* Hs688(B).T | 0.0 | Gastric ca. (liver met.) NCI-N87 | 0.4 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 0.3 |
| Squamous cell carcinoma SCC-4 | 0.0 | Colon ca.* (SW480 met) SW620 | 0.3 |
| Testis Pool | 1.7 | Colon ca. HT29 | 0.1 |
| Prostate ca.* (bone met) PC-3 | 0.0 | Colon ca. HCT-116 | 0.0 |
| Prostate Pool | 0.5 | Colon ca. CaCo-2 | 0.0 |
| Placenta | 0.0 | Colon cancer tissue | 0.0 |
| Uterus Pool | 0.0 | Colon ca. SW1116 | 0.0 |
| Ovarian ca. OVCAR-3 | 0.0 | Colon ca. Colo-205 | 0.1 |
| Ovarian ca. SK-OV-3 | 0.0 | Colon ca. SW-48 | 0.3 |
| Ovarian ca. OVCAR-4 | 0.0 | Colon Pool | 0.1 |
| Ovarian ca. OVCAR-5 | 1.5 | Small Intestine Pool | 0.2 |
| Ovarian ca. IGROV-1 | 0.1 | Stomach Pool | 0.1 |
| Ovarian ca. OVCAR-8 | 0.2 | Bone Marrow Pool | 0.1 |
| Ovary | 0.0 | Fetal Heart | 0.0 |
| Breast ca. MCF-7 | 1.8 | Heart Pool | 0.1 |
| Breast ca. MDA-MB-231 | 0.3 | Lymph Node Pool | 0.2 |
| Breast ca. BT 549 | 0.1 | Fetal Skeletal Muscle | 0.9 |
| Breast ca. T47D | 2.4 | Skeletal Muscle Pool | 22.5 |
| Breast ca. MDA-N | 0.0 | Spleen Pool | 0.4 |
| Breast Pool | 0.1 | Thymus Pool | 0.7 |
| Trachea | 0.9 | CNS cancer (glio/astro) U87-MG | 0.1 |
| Lung | 0.0 | CNS cancer (glio/astro) U-118-MG | 0.1 |
| Fetal Lung | 1.6 | CNS cancer (neuro; met) SK-N-AS | 0.3 |
| Lung ca. NCI-N417 | 0.0 | CNS cancer (astro) SF-539 | 0.0 |
| Lung ca. LX-1 | 0.4 | CNS cancer (astro) SNB-75 | 0.0 |
| Lung ca. NCI-H146 | 0.0 | CNS cancer (glio) SNB-19 | 0.0 |
| Lung ca. SHP-77 | 0.2 | CNS cancer (glio) SF-295 | 0.0 |
| Lung ca. A549 | 0.0 | Brain (Amygdala) Pool | 0.3 |
| Lung ca. NCI-H526 | 0.1 | Brain (cerebellum) | 100.0 |
| Lung ca. NCI-H23 | 0.1 | Brain (fetal) | 0.1 |
| Lung ca. NCI-H460 | 0.1 | Brain (Hippocampus) Pool | 0.1 |
| Lung ca. HOP-62 | 0.0 | Cerebral Cortex Pool | 0.0 |
| Lung ca. NCI-H522 | 0.0 | Brain (Substantia nigra) Pool | 0.1 |
| Liver | 0.7 | Brain (Thalamus) Pool | 1.1 |
| Fetal Liver | 0.2 | Brain (whole) | 1.6 |
| Liver ca. HepG2 | 0.0 | Spinal Cord Pool | 4.2 |
| Kidney Pool | 0.2 | Adrenal Gland | 1.4 |
| Fetal Kidney | 0.1 | Pituitary gland Pool | 0.9 |
| Renal ca. 786-0 | 0.2 | Salivary Gland | 1.3 |
| Renal ca. A498 | 0.0 | Thyroid (female) | 0.7 |
| Renal ca. ACHN | 0.1 | Pancreatic ca. CAPAN2 | 0.1 |
| Renal ca. UO-31 | 0.1 | Pancreas Pool | 0.9 |

TABLE OE

General_screening_panel_v1.6

| Tissue Name | Rel. Exp. (%) Ag6885, Run 278388126 | Tissue Name | Rel. Exp. (%) Ag6885, Run 278388126 |
|---|---|---|---|
| Adipose | 0.5 | Renal ca. TK-10 | 0.0 |
| Melanoma* Hs688(A).T | 0.0 | Bladder | 0.7 |
| Melanoma* Hs688(B).T | 0.0 | Gastric ca. (liver met.) NCI-N87 | 1.0 |
| Melanoma* M14 | 0.0 | Gastric ca. KATO III | 0.0 |
| Melanoma* LOXIMVI | 0.0 | Colon ca. SW-948 | 0.3 |
| Melanoma* SK-MEL-5 | 0.0 | Colon ca. SW480 | 0.6 |
| Squamous cell carcinoma SCC-4 | 0.0 | Colon ca.* (SW480 met) SW620 | 0.1 |
| Testis Pool | 2.8 | Colon ca. HT29 | 0.1 |
| Prostate ca.* (bone met) PC-3 | 0.0 | Colon ca. HCT-116 | 0.0 |
| Prostate Pool | 0.7 | Colon ca. CaCo-2 | 0.0 |
| Placenta | 0.0 | Colon cancer tissue | 0.0 |
| Uterus Pool | 0.0 | Colon ca. SW1116 | 0.0 |
| Ovarian ca. OVCAR-3 | 0.1 | Colon ca. Colo-205 | 0.1 |
| Ovarian ca. SK-OV-3 | 0.1 | Colon ca. SW-48 | 0.0 |
| Ovarian ca. OVCAR-4 | 0.1 | Colon Pool | 0.1 |
| Ovarian ca. OVCAR-5 | 0.8 | Small Intestine Pool | 0.3 |
| Ovarian ca. IGROV-1 | 0.0 | Stomach Pool | 0.4 |
| Ovarian ca. OVCAR-8 | 0.1 | Bone Marrow Pool | 0.3 |
| Ovary | 0.1 | Fetal Heart | 0.2 |
| Breast ca. MCF-7 | 0.9 | Heart Pool | 0.5 |
| Breast ca. MDA-MB-231 | 0.0 | Lymph Node Pool | 0.1 |
| Breast ca. BT 549 | 0.1 | Fetal Skeletal Muscle | 1.1 |
| Breast ca. T47D | 1.0 | Skeletal Muscle Pool | 8.2 |
| Breast ca. MDA-N | 0.0 | Spleen Pool | 0.5 |
| Breast Pool | 0.2 | Thymus Pool | 1.5 |
| Trachea | 1.0 | CNS cancer (glio/astro) U87-MG | 0.0 |
| Lung | 0.0 | CNS cancer (glio/astro) U-118-MG | 0.2 |
| Fetal Lung | 1.2 | CNS cancer (neuro;met) SK-N-AS | 0.5 |
| Lung ca. NCI-N417 | 0.1 | CNS cancer (astro) SF-539 | 0.0 |
| Lung ca. LX-1 | 1.3 | CNS cancer (astro) SNB-75 | 0.1 |
| Lung ca. NCI-H146 | 0.0 | CNS cancer (glio) SNB-19 | 0.0 |
| Lung ca. SHP-77 | 0.1 | CNS cancer (glio) SF-295 | 0.1 |
| Lung ca. A549 | 0.1 | Brain (Amygdala) Pool | 0.1 |
| Lung ca. NCI-H526 | 0.0 | Brain (cerebellum) | 100.0 |
| Lung ca. NCI-H23 | 0.0 | Brain (fetal) | 0.1 |
| Lung ca. NCI-H460 | 0.0 | Brain (Hippocampus) Pool | 0.3 |
| Lung ca. HOP-62 | 0.0 | Cerebral Cortex Pool | 0.3 |
| Lung ca. NCI-H522 | 0.1 | Brain (Substantia nigra) Pool | 0.3 |
| Liver | 1.0 | Brain (Thalamus) Pool | 0.5 |
| Fetal Liver | 0.0 | Brain (whole) | 1.7 |
| Liver ca. HepG2 | 0.0 | Spinal Cord Pool | 3.8 |
| Kidney Pool | 0.2 | Adrenal Gland | 2.6 |
| Fetal Kidney | 0.5 | Pituitary gland Pool | 1.6 |
| Renal ca. 786-0 | 0.0 | Salivary Gland | 2.2 |
| Renal ca. A498 | 0.1 | Thyroid (female) | 2.4 |
| Renal ca. ACHN | 0.1 | Pancreatic ca. CAPAN2 | 0.1 |
| Renal ca. UO-31 | 0.0 | Pancreas Pool | 0.6 |

TABLE OF

Panel 4.1D

| Tissue Name | Rel. Exp. (%) Ag4386, Run 186506628 | Tissue Name | Rel. Exp. (%) Ag4386, Run 186506628 |
|---|---|---|---|
| Secondary Th1 act | 0.0 | HUVEC IL-1 beta | 0.0 |
| Secondary Th2 act | 0.0 | HUVEC IFN gamma | 0.0 |
| Secondary Tr1 act | 1.3 | HUVEC TNF alpha + IFN gamma | 0.0 |
| Secondary Th1 rest | 0.0 | HUVEC TNF alpha + IL4 | 0.4 |
| Secondary Th2 rest | 0.5 | HUVEC IL-11 | 0.0 |
| Secondary Tr1 rest | 0.0 | Lung Microvascular EC none | 0.5 |
| Primary Th1 act | 0.0 | Lung Microvascular EC TNF alpha + IL-1 beta | 0.0 |
| Primary Th2 act | 0.8 | Microvascular Dermal EC none | 0.0 |
| Primary Tr1 act | 0.0 | Microsvasular Dermal EC TNF alpha + IL-1 beta | 0.0 |
| Primary Th1 rest | 0.8 | Bronchial epithelium TNF alpha + IL1 beta | 1.0 |
| Primary Th2 rest | 0.6 | Small airway epithelium none | 0.0 |
| Primary Tr1 rest | 0.0 | Small airway epithelium TNF alpha + IL-1 beta | 0.0 |
| CD45RA CD4 lymphocyte act | 1.0 | Coronery artery SMC rest | 0.5 |
| CD45RO CD4 lymphocyte act | 4.8 | Coronery artery SMC TNF alpha + IL-1 beta | 0.0 |
| CD8 lymphocyte act | 2.0 | Astrocytes rest | 1.0 |
| Secondary CD8 lymphocyte rest | 4.7 | Astrocytes TNF alpha + IL-1 beta | 0.0 |
| Secondary CD8 lymphocyte act | 0.4 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.5 | CCD1106 (Keratinocytes) none | 0.0 |
| LAK cells rest | 0.5 | CCD1106 (Keratinocytes) TNF alpha + IL-1 beta | 0.0 |
| LAK cells IL-2 | 0.0 | Liver cirrhosis | 1.0 |
| LAK cells IL-2 + IL-12 | 0.0 | NCI-H292 none | 1.9 |
| LAK cells IL-2 + IFN gamma | 2.4 | NCI-H292 IL-4 | 0.7 |
| LAK cells IL-2 + IL-18 | 0.0 | NCI-H292 IL-9 | 0.6 |
| LAK cells PMA/ionomycin | 3.6 | NCI-H292 IL-13 | 0.0 |
| NK Cells IL-2 rest | 3.7 | NCI-H292 IFN gamma | 0.0 |
| Two Way MLR 3 day | 1.2 | HPAEC none | 0.0 |
| Two Way MLR 5 day | 0.5 | HPAEC TNF alpha + IL-1 beta | 0.7 |
| Two Way MLR 7 day | 0.0 | Lung fibroblast none | 0.0 |
| PBMC rest | 0.0 | Lung fibroblast TNF alpha + IL-1 beta | 0.0 |
| PBMC PWM | 14.9 | Lung fibroblast IL-4 | 0.0 |
| PBMC PHA-L | 5.0 | Lung fibroblast IL-9 | 0.0 |
| Ramos (B cell) none | 0.0 | Lung fibroblast IL-13 | 0.0 |
| Ramos (B cell) ionomycin | 0.5 | Lung fibroblast IFN gamma | 0.0 |
| B lymphocytes PWM | 1.5 | Dermal fibroblast CCD1070 rest | 0.0 |
| B lymphocytes CD40L and IL-4 | 0.4 | Dermal fibroblast CCD1070 TNF alpha | 0.0 |
| EOL-1 dbcAMP | 0.0 | Dermal fibroblast CCD1070 IL-1 beta | 0.5 |
| EOL-1 dbcAMP PMA/ionomycin | 0.0 | Dermal fibroblast IFN gamma | 1.0 |
| Dendritic cells none | 0.0 | Dermal fibroblast IL-4 | 0.3 |
| Dendritic cells LPS | 0.0 | Dermal Fibroblasts rest | 1.3 |
| Dendritic cells anti-CD40 | 0.0 | Neutrophils TNFa + LPS | 0.0 |
| Monocytes rest | 0.0 | Neutrophils rest | 0.0 |
| Monocytes LPS | 0.0 | Colon | 2.4 |
| Macrophages rest | 0.0 | Lung | 5.8 |

TABLE OF-continued

Panel 4.1D

| Tissue Name | Rel. Exp. (%) Ag4386, Run 186506628 | Tissue Name | Rel. Exp. (%) Ag4386, Run 186506628 |
|---|---|---|---|
| Macrophages LPS | 0.0 | Thymus | 15.2 |
| HUVEC none | 0.0 | Kidney | 100.0 |
| HUVEC starved | 0.0 | | |

CNS_neurodegeneration_v1.0 Summary: Ag4386 This panel confirms the expression of the NOV16A gene at low levels in the brains with highest expression in hippocampus of an Alzheimer patient (CT=34.6). Therefore, therapeutic modulation of this gene may be beneficial in the treatment of Alzheimer's disease.

General_screening_panel_v1.4 Summary: Ag4386 Highest expression of the NOV16A gene is detected in brain (cerebellum) (CT=27.4). In addition, moderate expression of this gene is also detected thalamus, whole brain and spinal cord. Therefore, therapeutic modulation of this gene product may be beneficial in the treatment of neurological disorders such as Alzheimer's disease, Parkinson's disease, epilepsy, multiple sclerosis, schizophrenia and depression.

The NOV16A gene encodes a homolog of neuronal leucine rich repeat protein (NLRR). In zebra fish the NLRR functions as a neuronal-specific adhesion molecule or soluble ligand binding receptor, primarily during restoration of the nervous system after injury (Bormann et al., 1999, Mol Cell Neurosci 13(3):167–79, PMII): 10328879). Thus, NLRR encoded by this gene may also play similar role in restoration of nervous system after injury.

Among tissues with metabolic or endocrine function, this gene is expressed at low to moderate levels in pancreas, adrenal gland, thyroid, pituitary gland, skeletal muscle, and liver. Therefore, therapeutic modulation of the activity of this gene may prove useful in the treatment of endocrine/metabolically related diseases, such as obesity and diabetes.

Interestingly, this gene is expressed at much higher levels in adult (CT=29.5) when compared to fetal skeletal muscle (CT=34.3). This observation suggests that expression of this gene can be used to distinguish fetal from adult skeletal muscle.

General_screening_panel_v1.6 Summary: Ag4386 Highest expression of this gene is seen in the cerebellum (CT=26.7). This is in agreement with expression seen in Panel 1.4. Overall, expression in this panel is in agreement with expression in Panel 1.5. Please see that panel for further description and utility of this gene in metabolic and CNS disorders.

Panel 4.1D Summary: Ag4386 Highest expression of the NOV16A gene is detected in kidney (CT=30.7). Thus, expression of this gene may be used to distinguish kidney sample from other samples in this panel. In addition, low expression of this gene is also seen in lung, thymus and PWM treated PBMC cells. Therefore, therapeutic modulation of this gene product may be useful in the treatment of inflammatory and autoimmune diseases affecting kidney and lung such as lupus, glomerulonephritis, asthma, allergy, and COPD.

P. NOV17A: Immunoglobulin Domains Containing Protein

Expression of gene NOV17A was assessed using the primer-probe set Ag4389, described in Table PA. Results of the RTQ-PCR runs are shown in Tables PB, PC and PD.

TABLE PA

Probe Name Ag4389

| Primers | Sequences | Length | Start Position | SEQ ID No |
|---|---|---|---|---|
| Forward | 5'-agagcctggaaattaccaatgt-3' | 22 | 250 | 196 |
| Probe | TET-5'-agacccgaggatcctccctcagtgat-3'-TAMRA | 26 | 273 | 197 |
| Reverse | 5'-cagtcaggtgaaaattccacat-3' | 22 | 306 | 198 |

TABLE PB

General_screening_panel_v1.4

| Tissue Name | Rel. Exp. (%) Ag4389, Run 222641235 | Tissue Name | Rel. Exp. (%) Ag4389, Run 222641235 |
|---|---|---|---|
| Adipose | 6.3 | Renal ca. TK-10 | 0.0 |
| Melanoma* Hs688(A).T | 0.0 | Bladder | 4.0 |
| Melanoma* Hs688(B).T | 0.0 | Gastric ca. (liver met.) NCI-N87 | 0.0 |
| Melanoma* M14 | 0.0 | Gastric ca. KATO III | 0.0 |
| Melanoma* | 0.0 | Colon ca. SW-948 | 0.0 |

TABLE PB-continued

General_screening_panel_v1.4

| Tissue Name | Rel. Exp. (%) Ag4389, Run 222641235 | Tissue Name | Rel. Exp. (%) Ag4389, Run 222641235 |
|---|---|---|---|
| LOXIMVI Melanoma* SK-MEL-5 | 0.5 | Colon ca. SW480 | 0.0 |
| Squamous cell carcinoma SCC-4 | 0.2 | Colon ca.* (SW480 met) SW620 | 0.0 |
| Testis Pool | 0.9 | Colon ca. HT29 | 0.0 |
| Prostate ca.* (bone met) PC-3 | 0.0 | Colon ca. HCT-116 | 0.0 |
| Prostate Pool | 0.7 | Colon ca. CaCo-2 | 0.0 |
| Placenta | 1.0 | Colon cancer tissue | 1.4 |
| Uterus Pool | 0.6 | Colon ca. SW1116 | 0.0 |
| Ovarian ca. OVCAR-3 | 0.0 | Colon ca. Colo-205 | 0.0 |
| Ovarian ca. SK-OV-3 | 0.0 | Colon ca. SW-48 | 0.0 |
| Ovarian ca. OVCAR-4 | 0.0 | Colon Pool | 0.5 |
| Ovarian ca. OVCAR-5 | 1.7 | Small Intestine Pool | 1.0 |
| Ovarian ca. IGROV-1 | 0.0 | Stomach Pool | 1.5 |
| Ovarian ca. OVCAR-8 | 0.0 | Bone Marrow Pool | 0.7 |
| Ovary | 0.0 | Fetal Heart | 0.2 |
| Breast ca. MCF-7 | 0.0 | Heart Pool | 0.2 |
| Breast ca. MDA-MB-231 | 0.0 | Lymph Node Pool | 1.2 |
| Breast ca. BT 549 | 0.0 | Fetal Skeletal Muscle | 0.0 |
| Breast ca. T47D | 2.0 | Skeletal Muscle Pool | 0.3 |
| Breast ca. MDA-N | 0.0 | Spleen Pool | 100.0 |
| Breast Pool | 0.4 | Thymus Pool | 14.9 |
| Trachea | 6.8 | CNS cancer (glio/astro) U87-MG | 0.0 |
| Lung | 0.0 | CNS cancer (glio/astro) U-118-MG | 0.2 |
| Fetal Lung | 8.5 | CNS cancer (neuro;met) SK-N-AS | 0.4 |
| Lung ca. NCI-N417 | 0.0 | CNS cancer (astro) SF-539 | 0.0 |
| Lung ca. LX-1 | 0.0 | CNS cancer (astro) SNB-75 | 0.0 |
| Lung ca. NCI-H146 | 0.0 | CNS cancer (glio) SNB-19 | 0.0 |
| Lung ca. SHP-77 | 0.0 | CNS cancer (glio) SF-295 | 0.0 |
| Lung ca. A549 | 0.0 | Brain (Amygdala) Pool | 0.0 |
| Lung ca. NCI-H526 | 0.0 | Brain (cerebellum) | 0.0 |
| Lung ca. NCI-H23 | 0.0 | Brain (fetal) | 0.7 |
| Lung ca. NCI-H460 | 0.0 | Brain (Hippocampus) Pool | 0.0 |
| Lung ca. HOP-62 | 0.0 | Cerebral Cortex Pool | 0.2 |
| Lung ca. NCI-H522 | 0.0 | Brain (Substantia nigra) Pool | 0.0 |
| Liver | 0.7 | Brain (Thalamus) Pool | 0.5 |
| Fetal Liver | 2.0 | Brain (whole) | 0.5 |
| Liver ca. HepG2 | 0.0 | Spinal Cord Pool | 0.0 |
| Kidney Pool | 1.4 | Adrenal Gland | 0.6 |
| Fetal Kidney | 0.0 | Pituitary gland Pool | 0.0 |
| Renal ca. 786-0 | 0.0 | Salivary Gland | 1.5 |
| Renal ca. A498 | 0.0 | Thyroid (female) | 0.2 |
| Renal ca. ACHN | 0.0 | Pancreatic ca. CAPAN2 | 0.0 |
| Renal ca. UO-31 | 0.0 | Pancreas Pool | 0.5 |

TABLE PC

Panel 4.1D

| Tissue Name | Rel. Exp. (%) Ag4389, Run 186502087 | Tissue Name | Rel. Exp. (%) Ag4389, Run 186502087 |
|---|---|---|---|
| Secondary Th1 act | 0.0 | HUVEC IL-1 beta | 0.0 |
| Secondary Th2 act | 0.1 | HUVEC IFN gamma | 0.0 |
| Secondary Tr1 act | 0.1 | HUVEC TNF alpha + IFN gamma | 0.0 |
| Secondary Th1 rest | 0.7 | HUVEC TNF alpha + IL4 | 0.0 |
| Secondary Th2 rest | 5.5 | HUVEC IL-11 | 0.5 |
| Secondary Tr1 rest | 0.0 | Lung Microvascular EC none | 0.0 |
| Primary Th1 act | 1.0 | Lung Microvascular EC TNF alpha + IL-1 beta | 0.0 |
| Primary Th2 act | 4.5 | Microvascular Dermal EC none | 0.1 |
| Primary Tr1 act | 0.5 | Microsvascular Dermal EC TNF alpha + IL-1 beta | 0.1 |
| Primary Th1 rest | 0.3 | Bronchial epithelium TNF alpha + IL1 beta | 0.0 |
| Primary Th2 rest | 1.5 | Small airway epithelium none | 0.0 |
| Primary Tr1 rest | 0.0 | Small airway epithelium TNF alpha + IL-1 beta | 0.0 |
| CD45RA CD4 lymphocyte act | 3.8 | Coronery artery SMC rest | 0.0 |
| CD45RO CD4 lymphocyte act | 7.0 | Coronery artery SMC TNF alpha + IL-1 beta | 0.0 |
| CD8 lymphocyte act | 14.4 | Astrocytes rest | 0.0 |
| Secondary CD8 lymphocyte rest | 2.3 | Astrocytes TNF alpha + IL-1 beta | 0.0 |
| Secondary CD8 lymphocyte act | 5.9 | KU-812 (Basophil) rest | 0.0 |
| CD4 lymphocyte none | 6.9 | KU-812 (Basophil) PMA/ionomycin | 0.0 |
| 2ry Th1/Th2/Tr1_anti-CD95 CH11 | 1.4 | CCD1106 (Keratinocytes) none | 0.0 |
| LAK cells rest | 15.1 | CCD1106 (Keratinocytes) TNF alpha + IL-1 beta | 0.0 |
| LAK cells IL-2 | 26.8 | Liver cirrhosis | 1.0 |
| LAK cells IL-2 + IL-12 | 12.2 | NCI-H292 none | 0.0 |
| LAK cells IL-2 + IFN gamma | 16.0 | NCI-H292 IL-4 | 0.0 |
| LAK cells IL-2 + IL-18 | 15.9 | NCI-H292 IL-9 | 0.0 |
| LAK cells PMA/ionomycin | 26.8 | NCI-H292 IL-13 | 0.0 |
| NK Cells IL-2 rest | 59.5 | NCI-H292 IFN gamma | 0.0 |
| Two Way MLR 3 day | 31.2 | HPAEC none | 0.1 |
| Two Way MLR 5 day | 8.4 | HPAEC TNF alpha + IL-1 beta | 0.0 |
| Two Way MLR 7 day | 5.6 | Lung fibroblast none | 0.0 |
| PBMC rest | 17.1 | Lung fibroblast TNF alpha + IL-1 beta | 0.0 |
| PBMC PWM | 5.5 | Lung fibroblast IL-4 | 0.0 |
| PBMC PHA-L | 2.5 | Lung fibroblast IL-9 | 0.0 |
| Ramos (B cell) none | 1.8 | Lung fibroblast IL-13 | 0.0 |
| Ramos (B cell) ionomycin | 4.0 | Lung fibroblast IFN gamma | 0.0 |
| B lymphocytes PWM | 8.5 | Dermal fibroblast CCD1070 rest | 0.6 |
| B lymphocytes CD40L and IL-4 | 100.0 | Dermal fibroblast CCD1070 TNF alpha | 0.7 |
| EOL-1 dbcAMP | 0.0 | Dermal fibroblast CCD1070 IL-1 beta | 0.0 |
| EOL-1 dbcAMP PMA/ionomycin | 0.1 | Dermal fibroblast IFN gamma | 0.5 |
| Dendritic cells none | 7.3 | Dermal fibroblast IL-4 | 0.0 |
| Dendritic cells LPS | 1.0 | Dermal Fibroblasts rest | 0.0 |
| Dendritic cells anti-CD40 | 0.2 | Neutrophils TNFa + LPS | 1.4 |
| Monocytes rest | 2.8 | Neutrophils rest | 2.0 |
| Monocytes LPS | 3.7 | Colon | 8.0 |
| Macrophages rest | 19.1 | Lung | 1.4 |

TABLE PC-continued

Panel 4.1D

| Tissue Name | Rel. Exp. (%) Ag4389, Run 186502087 | Tissue Name | Rel. Exp. (%) Ag4389, Run 186502087 |
|---|---|---|---|
| Macrophages LPS | 0.3 | Thymus | 7.3 |
| HUVEC none | 0.0 | Kidney | 25.9 |
| HUVEC starved | 0.0 | | |

TABLE PD

Panel CNS_1.1

| Tissue Name | Rel. Exp. (%) Ag4389, Run 190028469 | Tissue Name | Rel. Exp. (%) Ag4389, Run 190028469 |
|---|---|---|---|
| Cing Gyr Depression2 | 0.0 | BA17 PSP2 | 0.0 |
| Cing Gyr Depression | 0.0 | BA17 PSP | 0.0 |
| Cing Gyr PSP2 | 0.0 | BA17 Huntington's2 | 0.0 |
| Cing Gyr PSP | 0.0 | BA17 Huntington's | 1.2 |
| Cing Gyr Huntington's2 | 0.0 | BA17 Parkinson's2 | 0.0 |
| Cing Gyr Huntington's | 0.0 | BA17 Parkinson's | 0.0 |
| Cing Gyr Parkinson's2 | 0.0 | BA17 Alzheimer's2 | 4.2 |
| Cing Gyr Parkinson's | 0.0 | BA17 Control2 | 0.0 |
| Cing Gyr Alzheimer's2 | 0.0 | BA17 Control | 0.0 |
| Cing Gyr Alzheimer's | 0.0 | BA9 Depression2 | 0.0 |
| Cing Gyr Control2 | 0.0 | BA9 Depression | 0.0 |
| Cing Gyr Control | 0.0 | BA9 PSP2 | 0.0 |
| Temp Pole Depression2 | 0.0 | BA9 PSP | 0.0 |
| Temp Pole PSP2 | 0.0 | BA9 Huntington's2 | 6.0 |
| Temp Pole PSP | 0.0 | BA9 Huntington's | 0.0 |
| Temp Pole Huntington's | 0.0 | BA9 Parkinson's2 | 0.0 |
| Temp Pole Parkinson's2 | 0.0 | BA9 Parkinson's | 0.0 |
| Temp Pole Parkinson's | 0.0 | BA9 Alzheimer's2 | 0.0 |
| Temp Pole Alzheimer's2 | 0.0 | BA9 Alzheimer's | 0.0 |
| Temp Pole Alzheimer's | 0.0 | BA9 Control2 | 5.4 |
| Temp Pole Control2 | 0.0 | BA9 Control | 0.0 |
| Temp Pole Control | 0.0 | BA7 Depression | 0.0 |
| Glob Palladus Depression | 0.0 | BA7 PSP2 | 0.0 |
| Glob Palladus PSP2 | 0.0 | BA7 PSP | 0.0 |
| Glob Palladus PSP | 0.0 | BA7 Huntington's2 | 0.0 |
| Glob Palladus Parkinson's2 | 0.0 | BA7 Huntington's | 0.0 |
| Glob Palladus Parkinson's | 0.0 | BA7 Parkinson's2 | 0.0 |
| Glob Palladus Alzheimer's2 | 0.0 | BA7 Parkinson's | 100.0 |
| Glob Palladus Alzheimer's | 0.0 | BA7 Alzheimer's2 | 0.0 |
| Glob Palladus Control2 | 0.0 | BA7 Control2 | 0.0 |
| Glob Palladus Control | 0.0 | BA7 Control | 0.0 |
| Sub Nigra Depression2 | 0.0 | BA4 Depression2 | 0.0 |

TABLE PD-continued

Panel CNS_1.1

| Tissue Name | Rel. Exp. (%) Ag4389, Run 190028469 | Tissue Name | Rel. Exp. (%) Ag4389, Run 190028469 |
|---|---|---|---|
| Sub Nigra Depression | 0.0 | BA4 Depression | 0.0 |
| Sub Nigra PSP2 | 0.0 | BA4 PSP2 | 0.0 |
| Sub Nigra Huntington's2 | 0.0 | BA4 PSP | 0.0 |
| Sub Nigra Huntington's | 0.0 | BA4 Huntington's2 | 0.0 |
| Sub Nigra Parkinson's2 | 0.0 | BA4 Huntington's | 0.0 |
| Sub Nigra Alzheimer's2 | 0.0 | BA4 Parkinson's2 | 0.0 |
| Sub Nigra Control2 | 0.0 | BA4 Parkinson's | 0.0 |
| Sub Nigra Control | 0.0 | BA4 Alzheimer's2 | 0.0 |
| BA17 Depression2 | 0.0 | BA4 Control2 | 0.0 |
| BA17 Depression | 0.0 | BA4 Control | 0.0 |

CNS_neurodegeneration_v1.0 Summary: Ag4389 Expression of the NOV17A gene is low/undetectable (CTs>35) across all of the samples on this panel (data not shown).

General_screening_panel_v1.4 Summary: Ag4389 Highest expression of the NOV17A gene is detected in spleen (CT=29). Moderate expression of this gene is also detected in thymus. The NOV17A gene encodes a protein similar to the immunoglobulin receptor translocation associated (IRTA) protein. IRTA proteins are immunoreceptors implicated in B cell development and lymphomagenesis (Hatzivassiliou et al., 2001, Immunity 14(3):277–89, PMID: 11290337). Therefore, therapeutic modulation of IRTA-like protein encoded by this gene may be beneficial in the treatment of diseases associated with B cells including B-cell non-Hodgkin lymphoma and multiple myeloma.

In addition, low expression of this gene is also seen in adipose, and fetal liver. Therefore, therapeutic modulation of the activity of this gene may prove useful in the treatment of endocrine/metabolically related diseases, such as obesity and diabetes.

Significant expression of this gene is also detected in fetal lung (CT=32.6). Interestingly, this gene is expressed at much higher levels in fetal when compared to adult lung (CT=40). This observation suggests that expression of this gene can be used to distinguish fetal from adult lung. In addition, the relative overexpression of this gene in fetal lung suggests that the protein product may enhance lung growth or development in the fetus and thus may also act in a regenerative capacity in the adult. Therefore, therapeutic modulation of the protein encoded by this gene could be useful in treatment of lung related diseases.

Panel 4.1D Summary: Ag4389 Highest expression of the NOV17A gene is detected in CD40L and IL4 treated B lymphocytes (CT=28.5). In addition, significant expression of this gene is also seen in monocytes, resting macrophages, PWM treated B lymphocytes, Ramos B cells, LAK cells, Two Way MLR cells, IL2 treated NK cells, PWM/PHA treated and resting PBMC cells, CD4 and CD8 lymphocytes, primary and secondary Th2 cells and in normal tissues represented by colon, lung, thymus and kidney. Therefore, therapeutic modulation of this gene product may be beneficial in the treatment of autoimmune and inflammatory diseases in which B and Th2 cells play a part in the initiation or progression of the disease process, such as systemic lupus erythematosus, Crohn's disease, ulcerative colitis, multiple sclerosis, chronic obstructive pulmonary disease, asthma, emphysema, rheumatoid arthritis, or psoriasis.

Panel CNS_1 Summary: Ag4389 Expression of the NOV17A gene is low/undetectable (CTs>35) across all of the samples on this panel (data not shown).

Panel CNS_1.1 Summary: Ag4389 This panel confirms the expression of the NOV17A gene at very low levels in the brain of an independent group of individuals, with highest expression in a sample from Parkinson's patient. Therefore, therapeutic modulation of this gene product may be beneficial in the treatment of Parkinson's disease.

Q. NOV18A, NOV18B and NOV18C: Small Inducible Cytokine B14 Precursor (Chemokine BRAK)

Expression of gene NOV18A and variants NOV18B and NOV18C was assessed using the primer-probe set Ag953, described in Table QA. Results of the RTQ-PCR runs are shown in Tables QB, QC, QD and QE. Please note that NOV18A and NOV18C represent full-length physical clones.

TABLE QA

Probe Name Ag953

| Primers | Sequences | Length | Start Position | SEQ ID No |
|---|---|---|---|---|
| Forward | 5'-ccaagagcgtgtccaggta-3' | 19 | 110 | 199 |
| Probe | TET-5'-agagcaccaagcgcttcatcaagtg-3'-TAMRA | 25 | 164 | 200 |
| Reverse | 5'-ctcgttccaggcgttgtac-3' | 19 | 189 | 201 |

TABLE QB

AI_comprehensive_panel_v1.0

| Tissue Name | Rel. Exp. (%) Ag953, Run 247834379 | Tissue name | Rel. Exp. (%) Ag953, Run 247834379 |
|---|---|---|---|
| 110967 COPD-F | 0.0 | 112427 Match Control Psoriasis-F | 0.2 |
| 110980 COPD-F | 0.2 | 112418 Psoriasis-M | 0.1 |
| 110968 COPD-M | 0.0 | 112723 Match Control Psoriasis-M | 0.0 |
| 110977 COPD-M | 0.2 | 112419 Psoriasis-M | 0.1 |
| 110989 Emphysema-F | 0.1 | 112424 Match Control Psoriasis-M | 0.2 |
| 110992 Emphysema-F | 42.3 | 112420 Psoriasis-M | 1.1 |
| 110993 Emphysema-F | 0.1 | 112425 Match Control Psoriasis-M | 0.1 |
| 110994 Emphysema-F | 0.1 | 104689 (MF) OA Bone-Backus | 5.0 |
| 110995 Emphysema-F | 100.0 | 104690 (MF) Adj "Normal" Bone-Backus | 4.4 |
| 110996 Emphysema-F | 22.7 | 104691 (MF) OA Synovium-Backus | 12.1 |
| 110997 Asthma-M | 6.8 | 104692 (BA) OA Cartilage-Backus | 2.5 |
| 111001 Asthma-F | 0.5 | 104694 (BA) OA Bone-Backus | 3.9 |
| 111002 Asthma-F | 0.4 | 104695 (BA) Adj "Normal" Bone-Backus | 1.0 |
| 111003 Atopic Asthma-F | 0.2 | 104696 (BA) OA Synovium-Backus | 31.6 |
| 111004 Atopic Asthma-F | 0.3 | 104700 (SS) OA Bone-Backus | 2.6 |
| 111005 Atopic Asthma-F | 0.2 | 104701 (SS) Adj "Normal" Bone-Backus | 4.0 |
| 111006 Atopic Asthma-F | 0.0 | 104702 (SS) OA Synovium-Backus | 14.2 |
| 111417 Allergy-M | 0.1 | 117093 OA Cartilage Rep7 | 0.6 |
| 112347 Allergy-M | 0.1 | 112672 OA Bone5 | 0.1 |
| 112349 Normal Lung-F | 0.2 | 112673 OA Synovium5 | 0.0 |
| 112357 Normal Lung-F | 0.1 | 112674 OA Synovial Fluid cells5 | 0.0 |
| 112354 Normal Lung-M | 0.7 | 117100 OA Cartilage Rep14 | 0.1 |
| 112374 Crohns-F | 1.5 | 112756 OA Bone9 | 0.0 |
| 112389 Match Control Crohns-F | 15.3 | 112757 OA Synovium9 | 3.1 |
| 112375 Crohns-F | 1.2 | 112758 OA Synovial Fluid Cells9 | 1.3 |
| 112732 Match Control Crohns-F | 2.6 | 117125 RA Cartilage Rep2 | 0.1 |
| 112725 Crohns-M | 0.1 | 113492 Bone2 RA | 0.6 |
| 112387 Match Control Crohns-M | 0.9 | 113493 Synovium2 RA | 0.4 |
| 112378 Crohns-M | 0.2 | 113494 Syn Fluid Cells RA | 0.6 |
| 112390 Match Control Crohns-M | 0.2 | 113499 Cartilage4 RA | 0.2 |
| 112726 Crohns-M | 2.5 | 113500 Bone4 RA | 0.2 |
| 112731 Match Control Crohns-M | 3.0 | 113501 Synovium4 RA | 0.1 |
| 112380 Ulcer Col-F | 0.1 | 113502 Syn Fluid Cells4 RA | 0.1 |
| 112734 Match Control Ulcer Col-F | 7.1 | 113495 Cartilage3 RA | 0.1 |
| 112384 Ulcer Col-F | 48.3 | 113496 Bone3 RA | 0.1 |
| 112737 Match Control Ulcer Col-F | 2.2 | 113497 Synovium3 RA | 0.0 |
| 112386 Ulcer Col-F | 1.1 | 113498 Syn Fluid Cells3 RA | 0.1 |
| 112738 Match Control Ulcer Col-F | 1.3 | 117106 Normal Cartilage Rep20 | 0.0 |
| 112381 Ulcer Col-M | 1.0 | 113663 Bone3 Normal | 0.1 |
| 112735 Match Control Ulcer Col-M | 0.8 | 113664 Synovium3 Normal | 0.0 |

TABLE QB-continued

AI_comprehensive panel_v1.0

| Tissue Name | Rel. Exp. (%) Ag953, Run 247834379 | Tissue name | Rel. Exp. (%) Ag953, Run 247834379 |
|---|---|---|---|
| 112382 Ulcer Col-M | 11.5 | 113665 Syn Fluid Cells3 Normal | 0.0 |
| 112394 Match Control Ulcer Col-M | 1.0 | 117107 Normal Cartilage Rep22 | 0.2 |
| 112383 Ulcer Col-M | 35.4 | 113667 Bone4 Normal | 0.5 |
| 112736 Match Control Ulcer Col-M | 8.4 | 113668 Synovium4 Normal | 0.7 |
| 112423 Psoriasis-F | 0.3 | 113669 Syn Fluid Cells4 Normal | 0.7 |

TABLE QC

Panel 2D

| Tissue Name | Rel. Exp. (%) Ag953, Run 170849612 | Tissue Name | Rel. Exp. (%) Ag953, Run 170849612 |
|---|---|---|---|
| Normal Colon | 36.6 | Kidney Margin 8120608 | 43.8 |
| CC Well to Mod Diff (ODO3866) | 0.4 | Kidney Cancer 8120613 | 0.1 |
| CC Margin (ODO3866) | 8.3 | Kidney Margin 8120614 | 43.8 |
| CC Gr.2 rectosigmoid (ODO3868) | 1.3 | Kidney Cancer 9010320 | 3.1 |
| CC Margin (ODO3868) | 0.3 | Kidney Margin 9010321 | 81.2 |
| CC Mod Diff (ODO3920) | 4.4 | Normal Uterus | 0.1 |
| CC Margin (ODO3920) | 1.6 | Uterus Cancer 064011 | 2.2 |
| CC Gr.2 ascend colon (ODO3921) | 28.3 | Normal Thyroid | 3.7 |
| CC Margin (ODO3921) | 4.3 | Thyroid Cancer 064010 | 0.1 |
| CC from Partial Hepatectomy (ODO4309) Mets | 2.3 | Thyroid Cancer A302152 | 1.1 |
| Liver Margin (ODO4309) | 3.1 | Thyroid Margin A302153 | 1.6 |
| Colon mets to lung (OD04451-01) | 0.2 | Normal Breast | 17.2 |
| Lung Margin (OD04451-02) | 0.0 | Breast Cancer (OD04566) | 43.8 |
| Normal Prostate 6546-1 | 2.8 | Breast Cancer (OD04590-01) | 9.0 |
| Prostate Cancer (OD04410) | 8.7 | Breast Cancer Mets (OD04590-03) | 14.9 |
| Prostate Margin (OD04410) | 0.5 | Breast Cancer Metastasis (OD04655-05) | 4.1 |
| Prostate Cancer (OD04720-01) | 3.0 | Breast Cancer 064006 | 28.7 |
| Prostate Margin (OD04720-02) | 1.8 | Breast Cancer 1024 | 14.4 |
| Normal Lung 061010 | 5.2 | Breast Cancer 9100266 | 16.5 |
| Lung Met to Muscle (ODO4286) | 0.1 | Breast Margin 9100265 | 20.7 |
| Muscle Margin (ODO4286) | 22.8 | Breast Cancer A209073 | 10.5 |
| Lung Malignant Cancer (OD03126) | 3.9 | Breast Margin A209073 | 10.4 |
| Lung Margin (OD03126) | 0.5 | Normal Liver | 4.6 |
| Lung Cancer (OD04404) | 27.4 | Liver Cancer 064003 | 0.1 |
| Lung Margin (OD04404) | 3.0 | Liver Cancer 1025 | 3.5 |
| Lung Cancer (OD04565) | 27.2 | Liver Cancer 1026 | 0.7 |
| Lung Margin (OD04565) | 0.0 | Liver Cancer 6004-T | 4.5 |
| Lung Cancer (OD04237-01) | 7.5 | Liver Tissue 6004-N | 0.3 |
| Lung Margin (OD04237- | 0.2 | Liver Cancer 6005-T | 0.5 |

TABLE QC-continued

Panel 2D

| Tissue Name | Rel. Exp. (%) Ag953, Run 170849612 | Tissue Name | Rel. Exp. (%) Ag953, Run 170849612 |
|---|---|---|---|
| 02) | | | |
| Ocular Mel Met to Liver (OD04310) | 0.0 | Liver Tissue 6005-N | 1.2 |
| Liver Margin (OD04310) | 2.5 | Normal Bladder | 2.8 |
| Melanoma Mets to Lung (OD04321) | 0.2 | Bladder Cancer 1023 | 1.6 |
| Lung Margin (OD04321) | 0.5 | Bladder Cancer A302173 | 45.4 |
| Normal Kidney | 63.3 | Bladder Cancer (OD04718-01) | 0.1 |
| Kidney Ca, Nuclear grade 2 (OD04338) | 23.2 | Bladder Normal Adjacent (OD04718-03) | 12.3 |
| Kidney Margin (OD04338) | 22.2 | Normal Ovary | 0.2 |
| Kidney Ca Nuclear grade 1/2 (OD04339) | 20.4 | Ovarian Cancer 064008 | 21.5 |
| Kidney Margin (OD04339) | 100.0 | Ovarian Cancer (OD04768-07) | 0.0 |
| Kidney Ca, Clear cell type (OD04340) | 39.8 | Ovary Margin (OD04768-08) | 2.3 |
| Kidney Margin (OD04340) | 26.6 | Normal Stomach | 8.9 |
| Kidney Ca, Nuclear grade 3 (OD04348) | 1.0 | Gastric Cancer 9060358 | 3.5 |
| Kidney Margin (OD04348) | 12.1 | Stomach Margin 9060359 | 10.6 |
| Kidney Cancer (OD04622-01) | 32.1 | Gastric Cancer 9060395 | 3.1 |
| Kidney Margin (OD04622-03) | 6.3 | Stomach Margin 9060394 | 11.4 |
| Kidney Cancer (OD04450-01) | 9.0 | Gastric Cancer 9060397 | 12.9 |
| Kidney Margin (OD04450-03) | 31.6 | Stomach Margin 9060396 | 4.0 |
| Kidney Cancer 8120607 | 1.2 | Gastric Cancer 064005 | 6.3 |

TABLE QD

Panel 3D

| Tissue Name | Rel. Exp. (%) Ag953, Run 168032587 | Tissue Name | Rel. Exp. (%) Ag953, Run 168032587 |
|---|---|---|---|
| Daoy-Medulloblastoma | 0.7 | Ca Ski-Cervical epidermoid carcinoma (metastasis) | 0.0 |
| TE671-Medulloblastoma | 0.0 | ES-2-Ovarian clear cell carcinoma | 0.0 |
| D283 Med-Medulloblastoma | 0.0 | Ramos-Stimulated with PMA/ionomycin 6 h | 0.0 |
| PFSK-1-Primitive Neuroectodermal | 0.0 | Ramos-Stimulated with PMA/ionomycin 14 h | 0.0 |
| XF-498-CNS | 0.5 | MEG-01-Chronic myelogenous leukemia (megokaryoblast) | 1.6 |
| SNB-78-Glioma | 0.0 | Raji-Burkitt's lymphoma | 0.0 |
| SF-268-Glioblastoma | 0.0 | Daudi-Burkitt's lymphoma | 0.0 |
| T98G-Glioblastoma | 4.0 | U266-B-cell plasmacytoma | 0.0 |
| SK-N-SH-Neuroblastoma (metastasis) | 0.0 | CA46-Burkitt's lymphoma | 0.1 |
| SF-295-Glioblastoma | 0.0 | RL-non-Hodgkin's B-cell lymphoma | 0.0 |
| Cerebellum | 2.6 | JM1-pre-B-cell lymphoma | 0.0 |
| Cerebellum | 2.4 | Jurkat-T cell leukemia | 0.0 |
| NCI-H292-Mucoepidermoid lung carcinoma | 0.0 | TF-1-Erythroleukemia | 1.7 |

TABLE QD-continued

Panel 3D

| Tissue Name | Rel. Exp. (%) Ag953, Run 168032587 | Tissue Name | Rel. Exp. (%) Ag953, Run 168032587 |
|---|---|---|---|
| DMS-114-Small cell lung cancer | 0.0 | HUT 78-T-cell lymphoma | 0.1 |
| DMS-79-Small cell lung cancer | 1.2 | U937-Histiocytic lymphoma | 0.1 |
| NCI-H146-Small cell lung cancer | 9.7 | KU-812-Myelogenous leukemia | 1.9 |
| NCI-H526-Small cell lung cancer | 0.4 | 769-P-Clear cell renal carcinoma | 0.3 |
| NCI-N417-Small cell lung cancer | 0.5 | Caki-2-Clear cell renal carcinoma | 0.0 |
| NCI-H82-Small cell lung cancer | 0.2 | SW 839-Clear cell renal carcinoma | 0.1 |
| NCI-H157-Squamous cell lung cancer (metastasis) | 0.0 | G401-Wilms' tumor | 0.0 |
| NCI-H1155-Large cell lung cancer | 0.0 | Hs766T-Pancreatic carcinoma (LN metastasis) | 0.0 |
| NCI-H1299-Large cell lung cancer | 0.0 | CAPAN-1-Pancreatic adenocarcinoma (liver metastasis) | 0.0 |
| NCI-H727-Lung carcinoid | 0.0 | SU86.86-Pancreatic carcinoma (liver metastasis) | 0.1 |
| NCI-UMC-11-Lung carcinoid | 0.0 | BxPC-3-Pancreatic adenocarcinoma | 4.1 |
| LX-1-Small cell lung cancer | 0.0 | HPAC-Pancreatic adenocarcinoma | 100.0 |
| Colo-205-Colon cancer | 0.0 | MIA PaCa-2-Pancreatic carcinoma | 0.1 |
| KM12-Colon cancer | 0.0 | CFPAC-1-Pancreatic ductal adenocarcinoma | 74.2 |
| KM20L2-Colon cancer | 0.0 | PANC-1-Pancreatic epithelioid ductal carcinoma | 0.0 |
| NCI-H716-Colon cancer | 0.0 | T24-Bladder carcinma (transitional cell) | 0.0 |
| SW-48-Colon adenocarcinoma | 11.2 | 5637-Bladder carcinoma | 0.0 |
| SW1116-Colon adenocarcinoma | 0.0 | HT-1197-Bladder carcinoma | 0.0 |
| LS 174T-Colon adenocarcinoma | 76.3 | UM-UC-3-Bladder carcinma (transitional cell) | 0.0 |
| SW-948-Colon adenocarcinoma | 0.0 | A204-Rhabdomyosarcoma | 0.0 |
| SW-480-Colon adenocarcinoma | 0.0 | HT-1080-Fibrosarcoma | 0.0 |
| NCI-SNU-5-Gastric carcinoma | 0.9 | MG-63-Osteosarcoma | 0.7 |
| KATO III-Gastric carcinoma | 0.0 | SK-LMS-1-Leiomyosarcoma (vulva) | 0.0 |
| NCI-SNU-16-Gastric carcinoma | 0.0 | SJRH30-Rhabdomyosarcoma (met to bone marrow | 0.0 |
| NCI-SNU-1-Gastric carcinoma | 0.0 | A431-Epidermoid carcinoma | 0.0 |
| RF-1-Gastric adenocarcinoma | 0.0 | WM266-4-Melanoma | 0.3 |
| RF-48-Gastric adenocarcinoma | 0.0 | DU 145-Prostate carcinoma (brain metastasis) | 0.0 |
| MKN-45-Gastric carcinoma | 0.0 | MDA-MB-468-Breast adenocarcinoma | 0.0 |
| NCI-N87-Gastric carcinoma | 0.8 | SCC-4-Squamous cell carcinoma of tongue | 0.0 |
| OVCAR-5-Ovarian carcinoma | 0.0 | SCC-9-Squamous cell carcinoma of tongue | 0.0 |
| RL95-2-Uterine carcinoma | 0.0 | SCC-15-Squamous cell carcinoma of tongue | 0.0 |
| HelaS3-Cervical adenocarcinoma | 0.0 | CAL 27-Squamous cell carcinoma of tongue | 0.4 |

TABLE QE

Panel 4D

| Tissue Name | Rel. Exp. (%) Ag953, Run 168033522 | Tissue Name | Rel. Exp. (%) Ag953, Run 168033522 |
|---|---|---|---|
| Secondary Th1 act | 0.0 | HUVEC IL-1 beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1 beta | 0.0 |
| Primary Th2 act | 0.0 | Microvascular Dermal EC none | 0.0 |
| Primary Tr1 act | 0.0 | Microsvascular Dermal EC TNF alpha + IL-1 beta | 0.0 |
| Primary Th1 rest | 0.0 | Bronchial epithelium TNF alpha + IL1 beta | 5.4 |
| Primary Th2 rest | 0.0 | Small airway epithelium none | 1.9 |
| Primary Tr1 rest | 0.0 | Small airway epithelium TNF alpha + IL-1 beta | 10.2 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1 beta | 0.0 |
| CD8 lymphocyte act | 0.0 | Astrocytes rest | 1.7 |
| Secondary CD8 lymphocyte rest | 0.0 | Astrocytes TNF alpha + IL-1 beta | 0.4 |
| Secondary CD8 lymphocyte act | 0.0 | KU-812 (Basophil) rest | 0.4 |
| CD4 lymphocyte none | 0.0 | KU-812 (Basophil) PMA/ionomycin | 0.4 |
| 2ry Th1/Th2/Tr1_anti-CD95 CH11 | 0.0 | CCD1106 (Keratinocytes) none | 0.1 |
| LAK cells rest | 0.0 | CCD1106 (Keratinocytes) TNF alpha + IL-1 beta | 0.3 |
| LAK cells IL-2 | 0.0 | Liver cirrhosis | 0.8 |
| LAK cells IL-2 + IL-12 | 0.0 | Lupus kidney | 5.1 |
| LAK cells IL-2 + IFN gamma | 0.0 | NCI-H292 none | 0.0 |
| LAK cells IL-2 + IL-18 | 0.0 | NCI-H292 IL-4 | 0.0 |
| LAK cells PMA/ionomycin | 0.0 | NCI-H292 IL-9 | 0.0 |
| NK Cells IL-2 rest | 0.0 | NCI-H292 IL-13 | 0.0 |
| Two Way MLR 3 day | 0.0 | NCI-H292 IFN gamma | 0.0 |
| Two Way MLR 5 day | 0.0 | HPAEC none | 0.0 |
| Two Way MLR 7 day | 0.0 | HPAEC TNF alpha + IL-1 beta | 0.0 |
| PBMC rest | 0.0 | Lung fibroblast none | 0.0 |
| PBMC PWM | 0.0 | Lung fibroblast TNF alpha + IL-1 beta | 0.0 |
| PBMC PHA-L | 0.0 | Lung fibroblast IL-4 | 0.1 |
| Ramos (B cell) none | 0.0 | Lung fibroblast IL-9 | 0.0 |
| Ramos (B cell) ionomycin | 0.0 | Lung fibroblast IL-13 | 0.0 |
| B lymphocytes PWM | 0.0 | Lung fibroblast IFN gamma | 0.0 |
| B lymphocytes CD40L and IL-4 | 0.0 | Dermal fibroblast CCD1070 rest | 0.9 |
| EOL-1 dbcAMP | 0.0 | Dermal fibroblast CCD1070 TNF alpha | 0.6 |
| EOL-1 dbcAMP PMA/ionomycin | 0.0 | Dermal fibroblast CCD1070 IL-1 beta | 0.3 |
| Dendritic cells none | 0.0 | Dermal fibroblast IFN gamma | 0.0 |
| Dendritic cells LPS | 0.0 | Dermal fibroblast IL-4 | 0.1 |
| Dendritic cells anti-CD40 | 0.0 | IBD Colitis 2 | 1.4 |
| Monocytes rest | 0.0 | IBD Crohn's | 1.1 |
| Monocytes LPS | 0.0 | Colon | 21.0 |
| Macrophages rest | 0.0 | Lung | 1.3 |
| Macrophages LPS | 0.0 | Thymus | 100.0 |

TABLE QE-continued

Panel 4D

| Tissue Name | Rel. Exp. (%) Ag953, Run 168033522 | Tissue Name | Rel. Exp. (%) Ag953, Run 168033522 |
| --- | --- | --- | --- |
| HUVEC none | 0.0 | Kidney | 5.0 |
| HUVEC starved | 0.0 | | |

A1_comprehensive panel_v1.0 Summary: Ag953 Highest expression of the NOV18B gene is seen in emphysema (CT=23). Moderate levels of expression are seen in many of the samples on this panel suggesting a role for this protein product in the immune system. Please see Panel 4D for discussion of utility of this gene in autoimmunity.

Panel 1.3D Summary: Ag953 Results from one experiment with the CG56003-01 gene are not included. The amp plot indicates that there were experimental difficulties with this run (data not shown).

Panel 2D Summary: Ag953 Highest expression of the CG51213-02 gene is seen in normal kidney adjacent to a tumor (CT=24.8). In addition, this gene appears to be overexpressed in normal kidney when compared to expression in adjacent tumor. In contrast, expression of this gene appears to be higher in lung and colon cancer than in the adjacent tissue. High levels of expression are also seen in bladder and ovarian cancers. This gene encodes a protein with homology to cytokines which are molecular growth factors involved in the regulation of cell proliferation. Thus, this gene product may potentially be involved in the growth regulation of cancer cells. Since blockade of the action of this factor may interfere with cancer cell proliferation, therapeutic targeting with a human monoclonal antibody may be beneficial especially in those cancers where the gene is overexpressed in the tumor compared to the normal adjacent tissue. Additionally, application of the protein encoded by this gene may be useful as a therapeutic for cancers where the gene is overexpressed in the normal adjacent tissue compared to the tumor.

Panel 3D Summary: Ag953 Highest expression of the CG51213-02 gene is seen in a pancreatic cancer cell line (CT=28.1). Moderate levels of expression are also seen in a colon cancer and a lung cell line. Thus, expression of this gene could be used to differentiate these samples from other samples on this panel.

Panel 4D Summary: Ag953 High expression of the CG51213-02 gene is seen the thymus (CT=25) and colon. Moderate levels of expression are seen in kidney, lung, Crohn's, colitis, resting dermal fibroblasts, lupus kidney, resting astrocytes, activated bronchial epithelium, and treated and untreated small airway epithelium. Low but significant levels of expression are seen in activated dermal fibroblasts and astrocytes, and treated and untreated basophils and keratinocytes. The high levels of expression in the thymus suggest that expression of this could be used to differentiate this sample from other samples and as a marker of thymic tissue. Therapeutic modulation of the protein encoded by this gene could potentially be utilized to modulate immune function (T cell development) and be important for organ transplant, AIDS treatment or post chemotherapy immune reconstitution.

Example D

Identification of Single Nucleotide Polymorphisms in NOVX Nucleic Acid Sequences Variant sequences are also included in this application. A variant sequence can include a single nucleotide polymorphism (SNP). A SNP can, in some instances, be referred to as a "cSNP" to denote that the nucleotide sequence containing the SNP originates as a cDNA. A SNP can arise in several ways. For example, a SNP may be due to a substitution of one nucleotide for another at the polymorphic site. Such a substitution can be either a transition or a transversion. A SNP can also arise from a deletion of a nucleotide or an insertion of a nucleotide, relative to a reference allele. In this case, the polymorphic site is a site at which one allele bears a gap with respect to a particular nucleotide in another allele. SNPs occurring within genes may result in an alteration of the amino acid encoded by the gene at the position of the SNP. Intragenic SNPs may also be silent, when a codon including a SNP encodes the same amino acid as a result of the redundancy of the genetic code. SNPs occurring outside the region of a gene, or in an intron within a gene, do not result in changes in any amino acid sequence of a protein but may result in altered regulation of the expression pattern. Examples include alteration in temporal expression, physiological response regulation, cell type expression regulation, intensity of expression, and stability of transcribed message.

SeqCalling assemblies produced by the exon linking process were selected and extended using the following criteria. Genomic clones having regions with 98% identity to all or part of the initial or extended sequence were identified by BLASTN searches using the relevant sequence to query human genomic databases. The genomic clones that resulted were selected for further analysis because this identity indicates that these clones contain the genomic locus for these SeqCalling assemblies. These sequences were analyzed for putative coding regions as well as for similarity to the known DNA and protein sequences. Programs used for these analyses include Grail, Genscan, BLAST, HMMER, FASTA, Hybrid and other relevant programs.

Some additional genomic regions may have also been identified because selected SeqCalling assemblies map to those regions. Such SeqCalling sequences may have overlapped with regions defined by homology or exon prediction. They may also be included because the location of the fragment was in the vicinity of genomic regions identified by similarity or exon prediction that had been included in the original predicted sequence. The sequence so identified was manually assembled and then may have been extended using one or more additional sequences taken from CuraGen Corporation's human SeqCalling database. SeqCalling fragments suitable for inclusion were identified by the CuraTools™ program SeqExtend or by identifying SeqCalling fragments mapping to the appropriate regions of the genomic clones analyzed.

The regions defined by the procedures described above were then manually integrated and corrected for apparent inconsistencies that may have arisen, for example, from miscalled bases in the original fragments or from discrepancies between predicted exon junctions, EST locations and regions of sequence similarity, to derive the final sequence disclosed herein. When necessary, the process to identify and analyze SeqCalling assemblies and genomic clones was reiterated to derive the full length sequence (Alderborn et al., Determination of Single Nucleotide Polymorphisms by Real-time Pyrophosphate DNA Sequencing. Genome Research. 10 (8) 1249–1265, 2000).

Variants are reported individually but any combination of all or a select subset of variants are also included as contemplated NOVX embodiments of the invention.

NOV3a SNP Data:

NOV3a has one SNP variant, whose variant positions for its nucleotide and amino acid sequences is numbered according to SEQ ID NOs:25 and 26, respectively. The nucleotide sequence of the NOV3a variant differs as shown in Table 20A.

TABLE 20A data for NOV3a

| | Nucleotides | | | Amino Acids | | |
|---|---|---|---|---|---|---|
| Variant | Position | Initial | Modified | Position | Initial | Modified |
| 13379134 | 370 | T | C | 115 | Cys | Arg |

NOV5a SNP Data:

NOV5a has three SNP variants, whose variant positions for its nucleotide and amino acid sequences is numbered according to SEQ ID NOs:29 and 30, respectively. The nucleotide sequence of the NOV5a variant differs as shown in Table 20B.

TABLE 20B data for NOV5a

| | Nucleotides | | | Amino Acids | | |
|---|---|---|---|---|---|---|
| Variant | Position | Initial | Modified | Position | Initial | Modified |
| 13379138 | 534 | G | A | 177 | Lys | Lys |
| 13379139 | 560 | G | T | 186 | Cys | Phe |
| 13379140 | 1124 | C | T | 0 | | |

NOV10a SNP Data:

NOV10a has three SNP variants, whose variant positions for its nucleotide and amino acid sequences is numbered according to SEQ ID NOs:53 and 54, respectively The nucleotide sequence of the NOV10a variant differs as shown in Table 20C.

TABLE 20C data for NOV10a

| | Nucleotides | | | Amino Acids | | |
|---|---|---|---|---|---|---|
| Variant | Position | Initial | Modified | Position | Initial | Modified |
| 13379143 | 172 | G | C | 57 | Ala | Pro |
| 13379142 | 197 | A | G | 65 | Asp | Gly |
| 13379141 | 398 | G | A | 132 | Ser | Asn |

NOV12a SNP Data:

NOV12a has seven SNP variants, whose variant positions for its nucleotide and amino acid sequences is numbered according to SEQ ID NOs:69 and 70, respectively. The nucleotide sequence of the NOV12a variant differs as shown in Table 20D.

TABLE 20D data for NOV12a

| | Nucleotides | | | Amino Acids | | |
|---|---|---|---|---|---|---|
| Variant | Position | Initial | Modified | Position | Initial | Modified |
| 13379160 | 237 | A | G | 79 | Thr | Thr |
| 13379161 | 446 | C | T | 149 | Thr | Met |
| 13376279 | 636 | T | G | 212 | Ile | Met |
| 13379162 | 710 | G | A | 237 | Gly | Asp |
| 13376278 | 893 | C | T | 298 | Thr | Ile |
| 13375449 | 1177 | T | C | 393 | Ser | Pro |
| 13379150 | 1194 | T | C | 398 | Ser | Ser |

NOV13a SNP Data:

NOV13a has one SNP variant, whose variant positions for its nucleotide and amino acid sequences is numbered according to SEQ ID NOs:85 and 86, respectively. The nucleotide sequence of the NOV13a variant differs as shown in Table 20E.

TABLE 20E data for NOV13a

| | Nucleotides | | | Amino Acids | | |
|---|---|---|---|---|---|---|
| Variant | Position | Initial | Modified | Position | Initial | Modified |
| 13379144 | 915 | G | A | 232 | Leu | Leu |

NOV14a SNP Data:

NOV 14a has four SNP variants, whose variant positions for its nucleotide and amino acid sequences is numbered according to SEQ ID NOs:87 and 88, respectively. The nucleotide sequence of the NOV14a variant differs as shown in Table 20F.

TABLE 20F data for NOV14a

| | Nucleotides | | | Amino Acids | | |
|---|---|---|---|---|---|---|
| Variant | Position | Initial | Modified | Position | Initial | Modified |
| 13379164 | 33 | C | T | 8 | Pro | Pro |
| 13379165 | 117 | T | C | 36 | Ala | Ala |
| 13379167 | 575 | T | C | 189 | Leu | Pro |
| 13379168 | 686 | T | C | 226 | Leu | Ser |

NOV17a SNP Data:

NOV 17a has four SNP variants, whose variant positions for its nucleotide and amino acid sequences is numbered according to SEQ ID NOs:93 and 94, respectively. The nucleotide sequence of the NOV17a variant differs as shown in Table 20G.

TABLE 20G

| | data for NOV17a | | | | | |
|---|---|---|---|---|---|---|
| | Nucleotides | | | Amino Acids | | |
| Variant | Position | Initial | Modified | Position | Initial | Modified |
| 13377348 | 521 | T | C | 166 | Tyr | His |
| 13377349 | 1731 | C | A | 569 | Pro | His |

NOV18b SNP Data:

NOV 18b has two SNP variants, whose variant positions for its nucleotide and amino acid sequences is numbered according to SEQ ID NOs:93 and 94, respectively. The nucleotide sequence of the NOV18b variant differs as shown in Table 20H.

TABLE 20H

| | data for NOV18b | | | | | |
|---|---|---|---|---|---|---|
| | Nucleotides | | | Amino Acids | | |
| Variant | Position | Initial | Modified | Position | Initial | Modified |
| 13379152 | 114 | G | T | 38 | Lys | Asn |
| 13379151 | 222 | C | T | 74 | Tyr | Tyr |

NOV19a SNP Data:

NOV19a has one SNP variant, whose variant positions for its nucleotide and amino acid sequences is numbered according to SEQ ID NOs:107 and 108, respectively. The nucleotide sequence of the NOV19a variant differs as shown in Table 20I.

TABLE 20I

| | data for NOV19a | | | | | |
|---|---|---|---|---|---|---|
| | Nucleotides | | | Amino Acids | | |
| Variant | Position | Initial | Modified | Position | Initial | Modified |
| 13379148 | 441 | T | C | 147 | His | His |

Other Embodiments

Although particular embodiments have been disclosed herein in detail, this has ben done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims. The claims presented are representative of the inventions disclosed herein. Other, unclaimed inventions are also contemplated. Applicants reserve the right to pursue such inventions in later claims.

We claim:

1. An isolated nucleic acid molecule comprising a nucleic acid sequence of SEQ ID NO:47.

2. An isolated nucleic acid molecule, wherein the nucleic acid molecule differs by a single nucleotide from a nucleic acid sequence comprising SEQ ID NO:47.

3. An isolated nucleic acid molecule comprising an open reading frame that encodes a polypeptide having an amino acid sequence of SEQ ID NO:48.

4. An isolated nucleic acid molecule consisting of a nucleic acid sequence of SEQ ID NO:47.

5. An isolated nucleic acid molecule, wherein said nucleic acid molecule hybridizes under stringent conditions to the nucleotide sequence of SEQ ID NO: 47, or a complement of said nucleotide sequence, and wherein said stringent conditions comprises a hybridization buffer of 6×SSC, 50 mM Tris HCl (pH 7.5), 1 mM EDTA, and 500 mg/ml denatured salmon sperm DNA at 65° C., followed by one or more washes in 0.2×SSC, 0.01% BSA at 50° C.

6. A vector comprising the nucleic acid molecule of claim 1.

7. The vector of claim 6, further comprising a promoter operably linked to said nucleic acid molecule.

8. A cell comprising the vector of claim 6.

9. A method of producing the polypeptide encoded by the nucleic acid of claim 1, the method comprising culturing a cell under conditions that lead to expression of the polypeptide, wherein said cell comprises a vector comprising an isolated nucleic acid molecule comprising a nucleic acid sequence of SEQ ID NO:47.

10. The method of claim 9 wherein the cell is a bacterial cell.

11. The method of claim 9 wherein the cell is an insect cell.

12. The method of claim 9 wherein the cell is a yeast cell.

13. The method of claim 9 wherein the cell is a mammalian cell.

* * * * *

SEQUENCE LISTING

```
<160> NUMBER OF SEQ ID NOS: 201

<210> SEQ ID NO 1
<211> LENGTH: 1239
<212> TYPE: DNA
<213> ORGANISM: Homo sapiens
<220> FEATURE:
<221> NAME/KEY: CDS
<222> LOCATION: (51)..(1167)

<400> SEQUENCE: 1
aaccagggcc ttatccaggg ccacgcttac agaactccca cggacacacc atg att          56
                                                        Met Ile
                                                          1 agg acc ctg ctg ctg tcc act ttg gtg gcc ctc agt tgt ggg gtc tcc        104
Arg Thr Leu Leu Leu Ser Thr Leu Val Ala Leu Ser Cys Gly Val Ser
          5                  10                  15 act tac gcg cct gat atg tct agg atg ctt gga ggt gaa gaa gcg agg        152
Thr Tyr Ala Pro Asp Met Ser Arg Met Leu Gly Gly Glu Glu Ala Arg
     20                  25                  30 ccc aac agc tgg ccc tgg cag gtg agt ctg cag tac agc tcc aat ggc        200
Pro Asn Ser Trp Pro Trp Gln Val Ser Leu Gln Tyr Ser Ser Asn Gly
 35                  40                  45                  50 cag tgg tac cac acc tgc gga ggg tcc ctg ata gcc aac agc tgg gtc        248
Gln Trp Tyr His Thr Cys Gly Gly Ser Leu Ile Ala Asn Ser Trp Val
                 55                  60                  65 ctg acg gct gcc cac tgc atc agc tcc tcc ggg atc tac cgc gtg atg        296
Leu Thr Ala Ala His Cys Ile Ser Ser Ser Gly Ile Tyr Arg Val Met
             70                  75                  80
```

```
ctg ggc cag cat aac ctc tac gtt gca gag tcc ggc tcg ctg gcc gtc        344
Leu Gly Gln His Asn Leu Tyr Val Ala Glu Ser Gly Ser Leu Ala Val
         85                  90                  95 agt gtc tct aag att gtg gtc cac aag gac tgg aac tcc gac cag gtc        392
Ser Val Ser Lys Ile Val Val His Lys Asp Trp Asn Ser Asp Gln Val
100                 105                 110 tcc aaa ggg aac gac att gcc ctg ctc aaa ctg gct aac ccc gtc tcc        440
Ser Lys Gly Asn Asp Ile Ala Leu Leu Lys Leu Ala Asn Pro Val Ser
115                 120                 125                 130 ctc acc gac aag atc cag ctg gcc tgc ctc cct cct gcc ggc acc att        488
Leu Thr Asp Lys Ile Gln Leu Ala Cys Leu Pro Pro Ala Gly Thr Ile
                135                 140                 145 cta ccc aac aac tac ccc tgc tac gtc acg ggc tgg gga agg ctg cag        536
Leu Pro Asn Asn Tyr Pro Cys Tyr Val Thr Gly Trp Gly Arg Leu Gln
            150                 155                 160 agt aac ggg gct ctc cct gat gac ctg aag cag ggc cag ttg ctg gtt        584
Ser Asn Gly Ala Leu Pro Asp Asp Leu Lys Gln Gly Gln Leu Leu Val
        165                 170                 175 gtg gac tat gcc acc tgc tcc agc tct ggc tgg tgg ggc agc acc gtg        632
Val Asp Tyr Ala Thr Cys Ser Ser Ser Gly Trp Trp Gly Ser Thr Val
180                 185                 190 aag acg aat atg atc tgt gct ggg ggt gat ggc gtg ata tgc acc tgc        680
Lys Thr Asn Met Ile Cys Ala Gly Gly Asp Gly Val Ile Cys Thr Cys
195                 200                 205                 210 aac gga gac tcc ggt ggg ccg ctg aac tgt cag gca tct gac ggc cgg        728
Asn Gly Asp Ser Gly Gly Pro Leu Asn Cys Gln Ala Ser Asp Gly Arg
                215                 220                 225 tgg gag gtg cat ggc atc ggc agc ctc acg tcg gtc ctt ggt tgc aac        776
Trp Glu Val His Gly Ile Gly Ser Leu Thr Ser Val Leu Gly Cys Asn
            230                 235                 240 tac tac tac aag ccc tcc atc ttc acg cgg gtc tcc aac tac aac gac        824
Tyr Tyr Tyr Lys Pro Ser Ile Phe Thr Arg Val Ser Asn Tyr Asn Asp
        245                 250                 255 tgg atc aat tcg gta aga acc gga gca gcc ctg agc ccc aag gca ctg        872
Trp Ile Asn Ser Val Arg Thr Gly Ala Ala Leu Ser Pro Lys Ala Leu
260                 265                 270 acc tgc tca cct ggc ctc ggg agt gcc atg ccc acc tgg cga ctg aga        920
Thr Cys Ser Pro Gly Leu Gly Ser Ala Met Pro Thr Trp Arg Leu Arg
275                 280                 285                 290 acc ccc tcc ttc ctc ttg aga gct aga tgg gaa ccc ctt gga gga ggc        968
Thr Pro Ser Phe Leu Leu Arg Ala Arg Trp Glu Pro Leu Gly Gly Gly
                295                 300                 305 tgc aga cct tgg caa ctg ctg agt ccc cca tgg gtc ccc aaa att tct       1016
Cys Arg Pro Trp Gln Leu Leu Ser Pro Pro Trp Val Pro Lys Ile Ser
            310                 315                 320 gtg tgg gta aag ctg agt gaa aag gaa cat gag agt atg gcc ttg tcc       1064
Val Trp Val Lys Leu Ser Glu Lys Glu His Glu Ser Met Ala Leu Ser
        325                 330                 335 aaa gac gtt gga cac tcc tca ggt acg tta aga gtg agt tcc aca gga       1112
Lys Asp Val Gly His Ser Ser Gly Thr Leu Arg Val Ser Ser Thr Gly
340                 345                 350 atg att tta ttt ttg tgt att tgt gtg tgg ccc aga ctc tac cat cca       1160
Met Ile Leu Phe Leu Cys Ile Cys Val Trp Pro Arg Leu Tyr His Pro
355                 360                 365                 370 gtg cta taaatgggta tatgtctgca aacccaaaa cctgatactt tgagacccccc        1216
Val Leu atagcattaa ttattggaaa tta                                             1239
```

```
<210> SEQ ID NO 2
<211> LENGTH: 372
<212> TYPE: PRT
<213> ORGANISM: Homo sapiens

<400> SEQUENCE: 2

Met Ile Arg Thr Leu Leu Ser Thr Leu Val Ala Leu Ser Cys Gly
  1               5                  10                  15

Val Ser Thr Tyr Ala Pro Asp Met Ser Arg Met Leu Gly Gly Glu Glu
             20                  25                  30

Ala Arg Pro Asn Ser Trp Pro Trp Gln Val Ser Leu Gln Tyr Ser Ser
         35                  40                  45

Asn Gly Gln Trp Tyr His Thr Cys Gly Gly Ser Leu Ile Ala Asn Ser
     50                  55                  60

Trp Val Leu Thr Ala Ala His Cys Ile Ser Ser Gly Ile Tyr Arg
 65                  70                  75                  80

Val Met Leu Gly Gln His Asn Leu Tyr Val Ala Glu Ser Gly Ser Leu
                 85                  90                  95

Ala Val Ser Val Ser Lys Ile Val His Lys Asp Trp Asn Ser Asp
            100                 105                 110

Gln Val Ser Lys Gly Asn Asp Ile Ala Leu Leu Lys Leu Ala Asn Pro
        115                 120                 125

Val Ser Leu Thr Asp Lys Ile Gln Leu Ala Cys Leu Pro Pro Ala Gly
    130                 135                 140

Thr Ile Leu Pro Asn Asn Tyr Pro Cys Tyr Val Thr Gly Trp Gly Arg
145                 150                 155                 160

Leu Gln Ser Asn Gly Ala Leu Pro Asp Asp Leu Lys Gln Gly Gln Leu
                165                 170                 175

Leu Val Val Asp Tyr Ala Thr Cys Ser Ser Ser Gly Trp Trp Gly Ser
                180                 185                 190

Thr Val Lys Thr Asn Met Ile Cys Ala Gly Gly Asp Gly Val Ile Cys
            195                 200                 205

Thr Cys Asn Gly Asp Ser Gly Gly Pro Leu Asn Cys Gln Ala Ser Asp
    210                 215                 220

Gly Arg Trp Glu Val His Gly Ile Gly Ser Leu Thr Ser Val Leu Gly
225                 230                 235                 240

Cys Asn Tyr Tyr Tyr Lys Pro Ser Ile Phe Thr Arg Val Ser Asn Tyr
                245                 250                 255

Asn Asp Trp Ile Asn Ser Val Arg Thr Gly Ala Ala Leu Ser Pro Lys
            260                 265                 270

Ala Leu Thr Cys Ser Pro Gly Leu Gly Ser Ala Met Pro Thr Trp Arg
        275                 280                 285

Leu Arg Thr Pro Ser Phe Leu Leu Arg Ala Arg Trp Glu Pro Leu Gly
    290                 295                 300

Gly Gly Cys Arg Pro Trp Gln Leu Leu Ser Pro Pro Val Pro Lys
305                 310                 315                 320

Ile Ser Val Trp Val Lys Leu Ser Glu Lys Glu His Glu Ser Met Ala
                325                 330                 335

Leu Ser Lys Asp Val Gly His Ser Ser Gly Thr Leu Arg Val Ser Ser
            340                 345                 350

Thr Gly Met Ile Leu Phe Leu Cys Ile Cys Val Trp Pro Arg Leu Tyr
        355                 360                 365

His Pro Val Leu
    370
```

<210> SEQ ID NO 3
<211> LENGTH: 1188
<212> TYPE: DNA
<213> ORGANISM: Homo sapiens
<220> FEATURE:
<221> NAME/KEY: CDS
<222> LOCATION: (1)..(868)

<400> SEQUENCE: 3

| | | | | | | | | | | | | | | | | |
|---|---|---|---|---|---|---|---|---|---|---|---|---|---|---|---|---|
| atg | att | agg | acc | ctg | ctg | ctg | tcc | act | ttg | gtg | gct | gga | gcc | ctc | agt | 48 |
| Met | Ile | Arg | Thr | Leu | Leu | Leu | Ser | Thr | Leu | Val | Ala | Gly | Ala | Leu | Ser | |
| 1 | | | | 5 | | | | | 10 | | | | | 15 | | |
| tgt | ggg | gtc | tcc | act | tac | gcg | cct | gat | atg | tct | agg | atg | ctt | gga | ggt | 96 |
| Cys | Gly | Val | Ser | Thr | Tyr | Ala | Pro | Asp | Met | Ser | Arg | Met | Leu | Gly | Gly | |
| | | | 20 | | | | | 25 | | | | | 30 | | | |
| gaa | gaa | gcg | agg | ccc | aac | agc | tgg | ccc | tgg | cag | gtg | agt | ctg | cag | tac | 144 |
| Glu | Glu | Ala | Arg | Pro | Asn | Ser | Trp | Pro | Trp | Gln | Val | Ser | Leu | Gln | Tyr | |
| | | 35 | | | | | 40 | | | | | 45 | | | | |
| agc | tcc | aat | ggc | cag | tgg | tac | cac | acc | tgc | gga | ggg | tcc | ctg | ata | gcc | 192 |
| Ser | Ser | Asn | Gly | Gln | Trp | Tyr | His | Thr | Cys | Gly | Gly | Ser | Leu | Ile | Ala | |
| | 50 | | | | | 55 | | | | | 60 | | | | | |
| aac | agc | tgg | gtc | ctg | acg | gct | gcc | cac | tgc | atc | agc | tcc | tcc | ggg | atc | 240 |
| Asn | Ser | Trp | Val | Leu | Thr | Ala | Ala | His | Cys | Ile | Ser | Ser | Ser | Gly | Ile | |
| 65 | | | | | 70 | | | | | 75 | | | | | 80 | |
| tac | cgc | gtg | atg | ctg | ggc | cag | cat | aac | ctc | tac | gtt | gca | gag | tcc | ggc | 288 |
| Tyr | Arg | Val | Met | Leu | Gly | Gln | His | Asn | Leu | Tyr | Val | Ala | Glu | Ser | Gly | |
| | | | | 85 | | | | | 90 | | | | | 95 | | |
| tcg | ctg | gcc | gtc | agt | gtc | tct | aag | att | gtg | gtg | cac | aag | gac | tgg | aac | 336 |
| Ser | Leu | Ala | Val | Ser | Val | Ser | Lys | Ile | Val | Val | His | Lys | Asp | Trp | Asn | |
| | | | 100 | | | | | 105 | | | | | 110 | | | |
| tcc | gac | cag | gtc | tcc | aaa | ggg | aac | gac | att | gcc | ctg | ctc | aaa | ctg | gct | 384 |
| Ser | Asp | Gln | Val | Ser | Lys | Gly | Asn | Asp | Ile | Ala | Leu | Leu | Lys | Leu | Ala | |
| | | 115 | | | | | 120 | | | | | 125 | | | | |
| aac | ccc | gtc | tcc | ctc | acc | gac | aag | atc | cag | ctg | gcc | tgc | ctc | cct | cct | 432 |
| Asn | Pro | Val | Ser | Leu | Thr | Asp | Lys | Ile | Gln | Leu | Ala | Cys | Leu | Pro | Pro | |
| | 130 | | | | | 135 | | | | | 140 | | | | | |
| gcc | ggc | acc | att | cta | ccc | aac | aac | tac | ccc | tgc | tac | gtc | acg | ggc | tgg | 480 |
| Ala | Gly | Thr | Ile | Leu | Pro | Asn | Asn | Tyr | Pro | Cys | Tyr | Val | Thr | Gly | Trp | |
| 145 | | | | | 150 | | | | | 155 | | | | | 160 | |
| gga | agg | ctg | cag | acc | aac | ggg | gct | ctc | cct | gat | gac | ctg | aag | cag | ggc | 528 |
| Gly | Arg | Leu | Gln | Thr | Asn | Gly | Ala | Leu | Pro | Asp | Asp | Leu | Lys | Gln | Gly | |
| | | | | 165 | | | | | 170 | | | | | 175 | | |
| cag | ttg | ctg | gtt | gtg | gac | tat | gcc | acc | tgc | tcc | agc | tct | ggc | tgg | tgg | 576 |
| Gln | Leu | Leu | Val | Val | Asp | Tyr | Ala | Thr | Cys | Ser | Ser | Ser | Gly | Trp | Trp | |
| | | | 180 | | | | | 185 | | | | | 190 | | | |
| ggc | agc | acc | gtg | aag | acg | aat | atg | atc | tgt | gct | ggg | ggt | aat | ggc | gtg | 624 |
| Gly | Ser | Thr | Val | Lys | Thr | Asn | Met | Ile | Cys | Ala | Gly | Gly | Asn | Gly | Val | |
| | | 195 | | | | | 200 | | | | | 205 | | | | |
| ata | tgc | acc | tgc | aac | gga | gac | tct | ggc | ggg | cca | ctg | aac | tgt | cag | gcg | 672 |
| Ile | Cys | Thr | Cys | Asn | Gly | Asp | Ser | Gly | Gly | Pro | Leu | Asn | Cys | Gln | Ala | |
| | 210 | | | | | 215 | | | | | 220 | | | | | |
| tct | gac | ggc | cgg | tgg | cag | gtg | cac | ggc | atc | gtc | agc | ttc | ggg | tct | cgc | 720 |
| Ser | Asp | Gly | Arg | Trp | Gln | Val | His | Gly | Ile | Val | Ser | Phe | Gly | Ser | Arg | |
| 225 | | | | | 230 | | | | | 235 | | | | | 240 | |
| ctc | ggc | tgc | aac | tac | tac | cac | aag | ccc | tcc | gtc | ttc | acg | cgg | gtc | tcc | 768 |
| Leu | Gly | Cys | Asn | Tyr | Tyr | His | Lys | Pro | Ser | Val | Phe | Thr | Arg | Val | Ser | |
| | | | | 245 | | | | | 250 | | | | | 255 | | |
| aat | tac | atc | gac | tgg | atc | aat | tcg | gta | aga | acc | gga | cca | gcc | ttg | agc | 816 |
| Asn | Tyr | Ile | Asp | Trp | Ile | Asn | Ser | Val | Arg | Thr | Gly | Pro | Ala | Leu | Ser | |
| | | | 260 | | | | | 265 | | | | | 270 | | | |

-continued

```
ccc aag gca cta ccc tgc tca cct ggc ctc ggg agt gcc atg ccc acc    864
Pro Lys Ala Leu Pro Cys Ser Pro Gly Leu Gly Ser Ala Met Pro Thr
        275                 280                 285 tgg tgactgagaa tccctccttt cctcttgaga gctagatggg aaccccttgg         917
Trp aggaggctgc agacctgagt aactgctggg cctgccatgg gtccccccaaa            967 tttctgtgtg gataaagctg agtgaaaagg aacatagagg gtggccttgt            1017
ccaaagaggt tggacactcc tcaggcatat gaagagtgag ttccgctggg            1067
cgccgtggct catgcctgta atcccagctc tttgggaggc caaggcgggc            1117
agatcacgag gtcagaagtt caagaccagc ctgaccaacc tggcaaaacc            1167
ccatgtctac taaaaaaatc c                                           1188

<210> SEQ ID NO 4
<211> LENGTH: 289
<212> TYPE: PRT
<213> ORGANISM: Homo sapiens

<400> SEQUENCE: 4

Met Ile Arg Thr Leu Leu Leu Ser Thr Leu Val Ala Gly Ala Leu Ser
 1               5                  10                  15

Cys Gly Val Ser Thr Tyr Ala Pro Asp Met Ser Arg Met Leu Gly Gly
                20                  25                  30

Glu Glu Ala Arg Pro Asn Ser Trp Pro Trp Gln Val Ser Leu Gln Tyr
            35                  40                  45

Ser Ser Asn Gly Gln Trp Tyr His Thr Cys Gly Gly Ser Leu Ile Ala
        50                  55                  60

Asn Ser Trp Val Leu Thr Ala Ala His Cys Ile Ser Ser Ser Gly Ile
 65                  70                  75                  80

Tyr Arg Val Met Leu Gly Gln His Asn Leu Tyr Val Ala Glu Ser Gly
                 85                  90                  95

Ser Leu Ala Val Ser Val Ser Lys Ile Val Val His Lys Asp Trp Asn
            100                 105                 110

Ser Asp Gln Val Ser Lys Gly Asn Asp Ile Ala Leu Leu Lys Leu Ala
        115                 120                 125

Asn Pro Val Ser Leu Thr Asp Lys Ile Gln Leu Ala Cys Leu Pro Pro
    130                 135                 140

Ala Gly Thr Ile Leu Pro Asn Asn Tyr Pro Cys Tyr Val Thr Gly Trp
145                 150                 155                 160

Gly Arg Leu Gln Thr Asn Gly Ala Leu Pro Asp Leu Lys Gln Gly
                165                 170                 175

Gln Leu Leu Val Val Asp Tyr Ala Thr Cys Ser Ser Ser Gly Trp Trp
            180                 185                 190

Gly Ser Thr Val Lys Thr Asn Met Ile Cys Ala Gly Gly Asn Gly Val
        195                 200                 205

Ile Cys Thr Cys Asn Gly Asp Ser Gly Gly Pro Leu Asn Cys Gln Ala
    210                 215                 220

Ser Asp Gly Arg Trp Gln Val His Gly Ile Val Ser Phe Gly Ser Arg
225                 230                 235                 240

Leu Gly Cys Asn Tyr Tyr His Lys Pro Ser Val Phe Thr Arg Val Ser
                245                 250                 255

Asn Tyr Ile Asp Trp Ile Asn Ser Val Arg Thr Gly Pro Ala Leu Ser
            260                 265                 270

Pro Lys Ala Leu Pro Cys Ser Pro Gly Leu Gly Ser Ala Met Pro Thr
```

```
                    275                 280                 285
Trp

<210> SEQ ID NO 5
<211> LENGTH: 889
<212> TYPE: DNA
<213> ORGANISM: Homo sapiens
<220> FEATURE:
<221> NAME/KEY: CDS
<222> LOCATION: (1)..(799)

<400> SEQUENCE: 5 atg att agg acc ctg ctg ctg tcc act ttg gtg gct gga gcc ctc agt      48
Met Ile Arg Thr Leu Leu Leu Ser Thr Leu Val Ala Gly Ala Leu Ser
 1               5                  10                  15 tgt ggg gtc tcc act tac gcg cct gat atg tct agg atg ctt gga ggt      96
Cys Gly Val Ser Thr Tyr Ala Pro Asp Met Ser Arg Met Leu Gly Gly
             20                  25                  30 gaa gaa gcg agg ccc aac agc tgg ccc tgg cag gtg agt ctg cag tac     144
Glu Glu Ala Arg Pro Asn Ser Trp Pro Trp Gln Val Ser Leu Gln Tyr
         35                  40                  45 agc tcc aat ggc cag tgg tac cac acc tgc gga ggg tcc ctg ata gcc     192
Ser Ser Asn Gly Gln Trp Tyr His Thr Cys Gly Gly Ser Leu Ile Ala
     50                  55                  60 aac agc tgg gtc ctg acg gct gcc cac tgc atc agc tcc tcc ggg atc     240
Asn Ser Trp Val Leu Thr Ala Ala His Cys Ile Ser Ser Ser Gly Ile
 65                  70                  75                  80 tac cgc gtg atg ctg ggc cag cat aac ctc tac gtt gca gag tcc ggc     288
Tyr Arg Val Met Leu Gly Gln His Asn Leu Tyr Val Ala Glu Ser Gly
                 85                  90                  95 tcg ctg gcc gtc agt gtc tct aag att gtg gtg cac aag gac tgg aac     336
Ser Leu Ala Val Ser Val Ser Lys Ile Val Val His Lys Asp Trp Asn
            100                 105                 110 tcc gac cag gtc tcc aaa ggg aac gac att gcc ctg ctc aaa ctg gct     384
Ser Asp Gln Val Ser Lys Gly Asn Asp Ile Ala Leu Leu Lys Leu Ala
        115                 120                 125 aac ccc gtc tcc ctc acc gac aag atc cag ctg gcc tgc ctc cct cct     432
Asn Pro Val Ser Leu Thr Asp Lys Ile Gln Leu Ala Cys Leu Pro Pro
    130                 135                 140 gcc ggc acc att cta ccc aac aac tac ccc tgc tac gtc acg ggc tgg     480
Ala Gly Thr Ile Leu Pro Asn Asn Tyr Pro Cys Tyr Val Thr Gly Trp
145                 150                 155                 160 gga agg ctg cag acc aac ggg gct ctc cct gat gac ctg aag cag ggc     528
Gly Arg Leu Gln Thr Asn Gly Ala Leu Pro Asp Asp Leu Lys Gln Gly
                165                 170                 175 cag ttg ctg gtt gtg gac tat gcc acc tgc tcc agc tct ggc tgg tgg     576
Gln Leu Leu Val Val Asp Tyr Ala Thr Cys Ser Ser Ser Gly Trp Trp
            180                 185                 190 ggc agc acc gtg aag acg aat atg atc tgt gct ggg ggt aat ggc gtg     624
Gly Ser Thr Val Lys Thr Asn Met Ile Cys Ala Gly Gly Asn Gly Val
        195                 200                 205 ata tgc acc tgc aac gga gac tct ggc ggg cca ctg aac tgt cag gcg     672
Ile Cys Thr Cys Asn Gly Asp Ser Gly Gly Pro Leu Asn Cys Gln Ala
    210                 215                 220 tct gac ggc cgg tgg cag gtg cac ggc atc gtc agc ttc ggg tct cgc     720
Ser Asp Gly Arg Trp Gln Val His Gly Ile Val Ser Phe Gly Ser Arg
225                 230                 235                 240 ctc ggc tgc aac tac tac cac aag ccc tcc gtc ttc acg cgg gtc tcc     768
Leu Gly Cys Asn Tyr Tyr His Lys Pro Ser Val Phe Thr Arg Val Ser
                245                 250                 255
```

```
aat tac atc gac tgg atg att gca aat aac taaccaaaag aagtccctgg      818
Asn Tyr Ile Asp Trp Met Ile Ala Asn Asn
        260                 265 gactgtttca gacttggaaa ggtcacggaa ggaaaataat ataataaagt              868
ggcaactatg caaaaaaaaa a                                             889
```

<210> SEQ ID NO 6
<211> LENGTH: 266
<212> TYPE: PRT
<213> ORGANISM: Homo sapiens

<400> SEQUENCE: 6

```
Met Ile Arg Thr Leu Leu Leu Ser Thr Leu Val Ala Gly Ala Leu Ser
 1               5                  10                  15

Cys Gly Val Ser Thr Tyr Ala Pro Asp Met Ser Arg Met Leu Gly Gly
            20                  25                  30

Glu Glu Ala Arg Pro Asn Ser Trp Pro Trp Gln Val Ser Leu Gln Tyr
        35                  40                  45

Ser Ser Asn Gly Gln Trp Tyr His Thr Cys Gly Gly Ser Leu Ile Ala
    50                  55                  60

Asn Ser Trp Val Leu Thr Ala Ala His Cys Ile Ser Ser Gly Ile
 65                  70                  75                  80

Tyr Arg Val Met Leu Gly Gln His Asn Leu Tyr Val Ala Glu Ser Gly
                85                  90                  95

Ser Leu Ala Val Ser Val Ser Lys Ile Val His Lys Asp Trp Asn
            100                 105                 110

Ser Asp Gln Val Ser Lys Gly Asn Asp Ile Ala Leu Leu Lys Leu Ala
        115                 120                 125

Asn Pro Val Ser Leu Thr Asp Lys Ile Gln Leu Ala Cys Leu Pro Pro
    130                 135                 140

Ala Gly Thr Ile Leu Pro Asn Asn Tyr Pro Cys Tyr Val Thr Gly Trp
145                 150                 155                 160

Gly Arg Leu Gln Thr Asn Gly Ala Leu Pro Asp Asp Leu Lys Gln Gly
                165                 170                 175

Gln Leu Leu Val Val Asp Tyr Ala Thr Cys Ser Ser Ser Gly Trp Trp
            180                 185                 190

Gly Ser Thr Val Lys Thr Asn Met Ile Cys Ala Gly Gly Asn Gly Val
        195                 200                 205

Ile Cys Thr Cys Asn Gly Asp Ser Gly Gly Pro Leu Asn Cys Gln Ala
    210                 215                 220

Ser Asp Gly Arg Trp Gln Val His Gly Ile Val Ser Phe Gly Ser Arg
225                 230                 235                 240

Leu Gly Cys Asn Tyr Tyr His Lys Pro Ser Val Phe Thr Arg Val Ser
                245                 250                 255

Asn Tyr Ile Asp Trp Met Ile Ala Asn Asn
            260                 265
```

<210> SEQ ID NO 7
<211> LENGTH: 1188
<212> TYPE: DNA
<213> ORGANISM: Homo sapiens
<220> FEATURE:
<221> NAME/KEY: CDS
<222> LOCATION: (1)..(868)

<400> SEQUENCE: 7

```
atg att agg acc ctg ctg ctg tcc act ttg gtg gct gga gcc ctc agt    48
```

```
Met Ile Arg Thr Leu Leu Leu Ser Thr Leu Val Ala Gly Ala Leu Ser
 1               5                  10                  15 tgt ggg gac ccc act tac cca cct tat gtg act agg gtg gtt ggc ggt    96
Cys Gly Asp Pro Thr Tyr Pro Pro Tyr Val Thr Arg Val Val Gly Gly
             20                  25                  30 gaa gaa gcg agg ccc aac agc tgg ccc tgg cag gtg agt ctg cag tac   144
Glu Glu Ala Arg Pro Asn Ser Trp Pro Trp Gln Val Ser Leu Gln Tyr
         35                  40                  45 agc tcc aat ggc cag tgg tac cac acc tgc gga ggg tcc ctg ata gcc   192
Ser Ser Asn Gly Gln Trp Tyr His Thr Cys Gly Gly Ser Leu Ile Ala
     50                  55                  60 aac agc tgg gtc ctg acg gct gcc cac tgc atc agc tcc tcc ggg atc   240
Asn Ser Trp Val Leu Thr Ala Ala His Cys Ile Ser Ser Ser Gly Ile
 65                  70                  75                  80 tac cgc gtg atg ctg ggc cag cat aac ctc tac gtt gca gag tcc ggc   288
Tyr Arg Val Met Leu Gly Gln His Asn Leu Tyr Val Ala Glu Ser Gly
                 85                  90                  95 tcg ctg gcc gtc agt gtc tct aag att gtg gtg cac aag gac tgg aac   336
Ser Leu Ala Val Ser Val Ser Lys Ile Val Val His Lys Asp Trp Asn
             100                 105                 110 tcc gac cag gtc tcc aaa ggg aac gac att gcc ctg ctc aaa ctg gct   384
Ser Asp Gln Val Ser Lys Gly Asn Asp Ile Ala Leu Leu Lys Leu Ala
         115                 120                 125 aac ccc gtc tcc ctc acc gac aag atc cag ctg gcc tgc ctc cct cct   432
Asn Pro Val Ser Leu Thr Asp Lys Ile Gln Leu Ala Cys Leu Pro Pro
     130                 135                 140 gcc ggc acc att cta ccc aac aac tac ccc tgc tac gtc acg ggc tgg   480
Ala Gly Thr Ile Leu Pro Asn Asn Tyr Pro Cys Tyr Val Thr Gly Trp
145                 150                 155                 160 gga agg ctg cag gcc aac ggg gct ctc cct gat gac ctg aag cag ggc   528
Gly Arg Leu Gln Ala Asn Gly Ala Leu Pro Asp Asp Leu Lys Gln Gly
                 165                 170                 175 cag ttg ctg gtt gtg gac tat gcc acc tgc tcc agc tct ggc tgg tgg   576
Gln Leu Leu Val Val Asp Tyr Ala Thr Cys Ser Ser Ser Gly Trp Trp
             180                 185                 190 ggc agc acc gtg aag acg aat atg atc tgt gct ggg ggt aat ggc gtg   624
Gly Ser Thr Val Lys Thr Asn Met Ile Cys Ala Gly Gly Asn Gly Val
         195                 200                 205 ata tgc acc tgc aac gga gac tct ggc ggg cca ctg aac tgt cag gcg   672
Ile Cys Thr Cys Asn Gly Asp Ser Gly Gly Pro Leu Asn Cys Gln Ala
     210                 215                 220 tct gac ggc cgg tgg cag gtg cac ggc atc gtc agc ttc ggg tct cgc   720
Ser Asp Gly Arg Trp Gln Val His Gly Ile Val Ser Phe Gly Ser Arg
225                 230                 235                 240 ctc ggc tgc aac tac tac cac aag ccc tcc gtc ttc acg cgg gtc tcc   768
Leu Gly Cys Asn Tyr Tyr His Lys Pro Ser Val Phe Thr Arg Val Ser
                 245                 250                 255 aat tac atc gac tgg atc aat tcg gta aga acc gga cca gcc ttg agc   816
Asn Tyr Ile Asp Trp Ile Asn Ser Val Arg Thr Gly Pro Ala Leu Ser
             260                 265                 270 ccc aag gca cta ccc tgc tca cct ggc ctc ggg agt gcc atg ccc acc   864
Pro Lys Ala Leu Pro Cys Ser Pro Gly Leu Gly Ser Ala Met Pro Thr
         275                 280                 285 tgg tgactgagaa tcccctcctt cctcttgaga gctagatggg aaccccttgg         917
Trp aggaggctgc agacctgagt aactgctggg cctgccatgg gtcccccaaa             967
tttctgtgtg gataaagctg agtgaaaagg aacatagagg gtggccttgt            1017
ccaaagaggt tggacactcc tcaggcatat gaagagtgag ttccgctggg            1067
```

-continued cgccgtggct catgcctgta atcccagctc tttgggaggc caaggcgggc    1117
agatcacgag gtcagaagtt caagaccagc ctgaccaacc tggcaaaacc    1167
ccatgtctac taaaaaaatc c    1188

<210> SEQ ID NO 8
<211> LENGTH: 289
<212> TYPE: PRT
<213> ORGANISM: Homo sapiens

<400> SEQUENCE: 8

Met Ile Arg Thr Leu Leu Ser Thr Leu Val Ala Gly Ala Leu Ser
1               5                   10                  15

Cys Gly Asp Pro Thr Tyr Pro Pro Tyr Val Thr Arg Val Val Gly Gly
                20                  25                  30

Glu Glu Ala Arg Pro Asn Ser Trp Pro Trp Gln Val Ser Leu Gln Tyr
            35                  40                  45

Ser Ser Asn Gly Gln Trp Tyr His Thr Cys Gly Gly Ser Leu Ile Ala
        50                  55                  60

Asn Ser Trp Val Leu Thr Ala Ala His Cys Ile Ser Ser Ser Gly Ile
65                  70                  75                  80

Tyr Arg Val Met Leu Gly Gln His Asn Leu Tyr Val Ala Glu Ser Gly
                85                  90                  95

Ser Leu Ala Val Ser Val Ser Lys Ile Val His Lys Asp Trp Asn
            100                 105                 110

Ser Asp Gln Val Ser Lys Gly Asn Asp Ile Ala Leu Leu Lys Leu Ala
        115                 120                 125

Asn Pro Val Ser Leu Thr Asp Lys Ile Gln Leu Ala Cys Leu Pro Pro
    130                 135                 140

Ala Gly Thr Ile Leu Pro Asn Asn Tyr Pro Cys Tyr Val Thr Gly Trp
145                 150                 155                 160

Gly Arg Leu Gln Ala Asn Gly Ala Leu Pro Asp Leu Lys Gln Gly
                165                 170                 175

Gln Leu Leu Val Val Asp Tyr Ala Thr Cys Ser Ser Ser Gly Trp Trp
            180                 185                 190

Gly Ser Thr Val Lys Thr Asn Met Ile Cys Ala Gly Gly Asn Gly Val
        195                 200                 205

Ile Cys Thr Cys Asn Gly Asp Ser Gly Gly Pro Leu Asn Cys Gln Ala
    210                 215                 220

Ser Asp Gly Arg Trp Gln Val His Gly Ile Val Ser Phe Gly Ser Arg
225                 230                 235                 240

Leu Gly Cys Asn Tyr Tyr His Lys Pro Ser Val Phe Thr Arg Val Ser
                245                 250                 255

Asn Tyr Ile Asp Trp Ile Asn Ser Val Arg Thr Gly Pro Ala Leu Ser
            260                 265                 270

Pro Lys Ala Leu Pro Cys Ser Pro Gly Leu Gly Ser Ala Met Pro Thr
        275                 280                 285

Trp

<210> SEQ ID NO 9
<211> LENGTH: 889
<212> TYPE: DNA
<213> ORGANISM: Homo sapiens
<220> FEATURE:
<221> NAME/KEY: CDS
<222> LOCATION: (1)..(799)

<400> SEQUENCE: 9

```
atg att agg acc ctg ctg ctg tcc act ttg gtg gct gga gcc ctc agt       48
Met Ile Arg Thr Leu Leu Leu Ser Thr Leu Val Ala Gly Ala Leu Ser
 1               5                  10                  15 tgt ggg gac ccc act tac cca cct tat gtg act agg gtg gtt ggc ggt       96
Cys Gly Asp Pro Thr Tyr Pro Pro Tyr Val Thr Arg Val Val Gly Gly
             20                  25                  30 gaa gaa gcg agg ccc aac agc tgg ccc tgg cag gtg agt ctg cag tac      144
Glu Glu Ala Arg Pro Asn Ser Trp Pro Trp Gln Val Ser Leu Gln Tyr
         35                  40                  45 agc tcc aat ggc cag tgg tac cac acc tgc gga ggg tcc ctg ata gcc      192
Ser Ser Asn Gly Gln Trp Tyr His Thr Cys Gly Gly Ser Leu Ile Ala
     50                  55                  60 aac agc tgg gtc ctg acg gct gcc cac tgc atc agc tcc ggg atc          240
Asn Ser Trp Val Leu Thr Ala Ala His Cys Ile Ser Ser Gly Ile
 65                  70                  75                  80 tac cgc gtg atg ctg ggc cag cat aac ctc tac gtt gca gag tcc ggc      288
Tyr Arg Val Met Leu Gly Gln His Asn Leu Tyr Val Ala Glu Ser Gly
                 85                  90                  95 tcg ctg gcc gtc agt gtc tct aag att gtg gtg cac aag gac tgg aac      336
Ser Leu Ala Val Ser Val Ser Lys Ile Val Val His Lys Asp Trp Asn
             100                 105                 110 tcc gac cag gtc tcc aaa ggg aac gac att gcc ctg ctc aaa ctg gct      384
Ser Asp Gln Val Ser Lys Gly Asn Asp Ile Ala Leu Leu Lys Leu Ala
         115                 120                 125 aac ccc gtc tcc ctc acc gac aag atc cag ctg gcc tgc ctc cct cct      432
Asn Pro Val Ser Leu Thr Asp Lys Ile Gln Leu Ala Cys Leu Pro Pro
     130                 135                 140 gcc ggc acc att cta ccc aac aac tac ccc tgc tac gtc acg ggc tgg      480
Ala Gly Thr Ile Leu Pro Asn Asn Tyr Pro Cys Tyr Val Thr Gly Trp
145                 150                 155                 160 gga agg ctg cag gcc aac ggg gct ctc cct gat gac ctg aag cag ggc      528
Gly Arg Leu Gln Ala Asn Gly Ala Leu Pro Asp Asp Leu Lys Gln Gly
                165                 170                 175 cag ttg ctg gtt gtg gac tat gcc acc tgc tcc agc tct ggc tgg tgg      576
Gln Leu Leu Val Val Asp Tyr Ala Thr Cys Ser Ser Ser Gly Trp Trp
            180                 185                 190 ggc agc acc gtg aag acg aat atg atc tgt gct ggg ggt aat ggc gtg      624
Gly Ser Thr Val Lys Thr Asn Met Ile Cys Ala Gly Gly Asn Gly Val
        195                 200                 205 ata tgc acc tgc aac gga gac tct ggg ggg cca ctg aac tgt cag gcg      672
Ile Cys Thr Cys Asn Gly Asp Ser Gly Gly Pro Leu Asn Cys Gln Ala
    210                 215                 220 tct gac ggc cgg tgg cag gtg cac ggc atc gtc agc ttc ggg tct cgc      720
Ser Asp Gly Arg Trp Gln Val His Gly Ile Val Ser Phe Gly Ser Arg
225                 230                 235                 240 ctc ggc tgc aac tac tac cac aag ccc tcc gtc ttc acg cgg gtc tcc      768
Leu Gly Cys Asn Tyr Tyr His Lys Pro Ser Val Phe Thr Arg Val Ser
                245                 250                 255 aat tac atc gac tgg atg att gca aat aac taaccaaaag aagtccctgg        818
Asn Tyr Ile Asp Trp Met Ile Ala Asn Asn
            260                 265 gactgtttca gacttggaaa ggtcacggaa ggaaataat ataataaagt                 868 ggcaactatg caaaaaaaaa a                                               889
```

<210> SEQ ID NO 10
<211> LENGTH: 266
<212> TYPE: PRT

<213> ORGANISM: Homo sapiens

<400> SEQUENCE: 10

```
Met Ile Arg Thr Leu Leu Ser Thr Leu Val Ala Gly Ala Leu Ser
  1               5                  10                  15

Cys Gly Asp Pro Thr Tyr Pro Tyr Val Thr Arg Val Val Gly Gly
             20                  25                  30

Glu Glu Ala Arg Pro Asn Ser Trp Pro Trp Gln Val Ser Leu Gln Tyr
         35                  40                  45

Ser Ser Asn Gly Gln Trp Tyr His Thr Cys Gly Gly Ser Leu Ile Ala
 50                  55                  60

Asn Ser Trp Val Leu Thr Ala Ala His Cys Ile Ser Ser Ser Gly Ile
 65                  70                  75                  80

Tyr Arg Val Met Leu Gly Gln His Asn Leu Tyr Val Ala Glu Ser Gly
                 85                  90                  95

Ser Leu Ala Val Ser Val Ser Lys Ile Val His Lys Asp Trp Asn
            100                 105                 110

Ser Asp Gln Val Ser Lys Gly Asn Asp Ile Ala Leu Leu Lys Leu Ala
            115                 120                 125

Asn Pro Val Ser Leu Thr Asp Lys Ile Gln Leu Ala Cys Leu Pro Pro
130                 135                 140

Ala Gly Thr Ile Leu Pro Asn Asn Tyr Pro Cys Tyr Val Thr Gly Trp
145                 150                 155                 160

Gly Arg Leu Gln Ala Asn Gly Ala Leu Pro Asp Asp Leu Lys Gln Gly
                165                 170                 175

Gln Leu Leu Val Val Asp Tyr Ala Thr Cys Ser Ser Ser Gly Trp Trp
            180                 185                 190

Gly Ser Thr Val Lys Thr Asn Met Ile Cys Ala Gly Gly Asn Gly Val
            195                 200                 205

Ile Cys Thr Cys Asn Gly Asp Ser Gly Gly Pro Leu Asn Cys Gln Ala
210                 215                 220

Ser Asp Gly Arg Trp Gln Val His Gly Ile Val Ser Phe Gly Ser Arg
225                 230                 235                 240

Leu Gly Cys Asn Tyr Tyr His Lys Pro Ser Val Phe Thr Arg Val Ser
                245                 250                 255

Asn Tyr Ile Asp Trp Met Ile Ala Asn Asn
            260                 265
```

<210> SEQ ID NO 11
<211> LENGTH: 1080
<212> TYPE: DNA
<213> ORGANISM: Homo sapiens
<220> FEATURE:
<221> NAME/KEY: CDS
<222> LOCATION: (1)..(1080)

<400> SEQUENCE: 11

```
gga tcc gtc tcc act tac gcg cct gat atg tct agg atg ctt gga ggt      48
Gly Ser Val Ser Thr Tyr Ala Pro Asp Met Ser Arg Met Leu Gly Gly
  1               5                  10                  15 gaa gaa gcg agg ccc aac agc tgg ccc tgg cag atc tcc ctg cag tac      96
Glu Glu Ala Arg Pro Asn Ser Trp Pro Trp Gln Ile Ser Leu Gln Tyr
             20                  25                  30 agc tcc aat ggc cag tgg tac cac acc tgc gga ggg tcc ctg ata gcc     144
Ser Ser Asn Gly Gln Trp Tyr His Thr Cys Gly Gly Ser Leu Ile Ala
         35                  40                  45 aac agc tgg gtc ctg acg gct gcc cac tgc atc agc tcc tcc ggg atc     192
Asn Ser Trp Val Leu Thr Ala Ala His Cys Ile Ser Ser Ser Gly Ile
```

```
                    Asn Ser Trp Val Leu Thr Ala Ala His Cys Ile Ser Ser Gly Ile
                        50                  55                  60 tac cgc gtg atg ctg ggc cag cat aac ctc tac gtt gca gag tcc ggc        240
Tyr Arg Val Met Leu Gly Gln His Asn Leu Tyr Val Ala Glu Ser Gly
 65              70                  75                  80 tcg ctg gcc gtc agt gtc tct aag att gtg gtg cac aag gac tgg aac        288
Ser Leu Ala Val Ser Val Ser Lys Ile Val Val His Lys Asp Trp Asn
                 85                  90                  95 tcc gac cag gtc tcc aaa ggg aac gac att gcc ctg ctc aaa ctg gct        336
Ser Asp Gln Val Ser Lys Gly Asn Asp Ile Ala Leu Leu Lys Leu Ala
            100                 105                 110 aac ccc gtc tcc ctc gcc gac aag atc cag ctg gcc tgc ctc cct cct        384
Asn Pro Val Ser Leu Ala Asp Lys Ile Gln Leu Ala Cys Leu Pro Pro
        115                 120                 125 gcc ggc acc att cta ccc aac aac tac ccc tgc tac gtc acg ggc tgg        432
Ala Gly Thr Ile Leu Pro Asn Asn Tyr Pro Cys Tyr Val Thr Gly Trp
    130                 135                 140 gga agg ctg cag acc aac ggg gct ctc cct gat gac ctg aag cag ggc        480
Gly Arg Leu Gln Thr Asn Gly Ala Leu Pro Asp Asp Leu Lys Gln Gly
145                 150                 155                 160 cgg ttg ctg gtt gtg gac tat gcc acc tgc tcc agc tct ggc tgg tgg        528
Arg Leu Leu Val Val Asp Tyr Ala Thr Cys Ser Ser Ser Gly Trp Trp
                165                 170                 175 ggc agc acc gtg aag acg aat atg atc tgt gct ggg ggt gat ggc gtg        576
Gly Ser Thr Val Lys Thr Asn Met Ile Cys Ala Gly Gly Asp Gly Val
            180                 185                 190 ata tgc acc tgc aac gga gac tcc ggt ggg ccg ctg aac tgt cag gca        624
Ile Cys Thr Cys Asn Gly Asp Ser Gly Gly Pro Leu Asn Cys Gln Ala
        195                 200                 205 tct gac ggc cgg tgg gag gtg cat ggc atc ggc agc ctc acg tcg gtc        672
Ser Asp Gly Arg Trp Glu Val His Gly Ile Gly Ser Leu Thr Ser Val
    210                 215                 220 ctt ggt tgc aac tac tac tac aag ccc tcc atc ttc acg cgg gtc tcc        720
Leu Gly Cys Asn Tyr Tyr Tyr Lys Pro Ser Ile Phe Thr Arg Val Ser
225                 230                 235                 240 aac tac aac gac tgg atc aat tcg gta aga acc gga gca gcc ctg agc        768
Asn Tyr Asn Asp Trp Ile Asn Ser Val Arg Thr Gly Ala Ala Leu Ser
                245                 250                 255 ccc aag gca ctg acc tgc tca cct ggc ctc ggg agt gcc atg ccc acc        816
Pro Lys Ala Leu Thr Cys Ser Pro Gly Leu Gly Ser Ala Met Pro Thr
            260                 265                 270 tgg cga ctg aga acc ccc tcc ttc ctc ttg aga gct aga tgg gaa ccc        864
Trp Arg Leu Arg Thr Pro Ser Phe Leu Leu Arg Ala Arg Trp Glu Pro
        275                 280                 285 ctt gga gga ggc tgc aga cct tgg caa ctg ctg agt ccc cca tgg gtc        912
Leu Gly Gly Gly Cys Arg Pro Trp Gln Leu Leu Ser Pro Pro Trp Val
    290                 295                 300 ccc aaa att tct gtg tgg gta aag ctg agt gaa aag gaa cat gag agt        960
Pro Lys Ile Ser Val Trp Val Lys Leu Ser Glu Lys Glu His Glu Ser
305                 310                 315                 320 atg gcc ttg tcc aaa gac gtt gga cac tcc tca ggt acg tta aga gtg       1008
Met Ala Leu Ser Lys Asp Val Gly His Ser Ser Gly Thr Leu Arg Val
                325                 330                 335 agt tcc aca gga atg att tta ttt ttg tgt att tgt gtg tgg ccc aga       1056
Ser Ser Thr Gly Met Ile Leu Phe Leu Cys Ile Cys Val Trp Pro Arg
            340                 345                 350 ctc tac cat cca gtg cta ctc gag                                       1080
Leu Tyr His Pro Val Leu Leu Glu
        355                 360
```

```
<210> SEQ ID NO 12
<211> LENGTH: 360
<212> TYPE: PRT
<213> ORGANISM: Homo sapiens

<400> SEQUENCE: 12

Gly Ser Val Ser Thr Tyr Ala Pro Asp Met Ser Arg Met Leu Gly Gly
  1               5                  10                  15

Glu Glu Ala Arg Pro Asn Ser Trp Pro Trp Gln Ile Ser Leu Gln Tyr
             20                  25                  30

Ser Ser Asn Gly Gln Trp Tyr His Thr Cys Gly Gly Ser Leu Ile Ala
         35                  40                  45

Asn Ser Trp Val Leu Thr Ala Ala His Cys Ile Ser Ser Ser Gly Ile
     50                  55                  60

Tyr Arg Val Met Leu Gly Gln His Asn Leu Tyr Val Ala Glu Ser Gly
 65                  70                  75                  80

Ser Leu Ala Val Ser Val Ser Lys Ile Val His Lys Asp Trp Asn
                 85                  90                  95

Ser Asp Gln Val Ser Lys Gly Asn Asp Ile Ala Leu Leu Lys Leu Ala
            100                 105                 110

Asn Pro Val Ser Leu Ala Asp Lys Ile Gln Leu Ala Cys Leu Pro Pro
        115                 120                 125

Ala Gly Thr Ile Leu Pro Asn Asn Tyr Pro Cys Tyr Val Thr Gly Trp
    130                 135                 140

Gly Arg Leu Gln Thr Asn Gly Ala Leu Pro Asp Asp Leu Lys Gln Gly
145                 150                 155                 160

Arg Leu Leu Val Val Asp Tyr Ala Thr Cys Ser Ser Ser Gly Trp Trp
                165                 170                 175

Gly Ser Thr Val Lys Thr Asn Met Ile Cys Ala Gly Gly Asp Gly Val
            180                 185                 190

Ile Cys Thr Cys Asn Gly Asp Ser Gly Gly Pro Leu Asn Cys Gln Ala
        195                 200                 205

Ser Asp Gly Arg Trp Glu Val His Gly Ile Gly Ser Leu Thr Ser Val
    210                 215                 220

Leu Gly Cys Asn Tyr Tyr Tyr Lys Pro Ser Ile Phe Thr Arg Val Ser
225                 230                 235                 240

Asn Tyr Asn Asp Trp Ile Asn Ser Val Arg Thr Gly Ala Ala Leu Ser
                245                 250                 255

Pro Lys Ala Leu Thr Cys Ser Pro Gly Leu Gly Ser Ala Met Pro Thr
            260                 265                 270

Trp Arg Leu Arg Thr Pro Ser Phe Leu Leu Arg Ala Arg Trp Glu Pro
        275                 280                 285

Leu Gly Gly Gly Cys Arg Pro Trp Gln Leu Leu Ser Pro Pro Trp Val
    290                 295                 300

Pro Lys Ile Ser Val Trp Val Lys Leu Ser Glu Lys Glu His Glu Ser
305                 310                 315                 320

Met Ala Leu Ser Lys Asp Val Gly His Ser Ser Gly Thr Leu Arg Val
                325                 330                 335

Ser Ser Thr Gly Met Ile Leu Phe Leu Cys Ile Cys Val Trp Pro Arg
            340                 345                 350

Leu Tyr His Pro Val Leu Leu Glu
        355                 360

<210> SEQ ID NO 13
```

```
<211> LENGTH: 1080
<212> TYPE: DNA
<213> ORGANISM: Homo sapiens
<220> FEATURE:
<221> NAME/KEY: CDS
<222> LOCATION: (1)..(1080)

<400> SEQUENCE: 13 gga tcc gtc tcc act tac gcg cct gat atg tct agg atg cgt gga ggt       48
Gly Ser Val Ser Thr Tyr Ala Pro Asp Met Ser Arg Met Arg Gly Gly
 1               5                  10                  15 gaa gaa gcg agg ccc aac agc tgg ccc tgg cag gtc tcc ctg cag tac       96
Glu Glu Ala Arg Pro Asn Ser Trp Pro Trp Gln Val Ser Leu Gln Tyr
             20                  25                  30 agc tcc aat ggc cag tgg tac cac acc tgc gga ggg tcc ctg ata gcc      144
Ser Ser Asn Gly Gln Trp Tyr His Thr Cys Gly Gly Ser Leu Ile Ala
         35                  40                  45 aac agc tgg gtc ctg acg gct gcc cac tgc atc agc tcc ggg atc          192
Asn Ser Trp Val Leu Thr Ala Ala His Cys Ile Ser Ser Gly Ile
     50                  55                  60 tac cgc gtg atg ctg ggc cag cat aac ctc tac gtt gca gag tcc ggc      240
Tyr Arg Val Met Leu Gly Gln His Asn Leu Tyr Val Ala Glu Ser Gly
 65                  70                  75                  80 tcg ctg gcc gtc agt gtc tct aag att gtg gtg cac aag gac tgg aac      288
Ser Leu Ala Val Ser Val Ser Lys Ile Val Val His Lys Asp Trp Asn
                 85                  90                  95 tcc gac cag gtc tcc aaa ggg aac gac att gcc ctg ctc aaa ctg gct      336
Ser Asp Gln Val Ser Lys Gly Asn Asp Ile Ala Leu Leu Lys Leu Ala
            100                 105                 110 aac ccc gtc tcc ctc acc gac aag atc cag ctg gcc tgc ctc cct cct      384
Asn Pro Val Ser Leu Thr Asp Lys Ile Gln Leu Ala Cys Leu Pro Pro
        115                 120                 125 gcc ggc acc att cta ccc aac aac tac ccc tgc tac gtc acg ggc tgg      432
Ala Gly Thr Ile Leu Pro Asn Asn Tyr Pro Cys Tyr Val Thr Gly Trp
    130                 135                 140 gga agg ctg cag acc aac ggg gct ctc cct gat gac ctg aag cag ggc      480
Gly Arg Leu Gln Thr Asn Gly Ala Leu Pro Asp Asp Leu Lys Gln Gly
145                 150                 155                 160 cgg ttg ctg gtt gtg gac tat gcc acc tgc tcc agc tct ggc tgg tgg      528
Arg Leu Leu Val Val Asp Tyr Ala Thr Cys Ser Ser Ser Gly Trp Trp
                165                 170                 175 ggc agc acc gtg aag acg aat atg atc tgt gct ggg ggt gat ggc gtg      576
Gly Ser Thr Val Lys Thr Asn Met Ile Cys Ala Gly Gly Asp Gly Val
            180                 185                 190 ata tgc acc tgc aac gga gac tcc ggt ggg ccg ctg aac tgc cag gca      624
Ile Cys Thr Cys Asn Gly Asp Ser Gly Gly Pro Leu Asn Cys Gln Ala
        195                 200                 205 tct gac ggc cgg tgg gag gtg cat ggc atc ggc agc ctc acg tcg gtc      672
Ser Asp Gly Arg Trp Glu Val His Gly Ile Gly Ser Leu Thr Ser Val
    210                 215                 220 ctt ggt tgc aac tac tac tac aag ccc tcc atc ttc acg cgg gtc tcc      720
Leu Gly Cys Asn Tyr Tyr Tyr Lys Pro Ser Ile Phe Thr Arg Val Ser
225                 230                 235                 240 aac tac aac gac tgg atc aat tcg gta aga acc gga gca gcc ctg agt      768
Asn Tyr Asn Asp Trp Ile Asn Ser Val Arg Thr Gly Ala Ala Leu Ser
                245                 250                 255 ccc aag gca ctg ccc tgc tca cct ggc ctc ggg agt gcc atg ccc acc      816
Pro Lys Ala Leu Pro Cys Ser Pro Gly Leu Gly Ser Ala Met Pro Thr
            260                 265                 270 tgg cga ctg aga acc ccc tcc ttc ctc ttg aga gct aga tgg gaa ccc      864
Trp Arg Leu Arg Thr Pro Ser Phe Leu Leu Arg Ala Arg Trp Glu Pro
```

-continued

```
            275                 280                 285
ctt gga gga ggc tgc aga cct tgg caa ctg ctg agt ccc cca tgg gtc    912
Leu Gly Gly Gly Cys Arg Pro Trp Gln Leu Leu Ser Pro Pro Trp Val
        290                 295                 300 ccc aaa att tct gtg tgg gta aag ctg agt gaa aag gaa cat gag agt    960
Pro Lys Ile Ser Val Trp Val Lys Leu Ser Glu Lys Glu His Glu Ser
305                 310                 315                 320 atg gcc ttg tcc aaa gac gtt gga cac tcc tca ggt atg tta aga gtg   1008
Met Ala Leu Ser Lys Asp Val Gly His Ser Ser Gly Met Leu Arg Val
                325                 330                 335 agt tcc aca gga atg att tta ttt ttg tgt att tgt gaa tgg ccc aga   1056
Ser Ser Thr Gly Met Ile Leu Phe Leu Cys Ile Cys Glu Trp Pro Arg
            340                 345                 350 ctc tac cat cca gtg cta ctc gag                                   1080
Leu Tyr His Pro Val Leu Leu Glu
            355                 360

<210> SEQ ID NO 14
<211> LENGTH: 360
<212> TYPE: PRT
<213> ORGANISM: Homo sapiens

<400> SEQUENCE: 14

Gly Ser Val Ser Thr Tyr Ala Pro Asp Met Ser Arg Met Arg Gly Gly
1               5                   10                  15

Glu Glu Ala Arg Pro Asn Ser Trp Pro Trp Gln Val Ser Leu Gln Tyr
            20                  25                  30

Ser Ser Asn Gly Gln Trp Tyr His Thr Cys Gly Gly Ser Leu Ile Ala
        35                  40                  45

Asn Ser Trp Val Leu Thr Ala Ala His Cys Ile Ser Ser Ser Gly Ile
    50                  55                  60

Tyr Arg Val Met Leu Gly Gln His Asn Leu Tyr Val Ala Glu Ser Gly
65                  70                  75                  80

Ser Leu Ala Val Ser Val Ser Lys Ile Val His Lys Asp Trp Asn
                85                  90                  95

Ser Asp Gln Val Ser Lys Gly Asn Asp Ile Ala Leu Leu Lys Leu Ala
            100                 105                 110

Asn Pro Val Ser Leu Thr Asp Lys Ile Gln Leu Ala Cys Leu Pro Pro
        115                 120                 125

Ala Gly Thr Ile Leu Pro Asn Asn Tyr Pro Cys Tyr Val Thr Gly Trp
    130                 135                 140

Gly Arg Leu Gln Thr Asn Gly Ala Leu Pro Asp Asp Leu Lys Gln Gly
145                 150                 155                 160

Arg Leu Leu Val Val Asp Tyr Ala Thr Cys Ser Ser Ser Gly Trp Trp
                165                 170                 175

Gly Ser Thr Val Lys Thr Asn Met Ile Cys Ala Gly Gly Asp Gly Val
            180                 185                 190

Ile Cys Thr Cys Asn Gly Asp Ser Gly Gly Pro Leu Asn Cys Gln Ala
        195                 200                 205

Ser Asp Gly Arg Trp Glu Val His Gly Ile Gly Ser Leu Thr Ser Val
    210                 215                 220

Leu Gly Cys Asn Tyr Tyr Tyr Lys Pro Ser Ile Phe Thr Arg Val Ser
225                 230                 235                 240

Asn Tyr Asn Asp Trp Ile Asn Ser Val Arg Thr Gly Ala Ala Leu Ser
                245                 250                 255

Pro Lys Ala Leu Pro Cys Ser Pro Gly Leu Gly Ser Ala Met Pro Thr
```

```
                260                 265                 270
Trp Arg Leu Arg Thr Pro Ser Phe Leu Leu Arg Ala Arg Trp Glu Pro
            275                 280                 285

Leu Gly Gly Gly Cys Arg Pro Trp Gln Leu Leu Ser Pro Pro Trp Val
            290                 295                 300

Pro Lys Ile Ser Val Trp Val Lys Leu Ser Glu Lys Glu His Glu Ser
305                 310                 315                 320

Met Ala Leu Ser Lys Asp Val Gly His Ser Ser Gly Met Leu Arg Val
                325                 330                 335

Ser Ser Thr Gly Met Ile Leu Phe Leu Cys Ile Cys Glu Trp Pro Arg
            340                 345                 350

Leu Tyr His Pro Val Leu Leu Glu
            355                 360

<210> SEQ ID NO 15
<211> LENGTH: 1080
<212> TYPE: DNA
<213> ORGANISM: Homo sapiens
<220> FEATURE:
<221> NAME/KEY: CDS
<222> LOCATION: (1)..(1080)

<400> SEQUENCE: 15 gga tcc gtc tcc act tac gcg cct gat atg tct agg atg ctt gga ggt        48
Gly Ser Val Ser Thr Tyr Ala Pro Asp Met Ser Arg Met Leu Gly Gly
  1               5                  10                  15 gaa gaa gcg agg ccc aac agc tgg ccc tgg cag gtc tcc ctg cag tac        96
Glu Glu Ala Arg Pro Asn Ser Trp Pro Trp Gln Val Ser Leu Gln Tyr
             20                  25                  30 agc tcc aat ggc cag tgg tac cac acc tgc gga ggg tcc ctg ata gcc       144
Ser Ser Asn Gly Gln Trp Tyr His Thr Cys Gly Gly Ser Leu Ile Ala
         35                  40                  45 aac agc tgg gtc ctg acg gct gcc cac tgc atc agc tcc tcc agg atc       192
Asn Ser Trp Val Leu Thr Ala Ala His Cys Ile Ser Ser Ser Arg Ile
     50                  55                  60 tac cgc gtg atg ctg ggc cag cat aac ctc tac gtt gca gag tcc ggc       240
Tyr Arg Val Met Leu Gly Gln His Asn Leu Tyr Val Ala Glu Ser Gly
 65                  70                  75                  80 tcg cta gcc gtc agt gtc tct aag att gtg gtg cac aag gac tgg aac       288
Ser Leu Ala Val Ser Val Ser Lys Ile Val Val His Lys Asp Trp Asn
                 85                  90                  95 tcc aac cag gtc tcc aaa ggg aac gac att gcc ctg ctc aaa ctg gct       336
Ser Asn Gln Val Ser Lys Gly Asn Asp Ile Ala Leu Leu Lys Leu Ala
            100                 105                 110 aac ccc gtc tcc ctc acc gac aag atc cag ctg gcc tgc ctc cct cct       384
Asn Pro Val Ser Leu Thr Asp Lys Ile Gln Leu Ala Cys Leu Pro Pro
        115                 120                 125 gcc ggc acc att cta ccc aac aac tac ccc tgc tac gtc aca ggc tgg       432
Ala Gly Thr Ile Leu Pro Asn Asn Tyr Pro Cys Tyr Val Thr Gly Trp
    130                 135                 140 gga agg ctg cag acc aac ggg gct ctc cct gat gac ctg aag cag ggc       480
Gly Arg Leu Gln Thr Asn Gly Ala Leu Pro Asp Asp Leu Lys Gln Gly
145                 150                 155                 160 cgg ttg ctg gtt gtg gac tat gcc acc tgc tcc agc tct ggc tgg tgg       528
Arg Leu Leu Val Val Asp Tyr Ala Thr Cys Ser Ser Ser Gly Trp Trp
                165                 170                 175 ggc agc acc gtg aag acg aat atg att tgt gct ggg ggt gat ggc gtg       576
Gly Ser Thr Val Lys Thr Asn Met Ile Cys Ala Gly Gly Asp Gly Val
            180                 185                 190
```

```
ata tgc acc tgc aac gga gac tcc ggt ggg ccg ctg aac tgt cag gca        624
Ile Cys Thr Cys Asn Gly Asp Ser Gly Gly Pro Leu Asn Cys Gln Ala
        195                 200                 205 tct gac ggc cgg tgg gag gtg cat ggc atc ggc agc ctc acg tcg gtc        672
Ser Asp Gly Arg Trp Glu Val His Gly Ile Gly Ser Leu Thr Ser Val
210                 215                 220 ctt ggt tgc aac tac tac tac aag ccc tcc atc ttc acg cgg gtc tcc        720
Leu Gly Cys Asn Tyr Tyr Tyr Lys Pro Ser Ile Phe Thr Arg Val Ser
225                 230                 235                 240 aac tac aac gac tgg atc aat tcg gta aga acc gga gca gcc ctg agc        768
Asn Tyr Asn Asp Trp Ile Asn Ser Val Arg Thr Gly Ala Ala Leu Ser
                245                 250                 255 ccc aag gca ctg acc tgc tca cct ggc ctc ggg agt gcc atg ccc acc        816
Pro Lys Ala Leu Thr Cys Ser Pro Gly Leu Gly Ser Ala Met Pro Thr
        260                 265                 270 tgg cga ctg aga acc ccc tcc ttc ctc ttg aga gct aga tgg gaa ccc        864
Trp Arg Leu Arg Thr Pro Ser Phe Leu Leu Arg Ala Arg Trp Glu Pro
    275                 280                 285 ctt gga gga ggc tgc aga cct tgg caa ctg ctg agt ccc cca tgg gtc        912
Leu Gly Gly Gly Cys Arg Pro Trp Gln Leu Leu Ser Pro Pro Trp Val
290                 295                 300 ccc aaa att tct gtg tgg gta aag ctg agt gaa aag gaa cat gag agt        960
Pro Lys Ile Ser Val Trp Val Lys Leu Ser Glu Lys Glu His Glu Ser
305                 310                 315                 320 atg gcc ttg tcc aaa gac gtt gga cac tcc tca ggt atg tta aga gtg       1008
Met Ala Leu Ser Lys Asp Val Gly His Ser Ser Gly Met Leu Arg Val
                325                 330                 335 agt tcc aca gga atg att tta ttt ttg tgt att tgt gtg tgg ccc aga       1056
Ser Ser Thr Gly Met Ile Leu Phe Leu Cys Ile Cys Val Trp Pro Arg
        340                 345                 350 ctc tac cat cca gtg cta ctc gag                                        1080
Leu Tyr His Pro Val Leu Leu Glu
355                 360

<210> SEQ ID NO 16
<211> LENGTH: 360
<212> TYPE: PRT
<213> ORGANISM: Homo sapiens

<400> SEQUENCE: 16

Gly Ser Val Ser Thr Tyr Ala Pro Asp Met Ser Arg Met Leu Gly Gly
  1               5                  10                  15

Glu Glu Ala Arg Pro Asn Ser Trp Pro Trp Gln Val Ser Leu Gln Tyr
                20                  25                  30

Ser Ser Asn Gly Gln Trp Tyr His Thr Cys Gly Gly Ser Leu Ile Ala
            35                  40                  45

Asn Ser Trp Val Leu Thr Ala Ala His Cys Ile Ser Ser Arg Ile
        50                  55                  60

Tyr Arg Val Met Leu Gly Gln His Asn Leu Tyr Val Ala Glu Ser Gly
 65                  70                  75                  80

Ser Leu Ala Val Ser Val Ser Lys Ile Val His Lys Asp Trp Asn
                85                  90                  95

Ser Asn Gln Val Ser Lys Gly Asn Asp Ile Ala Leu Leu Lys Leu Ala
               100                 105                 110

Asn Pro Val Ser Leu Thr Asp Lys Ile Gln Leu Ala Cys Leu Pro Pro
           115                 120                 125

Ala Gly Thr Ile Leu Pro Asn Asn Tyr Pro Cys Tyr Val Thr Gly Trp
       130                 135                 140
```

```
Gly Arg Leu Gln Thr Asn Gly Ala Leu Pro Asp Asp Leu Lys Gln Gly
145                 150                 155                 160

Arg Leu Leu Val Val Asp Tyr Ala Thr Cys Ser Ser Gly Trp Trp
                165                 170                 175

Gly Ser Thr Val Lys Thr Asn Met Ile Cys Ala Gly Gly Asp Gly Val
            180                 185                 190

Ile Cys Thr Cys Asn Gly Asp Ser Gly Gly Pro Leu Asn Cys Gln Ala
        195                 200                 205

Ser Asp Gly Arg Trp Glu Val His Gly Ile Gly Ser Leu Thr Ser Val
    210                 215                 220

Leu Gly Cys Asn Tyr Tyr Lys Pro Ser Ile Phe Thr Arg Val Ser
225                 230                 235                 240

Asn Tyr Asn Asp Trp Ile Asn Ser Val Arg Thr Gly Ala Ala Leu Ser
                245                 250                 255

Pro Lys Ala Leu Thr Cys Ser Pro Gly Leu Gly Ser Ala Met Pro Thr
            260                 265                 270

Trp Arg Leu Arg Thr Pro Ser Phe Leu Leu Arg Ala Arg Trp Glu Pro
        275                 280                 285

Leu Gly Gly Gly Cys Arg Pro Trp Gln Leu Leu Ser Pro Pro Trp Val
    290                 295                 300

Pro Lys Ile Ser Val Trp Val Lys Leu Ser Glu Lys Glu His Glu Ser
305                 310                 315                 320

Met Ala Leu Ser Lys Asp Val Gly His Ser Ser Gly Met Leu Arg Val
                325                 330                 335

Ser Ser Thr Gly Met Ile Leu Phe Leu Cys Ile Cys Val Trp Pro Arg
            340                 345                 350

Leu Tyr His Pro Val Leu Leu Glu
        355                 360

<210> SEQ ID NO 17
<211> LENGTH: 1080
<212> TYPE: DNA
<213> ORGANISM: Homo sapiens
<220> FEATURE:
<221> NAME/KEY: CDS
<222> LOCATION: (1)..(1080)

<400> SEQUENCE: 17 gga tcc gtc tcc act tac gcg cct gat atg tct agg atg ctt gga ggt        48
Gly Ser Val Ser Thr Tyr Ala Pro Asp Met Ser Arg Met Leu Gly Gly
1               5                   10                  15 gaa gaa gcg agg ccc aac agc tgg ccc tgg cag gtc tcc ctg cag tac       96
Glu Glu Ala Arg Pro Asn Ser Trp Pro Trp Gln Val Ser Leu Gln Tyr
            20                  25                  30 agc tcc aat ggc cag tgg tac cac acc tgc gga ggg tcc ctg ata gcc      144
Ser Ser Asn Gly Gln Trp Tyr His Thr Cys Gly Gly Ser Leu Ile Ala
        35                  40                  45 aac agc tgg gtc ctg acg gct gcc cac tgc atc agc tcc ggg atc          192
Asn Ser Trp Val Leu Thr Ala Ala His Cys Ile Ser Ser Gly Ile
    50                  55                  60 tac cgc gtg atg ctg ggc cag cat aac ctc tac gtt gca gag tcc ggc      240
Tyr Arg Val Met Leu Gly Gln His Asn Leu Tyr Val Ala Glu Ser Gly
65                  70                  75                  80 tcg ctg gcc gtc agt gtc tct aag att gtg gtg cac aag gac tgg aac      288
Ser Leu Ala Val Ser Val Ser Lys Ile Val Val His Lys Asp Trp Asn
                85                  90                  95 tcc gac cag gtc tcc aaa ggg aac gac att gcc ctg ctc aaa ctg gct      336
Ser Asp Gln Val Ser Lys Gly Asn Asp Ile Ala Leu Leu Lys Leu Ala
```

| | | |
|---|---|---|
| aac ccc gtc tcc ctc acc gac aag atc cag ctg gcc tgc ctc cct cct<br>Asn Pro Val Ser Leu Thr Asp Lys Ile Gln Leu Ala Cys Leu Pro Pro<br>            115                  120                125 | 384 |
| gcc ggc acc att cta ccc aac aac tac ccc tgc tac gtc acg ggc tgg<br>Ala Gly Thr Ile Leu Pro Asn Asn Tyr Pro Cys Tyr Val Thr Gly Trp<br>130                  135                  140 | 432 |
| gga agg ctg cag acc aac ggg gct ctc cct gat gac ctg aag cag ggc<br>Gly Arg Leu Gln Thr Asn Gly Ala Leu Pro Asp Asp Leu Lys Gln Gly<br>145                  150                  155                160 | 480 |
| cgg ttg ctg gtt gtg gac tat gcc acc tgc tcc agc tct ggc tgg tgg<br>Arg Leu Leu Val Val Asp Tyr Ala Thr Cys Ser Ser Ser Gly Trp Trp<br>                  165                  170                175 | 528 |
| ggc agc acc gtg aag acg aat atg atc tgt gct ggg ggt gat ggc gtg<br>Gly Ser Thr Val Lys Thr Asn Met Ile Cys Ala Gly Gly Asp Gly Val<br>            180                  185                190 | 576 |
| ata tgc acc tgc aac gga gac tcc ggt ggg ccg ctg aac tgt cag gca<br>Ile Cys Thr Cys Asn Gly Asp Ser Gly Gly Pro Leu Asn Cys Gln Ala<br>                  195                  200                205 | 624 |
| tct gac ggc cgg tgg gag gtg cat ggc atc ggc agc ctc acg tcg gtc<br>Ser Asp Gly Arg Trp Glu Val His Gly Ile Gly Ser Leu Thr Ser Val<br>            210                  215                220 | 672 |
| ctt ggt tgc aac tac tac tac aag ccc tcc atc ttc acg cgg gtc tcc<br>Leu Gly Cys Asn Tyr Tyr Tyr Lys Pro Ser Ile Phe Thr Arg Val Ser<br>225                  230                  235                240 | 720 |
| aac tac aac gac tgg atc aat tcg gta aga acc gga gca gcc ctg agc<br>Asn Tyr Asn Asp Trp Ile Asn Ser Val Arg Thr Gly Ala Ala Leu Ser<br>                  245                  250                255 | 768 |
| ccc aag gca ctg ccc tgc tca cct ggc ctc ggg agt gcc atg ccc acc<br>Pro Lys Ala Leu Pro Cys Ser Pro Gly Leu Gly Ser Ala Met Pro Thr<br>            260                  265                270 | 816 |
| tgg cga ctg aga acc ccc tcc ttc ctc ttg aga gct aga tgg gaa ccc<br>Trp Arg Leu Arg Thr Pro Ser Phe Leu Leu Arg Ala Arg Trp Glu Pro<br>                  275                  280                285 | 864 |
| ctt gga gga ggc tgc aga cct tgg caa ctg ctg agt ccc cca tgg gtc<br>Leu Gly Gly Gly Cys Arg Pro Trp Gln Leu Leu Ser Pro Pro Trp Val<br>290                  295                  300 | 912 |
| ccc aaa att tct gtg tgg gta aag ctg agt gaa aag gaa cat gag agt<br>Pro Lys Ile Ser Val Trp Val Lys Leu Ser Glu Lys Glu His Glu Ser<br>305                  310                  315                320 | 960 |
| atg gcc ttg tcc aaa gac gtt gga cac tcc tca ggt atg tta aga gtg<br>Met Ala Leu Ser Lys Asp Val Gly His Ser Ser Gly Met Leu Arg Val<br>                  325                  330                335 | 1008 |
| agt tcc aca gga atg att tta ttt ttg tgt att tgt gtg tgg ccc aga<br>Ser Ser Thr Gly Met Ile Leu Phe Leu Cys Ile Cys Val Trp Pro Arg<br>            340                  345                350 | 1056 |
| ctc tac cat cca gtg cta ctc gag<br>Leu Tyr His Pro Val Leu Leu Glu<br>            355                  360 | 1080 |

<210> SEQ ID NO 18
<211> LENGTH: 360
<212> TYPE: PRT
<213> ORGANISM: Homo sapiens

<400> SEQUENCE: 18

Gly Ser Val Ser Thr Tyr Ala Pro Asp Met Ser Arg Met Leu Gly Gly
1               5                   10                  15

Glu Glu Ala Arg Pro Asn Ser Trp Pro Trp Gln Val Ser Leu Gln Tyr
            20                  25                  30

```
Ser Ser Asn Gly Gln Trp Tyr His Thr Cys Gly Gly Ser Leu Ile Ala
        35                  40                  45

Asn Ser Trp Val Leu Thr Ala Ala His Cys Ile Ser Ser Ser Gly Ile
        50                  55                  60

Tyr Arg Val Met Leu Gly Gln His Asn Leu Tyr Val Ala Glu Ser Gly
 65                  70                  75                  80

Ser Leu Ala Val Ser Val Ser Lys Ile Val His Lys Asp Trp Asn
                 85                  90                  95

Ser Asp Gln Val Ser Lys Gly Asn Asp Ile Ala Leu Leu Lys Leu Ala
                100                 105                 110

Asn Pro Val Ser Leu Thr Asp Lys Ile Gln Leu Ala Cys Leu Pro Pro
                115                 120                 125

Ala Gly Thr Ile Leu Pro Asn Asn Tyr Pro Cys Tyr Val Thr Gly Trp
        130                 135                 140

Gly Arg Leu Gln Thr Asn Gly Ala Leu Pro Asp Asp Leu Lys Gln Gly
145                 150                 155                 160

Arg Leu Val Val Asp Tyr Ala Thr Cys Ser Ser Gly Trp Trp
                165                 170                 175

Gly Ser Thr Val Lys Thr Asn Met Ile Cys Ala Gly Asp Gly Val
                180                 185                 190

Ile Cys Thr Cys Asn Gly Asp Ser Gly Gly Pro Leu Asn Cys Gln Ala
        195                 200                 205

Ser Asp Gly Arg Trp Glu Val His Gly Ile Gly Ser Leu Thr Ser Val
210                 215                 220

Leu Gly Cys Asn Tyr Tyr Tyr Lys Pro Ser Ile Phe Thr Arg Val Ser
225                 230                 235                 240

Asn Tyr Asn Asp Trp Ile Asn Ser Val Arg Thr Gly Ala Ala Leu Ser
                245                 250                 255

Pro Lys Ala Leu Pro Cys Ser Pro Gly Leu Gly Ser Ala Met Pro Thr
        260                 265                 270

Trp Arg Leu Arg Thr Pro Ser Phe Leu Leu Arg Ala Arg Trp Glu Pro
        275                 280                 285

Leu Gly Gly Gly Cys Arg Pro Trp Gln Leu Leu Ser Pro Pro Trp Val
        290                 295                 300

Pro Lys Ile Ser Val Trp Val Lys Leu Ser Glu Lys Glu His Glu Ser
305                 310                 315                 320

Met Ala Leu Ser Lys Asp Val Gly His Ser Ser Gly Met Leu Arg Val
                325                 330                 335

Ser Ser Thr Gly Met Ile Leu Phe Leu Cys Ile Cys Val Trp Pro Arg
        340                 345                 350

Leu Tyr His Pro Val Leu Leu Glu
        355                 360

<210> SEQ ID NO 19
<211> LENGTH: 1023
<212> TYPE: DNA
<213> ORGANISM: Homo sapiens
<220> FEATURE:
<221> NAME/KEY: CDS
<222> LOCATION: (1)..(1023)

<400> SEQUENCE: 19 gga tcc gtc tcc act tac gcg cct gat atg tct agg atg ctt gga ggt         48
Gly Ser Val Ser Thr Tyr Ala Pro Asp Met Ser Arg Met Leu Gly Gly
 1               5                  10                  15
```

```
gaa gaa gcg agg ccc aac agc cgg ccc tgg cag gtc tcc ctg cag tac    96
Glu Glu Ala Arg Pro Asn Ser Arg Pro Trp Gln Val Ser Leu Gln Tyr
            20                  25                  30 agc tcc aat ggc cag tgg tac cac acc tgc gga ggg tcc ctg ata gcc   144
Ser Ser Asn Gly Gln Trp Tyr His Thr Cys Gly Gly Ser Leu Ile Ala
        35                  40                  45 aac agc tgg gtc ctg acg gct gcc cac tgc atc agc tcc tcc ggg atc   192
Asn Ser Trp Val Leu Thr Ala Ala His Cys Ile Ser Ser Ser Gly Ile
    50                  55                  60 tac cgc gtg atg ctg ggc cag cat aac ctc tac gtt gca gag tcc ggc   240
Tyr Arg Val Met Leu Gly Gln His Asn Leu Tyr Val Ala Glu Ser Gly
65                  70                  75                  80 tcg ctg gcc gtc agt gtc tct aag att gtg gtg cac aag gac tgg aac   288
Ser Leu Ala Val Ser Val Ser Lys Ile Val Val His Lys Asp Trp Asn
                85                  90                  95 tcc gac cag gtc tcc aaa ggg aac gac att gcc ctg ctc aaa ctg gct   336
Ser Asp Gln Val Ser Lys Gly Asn Asp Ile Ala Leu Leu Lys Leu Ala
            100                 105                 110 aac ccc gtc tcc ctc acc gac aag atc cag ctg gcc tgc ctc cct cct   384
Asn Pro Val Ser Leu Thr Asp Lys Ile Gln Leu Ala Cys Leu Pro Pro
        115                 120                 125 gcc ggc acc att cta ccc aac aac tac ccc tgc tac gtc acg ggc tgg   432
Ala Gly Thr Ile Leu Pro Asn Asn Tyr Pro Cys Tyr Val Thr Gly Trp
    130                 135                 140 gga agg ctg cag acc aac ggg gct ctc cct gat gac ctg aag cag ggc   480
Gly Arg Leu Gln Thr Asn Gly Ala Leu Pro Asp Asp Leu Lys Gln Gly
145                 150                 155                 160 cgg ttg ctg gtt gtg gac tat gcc acc tgc tcc aac tct ggc tgg tgg   528
Arg Leu Leu Val Val Asp Tyr Ala Thr Cys Ser Asn Ser Gly Trp Trp
                165                 170                 175 ggc agc acc gtg aag acg aat atg atc tgt gct ggg ggt gat ggc gtg   576
Gly Ser Thr Val Lys Thr Asn Met Ile Cys Ala Gly Gly Asp Gly Val
            180                 185                 190 ata tgc acc tgc aac gga gac tcc ggt ggg ccg ctg aac tgt cag gca   624
Ile Cys Thr Cys Asn Gly Asp Ser Gly Gly Pro Leu Asn Cys Gln Ala
        195                 200                 205 tct gac ggc cgg tgg gag gtg cat ggc atc ggc agc ctc acg tcg gtc   672
Ser Asp Gly Arg Trp Glu Val His Gly Ile Gly Ser Leu Thr Ser Val
    210                 215                 220 ctt ggt tgc aac tac tac tac aag ccc tcc atc ttc acg cgg gtc tcc   720
Leu Gly Cys Asn Tyr Tyr Tyr Lys Pro Ser Ile Phe Thr Arg Val Ser
225                 230                 235                 240 aac tac aac gac tgg atc aat tcg gta aga acc gga gca gcc ctg agc   768
Asn Tyr Asn Asp Trp Ile Asn Ser Val Arg Thr Gly Ala Ala Leu Ser
                245                 250                 255 ccc aag gca ctg acc tgc tca cct ggc ctc ggg agt gcc atg ccc acc   816
Pro Lys Ala Leu Thr Cys Ser Pro Gly Leu Gly Ser Ala Met Pro Thr
            260                 265                 270 tgg cga ctg aga acc ccc tcc ttc ctc ttg aga act aga tgg gaa ccc   864
Trp Arg Leu Arg Thr Pro Ser Phe Leu Leu Arg Thr Arg Trp Glu Pro
        275                 280                 285 ctt gga gga ggc tgc aga cct tgg caa ctg ctg agt ccc cca tgg gtc   912
Leu Gly Gly Gly Cys Arg Pro Trp Gln Leu Leu Ser Pro Pro Trp Val
    290                 295                 300 ccc aaa att tct gtg tgg gta aag ctg agt gaa aag gaa cat gag agt   960
Pro Lys Ile Ser Val Trp Val Lys Leu Ser Glu Lys Glu His Glu Ser
305                 310                 315                 320 atg gcc ttg tcc aaa gac gtt gga cac tcc tca ggt acg tta aga gtg  1008
Met Ala Leu Ser Lys Asp Val Gly His Ser Ser Gly Thr Leu Arg Val
                325                 330                 335
```

```
agt tcc aca ctc gag                                              1023
Ser Ser Thr Leu Glu
        340
```

<210> SEQ ID NO 20
<211> LENGTH: 341
<212> TYPE: PRT
<213> ORGANISM: Homo sapiens

<400> SEQUENCE: 20

```
Gly Ser Val Ser Thr Tyr Ala Pro Asp Met Ser Arg Met Leu Gly Gly
 1               5                  10                  15

Glu Glu Ala Arg Pro Asn Ser Arg Pro Trp Gln Val Ser Leu Gln Tyr
            20                  25                  30

Ser Ser Asn Gly Gln Trp Tyr His Thr Cys Gly Gly Ser Leu Ile Ala
        35                  40                  45

Asn Ser Trp Val Leu Thr Ala Ala His Cys Ile Ser Ser Ser Gly Ile
    50                  55                  60

Tyr Arg Val Met Leu Gly Gln His Asn Leu Tyr Val Ala Glu Ser Gly
65                  70                  75                  80

Ser Leu Ala Val Ser Val Ser Lys Ile Val Val His Lys Asp Trp Asn
                85                  90                  95

Ser Asp Gln Val Ser Lys Gly Asn Asp Ile Ala Leu Leu Lys Leu Ala
            100                 105                 110

Asn Pro Val Ser Leu Thr Asp Lys Ile Gln Leu Ala Cys Leu Pro Pro
        115                 120                 125

Ala Gly Thr Ile Leu Pro Asn Asn Tyr Pro Cys Tyr Val Thr Gly Trp
    130                 135                 140

Gly Arg Leu Gln Thr Asn Gly Ala Leu Pro Asp Asp Leu Lys Gln Gly
145                 150                 155                 160

Arg Leu Leu Val Val Asp Tyr Ala Thr Cys Ser Asn Ser Gly Trp Trp
                165                 170                 175

Gly Ser Thr Val Lys Thr Asn Met Ile Cys Ala Gly Gly Asp Gly Val
            180                 185                 190

Ile Cys Thr Cys Asn Gly Asp Ser Gly Gly Pro Leu Asn Cys Gln Ala
        195                 200                 205

Ser Asp Gly Arg Trp Glu Val His Gly Ile Gly Ser Leu Thr Ser Val
    210                 215                 220

Leu Gly Cys Asn Tyr Tyr Tyr Lys Pro Ser Ile Phe Thr Arg Val Ser
225                 230                 235                 240

Asn Tyr Asn Asp Trp Ile Asn Ser Val Arg Thr Gly Ala Ala Leu Ser
                245                 250                 255

Pro Lys Ala Leu Thr Cys Ser Pro Gly Leu Gly Ser Ala Met Pro Thr
            260                 265                 270

Trp Arg Leu Arg Thr Pro Ser Phe Leu Leu Arg Thr Arg Trp Glu Pro
        275                 280                 285

Leu Gly Gly Gly Cys Arg Pro Trp Gln Leu Leu Ser Pro Pro Trp Val
    290                 295                 300

Pro Lys Ile Ser Val Trp Val Lys Leu Ser Glu Lys Glu His Glu Ser
305                 310                 315                 320

Met Ala Leu Ser Lys Asp Val Gly His Ser Ser Gly Thr Leu Arg Val
                325                 330                 335

Ser Ser Thr Leu Glu
            340
```

<210> SEQ ID NO 21
<211> LENGTH: 1800
<212> TYPE: DNA
<213> ORGANISM: Homo sapiens
<220> FEATURE:
<221> NAME/KEY: CDS
<222> LOCATION: (16)..(1762)

<400> SEQUENCE: 21

```
gagcctctct tcacc atg tgc ttc gtc ccc ctg gtg tgc tgg gtg gtg            48
                 Met Cys Phe Val Pro Leu Val Cys Trp Val Val
                  1               5                  10 tgt acc tgc ctc cag cag cag ctg gag ggt ggg ggg ctg ttg aga cag         96
Cys Thr Cys Leu Gln Gln Gln Leu Glu Gly Gly Gly Leu Leu Arg Gln
             15                  20                  25 acg tcc agg acc acc act gca gtg tac atg ctc tac ctg ctg agt ctg        144
Thr Ser Arg Thr Thr Thr Ala Val Tyr Met Leu Tyr Leu Leu Ser Leu
         30                  35                  40 atg caa ccc aag ccg ggg gcc ccg cgc ctc cag ccc cca ccc aac cag        192
Met Gln Pro Lys Pro Gly Ala Pro Arg Leu Gln Pro Pro Pro Asn Gln
     45                  50                  55 aga ggg ttg tgc tcc ttg gcg gca gat ggg ctc tgg aat cag aaa atc        240
Arg Gly Leu Cys Ser Leu Ala Ala Asp Gly Leu Trp Asn Gln Lys Ile
 60                  65                  70                  75 cta ttt gag gag cag gac ctc cgg aag cac ggc cta gac ggg gaa gac        288
Leu Phe Glu Glu Gln Asp Leu Arg Lys His Gly Leu Asp Gly Glu Asp
                 80                  85                  90 gtc tct gcc ttc ctc aac atg aac atc ttc cag aag gac atc aac tgt        336
Val Ser Ala Phe Leu Asn Met Asn Ile Phe Gln Lys Asp Ile Asn Cys
             95                 100                 105 gag agg tac tac agc ttc atc cac ttg agt ttc cag gaa ttc ttt gca        384
Glu Arg Tyr Tyr Ser Phe Ile His Leu Ser Phe Gln Glu Phe Phe Ala
        110                 115                 120 gct atg tac tat atc ctg gac gag ggg gag ggc ggg gca ggc cca gac        432
Ala Met Tyr Tyr Ile Leu Asp Glu Gly Glu Gly Gly Ala Gly Pro Asp
    125                 130                 135 cag gac gtg acc agg ctg ttg acc gag tac gcg ttt tct gaa agg agc        480
Gln Asp Val Thr Arg Leu Leu Thr Glu Tyr Ala Phe Ser Glu Arg Ser
140                 145                 150                 155 ttc ctg gca ctc acc agc cgc ttc ctg ttt gga ctc ctg aac gag gag        528
Phe Leu Ala Leu Thr Ser Arg Phe Leu Phe Gly Leu Leu Asn Glu Glu
                160                 165                 170 acc agg agc cac ctg gag aag agt ctc tgc tgg aag gtc tcg ccg cac        576
Thr Arg Ser His Leu Glu Lys Ser Leu Cys Trp Lys Val Ser Pro His
            175                 180                 185 atc aag atg gac ctg ttg cag tgg atc caa agc aaa gct cag agc gac        624
Ile Lys Met Asp Leu Leu Gln Trp Ile Gln Ser Lys Ala Gln Ser Asp
        190                 195                 200 ggc tcc acc ctg cag cag ggc tcc ttg gag ttc ttc agc tgc ttg tac        672
Gly Ser Thr Leu Gln Gln Gly Ser Leu Glu Phe Phe Ser Cys Leu Tyr
    205                 210                 215 gag atc cag gag gag gag ttt atc cag cag gcc ctg agc cac ttc cag        720
Glu Ile Gln Glu Glu Glu Phe Ile Gln Gln Ala Leu Ser His Phe Gln
220                 225                 230                 235 gtg atc gtg gtc agc aac att gcc tcc aag atg gag cac atg gtc tcc        768
Val Ile Val Val Ser Asn Ile Ala Ser Lys Met Glu His Met Val Ser
                240                 245                 250 tcg ttc tgt ctg aag cgc tgc agg agc gcc cag gtg ctg cac ttg tat        816
Ser Phe Cys Leu Lys Arg Cys Arg Ser Ala Gln Val Leu His Leu Tyr
            255                 260                 265
```

-continued

| | | |
|---|---|---|
| ggc gcc acc tac agc gcg gac ggg gaa gac cgc gcg agg tgc tcc gca<br>Gly Ala Thr Tyr Ser Ala Asp Gly Glu Asp Arg Ala Arg Cys Ser Ala<br>270                       275                     280 | 864 |
| gga gcg cac acg ctg ttg gtg cag ctg aga cca gag agg acc gtt ctg<br>Gly Ala His Thr Leu Leu Val Gln Leu Arg Pro Glu Arg Thr Val Leu<br>285                       290                     295 | 912 |
| ctg gac gcc tac agt gaa cat ctg gca gcg gcc ctg tgc acc aat cca<br>Leu Asp Ala Tyr Ser Glu His Leu Ala Ala Ala Leu Cys Thr Asn Pro<br>300                       305                     310                     315 | 960 |
| aac ctg ata gag ctg tct ctg tac cga aat gcc ctg ggc agc cgg ggg<br>Asn Leu Ile Glu Leu Ser Leu Tyr Arg Asn Ala Leu Gly Ser Arg Gly<br>                   320                     325                     330 | 1008 |
| gtg aag ctg ctc tgt caa gga ctc aga cac ccc aac tgc aaa ctt cag<br>Val Lys Leu Leu Cys Gln Gly Leu Arg His Pro Asn Cys Lys Leu Gln<br>               335                     340                     345 | 1056 |
| aac ctg agg agg ctg aag agg tgc cgc atc tcc agc tca gcc tgc gag<br>Asn Leu Arg Arg Leu Lys Arg Cys Arg Ile Ser Ser Ser Ala Cys Glu<br>350                       355                     360 | 1104 |
| gac ctc tct gca gct ctc ata gcc aat aag aat ttg aca agg atg gat<br>Asp Leu Ser Ala Ala Leu Ile Ala Asn Lys Asn Leu Thr Arg Met Asp<br>365                       370                     375 | 1152 |
| ctc agt ggc aac ggc gtt gga ttc cca ggc atg atg ctg ctt tgc gag<br>Leu Ser Gly Asn Gly Val Gly Phe Pro Gly Met Met Leu Leu Cys Glu<br>380                       385                     390                     395 | 1200 |
| ggc ctg cgg cat ccc cag tgc agg ctg cag atg att cag ttg agg aag<br>Gly Leu Arg His Pro Gln Cys Arg Leu Gln Met Ile Gln Leu Arg Lys<br>                   400                     405                     410 | 1248 |
| tgt cag ctg gag tcc ggg gct tgt cag gag atg gct tct gtg ctc ggc<br>Cys Gln Leu Glu Ser Gly Ala Cys Gln Glu Met Ala Ser Val Leu Gly<br>               415                     420                     425 | 1296 |
| acc aac cca cat ctg gtt gag ttg gac ctg aca gga aat gca ctg gag<br>Thr Asn Pro His Leu Val Glu Leu Asp Leu Thr Gly Asn Ala Leu Glu<br>430                       435                     440 | 1344 |
| gat ttg ggc ctg agg tta cta tgc cag gga ctg agg cac cca gtc tgc<br>Asp Leu Gly Leu Arg Leu Leu Cys Gln Gly Leu Arg His Pro Val Cys<br>445                       450                     455 | 1392 |
| aga cta cgg act ttg tgg tgc agg ctg aag atc tgc cgc ctc act gct<br>Arg Leu Arg Thr Leu Trp Cys Arg Leu Lys Ile Cys Arg Leu Thr Ala<br>460                       465                     470                     475 | 1440 |
| gct gcc tgt gac gag ctg gcc tca act ctc agt gtg aac cag agc ctg<br>Ala Ala Cys Asp Glu Leu Ala Ser Thr Leu Ser Val Asn Gln Ser Leu<br>                   480                     485                     490 | 1488 |
| aga gag ctg gac ctg agc ctg aat gag ctg ggg gac ctc ggg gtg ctg<br>Arg Glu Leu Asp Leu Ser Leu Asn Glu Leu Gly Asp Leu Gly Val Leu<br>               495                     500                     505 | 1536 |
| ctg ctg tgt gag ggc ctc agg cat ccc acg tgc aag ctc cag acc ctg<br>Leu Leu Cys Glu Gly Leu Arg His Pro Thr Cys Lys Leu Gln Thr Leu<br>510                       515                     520 | 1584 |
| cgg agg ttg ggc atc tgc cgg ctg ggc tct gcc gcc tgt gag ggt ctt<br>Arg Arg Leu Gly Ile Cys Arg Leu Gly Ser Ala Ala Cys Glu Gly Leu<br>525                       530                     535 | 1632 |
| tct gtg gtg ctc cag gcc aac cac aac ctc cgg gag ctg gac ttg agt<br>Ser Val Val Leu Gln Ala Asn His Asn Leu Arg Glu Leu Asp Leu Ser<br>540                       545                     550                     555 | 1680 |
| ttc aac gac ctg gga gac tgg ggc ctg tgg ttg ctg gct gag ggg ctg<br>Phe Asn Asp Leu Gly Asp Trp Gly Leu Trp Leu Leu Ala Glu Gly Leu<br>                   560                     565                     570 | 1728 |
| caa cat ccc gcc tgc aga ctc cag aaa ctg tgg tgagcatcgg<br>Gln His Pro Ala Cys Arg Leu Gln Lys Leu Trp<br>575                       580 | 1771 | ggagtgacgg ggtggcagtg gtcacgttt 1800

<210> SEQ ID NO 22
<211> LENGTH: 582
<212> TYPE: PRT
<213> ORGANISM: Homo sapiens

<400> SEQUENCE: 22

| | | | | | | | | | | | | | | |
|---|---|---|---|---|---|---|---|---|---|---|---|---|---|---|
| Met | Cys | Phe | Val | Pro | Leu | Val | Cys | Trp | Val | Cys | Thr | Cys | Leu | Gln |
| 1 | | | | 5 | | | | | 10 | | | | | 15 |
| Gln | Gln | Leu | Glu | Gly | Gly | Leu | Leu | Arg | Gln | Thr | Ser | Arg | Thr | Thr |
| | | | | 20 | | | | | 25 | | | | | 30 |
| Thr | Ala | Val | Tyr | Met | Leu | Tyr | Leu | Leu | Ser | Leu | Met | Gln | Pro | Lys | Pro |
| | | | 35 | | | | | 40 | | | | | 45 | | |
| Gly | Ala | Pro | Arg | Leu | Gln | Pro | Pro | Asn | Gln | Arg | Gly | Leu | Cys | Ser |
| | | 50 | | | | | 55 | | | | | 60 | | |
| Leu | Ala | Ala | Asp | Gly | Leu | Trp | Asn | Gln | Lys | Ile | Leu | Phe | Glu | Glu | Gln |
| 65 | | | | | 70 | | | | | 75 | | | | | 80 |
| Asp | Leu | Arg | Lys | His | Gly | Leu | Asp | Gly | Glu | Asp | Val | Ser | Ala | Phe | Leu |
| | | | | 85 | | | | | 90 | | | | | 95 | |
| Asn | Met | Asn | Ile | Phe | Gln | Lys | Asp | Ile | Asn | Cys | Glu | Arg | Tyr | Tyr | Ser |
| | | | 100 | | | | | 105 | | | | | 110 | | |
| Phe | Ile | His | Leu | Ser | Phe | Gln | Glu | Phe | Phe | Ala | Ala | Met | Tyr | Tyr | Ile |
| | | | 115 | | | | | 120 | | | | | 125 | | |
| Leu | Asp | Glu | Gly | Glu | Gly | Gly | Ala | Gly | Pro | Asp | Gln | Asp | Val | Thr | Arg |
| | 130 | | | | | 135 | | | | | 140 | | | | |
| Leu | Leu | Thr | Glu | Tyr | Ala | Phe | Ser | Glu | Arg | Ser | Phe | Leu | Ala | Leu | Thr |
| 145 | | | | | 150 | | | | | 155 | | | | | 160 |
| Ser | Arg | Phe | Leu | Phe | Gly | Leu | Leu | Asn | Glu | Glu | Thr | Arg | Ser | His | Leu |
| | | | | 165 | | | | | 170 | | | | | 175 | |
| Glu | Lys | Ser | Leu | Cys | Trp | Lys | Val | Ser | Pro | His | Ile | Lys | Met | Asp | Leu |
| | | | 180 | | | | | 185 | | | | | 190 | | |
| Leu | Gln | Trp | Ile | Gln | Ser | Lys | Ala | Gln | Ser | Asp | Gly | Ser | Thr | Leu | Gln |
| | | | 195 | | | | | 200 | | | | | 205 | | |
| Gln | Gly | Ser | Leu | Glu | Phe | Phe | Ser | Cys | Leu | Tyr | Glu | Ile | Gln | Glu | Glu |
| | 210 | | | | | 215 | | | | | 220 | | | | |
| Glu | Phe | Ile | Gln | Gln | Ala | Leu | Ser | His | Phe | Gln | Val | Ile | Val | Val | Ser |
| 225 | | | | | 230 | | | | | 235 | | | | | 240 |
| Asn | Ile | Ala | Ser | Lys | Met | Glu | His | Met | Val | Ser | Ser | Phe | Cys | Leu | Lys |
| | | | | 245 | | | | | 250 | | | | | 255 | |
| Arg | Cys | Arg | Ser | Ala | Gln | Val | Leu | His | Leu | Tyr | Gly | Ala | Thr | Tyr | Ser |
| | | | 260 | | | | | 265 | | | | | 270 | | |
| Ala | Asp | Gly | Glu | Asp | Arg | Ala | Arg | Cys | Ser | Ala | Gly | Ala | His | Thr | Leu |
| | | | 275 | | | | | 280 | | | | | 285 | | |
| Leu | Val | Gln | Leu | Arg | Pro | Glu | Arg | Thr | Val | Leu | Leu | Asp | Ala | Tyr | Ser |
| | | 290 | | | | | 295 | | | | | 300 | | | |
| Glu | His | Leu | Ala | Ala | Leu | Cys | Thr | Asn | Pro | Asn | Leu | Ile | Glu | Leu |
| 305 | | | | | 310 | | | | | 315 | | | | | 320 |
| Ser | Leu | Tyr | Arg | Asn | Ala | Leu | Gly | Ser | Arg | Gly | Val | Lys | Leu | Leu | Cys |
| | | | | 325 | | | | | 330 | | | | | 335 | |
| Gln | Gly | Leu | Arg | His | Pro | Asn | Cys | Lys | Leu | Gln | Asn | Leu | Arg | Arg | Leu |
| | | | | 340 | | | | | 345 | | | | | 350 | |
| Lys | Arg | Cys | Arg | Ile | Ser | Ser | Ser | Ala | Cys | Glu | Asp | Leu | Ser | Ala | Ala |
| | | | 355 | | | | | 360 | | | | | 365 | | |

```
Leu Ile Ala Asn Lys Asn Leu Thr Arg Met Asp Leu Ser Gly Asn Gly
        370                 375                 380

Val Gly Phe Pro Gly Met Met Leu Cys Glu Gly Leu Arg His Pro
385                 390                 395                 400

Gln Cys Arg Leu Gln Met Ile Gln Leu Arg Lys Cys Gln Leu Glu Ser
                405                 410                 415

Gly Ala Cys Gln Glu Met Ala Ser Val Leu Gly Thr Asn Pro His Leu
            420                 425                 430

Val Glu Leu Asp Leu Thr Gly Asn Ala Leu Glu Asp Leu Gly Leu Arg
        435                 440                 445

Leu Leu Cys Gln Gly Leu Arg His Pro Val Cys Arg Leu Arg Thr Leu
    450                 455                 460

Trp Cys Arg Leu Lys Ile Cys Arg Leu Thr Ala Ala Cys Asp Glu
465                 470                 475                 480

Leu Ala Ser Thr Leu Ser Val Asn Gln Ser Leu Arg Glu Leu Asp Leu
                485                 490                 495

Ser Leu Asn Glu Leu Gly Asp Leu Gly Val Leu Leu Leu Cys Glu Gly
            500                 505                 510

Leu Arg His Pro Thr Cys Lys Leu Gln Thr Leu Arg Arg Leu Gly Ile
        515                 520                 525

Cys Arg Leu Gly Ser Ala Ala Cys Glu Gly Leu Ser Val Val Leu Gln
    530                 535                 540

Ala Asn His Asn Leu Arg Glu Leu Asp Leu Ser Phe Asn Asp Leu Gly
545                 550                 555                 560

Asp Trp Gly Leu Trp Leu Leu Ala Glu Gly Leu Gln His Pro Ala Cys
                565                 570                 575

Arg Leu Gln Lys Leu Trp
            580

<210> SEQ ID NO 23
<211> LENGTH: 1683
<212> TYPE: DNA
<213> ORGANISM: Homo sapiens
<220> FEATURE:
<221> NAME/KEY: CDS
<222> LOCATION: (18)..(1581)

<400> SEQUENCE: 23
gcgcgcctct cttcacc atg tgc ttc gtc ccc ctg gtg tgc tgg gtg gtg     50
                   Met Cys Phe Val Pro Leu Val Cys Trp Val Val
                    1               5                  10 tgt acc tgc ctc cag cag cag ctg gag ggt ggg ggg ctg ttg aga cag    98
Cys Thr Cys Leu Gln Gln Gln Leu Glu Gly Gly Gly Leu Leu Arg Gln
            15                  20                  25 acg tcc agg acc acc act gca gtg tac atg ctc tac ctg ctg agt ctg   146
Thr Ser Arg Thr Thr Thr Ala Val Tyr Met Leu Tyr Leu Leu Ser Leu
        30                  35                  40 atg caa ccc aag ccg ggg gcc ccg cgc ctc cag ccc cca ccc aac cag   194
Met Gln Pro Lys Pro Gly Ala Pro Arg Leu Gln Pro Pro Pro Asn Gln
    45                  50                  55 aga ggg ttg tgc tcc ttg gcg gca gat ggg ctc tgg aat cag aaa atc   242
Arg Gly Leu Cys Ser Leu Ala Ala Asp Gly Leu Trp Asn Gln Lys Ile
60                  65                  70                  75 cta ttt gag gag cag gac ctc cgg aag cac ggc cta gac ggg gaa gac   290
Leu Phe Glu Glu Gln Asp Leu Arg Lys His Gly Leu Asp Gly Glu Asp
                80                  85                  90 gtc tct gcc ttc ctc aac atg aac atc ttc cag aag gac atc aac tgt   338
```

```
                                                            -continued

Val Ser Ala Phe Leu Asn Met Asn Ile Phe Gln Lys Asp Ile Asn Cys
            95                 100                 105 gag agg tac tac agc ttc atc cac ttg agt ttc cag gaa ttc ttt gca      386
Glu Arg Tyr Tyr Ser Phe Ile His Leu Ser Phe Gln Glu Phe Phe Ala
        110                 115                 120 gct atg tac tat atc ctg gac gag ggg gag ggc ggg gca ggc cca gac      434
Ala Met Tyr Tyr Ile Leu Asp Glu Gly Glu Gly Gly Ala Gly Pro Asp
    125                 130                 135 cag gac gtg acc agg ctg ttg acc gag tac gcg ttt tct gaa agg agc      482
Gln Asp Val Thr Arg Leu Leu Thr Glu Tyr Ala Phe Ser Glu Arg Ser
140                 145                 150                 155 ttc ctg gca ctc acc agc cgc ttc ctg ttt gga ctc ctg aac gag gag      530
Phe Leu Ala Leu Thr Ser Arg Phe Leu Phe Gly Leu Leu Asn Glu Glu
                160                 165                 170 acc agg agc cac ctg gag aag agt ctc tgc tgg aag gtc tcg ccg cac      578
Thr Arg Ser His Leu Glu Lys Ser Leu Cys Trp Lys Val Ser Pro His
            175                 180                 185 atc aag atg gac ctg ttg cag tgg atc caa agc aaa gct cag agc gac      626
Ile Lys Met Asp Leu Leu Gln Trp Ile Gln Ser Lys Ala Gln Ser Asp
        190                 195                 200 ggc tcc acc ctg cag cag ggc tcc ttg gag ttc ttc agc tgc ttg tac      674
Gly Ser Thr Leu Gln Gln Gly Ser Leu Glu Phe Phe Ser Cys Leu Tyr
    205                 210                 215 gag atc cag gag gag gag ttt atc cag cag gcc ctg agc cac ttc cag      722
Glu Ile Gln Glu Glu Glu Phe Ile Gln Gln Ala Leu Ser His Phe Gln
220                 225                 230                 235 gtg atc gtg gtc agc aac att gcc tcc aag atg gag cac atg gtc tcc      770
Val Ile Val Val Ser Asn Ile Ala Ser Lys Met Glu His Met Val Ser
                240                 245                 250 tcg ttc tgt ctg aag cgc tgc agg agc gcc cag gtg ctg cac ttg tat      818
Ser Phe Cys Leu Lys Arg Cys Arg Ser Ala Gln Val Leu His Leu Tyr
            255                 260                 265 ggc gcc acc tac agc gcg gac ggg gaa gac cgc gcg agg tgc tcc gca      866
Gly Ala Thr Tyr Ser Ala Asp Gly Glu Asp Arg Ala Arg Cys Ser Ala
        270                 275                 280 gga gcg cac acg ctg ttg gtg cag ctc aga cca gag agg acc gtt ctg      914
Gly Ala His Thr Leu Leu Val Gln Leu Arg Pro Glu Arg Thr Val Leu
    285                 290                 295 ctg gac gcc tac agt gaa cat ctg gca gcg gcc ctg tgc acc aat cca      962
Leu Asp Ala Tyr Ser Glu His Leu Ala Ala Ala Leu Cys Thr Asn Pro
300                 305                 310                 315 aac ctg ata gag ctg tct ctg tac cga aat gcc ctg ggc agc cgg ggg     1010
Asn Leu Ile Glu Leu Ser Leu Tyr Arg Asn Ala Leu Gly Ser Arg Gly
                320                 325                 330 gtg aag ctg ctc tgt caa gga ctc aga cac ccc aac tgc aaa ctt cag     1058
Val Lys Leu Leu Cys Gln Gly Leu Arg His Pro Asn Cys Lys Leu Gln
            335                 340                 345 aac ctg agg ctg aag agg tgc cgc atc tcc agc tca gcc tgc gag gac     1106
Asn Leu Arg Leu Lys Arg Cys Arg Ile Ser Ser Ser Ala Cys Glu Asp
        350                 355                 360 ctc tct gca gct ctc ata gcc aat aag aat ttg aca agg atg gat ctc     1154
Leu Ser Ala Ala Leu Ile Ala Asn Lys Asn Leu Thr Arg Met Asp Leu
    365                 370                 375 agt ggc aac ggc gtt gga ttc cca ggc atg atg ctg ctt tgc gag ggc     1202
Ser Gly Asn Gly Val Gly Phe Pro Gly Met Met Leu Leu Cys Glu Gly
380                 385                 390                 395 ctg cgg cat ccc caa tgc agg ctg cag atg att cag ctg aag atc tgc     1250
Leu Arg His Pro Gln Cys Arg Leu Gln Met Ile Gln Leu Lys Ile Cys
                400                 405                 410
```

-continued

| | | |
|---|---|---|
| cgc ctc act gct gct gcc tgt gac gag ctg gcc tca act ctc agt gtg<br>Arg Leu Thr Ala Ala Ala Cys Asp Glu Leu Ala Ser Thr Leu Ser Val<br>         415                        420                     425 | 1298 |
| aac cag agc ctg aga gag ctg gac ctg agc ctg aat gag ctg ggg gac<br>Asn Gln Ser Leu Arg Glu Leu Asp Leu Ser Leu Asn Glu Leu Gly Asp<br>        430                       435                     440 | 1346 |
| ctc ggg gtg ctg ctg ctg tgt gag ggc ctc agg cat ccc acg tgc aag<br>Leu Gly Val Leu Leu Leu Cys Glu Gly Leu Arg His Pro Thr Cys Lys<br>445                       450                     455 | 1394 |
| ctc cag acc ctg cgg ttg ggc atc tgc cgg ctg ggc tct gcc gcc tgt<br>Leu Gln Thr Leu Arg Leu Gly Ile Cys Arg Leu Gly Ser Ala Ala Cys<br>460                       465                     470                     475 | 1442 |
| gag ggt ctt tct gtg gtg ctc cag gcc aac cac aac ctc cgg gag ctg<br>Glu Gly Leu Ser Val Val Leu Gln Ala Asn His Asn Leu Arg Glu Leu<br>                   480                     485                     490 | 1490 |
| gac ttg agt ttc aac gac ctg gga gac tgg ggc ctg tgg ttg ctg gct<br>Asp Leu Ser Phe Asn Asp Leu Gly Asp Trp Gly Leu Trp Leu Leu Ala<br>                 495                     500                     505 | 1538 |
| gag ggg ctg caa cat ccc gcc tgc aga ctc cag aaa ctg tgg<br>Glu Gly Leu Gln His Pro Ala Cys Arg Leu Gln Lys Leu Trp<br>510                       515                     520 | 1580 |
| tgagcatcgg ggagtgacgg ggtggcagtg gtcacgtttg dacagtggaa | 1630 |
| gcgccttctc atccttcatt tttctatttta tgaactatcc tgcttcacta | 1680 |
| caa | 1683 |

<210> SEQ ID NO 24
<211> LENGTH: 521
<212> TYPE: PRT
<213> ORGANISM: Homo sapiens

<400> SEQUENCE: 24

Met Cys Phe Val Pro Leu Val Cys Trp Val Cys Thr Cys Leu Gln
1               5                   10                  15

Gln Gln Leu Glu Gly Gly Leu Leu Arg Gln Thr Ser Arg Thr Thr
            20                  25                  30

Thr Ala Val Tyr Met Leu Tyr Leu Ser Leu Met Gln Pro Lys Pro
        35                  40                  45

Gly Ala Pro Arg Leu Gln Pro Pro Asn Gln Arg Gly Leu Cys Ser
    50                  55                  60

Leu Ala Ala Asp Gly Leu Trp Asn Gln Lys Ile Leu Phe Glu Glu Gln
65                  70                  75                  80

Asp Leu Arg Lys His Gly Leu Asp Gly Glu Asp Val Ser Ala Phe Leu
                85                  90                  95

Asn Met Asn Ile Phe Gln Lys Asp Ile Asn Cys Glu Arg Tyr Tyr Ser
            100                 105                 110

Phe Ile His Leu Ser Phe Gln Glu Phe Phe Ala Ala Met Tyr Tyr Ile
        115                 120                 125

Leu Asp Glu Gly Glu Gly Gly Ala Gly Pro Asp Gln Asp Val Thr Arg
    130                 135                 140

Leu Leu Thr Glu Tyr Ala Phe Ser Glu Arg Ser Phe Leu Ala Leu Thr
145                 150                 155                 160

Ser Arg Phe Leu Phe Gly Leu Leu Asn Glu Glu Thr Arg Ser His Leu
                165                 170                 175

Glu Lys Ser Leu Cys Trp Lys Val Ser Pro His Ile Lys Met Asp Leu
            180                 185                 190

Leu Gln Trp Ile Gln Ser Lys Ala Gln Ser Asp Gly Ser Thr Leu Gln

```
                     195                 200                 205
Gln Gly Ser Leu Glu Phe Phe Ser Cys Leu Tyr Glu Ile Gln Glu Glu
    210                 215                 220

Glu Phe Ile Gln Gln Ala Leu Ser His Phe Gln Val Ile Val Val Ser
225                 230                 235                 240

Asn Ile Ala Ser Lys Met Glu His Met Val Ser Ser Phe Cys Leu Lys
                245                 250                 255

Arg Cys Arg Ser Ala Gln Val Leu His Leu Tyr Gly Ala Thr Tyr Ser
            260                 265                 270

Ala Asp Gly Glu Asp Arg Ala Arg Cys Ser Ala Gly Ala His Thr Leu
        275                 280                 285

Leu Val Gln Leu Arg Pro Glu Arg Thr Val Leu Leu Asp Ala Tyr Ser
    290                 295                 300

Glu His Leu Ala Ala Ala Leu Cys Thr Asn Pro Asn Leu Ile Glu Leu
305                 310                 315                 320

Ser Leu Tyr Arg Asn Ala Leu Gly Ser Arg Gly Val Lys Leu Leu Cys
                325                 330                 335

Gln Gly Leu Arg His Pro Asn Cys Lys Leu Gln Asn Leu Arg Leu Lys
            340                 345                 350

Arg Cys Arg Ile Ser Ser Ser Ala Cys Glu Asp Leu Ser Ala Ala Leu
        355                 360                 365

Ile Ala Asn Lys Asn Leu Thr Arg Met Asp Leu Ser Gly Asn Gly Val
    370                 375                 380

Gly Phe Pro Gly Met Met Leu Leu Cys Glu Gly Leu Arg His Pro Gln
385                 390                 395                 400

Cys Arg Leu Gln Met Ile Gln Leu Lys Ile Cys Arg Leu Thr Ala Ala
                405                 410                 415

Ala Cys Asp Glu Leu Ala Ser Thr Leu Ser Val Asn Gln Ser Leu Arg
            420                 425                 430

Glu Leu Asp Leu Ser Leu Asn Glu Leu Gly Asp Leu Gly Val Leu Leu
        435                 440                 445

Leu Cys Glu Gly Leu Arg His Pro Thr Cys Lys Leu Gln Thr Leu Arg
    450                 455                 460

Leu Gly Ile Cys Arg Leu Gly Ser Ala Ala Cys Glu Gly Leu Ser Val
465                 470                 475                 480

Val Leu Gln Ala Asn His Asn Leu Arg Glu Leu Asp Leu Ser Phe Asn
                485                 490                 495

Asp Leu Gly Asp Trp Gly Leu Trp Leu Leu Ala Glu Gly Leu Gln His
            500                 505                 510

Pro Ala Cys Arg Leu Gln Lys Leu Trp
        515                 520

<210> SEQ ID NO 25
<211> LENGTH: 481
<212> TYPE: DNA
<213> ORGANISM: Homo sapiens
<220> FEATURE:
<221> NAME/KEY: CDS
<222> LOCATION: (28)..(382)

<400> SEQUENCE: 25
cttgtcttgt tccagttctc agaggga atg ctt tca att ttt ctc tat tca      51
                            Met Leu Ser Ile Phe Leu Tyr Ser
                              1               5 gta tta tgt tgg ctg tgg gtt tgt cat aga ttg tgt gcc gtg agg gag   99
Val Leu Cys Trp Leu Trp Val Cys His Arg Leu Cys Ala Val Arg Glu
```

```
ttt act ttc ctg gcc aag aag cca ggc tgc agg ggc ctt cgg atc acc    147
Phe Thr Phe Leu Ala Lys Lys Pro Gly Cys Arg Gly Leu Arg Ile Thr
 25                  30                  35                  40 acg gat gcc tgc tgg ggt cgc tgt gag acc ttc tat cta tgg gga cag    195
Thr Asp Ala Cys Trp Gly Arg Cys Glu Thr Phe Tyr Leu Trp Gly Gln
                 45                  50                  55 aaa ccc att ctg gaa ccc ccc tat att gaa gcc cat cat cga gtc tgt    243
Lys Pro Ile Leu Glu Pro Pro Tyr Ile Glu Ala His His Arg Val Cys
             60                  65                  70 acc tac aac gag acc aaa cag gtg act gtc aag ctg ccc aac tgt gcc    291
Thr Tyr Asn Glu Thr Lys Gln Val Thr Val Lys Leu Pro Asn Cys Ala
         75                  80                  85 ccg gga gtc gac ccc ttc tac acc tat ccc gtg gcc atc cgc tgt gac    339
Pro Gly Val Asp Pro Phe Tyr Thr Tyr Pro Val Ala Ile Arg Cys Asp
     90                  95                 100 tgc gga gcc tgc tcc act gcc acc acg gag tgt gag acc atc            381
Cys Gly Ala Cys Ser Thr Ala Thr Thr Glu Cys Glu Thr Ile
105                 110                 115 tgaggccgct agctgctctc tgcagaccca cctgtgtgag cagcacatgc              431
agttatactt cctggatgca agactgttta atttcgacca cacccatgga              481
```

<210> SEQ ID NO 26
<211> LENGTH: 118
<212> TYPE: PRT
<213> ORGANISM: Homo sapiens

<400> SEQUENCE: 26

Met Leu Ser Ile Phe Leu Tyr Ser Val Leu Cys Trp Leu Trp Val Cys
 1               5                  10                  15

His Arg Leu Cys Ala Val Arg Glu Phe Thr Phe Leu Ala Lys Lys Pro
             20                  25                  30

Gly Cys Arg Gly Leu Arg Ile Thr Thr Asp Ala Cys Trp Gly Arg Cys
         35                  40                  45

Glu Thr Phe Tyr Leu Trp Gly Gln Lys Pro Ile Leu Glu Pro Pro Tyr
     50                  55                  60

Ile Glu Ala His His Arg Val Cys Thr Tyr Asn Glu Thr Lys Gln Val
 65                  70                  75                  80

Thr Val Lys Leu Pro Asn Cys Ala Pro Gly Val Asp Pro Phe Tyr Thr
                 85                  90                  95

Tyr Pro Val Ala Ile Arg Cys Asp Cys Gly Ala Cys Ser Thr Ala Thr
            100                 105                 110

Thr Glu Cys Glu Thr Ile
        115

<210> SEQ ID NO 27
<211> LENGTH: 682
<212> TYPE: DNA
<213> ORGANISM: Homo sapiens
<220> FEATURE:
<221> NAME/KEY: CDS
<222> LOCATION: (1)..(673)

<400> SEQUENCE: 27

```
atg aag acc ctg ttc ctg ggt gtc acg ctc ggc ctg gcc gct gcc ctg     48
Met Lys Thr Leu Phe Leu Gly Val Thr Leu Gly Leu Ala Ala Ala Leu
 1               5                  10                  15 tcc ttc acc ctg gag gag gag gat gtg cat cca gaa gaa aat cct gat     96
Ser Phe Thr Leu Glu Glu Glu Asp Val His Pro Glu Glu Asn Pro Asp
```

```
                   20                  25                  30
gcg gaa tgg ggg cag gaa gct cat gta cct gca gga gct gcc cag gag      144
Ala Glu Trp Gly Gln Glu Ala His Val Pro Ala Gly Ala Ala Gln Glu
         35                  40                  45 gga cca cta cat ctt tta ctg caa aga cca gca cca tgg ggg cct gct      192
Gly Pro Leu His Leu Leu Leu Gln Arg Pro Ala Pro Trp Gly Pro Ala
 50                  55                  60 cca cat ggg aaa gct tgt ggg tgc tcc ctg cag ggc cgt gcc gct gtc      240
Pro His Gly Lys Ala Cys Gly Cys Ser Leu Gln Gly Arg Ala Ala Val
 65                  70                  75                  80 ccc acg tcg gct cac ctg gcc acc tca cct gca ggt agg aat tct gat      288
Pro Thr Ser Ala His Leu Ala Thr Ser Pro Ala Gly Arg Asn Ser Asp
                 85                  90                  95 acc aac cgg gag gcc ctg gaa gaa ttt aag aaa ttg gtg cag cgc aag      336
Thr Asn Arg Glu Ala Leu Glu Glu Phe Lys Lys Leu Val Gln Arg Lys
            100                 105                 110 gga ctc tcg gag gag gac att ttc acg ccc ctg cag acg ggt gag gat      384
Gly Leu Ser Glu Glu Asp Ile Phe Thr Pro Leu Gln Thr Gly Glu Asp
        115                 120                 125 ggc tgt gcc cag tcc cct gtg tcc ctc tgc tgt gtc tgt cta tct           432
Gly Cys Ala Gln Ser Pro Val Ser Leu Cys Cys Val Cys Leu Leu Ser
    130                 135                 140 cca gtg tcc cat gac ccc cat gtc ctc cca tgt ccc ccg cat tcc cca      480
Pro Val Ser His Asp Pro His Val Leu Pro Cys Pro Pro His Ser Pro
145                 150                 155                 160 tgt gcc ccg agt ctc ctc gca ggg gct ccc ggg ccc tgt tta gcg tcc      528
Cys Ala Pro Ser Leu Leu Ala Gly Ala Pro Gly Pro Cys Leu Ala Ser
                165                 170                 175 tcc tca ttg gag gct ctg tgc tct ggg ctg cga tgg ggt ctg ggg ctc      576
Ser Ser Leu Glu Ala Leu Cys Ser Gly Leu Arg Trp Gly Leu Gly Leu
            180                 185                 190 cgc gct ctg ggc tgc gat ggg gtc tgg ggc tcc gca ctc tgg gct gcg      624
Arg Ala Leu Gly Cys Asp Gly Val Trp Gly Ser Ala Leu Trp Ala Ala
        195                 200                 205 atg ggg tct ggg gct ccg cgc tct ggg ctg cga tgg gct ctg ggg ctc      672
Met Gly Ser Gly Ala Pro Arg Ser Gly Leu Arg Trp Ala Leu Gly Leu
    210                 215                 220 tgagctctgg                                                           682

<210> SEQ ID NO 28
<211> LENGTH: 224
<212> TYPE: PRT
<213> ORGANISM: Homo sapiens

<400> SEQUENCE: 28

Met Lys Thr Leu Phe Leu Gly Val Thr Leu Gly Leu Ala Ala Ala Leu
 1               5                  10                  15

Ser Phe Thr Leu Glu Glu Glu Asp Val His Pro Glu Glu Asn Pro Asp
            20                  25                  30

Ala Glu Trp Gly Gln Glu Ala His Val Pro Ala Gly Ala Ala Gln Glu
        35                  40                  45

Gly Pro Leu His Leu Leu Leu Gln Arg Pro Ala Pro Trp Gly Pro Ala
    50                  55                  60

Pro His Gly Lys Ala Cys Gly Cys Ser Leu Gln Gly Arg Ala Ala Val
 65                  70                  75                  80

Pro Thr Ser Ala His Leu Ala Thr Ser Pro Ala Gly Arg Asn Ser Asp
                85                  90                  95

Thr Asn Arg Glu Ala Leu Glu Glu Phe Lys Lys Leu Val Gln Arg Lys
```

```
                    100                 105                 110
Gly Leu Ser Glu Glu Asp Ile Phe Thr Pro Leu Gln Thr Gly Glu Asp
            115                 120                 125
Gly Cys Ala Gln Ser Pro Val Ser Leu Cys Cys Val Cys Leu Leu Ser
        130                 135                 140
Pro Val Ser His Asp Pro His Val Leu Pro Cys Pro His Ser Pro
145                 150                 155                 160
Cys Ala Pro Ser Leu Leu Ala Gly Ala Pro Gly Pro Cys Leu Ala Ser
                165                 170                 175
Ser Ser Leu Glu Ala Leu Cys Ser Gly Leu Arg Trp Gly Leu Gly Leu
            180                 185                 190
Arg Ala Leu Gly Cys Asp Gly Val Trp Gly Ser Ala Leu Trp Ala Ala
        195                 200                 205
Met Gly Ser Gly Ala Pro Arg Ser Gly Leu Arg Trp Ala Leu Gly Leu
    210                 215                 220

<210> SEQ ID NO 29
<211> LENGTH: 1178
<212> TYPE: DNA
<213> ORGANISM: Homo sapiens
<220> FEATURE:
<221> NAME/KEY: CDS
<222> LOCATION: (4)..(994)

<400> SEQUENCE: 29 ggg atg gga aaa cta tgc ctg ggg ccg acg ctc tgc ccg gct gct gcc          48
    Met Gly Lys Leu Cys Leu Gly Pro Thr Leu Cys Pro Ala Ala Ala
    1               5                  10                  15 gct gag gaa agc cgg gac gcg gag ccc cgc cga gag ctt ctt tgc tcc          96
Ala Glu Glu Ser Arg Asp Ala Glu Pro Arg Arg Glu Leu Leu Cys Ser
            20                  25                  30 gga cgc ccc tgg acg tgg cgg gca gcc gcg agg gta acc acc atg atc        144
Gly Arg Pro Trp Thr Trp Arg Ala Ala Ala Arg Val Thr Thr Met Ile
        35                  40                  45 ccc tgg gtg ctc ctg gcc tgt gcc ctc ccc tgt gct gct gac cca ctg        192
Pro Trp Val Leu Leu Ala Cys Ala Leu Pro Cys Ala Ala Asp Pro Leu
    50                  55                  60 ctt ggc gcc ttt gct cgc agg gac ttc cgg aaa ggc tcc cct caa ctg        240
Leu Gly Ala Phe Ala Arg Arg Asp Phe Arg Lys Gly Ser Pro Gln Leu
65                  70                  75 gtc tgc agc ctg cct ggc ccc cag ggc cca ccc ggc ccc cca gga gcc        288
Val Cys Ser Leu Pro Gly Pro Gln Gly Pro Pro Gly Pro Pro Gly Ala
80                  85                  90                  95 cca ggg ccc tca gga atg atg gga cga atg ggc ttt cct ggc aaa gac        336
Pro Gly Pro Ser Gly Met Met Gly Arg Met Gly Phe Pro Gly Lys Asp
                100                 105                 110 ggc caa gat gga cac gac ggc gac cgg ggg gac agc gga gag gaa ggt        384
Gly Gln Asp Gly His Asp Gly Asp Arg Gly Asp Ser Gly Glu Glu Gly
            115                 120                 125 cca cct ggc cgg aca ggt aac cgg gga aag cca gga cca aag ggc aaa        432
Pro Pro Gly Arg Thr Gly Asn Arg Gly Lys Pro Gly Pro Lys Gly Lys
        130                 135                 140 gcc ggg gcc att ggg cgg gct ggc ccc cgt ggc ccc aag ggg gtc aac        480
Ala Gly Ala Ile Gly Arg Ala Gly Pro Arg Gly Pro Lys Gly Val Asn
145                 150                 155 ggt acc ccc ggg aag cat ggc aca cca ggc aag aag ggg ccc aag ggc        528
Gly Thr Pro Gly Lys His Gly Thr Pro Gly Lys Lys Gly Pro Lys Gly
160                 165                 170                 175 aag aag ggg gag cca ggc ctc cca ggc ccc tgc agc tgt ggc agt ggc        576
```

|  |  |
|---|---|
| Lys Lys Gly Glu Pro Gly Leu Pro Gly Pro Cys Ser Cys Gly Ser Gly<br>                180                        185                  190 |  |
| cat acc aag tca gct ttc tcg gtg gca gtg acc aag agc tac cca cgg<br>His Thr Lys Ser Ala Phe Ser Val Ala Val Thr Lys Ser Tyr Pro Arg<br>           195                    200                    205 | 624 |
| gag cgg ctg ccc atc aag ttt gac aag att ctg atg aac gag ggt ggc<br>Glu Arg Leu Pro Ile Lys Phe Asp Lys Ile Leu Met Asn Glu Gly Gly<br>        210                    215                    220 | 672 |
| cac tac aat gct tcc agc ggc aag ttc gtc tgc ggc gtg cct ggg atc<br>His Tyr Asn Ala Ser Ser Gly Lys Phe Val Cys Gly Val Pro Gly Ile<br>        225                    230                235 | 720 |
| tac tac ttc acc tac gac atc acg ctg gcc aac aag cac ctg gcc atc<br>Tyr Tyr Phe Thr Tyr Asp Ile Thr Leu Ala Asn Lys His Leu Ala Ile<br>240                  245                    250                255 | 768 |
| ggc ctg gtg cac aac ggc cag tac cgc atc cgg acc ttt gat gcc aac<br>Gly Leu Val His Asn Gly Gln Tyr Arg Ile Arg Thr Phe Asp Ala Asn<br>              260                    265                    270 | 816 |
| acc ggc aac cac gat gtg gcc tca ggc tcc acc atc ctg gct ctc aag<br>Thr Gly Asn His Asp Val Ala Ser Gly Ser Thr Ile Leu Ala Leu Lys<br>           275                    280                    285 | 864 |
| cag ggt gac gaa gtt tgg ctg cag atc ttc tac tca gag cag aac ggg<br>Gln Gly Asp Glu Val Trp Leu Gln Ile Phe Tyr Ser Glu Gln Asn Gly<br>        290                    295                    300 | 912 |
| ctc ttc tat gac cct tac tgg aca gac agc ctc ttt acg ggc ttc cta<br>Leu Phe Tyr Asp Pro Tyr Trp Thr Asp Ser Leu Phe Thr Gly Phe Leu<br>305                  310                    315 | 960 |
| atc tat gcc gac cag gat gac ccc aac gag gta tagacatgcc<br>Ile Tyr Ala Asp Gln Asp Asp Pro Asn Glu Val<br>320                  325                    330 | 1003 |
| acggcggtcc tccaggcagg gaacaagctt ctggacttgg gcttacagag | 1053 |
| caagaccccca caactgtagg ctgggggtgg gggtcgagt gagcggttct | 1103 |
| agcctcaggc tcacctcctc cgcctctttt ttttcccctt cattaaatcc | 1153 |
| aaaccttttt attcatccaa aaaaa | 1178 |

<210> SEQ ID NO 30
<211> LENGTH: 330
<212> TYPE: PRT
<213> ORGANISM: Homo sapiens

<400> SEQUENCE: 30

Met Gly Lys Leu Cys Leu Gly Pro Thr Leu Cys Pro Ala Ala Ala Ala
1               5                   10                  15

Glu Glu Ser Arg Asp Ala Glu Pro Arg Arg Glu Leu Leu Cys Ser Gly
            20                  25                  30

Arg Pro Trp Thr Trp Arg Ala Ala Arg Val Thr Thr Met Ile Pro
        35                  40                  45

Trp Val Leu Leu Ala Cys Ala Leu Pro Cys Ala Ala Asp Pro Leu Leu
    50                  55                  60

Gly Ala Phe Ala Arg Arg Asp Phe Arg Lys Gly Ser Pro Gln Leu Val
65                  70                  75                  80

Cys Ser Leu Pro Gly Pro Gln Gly Pro Pro Gly Pro Gly Ala Pro
                85                  90                  95

Gly Pro Ser Gly Met Met Gly Arg Met Gly Phe Pro Gly Lys Asp Gly
            100                 105                 110

Gln Asp Gly His Asp Gly Asp Arg Gly Asp Ser Gly Glu Glu Gly Pro
        115                 120                 125

```
Pro Gly Arg Thr Gly Asn Arg Gly Lys Pro Gly Pro Lys Gly Lys Ala
    130                 135                 140
Gly Ala Ile Gly Arg Ala Gly Pro Arg Gly Pro Lys Gly Val Asn Gly
145                 150                 155                 160
Thr Pro Gly Lys His Gly Thr Pro Gly Lys Lys Gly Pro Lys Gly Lys
                165                 170                 175
Lys Gly Glu Pro Gly Leu Pro Gly Pro Cys Ser Cys Gly Ser Gly His
            180                 185                 190
Thr Lys Ser Ala Phe Ser Val Ala Val Thr Lys Ser Tyr Pro Arg Glu
        195                 200                 205
Arg Leu Pro Ile Lys Phe Asp Lys Ile Leu Met Asn Glu Gly Gly His
    210                 215                 220
Tyr Asn Ala Ser Ser Gly Lys Phe Val Cys Gly Val Pro Gly Ile Tyr
225                 230                 235                 240
Tyr Phe Thr Tyr Asp Ile Thr Leu Ala Asn Lys His Leu Ala Ile Gly
                245                 250                 255
Leu Val His Asn Gly Gln Tyr Arg Ile Arg Thr Phe Asp Ala Asn Thr
            260                 265                 270
Gly Asn His Asp Val Ala Ser Gly Ser Thr Ile Leu Ala Leu Lys Gln
        275                 280                 285
Gly Asp Glu Val Trp Leu Gln Ile Phe Tyr Ser Glu Gln Asn Gly Leu
    290                 295                 300
Phe Tyr Asp Pro Tyr Trp Thr Asp Ser Leu Phe Thr Gly Phe Leu Ile
305                 310                 315                 320
Tyr Ala Asp Gln Asp Asp Pro Asn Glu Val
                325                 330

<210> SEQ ID NO 31
<211> LENGTH: 1611
<212> TYPE: DNA
<213> ORGANISM: Homo sapiens
<220> FEATURE:
<221> NAME/KEY: CDS
<222> LOCATION: (42)..(1512)

<400> SEQUENCE: 31
ggagcgtctg ttgggtccgg gccgccggct tcgccctcgc c atg gcg ccc tgg          53
                                              Met Ala Pro Trp
                                                1 ctg cag ctc ctg tcg ctg ctg ggg ctg ctc ccg ggc gca gtg gcc gcc      101
Leu Gln Leu Leu Ser Leu Leu Gly Leu Leu Pro Gly Ala Val Ala Ala
  5                  10                  15                  20 ccc gcc cag ccc cga gcc gcc agc ttt cag gcc tgg ggg ccg ccg tcc      149
Pro Ala Gln Pro Arg Ala Ala Ser Phe Gln Ala Trp Gly Pro Pro Ser
                 25                  30                  35 ccg cag ctg ctg gcg ccc acc cgc ttc gcg ctg gag atg ttc aac cgc      197
Pro Gln Leu Leu Ala Pro Thr Arg Phe Ala Leu Glu Met Phe Asn Arg
             40                  45                  50 ggc cgg gct gcg ggg acg cgg gcc gtg ctg ggc ctt gtg cgc gac cgt      245
Gly Arg Ala Ala Gly Thr Arg Ala Val Leu Gly Leu Val Arg Asp Arg
         55                  60                  65 ccg cgc ctc acc tac tcc tct ctc cag gcg ggc cag ggg tcg ctg tac      293
Pro Arg Leu Thr Tyr Ser Ser Leu Gln Ala Gly Gln Gly Ser Leu Tyr
     70                  75                  80 tcc ctg gag gcc acc ctg gag gag cca ccc tgc aac gac ccc atg gtg      341
Ser Leu Glu Ala Thr Leu Glu Glu Pro Pro Cys Asn Asp Pro Met Val
 85                  90                  95                 100 tgc cgg ctc ccc gtg tcc aag aaa acc ctg gtg act ttc aaa gtc ctg      389
```

```
Cys Arg Leu Pro Val Ser Lys Lys Thr Leu Val Thr Phe Lys Val Leu
                105                 110                 115 gat gag ctc ggg ggg cgc gtg ctg ctg cgg aag gac tgt ggc cca gtg      437
Asp Glu Leu Gly Gly Arg Val Leu Leu Arg Lys Asp Cys Gly Pro Val
            120                 125                 130 gac acc aag gtt cca ggt gct ggg gag ccc aag tca gcc ttc act cag      485
Asp Thr Lys Val Pro Gly Ala Gly Glu Pro Lys Ser Ala Phe Thr Gln
        135                 140                 145 ggc tca gcc atg att tct tct ctg tcc caa aac cat cca gac aac aga      533
Gly Ser Ala Met Ile Ser Ser Leu Ser Gln Asn His Pro Asp Asn Arg
    150                 155                 160 aac gag act ttc agc tca gtc att tcc ctg ttg aat gag gat ccc ctg      581
Asn Glu Thr Phe Ser Ser Val Ile Ser Leu Leu Asn Glu Asp Pro Leu
165                 170                 175                 180 tcc cag gac ttg cct gtg aag atg gct tca atc ttc aag aac ttt gtc      629
Ser Gln Asp Leu Pro Val Lys Met Ala Ser Ile Phe Lys Asn Phe Val
                185                 190                 195 att acc tat aac cgg aca tat gag tca aag gaa gaa gcc cgg tgg cgc      677
Ile Thr Tyr Asn Arg Thr Tyr Glu Ser Lys Glu Glu Ala Arg Trp Arg
            200                 205                 210 ctg tcc gtc ttt gtc aat aac atg gtg cga gca cag aag atc cag gcc      725
Leu Ser Val Phe Val Asn Asn Met Val Arg Ala Gln Lys Ile Gln Ala
        215                 220                 225 ctg gac cgt ggc aca gct cag tat gga gtc acc aag ttc agt gat ctc      773
Leu Asp Arg Gly Thr Ala Gln Tyr Gly Val Thr Lys Phe Ser Asp Leu
    230                 235                 240 aca gag gag gag ttc cgc act atc tac ctg aat act ctc ctg aga aaa      821
Thr Glu Glu Glu Phe Arg Thr Ile Tyr Leu Asn Thr Leu Leu Arg Lys
245                 250                 255                 260 gag cct ggc aac aag atg aag caa gcc aag tct gtg ggt gac ctc gcc      869
Glu Pro Gly Asn Lys Met Lys Gln Ala Lys Ser Val Gly Asp Leu Ala
                265                 270                 275 cca cct gaa tgg gac tgg agg agt aag ggg gct gtc aca aaa gtc aaa      917
Pro Pro Glu Trp Asp Trp Arg Ser Lys Gly Ala Val Thr Lys Val Lys
            280                 285                 290 gac cag ggc atg tgt ggc tcc tgc tgg gcc ttc tca gtc aca ggc aat      965
Asp Gln Gly Met Cys Gly Ser Cys Trp Ala Phe Ser Val Thr Gly Asn
        295                 300                 305 gtg gag ggc cag tgg ttt ctc aac cag ggg acc ctg ctc tcc ctc tct     1013
Val Glu Gly Gln Trp Phe Leu Asn Gln Gly Thr Leu Leu Ser Leu Ser
    310                 315                 320 gaa cag gag ctc ttg gac tgt gac aag atg gac aag gcc tgc atg ggc     1061
Glu Gln Glu Leu Leu Asp Cys Asp Lys Met Asp Lys Ala Cys Met Gly
325                 330                 335                 340 ggc ttg ccc tcc aat gcc tac tcg gcc ata aag aat ttg gga ggg ctg     1109
Gly Leu Pro Ser Asn Ala Tyr Ser Ala Ile Lys Asn Leu Gly Gly Leu
                345                 350                 355 gag aca gag gat gac tac agc tac cag ggt cac atg cag tcc tgc aac     1157
Glu Thr Glu Asp Asp Tyr Ser Tyr Gln Gly His Met Gln Ser Cys Asn
            360                 365                 370 ttc tca gca gag aag gcc aag gtc tac atc aat gac tcc gtg gag ctg     1205
Phe Ser Ala Glu Lys Ala Lys Val Tyr Ile Asn Asp Ser Val Glu Leu
        375                 380                 385 agc cag aac gag cag gag ctg gca gcc tgg ctg gcc aag aga ggc cca     1253
Ser Gln Asn Glu Gln Glu Leu Ala Ala Trp Leu Ala Lys Arg Gly Pro
    390                 395                 400 atc tcc gtg gcc atc aat gcc ttt ggc atg cag ttt tac cgc cac ggg     1301
Ile Ser Val Ala Ile Asn Ala Phe Gly Met Gln Phe Tyr Arg His Gly
405                 410                 415                 420
```

```
atc tcc cgc cct ctc cgg ccc ctc tgc agc cct tgc gtc att gac cat    1349
Ile Ser Arg Pro Leu Arg Pro Leu Cys Ser Pro Cys Val Ile Asp His
                425                 430                 435 gcg gtg ttg ctt gtg ggc tac gga acc gtg agt tct gac gtt ccc ttt    1397
Ala Val Leu Leu Val Gly Tyr Gly Thr Val Ser Ser Asp Val Pro Phe
            440                 445                 450 tgg gcc atc aag aac agc tgg ggc act gac tgg ggt gag aag ggt tac    1445
Trp Ala Ile Lys Asn Ser Trp Gly Thr Asp Trp Gly Glu Lys Gly Tyr
            455                 460                 465 tac tac ttg cat cgc ggg tcc ggg gca tgt ggc gtg aac acc atg gcc    1493
Tyr Tyr Leu His Arg Gly Ser Gly Ala Cys Gly Val Asn Thr Met Ala
        470                 475                 480 agc tcg gcg gtg gtg gac tgaagagggg cccccagctc gggacctggt           1541
Ser Ser Ala Val Val Asp
485                 490 gctgatcaga gtggctgctg ccccagcctg acatgtgtcc aggcccctcc             1591
ccgggaggta cagctggcag                                              1611

<210> SEQ ID NO 32
<211> LENGTH: 490
<212> TYPE: PRT
<213> ORGANISM: Homo sapiens

<400> SEQUENCE: 32

Met Ala Pro Trp Leu Gln Leu Leu Ser Leu Leu Gly Leu Leu Pro Gly
 1               5                  10                  15

Ala Val Ala Ala Pro Ala Gln Pro Arg Ala Ala Ser Phe Gln Ala Trp
            20                  25                  30

Gly Pro Pro Ser Pro Gln Leu Leu Ala Pro Thr Arg Phe Ala Leu Glu
        35                  40                  45

Met Phe Asn Arg Gly Arg Ala Ala Gly Thr Arg Ala Val Leu Gly Leu
    50                  55                  60

Val Arg Asp Arg Pro Arg Leu Thr Tyr Ser Ser Leu Gln Ala Gly Gln
65                  70                  75                  80

Gly Ser Leu Tyr Ser Leu Glu Ala Thr Leu Glu Glu Pro Pro Cys Asn
                85                  90                  95

Asp Pro Met Val Cys Arg Leu Pro Val Ser Lys Lys Thr Leu Val Thr
            100                 105                 110

Phe Lys Val Leu Asp Glu Leu Gly Gly Arg Val Leu Arg Lys Asp
        115                 120                 125

Cys Gly Pro Val Asp Thr Lys Val Pro Gly Ala Gly Glu Pro Lys Ser
    130                 135                 140

Ala Phe Thr Gln Gly Ser Ala Met Ile Ser Ser Leu Ser Gln Asn His
145                 150                 155                 160

Pro Asp Asn Arg Asn Glu Thr Phe Ser Ser Val Ile Ser Leu Leu Asn
                165                 170                 175

Glu Asp Pro Leu Ser Gln Asp Leu Pro Val Lys Met Ala Ser Ile Phe
            180                 185                 190

Lys Asn Phe Val Ile Thr Tyr Asn Arg Thr Tyr Glu Ser Lys Glu Glu
        195                 200                 205

Ala Arg Trp Arg Leu Ser Val Phe Val Asn Asn Met Val Arg Ala Gln
    210                 215                 220

Lys Ile Gln Ala Leu Asp Arg Gly Thr Ala Gln Tyr Gly Val Thr Lys
225                 230                 235                 240

Phe Ser Asp Leu Thr Glu Glu Phe Arg Thr Ile Tyr Leu Asn Thr
                245                 250                 255
```

```
Leu Leu Arg Lys Glu Pro Gly Asn Lys Met Lys Gln Ala Lys Ser Val
        260                 265                 270

Gly Asp Leu Ala Pro Pro Glu Trp Asp Trp Arg Ser Lys Gly Ala Val
    275                 280                 285

Thr Lys Val Lys Asp Gln Gly Met Cys Gly Ser Cys Trp Ala Phe Ser
290                 295                 300

Val Thr Gly Asn Val Glu Gly Gln Trp Phe Leu Asn Gln Gly Thr Leu
305                 310                 315                 320

Leu Ser Leu Ser Glu Gln Glu Leu Leu Asp Cys Asp Lys Met Asp Lys
                325                 330                 335

Ala Cys Met Gly Gly Leu Pro Ser Asn Ala Tyr Ser Ala Ile Lys Asn
        340                 345                 350

Leu Gly Gly Leu Glu Thr Glu Asp Asp Tyr Ser Tyr Gln Gly His Met
            355                 360                 365

Gln Ser Cys Asn Phe Ser Ala Glu Lys Ala Lys Val Tyr Ile Asn Asp
370                 375                 380

Ser Val Glu Leu Ser Gln Asn Glu Gln Glu Leu Ala Ala Trp Leu Ala
385                 390                 395                 400

Lys Arg Gly Pro Ile Ser Val Ala Ile Asn Ala Phe Gly Met Gln Phe
                405                 410                 415

Tyr Arg His Gly Ile Ser Arg Pro Leu Arg Pro Leu Cys Ser Pro Cys
            420                 425                 430

Val Ile Asp His Ala Val Leu Leu Val Gly Tyr Gly Thr Val Ser Ser
            435                 440                 445

Asp Val Pro Phe Trp Ala Ile Lys Asn Ser Trp Gly Thr Asp Trp Gly
450                 455                 460

Glu Lys Gly Tyr Tyr Tyr Leu His Arg Gly Ser Gly Ala Cys Gly Val
465                 470                 475                 480

Asn Thr Met Ala Ser Ser Ala Val Val Asp
                485                 490

<210> SEQ ID NO 33
<211> LENGTH: 1226
<212> TYPE: DNA
<213> ORGANISM: Homo sapiens
<220> FEATURE:
<221> NAME/KEY: CDS
<222> LOCATION: (15)..(1215)

<400> SEQUENCE: 33
gcttcgccct cgcc atg gcg ccc tgg ctg cag ctc ctg tcg ctg ctg ggg      50
                Met Ala Pro Trp Leu Gln Leu Leu Ser Leu Leu Gly
                1               5                   10 ctg ctc ccg ggc gca gtg gcc gcc ccc gcc cag ccc caa gtc ctg gat      98
Leu Leu Pro Gly Ala Val Ala Ala Pro Ala Gln Pro Gln Val Leu Asp
        15                  20                  25 gag ctc gga aga cac gtg ctg ctg cgg aag gac tgt ggc cca gtg gac     146
Glu Leu Gly Arg His Val Leu Leu Arg Lys Asp Cys Gly Pro Val Asp
    30                  35                  40 acc aag gtt cca ggt gct ggg gag ccc aag tca gcc ttc act cag ggc     194
Thr Lys Val Pro Gly Ala Gly Glu Pro Lys Ser Ala Phe Thr Gln Gly
45                  50                  55                  60 tca gcc atg att tct tct ctg tcc caa aac cat cca gac aac aga aac     242
Ser Ala Met Ile Ser Ser Leu Ser Gln Asn His Pro Asp Asn Arg Asn
                65                  70                  75 gag act ttc agc tca gtc att tcc ctg ttg aat gag gat ccc ctg tcc     290
Glu Thr Phe Ser Ser Val Ile Ser Leu Leu Asn Glu Asp Pro Leu Ser
```

```
                    80                  85                  90
cag gac ttg cct gtg aag atg gct tca atc ttc aag aac ttt gtc att    338
Gln Asp Leu Pro Val Lys Met Ala Ser Ile Phe Lys Asn Phe Val Ile
        95                  100                 105 acc tat aac cgg aca tat gag tca aag gaa gaa gcc cgg tgg cgc ctg    386
Thr Tyr Asn Arg Thr Tyr Glu Ser Lys Glu Glu Ala Arg Trp Arg Leu
110                 115                 120 tcc gtc ttt gtc aat aac atg gtg cga gca cag aag atc cag gcc ctg    434
Ser Val Phe Val Asn Asn Met Val Arg Ala Gln Lys Ile Gln Ala Leu
125                 130                 135                 140 gac cgt ggc aca gct cag tat gga gtc acc aag ttc agt gat ctc aca    482
Asp Arg Gly Thr Ala Gln Tyr Gly Val Thr Lys Phe Ser Asp Leu Thr
                145                 150                 155 gag gag gag ttc cgc act atc tac ctg aat act ctc ctg agg aaa gag    530
Glu Glu Glu Phe Arg Thr Ile Tyr Leu Asn Thr Leu Leu Arg Lys Glu
                160                 165                 170 cct ggc aac aag atg aag caa gcc aag tct gtg ggt gac ctc gcc cca    578
Pro Gly Asn Lys Met Lys Gln Ala Lys Ser Val Gly Asp Leu Ala Pro
                175                 180                 185 cct gaa tgg gac tgg agg agt aag ggg gct gtc aca aaa gtc aaa gac    626
Pro Glu Trp Asp Trp Arg Ser Lys Gly Ala Val Thr Lys Val Lys Asp
            190                 195                 200 cag ggc atg tgt ggc tcc tgc tgg gcc ttc tca gtc aca ggc aat gtg    674
Gln Gly Met Cys Gly Ser Cys Trp Ala Phe Ser Val Thr Gly Asn Val
205                 210                 215                 220 gag ggc cag tgg ttt ctc aac cag ggg acc ctg ctc tcc ctc tct gaa    722
Glu Gly Gln Trp Phe Leu Asn Gln Gly Thr Leu Leu Ser Leu Ser Glu
                225                 230                 235 cag gag ctc ttg gac tgt gac aag atg gac aag gcc tgc atg ggc ggc    770
Gln Glu Leu Leu Asp Cys Asp Lys Met Asp Lys Ala Cys Met Gly Gly
                240                 245                 250 ttg ccc tcc aat gcc tac tcg gcc ata aag aat ttg gga ggg ctg gag    818
Leu Pro Ser Asn Ala Tyr Ser Ala Ile Lys Asn Leu Gly Gly Leu Glu
            255                 260                 265 aca gag gat gac tac agc tac cag ggt cac atg cag tcc tgc aac ttc    866
Thr Glu Asp Asp Tyr Ser Tyr Gln Gly His Met Gln Ser Cys Asn Phe
270                 275                 280 tca gca gag aag gcc aag gtc tac atc aat gac tcc gtg gag ctg agc    914
Ser Ala Glu Lys Ala Lys Val Tyr Ile Asn Asp Ser Val Glu Leu Ser
285                 290                 295                 300 cag aac gag cag aag ctg gca gcc tgg ctg gcc aag aga ggc cca atc    962
Gln Asn Glu Gln Lys Leu Ala Ala Trp Leu Ala Lys Arg Gly Pro Ile
                305                 310                 315 tcc gtg gcc atc aat gcc ttt ggc atg cag ttt tac cgc cac ggg atc    1010
Ser Val Ala Ile Asn Ala Phe Gly Met Gln Phe Tyr Arg His Gly Ile
                320                 325                 330 tcc cgc cct ctc cgg ccc ctc tgc agc cct tgg ctc att gac cat gcg    1058
Ser Arg Pro Leu Arg Pro Leu Cys Ser Pro Trp Leu Ile Asp His Ala
            335                 340                 345 gtg ttg ctt gtg ggc tac ggc aac cgc tct gac gtt ccc ttt tgg gcc    1106
Val Leu Leu Val Gly Tyr Gly Asn Arg Ser Asp Val Pro Phe Trp Ala
350                 355                 360 atc aag aac agc tgg ggc act gac tgg ggt gag aag ggt tac tac tac    1154
Ile Lys Asn Ser Trp Gly Thr Asp Trp Gly Glu Lys Gly Tyr Tyr Tyr
365                 370                 375                 380 ttg cat cgc ggg tcc ggg gcc tgt ggc gtg aac acc atg gcc agc tcg    1202
Leu His Arg Gly Ser Gly Ala Cys Gly Val Asn Thr Met Ala Ser Ser
                385                 390                 395 gcg gtg gtg gac tgaagagggg cc                                      1226
Ala Val Val Asp
```

```
Ala Val Val Asp
            400

<210> SEQ ID NO 34
<211> LENGTH: 400
<212> TYPE: PRT
<213> ORGANISM: Homo sapiens

<400> SEQUENCE: 34

Met Ala Pro Trp Leu Gln Leu Leu Ser Leu Leu Gly Leu Leu Pro Gly
 1               5                  10                  15

Ala Val Ala Ala Pro Ala Gln Pro Gln Val Leu Asp Glu Leu Gly Arg
            20                  25                  30

His Val Leu Leu Arg Lys Asp Cys Gly Pro Val Asp Thr Lys Val Pro
        35                  40                  45

Gly Ala Gly Glu Pro Lys Ser Ala Phe Thr Gln Gly Ser Ala Met Ile
    50                  55                  60

Ser Ser Leu Ser Gln Asn His Pro Asp Asn Arg Asn Glu Thr Phe Ser
65                  70                  75                  80

Ser Val Ile Ser Leu Leu Asn Glu Asp Pro Leu Ser Gln Asp Leu Pro
                85                  90                  95

Val Lys Met Ala Ser Ile Phe Lys Asn Phe Val Ile Thr Tyr Asn Arg
            100                 105                 110

Thr Tyr Glu Ser Lys Glu Glu Ala Arg Trp Arg Leu Ser Val Phe Val
        115                 120                 125

Asn Asn Met Val Arg Ala Gln Lys Ile Gln Ala Leu Asp Arg Gly Thr
    130                 135                 140

Ala Gln Tyr Gly Val Thr Lys Phe Ser Asp Leu Thr Glu Glu Glu Phe
145                 150                 155                 160

Arg Thr Ile Tyr Leu Asn Thr Leu Leu Arg Lys Glu Pro Gly Asn Lys
                165                 170                 175

Met Lys Gln Ala Lys Ser Val Gly Asp Leu Ala Pro Pro Glu Trp Asp
            180                 185                 190

Trp Arg Ser Lys Gly Ala Val Thr Lys Val Lys Asp Gln Gly Met Cys
        195                 200                 205

Gly Ser Cys Trp Ala Phe Ser Val Thr Gly Asn Val Glu Gly Gln Trp
    210                 215                 220

Phe Leu Asn Gln Gly Thr Leu Leu Ser Leu Ser Glu Gln Glu Leu Leu
225                 230                 235                 240

Asp Cys Asp Lys Met Asp Lys Ala Cys Met Gly Gly Leu Pro Ser Asn
                245                 250                 255

Ala Tyr Ser Ala Ile Lys Asn Leu Gly Gly Leu Glu Thr Glu Asp Asp
            260                 265                 270

Tyr Ser Tyr Gln Gly His Met Gln Ser Cys Asn Phe Ser Ala Glu Lys
        275                 280                 285

Ala Lys Val Tyr Ile Asn Asp Ser Val Glu Leu Ser Gln Asn Glu Gln
    290                 295                 300

Lys Leu Ala Ala Trp Leu Ala Lys Arg Gly Pro Ile Ser Val Ala Ile
305                 310                 315                 320

Asn Ala Phe Gly Met Gln Phe Tyr Arg His Gly Ile Ser Arg Pro Leu
                325                 330                 335

Arg Pro Leu Cys Ser Pro Trp Leu Ile Asp His Ala Val Leu Leu Val
            340                 345                 350

Gly Tyr Gly Asn Arg Ser Asp Val Pro Phe Trp Ala Ile Lys Asn Ser
        355                 360                 365
```

-continued

```
Trp Gly Thr Asp Trp Gly Glu Lys Gly Tyr Tyr Leu His Arg Gly
    370                 375                 380

Ser Gly Ala Cys Gly Val Asn Thr Met Ala Ser Ser Ala Val Val Asp
385                 390                 395                 400

<210> SEQ ID NO 35
<211> LENGTH: 1704
<212> TYPE: DNA
<213> ORGANISM: Homo sapiens
<220> FEATURE:
<221> NAME/KEY: CDS
<222> LOCATION: (103)..(1666)

<400> SEQUENCE: 35
tggtagatgt ggcatttcca tgctgaggcc gcgagtcccg cctgaccccg              50
tcgctgcctc tccagggctt ctctgggccg cgcctctgca gactgcgcag             100 cc atg ctg cat ctg ctg gcg ctc ttc ctg cac tgc ctc cct ctg gcc    147
   Met Leu His Leu Leu Ala Leu Phe Leu His Cys Leu Pro Leu Ala
   1               5                   10                  15 tct ggg gac tat gac atc tgc aaa tcc tgg gtg acc aca gat gag ggc   195
Ser Gly Asp Tyr Asp Ile Cys Lys Ser Trp Val Thr Thr Asp Glu Gly
                20                  25                  30 ccc acc tgg gag ttc tac gcc tgc cag ccc aag gtg atg cgc ctg aag   243
Pro Thr Trp Glu Phe Tyr Ala Cys Gln Pro Lys Val Met Arg Leu Lys
            35                  40                  45 gac tac gtc aag gtg aag gtg gag ccc tca ggc atc aca tgt gga gac   291
Asp Tyr Val Lys Val Lys Val Glu Pro Ser Gly Ile Thr Cys Gly Asp
        50                  55                  60 ccc cct gag agg ttc tgc tcc cat ccc tac cta tgc agc aac gag tgt   339
Pro Pro Glu Arg Phe Cys Ser His Pro Tyr Leu Cys Ser Asn Glu Cys
    65                  70                  75 gac gcc tcc aac ccg gac ctg gcc cac ccg ccc agg ctc atg ttc gac   387
Asp Ala Ser Asn Pro Asp Leu Ala His Pro Pro Arg Leu Met Phe Asp
 80                  85                  90                  95 aag gag gag gag ggc ctg gcc acc tac tgg cag agc atc acc tgg agc   435
Lys Glu Glu Glu Gly Leu Ala Thr Tyr Trp Gln Ser Ile Thr Trp Ser
                100                 105                 110 cgc tac ccc agc ccg ctg gaa gcc aac atc acc ctt tcg tgg aac aag   483
Arg Tyr Pro Ser Pro Leu Glu Ala Asn Ile Thr Leu Ser Trp Asn Lys
            115                 120                 125 acc gtg gag ctg acc gac gac gtg gtg atg acc ttc gag tac ggc cgg   531
Thr Val Glu Leu Thr Asp Asp Val Val Met Thr Phe Glu Tyr Gly Arg
        130                 135                 140 ccc acg gtc atg gtc ctg gag aag tcc ctg gac aac ggg cgc acc tgg   579
Pro Thr Val Met Val Leu Glu Lys Ser Leu Asp Asn Gly Arg Thr Trp
    145                 150                 155 cag ccc tac cag ttc tac gcc gag gac tgc atg gag gcc ttc ggt atg   627
Gln Pro Tyr Gln Phe Tyr Ala Glu Asp Cys Met Glu Ala Phe Gly Met
160                 165                 170                 175 tcc gcc cgc cgg gcc cgc gac atg tca tcc tcc agc gcg cac cgc gtg   675
Ser Ala Arg Arg Ala Arg Asp Met Ser Ser Ser Ser Ala His Arg Val
                180                 185                 190 ctc tgc acc gag gag tac tcg cgc tgg gca ggc tcc aag aag gag aag   723
Leu Cys Thr Glu Glu Tyr Ser Arg Trp Ala Gly Ser Lys Lys Glu Lys
            195                 200                 205 cac gtg cgc ttc gag gtg cgg gac cgc ttc gcc atc ttt gcc ggc ccc   771
His Val Arg Phe Glu Val Arg Asp Arg Phe Ala Ile Phe Ala Gly Pro
        210                 215                 220 gac ctg cgc aac atg gac aac ctc tac acg cgg ctg gag agc gcc aag   819
Asp Leu Arg Asn Met Asp Asn Leu Tyr Thr Arg Leu Glu Ser Ala Lys
```

```
                Asp Leu Arg Asn Met Asp Asn Leu Tyr Thr Arg Leu Glu Ser Ala Lys
                    225                 230                 235 ggc ctc aag gag ttc ttc acc ctc acc gac ctg cgc atg cgg ctg ctg          867
Gly Leu Lys Glu Phe Phe Thr Leu Thr Asp Leu Arg Met Arg Leu Leu
240                 245                 250                 255 cgc ccg gcg ctg ggc ggc acc tat gtg cag cgg gag aac ctc tac aag          915
Arg Pro Ala Leu Gly Gly Thr Tyr Val Gln Arg Glu Asn Leu Tyr Lys
                260                 265                 270 tac ttc tac gcc atc tcc aac atc gag gtc atc ggc agg tgc aag tgc          963
Tyr Phe Tyr Ala Ile Ser Asn Ile Glu Val Ile Gly Arg Cys Lys Cys
            275                 280                 285 aac ctg cac gcc aac ctg tgc tcc atg cgc gag ggc agc ctg cag tgc         1011
Asn Leu His Ala Asn Leu Cys Ser Met Arg Glu Gly Ser Leu Gln Cys
        290                 295                 300 gag tgc gag cac aac acc acc ggc ccc gac tgc ggc aag tgc aag aag         1059
Glu Cys Glu His Asn Thr Thr Gly Pro Asp Cys Gly Lys Cys Lys Lys
    305                 310                 315 aat ttc cgc acc cgg tcc tgg cgg gcc ggc tcc tac ctg ccg ctg ccc         1107
Asn Phe Arg Thr Arg Ser Trp Arg Ala Gly Ser Tyr Leu Pro Leu Pro
320                 325                 330                 335 cat ggc tct ccc aac gcc tgt gac tgc gaa tgc tac ggt cac tcc aac         1155
His Gly Ser Pro Asn Ala Cys Asp Cys Glu Cys Tyr Gly His Ser Asn
                340                 345                 350 cgc tgc agc tac att gac ttc ctg aat gtg gtg acc tgc gtc agc tgc         1203
Arg Cys Ser Tyr Ile Asp Phe Leu Asn Val Val Thr Cys Val Ser Cys
                355                 360                 365 aag cac aac acg cga ggt cag cac tgc cag cac tgc cgg ctg ggc tac         1251
Lys His Asn Thr Arg Gly Gln His Cys Gln His Cys Arg Leu Gly Tyr
            370                 375                 380 tac cgc aac ggc tcg gca gag ctg gat gat gag aac gtc tgc att gag         1299
Tyr Arg Asn Gly Ser Ala Glu Leu Asp Asp Glu Asn Val Cys Ile Glu
        385                 390                 395 tgt aac tgc aac cag ata ggc tcc gtg cac gac cgg tgc aac gag acc         1347
Cys Asn Cys Asn Gln Ile Gly Ser Val His Asp Arg Cys Asn Glu Thr
    400                 405                 410                 415 ggc ttc tgc gag tgc cgc gag ggc gcg gcg ggc ccc aag tgc gac gac         1395
Gly Phe Cys Glu Cys Arg Glu Gly Ala Ala Gly Pro Lys Cys Asp Asp
                420                 425                 430 tgc ctc ccc acg cac tac tgg cgc cag ggc tgc tac ccc aac gtg tgc         1443
Cys Leu Pro Thr His Tyr Trp Arg Gln Gly Cys Tyr Pro Asn Val Cys
                435                 440                 445 gac gac gac cag ctg ctg tgc cag aac gga ggc acc tgc ctg cag aac         1491
Asp Asp Asp Gln Leu Leu Cys Gln Asn Gly Gly Thr Cys Leu Gln Asn
            450                 455                 460 cag cgc tgc gcc tgc ccg cgc ggc tac acc ggc gtg cgc tgc gag cag         1539
Gln Arg Cys Ala Cys Pro Arg Gly Tyr Thr Gly Val Arg Cys Glu Gln
        465                 470                 475 ccc cgc tgc gac ccc gcc gac gat gac ggc ggt ctg gac tgc gac cgc         1587
Pro Arg Cys Asp Pro Ala Asp Asp Asp Gly Gly Leu Asp Cys Asp Arg
    480                 485                 490                 495 gcg ccc ggg gcc gcc ccg cgc ccc gcc acc ctg ctc ggc tgc ctg ctg         1635
Ala Pro Gly Ala Ala Pro Arg Pro Ala Thr Leu Leu Gly Cys Leu Leu
                500                 505                 510 ctg ctg ggg ctg gcc gcc cgc ctg ggc cgc tgagccccgc ccggaggacg          1685
Leu Leu Gly Leu Ala Ala Arg Leu Gly Arg
                515                 520 ctccccgcac ccggaggcc                                                    1704

<210> SEQ ID NO 36
```

```
<211> LENGTH: 521
<212> TYPE: PRT
<213> ORGANISM: Homo sapiens

<400> SEQUENCE: 36

Met Leu His Leu Leu Ala Leu Phe Leu His Cys Leu Pro Leu Ala Ser
 1               5                  10                  15

Gly Asp Tyr Asp Ile Cys Lys Ser Trp Val Thr Thr Asp Glu Gly Pro
            20                  25                  30

Thr Trp Glu Phe Tyr Ala Cys Gln Pro Lys Val Met Arg Leu Lys Asp
        35                  40                  45

Tyr Val Lys Val Lys Val Glu Pro Ser Gly Ile Thr Cys Gly Asp Pro
    50                  55                  60

Pro Glu Arg Phe Cys Ser His Pro Tyr Leu Cys Ser Asn Glu Cys Asp
65                  70                  75                  80

Ala Ser Asn Pro Asp Leu Ala His Pro Pro Arg Leu Met Phe Asp Lys
                85                  90                  95

Glu Glu Glu Gly Leu Ala Thr Tyr Trp Gln Ser Ile Thr Trp Ser Arg
            100                 105                 110

Tyr Pro Ser Pro Leu Glu Ala Asn Ile Thr Leu Ser Trp Asn Lys Thr
        115                 120                 125

Val Glu Leu Thr Asp Asp Val Val Met Thr Phe Glu Tyr Gly Arg Pro
    130                 135                 140

Thr Val Met Val Leu Glu Lys Ser Leu Asp Asn Gly Arg Thr Trp Gln
145                 150                 155                 160

Pro Tyr Gln Phe Tyr Ala Glu Asp Cys Met Glu Ala Phe Gly Met Ser
                165                 170                 175

Ala Arg Arg Ala Arg Asp Met Ser Ser Ser Ala His Arg Val Leu
            180                 185                 190

Cys Thr Glu Glu Tyr Ser Arg Trp Ala Gly Ser Lys Lys Glu Lys His
        195                 200                 205

Val Arg Phe Glu Val Arg Asp Arg Phe Ala Ile Phe Ala Gly Pro Asp
    210                 215                 220

Leu Arg Asn Met Asp Asn Leu Tyr Thr Arg Leu Glu Ser Ala Lys Gly
225                 230                 235                 240

Leu Lys Glu Phe Phe Thr Leu Thr Asp Leu Arg Met Arg Leu Leu Arg
                245                 250                 255

Pro Ala Leu Gly Gly Thr Tyr Val Gln Arg Glu Asn Leu Tyr Lys Tyr
            260                 265                 270

Phe Tyr Ala Ile Ser Asn Ile Glu Val Ile Gly Arg Cys Lys Cys Asn
        275                 280                 285

Leu His Ala Asn Leu Cys Ser Met Arg Glu Gly Ser Leu Gln Cys Glu
    290                 295                 300

Cys Glu His Asn Thr Thr Gly Pro Asp Cys Gly Lys Cys Lys Lys Asn
305                 310                 315                 320

Phe Arg Thr Arg Ser Trp Arg Ala Gly Ser Tyr Leu Pro Leu Pro His
                325                 330                 335

Gly Ser Pro Asn Ala Cys Asp Cys Glu Cys Tyr Gly His Ser Asn Arg
            340                 345                 350

Cys Ser Tyr Ile Asp Phe Leu Asn Val Val Thr Cys Val Ser Cys Lys
        355                 360                 365

His Asn Thr Arg Gly Gln His Cys Gln His Cys Arg Leu Gly Tyr Tyr
    370                 375                 380

Arg Asn Gly Ser Ala Glu Leu Asp Asp Glu Asn Val Cys Ile Glu Cys
```

```
                385                 390                 395                 400
Asn Cys Asn Gln Ile Gly Ser Val His Asp Arg Cys Asn Glu Thr Gly
                    405                 410                 415

Phe Cys Glu Cys Arg Glu Gly Ala Ala Gly Pro Lys Cys Asp Asp Cys
                420                 425                 430

Leu Pro Thr His Tyr Trp Arg Gln Gly Cys Tyr Pro Asn Val Cys Asp
            435                 440                 445

Asp Gln Leu Leu Cys Gln Asn Gly Gly Thr Cys Leu Gln Asn Gln
        450                 455                 460

Arg Cys Ala Cys Pro Arg Gly Tyr Thr Gly Val Arg Cys Glu Gln Pro
465                 470                 475                 480

Arg Cys Asp Pro Ala Asp Asp Gly Leu Asp Cys Asp Arg Ala
                485                 490                 495

Pro Gly Ala Ala Pro Arg Pro Ala Thr Leu Leu Gly Cys Leu Leu Leu
                500                 505                 510

Leu Gly Leu Ala Ala Arg Leu Gly Arg
            515                 520

<210> SEQ ID NO 37
<211> LENGTH: 910
<212> TYPE: DNA
<213> ORGANISM: Homo sapiens
<220> FEATURE:
<221> NAME/KEY: CDS
<222> LOCATION: (31)..(826)

<400> SEQUENCE: 37
ggtccggggg ggctgccggt cccgggtacc atg tgt gac ggc gcc ctg ctg          51
                                Met Cys Asp Gly Ala Leu Leu
                                 1               5 cct ccg ctc gtc ctg ccc gtg ctg ctg ctg gtt tgg gga ctg gac          99
Pro Pro Leu Val Leu Pro Val Leu Leu Leu Val Trp Gly Leu Asp
        10                  15                  20 ccg ggc aca gct gtc ggc gac gcg gcg gcc gac gtg gag gtg gtg ctc    147
Pro Gly Thr Ala Val Gly Asp Ala Ala Ala Asp Val Glu Val Val Leu
        25                  30                  35 ccg tgg cgg gtg cgc ccc gac gac gtg cac ctg ccg ccg ctg ccc gca    195
Pro Trp Arg Val Arg Pro Asp Asp Val His Leu Pro Pro Leu Pro Ala
40                  45                  50                  55 gcc ccc ggg ccc cga cgg cgg cga cgc ccc cgc acg ccc cca gcc gcc    243
Ala Pro Gly Pro Arg Arg Arg Arg Pro Arg Thr Pro Pro Ala Ala
                60                  65                  70 ccg cgc gcc cgg ccc gga gag cgc gcc ctg ctg ctg cac ctg ccg gcc    291
Pro Arg Ala Arg Pro Gly Glu Arg Ala Leu Leu Leu His Leu Pro Ala
        75                  80                  85 ttc ggg cgc gac ctg tac ctt cag ctg cgc cgc gac ctg cgc ttc ctg    339
Phe Gly Arg Asp Leu Tyr Leu Gln Leu Arg Arg Asp Leu Arg Phe Leu
        90                  95                 100 tcc cga ggc ttc gag gtg gag gag gcg ggc gcg gcc cgg cgc cgc ggc    387
Ser Arg Gly Phe Glu Val Glu Glu Ala Gly Ala Ala Arg Arg Arg Gly
        105                 110                 115 cgc ccc gcc gag ctg tgc ttc tac tcg ggc cgt gtg ctc ggc cac ccc    435
Arg Pro Ala Glu Leu Cys Phe Tyr Ser Gly Arg Val Leu Gly His Pro
120                 125                 130                 135 ggc tcc ctc gtc tcg ctc agc gcc tgc ggc gcc gcc ggc ggc ctg gta    483
Gly Ser Leu Val Ser Leu Ser Ala Cys Gly Ala Ala Gly Gly Leu Val
                140                 145                 150 ctg ccc gcg cca cct ccg ggt cgg ccc gtc cgg tct gtt gcg acg cag    531
Leu Pro Ala Pro Pro Pro Gly Arg Pro Val Arg Ser Val Ala Thr Gln
```

```
                155                 160                 165
agt ggt cgc cgt gga ggg tgg ggg tgg ggc gcc tct gct gga agt cca          579
Ser Gly Arg Arg Gly Gly Trp Gly Trp Gly Ala Ser Ala Gly Ser Pro
        170                 175                 180 gcc tcc agg gga acc gga ggg aac ccc ctg cct ttc cac ctc tcc cca          627
Ala Ser Arg Gly Thr Gly Gly Asn Pro Leu Pro Phe His Leu Ser Pro
185                 190                 195 tcc ccc acc ccg gcc ttc ggt acc ctc tat agg caa agg ggg tgg gag          675
Ser Pro Thr Pro Ala Phe Gly Thr Leu Tyr Arg Gln Arg Gly Trp Glu
200                 205                 210                 215 ggg cag cat ccc agt cca gcg cct ctg cag ccc gtg aaa ccc gcg cgg          723
Gly Gln His Pro Ser Pro Ala Pro Leu Gln Pro Val Glu Pro Ala Arg
            220                 225                 230 agc tgg ggt tgc gtg ggg gta tac gcc gcc cgc tct agg gag cgc aga          771
Ser Trp Gly Cys Val Gly Val Tyr Ala Ala Arg Ser Arg Glu Arg Arg
            235                 240                 245 tct ggc agg gat gaa act gtc agg gcc ctg gac aga ggc gcc ttg gcc          819
Ser Gly Arg Asp Glu Thr Val Arg Ala Leu Asp Arg Gly Ala Leu Ala
            250                 255                 260 cca atg tagagaacac tgcatctgca ccgccgtgtc aaagtgtatg tcacgggagt          875
Pro Met
    265 acctgtgtac gtgtaggtgt tatgttcttg gactt                                   910

<210> SEQ ID NO 38
<211> LENGTH: 265
<212> TYPE: PRT
<213> ORGANISM: Homo sapiens

<400> SEQUENCE: 38

Met Cys Asp Gly Ala Leu Leu Pro Pro Leu Val Pro Val Leu Leu
 1               5                  10                  15

Leu Leu Val Trp Gly Leu Asp Pro Gly Thr Ala Val Gly Asp Ala Ala
            20                  25                  30

Ala Asp Val Glu Val Val Leu Pro Trp Arg Val Arg Pro Asp Asp Val
        35                  40                  45

His Leu Pro Pro Leu Pro Ala Ala Pro Gly Pro Arg Arg Arg Arg Arg
    50                  55                  60

Pro Arg Thr Pro Pro Ala Ala Pro Arg Ala Arg Pro Gly Glu Arg Ala
65                  70                  75                  80

Leu Leu Leu His Leu Pro Ala Phe Gly Arg Asp Leu Tyr Leu Gln Leu
                85                  90                  95

Arg Arg Asp Leu Arg Phe Leu Ser Arg Gly Phe Glu Val Glu Glu Ala
            100                 105                 110

Gly Ala Ala Arg Arg Gly Arg Pro Ala Glu Leu Cys Phe Tyr Ser
        115                 120                 125

Gly Arg Val Leu Gly His Pro Gly Ser Leu Val Ser Leu Ser Ala Cys
    130                 135                 140

Gly Ala Ala Gly Gly Leu Val Leu Pro Ala Pro Pro Gly Arg Pro
145                 150                 155                 160

Val Arg Ser Val Ala Thr Gln Ser Gly Arg Arg Gly Trp Gly Trp
                165                 170                 175

Gly Ala Ser Ala Gly Ser Pro Ala Ser Arg Gly Thr Gly Gly Asn Pro
            180                 185                 190

Leu Pro Phe His Leu Ser Pro Ser Pro Thr Pro Ala Phe Gly Thr Leu
        195                 200                 205
```

```
Tyr Arg Gln Arg Gly Trp Glu Gly Gln His Pro Ser Pro Ala Pro Leu
    210                 215                 220

Gln Pro Val Glu Pro Ala Arg Ser Trp Gly Cys Val Gly Val Tyr Ala
225                 230                 235                 240

Ala Arg Ser Arg Glu Arg Arg Ser Gly Arg Asp Glu Thr Val Arg Ala
                245                 250                 255

Leu Asp Arg Gly Ala Leu Ala Pro Met
            260                 265

<210> SEQ ID NO 39
<211> LENGTH: 958
<212> TYPE: DNA
<213> ORGANISM: Homo sapiens
<220> FEATURE:
<221> NAME/KEY: CDS
<222> LOCATION: (31)..(931)

<400> SEQUENCE: 39
gcagcacccg cagccagagc cgcgctcggc atg atg ccc ggg gcg ccg ctc            51
                                Met Met Pro Gly Ala Pro Leu
                                  1               5 ctg cgg ctg ctg acc gcg gtc tct gcg gca gtg gca gtg gca gtg gcc        99
Leu Arg Leu Leu Thr Ala Val Ser Ala Ala Val Ala Val Ala Val Ala
        10                  15                  20 ggg gcg ccc ggg acg gta atg ccc ccc acc acg ggg gac gcc acc ctg       147
Gly Ala Pro Gly Thr Val Met Pro Pro Thr Thr Gly Asp Ala Thr Leu
 25                  30                  35 gcc ttc gtc ttc gac gtc acc ggc tcc atg tgg gac gaa ctg atg cag       195
Ala Phe Val Phe Asp Val Thr Gly Ser Met Trp Asp Glu Leu Met Gln
 40                  45                  50                  55 gtg atc gat ggc gcc tcg cgc att ctg gaa cgc agt ctg agc cgc cgc       243
Val Ile Asp Gly Ala Ser Arg Ile Leu Glu Arg Ser Leu Ser Arg Arg
                 60                  65                  70 agc cag gcc atc gcc aac tac gcg ctg gtg ccc ttc cac gac cca gat       291
Ser Gln Ala Ile Ala Asn Tyr Ala Leu Val Pro Phe His Asp Pro Asp
             75                  80                  85 att ggc cca gtg acc ctc acg gcg gac ccc aca gtg ttt cag agg gag       339
Ile Gly Pro Val Thr Leu Thr Ala Asp Pro Thr Val Phe Gln Arg Glu
         90                  95                 100 ctg aga gaa ctc tac gtg cag gga ggt ggt gac tgc ccg gag atg agt       387
Leu Arg Glu Leu Tyr Val Gln Gly Gly Gly Asp Cys Pro Glu Met Ser
    105                 110                 115 gtg ggg gcc att aag gct gcc gtg gag gtt gcc aac ccc gga tcc ttc       435
Val Gly Ala Ile Lys Ala Ala Val Glu Val Ala Asn Pro Gly Ser Phe
120                 125                 130                 135 atc tac gtc ttt tcg gat gcc cgc gcc aaa gac tat cac aag aag gaa       483
Ile Tyr Val Phe Ser Asp Ala Arg Ala Lys Asp Tyr His Lys Lys Glu
                140                 145                 150 gag ctg ctg cgg ctc ctg cag ctc aag caa tca cag gtg gtc ttt gtg       531
Glu Leu Leu Arg Leu Leu Gln Leu Lys Gln Ser Gln Val Val Phe Val
            155                 160                 165 ctg acg ggg gac tgt ggc gac cgc acc cat cct ggc tac ctg gct tat       579
Leu Thr Gly Asp Cys Gly Asp Arg Thr His Pro Gly Tyr Leu Ala Tyr
        170                 175                 180 gag gag atc gct gcc acc agc tct ggg cag gtg ttc cac ctg gac aag       627
Glu Glu Ile Ala Ala Thr Ser Ser Gly Gln Val Phe His Leu Asp Lys
    185                 190                 195 cag caa gtg aca gag gtg ctg aag tgg gtg gag tca gcg atc cag gcc       675
Gln Gln Val Thr Glu Val Leu Lys Trp Val Glu Ser Ala Ile Gln Ala
200                 205                 210                 215
```

-continued

```
tcc aag gtg cac ctg ctg tcc aca gac cac gag gag gag ggg gag cac      723
Ser Lys Val His Leu Leu Ser Thr Asp His Glu Glu Glu Gly Glu His
            220                 225                 230 aca tgg aga ctc ccc ttt gac ccc agc ctg aag gag gtc acc atc tca      771
Thr Trp Arg Leu Pro Phe Asp Pro Ser Leu Lys Glu Val Thr Ile Ser
        235                 240                 245 ttg agt ggg cca ggg cct gag att gaa gtc caa gat ccg ctg ggt atg      819
Leu Ser Gly Pro Gly Pro Glu Ile Glu Val Gln Asp Pro Leu Gly Met
    250                 255                 260 gac cac ccc ggg gct ggc ctc ctc ttt ggc ccc aag act gag gtg gaa      867
Asp His Pro Gly Ala Gly Leu Leu Phe Gly Pro Lys Thr Glu Val Glu
265                 270                 275 gcc cag gat ggg aca aag aaa gag acc aag ggt gac agg gct tca gac      915
Ala Gln Asp Gly Thr Lys Lys Glu Thr Lys Gly Asp Arg Ala Ser Asp
280                 285                 290                 295 atg agg ctc cag gaa tagggaaata tggggtgggg gggacacg                    958
Met Arg Leu Gln Glu
            300
```

<210> SEQ ID NO 40
<211> LENGTH: 300
<212> TYPE: PRT
<213> ORGANISM: Homo sapiens

<400> SEQUENCE: 40

```
Met Met Pro Gly Ala Pro Leu Leu Arg Leu Leu Thr Ala Val Ser Ala
 1               5                  10                  15

Ala Val Ala Val Ala Val Ala Gly Ala Pro Gly Thr Val Met Pro Pro
            20                  25                  30

Thr Thr Gly Asp Ala Thr Leu Ala Phe Val Phe Asp Val Thr Gly Ser
        35                  40                  45

Met Trp Asp Glu Leu Met Gln Val Ile Asp Gly Ala Ser Arg Ile Leu
    50                  55                  60

Glu Arg Ser Leu Ser Arg Arg Ser Gln Ala Ile Ala Asn Tyr Ala Leu
65                  70                  75                  80

Val Pro Phe His Asp Pro Asp Ile Gly Pro Val Thr Leu Thr Ala Asp
                85                  90                  95

Pro Thr Val Phe Gln Arg Glu Leu Arg Glu Leu Tyr Val Gln Gly Gly
            100                 105                 110

Gly Asp Cys Pro Glu Met Ser Val Gly Ala Ile Lys Ala Ala Val Glu
        115                 120                 125

Val Ala Asn Pro Gly Ser Phe Ile Tyr Val Phe Ser Asp Ala Arg Ala
    130                 135                 140

Lys Asp Tyr His Lys Lys Glu Glu Leu Leu Arg Leu Leu Gln Leu Lys
145                 150                 155                 160

Gln Ser Gln Val Val Phe Val Leu Thr Gly Asp Cys Gly Asp Arg Thr
                165                 170                 175

His Pro Gly Tyr Leu Ala Tyr Glu Glu Ile Ala Ala Thr Ser Ser Gly
            180                 185                 190

Gln Val Phe His Leu Asp Lys Gln Gln Val Thr Glu Val Leu Lys Trp
        195                 200                 205

Val Glu Ser Ala Ile Gln Ala Ser Lys Val His Leu Leu Ser Thr Asp
    210                 215                 220

His Glu Glu Gly Glu His Thr Trp Arg Leu Pro Phe Asp Pro Ser
225                 230                 235                 240

Leu Lys Glu Val Thr Ile Ser Leu Ser Gly Pro Gly Pro Glu Ile Glu
                245                 250                 255
```

-continued

```
Val Gln Asp Pro Leu Gly Met Asp His Pro Gly Ala Gly Leu Leu Phe
            260                 265                 270

Gly Pro Lys Thr Glu Val Glu Ala Gln Asp Gly Thr Lys Lys Glu Thr
        275                 280                 285

Lys Gly Asp Arg Ala Ser Asp Met Arg Leu Gln Glu
    290                 295                 300

<210> SEQ ID NO 41
<211> LENGTH: 2916
<212> TYPE: DNA
<213> ORGANISM: Homo sapiens
<220> FEATURE:
<221> NAME/KEY: CDS
<222> LOCATION: (31)..(2914)

<400> SEQUENCE: 41
gcagcacccg cagccagagc cgcgctcggc atg atg ccc ggg gcg ccg ctc          51
                                 Met Met Pro Gly Ala Pro Leu
                                   1               5 ctg cgg ctg ctg acc gcg gtc tct gcg gca gtg gca gtg gca gtg gcc      99
Leu Arg Leu Leu Thr Ala Val Ser Ala Ala Val Ala Val Ala Val Ala
             10                  15                  20 ggg gcg ccc ggg acg gta atg ccc ccc acg acg ggg gac gcc acc ctg     147
Gly Ala Pro Gly Thr Val Met Pro Pro Thr Thr Gly Asp Ala Thr Leu
         25                  30                  35 gcc ttc gtc ttc gac gtc acc ggc tcc atg tgg gac gaa ctg atg cag     195
Ala Phe Val Phe Asp Val Thr Gly Ser Met Trp Asp Glu Leu Met Gln
 40                  45                  50                  55 gtg atc gat ggc gcc tcg cgc att ctg gaa cgc agt ctg agc cgc cgc     243
Val Ile Asp Gly Ala Ser Arg Ile Leu Glu Arg Ser Leu Ser Arg Arg
                 60                  65                  70 agc cag gcc atc gcc aac tac gcg ctg gtg ccc ttc cac gac cca gat     291
Ser Gln Ala Ile Ala Asn Tyr Ala Leu Val Pro Phe His Asp Pro Asp
             75                  80                  85 att ggc cca gtg acc ctc acg gcg gac ccc aca gtg ttt cag agg gag     339
Ile Gly Pro Val Thr Leu Thr Ala Asp Pro Thr Val Phe Gln Arg Glu
         90                  95                 100 ctg aga gaa ctc tac gtg cag gga ggt ggt gac tgc ccg gag atg agt     387
Leu Arg Glu Leu Tyr Val Gln Gly Gly Gly Asp Cys Pro Glu Met Ser
     105                 110                 115 gtg ggg gcc att aag gct gcc gtg gag gtt gcc aac ccc gga tcc ttc     435
Val Gly Ala Ile Lys Ala Ala Val Glu Val Ala Asn Pro Gly Ser Phe
120                 125                 130                 135 atc tac gtc ttt tcg gat gcc cgc gcc aaa gac tat cac aag aag gaa     483
Ile Tyr Val Phe Ser Asp Ala Arg Ala Lys Asp Tyr His Lys Lys Glu
                 140                 145                 150 gag ctg ctg cgg ctc ctg cag ctc aag caa tca cag gtg gtc ttt gtg     531
Glu Leu Leu Arg Leu Leu Gln Leu Lys Gln Ser Gln Val Val Phe Val
             155                 160                 165 ctg acg ggg gac tgt ggc gac cgc acc cat cct ggc tac ctg gct tat     579
Leu Thr Gly Asp Cys Gly Asp Arg Thr His Pro Gly Tyr Leu Ala Tyr
         170                 175                 180 gag gag atc gct gcc acc agc tct ggg cag gtg ttc cac ctg gac aag     627
Glu Glu Ile Ala Ala Thr Ser Ser Gly Gln Val Phe His Leu Asp Lys
     185                 190                 195 cag caa gtg aca gag gca ggt gct tcc gtg ttt cca ggc aaa att gtg     675
Gln Gln Val Thr Glu Ala Gly Ala Ser Val Phe Pro Gly Lys Ile Val
200                 205                 210                 215 cag gag cac agg atc ctt tca ggg gcc agc tgg gaa atg atg aac aac     723
Gln Glu His Arg Ile Leu Ser Gly Ala Ser Trp Glu Met Met Asn Asn
```

```
                         220                 225                 230
gct ctc tct gga aag gac aag cac acc cat ttc cgt ggt ata aat gct      771
Ala Leu Ser Gly Lys Asp Lys His Thr His Phe Arg Gly Ile Asn Ala
            235                 240                 245 ccc acc tcg gct gat tcc aag tca gag ttg gga agt gac gct gac act      819
Pro Thr Ser Ala Asp Ser Lys Ser Glu Leu Gly Ser Asp Ala Asp Thr
            250                 255                 260 cag ctt tcc gga gcc tac aca agt ggc tcc cac aca cca ctg gat ccc      867
Gln Leu Ser Gly Ala Tyr Thr Ser Gly Ser His Thr Pro Leu Asp Pro
            265                 270                 275 gca cag gca cct ctc acc gcc agt tgg gtt aac gag agc ccc tac ctg      915
Ala Gln Ala Pro Leu Thr Ala Ser Trp Val Asn Glu Ser Pro Tyr Leu
280                 285                 290                 295 gtg ctg aag tgg gtg gag tca gcg atc cag gcc tcc aag gtg cac ctg      963
Val Leu Lys Trp Val Glu Ser Ala Ile Gln Ala Ser Lys Val His Leu
                300                 305                 310 ctg tcc aca gac cac gag gag gag ggg gag cac aca tgg aga ctc ccc     1011
Leu Ser Thr Asp His Glu Glu Glu Gly Glu His Thr Trp Arg Leu Pro
            315                 320                 325 ttt gac ccc agc ctg aag gag gtc acc atc tca ttg agt ggg cca ggg     1059
Phe Asp Pro Ser Leu Lys Glu Val Thr Ile Ser Leu Ser Gly Pro Gly
            330                 335                 340 cct gag att gaa gtc caa gat ccg ctg ggt atg gac cac ccc ggg gct     1107
Pro Glu Ile Glu Val Gln Asp Pro Leu Gly Met Asp His Pro Gly Ala
            345                 350                 355 ggc ctc ctc ttt ggc ccc aag act gag gtg gaa gcc cag gat ggg aca     1155
Gly Leu Leu Phe Gly Pro Lys Thr Glu Val Glu Ala Gln Asp Gly Thr
360                 365                 370                 375 aag aaa gag acc aag ggg agg atc ctg cag gag gac gag ggc ctc aac     1203
Lys Lys Glu Thr Lys Gly Arg Ile Leu Gln Glu Asp Glu Gly Leu Asn
                380                 385                 390 gtg ctt ctc aac atc cct gac tcg gcc aag gtc gta gcc ttt aag cct     1251
Val Leu Leu Asn Ile Pro Asp Ser Ala Lys Val Val Ala Phe Lys Pro
            395                 400                 405 gag cat ccg ggg ctg tgg tcc atc aag gtc tat agc agt ggc cgc cat     1299
Glu His Pro Gly Leu Trp Ser Ile Lys Val Tyr Ser Ser Gly Arg His
            410                 415                 420 tca gtg agg atc aca ggc gtc agc aac att gac ttc cga gcc ggc ttc     1347
Ser Val Arg Ile Thr Gly Val Ser Asn Ile Asp Phe Arg Ala Gly Phe
425                 430                 435 tcc act cag ccc ttg ctg gac ctc aac cac acc ctc gag tgg ccc ttg     1395
Ser Thr Gln Pro Leu Leu Asp Leu Asn His Thr Leu Glu Trp Pro Leu
440                 445                 450                 455 caa gga gtc ccc atc tcc ctg gtg atc aat tcc acg ggc ctg aag gca     1443
Gln Gly Val Pro Ile Ser Leu Val Ile Asn Ser Thr Gly Leu Lys Ala
                460                 465                 470 ccc ggc cgc cta gac tcg gtg gag ctg gca caa agc tca ggg aag ccc     1491
Pro Gly Arg Leu Asp Ser Val Glu Leu Ala Gln Ser Ser Gly Lys Pro
            475                 480                 485 ctc ctg act ctg ccc acg aag ccc ctc tcc aat ggc tcc acc cat cag     1539
Leu Leu Thr Leu Pro Thr Lys Pro Leu Ser Asn Gly Ser Thr His Gln
            490                 495                 500 ctg tgg ggc ggg ccg ccc ttc cac acc ccc aag gag cgc ttc tac ctc     1587
Leu Trp Gly Gly Pro Pro Phe His Thr Pro Lys Glu Arg Phe Tyr Leu
505                 510                 515 aag gtg aag ggc aag gac cat gag gga aac ccc ctc ctt cgt gtc tct     1635
Lys Val Lys Gly Lys Asp His Glu Gly Asn Pro Leu Leu Arg Val Ser
520                 525                 530                 535 gga gtg tcc tac agt ggg gtg gcc cca ggc gct ccc ctc gtc agc atg     1683
```

-continued

```
Gly Val Ser Tyr Ser Gly Val Ala Pro Gly Ala Pro Leu Val Ser Met
            540                 545                 550 gcc ccc agg atc cat ggc tac ctg cac cag ccc ctg ctg gtc tcc tgc      1731
Ala Pro Arg Ile His Gly Tyr Leu His Gln Pro Leu Leu Val Ser Cys
            555                 560                 565 tcg gtg cac agt gcc ctt ccc ttc cgg ctg cag ctg cgg cga ggt gaa      1779
Ser Val His Ser Ala Leu Pro Phe Arg Leu Gln Leu Arg Arg Gly Glu
            570                 575                 580 gcc agg ctg ggc gaa gag agg cac ttt cag gag tcg gga aac agc agc      1827
Ala Arg Leu Gly Glu Glu Arg His Phe Gln Glu Ser Gly Asn Ser Ser
585                 590                 595 tgg gag atc ctg cgg gcc tcc aag gcc gag gag ggc acg tac gag tgc      1875
Trp Glu Ile Leu Arg Ala Ser Lys Ala Glu Glu Gly Thr Tyr Glu Cys
600                 605                 610                 615 aca gcc gtc agc agg gct ggg acc ggg cga gca aag gcc cag att gtt      1923
Thr Ala Val Ser Arg Ala Gly Thr Gly Arg Ala Lys Ala Gln Ile Val
            620                 625                 630 gtc acc ctg cac ctc agg gtg ggg ttc ggg gca gca cca ggg ctt gca      1971
Val Thr Leu His Leu Arg Val Gly Phe Gly Ala Ala Pro Gly Leu Ala
            635                 640                 645 cga aga ccc cct ccc ttg cct cag ctc ctt ggt tcc tcc tgt gct cat      2019
Arg Arg Pro Pro Pro Leu Pro Gln Leu Leu Gly Ser Ser Cys Ala His
            650                 655                 660 gtc cct gca gac ccc ccg ccg cag ctg gtc cct gct ccc aac gtg acc      2067
Val Pro Ala Asp Pro Pro Pro Gln Leu Val Pro Ala Pro Asn Val Thr
665                 670                 675 gtg tcc cca ggg gag act gcc gtc cta tcc tgc cgg gtc cta ggc gag      2115
Val Ser Pro Gly Glu Thr Ala Val Leu Ser Cys Arg Val Leu Gly Glu
680                 685                 690                 695 gcc ccc tac aac ctg acg tgg gtc cgg gac tgg cga gtc ctg ccg gcc      2163
Ala Pro Tyr Asn Leu Thr Trp Val Arg Asp Trp Arg Val Leu Pro Ala
            700                 705                 710 tcg acg ggc cga gtt gcc cag ctg gct gac ctg tcc ctg gag atc agt      2211
Ser Thr Gly Arg Val Ala Gln Leu Ala Asp Leu Ser Leu Glu Ile Ser
            715                 720                 725 ggc atc atc ccc aca gac ggc ggg agg tac cag tgt gtg gcc agc aat      2259
Gly Ile Ile Pro Thr Asp Gly Gly Arg Tyr Gln Cys Val Ala Ser Asn
            730                 735                 740 gcc aat ggg gtc aca agg gca tcc gtc tgg ctc ctg gtg cga gag gcc      2307
Ala Asn Gly Val Thr Arg Ala Ser Val Trp Leu Leu Val Arg Glu Ala
745                 750                 755 cca cag gtc agc atc cac acc agc tcc cag cac ttc tcc caa ggt gtg      2355
Pro Gln Val Ser Ile His Thr Ser Ser Gln His Phe Ser Gln Gly Val
760                 765                 770                 775 gag gtg aag gtc agc tgc tca gcc tct gga tac ccc aca ccc cac atc      2403
Glu Val Lys Val Ser Cys Ser Ala Ser Gly Tyr Pro Thr Pro His Ile
            780                 785                 790 tcc tgg agc cgt gag agc caa gcc cta caa gag gac agc aga atc cat      2451
Ser Trp Ser Arg Glu Ser Gln Ala Leu Gln Glu Asp Ser Arg Ile His
            795                 800                 805 gtg gac gca cag gga acc ctg att att cag ggg gta gcc cca gag gat      2499
Val Asp Ala Gln Gly Thr Leu Ile Ile Gln Gly Val Ala Pro Glu Asp
            810                 815                 820 gct ggg aat tac agc tgc cag gcg act aat gag gtt ggc act gac cag      2547
Ala Gly Asn Tyr Ser Cys Gln Ala Thr Asn Glu Val Gly Thr Asp Gln
825                 830                 835 gag acg gtc acc ctc tac tac aca gac cca ccg tcg gtc tct gct gta      2595
Glu Thr Val Thr Leu Tyr Tyr Thr Asp Pro Pro Ser Val Ser Ala Val
840                 845                 850                 855
```

```
aat gcc gtg gtg ctg gtg gcc gtt ggg gag gag gct gtg ttg gtg tgt     2643
Asn Ala Val Val Leu Val Ala Val Gly Glu Glu Ala Val Leu Val Cys
            860                 865                 870 gag gca tct ggg gtt ccc ccg ccc cga gtc atc tgg tat cga ggg ggt     2691
Glu Ala Ser Gly Val Pro Pro Pro Arg Val Ile Trp Tyr Arg Gly Gly
        875                 880                 885 ctt gaa atg atc ctg gcc cct gag ggc tcc agc tct ggg aag ctg cgg     2739
Leu Glu Met Ile Leu Ala Pro Glu Gly Ser Ser Ser Gly Lys Leu Arg
    890                 895                 900 atc ccg gcg gct cag gag agg gat gct ggc acc tac acc tgc cgg gct     2787
Ile Pro Ala Ala Gln Glu Arg Asp Ala Gly Thr Tyr Thr Cys Arg Ala
905                 910                 915 gtc aat gag ttg ggt gac gcc tct gca gaa atc cag ctg gcg gtt gga     2835
Val Asn Glu Leu Gly Asp Ala Ser Ala Glu Ile Gln Leu Ala Val Gly
920                 925                 930                 935 cat gcg ccc cag ctg acg gag ctg ccc cgg gat gtc act gtg gaa ctg     2883
His Ala Pro Gln Leu Thr Glu Leu Pro Arg Asp Val Thr Val Glu Leu
                940                 945                 950 ggg agg agt gcc cag ctg cgg cgt ggg act taa                         2916
Gly Arg Ser Ala Gln Leu Arg Arg Gly Thr
            955                 960
```

<210> SEQ ID NO 42
<211> LENGTH: 961
<212> TYPE: PRT
<213> ORGANISM: Homo sapiens

<400> SEQUENCE: 42

```
Met Met Pro Gly Ala Pro Leu Leu Arg Leu Leu Thr Ala Val Ser Ala
1               5                   10                  15

Ala Val Ala Val Ala Val Ala Gly Ala Pro Gly Thr Val Met Pro Pro
            20                  25                  30

Thr Thr Gly Asp Ala Thr Leu Ala Phe Val Phe Asp Val Thr Gly Ser
        35                  40                  45

Met Trp Asp Glu Leu Met Gln Val Ile Asp Gly Ala Ser Arg Ile Leu
    50                  55                  60

Glu Arg Ser Leu Ser Arg Arg Ser Gln Ala Ile Ala Asn Tyr Ala Leu
65                  70                  75                  80

Val Pro Phe His Asp Pro Asp Ile Gly Pro Val Thr Leu Thr Ala Asp
                85                  90                  95

Pro Thr Val Phe Gln Arg Glu Leu Arg Glu Leu Tyr Val Gln Gly Gly
            100                 105                 110

Gly Asp Cys Pro Glu Met Ser Val Gly Ala Ile Lys Ala Ala Val Glu
        115                 120                 125

Val Ala Asn Pro Gly Ser Phe Ile Tyr Val Phe Ser Asp Ala Arg Ala
    130                 135                 140

Lys Asp Tyr His Lys Lys Glu Leu Leu Arg Leu Leu Gln Leu Lys
145                 150                 155                 160

Gln Ser Gln Val Val Phe Val Leu Thr Gly Asp Cys Gly Asp Arg Thr
                165                 170                 175

His Pro Gly Tyr Leu Ala Tyr Glu Glu Ile Ala Ala Thr Ser Ser Gly
            180                 185                 190

Gln Val Phe His Leu Asp Lys Gln Gln Val Thr Glu Ala Gly Ala Ser
        195                 200                 205

Val Phe Pro Gly Lys Ile Val Gln Glu His Arg Ile Leu Ser Gly Ala
    210                 215                 220

Ser Trp Glu Met Met Asn Asn Ala Leu Ser Gly Lys Asp Lys His Thr
```

-continued

```
            225                 230                 235                 240

His Phe Arg Gly Ile Asn Ala Pro Thr Ser Ala Asp Ser Lys Ser Glu
                245                 250                 255

Leu Gly Ser Asp Ala Asp Thr Gln Leu Ser Gly Ala Tyr Thr Ser Gly
                260                 265                 270

Ser His Thr Pro Leu Asp Pro Ala Gln Ala Pro Leu Thr Ala Ser Trp
                275                 280                 285

Val Asn Glu Ser Pro Tyr Leu Val Leu Lys Trp Val Glu Ser Ala Ile
        290                 295                 300

Gln Ala Ser Lys Val His Leu Leu Ser Thr Asp His Glu Glu Glu Gly
305                 310                 315                 320

Glu His Thr Trp Arg Leu Pro Phe Asp Pro Ser Leu Lys Glu Val Thr
                325                 330                 335

Ile Ser Leu Ser Gly Pro Gly Pro Glu Ile Glu Val Gln Asp Pro Leu
                340                 345                 350

Gly Met Asp His Pro Gly Ala Gly Leu Leu Phe Gly Pro Lys Thr Glu
                355                 360                 365

Val Glu Ala Gln Asp Gly Thr Lys Lys Glu Thr Lys Gly Arg Ile Leu
        370                 375                 380

Gln Glu Asp Glu Gly Leu Asn Val Leu Leu Asn Ile Pro Asp Ser Ala
385                 390                 395                 400

Lys Val Val Ala Phe Lys Pro Glu His Pro Gly Leu Trp Ser Ile Lys
                405                 410                 415

Val Tyr Ser Ser Gly Arg His Ser Val Arg Ile Thr Gly Val Ser Asn
                420                 425                 430

Ile Asp Phe Arg Ala Gly Phe Ser Thr Gln Pro Leu Leu Asp Leu Asn
                435                 440                 445

His Thr Leu Glu Trp Pro Leu Gln Gly Val Pro Ile Ser Leu Val Ile
        450                 455                 460

Asn Ser Thr Gly Leu Lys Ala Pro Gly Arg Leu Asp Ser Val Glu Leu
465                 470                 475                 480

Ala Gln Ser Ser Gly Lys Pro Leu Leu Thr Leu Pro Thr Lys Pro Leu
                485                 490                 495

Ser Asn Gly Ser Thr His Gln Leu Trp Gly Pro Pro Phe His Thr
                500                 505                 510

Pro Lys Glu Arg Phe Tyr Leu Lys Val Lys Gly Lys Asp His Glu Gly
                515                 520                 525

Asn Pro Leu Leu Arg Val Ser Gly Val Ser Tyr Ser Gly Val Ala Pro
        530                 535                 540

Gly Ala Pro Leu Val Ser Met Ala Pro Arg Ile His Gly Tyr Leu His
545                 550                 555                 560

Gln Pro Leu Leu Val Ser Cys Ser Val His Ser Ala Leu Pro Phe Arg
                565                 570                 575

Leu Gln Leu Arg Arg Gly Glu Ala Arg Leu Gly Glu Arg His Phe
                580                 585                 590

Gln Glu Ser Gly Asn Ser Ser Trp Glu Ile Leu Arg Ala Ser Lys Ala
                595                 600                 605

Glu Glu Gly Thr Tyr Glu Cys Thr Ala Val Ser Arg Ala Gly Thr Gly
                610                 615                 620

Arg Ala Lys Ala Gln Ile Val Thr Leu His Leu Arg Val Gly Phe
625                 630                 635                 640

Gly Ala Ala Pro Gly Leu Ala Arg Arg Pro Pro Leu Pro Gln Leu
                645                 650                 655
```

-continued

Leu Gly Ser Ser Cys Ala His Val Pro Ala Asp Pro Pro Gln Leu
              660                 665                 670

Val Pro Ala Pro Asn Val Thr Val Ser Pro Gly Glu Thr Ala Val Leu
          675                 680                 685

Ser Cys Arg Val Leu Gly Glu Ala Pro Tyr Asn Leu Thr Trp Val Arg
      690                 695                 700

Asp Trp Arg Val Leu Pro Ala Ser Thr Gly Arg Val Ala Gln Leu Ala
705                 710                 715                 720

Asp Leu Ser Leu Glu Ile Ser Gly Ile Ile Pro Thr Asp Gly Gly Arg
              725                 730                 735

Tyr Gln Cys Val Ala Ser Asn Ala Asn Gly Val Thr Arg Ala Ser Val
          740                 745                 750

Trp Leu Leu Val Arg Glu Ala Pro Gln Val Ser Ile His Thr Ser Ser
      755                 760                 765

Gln His Phe Ser Gln Gly Val Glu Val Lys Val Ser Cys Ser Ala Ser
  770                 775                 780

Gly Tyr Pro Thr Pro His Ile Ser Trp Ser Arg Glu Ser Gln Ala Leu
785                 790                 795                 800

Gln Glu Asp Ser Arg Ile His Val Asp Ala Gln Gly Thr Leu Ile Ile
              805                 810                 815

Gln Gly Val Ala Pro Glu Asp Ala Gly Asn Tyr Ser Cys Gln Ala Thr
          820                 825                 830

Asn Glu Val Gly Thr Asp Gln Glu Thr Val Thr Leu Tyr Tyr Thr Asp
      835                 840                 845

Pro Pro Ser Val Ser Ala Val Asn Ala Val Val Leu Ala Val Gly
850                 855                 860

Glu Glu Ala Val Leu Val Cys Glu Ala Ser Gly Val Pro Pro Pro Arg
865                 870                 875                 880

Val Ile Trp Tyr Arg Gly Gly Leu Glu Met Ile Leu Ala Pro Glu Gly
              885                 890                 895

Ser Ser Ser Gly Lys Leu Arg Ile Pro Ala Ala Gln Glu Arg Asp Ala
          900                 905                 910

Gly Thr Tyr Thr Cys Arg Ala Val Asn Glu Leu Gly Asp Ala Ser Ala
      915                 920                 925

Glu Ile Gln Leu Ala Val Gly His Ala Pro Gln Leu Thr Glu Leu Pro
  930                 935                 940

Arg Asp Val Thr Val Glu Leu Gly Arg Ser Ala Gln Leu Arg Arg Gly
945                 950                 955                 960

Thr

<210> SEQ ID NO 43
<211> LENGTH: 1023
<212> TYPE: DNA
<213> ORGANISM: Homo sapiens
<220> FEATURE:
<221> NAME/KEY: CDS
<222> LOCATION: (628)..(1023)

<400> SEQUENCE: 43
ctcgagtgtg gaactcactc ttaacgtacc tgaggagtgt ccaacgtctt         50
tggacaaggc catactctca tgttcctttt cactcagctt tacccacaca         100
gaaattttgg ggacccatgg gggactcagc agttgccaag gtctgcagcc         150
tcctccaagg ggttcccatc tagttctcaa gaggaaggag ggggtctca          200

```
gtcgccaggt gggcatggca ctcccgaggc caggtgagca ggtcagtgcc          250
ttggggctca gggctgctcc ggttcttacc gaattgatcc agtcgttgta          300
gttggagacc cgcgtgaaga tggagggctt gtagtagtag ttgcaaccaa          350
ggaccgacgt gaggctgccg atgccatgca cctcccaccg gccgtcagat          400
gcctgacagt tcagcggccc accggagtct ccgttgcagg tgcatatcac          450
gccatcaccc ccagcacaga tcatattcgt cttcacggtg ctgccccacc          500
agccagagtt ggagcaggtg gcatagtcca caaccagcaa ccggccctgc          550
ttcaggtcat cagggagagc cccgttggtc tgcagccttc cccagcccgt          600
gacgtagcag ggtagttgt tgggtag aat ggt gcc ggc agg agg gag gca     651
                              Asn Gly Ala Gly Arg Arg Glu Ala
                                1               5 ggc cag ctg gat ctt gtc ggt gag gga gac ggg gtt agc cag ttt gag  699
Gly Gln Leu Asp Leu Val Gly Glu Gly Asp Gly Val Ser Gln Phe Glu
         10                  15                  20 cag ggc aat gtc gtt ccc ttt gga gac ctg gtc gga gtt cca gtc ctt  747
Gln Gly Asn Val Val Pro Phe Gly Asp Leu Val Gly Val Pro Val Leu
 25                  30                  35                  40 gtg cac cac aat ctt aga gac act gac ggc cag cga gcc gga ctc tgc  795
Val His His Asn Leu Arg Asp Thr Asp Gly Gln Arg Ala Gly Leu Cys
                 45                  50                  55 aac gta gag gtt atg ctg gcc cag cat cac gcg gta gat ccc gga gga  843
Asn Val Glu Val Met Leu Ala Gln His His Ala Val Asp Pro Gly Gly
             60                  65                  70 gct gat gca gtg ggc agc cgt cag gac cca gct gtt ggc tat cag gga  891
Ala Asp Ala Val Gly Ser Arg Gln Asp Pro Ala Val Gly Tyr Gln Gly
         75                  80                  85 ccc tcc gca ggt gtg gta cca ctg gcc att gga gct gta ctg cag gga  939
Pro Ser Ala Gly Val Val Pro Leu Ala Ile Gly Ala Val Leu Gln Gly
 90                  95                 100 gac ctg cca ggg ccg gct gtt ggg cct cgc ttc ttc acc tcc aag cat  987
Asp Leu Pro Gly Pro Ala Val Gly Pro Arg Phe Phe Thr Ser Lys His
105                 110                 115                 120 cct aga cat atc agg cgc gta agt gga gac gga tcc                  1023
Pro Arg His Ile Arg Arg Val Ser Gly Asp Gly Ser
                125                 130

<210> SEQ ID NO 44
<211> LENGTH: 132
<212> TYPE: PRT
<213> ORGANISM: Homo sapiens

<400> SEQUENCE: 44

Asn Gly Ala Gly Arg Arg Glu Ala Gly Gln Leu Asp Leu Val Gly Glu
  1               5                  10                  15

Gly Asp Gly Val Ser Gln Phe Glu Gln Gly Asn Val Val Pro Phe Gly
             20                  25                  30

Asp Leu Val Gly Val Pro Val Leu Val His His Asn Leu Arg Asp Thr
         35                  40                  45

Asp Gly Gln Arg Ala Gly Leu Cys Asn Val Glu Val Met Leu Ala Gln
     50                  55                  60

His His Ala Val Asp Pro Gly Gly Ala Asp Ala Val Gly Ser Arg Gln
 65                  70                  75                  80

Asp Pro Ala Val Gly Tyr Gln Gly Pro Ser Ala Gly Val Val Pro Leu
                 85                  90                  95

Ala Ile Gly Ala Val Leu Gln Gly Asp Leu Pro Gly Pro Ala Val Gly
```

```
                    100                 105                 110
Pro Arg Phe Phe Thr Ser Lys His Pro Arg His Ile Arg Arg Val Ser
        115                 120                 125

Gly Asp Gly Ser
    130

<210> SEQ ID NO 45
<211> LENGTH: 2058
<212> TYPE: DNA
<213> ORGANISM: Homo sapiens
<220> FEATURE:
<221> NAME/KEY: CDS
<222> LOCATION: (1)..(2058)

<400> SEQUENCE: 45 aag ctt gtg gca gtg gcc ggg gcg ccc ggg acg gta atg ccc ccc acc      48
Lys Leu Val Ala Val Ala Gly Ala Pro Gly Thr Val Met Pro Pro Thr
  1               5                  10                  15 acg ggg gac gcc acc ctg gcc ttc gtc ttc gac gtc acc ggc tcc atg      96
Thr Gly Asp Ala Thr Leu Ala Phe Val Phe Asp Val Thr Gly Ser Met
             20                  25                  30 tgg gac gaa ctg atg cag gtg atc gat ggc gcc tcg cgc att ctg gaa     144
Trp Asp Glu Leu Met Gln Val Ile Asp Gly Ala Ser Arg Ile Leu Glu
         35                  40                  45 cgc agt ctg agc cgc cgc agc cag gcc atc gcc aac tac gcg ctg gtg     192
Arg Ser Leu Ser Arg Arg Ser Gln Ala Ile Ala Asn Tyr Ala Leu Val
     50                  55                  60 ccc ttc cac gac cca gat att ggc cca gtg acc ctc acg gcg gac ccc     240
Pro Phe His Asp Pro Asp Ile Gly Pro Val Thr Leu Thr Ala Asp Pro
 65                  70                  75                  80 aca gtg ttt cag agg gag ctg aga gaa ctc tac gtg cag gga ggt ggt     288
Thr Val Phe Gln Arg Glu Leu Arg Glu Leu Tyr Val Gln Gly Gly Gly
                 85                  90                  95 gac tgc ccg gag atg agt gtg ggg gcc att aag gct gcc gtg gag gtt     336
Asp Cys Pro Glu Met Ser Val Gly Ala Ile Lys Ala Ala Val Glu Val
            100                 105                 110 gcc aac ccc gga tcc ttc atc tac gtc ttt tcg gat gcc cgc gcc aaa     384
Ala Asn Pro Gly Ser Phe Ile Tyr Val Phe Ser Asp Ala Arg Ala Lys
        115                 120                 125 gac tat cac aag aag gaa gag ctg ctg cgg ctc ctg cag ctc aag caa     432
Asp Tyr His Lys Lys Glu Glu Leu Leu Arg Leu Leu Gln Leu Lys Gln
    130                 135                 140 tca cag gtg gtc ttt gtg ctg acg ggg gac tgt ggc gac cac acc cat     480
Ser Gln Val Val Phe Val Leu Thr Gly Asp Cys Gly Asp His Thr His
145                 150                 155                 160 cct ggc tac ctg gct tat gag gag atc gct gcc acc agc tct ggg cag     528
Pro Gly Tyr Leu Ala Tyr Glu Glu Ile Ala Ala Thr Ser Ser Gly Gln
                165                 170                 175 gtg ttc cac ctg gac aag cag caa gtg aca gag gtg ctg aag tgg gtg     576
Val Phe His Leu Asp Lys Gln Gln Val Thr Glu Val Leu Lys Trp Val
            180                 185                 190 gag tca gcg atc cag gcc tcc aag gtg cac ctg ctg tcc aca gac cac     624
Glu Ser Ala Ile Gln Ala Ser Lys Val His Leu Leu Ser Thr Asp His
        195                 200                 205 gag gag gag ggg gag cac aca tgg aga ctc ccc ttt gac ccc agc ctg     672
Glu Glu Glu Gly Glu His Thr Trp Arg Leu Pro Phe Asp Pro Ser Leu
    210                 215                 220 aag gag gtc acc atc tca ttg agt ggg cca ggg cct gag att gaa gtc     720
Lys Glu Val Thr Ile Ser Leu Ser Gly Pro Gly Pro Glu Ile Glu Val
225                 230                 235                 240
```

```
caa gat ccg ctg ggg agg atc ctg cag gag gac gag ggc ctc aac gtg         768
Gln Asp Pro Leu Gly Arg Ile Leu Gln Glu Asp Glu Gly Leu Asn Val
            245                 250                 255 ctt ctc aac atc cct gac tcg gcc aag gtc gta gcc ttt aag cct gag         816
Leu Leu Asn Ile Pro Asp Ser Ala Lys Val Val Ala Phe Lys Pro Glu
        260                 265                 270 cat ccg ggg ctg tgg tcc atc aag gtc tat agc agt ggc cgc cat tca         864
His Pro Gly Leu Trp Ser Ile Lys Val Tyr Ser Ser Gly Arg His Ser
    275                 280                 285 gtg agg atc aca ggc gtc agc aac att gac ttc cga gcc ggc ttc tcc         912
Val Arg Ile Thr Gly Val Ser Asn Ile Asp Phe Arg Ala Gly Phe Ser
290                 295                 300 act cag ccc ttg ctg gac ctc aac cac acc ctc gag tgg ccc ttg caa         960
Thr Gln Pro Leu Leu Asp Leu Asn His Thr Leu Glu Trp Pro Leu Gln
305                 310                 315                 320 gga gtc ccc atc tcc ctg gtg atc aat tcc acg ggc ctg aag gca ccc        1008
Gly Val Pro Ile Ser Leu Val Ile Asn Ser Thr Gly Leu Lys Ala Pro
                325                 330                 335 ggc cgc cta gac tcg gtg gag ctg gca caa agc tca ggg aag ccc ctc        1056
Gly Arg Leu Asp Ser Val Glu Leu Ala Gln Ser Ser Gly Lys Pro Leu
            340                 345                 350 ctg act ctg ccc acg aag ccc ctc tcc aat ggc tcc acc cat cag ctg        1104
Leu Thr Leu Pro Thr Lys Pro Leu Ser Asn Gly Ser Thr His Gln Leu
        355                 360                 365 tgg ggc ggg cca ccc ttc cac acc ccc aag gag cgc ttc tac ctc aag        1152
Trp Gly Gly Pro Pro Phe His Thr Pro Lys Glu Arg Phe Tyr Leu Lys
    370                 375                 380 gtg aag ggc aag gac cat gag gga aac ccc ctc ctt cgt gtc tct gga        1200
Val Lys Gly Lys Asp His Glu Gly Asn Pro Leu Leu Arg Val Ser Gly
385                 390                 395                 400 gtg tcc tac agt ggg gtg gcc cca ggc gct ccc ctc gtc agc atg gtc        1248
Val Ser Tyr Ser Gly Val Ala Pro Gly Ala Pro Leu Val Ser Met Val
                405                 410                 415 ccc agg atc cat ggc tac ctg cac cag ccc ctg ctg gtc tcc tgc tcg        1296
Pro Arg Ile His Gly Tyr Leu His Gln Pro Leu Leu Val Ser Cys Ser
            420                 425                 430 gtg cac agt gcc ctt ccc ttc cgg ctg cag ctg cga gga gaa gcc            1344
Val His Ser Ala Leu Pro Phe Arg Leu Gln Leu Arg Arg Gly Glu Ala
        435                 440                 445 agg ctg ggc gaa gag agg cac ttt cag gag tcg gga aac agt agc tgg        1392
Arg Leu Gly Glu Glu Arg His Phe Gln Glu Ser Gly Asn Ser Ser Trp
    450                 455                 460 gag atc ctg cgg gcc tcc aag gcc gag gag ggc acg tac gag tgc aca        1440
Glu Ile Leu Arg Ala Ser Lys Ala Glu Glu Gly Thr Tyr Glu Cys Thr
465                 470                 475                 480 gcc gtc agc agg gct ggg acc ggg cga gca aag gcc cag att gtt gtc        1488
Ala Val Ser Arg Ala Gly Thr Gly Arg Ala Lys Ala Gln Ile Val Val
                485                 490                 495 aca gac ccc ccg ccg cag ctg gtc cct gct ccc aac gtg acc gtg tcc        1536
Thr Asp Pro Pro Pro Gln Leu Val Pro Ala Pro Asn Val Thr Val Ser
            500                 505                 510 cca ggg gag act gcc gtc cta tcc tgc cgg gtc cta ggc gag gcc ccc        1584
Pro Gly Glu Thr Ala Val Leu Ser Cys Arg Val Leu Gly Glu Ala Pro
        515                 520                 525 tac aac ctg acg tgg gtc cgg gac tgg cga gtc ctg ccg gcc tcg acg        1632
Tyr Asn Leu Thr Trp Val Arg Asp Trp Arg Val Leu Pro Ala Ser Thr
    530                 535                 540 ggc cga gtt gcc cag ctg gct gac ctg tcc ctg gag atc agt ggc atc        1680
Gly Arg Val Ala Gln Leu Ala Asp Leu Ser Leu Glu Ile Ser Gly Ile
545                 550                 555                 560
```

-continued

| | | |
|---|---|---|
| atc ccc aca gac ggc ggg agg tac cag tgt gtg gcc agc aat gcc aat<br>Ile Pro Thr Asp Gly Gly Arg Tyr Gln Cys Val Ala Ser Asn Ala Asn<br>565 570 575 | | 1728 |
| ggg gtc aca agg gca tcc gtc tgg ctc ctg gtg cga gag gtc cca cag<br>Gly Val Thr Arg Ala Ser Val Trp Leu Leu Val Arg Glu Val Pro Gln<br>580 585 590 | | 1776 |
| gtc agc atc cac acc agc tcc cag cac ttc tcc caa ggt gtg gag gtg<br>Val Ser Ile His Thr Ser Ser Gln His Phe Ser Gln Gly Val Glu Val<br>595 600 605 | | 1824 |
| aag gtc agc tgc tca gcc tct gga tac ccc aca ccc cac atc tcc tgg<br>Lys Val Ser Cys Ser Ala Ser Gly Tyr Pro Thr Pro His Ile Ser Trp<br>610 615 620 | | 1872 |
| agc cgt gag agc caa gcc cta caa gag gac agc aga atc cat gtg gac<br>Ser Arg Glu Ser Gln Ala Leu Gln Glu Asp Ser Arg Ile His Val Asp<br>625 630 635 640 | | 1920 |
| gca cag gga acc ctg att att cag ggg gta gcc cca gag gat gct ggg<br>Ala Gln Gly Thr Leu Ile Ile Gln Gly Val Ala Pro Glu Asp Ala Gly<br>645 650 655 | | 1968 |
| aat tac agc tgc cag gcg act aat gag gtt ggc act gac cag gag acg<br>Asn Tyr Ser Cys Gln Ala Thr Asn Glu Val Gly Thr Asp Gln Glu Thr<br>660 665 670 | | 2016 |
| gtc acc ctc tac tac aca gac cca ccg tcg gtc tct gtc gac<br>Val Thr Leu Tyr Tyr Thr Asp Pro Pro Ser Val Ser Val Asp<br>675 680 685 | | 2058 |

<210> SEQ ID NO 46
<211> LENGTH: 686
<212> TYPE: PRT
<213> ORGANISM: Homo sapiens

<400> SEQUENCE: 46

```
Lys Leu Val Ala Val Ala Gly Ala Pro Gly Thr Val Met Pro Pro Thr
  1               5                  10                  15

Thr Gly Asp Ala Thr Leu Ala Phe Val Phe Asp Val Thr Gly Ser Met
                 20                  25                  30

Trp Asp Glu Leu Met Gln Val Ile Asp Gly Ala Ser Arg Ile Leu Glu
             35                  40                  45

Arg Ser Leu Ser Arg Arg Ser Gln Ala Ile Ala Asn Tyr Ala Leu Val
         50                  55                  60

Pro Phe His Asp Pro Asp Ile Gly Pro Val Thr Leu Thr Ala Asp Pro
 65                  70                  75                  80

Thr Val Phe Gln Arg Glu Leu Arg Glu Leu Tyr Val Gln Gly Gly Gly
                 85                  90                  95

Asp Cys Pro Glu Met Ser Val Gly Ala Ile Lys Ala Val Glu Val
                100                 105                 110

Ala Asn Pro Gly Ser Phe Ile Tyr Val Phe Ser Asp Ala Arg Ala Lys
            115                 120                 125

Asp Tyr His Lys Lys Glu Leu Leu Arg Leu Leu Gln Leu Lys Gln
        130                 135                 140

Ser Gln Val Val Phe Val Leu Thr Gly Asp Cys Gly Asp His Thr His
145                 150                 155                 160

Pro Gly Tyr Leu Ala Tyr Glu Glu Ile Ala Ala Thr Ser Ser Gly Gln
                165                 170                 175

Val Phe His Leu Asp Lys Gln Gln Val Thr Glu Val Leu Lys Trp Val
            180                 185                 190

Glu Ser Ala Ile Gln Ala Ser Lys Val His Leu Leu Ser Thr Asp His
        195                 200                 205
```

-continued

```
Glu Glu Glu Gly Glu His Thr Trp Arg Leu Pro Phe Asp Pro Ser Leu
    210                 215                 220
Lys Glu Val Thr Ile Ser Leu Ser Gly Pro Gly Pro Glu Ile Glu Val
225                 230                 235                 240
Gln Asp Pro Leu Gly Arg Ile Leu Gln Glu Asp Glu Gly Leu Asn Val
                245                 250                 255
Leu Leu Asn Ile Pro Asp Ser Ala Lys Val Val Ala Phe Lys Pro Glu
                260                 265                 270
His Pro Gly Leu Trp Ser Ile Lys Val Tyr Ser Ser Gly Arg His Ser
            275                 280                 285
Val Arg Ile Thr Gly Val Ser Asn Ile Asp Phe Arg Ala Gly Phe Ser
    290                 295                 300
Thr Gln Pro Leu Leu Asp Leu Asn His Thr Leu Glu Trp Pro Leu Gln
305                 310                 315                 320
Gly Val Pro Ile Ser Leu Val Ile Asn Ser Thr Gly Leu Lys Ala Pro
                325                 330                 335
Gly Arg Leu Asp Ser Val Glu Leu Ala Gln Ser Ser Gly Lys Pro Leu
                340                 345                 350
Leu Thr Leu Pro Thr Lys Pro Leu Ser Asn Gly Ser Thr His Gln Leu
            355                 360                 365
Trp Gly Gly Pro Pro Phe His Thr Pro Lys Glu Arg Phe Tyr Leu Lys
    370                 375                 380
Val Lys Gly Lys Asp His Glu Gly Asn Pro Leu Leu Arg Val Ser Gly
385                 390                 395                 400
Val Ser Tyr Ser Gly Val Ala Pro Gly Ala Pro Leu Val Ser Met Val
                405                 410                 415
Pro Arg Ile His Gly Tyr Leu His Gln Pro Leu Leu Val Ser Cys Ser
                420                 425                 430
Val His Ser Ala Leu Pro Phe Arg Leu Gln Leu Arg Arg Gly Glu Ala
            435                 440                 445
Arg Leu Gly Glu Glu Arg His Phe Gln Glu Ser Gly Asn Ser Ser Trp
    450                 455                 460
Glu Ile Leu Arg Ala Ser Lys Ala Glu Glu Gly Thr Tyr Glu Cys Thr
465                 470                 475                 480
Ala Val Ser Arg Ala Gly Thr Gly Arg Ala Lys Ala Gln Ile Val Val
                485                 490                 495
Thr Asp Pro Pro Pro Gln Leu Val Pro Ala Pro Asn Val Thr Val Ser
                500                 505                 510
Pro Gly Glu Thr Ala Val Leu Ser Cys Arg Val Leu Gly Glu Ala Pro
            515                 520                 525
Tyr Asn Leu Thr Trp Val Arg Asp Trp Arg Val Leu Pro Ala Ser Thr
    530                 535                 540
Gly Arg Val Ala Gln Leu Ala Asp Leu Ser Leu Glu Ile Ser Gly Ile
545                 550                 555                 560
Ile Pro Thr Asp Gly Gly Arg Tyr Gln Cys Val Ala Ser Asn Ala Asn
                565                 570                 575
Gly Val Thr Arg Ala Ser Val Trp Leu Leu Val Arg Glu Val Pro Gln
                580                 585                 590
Val Ser Ile His Thr Ser Ser Gln His Phe Ser Gln Gly Val Glu Val
            595                 600                 605
Lys Val Ser Cys Ser Ala Ser Gly Tyr Pro Thr Pro His Ile Ser Trp
    610                 615                 620
```

```
Ser Arg Glu Ser Gln Ala Leu Gln Glu Asp Ser Arg Ile His Val Asp
625                 630                 635                 640

Ala Gln Gly Thr Leu Ile Ile Gln Gly Val Ala Pro Glu Asp Ala Gly
            645                 650                 655

Asn Tyr Ser Cys Gln Ala Thr Asn Glu Val Gly Thr Asp Gln Glu Thr
                660                 665                 670

Val Thr Leu Tyr Tyr Thr Asp Pro Pro Ser Val Ser Val Asp
            675                 680                 685
```

<210> SEQ ID NO 47
<211> LENGTH: 2058
<212> TYPE: DNA
<213> ORGANISM: Homo sapiens
<220> FEATURE:
<221> NAME/KEY: CDS
<222> LOCATION: (1)..(2058)

<400> SEQUENCE: 47

```
aag ctt gtg gca gtg gcc ggg gcg ccc ggg acg gta atg ccc ccc acc        48
Lys Leu Val Ala Val Ala Gly Ala Pro Gly Thr Val Met Pro Pro Thr
  1               5                  10                  15 acg ggg gac gcc acc ctg gcc ttc gtc ttc gac gtc acc ggc tcc atg       96
Thr Gly Asp Ala Thr Leu Ala Phe Val Phe Asp Val Thr Gly Ser Met
             20                  25                  30 tgg gac gaa ctg atg cag gtg atc gat ggc gcc tcg cgc att ctg gaa      144
Trp Asp Glu Leu Met Gln Val Ile Asp Gly Ala Ser Arg Ile Leu Glu
         35                  40                  45 cgc agt ctg agc cgc cgc agc cag gcc atc gcc aac tac gcg ctg gtg      192
Arg Ser Leu Ser Arg Arg Ser Gln Ala Ile Ala Asn Tyr Ala Leu Val
     50                  55                  60 ccc ttc cac gac cca gat att ggc cca gtg acc ctc acg gcg gac ccc      240
Pro Phe His Asp Pro Asp Ile Gly Pro Val Thr Leu Thr Ala Asp Pro
 65                  70                  75                  80 aca gtg ttt cag agg gag ctg aga gaa ctc tac gtg cag gga ggt ggt      288
Thr Val Phe Gln Arg Glu Leu Arg Glu Leu Tyr Val Gln Gly Gly Gly
                 85                  90                  95 gac tgc ccg gag atg agt gtg ggg gcc att aag gct gcc gtg gag gtt      336
Asp Cys Pro Glu Met Ser Val Gly Ala Ile Lys Ala Ala Val Glu Val
            100                 105                 110 gcc aac ccc gga tcc ttc atc tac gtc ttt tcg gat gcc cgc gcc aaa      384
Ala Asn Pro Gly Ser Phe Ile Tyr Val Phe Ser Asp Ala Arg Ala Lys
        115                 120                 125 gac tat cac aag aag gaa gag ctg ctg cgg ctc ctg cag ctc aag caa      432
Asp Tyr His Lys Lys Glu Glu Leu Leu Arg Leu Leu Gln Leu Lys Gln
    130                 135                 140 tca cag gtg gtc ttt gtg ctg acg ggg gac tgt ggc gac cac acc cat      480
Ser Gln Val Val Phe Val Leu Thr Gly Asp Cys Gly Asp His Thr His
145                 150                 155                 160 cct ggc tac ctg gct tat gag gag atc gct gcc acc agc tct ggg cag      528
Pro Gly Tyr Leu Ala Tyr Glu Glu Ile Ala Ala Thr Ser Ser Gly Gln
                165                 170                 175 gtg ttc cac ctg gac aag cag caa gtg aca gag gtg ctg aag tgg gtg      576
Val Phe His Leu Asp Lys Gln Gln Val Thr Glu Val Leu Lys Trp Val
            180                 185                 190 gag tca gcg atc cag gcc tcc aag gtg cac ctg ctg tcc aca gac cac      624
Glu Ser Ala Ile Gln Ala Ser Lys Val His Leu Leu Ser Thr Asp His
        195                 200                 205 gag gag gag ggg gag cac aca tgg aga ctc ccc ttt gac ccc agc ctg      672
Glu Glu Glu Gly Glu His Thr Trp Arg Leu Pro Phe Asp Pro Ser Leu
    210                 215                 220
```

-continued

| | |
|---|---|
| aag gag gtc acc atc tca ttg agt ggg cca ggg cct gag att gaa gtc<br>Lys Glu Val Thr Ile Ser Leu Ser Gly Pro Gly Pro Glu Ile Glu Val<br>225                        230                     235                     240 | 720 |
| caa gat ccg ctg ggg agg atc ctg cag gag gac gag ggc ctc aac gtg<br>Gln Asp Pro Leu Gly Arg Ile Leu Gln Glu Asp Glu Gly Leu Asn Val<br>                     245                     250                     255 | 768 |
| ctt ctc aac atc cct gac tcg gcc aag gtc gta gcc ttt aag cct gag<br>Leu Leu Asn Ile Pro Asp Ser Ala Lys Val Val Ala Phe Lys Pro Glu<br>         260                     265                     270 | 816 |
| cat ccg ggg ctg tgg tcc atc aag gtc tat agc agt ggc cgc cat tca<br>His Pro Gly Leu Trp Ser Ile Lys Val Tyr Ser Ser Gly Arg His Ser<br>             275                     280                     285 | 864 |
| gtg agg atc aca ggc gtc agc aac att gac ttc cga gcc ggc ttc tcc<br>Val Arg Ile Thr Gly Val Ser Asn Ile Asp Phe Arg Ala Gly Phe Ser<br>290                        295                     300 | 912 |
| act cag ccc ttg ctg gac ctc aac cac acc ctc gag tgg ccc ttg caa<br>Thr Gln Pro Leu Leu Asp Leu Asn His Thr Leu Glu Trp Pro Leu Gln<br>305                        310                     315                     320 | 960 |
| gga gtc ccc atc tcc ctg gtg atc aat tcc acg ggc ctg aag gca ccc<br>Gly Val Pro Ile Ser Leu Val Ile Asn Ser Thr Gly Leu Lys Ala Pro<br>                     325                     330                     335 | 1008 |
| ggc cgc cta gac tcg gtg gag ctg gca caa agc tca ggg aag ccc ctc<br>Gly Arg Leu Asp Ser Val Glu Leu Ala Gln Ser Ser Gly Lys Pro Leu<br>         340                     345                     350 | 1056 |
| ctg act ctg ccc acg aag ccc ctc tcc aat ggc tcc acc cat cag ctg<br>Leu Thr Leu Pro Thr Lys Pro Leu Ser Asn Gly Ser Thr His Gln Leu<br>             355                     360                     365 | 1104 |
| tgg ggc ggg ccg ccc ttc cac acc ccc aag gag cgc ttc tac ctc aag<br>Trp Gly Gly Pro Pro Phe His Thr Pro Lys Glu Arg Phe Tyr Leu Lys<br>370                        375                     380 | 1152 |
| gtg aag ggc aag gac cat gag gga aac ccc ctc ctt cgt gtc tct gga<br>Val Lys Gly Lys Asp His Glu Gly Asn Pro Leu Leu Arg Val Ser Gly<br>385                        390                     395                     400 | 1200 |
| gtg tcc tac agt ggg gtg gcc cca ggc gct ccc ctc gtc agc atg gcc<br>Val Ser Tyr Ser Gly Val Ala Pro Gly Ala Pro Leu Val Ser Met Ala<br>                     405                     410                     415 | 1248 |
| ccc agg atc cat ggc tac ctg cac cag ccc ctg ctg gtc tcc tgc tcg<br>Pro Arg Ile His Gly Tyr Leu His Gln Pro Leu Leu Val Ser Cys Ser<br>             420                     425                     430 | 1296 |
| gtg cac agt gcc ctt ccc ttc cgg ctg cag ctg cgg cga ggt gaa gcc<br>Val His Ser Ala Leu Pro Phe Arg Leu Gln Leu Arg Arg Gly Glu Ala<br>             435                     440                     445 | 1344 |
| agg ctg ggc gaa gag agg cac ttt cag gag tcg gga aac agc agc tgg<br>Arg Leu Gly Glu Glu Arg His Phe Gln Glu Ser Gly Asn Ser Ser Trp<br>450                        455                     460 | 1392 |
| gag atc ctg cgg gcc tcc aag gcc gag gag ggc acg tac gag tgc aca<br>Glu Ile Leu Arg Ala Ser Lys Ala Glu Glu Gly Thr Tyr Glu Cys Thr<br>465                        470                     475                     480 | 1440 |
| gcc gtc agc agg gct ggg acc ggg cga gca aag gcc cag att gtt gtc<br>Ala Val Ser Arg Ala Gly Thr Gly Arg Ala Lys Ala Gln Ile Val Val<br>                     485                     490                     495 | 1488 |
| aca gac ccc ccg ccg cag ctg gtc cct gct ccc aac gtg acc gtg tcc<br>Thr Asp Pro Pro Pro Gln Leu Val Pro Ala Pro Asn Val Thr Val Ser<br>                     500                     505                     510 | 1536 |
| cca ggg gag act gcc gtc cta tcc tgc cgg gtc cta ggc gag gcc ccc<br>Pro Gly Glu Thr Ala Val Leu Ser Cys Arg Val Leu Gly Glu Ala Pro<br>             515                     520                     525 | 1584 |
| tac aac ctg acg tgg gtc cgg gac tgg cga gtc ctg ccg gcc tcg acg<br>Tyr Asn Leu Thr Trp Val Arg Asp Trp Arg Val Leu Pro Ala Ser Thr<br>530                        535                     540 | 1632 |

```
ggc cga gtt gcc cag ctg gct gac ctg tcc ctg gag atc agt ggc atc      1680
Gly Arg Val Ala Gln Leu Ala Asp Leu Ser Leu Glu Ile Ser Gly Ile
545                 550                 555                 560 atc ccc aca gac ggc ggg agg tac cag tgt gtg gcc agc aat gcc aat      1728
Ile Pro Thr Asp Gly Gly Arg Tyr Gln Cys Val Ala Ser Asn Ala Asn
                565                 570                 575 ggg gtc aca agg gca tcc gtc tgg ctc ctg gtg cga gag gcc cca cag      1776
Gly Val Thr Arg Ala Ser Val Trp Leu Leu Val Arg Glu Ala Pro Gln
            580                 585                 590 gtc agc atc cac acc agc tcc cag cac ttc tcc caa ggt gtg gag gtg      1824
Val Ser Ile His Thr Ser Ser Gln His Phe Ser Gln Gly Val Glu Val
        595                 600                 605 aag gtc agc tgc tca gcc tct gga tac ccc aca ccc cac atc tcc tgg      1872
Lys Val Ser Cys Ser Ala Ser Gly Tyr Pro Thr Pro His Ile Ser Trp
    610                 615                 620 agc cgt gag agc caa gcc cta caa gag gac agc aga atc cat gtg gac      1920
Ser Arg Glu Ser Gln Ala Leu Gln Glu Asp Ser Arg Ile His Val Asp
625                 630                 635                 640 gca cag gga acc ctg att att cag ggg gta gcc cca gag gat gct ggg      1968
Ala Gln Gly Thr Leu Ile Ile Gln Gly Val Ala Pro Glu Asp Ala Gly
                645                 650                 655 aat tac agc tgc cag gcg act aat gag gtt ggc act gac cag gag acg      2016
Asn Tyr Ser Cys Gln Ala Thr Asn Glu Val Gly Thr Asp Gln Glu Thr
            660                 665                 670 gtc acc ctc tac gac aca gac cca ccg tcg gtc tct gtc gac              2058
Val Thr Leu Tyr Asp Thr Asp Pro Pro Ser Val Ser Val Asp
        675                 680                 685

<210> SEQ ID NO 48
<211> LENGTH: 686
<212> TYPE: PRT
<213> ORGANISM: Homo sapiens

<400> SEQUENCE: 48

Lys Leu Val Ala Val Ala Gly Ala Pro Gly Thr Val Met Pro Pro Thr
1               5                   10                  15

Thr Gly Asp Ala Thr Leu Ala Phe Val Phe Asp Val Thr Gly Ser Met
            20                  25                  30

Trp Asp Glu Leu Met Gln Val Ile Asp Gly Ala Ser Arg Ile Leu Glu
        35                  40                  45

Arg Ser Leu Ser Arg Arg Ser Gln Ala Ile Ala Asn Tyr Ala Leu Val
    50                  55                  60

Pro Phe His Asp Pro Asp Ile Gly Pro Val Thr Leu Thr Ala Asp Pro
65                  70                  75                  80

Thr Val Phe Gln Arg Glu Leu Arg Glu Leu Tyr Val Gln Gly Gly Gly
                85                  90                  95

Asp Cys Pro Glu Met Ser Val Gly Ala Ile Lys Ala Val Glu Val
            100                 105                 110

Ala Asn Pro Gly Ser Phe Ile Tyr Val Phe Ser Asp Ala Arg Ala Lys
        115                 120                 125

Asp Tyr His Lys Lys Glu Glu Leu Leu Arg Leu Leu Gln Leu Lys Gln
    130                 135                 140

Ser Gln Val Val Phe Val Leu Thr Gly Asp Cys Gly Asp His Thr His
145                 150                 155                 160

Pro Gly Tyr Leu Ala Tyr Glu Glu Ile Ala Ala Thr Ser Ser Gly Gln
                165                 170                 175

Val Phe His Leu Asp Lys Gln Gln Val Thr Glu Val Leu Lys Trp Val
```

-continued

```
            180                 185                 190
Glu Ser Ala Ile Gln Ala Ser Lys Val His Leu Leu Ser Thr Asp His
            195                 200                 205
Glu Glu Glu Gly Glu His Thr Trp Arg Leu Pro Phe Asp Pro Ser Leu
210                 215                 220
Lys Glu Val Thr Ile Ser Leu Ser Gly Pro Gly Pro Glu Ile Glu Val
225                 230                 235                 240
Gln Asp Pro Leu Gly Arg Ile Leu Gln Glu Asp Gly Leu Asn Val
                    245                 250                 255
Leu Leu Asn Ile Pro Asp Ser Ala Lys Val Ala Phe Lys Pro Glu
                260                 265                 270
His Pro Gly Leu Trp Ser Ile Lys Val Tyr Ser Ser Gly Arg His Ser
                275                 280                 285
Val Arg Ile Thr Gly Val Ser Asn Ile Asp Phe Arg Ala Gly Phe Ser
290                 295                 300
Thr Gln Pro Leu Leu Asp Leu Asn His Thr Leu Glu Trp Pro Leu Gln
305                 310                 315                 320
Gly Val Pro Ile Ser Leu Val Ile Asn Ser Thr Gly Leu Lys Ala Pro
                325                 330                 335
Gly Arg Leu Asp Ser Val Glu Leu Ala Gln Ser Ser Gly Lys Pro Leu
                340                 345                 350
Leu Thr Leu Pro Thr Lys Pro Leu Ser Asn Gly Ser Thr His Gln Leu
                355                 360                 365
Trp Gly Gly Pro Pro Phe His Thr Pro Lys Glu Arg Phe Tyr Leu Lys
    370                 375                 380
Val Lys Gly Lys Asp His Glu Gly Asn Pro Leu Leu Arg Val Ser Gly
385                 390                 395                 400
Val Ser Tyr Ser Gly Val Ala Pro Gly Ala Pro Leu Val Ser Met Ala
                405                 410                 415
Pro Arg Ile His Gly Tyr Leu His Gln Pro Leu Leu Val Ser Cys Ser
                420                 425                 430
Val His Ser Ala Leu Pro Phe Arg Leu Gln Leu Arg Arg Gly Glu Ala
                435                 440                 445
Arg Leu Gly Glu Glu Arg His Phe Gln Glu Ser Gly Asn Ser Ser Trp
450                 455                 460
Glu Ile Leu Arg Ala Ser Lys Ala Glu Glu Gly Thr Tyr Glu Cys Thr
465                 470                 475                 480
Ala Val Ser Arg Ala Gly Thr Gly Arg Ala Lys Ala Gln Ile Val Val
                485                 490                 495
Thr Asp Pro Pro Pro Gln Leu Val Pro Ala Pro Asn Val Thr Val Ser
                500                 505                 510
Pro Gly Glu Thr Ala Val Leu Ser Cys Arg Val Leu Gly Glu Ala Pro
                515                 520                 525
Tyr Asn Leu Thr Trp Val Arg Asp Trp Arg Val Leu Pro Ala Ser Thr
                530                 535                 540
Gly Arg Val Ala Gln Leu Ala Asp Leu Ser Leu Glu Ile Ser Gly Ile
545                 550                 555                 560
Ile Pro Thr Asp Gly Gly Arg Tyr Gln Cys Val Ala Ser Asn Ala Asn
                    565                 570                 575
Gly Val Thr Arg Ala Ser Val Trp Leu Leu Val Arg Glu Ala Pro Gln
                580                 585                 590
Val Ser Ile His Thr Ser Ser Gln His Phe Ser Gln Gly Val Glu Val
                595                 600                 605
```

```
Lys Val Ser Cys Ser Ala Ser Gly Tyr Pro Thr Pro His Ile Ser Trp
    610                 615                 620
Ser Arg Glu Ser Gln Ala Leu Gln Glu Asp Ser Arg Ile His Val Asp
625                 630                 635                 640
Ala Gln Gly Thr Leu Ile Ile Gln Gly Val Ala Pro Glu Asp Ala Gly
                    645                 650                 655
Asn Tyr Ser Cys Gln Ala Thr Asn Glu Val Gly Thr Asp Gln Glu Thr
                660                 665                 670
Val Thr Leu Tyr Asp Thr Asp Pro Pro Ser Val Ser Val Asp
            675                 680                 685

<210> SEQ ID NO 49
<211> LENGTH: 2058
<212> TYPE: DNA
<213> ORGANISM: Homo sapiens
<220> FEATURE:
<221> NAME/KEY: CDS
<222> LOCATION: (1)..(2058)

<400> SEQUENCE: 49 aag ctt gtg gca gtg gcc ggg gcg ccc ggg acg gta atg ccc ccc acc      48
Lys Leu Val Ala Val Ala Gly Ala Pro Gly Thr Val Met Pro Pro Thr
  1               5                  10                  15 acg ggg gac gcc acc ctg gcc ttc gtc ttc gac gtc acc ggc tcc atg      96
Thr Gly Asp Ala Thr Leu Ala Phe Val Phe Asp Val Thr Gly Ser Met
             20                  25                  30 tgg gac gaa ctg atg cag gtg atc gat ggc gcc tcg cgc att ctg gaa     144
Trp Asp Glu Leu Met Gln Val Ile Asp Gly Ala Ser Arg Ile Leu Glu
         35                  40                  45 cgc agt ctg agc cgc cgc agc cag gcc atc gcc aac tac gcg ctg gtg     192
Arg Ser Leu Ser Arg Arg Ser Gln Ala Ile Ala Asn Tyr Ala Leu Val
     50                  55                  60 ccc ttc cac gac cca gat att ggc cca gtg acc ctc acg gcg gac ccc     240
Pro Phe His Asp Pro Asp Ile Gly Pro Val Thr Leu Thr Ala Asp Pro
 65                  70                  75                  80 aca gtg ttt cag agg gag ctg aga gaa ctc tac gtg cag gga ggt ggt     288
Thr Val Phe Gln Arg Glu Leu Arg Glu Leu Tyr Val Gln Gly Gly Gly
                 85                  90                  95 gac tgc ccg gag atg agt gtg ggg gcc att aag gct gcc gtg gag gtt     336
Asp Cys Pro Glu Met Ser Val Gly Ala Ile Lys Ala Ala Val Glu Val
            100                 105                 110 gcc aac ccc gga tcc ttc atc tac gtc ttt tcg gat gcc cgc gcc aaa     384
Ala Asn Pro Gly Ser Phe Ile Tyr Val Phe Ser Asp Ala Arg Ala Lys
        115                 120                 125 gac tat cac aag aag gaa gag ctg ctg cgg ctc ctg cag ctc aag caa     432
Asp Tyr His Lys Lys Glu Glu Leu Leu Arg Leu Leu Gln Leu Lys Gln
    130                 135                 140 tca cag gtg gtc ttt gtg ctg acg ggg gac tgt ggc gac cac acc cat     480
Ser Gln Val Val Phe Val Leu Thr Gly Asp Cys Gly Asp His Thr His
145                 150                 155                 160 cct ggc tac ctg gct tat gag gag atc gct gcc acc agc tct ggg cag     528
Pro Gly Tyr Leu Ala Tyr Glu Glu Ile Ala Ala Thr Ser Ser Gly Gln
                165                 170                 175 gtg ttc cac ctg gac aag cag caa gtg aca gag gtg ctg aag tgg gtg     576
Val Phe His Leu Asp Lys Gln Gln Val Thr Glu Val Leu Lys Trp Val
            180                 185                 190 gag tca gcg atc cag gcc tcc aag gtg cac ctg ctg tcc aca gac cac     624
Glu Ser Ala Ile Gln Ala Ser Lys Val His Leu Leu Ser Thr Asp His
        195                 200                 205
```

-continued

| | |
|---|---|
| gag gag gag ggg gag cac aca tgg aga ctc ccc ttt gac ccc agc ctg<br>Glu Glu Glu Gly Glu His Thr Trp Arg Leu Pro Phe Asp Pro Ser Leu<br>210                                   215                                220 | 672 |
| aag gag gtc acc atc tca ttg agt ggg cca ggg cct gag att gaa gtc<br>Lys Glu Val Thr Ile Ser Leu Ser Gly Pro Gly Pro Glu Ile Glu Val<br>225                                 230                         235                       240 | 720 |
| caa gat ccg ctg ggg agg atc ctg cag gag gac gag ggc ctc aac gtg<br>Gln Asp Pro Leu Gly Arg Ile Leu Gln Glu Asp Glu Gly Leu Asn Val<br>                          245                         250                       255 | 768 |
| ctt ctc aac atc cct gac tcg gcc aag gtc gta gcc ttt aag cct gag<br>Leu Leu Asn Ile Pro Asp Ser Ala Lys Val Val Ala Phe Lys Pro Glu<br>                 260                         265                       270 | 816 |
| cat ccg ggg ctg tgg tcc atc aag gtc tat agc agt ggc cgc cat tca<br>His Pro Gly Leu Trp Ser Ile Lys Val Tyr Ser Ser Gly Arg His Ser<br>              275                         280                       285 | 864 |
| gtg agg atc aca ggc gtc agc aac att gac ttc cga gcc ggc ttc tcc<br>Val Arg Ile Thr Gly Val Ser Asn Ile Asp Phe Arg Ala Gly Phe Ser<br>     290                       295                       300 | 912 |
| act cag ccc ttg ctg gac ctc aac cac acc ctc gag tgg ccc ttg caa<br>Thr Gln Pro Leu Leu Asp Leu Asn His Thr Leu Glu Trp Pro Leu Gln<br>305                                 310                         315                       320 | 960 |
| gga gtc ccc atc tcc ctg gtg atc aat tcc acg ggc ctg aag gca ccc<br>Gly Val Pro Ile Ser Leu Val Ile Asn Ser Thr Gly Leu Lys Ala Pro<br>                          325                         330                       335 | 1008 |
| ggc cgc cta gac tcg gtg gag ctg gca caa agc tca ggg aag ccc ctc<br>Gly Arg Leu Asp Ser Val Glu Leu Ala Gln Ser Ser Gly Lys Pro Leu<br>                 340                         345                       350 | 1056 |
| ctg act ctg ccc acg aag ccc ctc tcc aat ggc tcc acc cat cag ctg<br>Leu Thr Leu Pro Thr Lys Pro Leu Ser Asn Gly Ser Thr His Gln Leu<br>              355                         360                       365 | 1104 |
| tgg ggc ggg ccg ccc ttc cac acc ccc aag gag cgc ttc tac ctc aag<br>Trp Gly Gly Pro Pro Phe His Thr Pro Lys Glu Arg Phe Tyr Leu Lys<br>     370                       375                       380 | 1152 |
| gtg aag ggc aag gac cat gag gga aac ccc ctc ctt cgt gtc tct gga<br>Val Lys Gly Lys Asp His Glu Gly Asn Pro Leu Leu Arg Val Ser Gly<br>385                                 390                         395                       400 | 1200 |
| gtg tcc tac agt ggg gtg gcc cca ggc gct ccc ctc gtc agc atg gcc<br>Val Ser Tyr Ser Gly Val Ala Pro Gly Ala Pro Leu Val Ser Met Ala<br>                 405                         410                       415 | 1248 |
| ccc agg atc cat ggc tac ctg cac cag ccc ctg ctg gtc tcc tgc tcg<br>Pro Arg Ile His Gly Tyr Leu His Gln Pro Leu Leu Val Ser Cys Ser<br>              420                         425                       430 | 1296 |
| gtg cac agt gcc ctt ccc ttc cgg ctg cag ctg cgg cga ggt gaa gcc<br>Val His Ser Ala Leu Pro Phe Arg Leu Gln Leu Arg Arg Gly Glu Ala<br>            435                         440                       445 | 1344 |
| agg ctg ggc gaa gag agg cac ttt cag gag tcg gga aac agc agc tgg<br>Arg Leu Gly Glu Glu Arg His Phe Gln Glu Ser Gly Asn Ser Ser Trp<br>450                                 455                         460 | 1392 |
| gag atc ctg cgg gcc tcc aag gcc gag gag ggc acg tac gag tgc aca<br>Glu Ile Leu Arg Ala Ser Lys Ala Glu Glu Gly Thr Tyr Glu Cys Thr<br>465                                 470                         475                       480 | 1440 |
| gcc gtc agc agg gct ggg acc ggg cga gca aag gcc cag att gtt gtc<br>Ala Val Ser Arg Ala Gly Thr Gly Arg Ala Lys Ala Gln Ile Val Val<br>                 485                         490                       495 | 1488 |
| aca gac ccc ccg ccg cag ctg gtc cct gct ccc aac gtg acc gtg tcc<br>Thr Asp Pro Pro Pro Gln Leu Val Pro Ala Pro Asn Val Thr Val Ser<br>              500                         505                       510 | 1536 |
| cca ggg gag gct gcc gtc cta tcc tgc cgg gtc cta ggc gag gcc ccc<br>Pro Gly Glu Ala Ala Val Leu Ser Cys Arg Val Leu Gly Glu Ala Pro<br>     515                       520                       525 | 1584 |

```
tac aac ctg acg tgg gtc cgg gac tgg cga gtc ctg ccg gcc tcg acg      1632
Tyr Asn Leu Thr Trp Val Arg Asp Trp Arg Val Leu Pro Ala Ser Thr
530                 535                 540 ggc cga gtt gcc cag ctg gct gac ctg tcc ctg gag atc agt ggc atc      1680
Gly Arg Val Ala Gln Leu Ala Asp Leu Ser Leu Glu Ile Ser Gly Ile
545                 550                 555                 560 atc ccc aca gac ggc ggg agg tac cag tgt gtg gcc agc aat gcc aat      1728
Ile Pro Thr Asp Gly Gly Arg Tyr Gln Cys Val Ala Ser Asn Ala Asn
                565                 570                 575 ggg gtc aca agg gca tcc gtc tgg ctc ctg gtg cga gag gcc cca cag      1776
Gly Val Thr Arg Ala Ser Val Trp Leu Leu Val Arg Glu Ala Pro Gln
            580                 585                 590 gtc agc atc cac acc agc tcc cag cac ttc tcc caa ggt gtg gag gtg      1824
Val Ser Ile His Thr Ser Ser Gln His Phe Ser Gln Gly Val Glu Val
        595                 600                 605 aag gtc agc tgc tca gcc tct gga tac ccc aca ccc cac atc tcc tgg      1872
Lys Val Ser Cys Ser Ala Ser Gly Tyr Pro Thr Pro His Ile Ser Trp
610                 615                 620 agc cgt gag agc caa gcc cta caa gag gac agc aga atc cat gtg gac      1920
Ser Arg Glu Ser Gln Ala Leu Gln Glu Asp Ser Arg Ile His Val Asp
625                 630                 635                 640 gca cag gga acc ctg att att cag ggg gta gcc cca gag gat gct ggg      1968
Ala Gln Gly Thr Leu Ile Ile Gln Gly Val Ala Pro Glu Asp Ala Gly
                645                 650                 655 aat tac agc tgc cag gcg act aat gag gtt ggc act gac cag gag acg      2016
Asn Tyr Ser Cys Gln Ala Thr Asn Glu Val Gly Thr Asp Gln Glu Thr
            660                 665                 670 gtc acc ctc tac tac aca gac cca ccg tcg gtc tct gtc gac              2058
Val Thr Leu Tyr Tyr Thr Asp Pro Pro Ser Val Ser Val Asp
        675                 680                 685

<210> SEQ ID NO 50
<211> LENGTH: 686
<212> TYPE: PRT
<213> ORGANISM: Homo sapiens

<400> SEQUENCE: 50

Lys Leu Val Ala Val Ala Gly Ala Pro Gly Thr Val Met Pro Pro Thr
1               5                   10                  15

Thr Gly Asp Ala Thr Leu Ala Phe Val Phe Asp Val Thr Gly Ser Met
            20                  25                  30

Trp Asp Glu Leu Met Gln Val Ile Asp Gly Ala Ser Arg Ile Leu Glu
        35                  40                  45

Arg Ser Leu Ser Arg Arg Ser Gln Ala Ile Ala Asn Tyr Ala Leu Val
    50                  55                  60

Pro Phe His Asp Pro Asp Ile Gly Pro Val Thr Leu Thr Ala Asp Pro
65                  70                  75                  80

Thr Val Phe Gln Arg Glu Leu Arg Glu Leu Tyr Val Gln Gly Gly Gly
                85                  90                  95

Asp Cys Pro Glu Met Ser Val Gly Ala Ile Lys Ala Val Glu Val
            100                 105                 110

Ala Asn Pro Gly Ser Phe Ile Tyr Val Phe Ser Asp Ala Arg Ala Lys
        115                 120                 125

Asp Tyr His Lys Lys Glu Glu Leu Leu Arg Leu Leu Gln Leu Lys Gln
    130                 135                 140

Ser Gln Val Val Phe Val Leu Thr Gly Asp Cys Gly Asp His Thr His
145                 150                 155                 160
```

-continued

```
Pro Gly Tyr Leu Ala Tyr Glu Ile Ala Ala Thr Ser Ser Gly Gln
            165                 170                 175

Val Phe His Leu Asp Lys Gln Gln Val Thr Glu Val Leu Lys Trp Val
        180                 185                 190

Glu Ser Ala Ile Gln Ala Ser Lys Val His Leu Leu Ser Thr Asp His
            195                 200                 205

Glu Glu Glu Gly Glu His Thr Trp Arg Leu Pro Phe Asp Pro Ser Leu
    210                 215                 220

Lys Glu Val Thr Ile Ser Leu Ser Gly Pro Gly Pro Glu Ile Glu Val
225                 230                 235                 240

Gln Asp Pro Leu Gly Arg Ile Leu Gln Glu Asp Gly Leu Asn Val
            245                 250                 255

Leu Leu Asn Ile Pro Asp Ser Ala Lys Val Val Ala Phe Lys Pro Glu
            260                 265                 270

His Pro Gly Leu Trp Ser Ile Lys Val Tyr Ser Ser Gly Arg His Ser
            275                 280                 285

Val Arg Ile Thr Gly Val Ser Asn Ile Asp Phe Arg Ala Gly Phe Ser
        290                 295                 300

Thr Gln Pro Leu Leu Asp Leu Asn His Thr Leu Glu Trp Pro Leu Gln
305                 310                 315                 320

Gly Val Pro Ile Ser Leu Val Ile Asn Ser Thr Gly Leu Lys Ala Pro
                325                 330                 335

Gly Arg Leu Asp Ser Val Glu Leu Ala Gln Ser Ser Gly Lys Pro Leu
            340                 345                 350

Leu Thr Leu Pro Thr Lys Pro Leu Ser Asn Gly Ser Thr His Gln Leu
        355                 360                 365

Trp Gly Gly Pro Pro Phe His Thr Pro Lys Glu Arg Phe Tyr Leu Lys
    370                 375                 380

Val Lys Gly Lys Asp His Glu Gly Asn Pro Leu Leu Arg Val Ser Gly
385                 390                 395                 400

Val Ser Tyr Ser Gly Val Ala Pro Gly Ala Pro Leu Val Ser Met Ala
                405                 410                 415

Pro Arg Ile His Gly Tyr Leu His Gln Pro Leu Leu Val Ser Cys Ser
            420                 425                 430

Val His Ser Ala Leu Pro Phe Arg Leu Gln Leu Arg Arg Gly Glu Ala
        435                 440                 445

Arg Leu Gly Glu Glu Arg His Phe Gln Glu Ser Gly Asn Ser Ser Trp
450                 455                 460

Glu Ile Leu Arg Ala Ser Lys Ala Glu Glu Gly Thr Tyr Glu Cys Thr
465                 470                 475                 480

Ala Val Ser Arg Ala Gly Thr Gly Arg Ala Lys Ala Gln Ile Val Val
                485                 490                 495

Thr Asp Pro Pro Gln Leu Val Pro Ala Pro Asn Val Thr Val Ser
            500                 505                 510

Pro Gly Glu Ala Ala Val Leu Ser Cys Arg Val Leu Gly Glu Ala Pro
        515                 520                 525

Tyr Asn Leu Thr Trp Val Arg Asp Trp Arg Val Leu Pro Ala Ser Thr
    530                 535                 540

Gly Arg Val Ala Gln Leu Ala Asp Leu Ser Leu Glu Ile Ser Gly Ile
545                 550                 555                 560

Ile Pro Thr Asp Gly Arg Tyr Gln Cys Val Ala Ser Asn Ala Asn
            565                 570                 575

Gly Val Thr Arg Ala Ser Val Trp Leu Leu Val Arg Glu Ala Pro Gln
```

```
                  580                 585                 590
Val Ser Ile His Thr Ser Ser Gln His Phe Ser Gln Gly Val Glu Val
            595                 600                 605

Lys Val Ser Cys Ser Ala Ser Gly Tyr Pro Thr Pro His Ile Ser Trp
610                 615                 620

Ser Arg Glu Ser Gln Ala Leu Gln Glu Asp Ser Arg Ile His Val Asp
625                 630                 635                 640

Ala Gln Gly Thr Leu Ile Ile Gln Gly Val Ala Pro Glu Asp Ala Gly
            645                 650                 655

Asn Tyr Ser Cys Gln Ala Thr Asn Glu Val Gly Thr Asp Gln Glu Thr
                660                 665                 670

Val Thr Leu Tyr Tyr Thr Asp Pro Pro Ser Val Ser Val Asp
            675                 680                 685

<210> SEQ ID NO 51
<211> LENGTH: 2058
<212> TYPE: DNA
<213> ORGANISM: Homo sapiens
<220> FEATURE:
<221> NAME/KEY: CDS
<222> LOCATION: (1)..(2058)

<400> SEQUENCE: 51 aag ctt gtg gca gtg gcc ggg gcg ccc ggg acg gta atg ccc ccc acc     48
Lys Leu Val Ala Val Ala Gly Ala Pro Gly Thr Val Met Pro Pro Thr
 1               5                  10                  15 acg ggg gac gcc acc ctg gcc ttc gtc ttc gac gtc acc ggc tcc atg     96
Thr Gly Asp Ala Thr Leu Ala Phe Val Phe Asp Val Thr Gly Ser Met
                20                  25                  30 tgg gac gaa ctg atg cag gtg atc gat ggc gcc tcg cgc att ctg gaa    144
Trp Asp Glu Leu Met Gln Val Ile Asp Gly Ala Ser Arg Ile Leu Glu
            35                  40                  45 cgc agt ctg agc cgc cgc agc cag gcc atc gcc aac tac gcg ctg gtg    192
Arg Ser Leu Ser Arg Arg Ser Gln Ala Ile Ala Asn Tyr Ala Leu Val
        50                  55                  60 ccc ttc cac gac cca gat att ggc cca gtg acc ctc acg gcg gac ccc    240
Pro Phe His Asp Pro Asp Ile Gly Pro Val Thr Leu Thr Ala Asp Pro
65                  70                  75                  80 aca gtg ttt cag agg gag ctg aga gaa ctc tac gtg cag gga ggt ggt    288
Thr Val Phe Gln Arg Glu Leu Arg Glu Leu Tyr Val Gln Gly Gly Gly
                85                  90                  95 gac tgc ccg gag atg agt gtg ggg gcc att aag gct gcc gtg gag gtt    336
Asp Cys Pro Glu Met Ser Val Gly Ala Ile Lys Ala Ala Val Glu Val
            100                 105                 110 gcc aac ccc gga tcc ttc atc tac gtc ttt tcg gat gcc cgc gcc aaa    384
Ala Asn Pro Gly Ser Phe Ile Tyr Val Phe Ser Asp Ala Arg Ala Lys
        115                 120                 125 gac tat cac aag aag gaa gag ctg ctg cgg ctc ctg cag ctc aag caa    432
Asp Tyr His Lys Lys Glu Glu Leu Leu Arg Leu Leu Gln Leu Lys Gln
    130                 135                 140 tca cag gtg gtc ttt gtg ctg acg ggg gac tgt ggc gac cac acc cat    480
Ser Gln Val Val Phe Val Leu Thr Gly Asp Cys Gly Asp His Thr His
145                 150                 155                 160 cct ggc tac ctg gct tat gag gag atc gct gcc acc agc tct ggg cag    528
Pro Gly Tyr Leu Ala Tyr Glu Glu Ile Ala Ala Thr Ser Ser Gly Gln
                165                 170                 175 gtg ttc cac ctg gac aag cag caa gtg aca gag gtg ctg aag tgg gtg    576
Val Phe His Leu Asp Lys Gln Gln Val Thr Glu Val Leu Lys Trp Val
            180                 185                 190
```

```
                                                         -continued gag tca gcg atc cag gcc tcc aag gtg cac ctg ctg tcc aca gac cac      624
Glu Ser Ala Ile Gln Ala Ser Lys Val His Leu Leu Ser Thr Asp His
        195                 200                 205 gag gag gag ggg gag cac aca tgg aga ctc ccc ttt gac ccc agc ctg      672
Glu Glu Glu Gly Glu His Thr Trp Arg Leu Pro Phe Asp Pro Ser Leu
    210                 215                 220 aag gag gtc acc atc tca ttg agt ggg cca ggg cct gag att gaa gtc      720
Lys Glu Val Thr Ile Ser Leu Ser Gly Pro Gly Pro Glu Ile Glu Val
225                 230                 235                 240 caa gat ccg ctg ggg agg atc ctg cag gag gac gag ggc ctc aac gtg      768
Gln Asp Pro Leu Gly Arg Ile Leu Gln Glu Asp Glu Gly Leu Asn Val
                245                 250                 255 ctt ctc aac atc cct gac tcg gcc aag gtc gta gcc ttt aag cct gag      816
Leu Leu Asn Ile Pro Asp Ser Ala Lys Val Val Ala Phe Lys Pro Glu
            260                 265                 270 cat ccg ggg ctg tgg tcc atc aag gtc tat agc agt ggc cgc cat tca      864
His Pro Gly Leu Trp Ser Ile Lys Val Tyr Ser Ser Gly Arg His Ser
        275                 280                 285 gtg agg atc aca ggc gtc agc aac att gac ttc cga gcc ggc ttc tcc      912
Val Arg Ile Thr Gly Val Ser Asn Ile Asp Phe Arg Ala Gly Phe Ser
    290                 295                 300 act cag ccc ttg ctg gac ctc aac cac acc ctc gag tgg ccc ttg caa      960
Thr Gln Pro Leu Leu Asp Leu Asn His Thr Leu Glu Trp Pro Leu Gln
305                 310                 315                 320 gga gtc ccc atc tcc ctg gtg atc aat tcc acg ggc ctg aag gca ccc     1008
Gly Val Pro Ile Ser Leu Val Ile Asn Ser Thr Gly Leu Lys Ala Pro
                325                 330                 335 ggc cgc cta gac tcg gtg gag ctg gca caa agc tca ggg aag ccc ctc     1056
Gly Arg Leu Asp Ser Val Glu Leu Ala Gln Ser Ser Gly Lys Pro Leu
            340                 345                 350 ctg act ctg ccc acg aag ccc ctc tcc aat ggc tcc acc cat cag ctg     1104
Leu Thr Leu Pro Thr Lys Pro Leu Ser Asn Gly Ser Thr His Gln Leu
        355                 360                 365 tgg ggc ggg ccg ccc ttc cac acc ccc aag gag cgc ttc tac ctc aag     1152
Trp Gly Gly Pro Pro Phe His Thr Pro Lys Glu Arg Phe Tyr Leu Lys
    370                 375                 380 gtg aag ggc aag gac cat gag gga aac ccc ctc ctt cgt gtc tct gga     1200
Val Lys Gly Lys Asp His Glu Gly Asn Pro Leu Leu Arg Val Ser Gly
385                 390                 395                 400 gtg tcc tac agt ggg gtg gcc cca ggc gct ccc ctc gtc agc atg gcc     1248
Val Ser Tyr Ser Gly Val Ala Pro Gly Ala Pro Leu Val Ser Met Ala
                405                 410                 415 ccc agg atc cat ggc tac ctg cac cag ccc ctg ctg gtc tcc tgc tcg     1296
Pro Arg Ile His Gly Tyr Leu His Gln Pro Leu Leu Val Ser Cys Ser
            420                 425                 430 gtg cac agt gcc ctt ccc ttc cgg ctg cag ctg cgg cga ggt gaa gcc     1344
Val His Ser Ala Leu Pro Phe Arg Leu Gln Leu Arg Arg Gly Glu Ala
        435                 440                 445 agg ctg ggc gaa gag agg cac ttt cag gag tcg gga aac agc agc tgg     1392
Arg Leu Gly Glu Glu Arg His Phe Gln Glu Ser Gly Asn Ser Ser Trp
    450                 455                 460 gag atc ctg cgg gcc tcc aag gcc gag gag ggc acg tac gag tgc aca     1440
Glu Ile Leu Arg Ala Ser Lys Ala Glu Glu Gly Thr Tyr Glu Cys Thr
465                 470                 475                 480 gcc gtc agc agg gct ggg acc ggg cga gca aag gcc cag att gtt gtc     1488
Ala Val Ser Arg Ala Gly Thr Gly Arg Ala Lys Ala Gln Ile Val Val
                485                 490                 495 aca gac ccc ccg ccg cag ctg gtc cct gct ccc aac gtg acc gtg tcc     1536
Thr Asp Pro Pro Pro Gln Leu Val Pro Ala Pro Asn Val Thr Val Ser
            500                 505                 510
```

```
cca ggg gag act gcc gtc cta tcc tgc cgg gtc cta ggc gag gcc ccc      1584
Pro Gly Glu Thr Ala Val Leu Ser Cys Arg Val Leu Gly Glu Ala Pro
        515                 520                 525 tac aac ctg acg tgg gtc cgg gac tgg cga gtc ctg ccg gcc tcg acg      1632
Tyr Asn Leu Thr Trp Val Arg Asp Trp Arg Val Leu Pro Ala Ser Thr
530                 535                 540 ggc cga gtt gcc cag ctg gct gac ctg tcc ctg gag atc agt ggc atc      1680
Gly Arg Val Ala Gln Leu Ala Asp Leu Ser Leu Glu Ile Ser Gly Ile
545                 550                 555                 560 atc ccc aca gac ggc ggg agg tac cag tgt gtg gcc agc aat gcc aat      1728
Ile Pro Thr Asp Gly Gly Arg Tyr Gln Cys Val Ala Ser Asn Ala Asn
                565                 570                 575 ggg gtc aca agg aca tcc gtc tgg ctc ctg gtg cga gag gcc cca cag      1776
Gly Val Thr Arg Thr Ser Val Trp Leu Leu Val Arg Glu Ala Pro Gln
            580                 585                 590 gtc agc atc cac acc agc tcc cag cac ttc tcc caa ggt gtg gag gtg      1824
Val Ser Ile His Thr Ser Ser Gln His Phe Ser Gln Gly Val Glu Val
        595                 600                 605 aag gtc agc tgc tca gcc tct gga tac ccc aca ccc cac atc tcc tgg      1872
Lys Val Ser Cys Ser Ala Ser Gly Tyr Pro Thr Pro His Ile Ser Trp
610                 615                 620 agc cgt gag agc caa gcc cta caa gag gac agc aga atc cat gtg gac      1920
Ser Arg Glu Ser Gln Ala Leu Gln Glu Asp Ser Arg Ile His Val Asp
625                 630                 635                 640 gca cag gga acc ctg att att cag ggg gta gcc cca gag gat gct ggg      1968
Ala Gln Gly Thr Leu Ile Ile Gln Gly Val Ala Pro Glu Asp Ala Gly
                645                 650                 655 aat tac agc tgc cag gcg act aat gag gtt ggc act gac cag gag acg      2016
Asn Tyr Ser Cys Gln Ala Thr Asn Glu Val Gly Thr Asp Gln Glu Thr
            660                 665                 670 gtc acc ctc tac tac aca gac cca ccg tcg gtc tct gtc gac              2058
Val Thr Leu Tyr Tyr Thr Asp Pro Pro Ser Val Ser Val Asp
        675                 680                 685

<210> SEQ ID NO 52
<211> LENGTH: 686
<212> TYPE: PRT
<213> ORGANISM: Homo sapiens

<400> SEQUENCE: 52

Lys Leu Val Ala Val Ala Gly Ala Pro Gly Thr Val Met Pro Pro Thr
 1               5                  10                  15

Thr Gly Asp Ala Thr Leu Ala Phe Val Phe Asp Val Thr Gly Ser Met
            20                  25                  30

Trp Asp Glu Leu Met Gln Val Ile Asp Gly Ala Ser Arg Ile Leu Glu
        35                  40                  45

Arg Ser Leu Ser Arg Arg Ser Gln Ala Ile Ala Asn Tyr Ala Leu Val
    50                  55                  60

Pro Phe His Asp Pro Asp Ile Gly Pro Val Thr Leu Thr Ala Asp Pro
65                  70                  75                  80

Thr Val Phe Gln Arg Glu Leu Arg Glu Leu Tyr Val Gln Gly Gly Gly
                85                  90                  95

Asp Cys Pro Glu Met Ser Val Gly Ala Ile Lys Ala Val Glu Val
            100                 105                 110

Ala Asn Pro Gly Ser Phe Ile Tyr Val Phe Ser Asp Ala Arg Ala Lys
        115                 120                 125

Asp Tyr His Lys Lys Glu Glu Leu Leu Arg Leu Leu Gln Leu Lys Gln
    130                 135                 140
```

-continued

```
Ser Gln Val Val Phe Val Leu Thr Gly Asp Cys Gly Asp His Thr His
145                 150                 155                 160

Pro Gly Tyr Leu Ala Tyr Glu Ile Ala Ala Thr Ser Ser Gly Gln
            165                 170                 175

Val Phe His Leu Asp Lys Gln Val Thr Glu Val Leu Lys Trp Val
        180                 185                 190

Glu Ser Ala Ile Gln Ala Ser Lys Val His Leu Leu Ser Thr Asp His
    195                 200                 205

Glu Glu Glu Gly Glu His Thr Trp Arg Leu Pro Phe Asp Pro Ser Leu
210                 215                 220

Lys Glu Val Thr Ile Ser Leu Ser Gly Pro Gly Pro Glu Ile Glu Val
225                 230                 235                 240

Gln Asp Pro Leu Gly Arg Ile Leu Gln Glu Asp Gly Leu Asn Val
            245                 250                 255

Leu Leu Asn Ile Pro Asp Ser Ala Lys Val Val Ala Phe Lys Pro Glu
            260                 265                 270

His Pro Gly Leu Trp Ser Ile Lys Val Tyr Ser Ser Gly Arg His Ser
        275                 280                 285

Val Arg Ile Thr Gly Val Ser Asn Ile Asp Phe Arg Ala Gly Phe Ser
    290                 295                 300

Thr Gln Pro Leu Leu Asp Leu Asn His Thr Leu Glu Trp Pro Leu Gln
305                 310                 315                 320

Gly Val Pro Ile Ser Leu Val Ile Asn Ser Thr Gly Leu Lys Ala Pro
            325                 330                 335

Gly Arg Leu Asp Ser Val Glu Leu Ala Gln Ser Ser Gly Lys Pro Leu
            340                 345                 350

Leu Thr Leu Pro Thr Lys Pro Leu Ser Asn Gly Ser Thr His Gln Leu
        355                 360                 365

Trp Gly Gly Pro Pro Phe His Thr Pro Lys Glu Arg Phe Tyr Leu Lys
    370                 375                 380

Val Lys Gly Lys Asp His Glu Gly Asn Pro Leu Leu Arg Val Ser Gly
385                 390                 395                 400

Val Ser Tyr Ser Gly Val Ala Pro Gly Ala Pro Leu Val Ser Met Ala
            405                 410                 415

Pro Arg Ile His Gly Tyr Leu His Gln Pro Leu Leu Val Ser Cys Ser
            420                 425                 430

Val His Ser Ala Leu Pro Phe Arg Leu Gln Leu Arg Arg Gly Glu Ala
        435                 440                 445

Arg Leu Gly Glu Glu Arg His Phe Gln Glu Ser Gly Asn Ser Ser Trp
    450                 455                 460

Glu Ile Leu Arg Ala Ser Lys Ala Glu Glu Gly Thr Tyr Glu Cys Thr
465                 470                 475                 480

Ala Val Ser Arg Ala Gly Thr Gly Arg Ala Lys Ala Gln Ile Val Val
            485                 490                 495

Thr Asp Pro Pro Gln Leu Val Pro Ala Pro Asn Val Thr Val Ser
            500                 505                 510

Pro Gly Glu Thr Ala Val Leu Ser Cys Arg Val Leu Gly Glu Ala Pro
        515                 520                 525

Tyr Asn Leu Thr Trp Val Arg Asp Trp Arg Val Leu Pro Ala Ser Thr
    530                 535                 540

Gly Arg Val Ala Gln Leu Ala Asp Leu Ser Leu Glu Ile Ser Gly Ile
545                 550                 555                 560
```

```
Ile Pro Thr Asp Gly Gly Arg Tyr Gln Cys Val Ala Ser Asn Ala Asn
            565                 570                 575

Gly Val Thr Arg Thr Ser Val Trp Leu Leu Val Arg Glu Ala Pro Gln
        580                 585                 590

Val Ser Ile His Thr Ser Ser Gln His Phe Ser Gln Gly Val Glu Val
            595                 600                 605

Lys Val Ser Cys Ser Ala Ser Gly Tyr Pro Thr Pro His Ile Ser Trp
    610                 615                 620

Ser Arg Glu Ser Gln Ala Leu Gln Glu Asp Ser Arg Ile His Val Asp
625                 630                 635                 640

Ala Gln Gly Thr Leu Ile Ile Gln Gly Val Ala Pro Glu Asp Ala Gly
                645                 650                 655

Asn Tyr Ser Cys Gln Ala Thr Asn Glu Val Gly Thr Asp Gln Glu Thr
            660                 665                 670

Val Thr Leu Tyr Tyr Thr Asp Pro Pro Ser Val Ser Val Asp
        675                 680                 685

<210> SEQ ID NO 53
<211> LENGTH: 621
<212> TYPE: DNA
<213> ORGANISM: Homo sapiens
<220> FEATURE:
<221> NAME/KEY: CDS
<222> LOCATION: (4)..(598)

<400> SEQUENCE: 53 atc atg ccc cta ggt ctc ctg tgg ctg ggc cta gcc ctg ttg ggg gct      48
    Met Pro Leu Gly Leu Leu Trp Leu Gly Leu Ala Leu Leu Gly Ala
    1               5                   10                  15 ctg cat gcc cag gcc cag gac tcc acc tca gac ctg atc cca gcc cca      96
Leu His Ala Gln Ala Gln Asp Ser Thr Ser Asp Leu Ile Pro Ala Pro
                20                  25                  30 cct ctg agc aag gtc cct ctg cag cag aac ttc cag gac aac caa ttc     144
Pro Leu Ser Lys Val Pro Leu Gln Gln Asn Phe Gln Asp Asn Gln Phe
            35                  40                  45 cag ggg aag tgg tat gtg gta ggc ctg gca ggg aat gca att ctc aga     192
Gln Gly Lys Trp Tyr Val Val Gly Leu Ala Gly Asn Ala Ile Leu Arg
        50                  55                  60 gaa gac aaa gac ccg caa aag atg tat gcc acc atc tat gag ctg aaa     240
Glu Asp Lys Asp Pro Gln Lys Met Tyr Ala Thr Ile Tyr Glu Leu Lys
65                  70                  75 gaa gac aag agc tac aat gtc acc tcc gtc ctg ttt agg aaa aag aag     288
Glu Asp Lys Ser Tyr Asn Val Thr Ser Val Leu Phe Arg Lys Lys Lys
80                  85                  90                  95 tgt gac tac tgg atc agg act ttt gtt cca ggt tgc cag ccc ggc gag     336
Cys Asp Tyr Trp Ile Arg Thr Phe Val Pro Gly Cys Gln Pro Gly Glu
                100                 105                 110 ttc acg ctg ggc aac att aag agt tac cct gga tta acg agt tac ctc     384
Phe Thr Leu Gly Asn Ile Lys Ser Tyr Pro Gly Leu Thr Ser Tyr Leu
            115                 120                 125 gtc cga gtg gtg agc acc aac tac aac cag cat gct atg gtg ttc ttc     432
Val Arg Val Val Ser Thr Asn Tyr Asn Gln His Ala Met Val Phe Phe
        130                 135                 140 aag aaa gtt tct caa aac agg gag tac ttc aag atc acc ctc tac ggt     480
Lys Lys Val Ser Gln Asn Arg Glu Tyr Phe Lys Ile Thr Leu Tyr Gly
145                 150                 155 aga acc aag gag ctg act tcg gaa cta aag gag aac ttc atc cgc ttc     528
Arg Thr Lys Glu Leu Thr Ser Glu Leu Lys Glu Asn Phe Ile Arg Phe
160                 165                 170                 175
```

| | | |
|---|---|---|
| tcc aaa tct ctg ggc ctc cct gaa aac cac atc gtc ttc cct gtc cca<br>Ser Lys Ser Leu Gly Leu Pro Glu Asn His Ile Val Phe Pro Val Pro<br>180 185 190 | | 576 |
| atc ggt aat ggc cag tct gga tgaggggacg gggacatggg gact<br>Ile Gly Asn Gly Gln Ser Gly<br>195 | | 621 |

<210> SEQ ID NO 54
<211> LENGTH: 198
<212> TYPE: PRT
<213> ORGANISM: Homo sapiens

<400> SEQUENCE: 54

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro
            20                  25                  30

Leu Ser Lys Val Pro Leu Gln Gln Asn Phe Gln Asp Asn Gln Phe
        35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
    130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Gly Asn Gly Gln Ser Gly
        195

<210> SEQ ID NO 55
<211> LENGTH: 609
<212> TYPE: DNA
<213> ORGANISM: Homo sapiens
<220> FEATURE:
<221> NAME/KEY: CDS
<222> LOCATION: (4)..(598)

<400> SEQUENCE: 55

| | | |
|---|---|---|
| atc atg ccc cta ggt ctc ctg tgg ctg ggc cta gcc ctg ttg ggg gct<br>    Met Pro Leu Gly Leu Leu Trp Leu Gly Leu Ala Leu Leu Gly Ala<br>    1               5                   10                  15 | | 48 |
| ctg cat gcc cag gcc cag gac tcc acc tca gac ctg atc cca gcc cca<br>Leu His Ala Gln Ala Gln Asp Ser Thr Ser Asp Leu Ile Pro Ala Pro<br>            20                  25                  30 | | 96 |
| cct ctg agc aag gtc cct ctg cag cag aac ttc cag gac aac caa ttc<br>Pro Leu Ser Lys Val Pro Leu Gln Gln Asn Phe Gln Asp Asn Gln Phe<br>        35                  40                  45 | | 144 |
| cag ggg aag tgg tat gtg gta ggc ctg gca ggg aat gca att ctc aga<br> | | 192 |

```
Gln Gly Lys Trp Tyr Val Val Gly Leu Ala Gly Asn Ala Ile Leu Arg
         50                  55                  60 gaa gac aaa gac ccg caa aag atg tat gcc acc atc tat gag ctg aaa      240
Glu Asp Lys Asp Pro Gln Lys Met Tyr Ala Thr Ile Tyr Glu Leu Lys
 65                  70                  75 gaa gac aag agc tac aat gtc acc tcc gtc ctg ttt agg aaa aag aag      288
Glu Asp Lys Ser Tyr Asn Val Thr Ser Val Leu Phe Arg Lys Lys Lys
 80                  85                  90                  95 tgt gac tac tgg atc agg act ttt gtt cca ggt tgc cag ccc ggc gag      336
Cys Asp Tyr Trp Ile Arg Thr Phe Val Pro Gly Cys Gln Pro Gly Glu
                100                 105                 110 ttc acg ctg ggc aac att aag agt tac cct gga tta acg agt tac ctc      384
Phe Thr Leu Gly Asn Ile Lys Ser Tyr Pro Gly Leu Thr Ser Tyr Leu
            115                 120                 125 gtc cga gtg gtg agc acc aac tac aac cag cat gct atg gtg ttc ttc      432
Val Arg Val Val Ser Thr Asn Tyr Asn Gln His Ala Met Val Phe Phe
        130                 135                 140 aag aaa gtt tct caa aac agg gag tac ttc aag atc acc ctc tac ggg      480
Lys Lys Val Ser Gln Asn Arg Glu Tyr Phe Lys Ile Thr Leu Tyr Gly
    145                 150                 155 aga acc aag gag ctg act tcg gaa cta aag gag aac ttc atc cgc ttc      528
Arg Thr Lys Glu Leu Thr Ser Glu Leu Lys Glu Asn Phe Ile Arg Phe
160                 165                 170                 175 tcc aaa tct ctg ggc ctc cct gaa aac cac atc gtc ttc cct gtc cca      576
Ser Lys Ser Leu Gly Leu Pro Glu Asn His Ile Val Phe Pro Val Pro
                180                 185                 190 atc ggt aat ggc cag tct gga tgaggggacg gg                            609
Ile Gly Asn Gly Gln Ser Gly
                195

<210> SEQ ID NO 56
<211> LENGTH: 198
<212> TYPE: PRT
<213> ORGANISM: Homo sapiens

<400> SEQUENCE: 56

Met Pro Leu Gly Leu Leu Trp Leu Gly Leu Ala Leu Leu Gly Ala Leu
 1               5                  10                  15

His Ala Gln Ala Gln Asp Ser Thr Ser Asp Leu Ile Pro Ala Pro Pro
                20                  25                  30

Leu Ser Lys Val Pro Leu Gln Gln Asn Phe Gln Asp Asn Gln Phe Gln
            35                  40                  45

Gly Lys Trp Tyr Val Val Gly Leu Ala Gly Asn Ala Ile Leu Arg Glu
        50                  55                  60

Asp Lys Asp Pro Gln Lys Met Tyr Ala Thr Ile Tyr Glu Leu Lys Glu
 65                  70                  75                  80

Asp Lys Ser Tyr Asn Val Thr Ser Val Leu Phe Arg Lys Lys Lys Cys
                 85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
    130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175
```

```
Lys Ser Leu Gly Leu Pro Glu Asn His Ile Val Phe Pro Val Pro Ile
            180                 185                 190

Gly Asn Gly Gln Ser Gly
        195

<210> SEQ ID NO 57
<211> LENGTH: 477
<212> TYPE: DNA
<213> ORGANISM: Homo sapiens
<220> FEATURE:
<221> NAME/KEY: CDS
<222> LOCATION: (1)..(477)

<400> SEQUENCE: 57 cgc gga tcc caa ttc cag ggg aag tgg tat gtg gta ggc ctg gca ggg        48
Arg Gly Ser Gln Phe Gln Gly Lys Trp Tyr Val Val Gly Leu Ala Gly
 1               5                  10                  15 aat gca att ctc aga gga gac aaa gac ccg caa aag atg tat gcc acc        96
Asn Ala Ile Leu Arg Gly Asp Lys Asp Pro Gln Lys Met Tyr Ala Thr
            20                  25                  30 atc tat gag ctg aaa gaa gac aag agc tac aat gtc acc tcc gtc ctg       144
Ile Tyr Glu Leu Lys Glu Asp Lys Ser Tyr Asn Val Thr Ser Val Leu
        35                  40                  45 ttt agg aaa aag aag tgt gac tac tgg atc agg act ttt gtt cca ggt       192
Phe Arg Lys Lys Lys Cys Asp Tyr Trp Ile Arg Thr Phe Val Pro Gly
    50                  55                  60 tgc cag ccc ggc gag ttc acg ctg ggc aac att aag agt tac cct gga       240
Cys Gln Pro Gly Glu Phe Thr Leu Gly Asn Ile Lys Ser Tyr Pro Gly
65                  70                  75                  80 tta acg agt tac ctc gtc cga gtg gtg agc acc aac tac aac cag cat       288
Leu Thr Ser Tyr Leu Val Arg Val Val Ser Thr Asn Tyr Asn Gln His
                85                  90                  95 gct atg gtg ttc ttc aag aaa gtt tct caa aac agg gag tac ttc aag       336
Ala Met Val Phe Phe Lys Lys Val Ser Gln Asn Arg Glu Tyr Phe Lys
            100                 105                 110 atc acc ctc tac ggg aga acc aag gag ctg act tcg gaa cta aag gag       384
Ile Thr Leu Tyr Gly Arg Thr Lys Glu Leu Thr Ser Glu Leu Lys Glu
        115                 120                 125 aac ttc atc cgc ttc tcc aaa tct ctg ggc ctc cct gaa aac cac atc       432
Asn Phe Ile Arg Phe Ser Lys Ser Leu Gly Leu Pro Glu Asn His Ile
    130                 135                 140 gtc ttc cct gtc cca atc ggt aat ggc cag tct gga ctc gag gcg           477
Val Phe Pro Val Pro Ile Gly Asn Gly Gln Ser Gly Leu Glu Ala
145                 150                 155

<210> SEQ ID NO 58
<211> LENGTH: 159
<212> TYPE: PRT
<213> ORGANISM: Homo sapiens

<400> SEQUENCE: 58

Arg Gly Ser Gln Phe Gln Gly Lys Trp Tyr Val Val Gly Leu Ala Gly
 1               5                  10                  15

Asn Ala Ile Leu Arg Gly Asp Lys Asp Pro Gln Lys Met Tyr Ala Thr
            20                  25                  30

Ile Tyr Glu Leu Lys Glu Asp Lys Ser Tyr Asn Val Thr Ser Val Leu
        35                  40                  45

Phe Arg Lys Lys Lys Cys Asp Tyr Trp Ile Arg Thr Phe Val Pro Gly
    50                  55                  60

Cys Gln Pro Gly Glu Phe Thr Leu Gly Asn Ile Lys Ser Tyr Pro Gly
```

```
                 65                  70                  75                  80
Leu Thr Ser Tyr Leu Val Arg Val Ser Thr Asn Tyr Asn Gln His
                        85                  90                  95

Ala Met Val Phe Phe Lys Lys Val Ser Gln Asn Arg Glu Tyr Phe Lys
                100                 105                 110

Ile Thr Leu Tyr Gly Arg Thr Lys Glu Leu Thr Ser Glu Leu Lys Glu
            115                 120                 125

Asn Phe Ile Arg Phe Ser Lys Ser Leu Gly Leu Pro Glu Asn His Ile
        130                 135                 140

Val Phe Pro Val Pro Ile Gly Asn Gly Gln Ser Gly Leu Glu Ala
145                 150                 155

<210> SEQ ID NO 59
<211> LENGTH: 2210
<212> TYPE: DNA
<213> ORGANISM: Homo sapiens
<220> FEATURE:
<221> NAME/KEY: CDS
<222> LOCATION: (1)..(2194)

<400> SEQUENCE: 59 atg aca att tta aga gtg ttt aac caa gac tgt tcc ttt aaa tgt gtt        48
Met Thr Ile Leu Arg Val Phe Asn Gln Asp Cys Ser Phe Lys Cys Val
  1               5                  10                  15 ctt ttg ctg ctg ttt aat tat aca tgt caa tta ttt aca gat cct gtg       96
Leu Leu Leu Leu Phe Asn Tyr Thr Cys Gln Leu Phe Thr Asp Pro Val
                 20                  25                  30 gta ttg tgg aaa ttc cca gag gac ttt gga gac cag gaa ata cta cag      144
Val Leu Trp Lys Phe Pro Glu Asp Phe Gly Asp Gln Glu Ile Leu Gln
             35                  40                  45 agt gtg cca aag ttc tgt ttt ccc ttt gac gtt gaa agg tac agt ata      192
Ser Val Pro Lys Phe Cys Phe Pro Phe Asp Val Glu Arg Tyr Ser Ile
         50                  55                  60 agt caa gtt gga cag cac ttt acc ttt gta ctg aca gac att gaa agt      240
Ser Gln Val Gly Gln His Phe Thr Phe Val Leu Thr Asp Ile Glu Ser
 65                  70                  75                  80 aaa cag aga ttt gga ttc tgc aga ctg acg tca gga ggc aca att tgt      288
Lys Gln Arg Phe Gly Phe Cys Arg Leu Thr Ser Gly Gly Thr Ile Cys
                 85                  90                  95 tta tgc atc ctt agt tac ctt ccc tgg ttt gaa gtg tat tac aag ctt      336
Leu Cys Ile Leu Ser Tyr Leu Pro Trp Phe Glu Val Tyr Tyr Lys Leu
            100                 105                 110 cta aat act ctt gca gat tac ttg gct aag cat tcc tac ttc att gcc      384
Leu Asn Thr Leu Ala Asp Tyr Leu Ala Lys His Ser Tyr Phe Ile Ala
        115                 120                 125 cct gat gta act gga ctc cca aca ata ccc gag agt aga aat ctt aca      432
Pro Asp Val Thr Gly Leu Pro Thr Ile Pro Glu Ser Arg Asn Leu Thr
    130                 135                 140 gaa tat ttt gtt gcc gtg gat gtg aac aac atg ctg cag ctg tat gcc      480
Glu Tyr Phe Val Ala Val Asp Val Asn Asn Met Leu Gln Leu Tyr Ala
145                 150                 155                 160 agt atg ctg cat gaa agg cgc atc gtg att atc tcg agc aaa tta agc      528
Ser Met Leu His Glu Arg Arg Ile Val Ile Ile Ser Ser Lys Leu Ser
                165                 170                 175 act tta act gcc tgt atc cat gga tca gct gct ctt cta tac cca atg      576
Thr Leu Thr Ala Cys Ile His Gly Ser Ala Ala Leu Leu Tyr Pro Met
            180                 185                 190 tat tgg caa cac ata tac atc cca gtg ctt cct cca cac ctg ctg gac      624
Tyr Trp Gln His Ile Tyr Ile Pro Val Leu Pro Pro His Leu Leu Asp
        195                 200                 205
```

-continued

| | |
|---|---|
| tac tgc agt gcc cca atg cca tac ctg att gga ata cac tcc agc ctc<br>Tyr Cys Ser Ala Pro Met Pro Tyr Leu Ile Gly Ile His Ser Ser Leu<br>210                               215                           220 | 672 |
| ata gag aga gtg aaa aac aaa tca ttg gaa gat gtt gtt atg tta aat<br>Ile Glu Arg Val Lys Asn Lys Ser Leu Glu Asp Val Val Met Leu Asn<br>225                         230                       235                     240 | 720 |
| gtt gat aca aac aca tta gaa tca cca ttt agt gac ttg aac aac cta<br>Val Asp Thr Asn Thr Leu Glu Ser Pro Phe Ser Asp Leu Asn Asn Leu<br>                      245                       250                     255 | 768 |
| cca agt gat gtg gta agt gcc ttg aaa aat aaa ctg aag aag cag tct<br>Pro Ser Asp Val Val Ser Ala Leu Lys Asn Lys Leu Lys Lys Gln Ser<br>                 260                     265                     270 | 816 |
| aca gct acg ggt gat gga gta gct agg gcc ttt ctt aga gca cag gct<br>Thr Ala Thr Gly Asp Gly Val Ala Arg Ala Phe Leu Arg Ala Gln Ala<br>          275                     280                     285 | 864 |
| gct ttg ttt gga tcc tac aga gat gca ctg aga tac aaa cct ggt gag<br>Ala Leu Phe Gly Ser Tyr Arg Asp Ala Leu Arg Tyr Lys Pro Gly Glu<br>          290                     295                     300 | 912 |
| ccc atc act ttc tgt gag gag agt ttt gta aag cac cgc tca agc gtg<br>Pro Ile Thr Phe Cys Glu Glu Ser Phe Val Lys His Arg Ser Ser Val<br>305                               310                       315                     320 | 960 |
| atg aaa cag ttc ctg gaa act gcc att aac ctc cag ctt ttt aag cag<br>Met Lys Gln Phe Leu Glu Thr Ala Ile Asn Leu Gln Leu Phe Lys Gln<br>                      325                       330                     335 | 1008 |
| gta ttt atc gat ggt cga ctg gca aaa cta aat gca gga agg ggt ttc<br>Val Phe Ile Asp Gly Arg Leu Ala Lys Leu Asn Ala Gly Arg Gly Phe<br>                340                     345                     350 | 1056 |
| tct gat gta ttt gaa gaa gag atc act tca ggt ggc ttt tgt gga ggt<br>Ser Asp Val Phe Glu Glu Glu Ile Thr Ser Gly Gly Phe Cys Gly Gly<br>                      355                       360                     365 | 1104 |
| aaa gac aag tta caa tat aaa tat gtt tct gtt ttt ctt ttg cag aaa<br>Lys Asp Lys Leu Gln Tyr Lys Tyr Val Ser Val Phe Leu Leu Gln Lys<br>370                               375                       380 | 1152 |
| gga ggt gca ctg ttc aac aca gca atg acc aaa gca acc cct gct gta<br>Gly Gly Ala Leu Phe Asn Thr Ala Met Thr Lys Ala Thr Pro Ala Val<br>385                               390                       395                     400 | 1200 |
| cgg aca gca tat aaa ttt gca aaa aat cat gca aag ctg gga cta aag<br>Arg Thr Ala Tyr Lys Phe Ala Lys Asn His Ala Lys Leu Gly Leu Lys<br>                         405                       410                     415 | 1248 |
| gaa gtg aag agt aaa cta aaa cac aag gaa aat gaa gaa gat tat ggg<br>Glu Val Lys Ser Lys Leu Lys His Lys Glu Asn Glu Glu Asp Tyr Gly<br>                      420                     425                     430 | 1296 |
| acc tgt tct agt tct gta caa tat aca cca gtt tac aaa tta cac aat<br>Thr Cys Ser Ser Ser Val Gln Tyr Thr Pro Val Tyr Lys Leu His Asn<br>                         435                       440                     445 | 1344 |
| gaa aag gga gga aac tca gaa aag cgt aag ctt gct cag gca cgc tta<br>Glu Lys Gly Gly Asn Ser Glu Lys Arg Lys Leu Ala Gln Ala Arg Leu<br>450                               455                       460 | 1392 |
| aaa agg cct ctt aag agc ctt gat ggt gct cta tat gat gat gaa gat<br>Lys Arg Pro Leu Lys Ser Leu Asp Gly Ala Leu Tyr Asp Asp Glu Asp<br>465                             470                       475                     480 | 1440 |
| gat gat gac att gaa aga gca agc aag tta tct tct gaa gat ggt gaa<br>Asp Asp Asp Ile Glu Arg Ala Ser Lys Leu Ser Ser Glu Asp Gly Glu<br>                         485                       490                     495 | 1488 |
| gaa gct tct gct tat ctc tat gag agt gat gac tct gtt gaa aca aga<br>Glu Ala Ser Ala Tyr Leu Tyr Glu Ser Asp Asp Ser Val Glu Thr Arg<br>          500                     505                     510 | 1536 |
| gtg aag act cct tac tca ggt gaa atg gac tta cta gga gag att ctt<br>Val Lys Thr Pro Tyr Ser Gly Glu Met Asp Leu Leu Gly Glu Ile Leu | 1584 |

-continued

```
                515                 520                 525
gat aca ttg agc aca cac agc tca gat cag ggg aag ctg gca gct gca      1632
Asp Thr Leu Ser Thr His Ser Ser Asp Gln Gly Lys Leu Ala Ala Ala
        530                 535                 540 aag agc ttg gat ttc ttt aga tca atg gat gac att gat tac aaa cct      1680
Lys Ser Leu Asp Phe Phe Arg Ser Met Asp Asp Ile Asp Tyr Lys Pro
545                 550                 555                 560 acg aat aaa tct aat gct cct agt gag aat aac ctg gct ttc ctc tgt      1728
Thr Asn Lys Ser Asn Ala Pro Ser Glu Asn Asn Leu Ala Phe Leu Cys
                565                 570                 575 ggt ggt tct ggt gac caa gca gag tgg aat ctt ggg caa gac gat agt      1776
Gly Gly Ser Gly Asp Gln Ala Glu Trp Asn Leu Gly Gln Asp Asp Ser
            580                 585                 590 gcc ctc cat ggc aaa cac ctc cct cca tct cct agg aag cgg gtt tcc      1824
Ala Leu His Gly Lys His Leu Pro Pro Ser Pro Arg Lys Arg Val Ser
        595                 600                 605 tct agt ggt ttg aca gat tct ctg ttt atc ctg aga gag gaa aac agt      1872
Ser Ser Gly Leu Thr Asp Ser Leu Phe Ile Leu Arg Glu Glu Asn Ser
    610                 615                 620 aac aag cac ctc ggt gct gac aat gtg agt gac cct act tca gga ctg      1920
Asn Lys His Leu Gly Ala Asp Asn Val Ser Asp Pro Thr Ser Gly Leu
625                 630                 635                 640 gat ttc caa ctc act tcc cct gaa gtt tcc cag act gat aaa gga aaa      1968
Asp Phe Gln Leu Thr Ser Pro Glu Val Ser Gln Thr Asp Lys Gly Lys
                645                 650                 655 aca gaa aag agg gaa aca cta agc cag att tca gat gat ctg ctt ata      2016
Thr Glu Lys Arg Glu Thr Leu Ser Gln Ile Ser Asp Asp Leu Leu Ile
            660                 665                 670 ccc ggt ctt ggg cgg cat tca tcg act ttt gtt cct tgg gag aaa gaa      2064
Pro Gly Leu Gly Arg His Ser Ser Thr Phe Val Pro Trp Glu Lys Glu
        675                 680                 685 ggg aaa gaa gcc aaa gag act tca gaa gat att gga ctg ctc cat gaa      2112
Gly Lys Glu Ala Lys Glu Thr Ser Glu Asp Ile Gly Leu Leu His Glu
    690                 695                 700 gta gtg tca tta tgt cat atg aca tct gac ttc caa caa agc ttg aac      2160
Val Val Ser Leu Cys His Met Thr Ser Asp Phe Gln Gln Ser Leu Asn
705                 710                 715                 720 att tca gac aaa aac aca aat gga aac caa act taaatcttgc               2203
Ile Ser Asp Lys Asn Thr Asn Gly Asn Gln Thr
                725                 730 atccaag                                                              2210

<210> SEQ ID NO 60
<211> LENGTH: 731
<212> TYPE: PRT
<213> ORGANISM: Homo sapiens

<400> SEQUENCE: 60

Met Thr Ile Leu Arg Val Phe Asn Gln Asp Cys Ser Phe Lys Cys Val
 1               5                  10                  15

Leu Leu Leu Leu Phe Asn Tyr Thr Cys Gln Leu Phe Thr Asp Pro Val
                20                  25                  30

Val Leu Trp Lys Phe Pro Glu Asp Phe Gly Asp Gln Glu Ile Leu Gln
            35                  40                  45

Ser Val Pro Lys Phe Cys Phe Pro Phe Asp Val Glu Arg Tyr Ser Ile
        50                  55                  60

Ser Gln Val Gly Gln His Phe Thr Phe Val Leu Thr Asp Ile Glu Ser
 65                  70                  75                  80
```

-continued

```
Lys Gln Arg Phe Gly Phe Cys Arg Leu Thr Ser Gly Gly Thr Ile Cys
                 85                  90                  95
Leu Cys Ile Leu Ser Tyr Leu Pro Trp Phe Glu Val Tyr Tyr Lys Leu
                100                 105                 110
Leu Asn Thr Leu Ala Asp Tyr Leu Ala Lys His Ser Tyr Phe Ile Ala
                115                 120                 125
Pro Asp Val Thr Gly Leu Pro Thr Ile Pro Glu Ser Arg Asn Leu Thr
            130                 135                 140
Glu Tyr Phe Val Ala Val Asp Val Asn Asn Met Leu Gln Leu Tyr Ala
145                 150                 155                 160
Ser Met Leu His Glu Arg Arg Ile Val Ile Ile Ser Ser Lys Leu Ser
                165                 170                 175
Thr Leu Thr Ala Cys Ile His Gly Ser Ala Ala Leu Leu Tyr Pro Met
                180                 185                 190
Tyr Trp Gln His Ile Tyr Ile Pro Val Leu Pro Pro His Leu Leu Asp
            195                 200                 205
Tyr Cys Ser Ala Pro Met Pro Tyr Leu Ile Gly Ile His Ser Ser Leu
            210                 215                 220
Ile Glu Arg Val Lys Asn Lys Ser Leu Glu Asp Val Val Met Leu Asn
225                 230                 235                 240
Val Asp Thr Asn Thr Leu Glu Ser Pro Phe Ser Asp Leu Asn Asn Leu
                245                 250                 255
Pro Ser Asp Val Val Ser Ala Leu Lys Asn Lys Leu Lys Lys Gln Ser
            260                 265                 270
Thr Ala Thr Gly Asp Gly Val Ala Arg Ala Phe Leu Arg Ala Gln Ala
            275                 280                 285
Ala Leu Phe Gly Ser Tyr Arg Asp Ala Leu Arg Tyr Lys Pro Gly Glu
            290                 295                 300
Pro Ile Thr Phe Cys Glu Glu Ser Phe Val Lys His Arg Ser Ser Val
305                 310                 315                 320
Met Lys Gln Phe Leu Glu Thr Ala Ile Asn Leu Gln Leu Phe Lys Gln
                325                 330                 335
Val Phe Ile Asp Gly Arg Leu Ala Lys Leu Asn Ala Gly Arg Gly Phe
            340                 345                 350
Ser Asp Val Phe Glu Glu Glu Ile Thr Ser Gly Gly Phe Cys Gly Gly
            355                 360                 365
Lys Asp Lys Leu Gln Tyr Lys Tyr Val Ser Val Phe Leu Leu Gln Lys
            370                 375                 380
Gly Gly Ala Leu Phe Asn Thr Ala Met Thr Lys Ala Thr Pro Ala Val
385                 390                 395                 400
Arg Thr Ala Tyr Lys Phe Ala Lys Asn His Ala Lys Leu Gly Leu Lys
                405                 410                 415
Glu Val Lys Ser Lys Leu Lys His Lys Glu Asn Glu Glu Asp Tyr Gly
                420                 425                 430
Thr Cys Ser Ser Ser Val Gln Tyr Thr Pro Val Tyr Lys Leu His Asn
            435                 440                 445
Glu Lys Gly Gly Asn Ser Glu Lys Arg Lys Leu Ala Gln Ala Arg Leu
            450                 455                 460
Lys Arg Pro Leu Lys Ser Leu Asp Gly Ala Leu Tyr Asp Asp Glu Asp
465                 470                 475                 480
Asp Asp Asp Ile Glu Arg Ala Ser Lys Leu Ser Ser Glu Asp Gly Glu
                485                 490                 495
Glu Ala Ser Ala Tyr Leu Tyr Glu Ser Asp Asp Ser Val Glu Thr Arg
```

|   |   |   |   |   |   |   |   |   |   |   |   |
|---|---|---|---|---|---|---|---|---|---|---|---|
|   |   |   | 500 |   |   |   | 505 |   |   |   | 510 |
| Val | Lys | Thr | Pro | Tyr | Ser | Gly | Glu | Met | Asp | Leu | Leu | Gly | Glu | Ile | Leu |

Val Lys Thr Pro Tyr Ser Gly Glu Met Asp Leu Leu Gly Glu Ile Leu
                515                 520                 525

Asp Thr Leu Ser Thr His Ser Ser Asp Gln Gly Lys Leu Ala Ala Ala
        530                 535                 540

Lys Ser Leu Asp Phe Phe Arg Ser Met Asp Ile Asp Tyr Lys Pro
545                 550                 555                 560

Thr Asn Lys Ser Asn Ala Pro Ser Glu Asn Asn Leu Ala Phe Leu Cys
                565                 570                 575

Gly Gly Ser Gly Asp Gln Ala Glu Trp Asn Leu Gly Gln Asp Asp Ser
                580                 585                 590

Ala Leu His Gly Lys His Leu Pro Pro Ser Pro Arg Lys Arg Val Ser
                595                 600                 605

Ser Ser Gly Leu Thr Asp Ser Leu Phe Ile Leu Arg Glu Glu Asn Ser
        610                 615                 620

Asn Lys His Leu Gly Ala Asp Asn Val Ser Asp Pro Thr Ser Gly Leu
625                 630                 635                 640

Asp Phe Gln Leu Thr Ser Pro Glu Val Ser Gln Thr Asp Lys Gly Lys
                645                 650                 655

Thr Glu Lys Arg Glu Thr Leu Ser Gln Ile Ser Asp Asp Leu Leu Ile
                660                 665                 670

Pro Gly Leu Gly Arg His Ser Ser Thr Phe Val Pro Trp Glu Lys Glu
        675                 680                 685

Gly Lys Glu Ala Lys Glu Thr Ser Glu Asp Ile Gly Leu Leu His Glu
        690                 695                 700

Val Val Ser Leu Cys His Met Thr Ser Asp Phe Gln Gln Ser Leu Asn
705                 710                 715                 720

Ile Ser Asp Lys Asn Thr Asn Gly Asn Gln Thr
                725                 730

<210> SEQ ID NO 61
<211> LENGTH: 2256
<212> TYPE: DNA
<213> ORGANISM: Homo sapiens
<220> FEATURE:
<221> NAME/KEY: CDS
<222> LOCATION: (1)..(2256)

<400> SEQUENCE: 61

```
aga tct gat cct gtg gta ttg tgg aaa ttc cca gag gac ttt gga gac      48
Arg Ser Asp Pro Val Val Leu Trp Lys Phe Pro Glu Asp Phe Gly Asp
  1               5                  10                  15 cag gaa ata cta cag agt gtg cca aag ttc tgt ttt ccc ttt gac gtt      96
Gln Glu Ile Leu Gln Ser Val Pro Lys Phe Cys Phe Pro Phe Asp Val
              20                  25                  30 gaa agg gtg tct cag aat caa gtt gga cag cac ttt acc ttt gta ctg     144
Glu Arg Val Ser Gln Asn Gln Val Gly Gln His Phe Thr Phe Val Leu
          35                  40                  45 aca gac att gaa agt aaa cag aga ttt gga ttc tgc aga ctg acg tca     192
Thr Asp Ile Glu Ser Lys Gln Arg Phe Gly Phe Cys Arg Leu Thr Ser
      50                  55                  60 gga ggc aca att tgt tta tgc atc ctt agt tac ctt ccc tgg ttt gaa     240
Gly Gly Thr Ile Cys Leu Cys Ile Leu Ser Tyr Leu Pro Trp Phe Glu
 65                  70                  75                  80 gtg tat tac aag ctt cta aat act ctt gca gat tac ttg gct aag gaa     288
Val Tyr Tyr Lys Leu Leu Asn Thr Leu Ala Asp Tyr Leu Ala Lys Glu
                  85                  90                  95
```

-continued

| | | |
|---|---|---|
| ctg gaa aat gat ttg aat gaa act ctc aga tca ctg tat aac cac cca<br>Leu Glu Asn Asp Leu Asn Glu Thr Leu Arg Ser Leu Tyr Asn His Pro<br>100                                   105                       110 | 336 |
| gta cca aag gca aat act cct gta aat ttg agt gtg aac caa gag ata<br>Val Pro Lys Ala Asn Thr Pro Val Asn Leu Ser Val Asn Gln Glu Ile<br>115                       120                         125 | 384 |
| ttt att acc tgt gag caa gtt ctg aaa gat cag cct gct cta cta ccg<br>Phe Ile Thr Cys Glu Gln Val Leu Lys Asp Gln Pro Ala Leu Leu Pro<br>130                         135                       140 | 432 |
| cat tcc tac ttc att gcc cct gat gta act gga ctc cca aca ata ccc<br>His Ser Tyr Phe Ile Ala Pro Asp Val Thr Gly Leu Pro Thr Ile Pro<br>145                     150                     155               160 | 480 |
| gag agt aga aat ctt aca gaa tat ttt gtt gcc gtg gat gtg aac aac<br>Glu Ser Arg Asn Leu Thr Glu Tyr Phe Val Ala Val Asp Val Asn Asn<br>                       165                     170                     175 | 528 |
| atg ctg cag ctg tat gcc agt atg ctg cat gaa agg cgc atc gtg att<br>Met Leu Gln Leu Tyr Ala Ser Met Leu His Glu Arg Arg Ile Val Ile<br>                180                     185                     190 | 576 |
| atc tcg agc aaa tta agc act tta act gcc tgt atc cat gga tca gct<br>Ile Ser Ser Lys Leu Ser Thr Leu Thr Ala Cys Ile His Gly Ser Ala<br>                   195                     200                   205 | 624 |
| gct ctt cta tac cca atg tat tgg caa cac ata tac atc cca gtg ctt<br>Ala Leu Leu Tyr Pro Met Tyr Trp Gln His Ile Tyr Ile Pro Val Leu<br>210                       215                       220 | 672 |
| cct cca cac ctg ctg gac tac tgc tgt gcc cca atg cca tac ctg att<br>Pro Pro His Leu Leu Asp Tyr Cys Cys Ala Pro Met Pro Tyr Leu Ile<br>225                     230                     235               240 | 720 |
| gga ata cac tcc agc ctc ata gag aga gtg aaa aac aaa tca ttg gaa<br>Gly Ile His Ser Ser Leu Ile Glu Arg Val Lys Asn Lys Ser Leu Glu<br>                   245                     250                   255 | 768 |
| gat gtt gtt atg tta aat gtt gat aca aac aca tta gaa tca cca ttt<br>Asp Val Val Met Leu Asn Val Asp Thr Asn Thr Leu Glu Ser Pro Phe<br>260                       265                     270 | 816 |
| agt gac ttg aac aac cta cca agt gat gtg gtc tcg gcc ttg aaa aat<br>Ser Asp Leu Asn Asn Leu Pro Ser Asp Val Val Ser Ala Leu Lys Asn<br>                275                     280                   285 | 864 |
| aaa ctg aag aag cag tct aca gct acg ggt gat gga gta gct agg gcc<br>Lys Leu Lys Lys Gln Ser Thr Ala Thr Gly Asp Gly Val Ala Arg Ala<br>290                       295                     300 | 912 |
| ttt ctt aga gca cag gct gct ttg ttt gga tcc tac aga gat gca ctg<br>Phe Leu Arg Ala Gln Ala Ala Leu Phe Gly Ser Tyr Arg Asp Ala Leu<br>305                       310                     315               320 | 960 |
| aga tac aaa cct ggt gag ccc atc act ttc tgt gag gag agt ttt gta<br>Arg Tyr Lys Pro Gly Glu Pro Ile Thr Phe Cys Glu Glu Ser Phe Val<br>                   325                     330                   335 | 1008 |
| aag cac cgc tca agc gtg atg aaa cag ttc ctg gaa act gcc att aac<br>Lys His Arg Ser Ser Val Met Lys Gln Phe Leu Glu Thr Ala Ile Asn<br>                340                     345                   350 | 1056 |
| ctc cag ctt ttt aag cag ttt atc gat ggt cga ctg gca aaa cta aat<br>Leu Gln Leu Phe Lys Gln Phe Ile Asp Gly Arg Leu Ala Lys Leu Asn<br>                   355                     360                   365 | 1104 |
| gca gga agg ggt ttc tct gat gta ttt gaa gaa gag atc act tca ggt<br>Ala Gly Arg Gly Phe Ser Asp Val Phe Glu Glu Glu Ile Thr Ser Gly<br>370                       375                     380 | 1152 |
| ggc ttt tgt gga ggg aac ccg agg tca tat caa caa tgg gtg cat aca<br>Gly Phe Cys Gly Gly Asn Pro Arg Ser Tyr Gln Gln Trp Val His Thr<br>385                     390                     395               400 | 1200 |
| gtc aag aaa gga ggt gca ctg ttc aac aca gca atg acc aaa gca acc<br>Val Lys Lys Gly Gly Ala Leu Phe Asn Thr Ala Met Thr Lys Ala Thr<br>                   405                     410                   415 | 1248 |

```
cct gct gta cgg aca gca tat aaa ttt gca aaa aat cat gca aag ctg         1296
Pro Ala Val Arg Thr Ala Tyr Lys Phe Ala Lys Asn His Ala Lys Leu
            420                 425                 430 gga cta aag gaa gtg aag agt aaa cta aaa cac aag gaa aat gaa gaa         1344
Gly Leu Lys Glu Val Lys Ser Lys Leu Lys His Lys Glu Asn Glu Glu
        435                 440                 445 gat tat ggg acc tgt tct agt tct gta caa tat aca cca gtt tac aaa         1392
Asp Tyr Gly Thr Cys Ser Ser Ser Val Gln Tyr Thr Pro Val Tyr Lys
    450                 455                 460 tta cac aat gaa aag gga gga aac tca gaa aag cgt aag ctt gct cag         1440
Leu His Asn Glu Lys Gly Gly Asn Ser Glu Lys Arg Lys Leu Ala Gln
465                 470                 475                 480 gca cgc tta aaa agg cct ctt aag agc ctt gat ggt gct cta tat gat         1488
Ala Arg Leu Lys Arg Pro Leu Lys Ser Leu Asp Gly Ala Leu Tyr Asp
                485                 490                 495 gat gaa gat gat gat gac att gaa aga gca agc aag tta tct tct gaa         1536
Asp Glu Asp Asp Asp Asp Ile Glu Arg Ala Ser Lys Leu Ser Ser Glu
            500                 505                 510 gat ggt gaa gaa gct tct gct tat ctc tat gag agt gat gac tct gtt         1584
Asp Gly Glu Glu Ala Ser Ala Tyr Leu Tyr Glu Ser Asp Asp Ser Val
        515                 520                 525 gaa aca aga gtg aag act cct tac tca ggt gaa atg gac tta cta gga         1632
Glu Thr Arg Val Lys Thr Pro Tyr Ser Gly Glu Met Asp Leu Leu Gly
    530                 535                 540 gag att ctt gat aca ttg agc aca cac agc tca gat cag ggg agg ctg         1680
Glu Ile Leu Asp Thr Leu Ser Thr His Ser Ser Asp Gln Gly Arg Leu
545                 550                 555                 560 gca gct gca aag agc ttg gat ttc ttt aga tca atg gac gac att gat         1728
Ala Ala Ala Lys Ser Leu Asp Phe Phe Arg Ser Met Asp Asp Ile Asp
                565                 570                 575 tac aaa cct acg aat aaa tct aat gct cct agt gag aat aac ctg gct         1776
Tyr Lys Pro Thr Asn Lys Ser Asn Ala Pro Ser Glu Asn Asn Leu Ala
            580                 585                 590 ttc ctc tgt ggt ggt tct ggt gac caa gca gag tgg aat ctt ggg caa         1824
Phe Leu Cys Gly Gly Ser Gly Asp Gln Ala Glu Trp Asn Leu Gly Gln
        595                 600                 605 gac gat agt gcc ctc cat ggc aaa cac ctc cct cca tct cct agg aag         1872
Asp Asp Ser Ala Leu His Gly Lys His Leu Pro Pro Ser Pro Arg Lys
    610                 615                 620 cgg gtt tcc tct agt ggt ttg aca gat tct ctg ttt atc ctg aaa gag         1920
Arg Val Ser Ser Ser Gly Leu Thr Asp Ser Leu Phe Ile Leu Lys Glu
625                 630                 635                 640 gaa aac agt aac aag cac ctc ggt gct gac aat gtg agt gac cct act         1968
Glu Asn Ser Asn Lys His Leu Gly Ala Asp Asn Val Ser Asp Pro Thr
                645                 650                 655 tca gga ctg gat ttc caa ctc act tcc cct gaa gtt tcc cag act gat         2016
Ser Gly Leu Asp Phe Gln Leu Thr Ser Pro Glu Val Ser Gln Thr Asp
            660                 665                 670 aaa gga aaa aca gaa aag agg gaa aca cta agc cag att tca gat gat         2064
Lys Gly Lys Thr Glu Lys Arg Glu Thr Leu Ser Gln Ile Ser Asp Asp
        675                 680                 685 ctg ctt ata ccc ggt ctt ggg cgg cat tca tcg act ttt gtt cct tgg         2112
Leu Leu Ile Pro Gly Leu Gly Arg His Ser Ser Thr Phe Val Pro Trp
    690                 695                 700 gag aaa gaa ggg aaa gaa gcc aaa gag act tca gaa gat att gga ctg         2160
Glu Lys Glu Gly Lys Glu Ala Lys Glu Thr Ser Glu Asp Ile Gly Leu
705                 710                 715                 720 ctc cat gaa gta gtg tca tta tgt cat atg aca tct gac ttc caa caa         2208
Leu His Glu Val Val Ser Leu Cys His Met Thr Ser Asp Phe Gln Gln
```

```
                      725                 730                 735
agc ttg aac att tca gac aaa aac aca aat gga aac caa act aga tct    2256
Ser Leu Asn Ile Ser Asp Lys Asn Thr Asn Gly Asn Gln Thr Arg Ser
            740                 745                 750
```

<210> SEQ ID NO 62
<211> LENGTH: 752
<212> TYPE: PRT
<213> ORGANISM: Homo sapiens

<400> SEQUENCE: 62

```
Arg Ser Asp Pro Val Val Leu Trp Lys Phe Pro Glu Asp Phe Gly Asp
  1               5                  10                  15

Gln Glu Ile Leu Gln Ser Val Pro Lys Phe Cys Phe Pro Phe Asp Val
             20                  25                  30

Glu Arg Val Ser Gln Asn Gln Val Gly Gln His Phe Thr Phe Val Leu
         35                  40                  45

Thr Asp Ile Glu Ser Lys Gln Arg Phe Gly Phe Cys Arg Leu Thr Ser
     50                  55                  60

Gly Gly Thr Ile Cys Leu Cys Ile Leu Ser Tyr Leu Pro Trp Phe Glu
 65                  70                  75                  80

Val Tyr Tyr Lys Leu Leu Asn Thr Leu Ala Asp Tyr Leu Ala Lys Glu
                 85                  90                  95

Leu Glu Asn Asp Leu Asn Glu Thr Leu Arg Ser Leu Tyr Asn His Pro
            100                 105                 110

Val Pro Lys Ala Asn Thr Pro Val Asn Leu Ser Val Asn Gln Glu Ile
        115                 120                 125

Phe Ile Thr Cys Glu Gln Val Leu Lys Asp Gln Pro Ala Leu Leu Pro
    130                 135                 140

His Ser Tyr Phe Ile Ala Pro Asp Val Thr Gly Leu Pro Thr Ile Pro
145                 150                 155                 160

Glu Ser Arg Asn Leu Thr Glu Tyr Phe Val Ala Val Asp Val Asn Asn
                165                 170                 175

Met Leu Gln Leu Tyr Ala Ser Met Leu His Glu Arg Arg Ile Val Ile
            180                 185                 190

Ile Ser Ser Lys Leu Ser Thr Leu Thr Ala Cys Ile His Gly Ser Ala
        195                 200                 205

Ala Leu Leu Tyr Pro Met Tyr Trp Gln His Ile Tyr Ile Pro Val Leu
    210                 215                 220

Pro Pro His Leu Leu Asp Tyr Cys Cys Ala Pro Met Pro Tyr Leu Ile
225                 230                 235                 240

Gly Ile His Ser Ser Leu Ile Glu Arg Val Lys Asn Lys Ser Leu Glu
                245                 250                 255

Asp Val Val Met Leu Asn Val Asp Thr Asn Thr Leu Glu Ser Pro Phe
            260                 265                 270

Ser Asp Leu Asn Asn Leu Pro Ser Asp Val Val Ser Ala Leu Lys Asn
        275                 280                 285

Lys Leu Lys Lys Gln Ser Thr Ala Thr Gly Asp Gly Val Ala Arg Ala
    290                 295                 300

Phe Leu Arg Ala Gln Ala Ala Leu Phe Gly Ser Tyr Arg Asp Ala Leu
305                 310                 315                 320

Arg Tyr Lys Pro Gly Glu Pro Ile Thr Phe Cys Glu Glu Ser Phe Val
                325                 330                 335

Lys His Arg Ser Ser Val Met Lys Gln Phe Leu Glu Thr Ala Ile Asn
            340                 345                 350
```

-continued

```
Leu Gln Leu Phe Lys Gln Phe Ile Asp Gly Arg Leu Ala Lys Leu Asn
            355                 360                 365
Ala Gly Arg Gly Phe Ser Asp Val Phe Glu Glu Ile Thr Ser Gly
        370                 375                 380
Gly Phe Cys Gly Gly Asn Pro Arg Ser Tyr Gln Gln Trp Val His Thr
385                 390                 395                 400
Val Lys Lys Gly Gly Ala Leu Phe Asn Thr Ala Met Thr Lys Ala Thr
                405                 410                 415
Pro Ala Val Arg Thr Ala Tyr Lys Phe Ala Lys Asn His Ala Lys Leu
            420                 425                 430
Gly Leu Lys Glu Val Lys Ser Lys Leu Lys His Lys Glu Asn Glu Glu
        435                 440                 445
Asp Tyr Gly Thr Cys Ser Ser Val Gln Tyr Thr Pro Val Tyr Lys
450                 455                 460
Leu His Asn Glu Lys Gly Gly Asn Ser Glu Lys Arg Lys Leu Ala Gln
465                 470                 475                 480
Ala Arg Leu Lys Arg Pro Leu Lys Ser Leu Asp Gly Ala Leu Tyr Asp
            485                 490                 495
Asp Glu Asp Asp Asp Ile Glu Arg Ala Ser Lys Leu Ser Ser Glu
        500                 505                 510
Asp Gly Glu Glu Ala Ser Ala Tyr Leu Tyr Glu Ser Asp Asp Ser Val
        515                 520                 525
Glu Thr Arg Val Lys Thr Pro Tyr Ser Gly Glu Met Asp Leu Leu Gly
    530                 535                 540
Glu Ile Leu Asp Thr Leu Ser Thr His Ser Ser Asp Gln Gly Arg Leu
545                 550                 555                 560
Ala Ala Ala Lys Ser Leu Asp Phe Phe Arg Ser Met Asp Ile Asp
            565                 570                 575
Tyr Lys Pro Thr Asn Lys Ser Asn Ala Pro Ser Glu Asn Asn Leu Ala
            580                 585                 590
Phe Leu Cys Gly Gly Ser Gly Asp Gln Ala Glu Trp Asn Leu Gly Gln
        595                 600                 605
Asp Asp Ser Ala Leu His Gly Lys His Leu Pro Pro Ser Pro Arg Lys
    610                 615                 620
Arg Val Ser Ser Ser Gly Leu Thr Asp Ser Leu Phe Ile Leu Lys Glu
625                 630                 635                 640
Glu Asn Ser Asn Lys His Leu Gly Ala Asp Asn Val Ser Asp Pro Thr
            645                 650                 655
Ser Gly Leu Asp Phe Gln Leu Thr Ser Pro Glu Val Ser Gln Thr Asp
        660                 665                 670
Lys Gly Lys Thr Glu Lys Arg Glu Thr Leu Ser Gln Ile Ser Asp Asp
    675                 680                 685
Leu Leu Ile Pro Gly Leu Gly Arg His Ser Ser Thr Phe Val Pro Trp
        690                 695                 700
Glu Lys Glu Gly Lys Glu Ala Lys Glu Thr Ser Glu Asp Ile Gly Leu
705                 710                 715                 720
Leu His Glu Val Val Ser Leu Cys His Met Thr Ser Asp Phe Gln Gln
            725                 730                 735
Ser Leu Asn Ile Ser Asp Lys Asn Thr Asn Gly Asn Gln Thr Arg Ser
            740                 745                 750
```

<210> SEQ ID NO 63
<211> LENGTH: 2256

-continued

```
<212> TYPE: DNA
<213> ORGANISM: Homo sapiens
<220> FEATURE:
<221> NAME/KEY: CDS
<222> LOCATION: (1)..(2256)

<400> SEQUENCE: 63 aga tct gat cct gtg gta ttg tgg aaa ttc cca gag gac ttt gga gac       48
Arg Ser Asp Pro Val Val Leu Trp Lys Phe Pro Glu Asp Phe Gly Asp
 1               5                  10                  15 cag gaa ata cta cag agt gtg cca aag ttc tgt ttt ccc ttt gac gtt       96
Gln Glu Ile Leu Gln Ser Val Pro Lys Phe Cys Phe Pro Phe Asp Val
             20                  25                  30 gaa agg gtg tct cag aat caa gtt gga cag cac ttt acc ttt gta ctg      144
Glu Arg Val Ser Gln Asn Gln Val Gly Gln His Phe Thr Phe Val Leu
         35                  40                  45 aca gac att gaa agt aaa cag aga ttt gga ttc tgc aga ctg acg tca      192
Thr Asp Ile Glu Ser Lys Gln Arg Phe Gly Phe Cys Arg Leu Thr Ser
     50                  55                  60 gga ggc aca att tgt tta tgc atc ctt agt tac ctt ccc tgg ttt gaa      240
Gly Gly Thr Ile Cys Leu Cys Ile Leu Ser Tyr Leu Pro Trp Phe Glu
 65                  70                  75                  80 gtg tat tac aag ctt cta aat act ctt gca gat tac ttg gct aag gaa      288
Val Tyr Tyr Lys Leu Leu Asn Thr Leu Ala Asp Tyr Leu Ala Lys Glu
                 85                  90                  95 ctg gaa aat gat ttg aat gaa act ctc aga tca ctg tat aac cac cca      336
Leu Glu Asn Asp Leu Asn Glu Thr Leu Arg Ser Leu Tyr Asn His Pro
            100                 105                 110 gta cca aag gca aat act cct gta aat ttg agt gtg aac caa gag ata      384
Val Pro Lys Ala Asn Thr Pro Val Asn Leu Ser Val Asn Gln Glu Ile
        115                 120                 125 ttt att acc tgt gag caa gtt ctg aaa gat cag cct gct cta cta ccg      432
Phe Ile Thr Cys Glu Gln Val Leu Lys Asp Gln Pro Ala Leu Leu Pro
    130                 135                 140 cat tcc tac ttc att gcc cct gat gta act gga ctc cca aca ata ccc      480
His Ser Tyr Phe Ile Ala Pro Asp Val Thr Gly Leu Pro Thr Ile Pro
145                 150                 155                 160 gag agt aga aat ctt aca gaa tat ttt gtt gcc gtg gat gtg aac aac      528
Glu Ser Arg Asn Leu Thr Glu Tyr Phe Val Ala Val Asp Val Asn Asn
                165                 170                 175 atg ctg cag ctg tat gcc agt atg ctg cat gaa agg cgc atc gtg att      576
Met Leu Gln Leu Tyr Ala Ser Met Leu His Glu Arg Arg Ile Val Ile
            180                 185                 190 atc tcg agc aaa tta agc act tta act gcc tgt atc cat gga tca gct      624
Ile Ser Ser Lys Leu Ser Thr Leu Thr Ala Cys Ile His Gly Ser Ala
        195                 200                 205 gct ctt cta tac cca atg tat tgg caa cac ata tac atc cca gtg ctt      672
Ala Leu Leu Tyr Pro Met Tyr Trp Gln His Ile Tyr Ile Pro Val Leu
    210                 215                 220 cct cca cac ctg ctg gac tac tgc tgt gcc cca atg cca tac ctg att      720
Pro Pro His Leu Leu Asp Tyr Cys Cys Ala Pro Met Pro Tyr Leu Ile
225                 230                 235                 240 gga ata cac tcc agc ctc ata gag aga gtg aaa aac aaa tca ttg gaa      768
Gly Ile His Ser Ser Leu Ile Glu Arg Val Lys Asn Lys Ser Leu Glu
                245                 250                 255 gat gtt gtt atg tta aat gtt gat aca aac aca tta gaa tca cca ttt      816
Asp Val Val Met Leu Asn Val Asp Thr Asn Thr Leu Glu Ser Pro Phe
            260                 265                 270 agt gac ttg aac aac cta cca agt gat gtg gtc tcg gcc ttg aaa aat      864
Ser Asp Leu Asn Asn Leu Pro Ser Asp Val Val Ser Ala Leu Lys Asn
        275                 280                 285
```

|   |   |
|---|---|
| aaa ctg aag aag cag tct aca gct acg ggt gat gga gta gct agg gcc<br>Lys Leu Lys Lys Gln Ser Thr Ala Thr Gly Asp Gly Val Ala Arg Ala<br>290                         295                    300 | 912 |
| ttt ctt aga gca cag gct gct ttg ttt gga tcc tac aga gat gca ctg<br>Phe Leu Arg Ala Gln Ala Ala Leu Phe Gly Ser Tyr Arg Asp Ala Leu<br>305                        310                    315               320 | 960 |
| aga tac aaa cct ggt gag ccc atc act ttc tgt gag gag agt ttt gta<br>Arg Tyr Lys Pro Gly Glu Pro Ile Thr Phe Cys Glu Glu Ser Phe Val<br>                 325                    330                    335 | 1008 |
| aag cac cgc tca agc gtg atg aaa cag ttc ctg gaa act gcc att aac<br>Lys His Arg Ser Ser Val Met Lys Gln Phe Leu Glu Thr Ala Ile Asn<br>              340                    345                   350 | 1056 |
| ctc cag ctt ttt aag cag ttt atc gat ggt cga ctg gca aaa cta aat<br>Leu Gln Leu Phe Lys Gln Phe Ile Asp Gly Arg Leu Ala Lys Leu Asn<br>          355                    360                   365 | 1104 |
| gca gga agg ggt ttc tct gat gta ttt gaa gaa gag atc act tca ggt<br>Ala Gly Arg Gly Phe Ser Asp Val Phe Glu Glu Glu Ile Thr Ser Gly<br>370                         375                    380 | 1152 |
| ggc ttt tgt gga ggg aac ccg agg tca tat caa caa tgg gtg cat aca<br>Gly Phe Cys Gly Gly Asn Pro Arg Ser Tyr Gln Gln Trp Val His Thr<br>385                         390                    395               400 | 1200 |
| gtc aag aaa gga ggt gca ctg ttc aac aca gca atg acc aaa gca acc<br>Val Lys Lys Gly Gly Ala Leu Phe Asn Thr Ala Met Thr Lys Ala Thr<br>                    405                    410                   415 | 1248 |
| cct gct gta cgg aca gca tat aaa ttt gca aaa aat cat gca aag ctg<br>Pro Ala Val Arg Thr Ala Tyr Lys Phe Ala Lys Asn His Ala Lys Leu<br>              420                    425                   430 | 1296 |
| gga cta aag gaa gtg aag agt aaa cta aaa cac aag gaa aat gaa gaa<br>Gly Leu Lys Glu Val Lys Ser Lys Leu Lys His Lys Glu Asn Glu Glu<br>          435                    440                   445 | 1344 |
| gat tat ggg acc tgt tct agt tct gta caa tat aca cca gtt tac aaa<br>Asp Tyr Gly Thr Cys Ser Ser Ser Val Gln Tyr Thr Pro Val Tyr Lys<br>450                         455                    460 | 1392 |
| tta cac aat gaa aag gga gga aac tca gaa aag cgt aag ctt gct cag<br>Leu His Asn Glu Lys Gly Gly Asn Ser Glu Lys Arg Lys Leu Ala Gln<br>465                         470                    475               480 | 1440 |
| gca cgc tta aaa agg cct ctt aag agc ctt gat ggt gct cta tat gat<br>Ala Arg Leu Lys Arg Pro Leu Lys Ser Leu Asp Gly Ala Leu Tyr Asp<br>                    485                    490                   495 | 1488 |
| gat gaa gat gat gat gac att gaa aga gca agc aag tta tct tct gaa<br>Asp Glu Asp Asp Asp Asp Ile Glu Arg Ala Ser Lys Leu Ser Ser Glu<br>              500                    505                   510 | 1536 |
| gat ggt gaa gaa gct tct gct tat ctc tat gag agt gat gac tct gtt<br>Asp Gly Glu Glu Ala Ser Ala Tyr Leu Tyr Glu Ser Asp Asp Ser Val<br>          515                    520                   525 | 1584 |
| gaa aca aga gtg aag act cct tac tca ggt gaa atg gac tta cta gga<br>Glu Thr Arg Val Lys Thr Pro Tyr Ser Gly Glu Met Asp Leu Leu Gly<br>530                         535                    540 | 1632 |
| gag att ctt gat aca ttg agc aca cac agc tca gat cag ggg agg ctg<br>Glu Ile Leu Asp Thr Leu Ser Thr His Ser Ser Asp Gln Gly Arg Leu<br>545                         550                    555               560 | 1680 |
| gca gct gca aag agc ttg gat ttc ttt aga tca atg gac gac att gat<br>Ala Ala Ala Lys Ser Leu Asp Phe Phe Arg Ser Met Asp Asp Ile Asp<br>                    565                    570                   575 | 1728 |
| tac aaa cct acg aat aaa tct aat gct cct agt gag aat aac ctg gct<br>Tyr Lys Pro Thr Asn Lys Ser Asn Ala Pro Ser Glu Asn Asn Leu Ala<br>              580                    585                   590 | 1776 |
| ttc ctc tgt ggt ggt tct ggt gac caa gca gag tgg aat ctt ggg caa<br>Phe Leu Cys Gly Gly Ser Gly Asp Gln Ala Glu Trp Asn Leu Gly Gln | 1824 |

-continued

```
              595                 600                 605
gac gat agt gcc ctc cat ggc aaa cac ctc cct cca tct cct agg aag       1872
Asp Asp Ser Ala Leu His Gly Lys His Leu Pro Pro Ser Pro Arg Lys
610                 615                 620 cgg gtt tcc tct agt ggt ttg aca gat tct ctg ttt atc ctg aaa gag       1920
Arg Val Ser Ser Ser Gly Leu Thr Asp Ser Leu Phe Ile Leu Lys Glu
625                 630                 635                 640 gaa aac agt aac aag cac ctc ggt gct gac aat gtg agt gac cct act       1968
Glu Asn Ser Asn Lys His Leu Gly Ala Asp Asn Val Ser Asp Pro Thr
                645                 650                 655 tca gga ctg gat ttc caa ctc act tcc cct gaa gtt tcc cag act gat       2016
Ser Gly Leu Asp Phe Gln Leu Thr Ser Pro Glu Val Ser Gln Thr Asp
                660                 665                 670 aaa gga aaa aca gaa aag agg gaa aca cta agc cag att tca gat gat       2064
Lys Gly Lys Thr Glu Lys Arg Glu Thr Leu Ser Gln Ile Ser Asp Asp
                675                 680                 685 ctg ctt ata ccc ggt ctt ggg cgg cat tca tcg act ttt gtt cct tgg       2112
Leu Leu Ile Pro Gly Leu Gly Arg His Ser Ser Thr Phe Val Pro Trp
690                 695                 700 gag aaa gaa ggg aaa gaa gcc aaa gag act tca gaa gat att gga ctg       2160
Glu Lys Glu Gly Lys Glu Ala Lys Glu Thr Ser Glu Asp Ile Gly Leu
705                 710                 715                 720 ctc cat gaa gta gtg tca tta tgt cat atg aca tct gac ttc caa caa       2208
Leu His Glu Val Val Ser Leu Cys His Met Thr Ser Asp Phe Gln Gln
                725                 730                 735 agc ttg aac att tca gac aaa aac aca aat gga aac caa act aga tct       2256
Ser Leu Asn Ile Ser Asp Lys Asn Thr Asn Gly Asn Gln Thr Arg Ser
                740                 745                 750
```

<210> SEQ ID NO 64
<211> LENGTH: 752
<212> TYPE: PRT
<213> ORGANISM: Homo sapiens

<400> SEQUENCE: 64

```
Arg Ser Asp Pro Val Val Leu Trp Lys Phe Pro Glu Asp Phe Gly Asp
1               5                   10                  15

Gln Glu Ile Leu Gln Ser Val Pro Lys Phe Cys Pro Phe Asp Val
            20                  25                  30

Glu Arg Val Ser Gln Asn Gln Val Gly Gln His Phe Thr Phe Val Leu
        35                  40                  45

Thr Asp Ile Glu Ser Lys Gln Arg Phe Gly Phe Cys Arg Leu Thr Ser
    50                  55                  60

Gly Gly Thr Ile Cys Leu Cys Ile Leu Ser Tyr Leu Pro Trp Phe Glu
65                  70                  75                  80

Val Tyr Tyr Lys Leu Leu Asn Thr Leu Ala Asp Tyr Leu Ala Lys Glu
                85                  90                  95

Leu Glu Asn Asp Leu Asn Glu Thr Leu Arg Ser Leu Tyr Asn His Pro
            100                 105                 110

Val Pro Lys Ala Asn Thr Pro Val Asn Leu Ser Val Asn Gln Glu Ile
        115                 120                 125

Phe Ile Thr Cys Glu Gln Val Leu Lys Asp Gln Pro Ala Leu Leu Pro
    130                 135                 140

His Ser Tyr Phe Ile Ala Pro Asp Val Thr Gly Leu Pro Thr Ile Pro
145                 150                 155                 160

Glu Ser Arg Asn Leu Thr Glu Tyr Phe Val Ala Val Asp Val Asn Asn
                165                 170                 175
```

```
Met Leu Gln Leu Tyr Ala Ser Met Leu His Glu Arg Arg Ile Val Ile
                180                 185                 190
Ile Ser Ser Lys Leu Ser Thr Leu Thr Ala Cys Ile His Gly Ser Ala
            195                 200                 205
Ala Leu Leu Tyr Pro Met Tyr Trp Gln His Ile Tyr Ile Pro Val Leu
        210                 215                 220
Pro Pro His Leu Leu Asp Tyr Cys Cys Ala Pro Met Pro Tyr Leu Ile
225                 230                 235                 240
Gly Ile His Ser Ser Leu Ile Glu Arg Val Lys Asn Lys Ser Leu Glu
                245                 250                 255
Asp Val Val Met Leu Asn Val Asp Thr Asn Thr Leu Glu Ser Pro Phe
            260                 265                 270
Ser Asp Leu Asn Asn Leu Pro Ser Asp Val Val Ser Ala Leu Lys Asn
        275                 280                 285
Lys Leu Lys Lys Gln Ser Thr Ala Thr Gly Asp Gly Val Ala Arg Ala
    290                 295                 300
Phe Leu Arg Ala Gln Ala Ala Leu Phe Gly Ser Tyr Arg Asp Ala Leu
305                 310                 315                 320
Arg Tyr Lys Pro Gly Glu Pro Ile Thr Phe Cys Glu Glu Ser Phe Val
                325                 330                 335
Lys His Arg Ser Ser Val Met Lys Gln Phe Leu Glu Thr Ala Ile Asn
            340                 345                 350
Leu Gln Leu Phe Lys Gln Phe Ile Asp Gly Arg Leu Ala Lys Leu Asn
        355                 360                 365
Ala Gly Arg Gly Phe Ser Asp Val Phe Glu Glu Ile Thr Ser Gly
    370                 375                 380
Gly Phe Cys Gly Gly Asn Pro Arg Ser Tyr Gln Gln Trp Val His Thr
385                 390                 395                 400
Val Lys Lys Gly Gly Ala Leu Phe Asn Thr Ala Met Thr Lys Ala Thr
                405                 410                 415
Pro Ala Val Arg Thr Ala Tyr Lys Phe Ala Lys Asn His Ala Lys Leu
            420                 425                 430
Gly Leu Lys Glu Val Lys Ser Lys Leu Lys His Lys Glu Asn Glu Glu
        435                 440                 445
Asp Tyr Gly Thr Cys Ser Ser Val Gln Tyr Thr Pro Val Tyr Lys
    450                 455                 460
Leu His Asn Glu Lys Gly Gly Asn Ser Glu Lys Arg Lys Leu Ala Gln
465                 470                 475                 480
Ala Arg Leu Lys Arg Pro Leu Lys Ser Leu Asp Gly Ala Leu Tyr Asp
                485                 490                 495
Asp Glu Asp Asp Asp Ile Glu Arg Ala Ser Lys Leu Ser Ser Glu
            500                 505                 510
Asp Gly Glu Glu Ala Ser Ala Tyr Leu Tyr Glu Ser Asp Asp Ser Val
        515                 520                 525
Glu Thr Arg Val Lys Thr Pro Tyr Ser Gly Glu Met Asp Leu Leu Gly
    530                 535                 540
Glu Ile Leu Asp Thr Leu Ser Thr His Ser Ser Asp Gln Gly Arg Leu
545                 550                 555                 560
Ala Ala Ala Lys Ser Leu Asp Phe Phe Arg Ser Met Asp Ile Asp
                565                 570                 575
Tyr Lys Pro Thr Asn Lys Ser Asn Ala Pro Ser Glu Asn Asn Leu Ala
            580                 585                 590
Phe Leu Cys Gly Gly Ser Gly Asp Gln Ala Glu Trp Asn Leu Gly Gln
```

-continued 595                 600                 605

Asp Asp Ser Ala Leu His Gly Lys His Leu Pro Pro Ser Pro Arg Lys
    610                 615                 620

Arg Val Ser Ser Ser Gly Leu Thr Asp Ser Leu Phe Ile Leu Lys Glu
625                 630                 635                 640

Glu Asn Ser Asn Lys His Leu Gly Ala Asp Asn Val Ser Asp Pro Thr
                645                 650                 655

Ser Gly Leu Asp Phe Gln Leu Thr Ser Pro Glu Val Ser Gln Thr Asp
                660                 665                 670

Lys Gly Lys Thr Glu Lys Arg Glu Thr Leu Ser Gln Ile Ser Asp Asp
            675                 680                 685

Leu Leu Ile Pro Gly Leu Gly Arg His Ser Ser Thr Phe Val Pro Trp
690                 695                 700

Glu Lys Glu Gly Lys Glu Ala Lys Glu Thr Ser Glu Asp Ile Gly Leu
705                 710                 715                 720

Leu His Glu Val Val Ser Leu Cys His Met Thr Ser Asp Phe Gln Gln
                725                 730                 735

Ser Leu Asn Ile Ser Asp Lys Asn Thr Asn Gly Asn Gln Thr Arg Ser
                740                 745                 750

<210> SEQ ID NO 65
<211> LENGTH: 2259
<212> TYPE: DNA
<213> ORGANISM: Homo sapiens
<220> FEATURE:
<221> NAME/KEY: CDS
<222> LOCATION: (1)..(2259)

<400> SEQUENCE: 65 aga tct gat cct gtg gta ttg tgg aaa ttc cca gag gac ttt gga gac        48
Arg Ser Asp Pro Val Val Leu Trp Lys Phe Pro Glu Asp Phe Gly Asp
 1               5                  10                  15 cag gaa ata cta cag agt gtg cca aag ttc tgt ttt ccc ttt gac gtt        96
Gln Glu Ile Leu Gln Ser Val Pro Lys Phe Cys Phe Pro Phe Asp Val
             20                  25                  30 gaa agg gtg tct cag aat caa gtt gga cag cac ttt acc ttt gta ctg       144
Glu Arg Val Ser Gln Asn Gln Val Gly Gln His Phe Thr Phe Val Leu
         35                  40                  45 aca gac att gaa agt aaa cag aga ttt gga ttc tgc aga ctg acg tca       192
Thr Asp Ile Glu Ser Lys Gln Arg Phe Gly Phe Cys Arg Leu Thr Ser
     50                  55                  60 gga ggc aca att tgt tta tgc atc ctt agt tac ctt ccc tgg ttt gaa       240
Gly Gly Thr Ile Cys Leu Cys Ile Leu Ser Tyr Leu Pro Trp Phe Glu
 65                  70                  75                  80 gtg tat tac aag ctt cta aat act ctt gca gat tac ttg gct aag gaa       288
Val Tyr Tyr Lys Leu Leu Asn Thr Leu Ala Asp Tyr Leu Ala Lys Glu
                 85                  90                  95 ctg gaa aat gat ttg aat gaa act ctc aga tca ctg tat aac cac cca       336
Leu Glu Asn Asp Leu Asn Glu Thr Leu Arg Ser Leu Tyr Asn His Pro
            100                 105                 110 gta cca aag gca aat act cct gta aat ttg agt gtg aac caa gag ata       384
Val Pro Lys Ala Asn Thr Pro Val Asn Leu Ser Val Asn Gln Glu Ile
        115                 120                 125 ttt att gcc tgt gag caa gtt ctg aaa gat cag cct gct cta gta ccg       432
Phe Ile Ala Cys Glu Gln Val Leu Lys Asp Gln Pro Ala Leu Val Pro
    130                 135                 140 cat tcc tac ttc att gcc cct gat gta act gga ctc cca aca ata ccc       480
His Ser Tyr Phe Ile Ala Pro Asp Val Thr Gly Leu Pro Thr Ile Pro
145                 150                 155                 160

-continued

| | |
|---|---|
| gag agt aga aat ctt aca gaa tat ttt gtt gcc gtg gat gtg aac aac<br>Glu Ser Arg Asn Leu Thr Glu Tyr Phe Val Ala Val Asp Val Asn Asn<br>               165                    170                   175 | 528 |
| atg ctg cag ctg tat gcc agt atg ctg cat gaa agg cgc atc gtg att<br>Met Leu Gln Leu Tyr Ala Ser Met Leu His Glu Arg Arg Ile Val Ile<br>           180                    185                   190 | 576 |
| atc tcg agc aaa tta agc act tta act gcc tgt atc cat gga tca gct<br>Ile Ser Ser Lys Leu Ser Thr Leu Thr Ala Cys Ile His Gly Ser Ala<br>       195                  200                  205 | 624 |
| gct ctt cta tac cca atg tat tgg caa cac ata tac atc cca gtg ctt<br>Ala Leu Leu Tyr Pro Met Tyr Trp Gln His Ile Tyr Ile Pro Val Leu<br>210                   215                  220 | 672 |
| cct cca cac ctg ctg gac tac tgc tgt gcc cca atg cca tac ctg att<br>Pro Pro His Leu Leu Asp Tyr Cys Cys Ala Pro Met Pro Tyr Leu Ile<br>225                   230                  235                  240 | 720 |
| gga ata cac tcc agc ctc ata gag aga gtg aaa aac aaa tca ttg gaa<br>Gly Ile His Ser Ser Leu Ile Glu Arg Val Lys Asn Lys Ser Leu Glu<br>               245                  250                  255 | 768 |
| gat gtt gtt atg tta aat gtt gat aca aac aca tta gaa tca cca ttt<br>Asp Val Val Met Leu Asn Val Asp Thr Asn Thr Leu Glu Ser Pro Phe<br>           260                    265                   270 | 816 |
| agt gac ttg aac aac cta cca agt gat gtg gtc tcg gcc ttg aaa aat<br>Ser Asp Leu Asn Asn Leu Pro Ser Asp Val Val Ser Ala Leu Lys Asn<br>275                   280                  285 | 864 |
| aaa ctg aag aag cag tct aca gct acg ggt gat gga gta gct agg gcc<br>Lys Leu Lys Lys Gln Ser Thr Ala Thr Gly Asp Gly Val Ala Arg Ala<br>       290                  295                  300 | 912 |
| ttt ctt aga gca cag gct gct ttg ttt gga tcc tac aga gat gca ctg<br>Phe Leu Arg Ala Gln Ala Ala Leu Phe Gly Ser Tyr Arg Asp Ala Leu<br>305                   310                  315                  320 | 960 |
| aga tac aaa cct ggt gag ccc atc act ttc tgt gag gag agt ttt gta<br>Arg Tyr Lys Pro Gly Glu Pro Ile Thr Phe Cys Glu Glu Ser Phe Val<br>               325                  330                  335 | 1008 |
| aag cac cgc tca agc gtg atg aaa cag ttc ctg gaa act gcc att aac<br>Lys His Arg Ser Ser Val Met Lys Gln Phe Leu Glu Thr Ala Ile Asn<br>           340                    345                   350 | 1056 |
| ctc cag ctt ttt aag cag ttt atc gat ggt cga ctg gca aaa cta aat<br>Leu Gln Leu Phe Lys Gln Phe Ile Asp Gly Arg Leu Ala Lys Leu Asn<br>       355                  360                  365 | 1104 |
| gca gga agg ggt ttc tct gat gta ttt gaa gaa gag atc act tca ggt<br>Ala Gly Arg Gly Phe Ser Asp Val Phe Glu Glu Glu Ile Thr Ser Gly<br>370                   375                  380 | 1152 |
| ggc ttt tgt gga ggg aac ccg agg tca tat caa caa tgg gtg cat aca<br>Gly Phe Cys Gly Gly Asn Pro Arg Ser Tyr Gln Gln Trp Val His Thr<br>385                   390                  395                  400 | 1200 |
| gtc aag aaa gga ggt gca ctg ttc aac aca gca atg acc aaa gca acc<br>Val Lys Lys Gly Gly Ala Leu Phe Asn Thr Ala Met Thr Lys Ala Thr<br>               405                  410                  415 | 1248 |
| cct gct gta cgg aca gca tat aaa ttt gca aaa aat cat gca aag ctg<br>Pro Ala Val Arg Thr Ala Tyr Lys Phe Ala Lys Asn His Ala Lys Leu<br>           420                    425                   430 | 1296 |
| gga cta aag gaa gtg aag agt aaa cta aaa cac aag gaa aat gaa gaa<br>Gly Leu Lys Glu Val Lys Ser Lys Leu Lys His Lys Glu Asn Glu Glu<br>       435                  440                  445 | 1344 |
| gat tat ggg acc tgt tct agt tct gta caa tat aca cca gtt tac aaa<br>Asp Tyr Gly Thr Cys Ser Ser Ser Val Gln Tyr Thr Pro Val Tyr Lys<br>450                   455                  460 | 1392 |
| tta cac aat gaa aag gga gga aac tca gaa aag cgt aag ctt gct cag<br>Leu His Asn Glu Lys Gly Gly Asn Ser Glu Lys Arg Lys Leu Ala Gln | 1440 |

```
                    465                 470                 475                 480
gca cgc tta aaa agg cct ctt aag agc ctt gat ggt gct cta tat gat          1488
Ala Arg Leu Lys Arg Pro Leu Lys Ser Leu Asp Gly Ala Leu Tyr Asp
                485                 490                 495 gat gaa gat gat gat gac att gaa aga gca agc aag tta tct tct gaa          1536
Asp Glu Asp Asp Asp Asp Ile Glu Arg Ala Ser Lys Leu Ser Ser Glu
        500                 505                 510 gat ggt gaa gaa gct tct gct tat ctc tat gag agt gat gac tct gtt          1584
Asp Gly Glu Glu Ala Ser Ala Tyr Leu Tyr Glu Ser Asp Asp Ser Val
    515                 520                 525 gaa aca aga gtg aag act cct tac tca ggt gaa atg gac tta cta gga          1632
Glu Thr Arg Val Lys Thr Pro Tyr Ser Gly Glu Met Asp Leu Leu Gly
530                 535                 540 gag att ctt gat aca ttg agc aca cac agc tca gat cag ggg aag ctg          1680
Glu Ile Leu Asp Thr Leu Ser Thr His Ser Ser Asp Gln Gly Lys Leu
545                 550                 555                 560 gca gct gca aag agc ttg gat ttc ttt aga tca atg gat gac att gat          1728
Ala Ala Ala Lys Ser Leu Asp Phe Phe Arg Ser Met Asp Asp Ile Asp
                565                 570                 575 tac aaa cct acg aat aaa tct aat gct cct agt gag aat aac ctg gct          1776
Tyr Lys Pro Thr Asn Lys Ser Asn Ala Pro Ser Glu Asn Asn Leu Ala
                580                 585                 590 ttc ctc tgt agt ggt tct ggt gac caa gca gag tgg aat ctt ggg caa          1824
Phe Leu Cys Ser Gly Ser Gly Asp Gln Ala Glu Trp Asn Leu Gly Gln
        595                 600                 605 gac gat agt gcc ctc cat ggc aaa cac ctc cct cca tct cct agg aag          1872
Asp Asp Ser Ala Leu His Gly Lys His Leu Pro Pro Ser Pro Arg Lys
    610                 615                 620 cgg gtt tcc tct agt ggt ttg aca gat tct ctg tct atc ctg aaa gag          1920
Arg Val Ser Ser Ser Gly Leu Thr Asp Ser Leu Ser Ile Leu Lys Glu
625                 630                 635                 640 gaa aac agt aac aag cac ctc ggt gct gac aat gtg agt gac cct act          1968
Glu Asn Ser Asn Lys His Leu Gly Ala Asp Asn Val Ser Asp Pro Thr
                645                 650                 655 tca gga ctg gat ttc caa ctc act tcc cct gaa gtt tcc cag act gat          2016
Ser Gly Leu Asp Phe Gln Leu Thr Ser Pro Glu Val Ser Gln Thr Asp
                660                 665                 670 aaa gga aaa aca gaa aag agg gaa aca cta agc cag att tca gat gat          2064
Lys Gly Lys Thr Glu Lys Arg Glu Thr Leu Ser Gln Ile Ser Asp Asp
        675                 680                 685 ctg ctt ata ccc ggt ctt ggg cgg cat tca tcg act ttt gtt cct tgg          2112
Leu Leu Ile Pro Gly Leu Gly Arg His Ser Ser Thr Phe Val Pro Trp
    690                 695                 700 gag aaa gaa ggg aaa gaa gcc aaa gag act tca gaa gat att gga ctg          2160
Glu Lys Glu Gly Lys Glu Ala Lys Glu Thr Ser Glu Asp Ile Gly Leu
705                 710                 715                 720 ctc cat gaa gta gtg tca tta tgt cat atg aca tct gac ttc caa gct          2208
Leu His Glu Val Val Ser Leu Cys His Met Thr Ser Asp Phe Gln Ala
                725                 730                 735 aaa gct tgg aac att tca gac aaa aac aca aat gga aac caa act aga          2256
Lys Ala Trp Asn Ile Ser Asp Lys Asn Thr Asn Gly Asn Gln Thr Arg
                740                 745                 750 tct                                                                      2259
Ser <210> SEQ ID NO 66
<211> LENGTH: 753
<212> TYPE: PRT
<213> ORGANISM: Homo sapiens
```

-continued

<400> SEQUENCE: 66

```
Arg Ser Asp Pro Val Val Leu Trp Lys Phe Pro Glu Asp Phe Gly Asp
  1               5                  10                  15

Gln Glu Ile Leu Gln Ser Val Pro Lys Phe Cys Phe Pro Phe Asp Val
             20                  25                  30

Glu Arg Val Ser Gln Asn Gln Val Gly Gln His Phe Thr Phe Val Leu
         35                  40                  45

Thr Asp Ile Glu Ser Lys Gln Arg Phe Gly Phe Cys Arg Leu Thr Ser
     50                  55                  60

Gly Gly Thr Ile Cys Leu Cys Ile Leu Ser Tyr Leu Pro Trp Phe Glu
 65                  70                  75                  80

Val Tyr Tyr Lys Leu Leu Asn Thr Leu Ala Asp Tyr Leu Ala Lys Glu
                 85                  90                  95

Leu Glu Asn Asp Leu Asn Glu Thr Leu Arg Ser Leu Tyr Asn His Pro
             100                 105                 110

Val Pro Lys Ala Asn Thr Pro Val Asn Leu Ser Val Asn Gln Glu Ile
         115                 120                 125

Phe Ile Ala Cys Glu Gln Val Leu Lys Asp Gln Pro Ala Leu Val Pro
    130                 135                 140

His Ser Tyr Phe Ile Ala Pro Asp Val Thr Gly Leu Pro Thr Ile Pro
145                 150                 155                 160

Glu Ser Arg Asn Leu Thr Glu Tyr Phe Val Ala Val Asp Val Asn Asn
                165                 170                 175

Met Leu Gln Leu Tyr Ala Ser Met Leu His Glu Arg Arg Ile Val Ile
            180                 185                 190

Ile Ser Ser Lys Leu Ser Thr Leu Thr Ala Cys Ile His Gly Ser Ala
        195                 200                 205

Ala Leu Leu Tyr Pro Met Tyr Trp Gln His Ile Tyr Ile Pro Val Leu
    210                 215                 220

Pro Pro His Leu Leu Asp Tyr Cys Cys Ala Pro Met Pro Tyr Leu Ile
225                 230                 235                 240

Gly Ile His Ser Ser Leu Ile Glu Arg Val Lys Asn Lys Ser Leu Glu
                245                 250                 255

Asp Val Val Met Leu Asn Val Asp Thr Asn Thr Leu Glu Ser Pro Phe
            260                 265                 270

Ser Asp Leu Asn Asn Leu Pro Ser Asp Val Val Ser Ala Leu Lys Asn
        275                 280                 285

Lys Leu Lys Lys Gln Ser Thr Ala Thr Gly Asp Gly Val Ala Arg Ala
    290                 295                 300

Phe Leu Arg Ala Gln Ala Ala Leu Phe Gly Ser Tyr Arg Asp Ala Leu
305                 310                 315                 320

Arg Tyr Lys Pro Gly Glu Pro Ile Thr Phe Cys Glu Glu Ser Phe Val
                325                 330                 335

Lys His Arg Ser Ser Val Met Lys Gln Phe Leu Glu Thr Ala Ile Asn
            340                 345                 350

Leu Gln Leu Phe Lys Gln Phe Ile Asp Gly Arg Leu Ala Lys Leu Asn
        355                 360                 365

Ala Gly Arg Gly Phe Ser Asp Val Phe Glu Glu Ile Thr Ser Gly
    370                 375                 380

Gly Phe Cys Gly Gly Asn Pro Arg Ser Tyr Gln Gln Trp Val His Thr
385                 390                 395                 400

Val Lys Lys Gly Gly Ala Leu Phe Asn Thr Ala Met Thr Lys Ala Thr
                405                 410                 415
```

-continued

```
Pro Ala Val Arg Thr Ala Tyr Lys Phe Ala Lys Asn His Ala Lys Leu
            420                 425                 430
Gly Leu Lys Glu Val Lys Ser Lys Leu Lys His Lys Glu Asn Glu Glu
        435                 440                 445
Asp Tyr Gly Thr Cys Ser Ser Val Gln Tyr Thr Pro Val Tyr Lys
    450                 455                 460
Leu His Asn Glu Lys Gly Gly Asn Ser Glu Lys Arg Lys Leu Ala Gln
465                 470                 475                 480
Ala Arg Leu Lys Arg Pro Leu Lys Ser Leu Asp Gly Ala Leu Tyr Asp
                485                 490                 495
Asp Glu Asp Asp Asp Ile Glu Arg Ala Ser Lys Leu Ser Ser Glu
            500                 505                 510
Asp Gly Glu Glu Ala Ser Ala Tyr Leu Tyr Glu Ser Asp Asp Ser Val
        515                 520                 525
Glu Thr Arg Val Lys Thr Pro Tyr Ser Gly Met Asp Leu Leu Gly
    530                 535                 540
Glu Ile Leu Asp Thr Leu Ser Thr His Ser Ser Asp Gln Gly Lys Leu
545                 550                 555                 560
Ala Ala Ala Lys Ser Leu Asp Phe Phe Arg Ser Met Asp Asp Ile Asp
                565                 570                 575
Tyr Lys Pro Thr Asn Lys Ser Asn Ala Pro Ser Glu Asn Asn Leu Ala
            580                 585                 590
Phe Leu Cys Ser Gly Ser Gly Asp Gln Ala Glu Trp Asn Leu Gly Gln
        595                 600                 605
Asp Asp Ser Ala Leu His Gly Lys His Leu Pro Pro Ser Pro Arg Lys
    610                 615                 620
Arg Val Ser Ser Ser Gly Leu Thr Asp Ser Leu Ser Ile Leu Lys Glu
625                 630                 635                 640
Glu Asn Ser Asn Lys His Leu Gly Ala Asp Asn Val Ser Asp Pro Thr
                645                 650                 655
Ser Gly Leu Asp Phe Gln Leu Thr Ser Pro Glu Val Ser Gln Thr Asp
            660                 665                 670
Lys Gly Lys Thr Glu Lys Arg Glu Thr Leu Ser Gln Ile Ser Asp Asp
        675                 680                 685
Leu Leu Ile Pro Gly Leu Gly Arg His Ser Ser Thr Phe Val Pro Trp
    690                 695                 700
Glu Lys Glu Gly Lys Glu Ala Lys Glu Thr Ser Glu Asp Ile Gly Leu
705                 710                 715                 720
Leu His Glu Val Val Ser Leu Cys His Met Thr Ser Asp Phe Gln Ala
                725                 730                 735
Lys Ala Trp Asn Ile Ser Asp Lys Asn Thr Asn Gly Asn Gln Thr Arg
            740                 745                 750
Ser
```

<210> SEQ ID NO 67
<211> LENGTH: 2256
<212> TYPE: DNA
<213> ORGANISM: Homo sapiens
<220> FEATURE:
<221> NAME/KEY: CDS
<222> LOCATION: (1)..(2256)

<400> SEQUENCE: 67

```
aga tct gat cct gtg gta ttg tgg aaa ttc cca gag gac ttt gga gac      48
Arg Ser Asp Pro Val Val Leu Trp Lys Phe Pro Glu Asp Phe Gly Asp
```

```
  1                   5                    10                   15
cag gaa ata cta cag agt gtg cca aag ttc tgt ttt ccc ttt gac gtt        96
Gln Glu Ile Leu Gln Ser Val Pro Lys Phe Cys Phe Pro Phe Asp Val
            20                  25                  30 gaa agg gtg tct cag aat caa gtt gga cag cac ttt acc ttt gta ctg       144
Glu Arg Val Ser Gln Asn Gln Val Gly Gln His Phe Thr Phe Val Leu
        35                  40                  45 aca gac att gaa agt aaa cag aga ttt gga ttc tgc aga ctg acg tca       192
Thr Asp Ile Glu Ser Lys Gln Arg Phe Gly Phe Cys Arg Leu Thr Ser
    50                  55                  60 gga ggc aca att tgt tta tgc atc ctt agt tac ctt ccc tgg ttt gaa       240
Gly Gly Thr Ile Cys Leu Cys Ile Leu Ser Tyr Leu Pro Trp Phe Glu
65                  70                  75                  80 gtg tat tac aag ctt cta aat act ctt gca gat tac ttg gct aag gaa       288
Val Tyr Tyr Lys Leu Leu Asn Thr Leu Ala Asp Tyr Leu Ala Lys Glu
                85                  90                  95 ctg gaa aat gat ttg aat gaa act ctc aga tca ctg tat aac cac cca       336
Leu Glu Asn Asp Leu Asn Glu Thr Leu Arg Ser Leu Tyr Asn His Pro
            100                 105                 110 gta cca aag gca aat act cct gta aat ttg agt gtg aac caa gag ata       384
Val Pro Lys Ala Asn Thr Pro Val Asn Leu Ser Val Asn Gln Glu Ile
        115                 120                 125 ttt att gcc tgt gag caa gtt ctg aaa gat cag cct gct cta gta ccg       432
Phe Ile Ala Cys Glu Gln Val Leu Lys Asp Gln Pro Ala Leu Val Pro
    130                 135                 140 cat tcc tac ttc att gcc cct gat gta act gga ctc cca aca ata ccc       480
His Ser Tyr Phe Ile Ala Pro Asp Val Thr Gly Leu Pro Thr Ile Pro
145                 150                 155                 160 gag agt aga aat ctt aca gaa tat ttt gtt gcc gtg gat gtg aac aac       528
Glu Ser Arg Asn Leu Thr Glu Tyr Phe Val Ala Val Asp Val Asn Asn
                165                 170                 175 atg ctg cag ctg tat gcc agt atg ctg cat gaa agg cgc atc gtg att       576
Met Leu Gln Leu Tyr Ala Ser Met Leu His Glu Arg Arg Ile Val Ile
            180                 185                 190 atc tcg agc aaa tta agc act tta act gcc tgt atc cat gga tca gct       624
Ile Ser Ser Lys Leu Ser Thr Leu Thr Ala Cys Ile His Gly Ser Ala
        195                 200                 205 gct ctt cta tac cca atg tat tgg caa cac ata tac atc cca gtg ctt       672
Ala Leu Leu Tyr Pro Met Tyr Trp Gln His Ile Tyr Ile Pro Val Leu
    210                 215                 220 cct cca cac ctg ctg gac tac tgc tgt gcc cca atg cca tac ctg att       720
Pro Pro His Leu Leu Asp Tyr Cys Cys Ala Pro Met Pro Tyr Leu Ile
225                 230                 235                 240 gga ata cac tcc agc ctc ata gag aga gtg aaa aac aaa tca ttg gaa       768
Gly Ile His Ser Ser Leu Ile Glu Arg Val Lys Asn Lys Ser Leu Glu
                245                 250                 255 gat gtt gtt atg tta aat gtt gat aca aac aca tta gaa tca cca ttt       816
Asp Val Val Met Leu Asn Val Asp Thr Asn Thr Leu Glu Ser Pro Phe
            260                 265                 270 agt gac ttg aac aac cta cca agt gat gtg gtc tcg gcc ttg aaa aat       864
Ser Asp Leu Asn Asn Leu Pro Ser Asp Val Val Ser Ala Leu Lys Asn
        275                 280                 285 aaa ctg aag aag cag tct aca gct acg ggt gat gga gta gct agg gcc       912
Lys Leu Lys Lys Gln Ser Thr Ala Thr Gly Asp Gly Val Ala Arg Ala
    290                 295                 300 ttt ctt aga gca cag gct gct ttg ttt gga tcc tac aga gat gca ctg       960
Phe Leu Arg Ala Gln Ala Ala Leu Phe Gly Ser Tyr Arg Asp Ala Leu
305                 310                 315                 320 aga tac aaa cct ggt gag ccc atc act ttc tgt gag gag agt ttt gta      1008
```

```
                Arg Tyr Lys Pro Gly Glu Pro Ile Thr Phe Cys Glu Ser Phe Val
                            325                 330                 335 aag cac cgc tca agc gtg atg aaa cag ttc ctg gaa act gcc att aac          1056
Lys His Arg Ser Ser Val Met Lys Gln Phe Leu Glu Thr Ala Ile Asn
            340                 345                 350 ctc cag ctt ttt aag cag ttt atc gat ggt cga ctg gca aaa cta aat          1104
Leu Gln Leu Phe Lys Gln Phe Ile Asp Gly Arg Leu Ala Lys Leu Asn
            355                 360                 365 gca gga agg ggt ttc tct gat gta ttt gaa gaa gag atc act tca ggt          1152
Ala Gly Arg Gly Phe Ser Asp Val Phe Glu Glu Glu Ile Thr Ser Gly
            370                 375             380 ggc ttt tgt gga ggg aac ccg agg tca tat caa caa tgg gtg cat aca          1200
Gly Phe Cys Gly Gly Asn Pro Arg Ser Tyr Gln Gln Trp Val His Thr
385                 390                 395                 400 gtc aag aaa gga ggt gca ctg ttc aac aca gca atg acc aaa gca acc          1248
Val Lys Lys Gly Gly Ala Leu Phe Asn Thr Ala Met Thr Lys Ala Thr
                405                 410                 415 cct gct gta cgg aca gca tat aaa ttt gca aaa aat cat gca aag ctg          1296
Pro Ala Val Arg Thr Ala Tyr Lys Phe Ala Lys Asn His Ala Lys Leu
                420                 425                 430 gga cta aag gaa gtg aag agt aaa cta aaa cac aag gaa aat gaa gaa          1344
Gly Leu Lys Glu Val Lys Ser Lys Leu Lys His Lys Glu Asn Glu Glu
            435                 440                 445 gat tat ggg acc tgt tct agt tct gta caa tat aca cca gtt tac aaa          1392
Asp Tyr Gly Thr Cys Ser Ser Ser Val Gln Tyr Thr Pro Val Tyr Lys
        450                 455                 460 tta cac aat gaa aag gga gga aac tca gaa aag cgt aag ctt gct cag          1440
Leu His Asn Glu Lys Gly Gly Asn Ser Glu Lys Arg Lys Leu Ala Gln
465                 470                 475                 480 gca cgc tta aaa agg cct ctt aag agc ctt gat ggt gct cta tat gat          1488
Ala Arg Leu Lys Arg Pro Leu Lys Ser Leu Asp Gly Ala Leu Tyr Asp
                485                 490                 495 gat gaa gat gat gat gac att gaa aga gca agc aag tta tct tct gaa          1536
Asp Glu Asp Asp Asp Asp Ile Glu Arg Ala Ser Lys Leu Ser Ser Glu
            500                 505                 510 gat ggt gaa gaa gct tct gct tat ctc tat gag agt gat gac tct gtt          1584
Asp Gly Glu Glu Ala Ser Ala Tyr Leu Tyr Glu Ser Asp Asp Ser Val
        515                 520                 525 gaa aca aga gtg aag act cct tac tca ggt gaa atg gac tta cta gga          1632
Glu Thr Arg Val Lys Thr Pro Tyr Ser Gly Glu Met Asp Leu Leu Gly
        530                 535                 540 gag att ctt gat aca ttg agc aca cac agc tca gat cag ggg aag ctg          1680
Glu Ile Leu Asp Thr Leu Ser Thr His Ser Ser Asp Gln Gly Lys Leu
545                 550                 555                 560 gca gct gca aag agc ttg gat ttc ttt aga tca atg gat gac att gat          1728
Ala Ala Ala Lys Ser Leu Asp Phe Phe Arg Ser Met Asp Asp Ile Asp
                565                 570                 575 tac aaa cct acg aat aaa tct aat gct cct agt gag aat aac ctg gct          1776
Tyr Lys Pro Thr Asn Lys Ser Asn Ala Pro Ser Glu Asn Asn Leu Ala
            580                 585                 590 ttc ctc tgt ggt ggt tct ggt gac caa gca gag tgg aat ctt ggg caa          1824
Phe Leu Cys Gly Gly Ser Gly Asp Gln Ala Glu Trp Asn Leu Gly Gln
            595                 600                 605 gac gat agt gcc ctc cat ggc aaa cac ctc cct cca tct cct agg aag          1872
Asp Asp Ser Ala Leu His Gly Lys His Leu Pro Pro Ser Pro Arg Lys
610                 615                 620 cgg gtt tcc tct agt ggt ttg aca gat tct ctg ttt atc ctg aaa gag          1920
Arg Val Ser Ser Ser Gly Leu Thr Asp Ser Leu Phe Ile Leu Lys Glu
625                 630                 635                 640
```

| | | | | | | | | | | | | | | |
|---|---|---|---|---|---|---|---|---|---|---|---|---|---|---|
| gaa | aac | agt | aac | aag | cac | ctc | ggt | gct | gac | aat | gtg | agt | gac | cct | act | 1968 |
| Glu | Asn | Ser | Asn | Lys | His | Leu | Gly | Ala | Asp | Asn | Val | Ser | Asp | Pro | Thr | |
| | | | 645 | | | | | 650 | | | | | 655 | | | |

| | | | | | | | | | | | | | | |
|---|---|---|---|---|---|---|---|---|---|---|---|---|---|---|
| tca | gga | ctg | gat | ttc | caa | ctc | act | tcc | cct | gaa | gtt | tcc | cag | act | gat | 2016 |
| Ser | Gly | Leu | Asp | Phe | Gln | Leu | Thr | Ser | Pro | Glu | Val | Ser | Gln | Thr | Asp | |
| | | 660 | | | | | 665 | | | | | 670 | | | | |

| | | | | | | | | | | | | | | |
|---|---|---|---|---|---|---|---|---|---|---|---|---|---|---|
| aaa | gga | aaa | aca | gaa | aag | agg | gaa | aca | cta | agc | cag | att | tca | gat | gat | 2064 |
| Lys | Gly | Lys | Thr | Glu | Lys | Arg | Glu | Thr | Leu | Ser | Gln | Ile | Ser | Asp | Asp | |
| | | | 675 | | | | | 680 | | | | | 685 | | | |

| | | | | | | | | | | | | | | |
|---|---|---|---|---|---|---|---|---|---|---|---|---|---|---|
| ctg | ctt | ata | ccc | ggt | ctt | ggg | cgg | cat | tcg | act | ttt | gtt | cct | tgg | | 2112 |
| Leu | Leu | Ile | Pro | Gly | Leu | Gly | Arg | His | Ser | Ser | Thr | Phe | Val | Pro | Trp | |
| | | 690 | | | | | 695 | | | | | 700 | | | | |

| | | | | | | | | | | | | | | |
|---|---|---|---|---|---|---|---|---|---|---|---|---|---|---|
| gag | aaa | gaa | ggg | aaa | gaa | gcc | aaa | gag | act | tca | gaa | gat | att | gga | ctg | 2160 |
| Glu | Lys | Glu | Gly | Lys | Glu | Ala | Lys | Glu | Thr | Ser | Glu | Asp | Ile | Gly | Leu | |
| 705 | | | | | 710 | | | | | 715 | | | | | 720 | |

| | | | | | | | | | | | | | | |
|---|---|---|---|---|---|---|---|---|---|---|---|---|---|---|
| ctc | cat | gaa | gta | gtg | tca | tta | tgt | cat | atg | aca | tct | gac | ttc | caa | caa | 2208 |
| Leu | His | Glu | Val | Val | Ser | Leu | Cys | His | Met | Thr | Ser | Asp | Phe | Gln | Gln | |
| | | | | 725 | | | | | 730 | | | | | 735 | | |

| | | | | | | | | | | | | | | |
|---|---|---|---|---|---|---|---|---|---|---|---|---|---|---|
| agc | ttg | aac | att | tca | gac | aaa | aac | aca | aat | gga | aac | caa | act | aga | tct | 2256 |
| Ser | Leu | Asn | Ile | Ser | Asp | Lys | Asn | Thr | Asn | Gly | Asn | Gln | Thr | Arg | Ser | |
| | | | 740 | | | | | 745 | | | | | 750 | | | |

<210> SEQ ID NO 68
<211> LENGTH: 752
<212> TYPE: PRT
<213> ORGANISM: Homo sapiens

<400> SEQUENCE: 68

```
Arg Ser Asp Pro Val Val Leu Trp Lys Phe Pro Glu Asp Phe Gly Asp
 1               5                  10                  15

Gln Glu Ile Leu Gln Ser Val Pro Lys Phe Cys Phe Pro Phe Asp Val
                20                  25                  30

Glu Arg Val Ser Gln Asn Gln Val Gly Gln His Phe Thr Phe Val Leu
            35                  40                  45

Thr Asp Ile Glu Ser Lys Gln Arg Phe Gly Phe Cys Arg Leu Thr Ser
        50                  55                  60

Gly Gly Thr Ile Cys Leu Cys Ile Leu Ser Tyr Leu Pro Trp Phe Glu
 65                  70                  75                  80

Val Tyr Tyr Lys Leu Leu Asn Thr Leu Ala Asp Tyr Leu Ala Lys Glu
                85                  90                  95

Leu Glu Asn Asp Leu Asn Glu Thr Leu Arg Ser Leu Tyr Asn His Pro
            100                 105                 110

Val Pro Lys Ala Asn Thr Pro Val Asn Leu Ser Val Asn Gln Glu Ile
        115                 120                 125

Phe Ile Ala Cys Glu Gln Val Leu Lys Asp Gln Pro Ala Leu Val Pro
    130                 135                 140

His Ser Tyr Phe Ile Ala Pro Asp Val Thr Gly Leu Pro Thr Ile Pro
145                 150                 155                 160

Glu Ser Arg Asn Leu Thr Glu Tyr Phe Val Ala Val Asp Val Asn Asn
                165                 170                 175

Met Leu Gln Leu Tyr Ala Ser Met Leu His Glu Arg Arg Ile Val Ile
            180                 185                 190

Ile Ser Ser Lys Leu Ser Thr Leu Thr Ala Cys Ile His Gly Ser Ala
        195                 200                 205

Ala Leu Leu Tyr Pro Met Tyr Trp Gln His Ile Tyr Ile Pro Val Leu
    210                 215                 220

Pro Pro His Leu Leu Asp Tyr Cys Cys Ala Pro Met Pro Tyr Leu Ile
```

```
225                 230                 235                 240
Gly Ile His Ser Ser Leu Ile Glu Arg Val Lys Asn Lys Ser Leu Glu
                245                 250                 255
Asp Val Val Met Leu Asn Val Asp Thr Asn Thr Leu Glu Ser Pro Phe
                260                 265                 270
Ser Asp Leu Asn Asn Leu Pro Ser Asp Val Val Ser Ala Leu Lys Asn
                275                 280                 285
Lys Leu Lys Lys Gln Ser Thr Ala Thr Gly Asp Gly Val Ala Arg Ala
            290                 295                 300
Phe Leu Arg Ala Gln Ala Ala Leu Phe Gly Ser Tyr Arg Asp Ala Leu
305                 310                 315                 320
Arg Tyr Lys Pro Gly Glu Pro Ile Thr Phe Cys Glu Glu Ser Phe Val
                325                 330                 335
Lys His Arg Ser Ser Val Met Lys Gln Phe Leu Glu Thr Ala Ile Asn
                340                 345                 350
Leu Gln Leu Phe Lys Gln Phe Ile Asp Gly Arg Leu Ala Lys Leu Asn
                355                 360                 365
Ala Gly Arg Gly Phe Ser Asp Val Phe Glu Glu Ile Thr Ser Gly
            370                 375                 380
Gly Phe Cys Gly Gly Asn Pro Arg Ser Tyr Gln Gln Trp Val His Thr
385                 390                 395                 400
Val Lys Lys Gly Gly Ala Leu Phe Asn Thr Ala Met Thr Lys Ala Thr
                405                 410                 415
Pro Ala Val Arg Thr Ala Tyr Lys Phe Ala Lys Asn His Ala Lys Leu
                420                 425                 430
Gly Leu Lys Glu Val Lys Ser Lys Leu Lys His Lys Glu Asn Glu Glu
            435                 440                 445
Asp Tyr Gly Thr Cys Ser Ser Val Gln Tyr Thr Pro Val Tyr Lys
        450                 455                 460
Leu His Asn Glu Lys Gly Gly Asn Ser Glu Lys Arg Lys Leu Ala Gln
465                 470                 475                 480
Ala Arg Leu Lys Arg Pro Leu Lys Ser Leu Asp Gly Ala Leu Tyr Asp
                485                 490                 495
Asp Glu Asp Asp Asp Ile Glu Arg Ala Ser Lys Leu Ser Ser Glu
            500                 505                 510
Asp Gly Glu Glu Ala Ser Ala Tyr Leu Tyr Glu Ser Asp Asp Ser Val
        515                 520                 525
Glu Thr Arg Val Lys Thr Pro Tyr Ser Gly Met Asp Leu Leu Gly
    530                 535                 540
Glu Ile Leu Asp Thr Leu Ser Thr His Ser Ser Asp Gln Gly Lys Leu
545                 550                 555                 560
Ala Ala Ala Lys Ser Leu Asp Phe Phe Arg Ser Met Asp Ile Asp
                565                 570                 575
Tyr Lys Pro Thr Asn Lys Ser Asn Ala Pro Ser Glu Asn Asn Leu Ala
                580                 585                 590
Phe Leu Cys Gly Gly Ser Gly Asp Gln Ala Glu Trp Asn Leu Gly Gln
                595                 600                 605
Asp Asp Ser Ala Leu His Gly Lys His Leu Pro Pro Ser Pro Arg Lys
                610                 615                 620
Arg Val Ser Ser Gly Leu Thr Asp Ser Leu Phe Ile Leu Lys Glu
625                 630                 635                 640
Glu Asn Ser Asn Lys His Leu Gly Ala Asp Asn Val Ser Asp Pro Thr
                645                 650                 655
```

Ser Gly Leu Asp Phe Gln Leu Thr Ser Pro Glu Val Ser Gln Thr Asp
                660                 665                 670

Lys Gly Lys Thr Glu Lys Arg Glu Thr Leu Ser Gln Ile Ser Asp Asp
            675                 680                 685

Leu Leu Ile Pro Gly Leu Gly Arg His Ser Ser Thr Phe Val Pro Trp
        690                 695                 700

Glu Lys Glu Gly Lys Glu Ala Lys Glu Thr Ser Glu Asp Ile Gly Leu
705                 710                 715                 720

Leu His Glu Val Val Ser Leu Cys His Met Thr Ser Asp Phe Gln Gln
                725                 730                 735

Ser Leu Asn Ile Ser Asp Lys Asn Thr Asn Gly Asn Gln Thr Arg Ser
            740                 745                 750

<210> SEQ ID NO 69
<211> LENGTH: 1357
<212> TYPE: DNA
<213> ORGANISM: Homo sapiens
<220> FEATURE:
<221> NAME/KEY: CDS
<222> LOCATION: (1)..(1195)

<400> SEQUENCE: 69

```
atg aaa cta att acc atc ctt ttc ctc tgc tcc agg cta cta cta agt       48
Met Lys Leu Ile Thr Ile Leu Phe Leu Cys Ser Arg Leu Leu Leu Ser
 1               5                  10                  15 tta acc cag gaa tca cag tcc gag gaa att gat gac tgc aat gac aag       96
Leu Thr Gln Glu Ser Gln Ser Glu Glu Ile Asp Asp Cys Asn Asp Lys
             20                  25                  30 gat tta ttt aaa gct gtg gat gct gct ctg aag aaa tat aac agt caa      144
Asp Leu Phe Lys Ala Val Asp Ala Ala Leu Lys Lys Tyr Asn Ser Gln
         35                  40                  45 aac caa agt aac aac cag ttt gta ttg tac cgc aaa acc tgg cag gac      192
Asn Gln Ser Asn Asn Gln Phe Val Leu Tyr Arg Lys Thr Trp Gln Asp
     50                  55                  60 tgt gag tac aag gat gct gca aaa gca gcc act gga gaa tgc aca gca      240
Cys Glu Tyr Lys Asp Ala Ala Lys Ala Ala Thr Gly Glu Cys Thr Ala
 65                  70                  75                  80 acc gtg ggg aag agg agc agt acg aaa ttc tcc gtg gct acc cag acc      288
Thr Val Gly Lys Arg Ser Ser Thr Lys Phe Ser Val Ala Thr Gln Thr
                 85                  90                  95 tgc cag att act cca gcc gag ggc cct gtg gtg aca gcc cag tac gac      336
Cys Gln Ile Thr Pro Ala Glu Gly Pro Val Val Thr Ala Gln Tyr Asp
            100                 105                 110 tgc ctc ggc tgt gtg cat cct ata tca acg cag agc cca gac ctg gag      384
Cys Leu Gly Cys Val His Pro Ile Ser Thr Gln Ser Pro Asp Leu Glu
        115                 120                 125 ccc att ctg aga cac ggc att cag tac ttt aac aac aac act caa cat      432
Pro Ile Leu Arg His Gly Ile Gln Tyr Phe Asn Asn Asn Thr Gln His
    130                 135                 140 tcc tcc ctc ttc acg ctt aat gaa gta aaa cgg gcc caa aga cag gtg      480
Ser Ser Leu Phe Thr Leu Asn Glu Val Lys Arg Ala Gln Arg Gln Val
145                 150                 155                 160 gtg gct gga ttg aac ttt cga att acc tac tca att gtg caa acg aat      528
Val Ala Gly Leu Asn Phe Arg Ile Thr Tyr Ser Ile Val Gln Thr Asn
                165                 170                 175 tgt tcc aaa gag aat ttt ctg ttc tta act cca gac tgc aag tcc ctt      576
Cys Ser Lys Glu Asn Phe Leu Phe Leu Thr Pro Asp Cys Lys Ser Leu
            180                 185                 190 tgg aat ggt gat acc ggt gaa tgt aca gat aat gca tac atc gat att      624
```

-continued

```
                Trp Asn Gly Asp Thr Gly Glu Cys Thr Asp Asn Ala Tyr Ile Asp Ile
                                195                 200                 205 cag cta cga att gct tcc ttc tca cag aac tgt gac att tat cca ggg          672
Gln Leu Arg Ile Ala Ser Phe Ser Gln Asn Cys Asp Ile Tyr Pro Gly
    210                 215                 220 aag gat ttt gta caa cca cct acc aag att tgc gtg ggc tgc ccc aga          720
Lys Asp Phe Val Gln Pro Pro Thr Lys Ile Cys Val Gly Cys Pro Arg
225                 230                 235                 240 gat ata ccc acc aac agc cca gag ctg gag gag aca ctg act cac acc          768
Asp Ile Pro Thr Asn Ser Pro Glu Leu Glu Glu Thr Leu Thr His Thr
                245                 250                 255 atc aca aag ctt aat gca gag aat aac gca act ttc tat ttc aag att          816
Ile Thr Lys Leu Asn Ala Glu Asn Asn Ala Thr Phe Tyr Phe Lys Ile
            260                 265                 270 gac aat gtg aaa aaa gca aga gta cag gtg gtg gct ggc aag aaa tat          864
Asp Asn Val Lys Lys Ala Arg Val Gln Val Val Ala Gly Lys Lys Tyr
        275                 280                 285 ttt att gac ttc gtg gcc agg gaa acc aca tgt tcc aag gaa agt aat          912
Phe Ile Asp Phe Val Ala Arg Glu Thr Thr Cys Ser Lys Glu Ser Asn
    290                 295                 300 gaa gag ttg acc gaa agc tgt gag acc aaa aaa ctt ggc caa agc cta          960
Glu Glu Leu Thr Glu Ser Cys Glu Thr Lys Lys Leu Gly Gln Ser Leu
305                 310                 315                 320 gat tgc aac gct gaa gtt tat gtg gta ccc tgg gag aaa aaa att tac         1008
Asp Cys Asn Ala Glu Val Tyr Val Val Pro Trp Glu Lys Lys Ile Tyr
                325                 330                 335 cct act gtc aac tgt caa cca ctg gga atg atc tca ctg atg aaa agg         1056
Pro Thr Val Asn Cys Gln Pro Leu Gly Met Ile Ser Leu Met Lys Arg
            340                 345                 350 cct cca ggt ttt tca cct ttc cga tca tca cga ata ggg gaa ata aaa         1104
Pro Pro Gly Phe Ser Pro Phe Arg Ser Ser Arg Ile Gly Glu Ile Lys
        355                 360                 365 gaa gaa aca act agt cac cta agg tcc tgc gag tac aag ggt cga ccc         1152
Glu Glu Thr Thr Ser His Leu Arg Ser Cys Glu Tyr Lys Gly Arg Pro
    370                 375                 380 cca aag gca ggg gca gag cca gca tct gag agg gag gtc tct                 1194
Pro Lys Ala Gly Ala Glu Pro Ala Ser Glu Arg Glu Val Ser
385                 390                 395 tgaccaatgg gcagaatctt cactccaggc acatagcccc aaccacctct                  1244
gccagcaacc ttgagaggaa ggacaagaag aaagatggga tagaatttaa                  1294
atagagaaga atgccatttt atcactctgc ctctgggtga ataaagatc                   1344 agtcttgatg ttc                                                          1357

<210> SEQ ID NO 70
<211> LENGTH: 398
<212> TYPE: PRT
<213> ORGANISM: Homo sapiens

<400> SEQUENCE: 70

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Asp Cys Asn Asp Lys
            20                  25                  30

Asp Leu Phe Lys Ala Val Asp Ala Ala Leu Lys Lys Tyr Asn Ser Gln
        35                  40                  45

Asn Gln Ser Asn Asn Gln Phe Val Leu Tyr Arg Lys Thr Trp Gln Asp
    50                  55                  60
```

```
Cys Glu Tyr Lys Asp Ala Ala Lys Ala Ala Thr Gly Glu Cys Thr Ala
 65                  70                  75                  80

Thr Val Gly Lys Arg Ser Ser Thr Lys Phe Ser Val Ala Thr Gln Thr
                 85                  90                  95

Cys Gln Ile Thr Pro Ala Glu Gly Pro Val Val Thr Ala Gln Tyr Asp
            100                 105                 110

Cys Leu Gly Cys Val His Pro Ile Ser Thr Gln Ser Pro Asp Leu Glu
        115                 120                 125

Pro Ile Leu Arg His Gly Ile Gln Tyr Phe Asn Asn Thr Gln His
130                 135                 140

Ser Ser Leu Phe Thr Leu Asn Glu Val Lys Arg Ala Gln Arg Gln Val
145                 150                 155                 160

Val Ala Gly Leu Asn Phe Arg Ile Thr Tyr Ser Ile Val Gln Thr Asn
                165                 170                 175

Cys Ser Lys Glu Asn Phe Leu Phe Leu Thr Pro Asp Cys Lys Ser Leu
            180                 185                 190

Trp Asn Gly Asp Thr Gly Glu Cys Thr Asp Asn Ala Tyr Ile Asp Ile
        195                 200                 205

Gln Leu Arg Ile Ala Ser Phe Ser Gln Asn Cys Asp Ile Tyr Pro Gly
210                 215                 220

Lys Asp Phe Val Gln Pro Pro Thr Lys Ile Cys Val Gly Cys Pro Arg
225                 230                 235                 240

Asp Ile Pro Thr Asn Ser Pro Glu Leu Glu Glu Thr Leu Thr His Thr
                245                 250                 255

Ile Thr Lys Leu Asn Ala Glu Asn Asn Ala Thr Phe Tyr Phe Lys Ile
            260                 265                 270

Asp Asn Val Lys Lys Ala Arg Val Gln Val Val Ala Gly Lys Lys Tyr
        275                 280                 285

Phe Ile Asp Phe Val Ala Arg Glu Thr Thr Cys Ser Lys Glu Ser Asn
290                 295                 300

Glu Glu Leu Thr Glu Ser Cys Glu Thr Lys Lys Leu Gly Gln Ser Leu
305                 310                 315                 320

Asp Cys Asn Ala Glu Val Tyr Val Val Pro Trp Glu Lys Lys Ile Tyr
                325                 330                 335

Pro Thr Val Asn Cys Gln Pro Leu Gly Met Ile Ser Leu Met Lys Arg
            340                 345                 350

Pro Pro Gly Phe Ser Pro Phe Arg Ser Arg Ile Gly Glu Ile Lys
        355                 360                 365

Glu Glu Thr Thr Ser His Leu Arg Ser Cys Glu Tyr Lys Gly Arg Pro
370                 375                 380

Pro Lys Ala Gly Ala Glu Pro Ala Ser Glu Arg Glu Val Ser
385                 390                 395
```

<210> SEQ ID NO 71
<211> LENGTH: 1848
<212> TYPE: DNA
<213> ORGANISM: Homo sapiens
<220> FEATURE:
<221> NAME/KEY: CDS
<222> LOCATION: (1)..(1846)

<400> SEQUENCE: 71

```
atg aaa cta att acc atc ctt ttc ctc tgc tcc agg cta cta cta agt      48
Met Lys Leu Ile Thr Ile Leu Phe Leu Cys Ser Arg Leu Leu Leu Ser
 1               5                  10                  15 tta acc cag gaa tca cag tcc gag gaa att gat gac tgc aat gac aag      96
```

```
                Leu Thr Gln Glu Ser Gln Ser Glu Glu Ile Asp Asp Cys Asn Asp Lys
                            20                  25                  30 gat tta ttt aaa gct gtg gat gct gct ctg aag aaa tat aac agt caa        144
Asp Leu Phe Lys Ala Val Asp Ala Ala Leu Lys Lys Tyr Asn Ser Gln
        35                  40                  45 aac caa agt aac aac cag ttt gta ttg tac cgc aaa acc tgg cag gac        192
Asn Gln Ser Asn Asn Gln Phe Val Leu Tyr Arg Lys Thr Trp Gln Asp
    50                  55                  60 tgt gag tac aag gat gct gca aaa gca gcc act gga gaa tgc aca gca        240
Cys Glu Tyr Lys Asp Ala Ala Lys Ala Ala Thr Gly Glu Cys Thr Ala
65                  70                  75                  80 acc gtg ggg aag agg agc agt acg aaa ttc tcc gtg gct acc cag acc        288
Thr Val Gly Lys Arg Ser Ser Thr Lys Phe Ser Val Ala Thr Gln Thr
                85                  90                  95 tgc cag att act cca gcc gag ggc cct gtg gtg aca gcc cag tac gac        336
Cys Gln Ile Thr Pro Ala Glu Gly Pro Val Val Thr Ala Gln Tyr Asp
            100                 105                 110 tgc ctc ggc tgt gtg cat cct ata tca acg cag agc cca gac ctg gag        384
Cys Leu Gly Cys Val His Pro Ile Ser Thr Gln Ser Pro Asp Leu Glu
        115                 120                 125 ccc att ctg aga cac ggc att cag tac ttt aac aac aac act caa cat        432
Pro Ile Leu Arg His Gly Ile Gln Tyr Phe Asn Asn Asn Thr Gln His
    130                 135                 140 tcc tcc ctc ttc acg ctt aat gaa gta aaa cgg gcc caa aga cag gtg        480
Ser Ser Leu Phe Thr Leu Asn Glu Val Lys Arg Ala Gln Arg Gln Val
145                 150                 155                 160 gtg gct gga ttg aac ttt cga att acc tac tca att gtg caa acg aat        528
Val Ala Gly Leu Asn Phe Arg Ile Thr Tyr Ser Ile Val Gln Thr Asn
                165                 170                 175 tgt tcc aaa gag aat ttt ctg ttc tta act cca gac tgc aag tcc ctt        576
Cys Ser Lys Glu Asn Phe Leu Phe Leu Thr Pro Asp Cys Lys Ser Leu
            180                 185                 190 tgg aat ggt gat acc ggt gaa tgt aca gat aat gca tac atc gat att        624
Trp Asn Gly Asp Thr Gly Glu Cys Thr Asp Asn Ala Tyr Ile Asp Ile
        195                 200                 205 cag cta cga att gct tcc ttc tca cag aac tgt gac att tat cca ggg        672
Gln Leu Arg Ile Ala Ser Phe Ser Gln Asn Cys Asp Ile Tyr Pro Gly
    210                 215                 220 aag gat ttt gta caa cca cct acc aag att tgc gtg ggc tgc ccc aga        720
Lys Asp Phe Val Gln Pro Pro Thr Lys Ile Cys Val Gly Cys Pro Arg
225                 230                 235                 240 gat ata ccc acc aac agc cca gag ctg gag gag aca ctg act cac acc        768
Asp Ile Pro Thr Asn Ser Pro Glu Leu Glu Glu Thr Leu Thr His Thr
                245                 250                 255 atc aca aag ctt aat gca gag aat aac gca act ttc tat ttc aag att        816
Ile Thr Lys Leu Asn Ala Glu Asn Asn Ala Thr Phe Tyr Phe Lys Ile
            260                 265                 270 gac aat gtg aaa aaa gca aga gta cag gtg gtg gct ggc aag aaa tat        864
Asp Asn Val Lys Lys Ala Arg Val Gln Val Val Ala Gly Lys Lys Tyr
        275                 280                 285 ttt att gac ttc gtg gcc agg gaa acc aca tgt tcc aag gaa agt aat        912
Phe Ile Asp Phe Val Ala Arg Glu Thr Thr Cys Ser Lys Glu Ser Asn
    290                 295                 300 gaa gag ttg acc gaa agc tgt gag acc aaa aaa ctt ggc caa agc cta        960
Glu Glu Leu Thr Glu Ser Cys Glu Thr Lys Lys Leu Gly Gln Ser Leu
305                 310                 315                 320 gat tgc aac gct gaa gtt tat gtg gta ccc tgg gag aaa aaa att tac       1008
Asp Cys Asn Ala Glu Val Tyr Val Val Pro Trp Glu Lys Lys Ile Tyr
                325                 330                 335
```

```
cct act gtc aac tgt caa cca ctg gga atg atc tca ctg atg aaa agg    1056
Pro Thr Val Asn Cys Gln Pro Leu Gly Met Ile Ser Leu Met Lys Arg
            340                 345                 350 cct cca ggt ttt tca cct ttc cga tca tca cga ata ggg gaa ata aaa    1104
Pro Pro Gly Phe Ser Pro Phe Arg Ser Ser Arg Ile Gly Glu Ile Lys
        355                 360                 365 gaa gaa aca act gta agt cca ccc cac act tcc atg gca cct gca caa    1152
Glu Glu Thr Thr Val Ser Pro Pro His Thr Ser Met Ala Pro Ala Gln
370                 375                 380 gat gaa gag cgg gat tca gga aaa gaa caa ggg cat act cgt aga cat    1200
Asp Glu Glu Arg Asp Ser Gly Lys Glu Gln Gly His Thr Arg Arg His
385                 390                 395                 400 gac tgg ggc cat gaa aaa caa aga aaa cat aat ctt ggc cat ggc cat    1248
Asp Trp Gly His Glu Lys Gln Arg Lys His Asn Leu Gly His Gly His
                405                 410                 415 aaa cat gaa cgt gac caa ggg cat ggg cac caa aga gga cat ggc ctt    1296
Lys His Glu Arg Asp Gln Gly His Gly His Gln Arg Gly His Gly Leu
            420                 425                 430 ggc cat gga cac gaa caa cag cat ggt ctt ggt cat gga cat aag ttc    1344
Gly His Gly His Glu Gln Gln His Gly Leu Gly His Gly His Lys Phe
        435                 440                 445 aaa ctt gat gat gat ctt gaa cac caa ggg ggc cat gtc ctt gac cat    1392
Lys Leu Asp Asp Asp Leu Glu His Gln Gly Gly His Val Leu Asp His
450                 455                 460 gga cat aag cat aag cat ggt cat ggc cac gga aaa cat aaa aat aaa    1440
Gly His Lys His Lys His Gly His Gly His Gly Lys His Lys Asn Lys
465                 470                 475                 480 ggc aaa aag aat gga aag cac aat ggt tgg aaa aca gag cat ttg gca    1488
Gly Lys Lys Asn Gly Lys His Asn Gly Trp Lys Thr Glu His Leu Ala
                485                 490                 495 agc tct tct gaa gac agt act aca cct tct gca cag aca caa gag aag    1536
Ser Ser Ser Glu Asp Ser Thr Thr Pro Ser Ala Gln Thr Gln Glu Lys
            500                 505                 510 aca gaa ggg cca aca ccc atc cct tcc cta gcc aag cca ggt gta aca    1584
Thr Glu Gly Pro Thr Pro Ile Pro Ser Leu Ala Lys Pro Gly Val Thr
        515                 520                 525 gtt acc ttt tct gac ttt cag gac tct gat ctc att gca act atg atg    1632
Val Thr Phe Ser Asp Phe Gln Asp Ser Asp Leu Ile Ala Thr Met Met
530                 535                 540 cct cct ata tca cca gct ccc ata cag agt gat gac gat tgg atc cct    1680
Pro Pro Ile Ser Pro Ala Pro Ile Gln Ser Asp Asp Asp Trp Ile Pro
545                 550                 555                 560 gat atc cag aca gac cca aat ggc ctt tca ttt aac cca ata tca gat    1728
Asp Ile Gln Thr Asp Pro Asn Gly Leu Ser Phe Asn Pro Ile Ser Asp
                565                 570                 575 ttt cca gac acg acc tcc cca aaa tgt cct gga cgc ccc tgg aag tca    1776
Phe Pro Asp Thr Thr Ser Pro Lys Cys Pro Gly Arg Pro Trp Lys Ser
            580                 585                 590 gtt agt gaa att aat cca acc aca caa atg aaa gaa tct tat tat ttc    1824
Val Ser Glu Ile Asn Pro Thr Thr Gln Met Lys Glu Ser Tyr Tyr Phe
        595                 600                 605 gat ctc act gat ggc ctt tct taa                                    1848
Asp Leu Thr Asp Gly Leu Ser
    610                 615

<210> SEQ ID NO 72
<211> LENGTH: 615
<212> TYPE: PRT
<213> ORGANISM: Homo sapiens

<400> SEQUENCE: 72
```

-continued

```
Met Lys Leu Ile Thr Ile Leu Phe Leu Cys Ser Arg Leu Leu Leu Ser
 1               5                   10                  15

Leu Thr Gln Glu Ser Gln Ser Glu Ile Asp Asp Cys Asn Asp Lys
            20                  25                  30

Asp Leu Phe Lys Ala Val Asp Ala Ala Leu Lys Lys Tyr Asn Ser Gln
            35                  40                  45

Asn Gln Ser Asn Asn Gln Phe Val Leu Tyr Arg Lys Thr Trp Gln Asp
        50                  55                  60

Cys Glu Tyr Lys Asp Ala Ala Lys Ala Ala Thr Gly Glu Cys Thr Ala
 65                  70                  75                  80

Thr Val Gly Lys Arg Ser Ser Thr Lys Phe Ser Val Ala Thr Gln Thr
                85                  90                  95

Cys Gln Ile Thr Pro Ala Glu Gly Pro Val Val Thr Ala Gln Tyr Asp
                100                 105                 110

Cys Leu Gly Cys Val His Pro Ile Ser Thr Gln Ser Pro Asp Leu Glu
            115                 120                 125

Pro Ile Leu Arg His Gly Ile Gln Tyr Phe Asn Asn Asn Thr Gln His
        130                 135                 140

Ser Leu Phe Thr Leu Asn Glu Val Lys Arg Ala Gln Arg Gln Val
145                 150                 155                 160

Val Ala Gly Leu Asn Phe Arg Ile Thr Tyr Ser Ile Val Gln Thr Asn
                165                 170                 175

Cys Ser Lys Glu Asn Phe Leu Phe Leu Thr Pro Asp Cys Lys Ser Leu
            180                 185                 190

Trp Asn Gly Asp Thr Gly Glu Cys Thr Asp Asn Ala Tyr Ile Asp Ile
            195                 200                 205

Gln Leu Arg Ile Ala Ser Phe Ser Gln Asn Cys Asp Ile Tyr Pro Gly
        210                 215                 220

Lys Asp Phe Val Gln Pro Pro Thr Lys Ile Cys Val Gly Cys Pro Arg
225                 230                 235                 240

Asp Ile Pro Thr Asn Ser Pro Glu Leu Glu Glu Thr Leu Thr His Thr
                245                 250                 255

Ile Thr Lys Leu Asn Ala Glu Asn Asn Ala Thr Phe Tyr Phe Lys Ile
            260                 265                 270

Asp Asn Val Lys Lys Ala Arg Val Gln Val Val Ala Gly Lys Lys Tyr
            275                 280                 285

Phe Ile Asp Phe Val Ala Arg Glu Thr Thr Cys Ser Lys Glu Ser Asn
        290                 295                 300

Glu Glu Leu Thr Glu Ser Cys Glu Thr Lys Lys Leu Gly Gln Ser Leu
305                 310                 315                 320

Asp Cys Asn Ala Glu Val Tyr Val Pro Trp Glu Lys Lys Ile Tyr
                325                 330                 335

Pro Thr Val Asn Cys Gln Pro Leu Gly Met Ile Ser Leu Met Lys Arg
                340                 345                 350

Pro Pro Gly Phe Ser Pro Phe Arg Ser Arg Ile Gly Glu Ile Lys
            355                 360                 365

Glu Glu Thr Thr Val Ser Pro Pro His Thr Ser Met Ala Pro Ala Gln
370                 375                 380

Asp Glu Glu Arg Asp Ser Gly Lys Glu Gln Gly His Thr Arg Arg His
385                 390                 395                 400

Asp Trp Gly His Glu Lys Gln Arg Lys His Asn Leu Gly His Gly His
            405                 410                 415
```

```
Lys His Glu Arg Asp Gln Gly His Gly His Gln Arg Gly His Gly Leu
            420                 425                 430

Gly His Gly His Glu Gln Gln His Gly Leu Gly His Gly His Lys Phe
        435                 440                 445

Lys Leu Asp Asp Asp Leu Glu His Gln Gly Gly His Val Leu Asp His
    450                 455                 460

Gly His Lys His Lys His Gly His Gly His Gly Lys His Lys Asn Lys
465                 470                 475                 480

Gly Lys Lys Asn Gly Lys His Asn Gly Trp Lys Thr Glu His Leu Ala
                485                 490                 495

Ser Ser Ser Glu Asp Ser Thr Thr Pro Ser Ala Gln Thr Gln Glu Lys
            500                 505                 510

Thr Glu Gly Pro Thr Pro Ile Pro Ser Leu Ala Lys Pro Gly Val Thr
        515                 520                 525

Val Thr Phe Ser Asp Phe Gln Asp Ser Asp Leu Ile Ala Thr Met Met
    530                 535                 540

Pro Pro Ile Ser Pro Ala Pro Ile Gln Ser Asp Asp Asp Trp Ile Pro
545                 550                 555                 560

Asp Ile Gln Thr Asp Pro Asn Gly Leu Ser Phe Asn Pro Ile Ser Asp
                565                 570                 575

Phe Pro Asp Thr Thr Ser Pro Lys Cys Pro Gly Arg Pro Trp Lys Ser
            580                 585                 590

Val Ser Glu Ile Asn Pro Thr Thr Gln Met Lys Glu Ser Tyr Tyr Phe
        595                 600                 605

Asp Leu Thr Asp Gly Leu Ser
    610                 615

<210> SEQ ID NO 73
<211> LENGTH: 1981
<212> TYPE: DNA
<213> ORGANISM: Homo sapiens
<220> FEATURE:
<221> NAME/KEY: CDS
<222> LOCATION: (50)..(1981)

<400> SEQUENCE: 73
aattccggtt gaaaccatcc ctcagctcct agagggagat tgttagatc atg aaa        55
                                                    Met Lys
                                                      1 cta att acc atc ctt ttc ctc tgc tcc agg cta cta cta agt tta acc    103
Leu Ile Thr Ile Leu Phe Leu Cys Ser Arg Leu Leu Leu Ser Leu Thr
          5                  10                  15 cag gaa tca cag tcc gag gaa att gac tgc aat gac aag gat tta ttt   151
Gln Glu Ser Gln Ser Glu Glu Ile Asp Cys Asn Asp Lys Asp Leu Phe
 20                  25                  30 aaa gct gtg gat gct gct ctg aag aaa tat aac agt caa aac caa agt   199
Lys Ala Val Asp Ala Ala Leu Lys Lys Tyr Asn Ser Gln Asn Gln Ser
 35                  40                  45                  50 aac aac cag ttt gta ttg tac cgc ata act gaa gcc act aag acg gtt   247
Asn Asn Gln Phe Val Leu Tyr Arg Ile Thr Glu Ala Thr Lys Thr Val
                 55                  60                  65 ggc tct gac acg ttt tat tcc ttc aag tac gaa atc aag gag ggg gat   295
Gly Ser Asp Thr Phe Tyr Ser Phe Lys Tyr Glu Ile Lys Glu Gly Asp
         70                  75                  80 tgt cct gtt caa agt ggc aaa acc tgg cag gac tgt gag tac aag gat   343
Cys Pro Val Gln Ser Gly Lys Thr Trp Gln Asp Cys Glu Tyr Lys Asp
             85                  90                  95 gct gca aaa gca gcc act gga gaa tgc acg gca acc gtg ggg aag agg   391
```

```
Ala Ala Lys Ala Ala Thr Gly Glu Cys Thr Ala Thr Val Gly Lys Arg
    100                 105                 110 agc agt acg aaa ttc tcc gtg gct acc cag acc tgc cag att act cca    439
Ser Ser Thr Lys Phe Ser Val Ala Thr Gln Thr Cys Gln Ile Thr Pro
115                 120                 125                 130 gcc gag ggc cct gtg gtg aca gcc cag tac gac tgc ctc ggc tgt gtg    487
Ala Glu Gly Pro Val Val Thr Ala Gln Tyr Asp Cys Leu Gly Cys Val
                    135                 140                 145 cat cct ata tca acg cag agc cca gac ctg gag ccc att ctg aga cac    535
His Pro Ile Ser Thr Gln Ser Pro Asp Leu Glu Pro Ile Leu Arg His
                150                 155                 160 ggc att cag tac ttt aac aac aac act caa cat tcc tcc ctc ttc atg    583
Gly Ile Gln Tyr Phe Asn Asn Asn Thr Gln His Ser Ser Leu Phe Met
            165                 170                 175 ctt aat gaa gta aaa cgg gcc caa aga cag gtg gtg gct gga ttg aac    631
Leu Asn Glu Val Lys Arg Ala Gln Arg Gln Val Val Ala Gly Leu Asn
            180                 185                 190 ttt cga att acc tac tca att gtg caa acg aat tgt tcc aaa gag aat    679
Phe Arg Ile Thr Tyr Ser Ile Val Gln Thr Asn Cys Ser Lys Glu Asn
195                 200                 205                 210 ttt ctg ttc tta act cca gac tgc aag tcc ctt tgg aat ggt gat acc    727
Phe Leu Phe Leu Thr Pro Asp Cys Lys Ser Leu Trp Asn Gly Asp Thr
                    215                 220                 225 ggt gaa tgt aca gat aat gca tac atc gat att cag cta cga att gct    775
Gly Glu Cys Thr Asp Asn Ala Tyr Ile Asp Ile Gln Leu Arg Ile Ala
                230                 235                 240 tcc ttc tca cag aac tgt gac att tat cca ggg aag gat ttt gta caa    823
Ser Phe Ser Gln Asn Cys Asp Ile Tyr Pro Gly Lys Asp Phe Val Gln
            245                 250                 255 cca cct acc aag att tgc gtg ggc tgc ccc aga gat ata ccc acc aac    871
Pro Pro Thr Lys Ile Cys Val Gly Cys Pro Arg Asp Ile Pro Thr Asn
260                 265                 270 agc cca gag ctg gag gag aca ctg act cac acc atc aca aag ctt aat    919
Ser Pro Glu Leu Glu Glu Thr Leu Thr His Thr Ile Thr Lys Leu Asn
275                 280                 285                 290 gca gag aat aac gca act ttc tat ttc aag att gac aat gtg aaa aaa    967
Ala Glu Asn Asn Ala Thr Phe Tyr Phe Lys Ile Asp Asn Val Lys Lys
                    295                 300                 305 gca aga gta cag gtg gtg gct ggc aag aaa tat ttt att gac ttc gtg    1015
Ala Arg Val Gln Val Val Ala Gly Lys Lys Tyr Phe Ile Asp Phe Val
                310                 315                 320 gcc agg gaa acc aca tgt tcc aag gaa agt aat gaa gag ttg acc gaa    1063
Ala Arg Glu Thr Thr Cys Ser Lys Glu Ser Asn Glu Glu Leu Thr Glu
            325                 330                 335 agc tgt gag acc aaa aaa ctt ggc caa agc cta gat tgc aac gct gaa    1111
Ser Cys Glu Thr Lys Lys Leu Gly Gln Ser Leu Asp Cys Asn Ala Glu
        340                 345                 350 gtt tat gtg gta ccc tgg gag aaa aaa att tac cct act gtc aac tgt    1159
Val Tyr Val Val Pro Trp Glu Lys Lys Ile Tyr Pro Thr Val Asn Cys
355                 360                 365                 370 caa cca ctg gga atg atc tca ctg atg aaa agg cct cca ggt ttt tca    1207
Gln Pro Leu Gly Met Ile Ser Leu Met Lys Arg Pro Pro Gly Phe Ser
                    375                 380                 385 cct ttc cga tca tca cga ata ggg gaa ata aaa gaa gaa aca act gta    1255
Pro Phe Arg Ser Ser Arg Ile Gly Glu Ile Lys Glu Glu Thr Thr Val
                390                 395                 400 agt cca ccc cac act tcc atg gca cct gca caa gat gaa gag cgg gat    1303
Ser Pro Pro His Thr Ser Met Ala Pro Ala Gln Asp Glu Glu Arg Asp
            405                 410                 415
```

-continued

| | | |
|---|---|---|
| tca gga aaa gaa caa ggg cat act cgt aga cat gac tgg ggc cat gaa<br>Ser Gly Lys Glu Gln Gly His Thr Arg Arg His Asp Trp Gly His Glu<br>420                            425                        430 | 1351 |
| aaa caa aga aaa cat aat ctt ggc cat ggc cat aaa cat gaa cgt gac<br>Lys Gln Arg Lys His Asn Leu Gly His Gly His Lys His Glu Arg Asp<br>435                            440                        445                        450 | 1399 |
| caa ggg cat ggg cac caa aga gga cat ggc ctt ggc cat gga cac gaa<br>Gln Gly His Gly His Gln Arg Gly His Gly Leu Gly His Gly His Glu<br>                          455                        460                        465 | 1447 |
| caa cag cat ggt ctt ggt cat gga cat aag ttc aaa ctt gat gat gat<br>Gln Gln His Gly Leu Gly His Gly His Lys Phe Lys Leu Asp Asp Asp<br>                          470                        475                        480 | 1495 |
| ctt gaa cac caa ggg ggc cat gtc ctt gac cat gga cat aag cat aag<br>Leu Glu His Gln Gly Gly His Val Leu Asp His Gly His Lys His Lys<br>                          485                        490                        495 | 1543 |
| cat ggt cat ggc cac gga aaa cat aaa aat aaa ggc aaa aag aat gga<br>His Gly His Gly His Gly Lys His Lys Asn Lys Gly Lys Lys Asn Gly<br>500                            505                        510 | 1591 |
| aag cac aat ggt tgg aaa aca gag cat ttg gca agc tct tct gaa gac<br>Lys His Asn Gly Trp Lys Thr Glu His Leu Ala Ser Ser Ser Glu Asp<br>515                            520                        525                        530 | 1639 |
| agt act aca cct tct gca cag aca caa gag aag aca gaa ggg cca aca<br>Ser Thr Thr Pro Ser Ala Gln Thr Gln Glu Lys Thr Glu Gly Pro Thr<br>                          535                        540                        545 | 1687 |
| ccc atc cct tcc cta gcc aag cca ggt gta aca gtt acc ttt tct gac<br>Pro Ile Pro Ser Leu Ala Lys Pro Gly Val Thr Val Thr Phe Ser Asp<br>                          550                        555                        560 | 1735 |
| ttt cag gac tct gat ctc att gca act atg atg cct cct ata tca cca<br>Phe Gln Asp Ser Asp Leu Ile Ala Thr Met Met Pro Pro Ile Ser Pro<br>                          565                        570                        575 | 1783 |
| gct ccc ata cag agt gat gac gat tgg atc cct gat atc cag ata gac<br>Ala Pro Ile Gln Ser Asp Asp Asp Trp Ile Pro Asp Ile Gln Ile Asp<br>580                            585                        590 | 1831 |
| cca aat ggc ctt tca ttt aac cca ata tca gat ttt cca gac acg acc<br>Pro Asn Gly Leu Ser Phe Asn Pro Ile Ser Asp Phe Pro Asp Thr Thr<br>595                            600                        605                        610 | 1879 |
| tcc cca aaa tgt cct gga cgc ccc tgg aag tca gtt agt gaa att aat<br>Ser Pro Lys Cys Pro Gly Arg Pro Trp Lys Ser Val Ser Glu Ile Asn<br>                          615                        620                        625 | 1927 |
| cca acc aca caa atg aaa gaa tct tat tat ttc gat ctc act gat ggc<br>Pro Thr Thr Gln Met Lys Glu Ser Tyr Tyr Phe Asp Leu Thr Asp Gly<br>                          630                        635                        640 | 1975 |
| ctt tct<br>Leu Ser | 1981 |

<210> SEQ ID NO 74
<211> LENGTH: 644
<212> TYPE: PRT
<213> ORGANISM: Homo sapiens

<400> SEQUENCE: 74

Met Lys Leu Ile Thr Ile Leu Phe Leu Cys Ser Arg Leu Leu Leu Ser
1                   5                      10                     15

Leu Thr Gln Glu Ser Gln Ser Glu Glu Ile Asp Cys Asn Asp Lys Asp
                 20                     25                     30

Leu Phe Lys Ala Val Asp Ala Ala Leu Lys Lys Tyr Asn Ser Gln Asn
               35                     40                     45

Gln Ser Asn Asn Gln Phe Val Leu Tyr Arg Ile Thr Glu Ala Thr Lys
       50                     55                     60

-continued

```
Thr Val Gly Ser Asp Thr Phe Tyr Ser Phe Lys Tyr Glu Ile Lys Glu
 65                  70                  75                  80

Gly Asp Cys Pro Val Gln Ser Gly Lys Thr Trp Gln Asp Cys Glu Tyr
                 85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Thr Ala Gln Tyr Asp Cys Leu Gly
    130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Thr Gln His Ser Ser Leu
                165                 170                 175

Phe Met Leu Asn Glu Val Lys Arg Ala Gln Arg Gln Val Val Ala Gly
                180                 185                 190

Leu Asn Phe Arg Ile Thr Tyr Ser Ile Val Gln Thr Asn Cys Ser Lys
        195                 200                 205

Glu Asn Phe Leu Phe Leu Thr Pro Asp Cys Lys Ser Leu Trp Asn Gly
    210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
                260                 265                 270

Thr Asn Ser Pro Glu Leu Glu Glu Thr Leu Thr His Thr Ile Thr Lys
            275                 280                 285

Leu Asn Ala Glu Asn Asn Ala Thr Phe Tyr Phe Lys Ile Asp Asn Val
    290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
        355                 360                 365

Asn Cys Gln Pro Leu Gly Met Ile Ser Leu Met Lys Arg Pro Pro Gly
    370                 375                 380

Phe Ser Pro Phe Arg Ser Ser Arg Ile Gly Glu Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
            420                 425                 430

His Glu Lys Gln Arg Lys His Asn Leu Gly His Gly His Lys His Glu
        435                 440                 445

Arg Asp Gln Gly His Gly His Gln Arg Gly His Gly Leu Gly His Gly
    450                 455                 460

His Glu Gln Gln His Gly Leu Gly His Gly Lys Phe Lys Leu Asp
465                 470                 475                 480

Asp Asp Leu Glu His Gln Gly Gly His Val Leu Asp His Gly His Lys
```

-continued

```
                485                 490                 495
His Lys His Gly His Gly His Gly Lys His Lys Asn Lys Gly Lys Lys
            500                 505                 510
Asn Gly Lys His Asn Gly Trp Lys Thr Glu His Leu Ala Ser Ser Ser
            515                 520                 525
Glu Asp Ser Thr Thr Pro Ser Ala Gln Thr Gln Glu Lys Thr Glu Gly
            530                 535                 540
Pro Thr Pro Ile Pro Ser Leu Ala Lys Pro Gly Val Thr Val Thr Phe
545                 550                 555                 560
Ser Asp Phe Gln Asp Ser Asp Leu Ile Ala Thr Met Met Pro Pro Ile
                565                 570                 575
Ser Pro Ala Pro Ile Gln Ser Asp Asp Asp Trp Ile Pro Asp Ile Gln
            580                 585                 590
Ile Asp Pro Asn Gly Leu Ser Phe Asn Pro Ile Ser Asp Phe Pro Asp
            595                 600                 605
Thr Thr Ser Pro Lys Cys Pro Gly Arg Pro Trp Lys Ser Val Ser Glu
610                 615                 620
Ile Asn Pro Thr Thr Gln Met Lys Glu Ser Tyr Tyr Phe Asp Leu Thr
625                 630                 635                 640
Asp Gly Leu Ser
```

```
<210> SEQ ID NO 75
<211> LENGTH: 1297
<212> TYPE: DNA
<213> ORGANISM: Homo sapiens
<220> FEATURE:
<221> NAME/KEY: CDS
<222> LOCATION: (50)..(1295)

<400> SEQUENCE: 75
aattccggtt gaaaccatcc ctcagctcct agagggagat tgttagatc atg aaa         55
                                                    Met Lys
                                                      1 cta att acc atc ctt ttc ctc tgc tcc agg cta cta cta agt tta acc     103
Leu Ile Thr Ile Leu Phe Leu Cys Ser Arg Leu Leu Leu Ser Leu Thr
        5                  10                  15 cag gaa tca cag tcc gag gaa att gac tgc aat gac aag gat tta ttt    151
Gln Glu Ser Gln Ser Glu Glu Ile Asp Cys Asn Asp Lys Asp Leu Phe
 20                  25                  30 aaa gct gtg gat gct gct ctg aag aaa tat aac agt caa aac caa agt    199
Lys Ala Val Asp Ala Ala Leu Lys Lys Tyr Asn Ser Gln Asn Gln Ser
 35                  40                  45                  50 aac aac cag ttt gta ttg tac cgc ata act gaa gcc act aag acg gtt    247
Asn Asn Gln Phe Val Leu Tyr Arg Ile Thr Glu Ala Thr Lys Thr Val
                 55                  60                  65 ggc tct gac acg ttt tat tcc ttc aag tac gaa atc aag gag ggg gat    295
Gly Ser Asp Thr Phe Tyr Ser Phe Lys Tyr Glu Ile Lys Glu Gly Asp
             70                  75                  80 tgt cct gtt caa agt ggc aaa acc tgg cag gac tgt gag tac aag gat    343
Cys Pro Val Gln Ser Gly Lys Thr Trp Gln Asp Cys Glu Tyr Lys Asp
         85                  90                  95 gct gca aaa gca gcc act gga gaa tgc aca gca acc gtg ggg aag agg    391
Ala Ala Lys Ala Ala Thr Gly Glu Cys Thr Ala Thr Val Gly Lys Arg
    100                 105                 110 agc agt acg aaa ttc tcc gtg gct acc cag acc tgc cag att act cca    439
Ser Ser Thr Lys Phe Ser Val Ala Thr Gln Thr Cys Gln Ile Thr Pro
115                 120                 125                 130 gcc gag ggc cct gtg gtg aca gcc cag tac gac tgc ctc ggc tgt gtg    487
```

```
Ala Glu Gly Pro Val Val Thr Ala Gln Tyr Asp Cys Leu Gly Cys Val
                135                 140                 145 cat cct ata tca acg cag agc cca ggt ttt tca cct ttc cga tca tca      535
His Pro Ile Ser Thr Gln Ser Pro Gly Phe Ser Pro Phe Arg Ser Ser
            150                 155                 160 cga ata ggg gaa ata aaa gaa gaa aca act gta agt cca ccc cac act      583
Arg Ile Gly Glu Ile Lys Glu Glu Thr Thr Val Ser Pro Pro His Thr
        165                 170                 175 tcc atg gca cct gca caa gat gaa gag cgg gat tca gga aaa gaa caa      631
Ser Met Ala Pro Ala Gln Asp Glu Glu Arg Asp Ser Gly Lys Glu Gln
    180                 185                 190 ggg cat act cgt aga cat gac tgg ggc cat gaa aaa caa aga aaa cat      679
Gly His Thr Arg Arg His Asp Trp Gly His Glu Lys Gln Arg Lys His
195                 200                 205                 210 aat ctt ggc cat ggc cat aaa cat gaa cgt gac caa ggg cat ggg cac      727
Asn Leu Gly His Gly His Lys His Glu Arg Asp Gln Gly His Gly His
                215                 220                 225 caa aga gga cat ggc ctt ggc cat gga cac gaa caa cag cat ggt ctt      775
Gln Arg Gly His Gly Leu Gly His Gly His Glu Gln Gln His Gly Leu
            230                 235                 240 ggt cat gga cat aag ttc aaa ctt gat gat gat ctt gaa cac caa ggg      823
Gly His Gly His Lys Phe Lys Leu Asp Asp Asp Leu Glu His Gln Gly
        245                 250                 255 ggc cat gtc ctt gac cat gga cat aag cat aag cat ggt cat ggc cac      871
Gly His Val Leu Asp His Gly His Lys His Lys His Gly His Gly His
    260                 265                 270 gga aaa cat aaa aat aaa ggc aaa aag aat gga aag cac aat ggt tgg      919
Gly Lys His Lys Asn Lys Gly Lys Lys Asn Gly Lys His Asn Gly Trp
275                 280                 285                 290 aaa aca gag cat ttg gca agc tct tct gaa gac agt act aca cct tct      967
Lys Thr Glu His Leu Ala Ser Ser Ser Glu Asp Ser Thr Thr Pro Ser
                295                 300                 305 gca cag aca caa gag aag aca gaa ggg cca aca ccc atc cct tcc cta     1015
Ala Gln Thr Gln Glu Lys Thr Glu Gly Pro Thr Pro Ile Pro Ser Leu
            310                 315                 320 gcc aag cca ggt gta aca gtt acc ttt tct gac ttt cag gac tct gat     1063
Ala Lys Pro Gly Val Thr Val Thr Phe Ser Asp Phe Gln Asp Ser Asp
        325                 330                 335 ctc att gca act atg atg cct cct ata tca cca gct ccc ata cag agt     1111
Leu Ile Ala Thr Met Met Pro Pro Ile Ser Pro Ala Pro Ile Gln Ser
    340                 345                 350 gat gac gat tgg atc cct gat atc cag ata gac cca aat ggc ctt tca     1159
Asp Asp Asp Trp Ile Pro Asp Ile Gln Ile Asp Pro Asn Gly Leu Ser
355                 360                 365                 370 ttt aac cca ata tca gat ttt cca gac acg acc tcc cca aaa tgt cct     1207
Phe Asn Pro Ile Ser Asp Phe Pro Asp Thr Thr Ser Pro Lys Cys Pro
                375                 380                 385 gga cgc ccc tgg aag tca gtt agt gaa att aat cca acc aca caa atg     1255
Gly Arg Pro Trp Lys Ser Val Ser Glu Ile Asn Pro Thr Thr Gln Met
            390                 395                 400 aaa gaa tct tat tat ttc gat ctc act gat ggc ctt tct taa             1297
Lys Glu Ser Tyr Tyr Phe Asp Leu Thr Asp Gly Leu Ser
        405                 410                 415

<210> SEQ ID NO 76
<211> LENGTH: 415
<212> TYPE: PRT
<213> ORGANISM: Homo sapiens

<400> SEQUENCE: 76
```

-continued

```
Met Lys Leu Ile Thr Ile Leu Phe Leu Cys Ser Arg Leu Leu Leu Ser
 1               5                  10                  15

Leu Thr Gln Glu Ser Gln Ser Glu Glu Ile Asp Cys Asn Asp Lys Asp
                20                  25                  30

Leu Phe Lys Ala Val Asp Ala Ala Leu Lys Lys Tyr Asn Ser Gln Asn
            35                  40                  45

Gln Ser Asn Asn Gln Phe Val Leu Tyr Arg Ile Thr Glu Ala Thr Lys
        50                  55                  60

Thr Val Gly Ser Asp Thr Phe Tyr Ser Phe Lys Tyr Glu Ile Lys Glu
 65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Thr Ala Gln Tyr Asp Cys Leu Gly
    130                 135                 140

Cys Val His Pro Ile Ser Thr Gln Ser Pro Gly Phe Ser Pro Phe Arg
145                 150                 155                 160

Ser Ser Arg Ile Gly Glu Ile Lys Glu Glu Thr Thr Val Ser Pro Pro
                165                 170                 175

His Thr Ser Met Ala Pro Ala Gln Asp Glu Glu Arg Asp Ser Gly Lys
            180                 185                 190

Glu Gln Gly His Thr Arg Arg His Asp Trp Gly His Glu Lys Gln Arg
        195                 200                 205

Lys His Asn Leu Gly His Gly His Lys His Glu Arg Asp Gln Gly His
    210                 215                 220

Gly His Gln Arg Gly His Gly Leu Gly His Gly His Glu Gln Gln His
225                 230                 235                 240

Gly Leu Gly His Gly His Lys Phe Lys Leu Asp Asp Asp Leu Glu His
                245                 250                 255

Gln Gly Gly His Val Leu Asp His Gly His Lys His Lys His Gly His
            260                 265                 270

Gly His Gly Lys His Lys Asn Lys Gly Lys Lys Asn Gly Lys His Asn
        275                 280                 285

Gly Trp Lys Thr Glu His Leu Ala Ser Ser Glu Asp Ser Thr Thr
    290                 295                 300

Pro Ser Ala Gln Thr Gln Glu Lys Thr Glu Gly Pro Thr Pro Ile Pro
305                 310                 315                 320

Ser Leu Ala Lys Pro Gly Val Thr Val Thr Phe Ser Asp Phe Gln Asp
                325                 330                 335

Ser Asp Leu Ile Ala Thr Met Met Pro Pro Ile Ser Pro Ala Pro Ile
            340                 345                 350

Gln Ser Asp Asp Asp Trp Ile Pro Asp Ile Gln Ile Asp Pro Asn Gly
        355                 360                 365

Leu Ser Phe Asn Pro Ile Ser Asp Phe Pro Asp Thr Thr Ser Pro Lys
    370                 375                 380

Cys Pro Gly Arg Pro Trp Lys Ser Val Ser Glu Ile Asn Pro Thr Thr
385                 390                 395                 400

Gln Met Lys Glu Ser Tyr Tyr Phe Asp Leu Thr Asp Gly Leu Ser
                405                 410                 415
```

-continued

```
<210> SEQ ID NO 77
<211> LENGTH: 1892
<212> TYPE: DNA
<213> ORGANISM: Homo sapiens
<220> FEATURE:
<221> NAME/KEY: CDS
<222> LOCATION: (50)..(458)

<400> SEQUENCE: 77
```

| | | |
|---|---|---|
| aattccggtt gaaaccatcc ctcagctcct agagggagat tgttagatc atg aaa | | 55 |
| Met Lys | | |
| 1 | | |
| cta att acc atc ctt ttc ctc tgc tcc agg cta cta agt tta acc | | 103 |
| Leu Ile Thr Ile Leu Phe Leu Cys Ser Arg Leu Leu Ser Leu Thr | | |
| 5                     10                      15 | | |
| cag gaa tca cag tcc gag gaa att gac tgc aat gac aag gat tta ttt | | 151 |
| Gln Glu Ser Gln Ser Glu Glu Ile Asp Cys Asn Asp Lys Asp Leu Phe | | |
| 20                      25                      30 | | |
| aaa gct gtg gat gct gct ctg aag aaa tat aac agt caa aac caa agt | | 199 |
| Lys Ala Val Asp Ala Ala Leu Lys Lys Tyr Asn Ser Gln Asn Gln Ser | | |
| 35                      40                      45                      50 | | |
| aac aac cag ttt gta ttg tac cgc ata act gaa gcc act aag acg gtt | | 247 |
| Asn Asn Gln Phe Val Leu Tyr Arg Ile Thr Glu Ala Thr Lys Thr Val | | |
|                      55                      60                      65 | | |
| ggc tct gac acg ttt tat tcc ttc aag tac gaa atc aag gag ggg gat | | 295 |
| Gly Ser Asp Thr Phe Tyr Ser Phe Lys Tyr Glu Ile Lys Glu Gly Asp | | |
|                      70                      75                      80 | | |
| tgt cct gtt caa agt ggc aaa acc tgg cag gac tgt gag tac aag gat | | 343 |
| Cys Pro Val Gln Ser Gly Lys Thr Trp Gln Asp Cys Glu Tyr Lys Asp | | |
|           85                      90                      95 | | |
| gct gca aaa gca gcc act gga gaa tgc aca gca acc gtg gga aga gga | | 391 |
| Ala Ala Lys Ala Ala Thr Gly Glu Cys Thr Ala Thr Val Gly Arg Gly | | |
|           100                      105                      110 | | |
| gca gta cga aat tct ccg tgg cta ccc aga cct gga gcc cat tct gag | | 439 |
| Ala Val Arg Asn Ser Pro Trp Leu Pro Arg Pro Gly Ala His Ser Glu | | |
| 115                      120                      125                      130 | | |
| aca cgg cat tca gta ctt taacaacaac actcaacatt cctccctctt | | 487 |
| Thr Arg His Ser Val Leu | | |
|                      135 | | |
| cacgcttaat gaagtaaaac gggcccaaag acaggtggtg gctggattga | | 537 |
| actttcgaat tacctactca attgtgcaaa cgaattgttc caaagagaat | | 587 |
| tttctgttct taactccaga ctgcaagtcc ctttggaatg gtgataccgg | | 637 |
| tgaatgtaca gataatgcat acatcgatat tcagctacga attgcttcct | | 687 |
| tctcacagaa ctgtgacatt tatccaggga aggattttgt acaaccacct | | 737 |
| accaagattt gcgtgggctg ccccagagat atacccacca acagcccaga | | 787 |
| gctggaggag acactgactc acaccatcac aaagcttaat gcagagaata | | 837 |
| acgcaacttt ctatttcaag attgacaatg tgaaaaaagc aagagtacag | | 887 |
| gtggtggctg gcaagaaata ttttattgac ttcgtggcca gggaaaccac | | 937 |
| atgttccaag gaaagtaatg aagagttgac cgaaagctgt gagaccaaaa | | 987 |
| aacttggcca agcctagat tgcaacgctg aagtttatgt ggtaccctgg | | 1037 |
| gagaaaaaaa tttaccctac tgtcaactgt caaccactgg gaatgatctc | | 1087 |
| actgatgaaa aggcctccag gttttttcacc tttccgatca tcacgaatag | | 1137 |
| gggaaataaa agaagaaaca actgtaagtc caccccacac ttccatggca | | 1187 |
| cctgcacaag atgaagagcg ggattcagga aaagaacaag gcatactcg | | 1237 |

| | |
|---|---|
| tagacatgac tggggccatg aaaaacaaag aaaacataat cttggccatg | 1287 |
| gccataaaca tgaacgtgac caagggcatg ggcaccaaag aggacatggc | 1337 |
| cttggccatg gacacgaaca acagcatggt cttggtcatg gacataagtt | 1387 |
| caaacttgat gatgatcttg aacaccaagg gggccatgtc cttgaccatg | 1437 |
| gacataagca taagcatggt catggccacg gaaaacataa aaataaaggc | 1487 |
| aaaaagaatg gaaagcacaa tggttggaaa acagagcatt tggcaagctc | 1537 |
| ttctgaagac agtactacac cttctgcaca gacacaagag aagacagaag | 1587 |
| ggccaacacc catcccttcc ctagccaagc caggtgtaac agttaccttt | 1637 |
| tctgactttc aggactctga tctcattgca actatgatgc ctcctatatc | 1687 |
| accagctccc atacagagtg atgacgattg gatccctgat atccagatag | 1737 |
| acccaaatgg cctttcattt aacccaatat cagattttcc agacacgacc | 1787 |
| tccccaaaat gtcctggacg cccctggaag tcagttagtg aaattaatcc | 1837 |
| aaccacacaa atgaaagaat cttattattt cgatctcact gatggccttt | 1887 |
| cttaa | 1892 |

<210> SEQ ID NO 78
<211> LENGTH: 136
<212> TYPE: PRT
<213> ORGANISM: Homo sapiens

<400> SEQUENCE: 78

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Arg Gly Ala Val Arg Asn Ser Pro Trp Leu Pro Arg Pro Gly Ala His
        115                 120                 125

Ser Glu Thr Arg His Ser Val Leu
    130                 135

<210> SEQ ID NO 79
<211> LENGTH: 670
<212> TYPE: DNA
<213> ORGANISM: Homo sapiens
<220> FEATURE:
<221> NAME/KEY: CDS
<222> LOCATION: (1)..(508)

<400> SEQUENCE: 79

| | |
|---|---|
| atg aaa cta att acc atc ctt ttc ctc tgc tcc agg cta cta cta agt<br>Met Lys Leu Ile Thr Ile Leu Phe Leu Cys Ser Arg Leu Leu Leu Ser<br>1               5                   10                  15 | 48 |

```
tta acc cag gaa tca cag tcc gag gaa att gat gac tgc aat gac aag      96
Leu Thr Gln Glu Ser Gln Ser Glu Glu Ile Asp Asp Cys Asn Asp Lys
            20                  25                  30 gat tta ttt aaa gct gtg gat gct gct ctg aag aaa tat aac agt caa     144
Asp Leu Phe Lys Ala Val Asp Ala Ala Leu Lys Lys Tyr Asn Ser Gln
        35                  40                  45 aac caa agt aac aac cag ttt gta ttg tac cgc aaa acc tgg cag gac     192
Asn Gln Ser Asn Asn Gln Phe Val Leu Tyr Arg Lys Thr Trp Gln Asp
    50                  55                  60 tgt gag tac aag gat gct gca aaa gca gcc act gga gaa tgc aca gca     240
Cys Glu Tyr Lys Asp Ala Ala Lys Ala Ala Thr Gly Glu Cys Thr Ala
65                  70                  75                  80 acc gtg ggg aag agg agc agt acg aaa ttc tcc gtg gct acc cag acc     288
Thr Val Gly Lys Arg Ser Ser Thr Lys Phe Ser Val Ala Thr Gln Thr
                85                  90                  95 tgc cag att act cca gcc gag ggc cct gtg gtg aca gcc cag tac gac     336
Cys Gln Ile Thr Pro Ala Glu Gly Pro Val Val Thr Ala Gln Tyr Asp
            100                 105                 110 tgc ctc ggc tgt gtg cat cct ata tca acg cag agc cca ggt ttt tca     384
Cys Leu Gly Cys Val His Pro Ile Ser Thr Gln Ser Pro Gly Phe Ser
        115                 120                 125 cct ttc cga tca tca cga ata ggg gaa ata aaa gaa gaa aca act agt     432
Pro Phe Arg Ser Ser Arg Ile Gly Glu Ile Lys Glu Glu Thr Thr Ser
    130                 135                 140 cac cta agg tcc tgc gag tac aag ggt cga ccc cca aag gca ggg gca     480
His Leu Arg Ser Cys Glu Tyr Lys Gly Arg Pro Pro Lys Ala Gly Ala
145                 150                 155                 160 gag cca gca tct gag agg gag gtc tct tgaccaatgg gcagaatctt           527
Glu Pro Ala Ser Glu Arg Glu Val Ser
                165 cactccaggc acatagcccc aaccacctct gccagcaacc ttgagaggaa              577 ggacaagaag aaagatggga tagaatttaa atagagaaga atgccatttt              627 atcactctgc ctctgggtga ataaagatc agtcttgatg ttc                      670

<210> SEQ ID NO 80
<211> LENGTH: 169
<212> TYPE: PRT
<213> ORGANISM: Homo sapiens

<400> SEQUENCE: 80

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Asp Cys Asn Asp Lys
            20                  25                  30

Asp Leu Phe Lys Ala Val Asp Ala Ala Leu Lys Lys Tyr Asn Ser Gln
        35                  40                  45

Asn Gln Ser Asn Asn Gln Phe Val Leu Tyr Arg Lys Thr Trp Gln Asp
    50                  55                  60

Cys Glu Tyr Lys Asp Ala Ala Lys Ala Ala Thr Gly Glu Cys Thr Ala
65                  70                  75                  80

Thr Val Gly Lys Arg Ser Ser Thr Lys Phe Ser Val Ala Thr Gln Thr
                85                  90                  95

Cys Gln Ile Thr Pro Ala Glu Gly Pro Val Val Thr Ala Gln Tyr Asp
            100                 105                 110

Cys Leu Gly Cys Val His Pro Ile Ser Thr Gln Ser Pro Gly Phe Ser
        115                 120                 125

Pro Phe Arg Ser Ser Arg Ile Gly Glu Ile Lys Glu Glu Thr Thr Ser
```

```
               130                 135                 140
His Leu Arg Ser Cys Glu Tyr Lys Gly Arg Pro Lys Ala Gly Ala
145                 150                 155                 160

Glu Pro Ala Ser Glu Arg Glu Val Ser
                165

<210> SEQ ID NO 81
<211> LENGTH: 1193
<212> TYPE: DNA
<213> ORGANISM: Homo sapiens
<220> FEATURE:
<221> NAME/KEY: CDS
<222> LOCATION: (1)..(1171)

<400> SEQUENCE: 81 atg aaa cta att acc atc ctt ttc ctc tgc tcc agg cta cta cta agt      48
Met Lys Leu Ile Thr Ile Leu Phe Leu Cys Ser Arg Leu Leu Leu Ser
  1               5                  10                  15 tta acc cag gaa tca cag tcc gag gaa att gac tgc aat gac aag gat      96
Leu Thr Gln Glu Ser Gln Ser Glu Glu Ile Asp Cys Asn Asp Lys Asp
             20                  25                  30 tta ttt aaa gct gtg gat gct gct ctg aag aaa tat aac agt caa aac     144
Leu Phe Lys Ala Val Asp Ala Ala Leu Lys Lys Tyr Asn Ser Gln Asn
         35                  40                  45 caa agt aac aac cag ttt gta ttg tac cgc ata act gaa gcc act aag     192
Gln Ser Asn Asn Gln Phe Val Leu Tyr Arg Ile Thr Glu Ala Thr Lys
     50                  55                  60 acg gcc act gga gaa tgc acg gca acc gtg ggg aag agg agc agt acg     240
Thr Ala Thr Gly Glu Cys Thr Ala Thr Val Gly Lys Arg Ser Ser Thr
 65                  70                  75                  80 aaa ttc tcc gtg gct acc cag acc tgc cag att act cca gcc gag ggc     288
Lys Phe Ser Val Ala Thr Gln Thr Cys Gln Ile Thr Pro Ala Glu Gly
                 85                  90                  95 cct gtg gtg aca gcc cag tac gac tgc ctc ggc tgt gtg cat cct ata     336
Pro Val Val Thr Ala Gln Tyr Asp Cys Leu Gly Cys Val His Pro Ile
            100                 105                 110 tca acg cag agc cca gac ctg gag ccc att ctg aga cac ggc att cag     384
Ser Thr Gln Ser Pro Asp Leu Glu Pro Ile Leu Arg His Gly Ile Gln
        115                 120                 125 tac ttt aac aac aac act caa cat tcc tcc ctc ttc acg ctt aat gaa     432
Tyr Phe Asn Asn Asn Thr Gln His Ser Ser Leu Phe Thr Leu Asn Glu
    130                 135                 140 gta aaa cgg gcc caa aga cag gtg gtg gct gga ttg aac ttt cga att     480
Val Lys Arg Ala Gln Arg Gln Val Val Ala Gly Leu Asn Phe Arg Ile
145                 150                 155                 160 acc tac tca att gtg caa acg aat tgt tcc aaa gag aat ttt ctg ttc     528
Thr Tyr Ser Ile Val Gln Thr Asn Cys Ser Lys Glu Asn Phe Leu Phe
                165                 170                 175 tta act cca gac tgc gag tcc ctt tgg aat ggt gat acc ggt gaa tgt     576
Leu Thr Pro Asp Cys Glu Ser Leu Trp Asn Gly Asp Thr Gly Glu Cys
            180                 185                 190 aca gat aat gca tac atc gat att cag cta cga att gct tcc ttc tca     624
Thr Asp Asn Ala Tyr Ile Asp Ile Gln Leu Arg Ile Ala Ser Phe Ser
        195                 200                 205 cag aac tgt gac att tat cca ggg aag gat ttt gta caa cca cct acc     672
Gln Asn Cys Asp Ile Tyr Pro Gly Lys Asp Phe Val Gln Pro Pro Thr
    210                 215                 220 aag att tgc gtg ggc tgc ccc aga gat ata ccc acc aac agc cca gag     720
Lys Ile Cys Val Gly Cys Pro Arg Asp Ile Pro Thr Asn Ser Pro Glu
225                 230                 235                 240
```

-continued

```
ctg gag gag aca ctg act cac acc atc aca aag ctt aat gca gag aat    768
Leu Glu Glu Thr Leu Thr His Thr Ile Thr Lys Leu Asn Ala Glu Asn
            245                 250                 255 aac gca act ttc tat ttc aag att gac aat gtg aaa aaa gca aga gta    816
Asn Ala Thr Phe Tyr Phe Lys Ile Asp Asn Val Lys Lys Ala Arg Val
        260                 265                 270 cag gtg gtg gct ggc aag aaa tat ttt att gac ttc gtg gcc agg gaa    864
Gln Val Val Ala Gly Lys Lys Tyr Phe Ile Asp Phe Val Ala Arg Glu
    275                 280                 285 acc aca tgt tcc aag gaa agt aat gaa gag ttg acc gaa agc tgt gag    912
Thr Thr Cys Ser Lys Glu Ser Asn Glu Glu Leu Thr Glu Ser Cys Glu
290                 295                 300 acc aaa aaa ctt ggc caa agc cta gat tgc aac gct gaa gtt tat gtg    960
Thr Lys Lys Leu Gly Gln Ser Leu Asp Cys Asn Ala Glu Val Tyr Val
305                 310                 315                 320 gta ccc tgg gag aaa aaa att tac cct act gtc aac tgt caa cca ctg   1008
Val Pro Trp Glu Lys Lys Ile Tyr Pro Thr Val Asn Cys Gln Pro Leu
                325                 330                 335 gga atg atc tca ctg atg aaa agg cct cca ggt ttt tca cct ttc cga   1056
Gly Met Ile Ser Leu Met Lys Arg Pro Pro Gly Phe Ser Pro Phe Arg
            340                 345                 350 tca tca cga ata ggg gaa ata aaa gaa gaa aca act agt cac cta agg   1104
Ser Ser Arg Ile Gly Glu Ile Lys Glu Glu Thr Thr Ser His Leu Arg
        355                 360                 365 tcc tgc gag tac aag ggt cga ccc cca aag gca ggg gca gag cca gta   1152
Ser Cys Glu Tyr Lys Gly Arg Pro Pro Lys Ala Gly Ala Glu Pro Val
    370                 375                 380 tct gag agg gag gtc tct tgaccaatgg gcagaatctt cac                 1193
Ser Glu Arg Glu Val Ser
385                 390
```

<210> SEQ ID NO 82
<211> LENGTH: 390
<212> TYPE: PRT
<213> ORGANISM: Homo sapiens

<400> SEQUENCE: 82

```
Met Lys Leu Ile Thr Ile Leu Phe Leu Cys Ser Arg Leu Leu Leu Ser
 1               5                  10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Ala Thr Gly Glu Cys Thr Ala Thr Val Gly Lys Arg Ser Ser Thr
65                  70                  75                  80

Lys Phe Ser Val Ala Thr Gln Thr Cys Gln Ile Thr Pro Ala Glu Gly
                85                  90                  95

Pro Val Val Thr Ala Gln Tyr Asp Cys Leu Gly Cys Val His Pro Ile
            100                 105                 110

Ser Thr Gln Ser Pro Asp Leu Glu Pro Ile Leu Arg His Gly Ile Gln
        115                 120                 125

Tyr Phe Asn Asn Asn Thr Gln His Ser Ser Leu Phe Thr Leu Asn Glu
    130                 135                 140

Val Lys Arg Ala Gln Arg Gln Val Val Ala Gly Leu Asn Phe Arg Ile
145                 150                 155                 160

Thr Tyr Ser Ile Val Gln Thr Asn Cys Ser Lys Glu Asn Phe Leu Phe
```

```
                 165                 170                 175
Leu Thr Pro Asp Cys Glu Ser Leu Trp Asn Gly Asp Thr Gly Glu Cys
            180                 185                 190

Thr Asp Asn Ala Tyr Ile Asp Ile Gln Leu Arg Ile Ala Ser Phe Ser
            195                 200                 205

Gln Asn Cys Asp Ile Tyr Pro Gly Lys Asp Phe Val Gln Pro Pro Thr
            210                 215                 220

Lys Ile Cys Val Gly Cys Pro Arg Asp Ile Pro Thr Asn Ser Pro Glu
225                 230                 235                 240

Leu Glu Glu Thr Leu Thr His Thr Ile Thr Lys Leu Asn Ala Glu Asn
                245                 250                 255

Asn Ala Thr Phe Tyr Phe Lys Ile Asp Asn Val Lys Lys Ala Arg Val
            260                 265                 270

Gln Val Val Ala Gly Lys Lys Tyr Phe Ile Asp Phe Val Ala Arg Glu
            275                 280                 285

Thr Thr Cys Ser Lys Glu Ser Asn Glu Glu Leu Thr Glu Ser Cys Glu
            290                 295                 300

Thr Lys Lys Leu Gly Gln Ser Leu Asp Cys Asn Ala Glu Val Tyr Val
305                 310                 315                 320

Val Pro Trp Glu Lys Lys Ile Tyr Pro Thr Val Asn Cys Gln Pro Leu
                325                 330                 335

Gly Met Ile Ser Leu Met Lys Arg Pro Pro Gly Phe Ser Pro Phe Arg
            340                 345                 350

Ser Ser Arg Ile Gly Glu Ile Lys Glu Glu Thr Thr Ser His Leu Arg
            355                 360                 365

Ser Cys Glu Tyr Lys Gly Arg Pro Pro Lys Ala Gly Ala Glu Pro Val
370                 375                 380

Ser Glu Arg Glu Val Ser
385                 390

<210> SEQ ID NO 83
<211> LENGTH: 1984
<212> TYPE: DNA
<213> ORGANISM: Homo sapiens
<220> FEATURE:
<221> NAME/KEY: CDS
<222> LOCATION: (50)..(1982)

<400> SEQUENCE: 83
aattccggtt gaaaccatcc ctcagctcct agagggagat tgttagatc atg aaa          55
                                                    Met Lys
                                                      1 cta att acc atc ctt ttc ctc tgc tcc agg cta cta cta agt tta acc       103
Leu Ile Thr Ile Leu Phe Leu Cys Ser Arg Leu Leu Leu Ser Leu Thr
        5                   10                  15 cag gaa tca cag tcc gag gaa att gac tgc aat gac aag gat tta ttt      151
Gln Glu Ser Gln Ser Glu Glu Ile Asp Cys Asn Asp Lys Asp Leu Phe
            20                  25                  30 aaa gct gtg gat gct gct ctg aag aaa tat aac agt caa aac caa agt      199
Lys Ala Val Asp Ala Ala Leu Lys Lys Tyr Asn Ser Gln Asn Gln Ser
35                  40                  45                  50 aac aac cag ttt gta ttg tac cgc ata act gaa gcc act aag acg gtt      247
Asn Asn Gln Phe Val Leu Tyr Arg Ile Thr Glu Ala Thr Lys Thr Val
                55                  60                  65 ggc tct gac acg ttt tat tcc ttc aag tac gaa atc aag gag ggg gat      295
Gly Ser Asp Thr Phe Tyr Ser Phe Lys Tyr Glu Ile Lys Glu Gly Asp
            70                  75                  80
```

```
tgt cct gtt caa agt ggc aaa acc tgg cag gac tgt gag tac aag gat        343
Cys Pro Val Gln Ser Gly Lys Thr Trp Gln Asp Cys Glu Tyr Lys Asp
         85                  90                  95 gct gca aaa gca gcc act gga gaa tgc acg gca acc gtg ggg aag agg        391
Ala Ala Lys Ala Ala Thr Gly Glu Cys Thr Ala Thr Val Gly Lys Arg
    100                 105                 110 agc agt acg aaa ttc tcc gtg gct acc cag acc tgc cag att act cca        439
Ser Ser Thr Lys Phe Ser Val Ala Thr Gln Thr Cys Gln Ile Thr Pro
115                 120                 125                 130 gcc gag ggc cct gtg gtg aca gcc cag tac gac tgc ctc ggc tgt gtg        487
Ala Glu Gly Pro Val Val Thr Ala Gln Tyr Asp Cys Leu Gly Cys Val
                135                 140                 145 cat cct ata tca acg cag agc cca gac ctg gag ccc att ctg aga cac        535
His Pro Ile Ser Thr Gln Ser Pro Asp Leu Glu Pro Ile Leu Arg His
            150                 155                 160 ggc att cag tac ttt aac aac aac act caa cat tcc tcc ctc ttc atg        583
Gly Ile Gln Tyr Phe Asn Asn Asn Thr Gln His Ser Ser Leu Phe Met
        165                 170                 175 ctt aat gaa gta aaa cgg gcc caa aga cag gtg gtg gct gga ttg aac        631
Leu Asn Glu Val Lys Arg Ala Gln Arg Gln Val Val Ala Gly Leu Asn
180                 185                 190 ttt cga att acc tac tca att gtg caa acg aat tgt tcc aaa gag aat        679
Phe Arg Ile Thr Tyr Ser Ile Val Gln Thr Asn Cys Ser Lys Glu Asn
195                 200                 205                 210 ttt ctg ttc tta act cca gac tgc aag tcc ctt tgg aat ggt gat acc        727
Phe Leu Phe Leu Thr Pro Asp Cys Lys Ser Leu Trp Asn Gly Asp Thr
                215                 220                 225 ggt gaa tgt aca gat aat gca tac atc gat att cag cta cga att gct        775
Gly Glu Cys Thr Asp Asn Ala Tyr Ile Asp Ile Gln Leu Arg Ile Ala
            230                 235                 240 tcc ttc tca cag aac tgt gac att tat cca ggg aag gat ttt gta caa        823
Ser Phe Ser Gln Asn Cys Asp Ile Tyr Pro Gly Lys Asp Phe Val Gln
        245                 250                 255 cca cct acc aag att tgc gtg ggc tgc ccc aga gat ata ccc acc aac        871
Pro Pro Thr Lys Ile Cys Val Gly Cys Pro Arg Asp Ile Pro Thr Asn
260                 265                 270 agc cca gag ctg gag gag aca ctg act cac acc atc aca aag ctt aat        919
Ser Pro Glu Leu Glu Glu Thr Leu Thr His Thr Ile Thr Lys Leu Asn
275                 280                 285                 290 gca gag aat aac gca act ttc tat ttc aag att gac aat gtg aaa aaa        967
Ala Glu Asn Asn Ala Thr Phe Tyr Phe Lys Ile Asp Asn Val Lys Lys
                295                 300                 305 gca aga gta cag gtg gtg gct ggc aag aaa tat ttt att gac ttc gtg       1015
Ala Arg Val Gln Val Val Ala Gly Lys Lys Tyr Phe Ile Asp Phe Val
            310                 315                 320 gcc agg gaa acc aca tgt tcc aag gaa agt aat gaa gag ttg acc gaa       1063
Ala Arg Glu Thr Thr Cys Ser Lys Glu Ser Asn Glu Glu Leu Thr Glu
        325                 330                 335 agc tgt gag acc aaa aaa ctt ggc caa agc cta gat tgc aac gct gaa       1111
Ser Cys Glu Thr Lys Lys Leu Gly Gln Ser Leu Asp Cys Asn Ala Glu
340                 345                 350 gtt tat gtg gta ccc tgg gag aaa aaa att tac cct act gtc aac tgt       1159
Val Tyr Val Val Pro Trp Glu Lys Lys Ile Tyr Pro Thr Val Asn Cys
355                 360                 365                 370 caa cca ctg gga atg atc tca ctg atg aaa agg cct cca ggt ttt tca       1207
Gln Pro Leu Gly Met Ile Ser Leu Met Lys Arg Pro Pro Gly Phe Ser
                375                 380                 385 cct ttc cga tca tca cga ata ggg gaa ata aaa gaa gaa aca act gta       1255
Pro Phe Arg Ser Ser Arg Ile Gly Glu Ile Lys Glu Glu Thr Thr Val
            390                 395                 400
```

-continued

```
agt cca ccc cac act tcc atg gca cct gca caa gat gaa gag cgg gat    1303
Ser Pro Pro His Thr Ser Met Ala Pro Ala Gln Asp Glu Glu Arg Asp
        405                 410                 415 tca gga aaa gaa caa ggg cat act cgt aga cat gac tgg ggc cat gaa    1351
Ser Gly Lys Glu Gln Gly His Thr Arg Arg His Asp Trp Gly His Glu
420                 425                 430 aaa caa aga aaa cat aat ctt ggc cat ggc cat aaa cat gaa cgt gac    1399
Lys Gln Arg Lys His Asn Leu Gly His Gly His Lys His Glu Arg Asp
435                 440                 445                 450 caa ggg cat ggg cac caa aga gga cat ggc ctt ggc cat gga cac gaa    1447
Gln Gly His Gly His Gln Arg Gly His Gly Leu Gly His Gly His Glu
                455                 460                 465 caa cag cat ggt ctt ggt cat gga cat aag ttc aaa ctt gat gat gat    1495
Gln Gln His Gly Leu Gly His Gly His Lys Phe Lys Leu Asp Asp Asp
            470                 475                 480 ctt gaa cac caa ggg ggc cat gtc ctt gac cat gga cat aag cat aag    1543
Leu Glu His Gln Gly Gly His Val Leu Asp His Gly His Lys His Lys
        485                 490                 495 cat ggt cat ggc cac gga aaa cat aaa aat aaa ggc aaa aag aat gga    1591
His Gly His Gly His Gly Lys His Lys Asn Lys Gly Lys Lys Asn Gly
500                 505                 510 aag cac aat ggt tgg aaa aca gag cat ttg gca agc tct tct gaa gac    1639
Lys His Asn Gly Trp Lys Thr Glu His Leu Ala Ser Ser Ser Glu Asp
515                 520                 525                 530 agt act aca cct tct gca cag aca caa gag aag aca gaa ggg cca aca    1687
Ser Thr Thr Pro Ser Ala Gln Thr Gln Glu Lys Thr Glu Gly Pro Thr
                535                 540                 545 ccc atc cct tcc cta gcc aag cca ggt gta aca gtt acc ttt tct gac    1735
Pro Ile Pro Ser Leu Ala Lys Pro Gly Val Thr Val Thr Phe Ser Asp
            550                 555                 560 ttt cag gac tct gat ctc att gca act atg atg cct cct ata tca cca    1783
Phe Gln Asp Ser Asp Leu Ile Ala Thr Met Met Pro Pro Ile Ser Pro
        565                 570                 575 gct ccc ata cag agt gat gac gat tgg atc cct gat atc cag ata gac    1831
Ala Pro Ile Gln Ser Asp Asp Asp Trp Ile Pro Asp Ile Gln Ile Asp
580                 585                 590 cca aat ggc ctt tca ttt aac cca ata tca gat ttt cca gac acg acc    1879
Pro Asn Gly Leu Ser Phe Asn Pro Ile Ser Asp Phe Pro Asp Thr Thr
595                 600                 605                 610 tcc cca aaa tgt cct gga cgc ccc tgg aag tca gtt agt gaa att aat    1927
Ser Pro Lys Cys Pro Gly Arg Pro Trp Lys Ser Val Ser Glu Ile Asn
                615                 620                 625 cca acc aca caa atg aaa gaa tct tat tat ttc gat ctc act gat ggc    1975
Pro Thr Thr Gln Met Lys Glu Ser Tyr Tyr Phe Asp Leu Thr Asp Gly
            630                 635                 640 ctt tct taa                                                        1984
Leu Ser

<210> SEQ ID NO 84
<211> LENGTH: 644
<212> TYPE: PRT
<213> ORGANISM: Homo sapiens

<400> SEQUENCE: 84

Met Lys Leu Ile Thr Ile Leu Phe Leu Cys Ser Arg Leu Leu Leu Ser
 1               5                  10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
```

-continued

```
                35                  40                  45
Gln Ser Asn Asn Gln Phe Val Leu Tyr Arg Ile Thr Glu Ala Thr Lys
         50                  55                  60
Thr Val Gly Ser Asp Thr Phe Tyr Ser Phe Lys Tyr Glu Ile Lys Glu
 65                  70                  75                  80
Gly Asp Cys Pro Val Gln Ser Gly Lys Thr Trp Gln Asp Cys Glu Tyr
                 85                  90                  95
Lys Asp Ala Ala Lys Ala Ala Thr Gly Glu Cys Thr Ala Thr Val Gly
                100                 105                 110
Lys Arg Ser Ser Thr Lys Phe Ser Val Ala Thr Gln Thr Cys Gln Ile
            115                 120                 125
Thr Pro Ala Glu Gly Pro Val Thr Ala Gln Tyr Asp Cys Leu Gly
        130                 135                 140
Cys Val His Pro Ile Ser Thr Gln Ser Pro Asp Leu Glu Pro Ile Leu
145                 150                 155                 160
Arg His Gly Ile Gln Tyr Phe Asn Asn Thr Gln His Ser Ser Leu
                165                 170                 175
Phe Met Leu Asn Glu Val Lys Arg Ala Gln Arg Gln Val Val Ala Gly
            180                 185                 190
Leu Asn Phe Arg Ile Thr Tyr Ser Ile Val Gln Thr Asn Cys Ser Lys
            195                 200                 205
Glu Asn Phe Leu Phe Leu Thr Pro Asp Cys Lys Ser Leu Trp Asn Gly
    210                 215                 220
Asp Thr Gly Glu Cys Thr Asp Asn Ala Tyr Ile Asp Ile Gln Leu Arg
225                 230                 235                 240
Ile Ala Ser Phe Ser Gln Asn Cys Asp Ile Tyr Pro Gly Lys Asp Phe
                245                 250                 255
Val Gln Pro Pro Thr Lys Ile Cys Val Gly Cys Pro Arg Asp Ile Pro
                260                 265                 270
Thr Asn Ser Pro Glu Leu Glu Thr Leu Thr His Thr Ile Thr Lys
            275                 280                 285
Leu Asn Ala Glu Asn Asn Ala Thr Phe Tyr Phe Lys Ile Asp Asn Val
    290                 295                 300
Lys Lys Ala Arg Val Gln Val Ala Gly Lys Lys Tyr Phe Ile Asp
305                 310                 315                 320
Phe Val Ala Arg Glu Thr Thr Cys Ser Lys Glu Ser Asn Glu Glu Leu
                325                 330                 335
Thr Glu Ser Cys Glu Thr Lys Lys Leu Gly Gln Ser Leu Asp Cys Asn
            340                 345                 350
Ala Glu Val Tyr Val Val Pro Trp Glu Lys Lys Ile Tyr Pro Thr Val
            355                 360                 365
Asn Cys Gln Pro Leu Gly Met Ile Ser Leu Met Lys Arg Pro Pro Gly
    370                 375                 380
Phe Ser Pro Phe Arg Ser Arg Ile Gly Glu Ile Lys Glu Glu Thr
385                 390                 395                 400
Thr Val Ser Pro Pro His Thr Ser Met Ala Pro Ala Gln Asp Glu Glu
                405                 410                 415
Arg Asp Ser Gly Lys Glu Gln Gly His Thr Arg Arg His Asp Trp Gly
            420                 425                 430
His Glu Lys Gln Arg Lys His Asn Leu Gly His Gly His Lys His Glu
        435                 440                 445
Arg Asp Gln Gly His Gly His Gln Arg Gly His Gly Leu Gly His Gly
    450                 455                 460
```

```
His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
            500                 505                 510

Asn Gly Lys His Asn Gly Trp Lys Thr Glu His Leu Ala Ser Ser Ser
        515                 520                 525

Glu Asp Ser Thr Thr Pro Ser Ala Gln Thr Gln Glu Lys Thr Glu Gly
    530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Trp Ile Pro Asp Ile Gln
            580                 585                 590

Ile Asp Pro Asn Gly Leu Ser Phe Asn Pro Ile Ser Asp Phe Pro Asp
        595                 600                 605

Thr Thr Ser Pro Lys Cys Pro Gly Arg Pro Trp Lys Ser Val Ser Glu
610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 85
<211> LENGTH: 1272
<212> TYPE: DNA
<213> ORGANISM: Homo sapiens
<220> FEATURE:
<221> NAME/KEY: CDS
<222> LOCATION: (220)..(1249)

<400> SEQUENCE: 85
cttccccagg actccaggag acataaaact tgaaacggga gacttcgtgc               50
aaatcctgct ccggacgctg ctgaagctca gatttctccc actgcctgca              100
cagggtgctg cctgctggcg aatgtgactc tcctcctgtt cacccacaag              150
gctgattttt ccgtgttcct cctctggaaa gagcattgct ttctctcttc              200
cagcacttta cctacattc atg tct ttc agg tgg ctg ctt ctc tat tat       249
                      Met Ser Phe Arg Trp Leu Leu Leu Tyr Tyr
                        1               5                  10 gct ctg tgc ttc tcc ctg tca aag gct tca gcc cac acc gtg gag cta   297
Ala Leu Cys Phe Ser Leu Ser Lys Ala Ser Ala His Thr Val Glu Leu
            15                  20                  25 aac aat atg ttt ggc cag atc cag tcg cct ggt tat cca gac tcc tat   345
Asn Asn Met Phe Gly Gln Ile Gln Ser Pro Gly Tyr Pro Asp Ser Tyr
        30                  35                  40 ccc agt gat tca gag gtg act tgg aat atc act gtc cca gat ggg ttt   393
Pro Ser Asp Ser Glu Val Thr Trp Asn Ile Thr Val Pro Asp Gly Phe
    45                  50                  55 cgg atc aag ctt tac ttc atg cac ttc aac ttg gaa tcc tcc tac ctt   441
Arg Ile Lys Leu Tyr Phe Met His Phe Asn Leu Glu Ser Ser Tyr Leu
60                  65                  70 tgt gaa tat gac tat gtg aag gta gaa act gag gac act tcg aga gtg   489
Cys Glu Tyr Asp Tyr Val Lys Val Glu Thr Glu Asp Thr Ser Arg Val
            75                  80                  85                  90
```

| | | | |
|---|---|---|---|
| cca aat gac aag tgg ttt ggg agt ggg gcc ctg ctc tct gcg tcc tgg | | | 537 |
| Pro Asn Asp Lys Trp Phe Gly Ser Gly Ala Leu Leu Ser Ala Ser Trp | | | |
| 95 | 100 | 105 | |
| atc ctc aca gca gct cat gtg ctg cgc tcc cag cgt aga gac acc acg | | | 585 |
| Ile Leu Thr Ala Ala His Val Leu Arg Ser Gln Arg Arg Asp Thr Thr | | | |
| 110 | 115 | 120 | |
| gtg ata cca gtc tcc aag gag cat gtc acc gtc tac ctg ggc ttg cat | | | 633 |
| Val Ile Pro Val Ser Lys Glu His Val Thr Val Tyr Leu Gly Leu His | | | |
| 125 | 130 | 135 | |
| gat gtg cga gac aaa tcg ggg gca gtc aac agc tca gct gcc cga gtg | | | 681 |
| Asp Val Arg Asp Lys Ser Gly Ala Val Asn Ser Ser Ala Ala Arg Val | | | |
| 140 | 145 | 150 | |
| gtg ctc cac cca gac ttc aac atc caa aac tac aac cac gat ata gct | | | 729 |
| Val Leu His Pro Asp Phe Asn Ile Gln Asn Tyr Asn His Asp Ile Ala | | | |
| 155 | 160 | 165 | 170 |
| ctg gtg cag ctg cag gag cct gtg ccc ctg gga ccc cac gtt atg cct | | | 777 |
| Leu Val Gln Leu Gln Glu Pro Val Pro Leu Gly Pro His Val Met Pro | | | |
| 175 | 180 | 185 | |
| gtc tgc ctg cca agg ctt gag cct gaa ggc ccg gcc ccc cac atg ctg | | | 825 |
| Val Cys Leu Pro Arg Leu Glu Pro Glu Gly Pro Ala Pro His Met Leu | | | |
| 190 | 195 | 200 | |
| ggc ctg gtg gcc ggc tgg ggc atc tcc aat ccc aat gtg aca gtg gat | | | 873 |
| Gly Leu Val Ala Gly Trp Gly Ile Ser Asn Pro Asn Val Thr Val Asp | | | |
| 205 | 210 | 215 | |
| gag atc atc agc agt ggc aca cgg acc ttg tca gat gtc ctg cag tat | | | 921 |
| Glu Ile Ile Ser Ser Gly Thr Arg Thr Leu Ser Asp Val Leu Gln Tyr | | | |
| 220 | 225 | 230 | |
| gtc aag tta ccc gtg gtg cct cac gct gag tgc aaa act agc tat gag | | | 969 |
| Val Lys Leu Pro Val Val Pro His Ala Glu Cys Lys Thr Ser Tyr Glu | | | |
| 235 | 240 | 245 | 250 |
| tcc cgc tcg ggc aat tac agc gtc acg gag aac atg ttc tgt gct ggc | | | 1017 |
| Ser Arg Ser Gly Asn Tyr Ser Val Thr Glu Asn Met Phe Cys Ala Gly | | | |
| 255 | 260 | 265 | |
| tac tac gag ggc ggc aaa gac acg tgc ctt gga gat agc ggt ggg gcc | | | 1065 |
| Tyr Tyr Glu Gly Gly Lys Asp Thr Cys Leu Gly Asp Ser Gly Gly Ala | | | |
| 270 | 275 | 280 | |
| ttt gtc atc ttt gat gac ttg agc cag cgc tgg gtg gtg caa ggc ctg | | | 1113 |
| Phe Val Ile Phe Asp Asp Leu Ser Gln Arg Trp Val Val Gln Gly Leu | | | |
| 285 | 290 | 295 | |
| gtg tcc tgg ggg gga cct gaa gaa tgc ggc agc aag cag gtc tat gga | | | 1161 |
| Val Ser Trp Gly Gly Pro Glu Glu Cys Gly Ser Lys Gln Val Tyr Gly | | | |
| 300 | 305 | 310 | |
| gtc tac aca aag gtc tcc aat tac gtg gac tgg gtg tgg gag cag atg | | | 1209 |
| Val Tyr Thr Lys Val Ser Asn Tyr Val Asp Trp Val Trp Glu Gln Met | | | |
| 315 | 320 | 325 | 330 |
| ggc tta cca caa agt gtt gtg gag ccc cag gtg gaa cgg tgagctgact | | | 1258 |
| Gly Leu Pro Gln Ser Val Val Glu Pro Gln Val Glu Arg | | | |
| 335 | 340 | | |
| tacttcctcg cggg | | | 1272 |

<210> SEQ ID NO 86
<211> LENGTH: 343
<212> TYPE: PRT
<213> ORGANISM: Homo sapiens

<400> SEQUENCE: 86

Met Ser Phe Arg Trp Leu Leu Leu Tyr Tyr Ala Leu Cys Phe Ser Leu
1               5                   10                  15

Ser Lys Ala Ser Ala His Thr Val Glu Leu Asn Asn Met Phe Gly Gln
            20                  25                  30

```
Ile Gln Ser Pro Gly Tyr Pro Asp Ser Tyr Pro Ser Asp Ser Glu Val
        35                  40                  45

Thr Trp Asn Ile Thr Val Pro Asp Gly Phe Arg Ile Lys Leu Tyr Phe
 50                  55                  60

Met His Phe Asn Leu Glu Ser Ser Tyr Leu Cys Glu Tyr Asp Tyr Val
 65                  70                  75                  80

Lys Val Glu Thr Glu Asp Thr Ser Arg Val Pro Asn Asp Lys Trp Phe
                85                  90                  95

Gly Ser Gly Ala Leu Leu Ser Ala Ser Trp Ile Leu Thr Ala Ala His
                100                 105                 110

Val Leu Arg Ser Gln Arg Arg Asp Thr Thr Val Ile Pro Val Ser Lys
            115                 120                 125

Glu His Val Thr Val Tyr Leu Gly Leu His Asp Val Arg Asp Lys Ser
        130                 135                 140

Gly Ala Val Asn Ser Ser Ala Ala Arg Val Val Leu His Pro Asp Phe
145                 150                 155                 160

Asn Ile Gln Asn Tyr Asn His Asp Ile Ala Leu Val Gln Leu Gln Glu
                165                 170                 175

Pro Val Pro Leu Gly Pro His Val Met Pro Val Cys Leu Pro Arg Leu
                180                 185                 190

Glu Pro Glu Gly Pro Ala Pro His Met Leu Gly Leu Val Ala Gly Trp
            195                 200                 205

Gly Ile Ser Asn Pro Asn Val Thr Val Asp Glu Ile Ile Ser Ser Gly
        210                 215                 220

Thr Arg Thr Leu Ser Asp Val Leu Gln Tyr Val Lys Leu Pro Val Val
225                 230                 235                 240

Pro His Ala Glu Cys Lys Thr Ser Tyr Glu Ser Arg Ser Gly Asn Tyr
                245                 250                 255

Ser Val Thr Glu Asn Met Phe Cys Ala Gly Tyr Tyr Glu Gly Gly Lys
                260                 265                 270

Asp Thr Cys Leu Gly Asp Ser Gly Gly Ala Phe Val Ile Phe Asp Asp
            275                 280                 285

Leu Ser Gln Arg Trp Val Val Gln Gly Leu Val Ser Trp Gly Gly Pro
        290                 295                 300

Glu Glu Cys Gly Ser Lys Gln Val Tyr Gly Val Tyr Thr Lys Val Ser
305                 310                 315                 320

Asn Tyr Val Asp Trp Val Trp Glu Gln Met Gly Leu Pro Gln Ser Val
                325                 330                 335

Val Glu Pro Gln Val Glu Arg
            340

<210> SEQ ID NO 87
<211> LENGTH: 861
<212> TYPE: DNA
<213> ORGANISM: Homo sapiens
<220> FEATURE:
<221> NAME/KEY: CDS
<222> LOCATION: (10)..(775)

<400> SEQUENCE: 87 cagctcagc atg gct agg gta ctg gga gca ccc gtt gca ctg ggg ttg         48
          Met Ala Arg Val Leu Gly Ala Pro Val Ala Leu Gly Leu
           1               5                  10 tgg agc cta tgc tgg tct ctg gcc att gcc acc cct ctt cct ccg act       96
Trp Ser Leu Cys Trp Ser Leu Ala Ile Ala Thr Pro Leu Pro Pro Thr
 15                  20                  25
```

| | | | | | | | | | | | | | | | | |
|---|---|---|---|---|---|---|---|---|---|---|---|---|---|---|---|---|
| agt | gcc | cat | ggg | aat | gtt | gct | gaa | ggc | gag | acc | aag | cca | gac | cca | gac | 144 |
| Ser | Ala | His | Gly | Asn | Val | Ala | Glu | Gly | Glu | Thr | Lys | Pro | Asp | Pro | Asp | |
| 30 | | | | 35 | | | | | 40 | | | | | 45 | | |
| gtg | act | gaa | cgc | tgc | tca | gat | ggc | tgg | agc | ttt | gat | gct | acc | acc | ctg | 192 |
| Val | Thr | Glu | Arg | Cys | Ser | Asp | Gly | Trp | Ser | Phe | Asp | Ala | Thr | Thr | Leu | |
| | | | 50 | | | | | 55 | | | | | 60 | | | |
| gat | gac | aat | gga | acc | atg | ctg | ttt | ttt | aaa | ggg | acc | cac | tac | tgg | cgt | 240 |
| Asp | Asp | Asn | Gly | Thr | Met | Leu | Phe | Phe | Lys | Gly | Thr | His | Tyr | Trp | Arg | |
| | | | 65 | | | | | 70 | | | | | 75 | | | |
| ctg | gac | acc | agc | cgg | gat | ggc | tgg | cat | agc | tgg | ccc | att | gct | cat | cag | 288 |
| Leu | Asp | Thr | Ser | Arg | Asp | Gly | Trp | His | Ser | Trp | Pro | Ile | Ala | His | Gln | |
| | | 80 | | | | | 85 | | | | | 90 | | | | |
| tgg | ccc | cag | ggt | cct | tca | gca | gtg | gat | gct | gcc | ttt | tcc | tgg | gaa | gaa | 336 |
| Trp | Pro | Gln | Gly | Pro | Ser | Ala | Val | Asp | Ala | Ala | Phe | Ser | Trp | Glu | Glu | |
| | 95 | | | | | 100 | | | | | 105 | | | | | |
| aaa | ctc | tat | ctg | gtc | cag | ggc | acc | cag | gta | tat | gtc | ttc | ctg | aca | aag | 384 |
| Lys | Leu | Tyr | Leu | Val | Gln | Gly | Thr | Gln | Val | Tyr | Val | Phe | Leu | Thr | Lys | |
| 110 | | | | | 115 | | | | | 120 | | | | | 125 | |
| gga | ggc | tat | acc | cta | gta | agc | ggt | tat | ccg | aag | cgg | ctg | gag | aag | gaa | 432 |
| Gly | Gly | Tyr | Thr | Leu | Val | Ser | Gly | Tyr | Pro | Lys | Arg | Leu | Glu | Lys | Glu | |
| | | | 130 | | | | | 135 | | | | | 140 | | | |
| gtc | ggg | acc | cct | cat | ggg | att | atc | ctg | gac | tct | gtg | gat | gcg | gcc | ttt | 480 |
| Val | Gly | Thr | Pro | His | Gly | Ile | Ile | Leu | Asp | Ser | Val | Asp | Ala | Ala | Phe | |
| | | | 145 | | | | | 150 | | | | | 155 | | | |
| atc | tgc | cct | ggg | tct | tct | cgg | ctc | cat | atc | atg | gca | gga | cgg | cgg | ctg | 528 |
| Ile | Cys | Pro | Gly | Ser | Ser | Arg | Leu | His | Ile | Met | Ala | Gly | Arg | Arg | Leu | |
| | | | 160 | | | | | 165 | | | | | 170 | | | |
| tgg | tgg | ctg | gac | ctg | aag | tca | gga | gcc | caa | gcc | acg | tgg | aca | gag | ctt | 576 |
| Trp | Trp | Leu | Asp | Leu | Lys | Ser | Gly | Ala | Gln | Ala | Thr | Trp | Thr | Glu | Leu | |
| | 175 | | | | | 180 | | | | | 185 | | | | | |
| cct | tgg | ccc | cat | gag | aag | gta | gac | gga | gcc | ttg | tgt | atg | gaa | aag | tcc | 624 |
| Pro | Trp | Pro | His | Glu | Lys | Val | Asp | Gly | Ala | Leu | Cys | Met | Glu | Lys | Ser | |
| 190 | | | | | 195 | | | | | 200 | | | | | 205 | |
| ctt | ggc | cct | aac | tca | tgt | tcc | gcc | aat | ggt | ccc | ggc | ttg | tac | ctc | atc | 672 |
| Leu | Gly | Pro | Asn | Ser | Cys | Ser | Ala | Asn | Gly | Pro | Gly | Leu | Tyr | Leu | Ile | |
| | | | 210 | | | | | 215 | | | | | 220 | | | |
| cat | ggt | ccc | aat | ttg | tac | tgc | tac | agt | gat | gtg | gag | aaa | ctg | aat | gca | 720 |
| His | Gly | Pro | Asn | Leu | Tyr | Cys | Tyr | Ser | Asp | Val | Glu | Lys | Leu | Asn | Ala | |
| | | | 225 | | | | | 230 | | | | | 235 | | | |
| gcc | aag | gcc | ctt | ccg | caa | ccc | cag | aat | gtg | acc | agt | ctc | ctg | ggc | tgc | 768 |
| Ala | Lys | Ala | Leu | Pro | Gln | Pro | Gln | Asn | Val | Thr | Ser | Leu | Leu | Gly | Cys | |
| | | 240 | | | | | 245 | | | | | 250 | | | | |
| act | cac | tgaggggcct | tctgacatga | gtctggcctg | gccccacctc | ctagttcctc | | | | | | | | | | 824 |
| Thr | His | | | | | | | | | | | | | | | |
| | 255 | | | | | | | | | | | | | | | |
| ataataaaga | cagattgctt | cttcgcttct | cactgag | | | | | | | | | | | | | 861 |

<210> SEQ ID NO 88
<211> LENGTH: 255
<212> TYPE: PRT
<213> ORGANISM: Homo sapiens

<400> SEQUENCE: 88

| | | | | | | | | | | | | | | |
|---|---|---|---|---|---|---|---|---|---|---|---|---|---|---|
| Met | Ala | Arg | Val | Leu | Gly | Ala | Pro | Val | Ala | Leu | Gly | Leu | Trp | Ser | Leu |
| 1 | | | | 5 | | | | | 10 | | | | | 15 | |
| Cys | Trp | Ser | Leu | Ala | Ile | Ala | Thr | Pro | Leu | Pro | Pro | Thr | Ser | Ala | His |
| | | | 20 | | | | | 25 | | | | | 30 | | |
| Gly | Asn | Val | Ala | Glu | Gly | Glu | Thr | Lys | Pro | Asp | Pro | Asp | Val | Thr | Glu |
| | | 35 | | | | | 40 | | | | | 45 | | | |

```
Arg Cys Ser Asp Gly Trp Ser Phe Asp Ala Thr Thr Leu Asp Asp Asn
 50                  55                  60
Gly Thr Met Leu Phe Phe Lys Gly Thr His Tyr Trp Arg Leu Asp Thr
 65                  70                  75                  80
Ser Arg Asp Gly Trp His Ser Trp Pro Ile Ala His Gln Trp Pro Gln
                 85                  90                  95
Gly Pro Ser Ala Val Asp Ala Ala Phe Ser Trp Glu Glu Lys Leu Tyr
                100                 105                 110
Leu Val Gln Gly Thr Gln Val Tyr Val Phe Leu Thr Lys Gly Gly Tyr
                115                 120                 125
Thr Leu Val Ser Gly Tyr Pro Lys Arg Leu Glu Lys Glu Val Gly Thr
                130                 135                 140
Pro His Gly Ile Ile Leu Asp Ser Val Asp Ala Ala Phe Ile Cys Pro
145                 150                 155                 160
Gly Ser Ser Arg Leu His Ile Met Ala Gly Arg Arg Leu Trp Trp Leu
                165                 170                 175
Asp Leu Lys Ser Gly Ala Gln Ala Thr Trp Thr Glu Leu Pro Trp Pro
                180                 185                 190
His Glu Lys Val Asp Gly Ala Leu Cys Met Glu Lys Ser Leu Gly Pro
                195                 200                 205
Asn Ser Cys Ser Ala Asn Gly Pro Gly Leu Tyr Leu Ile His Gly Pro
210                 215                 220
Asn Leu Tyr Cys Tyr Ser Asp Val Glu Lys Leu Asn Ala Ala Lys Ala
225                 230                 235                 240
Leu Pro Gln Pro Gln Asn Val Thr Ser Leu Leu Gly Cys Thr His
                245                 250                 255

<210> SEQ ID NO 89
<211> LENGTH: 2671
<212> TYPE: DNA
<213> ORGANISM: Homo sapiens
<220> FEATURE:
<221> NAME/KEY: CDS
<222> LOCATION: (15)..(2652)

<400> SEQUENCE: 89
cccgccgggc gagc atg ggg cgc ctg gcc tcg agg ccg ctg ctg ctg gcg      50
                Met Gly Arg Leu Ala Ser Arg Pro Leu Leu Leu Ala
                  1               5                  10 ctc ctg tcg ttg gct ctt tgc cga ggg cgt gtg gtg aga gtc ccc aca      98
Leu Leu Ser Leu Ala Leu Cys Arg Gly Arg Val Val Arg Val Pro Thr
             15                  20                  25 gcg acc ctg gtt cga gtg gtg ggc act gag ctg gtc atc ccc tgc aac     146
Ala Thr Leu Val Arg Val Val Gly Thr Glu Leu Val Ile Pro Cys Asn
 30                  35                  40 gtc agt gac tat gat ggc ccc agc gag caa aac ttt gac tgg agc ttc     194
Val Ser Asp Tyr Asp Gly Pro Ser Glu Gln Asn Phe Asp Trp Ser Phe
 45                  50                  55                  60 tca tct ttg ggg agc agc ttt gtg gag ctt gca agc acc tgg gag gtg     242
Ser Ser Leu Gly Ser Ser Phe Val Glu Leu Ala Ser Thr Trp Glu Val
                 65                  70                  75 ggg ttc cca gcc caa ctg tac cag gag cgg ctg cag agg ggc gag atc     290
Gly Phe Pro Ala Gln Leu Tyr Gln Glu Arg Leu Gln Arg Gly Glu Ile
                 80                  85                  90 ctg tta agg cgg act gcc aac gac gcc gtg gag ctc cac ata aag aac     338
Leu Leu Arg Arg Thr Ala Asn Asp Ala Val Glu Leu His Ile Lys Asn
                 95                 100                 105
```

| | | |
|---|---|---|
| gtc cag cct tca gac caa ggc cac tac aaa tgt tca acc ccc agc aca<br>Val Gln Pro Ser Asp Gln Gly His Tyr Lys Cys Ser Thr Pro Ser Thr<br>110               115                  120 | 386 |
| gat gcc act gtc cag gga aac tat gag gac aca gtg cag gtt aaa gtg<br>Asp Ala Thr Val Gln Gly Asn Tyr Glu Asp Thr Val Gln Val Lys Val<br>125               130               135             140 | 434 |
| ctg gcc gac tcc ctg cac gtg ggc ccc agc gcg cgg ccc ccg ccg agc<br>Leu Ala Asp Ser Leu His Val Gly Pro Ser Ala Arg Pro Pro Pro Ser<br>               145                  150              155 | 482 |
| ctg agc ctg cgg gag ggg gag ccc ttc gag ctg cgc tgc acc gcc gcc<br>Leu Ser Leu Arg Glu Gly Glu Pro Phe Glu Leu Arg Cys Thr Ala Ala<br>                160                165              170 | 530 |
| tcc gcc tcg ccg ctg cac acg cac ctg gcg ctg ctg tgg gag gtg cac<br>Ser Ala Ser Pro Leu His Thr His Leu Ala Leu Leu Trp Glu Val His<br>175               180                  185 | 578 |
| cgc ggc ccg gcc agg cgg agc gtc ctc gcc ctg acc cac gag ggc agg<br>Arg Gly Pro Ala Arg Arg Ser Val Leu Ala Leu Thr His Glu Gly Arg<br>    190                  195              200 | 626 |
| ttc cac ccg ggc ctg ggg tac gag cag cgc tac cac agt ggg gac gtg<br>Phe His Pro Gly Leu Gly Tyr Glu Gln Arg Tyr His Ser Gly Asp Val<br>205               210               215             220 | 674 |
| cgc ctc gac acc gtg ggc agc gac gcc tac cgc ctc tca gtg tcc cgg<br>Arg Leu Asp Thr Val Gly Ser Asp Ala Tyr Arg Leu Ser Val Ser Arg<br>                    225               230             235 | 722 |
| gct ctg tct gcc gac cag ggc tcc tac agg tgt atc gtc agc gag tgg<br>Ala Leu Ser Ala Asp Gln Gly Ser Tyr Arg Cys Ile Val Ser Glu Trp<br>               240                  245             250 | 770 |
| atc gcc gag cag ggc aac tgg cag gaa atc caa gaa aag gcc gtg gaa<br>Ile Ala Glu Gln Gly Asn Trp Gln Glu Ile Gln Glu Lys Ala Val Glu<br>          255                260             265 | 818 |
| gtt gcc acc gtg gtg atc cag ccg aca gtt ctg cga gca gcc gtg ccc<br>Val Ala Thr Val Val Ile Gln Pro Thr Val Leu Arg Ala Ala Val Pro<br>270               275               280 | 866 |
| aag aat gtg tct gtg gct gaa gga aag gaa ctg gac ctg acc tgt aac<br>Lys Asn Val Ser Val Ala Glu Gly Lys Glu Leu Asp Leu Thr Cys Asn<br>285               290               295             300 | 914 |
| atc aca aca gac cga gcc gat gac gtc cgg ccc gag gtg acg tgg tcc<br>Ile Thr Thr Asp Arg Ala Asp Asp Val Arg Pro Glu Val Thr Trp Ser<br>                    305               310             315 | 962 |
| ttc agc agg atg cct gac agc acc cta cct ggc tcc cgc gtg ttg gcg<br>Phe Ser Arg Met Pro Asp Ser Thr Leu Pro Gly Ser Arg Val Leu Ala<br>                320                325              330 | 1010 |
| cgg ctt gac cgt gat tcc ctg gtg cac agc tcg cct cat gtt gct ttg<br>Arg Leu Asp Arg Asp Ser Leu Val His Ser Ser Pro His Val Ala Leu<br>335               340               345 | 1058 |
| agt cat gtg gat gca cgc tcc tac cat tta ctg gtt cgg gat gtt agc<br>Ser His Val Asp Ala Arg Ser Tyr His Leu Leu Val Arg Asp Val Ser<br>350               355               360 | 1106 |
| aaa gaa aac tct ggc tac tat tac tgc cac gtg tcc ctg tgg gca ccc<br>Lys Glu Asn Ser Gly Tyr Tyr Tyr Cys His Val Ser Leu Trp Ala Pro<br>365               370               375             380 | 1154 |
| gga cac aac agg agc tgg cac aaa gtg gca gag gcc gtg tct tcc cca<br>Gly His Asn Arg Ser Trp His Lys Val Ala Glu Ala Val Ser Ser Pro<br>                385               390             395 | 1202 |
| gct ggt gtg ggt gtg acc tgg cta gaa cca gac tac cag gtg tac ctg<br>Ala Gly Val Gly Val Thr Trp Leu Glu Pro Asp Tyr Gln Val Tyr Leu<br>               400               405             410 | 1250 |
| aat gct tcc aag gtc ccc ggg ttt gcg gat gac ccc aca gag ctg gca<br>Asn Ala Ser Lys Val Pro Gly Phe Ala Asp Asp Pro Thr Glu Leu Ala<br>               415                 420             425 | 1298 |

-continued

| | |
|---|---|
| tgc cgg gtg gtg gac acg aag agt ggg gag gcg aat gtc cga ttc acg<br>Cys Arg Val Val Asp Thr Lys Ser Gly Glu Ala Asn Val Arg Phe Thr<br>430                          435                            440 | 1346 |
| gtt tcg tgg tac tac agg atg aac cgc agc gac aat gtg gtg acc<br>Val Ser Trp Tyr Tyr Arg Met Asn Arg Arg Ser Asp Asn Val Val Thr<br>445                          450                          455                         460 | 1394 |
| agc gag ctg ctt gca gtc atg gac ggg gac tgg acg cta aaa tat gga<br>Ser Glu Leu Leu Ala Val Met Asp Gly Asp Trp Thr Leu Lys Tyr Gly<br>                        465                          470                         475 | 1442 |
| gag agg agc aag cag cgg gcc cag gat gga gac ttt att ttt tct aag<br>Glu Arg Ser Lys Gln Arg Ala Gln Asp Gly Asp Phe Ile Phe Ser Lys<br>                    480                          485                        490 | 1490 |
| gaa cat aca gac acg ttc aat ttc cgg atc caa agg act aca gag gaa<br>Glu His Thr Asp Thr Phe Asn Phe Arg Ile Gln Arg Thr Thr Glu Glu<br>                495                        500                        505 | 1538 |
| gac aga ggc aat tat tac tgt gtt gtg tct gcc tgg acc aaa cag cgg<br>Asp Arg Gly Asn Tyr Tyr Cys Val Val Ser Ala Trp Thr Lys Gln Arg<br>510                          515                            520 | 1586 |
| aac aac agc tgg gtg aaa agc aag gat gtc ttc tcc aag cct gtt aac<br>Asn Asn Ser Trp Val Lys Ser Lys Asp Val Phe Ser Lys Pro Val Asn<br>525                          530                          535                         540 | 1634 |
| ata ttt tgg gca tta gaa gat tcc gtg ctt gtg gtg aag gcg agg cag<br>Ile Phe Trp Ala Leu Glu Asp Ser Val Leu Val Val Lys Ala Arg Gln<br>                        545                          550                         555 | 1682 |
| cca aag cct ttc ttt gct gcc gga aat aca ttt gag atg act tgc aaa<br>Pro Lys Pro Phe Phe Ala Ala Gly Asn Thr Phe Glu Met Thr Cys Lys<br>                    560                          565                        570 | 1730 |
| gta tct tcc aag aat att aag tcg cca cgc tac tct gtt ctc atc atg<br>Val Ser Ser Lys Asn Ile Lys Ser Pro Arg Tyr Ser Val Leu Ile Met<br>                575                        580                        585 | 1778 |
| gct gag aag cct gtc ggc gac ctc tcc agt ccc aat gaa acg aag tac<br>Ala Glu Lys Pro Val Gly Asp Leu Ser Ser Pro Asn Glu Thr Lys Tyr<br>590                          595                            600 | 1826 |
| atc atc tct ctg gac cag gat tct gtg gtg aag ctg gag aat tgg aca<br>Ile Ile Ser Leu Asp Gln Asp Ser Val Val Lys Leu Glu Asn Trp Thr<br>605                          610                          615                         620 | 1874 |
| gat gca tca cgg gtg gat ggc gtt gtt tta gaa aaa gtg cag gag gat<br>Asp Ala Ser Arg Val Asp Gly Val Val Leu Glu Lys Val Gln Glu Asp<br>                        625                          630                         635 | 1922 |
| gag ttc cgc tat cga atg tac cag act cag gtc tca gac gca ggg ctg<br>Glu Phe Arg Tyr Arg Met Tyr Gln Thr Gln Val Ser Asp Ala Gly Leu<br>                    640                          645                        650 | 1970 |
| tac cgc tgc atg gtg aca gcc tgg tct cct gtc agg ggc agc ctt tgg<br>Tyr Arg Cys Met Val Thr Ala Trp Ser Pro Val Arg Gly Ser Leu Trp<br>                655                        660                        665 | 2018 |
| cga gaa gca gca acc agt ctc tcc aat cct att gag ata gac ttc caa<br>Arg Glu Ala Ala Thr Ser Leu Ser Asn Pro Ile Glu Ile Asp Phe Gln<br>670                          675                          680 | 2066 |
| acc tca ggt cct ata ttt aat gct tct gtg cat tca gac aca cca tca<br>Thr Ser Gly Pro Ile Phe Asn Ala Ser Val His Ser Asp Thr Pro Ser<br>685                          690                          695                         700 | 2114 |
| gta att cgg gga gat ctg atc aaa ttg ttc tgt atc atc act gtc gag<br>Val Ile Arg Gly Asp Leu Ile Lys Leu Phe Cys Ile Ile Thr Val Glu<br>                        705                          710                         715 | 2162 |
| gga gca gca ctg gat cca gat gac atg gcc ttt gat gtg tcc tgg ttt<br>Gly Ala Ala Leu Asp Pro Asp Asp Met Ala Phe Asp Val Ser Trp Phe<br>                    720                          725                        730 | 2210 |
| gcg gtg cac tct ttt ggc ctg gac aag gct cct gtg ctc ctg tct tcc<br>Ala Val His Ser Phe Gly Leu Asp Lys Ala Pro Val Leu Leu Ser Ser | 2258 |

```
                735                 740                 745
ctg gat cgg aag ggc atc gtg acc acc tcc cgg agg gac tgg aag agc      2306
Leu Asp Arg Lys Gly Ile Val Thr Thr Ser Arg Arg Asp Trp Lys Ser
    750                 755                 760 gac ctc agc ctg gag cgc gtg agt gtg ctg gaa ttc ttg ctg caa gtg      2354
Asp Leu Ser Leu Glu Arg Val Ser Val Leu Glu Phe Leu Leu Gln Val
765                 770                 775                 780 cat ggc tcc gag gac cag gac ttt ggc aac tac tac tgt tcc gtg act      2402
His Gly Ser Glu Asp Gln Asp Phe Gly Asn Tyr Tyr Cys Ser Val Thr
                785                 790                 795 cca tgg gtg aag tca cca aca ggt tcc tgg cag aag gag gca gag atc      2450
Pro Trp Val Lys Ser Pro Thr Gly Ser Trp Gln Lys Glu Ala Glu Ile
            800                 805                 810 cac tcc aag ccc gtt ttt ata act gtg aag atg gat gtg ctg aac gcc      2498
His Ser Lys Pro Val Phe Ile Thr Val Lys Met Asp Val Leu Asn Ala
        815                 820                 825 ttc aag tat ccc ttg ctg atc ggc gtc ggt ctg tcc acg gtc atc ggg      2546
Phe Lys Tyr Pro Leu Leu Ile Gly Val Gly Leu Ser Thr Val Ile Gly
830                 835                 840 ctc ctg tcc tgt ctc atc ggg tac tgc agc tcc cac tgg tgt tgt aag      2594
Leu Leu Ser Cys Leu Ile Gly Tyr Cys Ser Ser His Trp Cys Cys Lys
845                 850                 855                 860 aag gag gtt cag gag aca cgg cgc gag cgc cgc agg ctc atg tcg atg      2642
Lys Glu Val Gln Glu Thr Arg Arg Glu Arg Arg Arg Leu Met Ser Met
                865                 870                 875 gag atg gac taggctggcc cgggagggga                                     2671
Glu Met Asp <210> SEQ ID NO 90
<211> LENGTH: 879
<212> TYPE: PRT
<213> ORGANISM: Homo sapiens

<400> SEQUENCE: 90

Met Gly Arg Leu Ala Ser Arg Pro Leu Leu Leu Ala Leu Leu Ser Leu
1               5                   10                  15

Ala Leu Cys Arg Gly Arg Val Val Arg Val Pro Thr Ala Thr Leu Val
            20                  25                  30

Arg Val Val Gly Thr Glu Leu Val Ile Pro Cys Asn Val Ser Asp Tyr
        35                  40                  45

Asp Gly Pro Ser Glu Gln Asn Phe Asp Trp Ser Phe Ser Ser Leu Gly
    50                  55                  60

Ser Ser Phe Val Glu Leu Ala Ser Thr Trp Glu Val Gly Phe Pro Ala
65                  70                  75                  80

Gln Leu Tyr Gln Glu Arg Leu Gln Arg Gly Glu Ile Leu Leu Arg Arg
                85                  90                  95

Thr Ala Asn Asp Ala Val Glu Leu His Ile Lys Asn Val Gln Pro Ser
            100                 105                 110

Asp Gln Gly His Tyr Lys Cys Ser Thr Pro Ser Thr Asp Ala Thr Val
        115                 120                 125

Gln Gly Asn Tyr Glu Asp Thr Val Gln Val Lys Val Leu Ala Asp Ser
    130                 135                 140

Leu His Val Gly Pro Ser Ala Arg Pro Pro Ser Leu Ser Leu Arg
145                 150                 155                 160

Glu Gly Glu Pro Phe Glu Leu Arg Cys Thr Ala Ala Ser Ala Ser Pro
                165                 170                 175

Leu His Thr His Leu Ala Leu Leu Trp Glu Val His Arg Gly Pro Ala
```

```
                    180                 185                 190
Arg Arg Ser Val Leu Ala Leu Thr His Glu Gly Arg Phe His Pro Gly
        195                 200                 205
Leu Gly Tyr Glu Gln Arg Tyr His Ser Gly Asp Val Arg Leu Asp Thr
        210                 215                 220
Val Gly Ser Asp Ala Tyr Arg Leu Ser Val Ser Arg Ala Leu Ser Ala
225                 230                 235                 240
Asp Gln Gly Ser Tyr Arg Cys Ile Val Ser Glu Trp Ile Ala Glu Gln
                245                 250                 255
Gly Asn Trp Gln Glu Ile Gln Glu Lys Ala Val Glu Val Ala Thr Val
            260                 265                 270
Val Ile Gln Pro Thr Val Leu Arg Ala Val Pro Lys Asn Val Ser
        275                 280                 285
Val Ala Glu Gly Lys Glu Leu Asp Leu Thr Cys Asn Ile Thr Thr Asp
        290                 295                 300
Arg Ala Asp Asp Val Arg Pro Glu Val Thr Trp Ser Phe Ser Arg Met
305                 310                 315                 320
Pro Asp Ser Thr Leu Pro Gly Ser Arg Val Leu Ala Arg Leu Asp Arg
                325                 330                 335
Asp Ser Leu Val His Ser Ser Pro His Val Ala Leu Ser His Val Asp
                340                 345                 350
Ala Arg Ser Tyr His Leu Leu Val Arg Asp Val Ser Lys Glu Asn Ser
            355                 360                 365
Gly Tyr Tyr Tyr Cys His Val Ser Leu Trp Ala Pro Gly His Asn Arg
        370                 375                 380
Ser Trp His Lys Val Ala Glu Ala Val Ser Ser Pro Ala Gly Val Gly
385                 390                 395                 400
Val Thr Trp Leu Glu Pro Asp Tyr Gln Val Tyr Leu Asn Ala Ser Lys
                405                 410                 415
Val Pro Gly Phe Ala Asp Asp Pro Thr Glu Leu Ala Cys Arg Val Val
                420                 425                 430
Asp Thr Lys Ser Gly Glu Ala Asn Val Arg Phe Thr Val Ser Trp Tyr
            435                 440                 445
Tyr Arg Met Asn Arg Arg Ser Asp Asn Val Val Thr Ser Glu Leu Leu
        450                 455                 460
Ala Val Met Asp Gly Asp Trp Thr Leu Lys Tyr Gly Glu Arg Ser Lys
465                 470                 475                 480
Gln Arg Ala Gln Asp Gly Asp Phe Ile Phe Ser Lys Glu His Thr Asp
                485                 490                 495
Thr Phe Asn Phe Arg Ile Gln Arg Thr Thr Glu Glu Asp Arg Gly Asn
                500                 505                 510
Tyr Tyr Cys Val Val Ser Ala Trp Thr Lys Gln Arg Asn Asn Ser Trp
            515                 520                 525
Val Lys Ser Lys Asp Val Phe Ser Lys Pro Val Asn Ile Phe Trp Ala
        530                 535                 540
Leu Glu Asp Ser Val Leu Val Lys Ala Arg Gln Pro Lys Pro Phe
545                 550                 555                 560
Phe Ala Ala Gly Asn Thr Phe Glu Met Thr Cys Lys Val Ser Ser Lys
                565                 570                 575
Asn Ile Lys Ser Pro Arg Tyr Ser Val Leu Ile Met Ala Glu Lys Pro
            580                 585                 590
Val Gly Asp Leu Ser Ser Pro Asn Glu Thr Lys Tyr Ile Ile Ser Leu
        595                 600                 605
```

```
Asp Gln Asp Ser Val Val Lys Leu Glu Asn Trp Thr Asp Ala Ser Arg
        610                 615                 620

Val Asp Gly Val Val Leu Glu Lys Val Gln Glu Asp Glu Phe Arg Tyr
625                 630                 635                 640

Arg Met Tyr Gln Thr Gln Val Ser Asp Ala Gly Leu Tyr Arg Cys Met
                645                 650                 655

Val Thr Ala Trp Ser Pro Val Arg Gly Ser Leu Trp Arg Glu Ala Ala
            660                 665                 670

Thr Ser Leu Ser Asn Pro Ile Glu Ile Asp Phe Gln Thr Ser Gly Pro
        675                 680                 685

Ile Phe Asn Ala Ser Val His Ser Asp Thr Pro Ser Val Ile Arg Gly
    690                 695                 700

Asp Leu Ile Lys Leu Phe Cys Ile Ile Thr Val Glu Gly Ala Ala Leu
705                 710                 715                 720

Asp Pro Asp Asp Met Ala Phe Asp Val Ser Trp Phe Ala Val His Ser
                725                 730                 735

Phe Gly Leu Asp Lys Ala Pro Val Leu Leu Ser Ser Leu Asp Arg Lys
            740                 745                 750

Gly Ile Val Thr Thr Ser Arg Arg Asp Trp Lys Ser Asp Leu Ser Leu
        755                 760                 765

Glu Arg Val Ser Val Leu Glu Phe Leu Leu Gln Val His Gly Ser Glu
    770                 775                 780

Asp Gln Asp Phe Gly Asn Tyr Tyr Cys Ser Val Thr Pro Trp Val Lys
785                 790                 795                 800

Ser Pro Thr Gly Ser Trp Gln Lys Glu Ala Glu Ile His Ser Lys Pro
                805                 810                 815

Val Phe Ile Thr Val Lys Met Asp Val Leu Asn Ala Phe Lys Tyr Pro
            820                 825                 830

Leu Leu Ile Gly Val Gly Leu Ser Thr Val Ile Gly Leu Leu Ser Cys
        835                 840                 845

Leu Ile Gly Tyr Cys Ser Ser His Trp Cys Cys Lys Lys Glu Val Gln
    850                 855                 860

Glu Thr Arg Arg Glu Arg Arg Arg Leu Met Ser Met Glu Met Asp
865                 870                 875

<210> SEQ ID NO 91
<211> LENGTH: 1565
<212> TYPE: DNA
<213> ORGANISM: Homo sapiens
<220> FEATURE:
<221> NAME/KEY: CDS
<222> LOCATION: (4)..(1549)

<400> SEQUENCE: 91 gga atg ctc tcc cgc ctg agc ctg ctc cag gaa ttg gac ctc agc tac      48
    Met Leu Ser Arg Leu Ser Leu Leu Gln Glu Leu Asp Leu Ser Tyr
    1               5                   10                  15 aac cag ctc tca acc ctt gag cct ggg gcc ttc cat ggc cta caa agc      96
Asn Gln Leu Ser Thr Leu Glu Pro Gly Ala Phe His Gly Leu Gln Ser
                20                  25                  30 cta ctc acc ctg agg ctg cag ggc aat cgg ctc aga atc atg ggg cct     144
Leu Leu Thr Leu Arg Leu Gln Gly Asn Arg Leu Arg Ile Met Gly Pro
            35                  40                  45 ggg gtc ttc tca ggc ctc tct gct ctg acc ctg ctg gac ctc cgc ctc     192
Gly Val Phe Ser Gly Leu Ser Ala Leu Thr Leu Leu Asp Leu Arg Leu
        50                  55                  60
```

-continued

| | | |
|---|---|---|
| aac cag att gtt ctc ttc cta gat gga gct ttt ggg gag cta ggc agc<br>Asn Gln Ile Val Leu Phe Leu Asp Gly Ala Phe Gly Glu Leu Gly Ser<br>65                              70                            75 | | 240 |
| ctc cag aag ctg gag gtt ggg gac aac cac ctg gta ttt gtg gct ccg<br>Leu Gln Lys Leu Glu Val Gly Asp Asn His Leu Val Phe Val Ala Pro<br>80                              85                            90                        95 | | 288 |
| ggg gcc ttt gca ggg cta gcc aag ttg agc acc ctc acc ctg gag cgc<br>Gly Ala Phe Ala Gly Leu Ala Lys Leu Ser Thr Leu Thr Leu Glu Arg<br>                    100                         105                        110 | | 336 |
| tgc aac ctc agc aca gtg cct ggc cta gcc ctt gcc cgt ctc ccg gca<br>Cys Asn Leu Ser Thr Val Pro Gly Leu Ala Leu Ala Arg Leu Pro Ala<br>                115                         120                        125 | | 384 |
| cta gtg gcc cta agg ctt aga gaa ctg gat att ggg agg ctg cca gct<br>Leu Val Ala Leu Arg Leu Arg Glu Leu Asp Ile Gly Arg Leu Pro Ala<br>130                              135                            140 | | 432 |
| ggg gcc ctg cgg ggg ctg ggg cag ctc aag gag ctg gag atc cac ctc<br>Gly Ala Leu Arg Gly Leu Gly Gln Leu Lys Glu Leu Glu Ile His Leu<br>145                              150                            155 | | 480 |
| tgg cca tct ctg gag gct ctc gac cct ggg agc ctg gtt ggg ctc aat<br>Trp Pro Ser Leu Glu Ala Leu Asp Pro Gly Ser Leu Val Gly Leu Asn<br>160                              165                            170                        175 | | 528 |
| ctc agc agc ctg gcc atc act cgc tgc aat ctg agc tcg gtg ccc ttc<br>Leu Ser Ser Leu Ala Ile Thr Arg Cys Asn Leu Ser Ser Val Pro Phe<br>                180                         185                        190 | | 576 |
| caa gca ctg tac cac ctc agc ttc ctc agg gtc ctg gat ctg tcc cag<br>Gln Ala Leu Tyr His Leu Ser Phe Leu Arg Val Leu Asp Leu Ser Gln<br>                    195                         200                        205 | | 624 |
| aat ccc atc tca gcc atc cca gcc cga agg ctc agc ccc ctg gtg cgg<br>Asn Pro Ile Ser Ala Ile Pro Ala Arg Arg Leu Ser Pro Leu Val Arg<br>                210                         215                        220 | | 672 |
| ctc cag gag cta cgc ctg tca ggg gca tgc ctc acc tcc att gct gcc<br>Leu Gln Glu Leu Arg Leu Ser Gly Ala Cys Leu Thr Ser Ile Ala Ala<br>225                              230                            235 | | 720 |
| cat gcc ttc cat ggc ttg act gcc ttc cac ctc ctg gat gtg gca gat<br>His Ala Phe His Gly Leu Thr Ala Phe His Leu Leu Asp Val Ala Asp<br>240                              245                            250                        255 | | 768 |
| aac gcc ctt cag aca cta gag gaa aca gct ttc cct tct cca gac aaa<br>Asn Ala Leu Gln Thr Leu Glu Glu Thr Ala Phe Pro Ser Pro Asp Lys<br>                    260                         265                        270 | | 816 |
| ctg gtc acc ttg agg ctg tct ggc aac ccc cta acc tgt gac tgc cgc<br>Leu Val Thr Leu Arg Leu Ser Gly Asn Pro Leu Thr Cys Asp Cys Arg<br>                    275                         280                        285 | | 864 |
| ctc ctc tgg ctg ctc cgg ctc cgc cgc cac ctg gac ttt ggc atg tcc<br>Leu Leu Trp Leu Leu Arg Leu Arg Arg His Leu Asp Phe Gly Met Ser<br>                290                         295                        300 | | 912 |
| ccc cct gcc tgt gct ggc ccc cat cat gtc cag ggg aag agc ctg aag<br>Pro Pro Ala Cys Ala Gly Pro His His Val Gln Gly Lys Ser Leu Lys<br>305                              310                            315 | | 960 |
| gag ttt tca gac atc ctg cct cca ggg cac ttc acc tgc aaa cca gcc<br>Glu Phe Ser Asp Ile Leu Pro Pro Gly His Phe Thr Cys Lys Pro Ala<br>320                              325                            330                        335 | | 1008 |
| ctg atc cga aag tcg ggg cct cga tgg gtc att gca gag gag ggc ggg<br>Leu Ile Arg Lys Ser Gly Pro Arg Trp Val Ile Ala Glu Glu Gly Gly<br>                    340                         345                        350 | | 1056 |
| cat gcg gtt ttc tcc tgc tct gga gat gga gac cca gcc ccc act gtc<br>His Ala Val Phe Ser Cys Ser Gly Asp Gly Asp Pro Ala Pro Thr Val<br>                    355                         360                        365 | | 1104 |
| tcc tgg atg agg cct cat ggg gct tgg ctg ggc agg gct ggg aga gta<br>Ser Trp Met Arg Pro His Gly Ala Trp Leu Gly Arg Ala Gly Arg Val<br>                    370                         375                        380 | | 1152 |

-continued

```
agg gtc cta gag gat ggg aca ctg gag atc cgc tca gtg cag cta cgg      1200
Arg Val Leu Glu Asp Gly Thr Leu Glu Ile Arg Ser Val Gln Leu Arg
385                 390                 395 gac aga ggg gcc tat gtc tgt gtg gtt agc aat gtc gct ggg aat gac      1248
Asp Arg Gly Ala Tyr Val Cys Val Val Ser Asn Val Ala Gly Asn Asp
400                 405                 410                 415 tcc ctg agg acc tgg ctg gaa gtc atc cag gtg gaa cca cca aac ggc      1296
Ser Leu Arg Thr Trp Leu Glu Val Ile Gln Val Glu Pro Pro Asn Gly
            420                 425                 430 aca ctt tct gac ccc aac atc acc gtg cca ggg atc cca ggg cct ttt      1344
Thr Leu Ser Asp Pro Asn Ile Thr Val Pro Gly Ile Pro Gly Pro Phe
        435                 440                 445 ttt ctg gat agc aga ggt gtg gcc atg gtg ctg gca gtc ggc ttc ctc      1392
Phe Leu Asp Ser Arg Gly Val Ala Met Val Leu Ala Val Gly Phe Leu
    450                 455                 460 ccc ttc ctc acc tca gtg acc ctc tgc ttt ggc ctg att gcc ctt tgg      1440
Pro Phe Leu Thr Ser Val Thr Leu Cys Phe Gly Leu Ile Ala Leu Trp
465                 470                 475 agc aag ggc aaa ggt cgg gtc aaa cat cac atg acc ttt gac ttt gtg      1488
Ser Lys Gly Lys Gly Arg Val Lys His His Met Thr Phe Asp Phe Val
480                 485                 490                 495 gca cct cgg ccc tct ggg gat aaa aac tct ggg ggt aac cgg gtc act      1536
Ala Pro Arg Pro Ser Gly Asp Lys Asn Ser Gly Gly Asn Arg Val Thr
                500                 505                 510 gcc aag ctc ttc tgacctttcc ttcccca                                   1565
Ala Lys Leu Phe
            515

<210> SEQ ID NO 92
<211> LENGTH: 515
<212> TYPE: PRT
<213> ORGANISM: Homo sapiens

<400> SEQUENCE: 92

Met Leu Ser Arg Leu Ser Leu Leu Gln Glu Leu Asp Leu Ser Tyr Asn
1               5                   10                  15

Gln Leu Ser Thr Leu Glu Pro Gly Ala Phe His Gly Leu Gln Ser Leu
            20                  25                  30

Leu Thr Leu Arg Leu Gln Gly Asn Arg Leu Arg Ile Met Gly Pro Gly
        35                  40                  45

Val Phe Ser Gly Leu Ser Ala Leu Thr Leu Leu Asp Leu Arg Leu Asn
    50                  55                  60

Gln Ile Val Leu Phe Leu Asp Gly Ala Phe Gly Glu Leu Gly Ser Leu
65                  70                  75                  80

Gln Lys Leu Glu Val Gly Asp Asn His Leu Val Phe Val Ala Pro Gly
                85                  90                  95

Ala Phe Ala Gly Leu Ala Lys Leu Ser Thr Leu Thr Leu Glu Arg Cys
            100                 105                 110

Asn Leu Ser Thr Val Pro Gly Leu Ala Leu Ala Arg Leu Pro Ala Leu
        115                 120                 125

Val Ala Leu Arg Leu Arg Glu Leu Asp Ile Gly Arg Leu Pro Ala Gly
    130                 135                 140

Ala Leu Arg Gly Leu Gly Gln Leu Lys Glu Leu Glu Ile His Leu Trp
145                 150                 155                 160

Pro Ser Leu Glu Ala Leu Asp Pro Gly Ser Leu Val Gly Leu Asn Leu
                165                 170                 175

Ser Ser Leu Ala Ile Thr Arg Cys Asn Leu Ser Ser Val Pro Phe Gln
```

```
                  180                 185                 190
Ala Leu Tyr His Leu Ser Phe Leu Arg Val Leu Asp Leu Ser Gln Asn
        195                 200                 205
Pro Ile Ser Ala Ile Pro Ala Arg Arg Leu Ser Pro Leu Val Arg Leu
    210                 215                 220
Gln Glu Leu Arg Leu Ser Gly Ala Cys Leu Thr Ser Ile Ala Ala His
225                 230                 235                 240
Ala Phe His Gly Leu Thr Ala Phe His Leu Leu Asp Val Ala Asp Asn
                245                 250                 255
Ala Leu Gln Thr Leu Glu Glu Thr Ala Phe Pro Ser Pro Asp Lys Leu
            260                 265                 270
Val Thr Leu Arg Leu Ser Gly Asn Pro Leu Thr Cys Asp Cys Arg Leu
        275                 280                 285
Leu Trp Leu Leu Arg Leu Arg Arg His Leu Asp Phe Gly Met Ser Pro
    290                 295                 300
Pro Ala Cys Ala Gly Pro His Val Gln Gly Lys Ser Leu Lys Glu
305                 310                 315                 320
Phe Ser Asp Ile Leu Pro Pro Gly His Phe Thr Cys Lys Pro Ala Leu
                325                 330                 335
Ile Arg Lys Ser Gly Pro Arg Trp Val Ile Ala Glu Glu Gly Gly His
            340                 345                 350
Ala Val Phe Ser Cys Ser Gly Asp Gly Asp Pro Ala Pro Thr Val Ser
        355                 360                 365
Trp Met Arg Pro His Gly Ala Trp Leu Gly Arg Ala Gly Arg Val Arg
    370                 375                 380
Val Leu Glu Asp Gly Thr Leu Glu Ile Arg Ser Val Gln Leu Arg Asp
385                 390                 395                 400
Arg Gly Ala Tyr Val Cys Val Ser Asn Val Ala Gly Asn Asp Ser
                405                 410                 415
Leu Arg Thr Trp Leu Glu Val Ile Gln Val Glu Pro Pro Asn Gly Thr
            420                 425                 430
Leu Ser Asp Pro Asn Ile Thr Val Pro Gly Ile Pro Gly Pro Phe Phe
        435                 440                 445
Leu Asp Ser Arg Gly Val Ala Met Val Leu Ala Val Gly Phe Leu Pro
    450                 455                 460
Phe Leu Thr Ser Val Thr Leu Cys Phe Gly Leu Ile Ala Leu Trp Ser
465                 470                 475                 480
Lys Gly Lys Gly Arg Val Lys His His Met Thr Phe Asp Phe Val Ala
                485                 490                 495
Pro Arg Pro Ser Gly Asp Lys Asn Ser Gly Gly Asn Arg Val Thr Ala
            500                 505                 510
Lys Leu Phe
        515

<210> SEQ ID NO 93
<211> LENGTH: 1780
<212> TYPE: DNA
<213> ORGANISM: Homo sapiens
<220> FEATURE:
<221> NAME/KEY: CDS
<222> LOCATION: (26)..(1772)

<400> SEQUENCE: 93
ccaaccctct gcccggccgg tgccc atg ctt ctg tgg ctg ctg ctg atc        52
                            Met Leu Leu Trp Leu Leu Leu Ile
                              1               5
```

```
ctg act cct gga aga gaa caa tca ggg gtg gcc cca aaa gct gta ctt      100
Leu Thr Pro Gly Arg Glu Gln Ser Gly Val Ala Pro Lys Ala Val Leu
 10              15                  20                  25 ctc ctc aat cct cca tgg tcc aca gcc ttc aaa gga gaa aaa gtg gct      148
Leu Leu Asn Pro Pro Trp Ser Thr Ala Phe Lys Gly Glu Lys Val Ala
              30                  35                  40 ctc ata tgc agc agc ata tca cat tcc cta gcc cag gga gac aca tat      196
Leu Ile Cys Ser Ser Ile Ser His Ser Leu Ala Gln Gly Asp Thr Tyr
          45                  50                  55 tgg tat cac gat gag aag ttg ttg aaa ata aaa cat gac aag atc caa      244
Trp Tyr His Asp Glu Lys Leu Leu Lys Ile Lys His Asp Lys Ile Gln
      60                  65                  70 att aca gag cct gga aat tac caa tgt aag acc cga gga tcc tcc ctc      292
Ile Thr Glu Pro Gly Asn Tyr Gln Cys Lys Thr Arg Gly Ser Ser Leu
  75                  80                  85 agt gat gcc gtg cat gtg gaa ttt tca cct gac tgg ctg atc ctg cag      340
Ser Asp Ala Val His Val Glu Phe Ser Pro Asp Trp Leu Ile Leu Gln
 90                  95                 100                 105 gct tta cat cct gtc ttt gaa gga gac aat gtc att ctg aga tgt cag      388
Ala Leu His Pro Val Phe Glu Gly Asp Asn Val Ile Leu Arg Cys Gln
             110                 115                 120 ggg aaa gac aac aaa aac act cat caa aag gtt tac tac aag gat gga      436
Gly Lys Asp Asn Lys Asn Thr His Gln Lys Val Tyr Tyr Lys Asp Gly
         125                 130                 135 aaa cag ctt cct aat agt tat aat tta gag aag atc aca gtg aat tca      484
Lys Gln Leu Pro Asn Ser Tyr Asn Leu Glu Lys Ile Thr Val Asn Ser
         140                 145                 150 gtc tcc agg gat aat agc aaa tat cat tgt act gct tat agg aag ttt      532
Val Ser Arg Asp Asn Ser Lys Tyr His Cys Thr Ala Tyr Arg Lys Phe
 155                 160                 165 tac ata ctt gac att gaa gta act tca aaa ccc cta aat atc caa gtt      580
Tyr Ile Leu Asp Ile Glu Val Thr Ser Lys Pro Leu Asn Ile Gln Val
170                 175                 180                 185 caa gag ctg ttt cta cat cct gtg ctg aga gcc agc tct tcc acg ccc      628
Gln Glu Leu Phe Leu His Pro Val Leu Arg Ala Ser Ser Ser Thr Pro
             190                 195                 200 ata gag ggg agt ccc atg acc ctg acc tgt gag acc cag ctc tct cca      676
Ile Glu Gly Ser Pro Met Thr Leu Thr Cys Glu Thr Gln Leu Ser Pro
         205                 210                 215 cag agg cca gat gtc cag ctg caa ttc tcc ctc ttc aga gat agc cag      724
Gln Arg Pro Asp Val Gln Leu Gln Phe Ser Leu Phe Arg Asp Ser Gln
         220                 225                 230 acc ctc gga ttg ggc tgg agc agg tcc ccc aga ctc cag atc cct gcc      772
Thr Leu Gly Leu Gly Trp Ser Arg Ser Pro Arg Leu Gln Ile Pro Ala
 235                 240                 245 atg tgg act gaa gac tca ggg tct tac tgg tgt gag gtg gag aca gtg      820
Met Trp Thr Glu Asp Ser Gly Ser Tyr Trp Cys Glu Val Glu Thr Val
250                 255                 260                 265 act cac agc atc aaa aag agg agc ctg aga tct cag ata cgt gta cag      868
Thr His Ser Ile Lys Lys Arg Ser Leu Arg Ser Gln Ile Arg Val Gln
             270                 275                 280 aga gtc cct gtg tct aat gtg aat cta gag atc cgg ccc acc gga ggg      916
Arg Val Pro Val Ser Asn Val Asn Leu Glu Ile Arg Pro Thr Gly Gly
         285                 290                 295 cag ctg att gaa gga gaa aat atg gtc ctt att tgc tca gta gcc cag      964
Gln Leu Ile Glu Gly Glu Asn Met Val Leu Ile Cys Ser Val Ala Gln
         300                 305                 310 ggt tca ggg act gtc aca ttc tcc tgg cac aaa gaa gga aga gta aga     1012
Gly Ser Gly Thr Val Thr Phe Ser Trp His Lys Glu Gly Arg Val Arg
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 315 |     |     |     | 320 |     |     |     |     | 325 |     |     |     |     |      |
| agc | ctg | ggt | aga | aag | acc | cag | cgt | tcc | ctg | ttg | gca | gag | ctg | cat | gtt | 1060 |
| Ser | Leu | Gly | Arg | Lys | Thr | Gln | Arg | Ser | Leu | Leu | Ala | Glu | Leu | His | Val |      |
| 330 |     |     |     |     | 335 |     |     |     |     | 340 |     |     |     |     | 345 |      |
| ctc | acc | gtg | aag | gag | agt | gat | gca | ggg | aga | tac | tac | tgt | gca | gct | gat | 1108 |
| Leu | Thr | Val | Lys | Glu | Ser | Asp | Ala | Gly | Arg | Tyr | Tyr | Cys | Ala | Ala | Asp |      |
|     |     |     |     | 350 |     |     |     |     | 355 |     |     |     |     | 360 |     |      |
| aac | gtt | cac | agc | ccc | atc | ctc | agc | acg | tgg | att | cga | gtc | acc | gtg | aga | 1156 |
| Asn | Val | His | Ser | Pro | Ile | Leu | Ser | Thr | Trp | Ile | Arg | Val | Thr | Val | Arg |      |
|     |     | 365 |     |     |     |     | 370 |     |     |     |     | 375 |     |     |     |      |
| att | ccg | gta | tct | cac | cct | gtc | ctc | acc | ttc | agg | gct | ccc | agg | gcc | cac | 1204 |
| Ile | Pro | Val | Ser | His | Pro | Val | Leu | Thr | Phe | Arg | Ala | Pro | Arg | Ala | His |      |
| 380 |     |     |     |     | 385 |     |     |     |     | 390 |     |     |     |     |     |      |
| act | gtg | gtg | ggg | gac | ctg | ctg | gag | ctt | cac | tgt | gag | tcc | ctg | aga | ggc | 1252 |
| Thr | Val | Val | Gly | Asp | Leu | Leu | Glu | Leu | His | Cys | Glu | Ser | Leu | Arg | Gly |      |
|     | 395 |     |     |     |     | 400 |     |     |     |     | 405 |     |     |     |     |      |
| tct | ccc | ccg | atc | ctg | tac | cga | ttt | tat | cat | gag | gat | gtc | acc | ctg | ggg | 1300 |
| Ser | Pro | Pro | Ile | Leu | Tyr | Arg | Phe | Tyr | His | Glu | Asp | Val | Thr | Leu | Gly |      |
| 410 |     |     |     |     | 415 |     |     |     |     | 420 |     |     |     |     | 425 |      |
| aac | agc | tca | gcc | ccc | tct | gga | gga | gga | gcc | tcc | ttc | aac | ctc | tct | ctg | 1348 |
| Asn | Ser | Ser | Ala | Pro | Ser | Gly | Gly | Gly | Ala | Ser | Phe | Asn | Leu | Ser | Leu |      |
|     |     |     |     | 430 |     |     |     |     | 435 |     |     |     |     | 440 |     |      |
| act | gca | gaa | cat | tct | gga | aac | tac | tcc | tgt | gat | gca | gac | aat | ggc | ctg | 1396 |
| Thr | Ala | Glu | His | Ser | Gly | Asn | Tyr | Ser | Cys | Asp | Ala | Asp | Asn | Gly | Leu |      |
|     |     |     | 445 |     |     |     |     | 450 |     |     |     |     | 455 |     |     |      |
| ggg | gcc | cag | cac | agt | cat | gga | gtg | agt | ctc | agg | gtc | aca | gtt | ccg | gtg | 1444 |
| Gly | Ala | Gln | His | Ser | His | Gly | Val | Ser | Leu | Arg | Val | Thr | Val | Pro | Val |      |
|     |     | 460 |     |     |     |     | 465 |     |     |     |     | 470 |     |     |     |      |
| tct | cgc | ccc | gtc | ctc | acc | ctc | agg | gct | ccc | ggg | gcc | cag | gct | gtg | gtg | 1492 |
| Ser | Arg | Pro | Val | Leu | Thr | Leu | Arg | Ala | Pro | Gly | Ala | Gln | Ala | Val | Val |      |
| 475 |     |     |     |     | 480 |     |     |     |     | 485 |     |     |     |     |     |      |
| ggg | gac | ctg | ctg | gag | ctt | cac | tgt | gag | tcc | ctg | aga | ggc | tcc | ttc | ccg | 1540 |
| Gly | Asp | Leu | Leu | Glu | Leu | His | Cys | Glu | Ser | Leu | Arg | Gly | Ser | Phe | Pro |      |
| 490 |     |     |     |     | 495 |     |     |     |     | 500 |     |     |     |     | 505 |      |
| atc | ctg | tac | tgg | ttt | tat | cac | gag | gat | gac | acc | ttg | ggg | aac | atc | tcg | 1588 |
| Ile | Leu | Tyr | Trp | Phe | Tyr | His | Glu | Asp | Asp | Thr | Leu | Gly | Asn | Ile | Ser |      |
|     |     |     |     |     | 510 |     |     |     |     | 515 |     |     |     |     | 520 |      |
| gcc | cac | tct | gga | gga | ggg | gca | tcc | ttc | aac | ctc | tct | ctg | act | aca | gaa | 1636 |
| Ala | His | Ser | Gly | Gly | Gly | Ala | Ser | Phe | Asn | Leu | Ser | Leu | Thr | Thr | Glu |      |
|     |     |     | 525 |     |     |     |     | 530 |     |     |     |     | 535 |     |     |      |
| cat | tct | gga | aac | tac | tca | tgt | gag | gct | gac | aat | ggc | ctg | ggg | gcc | cag | 1684 |
| His | Ser | Gly | Asn | Tyr | Ser | Cys | Glu | Ala | Asp | Asn | Gly | Leu | Gly | Ala | Gln |      |
|     |     |     | 540 |     |     |     |     | 545 |     |     |     |     | 550 |     |     |      |
| cac | agt | aaa | gtg | gtg | aca | ctc | aat | gtt | aca | ggt | gtg | tta | ata | gta | cct | 1732 |
| His | Ser | Lys | Val | Val | Thr | Leu | Asn | Val | Thr | Gly | Val | Leu | Ile | Val | Pro |      |
|     | 555 |     |     |     |     | 560 |     |     |     |     | 565 |     |     |     |     |      |
| ggg | cta | gag | gtc | aca | gtt | atg | gta | aat | aaa | ata | gtt | atc | tgacagatt |     |     | 1780 |
| Gly | Leu | Glu | Val | Thr | Val | Met | Val | Asn | Lys | Ile | Val | Ile |     |     |     |      |
| 570 |     |     |     |     | 575 |     |     |     |     | 580 |     |     |     |     |     |      |

<210> SEQ ID NO 94
<211> LENGTH: 582
<212> TYPE: PRT
<213> ORGANISM: Homo sapiens
<400> SEQUENCE: 94

| Met | Leu | Leu | Trp | Leu | Leu | Leu | Ile | Leu | Thr | Pro | Gly | Arg | Glu | Gln |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ser | Gly | Val | Ala | Pro | Lys | Ala | Val | Leu | Leu | Leu | Asn | Pro | Pro | Trp | Ser |

-continued

```
                    20                  25                  30
Thr Ala Phe Lys Gly Glu Lys Val Ala Leu Ile Cys Ser Ser Ile Ser
            35                  40                  45

His Ser Leu Ala Gln Gly Asp Thr Tyr Trp Tyr His Asp Glu Lys Leu
    50                  55                  60

Leu Lys Ile Lys His Asp Lys Ile Gln Ile Thr Glu Pro Gly Asn Tyr
65                  70                  75                  80

Gln Cys Lys Thr Arg Gly Ser Ser Leu Ser Asp Ala Val His Val Glu
                85                  90                  95

Phe Ser Pro Asp Trp Leu Ile Leu Gln Ala Leu His Pro Val Phe Glu
            100                 105                 110

Gly Asp Asn Val Ile Leu Arg Cys Gln Gly Lys Asp Asn Lys Asn Thr
            115                 120                 125

His Gln Lys Val Tyr Tyr Lys Asp Gly Lys Gln Leu Pro Asn Ser Tyr
    130                 135                 140

Asn Leu Glu Lys Ile Thr Val Asn Ser Val Ser Arg Asp Asn Ser Lys
145                 150                 155                 160

Tyr His Cys Thr Ala Tyr Arg Lys Phe Tyr Ile Leu Asp Ile Glu Val
                165                 170                 175

Thr Ser Lys Pro Leu Asn Ile Gln Val Gln Glu Leu Phe Leu His Pro
            180                 185                 190

Val Leu Arg Ala Ser Ser Ser Thr Pro Ile Glu Gly Ser Pro Met Thr
            195                 200                 205

Leu Thr Cys Glu Thr Gln Leu Ser Pro Gln Arg Pro Asp Val Gln Leu
    210                 215                 220

Gln Phe Ser Leu Phe Arg Asp Ser Gln Thr Leu Gly Leu Gly Trp Ser
225                 230                 235                 240

Arg Ser Pro Arg Leu Gln Ile Pro Ala Met Trp Thr Glu Asp Ser Gly
                245                 250                 255

Ser Tyr Trp Cys Glu Val Glu Thr Val Thr His Ser Ile Lys Lys Arg
            260                 265                 270

Ser Leu Arg Ser Gln Ile Arg Val Gln Arg Val Pro Val Ser Asn Val
            275                 280                 285

Asn Leu Glu Ile Arg Pro Thr Gly Gly Gln Leu Ile Glu Gly Glu Asn
    290                 295                 300

Met Val Leu Ile Cys Ser Val Ala Gln Gly Ser Gly Thr Val Thr Phe
305                 310                 315                 320

Ser Trp His Lys Glu Gly Arg Val Arg Ser Leu Gly Arg Lys Thr Gln
                325                 330                 335

Arg Ser Leu Leu Ala Glu Leu His Val Leu Thr Val Lys Glu Ser Asp
            340                 345                 350

Ala Gly Arg Tyr Tyr Cys Ala Ala Asp Asn Val His Ser Pro Ile Leu
            355                 360                 365

Ser Thr Trp Ile Arg Val Thr Val Arg Ile Pro Val Ser His Pro Val
    370                 375                 380

Leu Thr Phe Arg Ala Pro Arg Ala His Thr Val Val Gly Asp Leu Leu
385                 390                 395                 400

Glu Leu His Cys Glu Ser Leu Arg Gly Ser Pro Pro Ile Leu Tyr Arg
                405                 410                 415

Phe Tyr His Glu Asp Val Thr Leu Gly Asn Ser Ser Ala Pro Ser Gly
            420                 425                 430

Gly Gly Ala Ser Phe Asn Leu Ser Leu Thr Ala Glu His Ser Gly Asn
            435                 440                 445
```

```
Tyr Ser Cys Asp Ala Asp Asn Gly Leu Gly Ala Gln His Ser His Gly
    450                 455                 460

Val Ser Leu Arg Val Thr Val Pro Val Ser Arg Pro Val Leu Thr Leu
465                 470                 475                 480

Arg Ala Pro Gly Ala Gln Ala Val Val Gly Asp Leu Leu Glu Leu His
                485                 490                 495

Cys Glu Ser Leu Arg Gly Ser Phe Pro Ile Leu Tyr Trp Phe Tyr His
            500                 505                 510

Glu Asp Asp Thr Leu Gly Asn Ile Ser Ala His Ser Gly Gly Gly Ala
        515                 520                 525

Ser Phe Asn Leu Ser Leu Thr Thr Glu His Ser Gly Asn Tyr Ser Cys
    530                 535                 540

Glu Ala Asp Asn Gly Leu Gly Ala Gln His Ser Lys Val Val Thr Leu
545                 550                 555                 560

Asn Val Thr Gly Val Leu Ile Val Pro Gly Leu Glu Val Thr Val Met
                565                 570                 575

Val Asn Lys Ile Val Ile
            580

<210> SEQ ID NO 95
<211> LENGTH: 1263
<212> TYPE: DNA
<213> ORGANISM: Homo sapiens
<220> FEATURE:
<221> NAME/KEY: CDS
<222> LOCATION: (1)..(1263)

<400> SEQUENCE: 95 aag ctt gga gaa aaa gtg gct ctc ata tgc agc agc ata tca cat tcc      48
Lys Leu Gly Glu Lys Val Ala Leu Ile Cys Ser Ser Ile Ser His Ser
 1               5                  10                  15 cta gcc cag gga gac aca tat tgg tat cac gat gag aag ttg ttg aaa      96
Leu Ala Gln Gly Asp Thr Tyr Trp Tyr His Asp Glu Lys Leu Leu Lys
             20                  25                  30 ata aaa cat gac aag atc caa att aca gag cct gga aat tac caa tgt     144
Ile Lys His Asp Lys Ile Gln Ile Thr Glu Pro Gly Asn Tyr Gln Cys
         35                  40                  45 aag acc cga gga tcc tcc ctc agt gat gcc gtg cat gtg gaa ttt tca     192
Lys Thr Arg Gly Ser Ser Leu Ser Asp Ala Val His Val Glu Phe Ser
     50                  55                  60 cct gac tgg ctg atc ctg cag gct tta cat cct gtc ttt gaa gga gac     240
Pro Asp Trp Leu Ile Leu Gln Ala Leu His Pro Val Phe Glu Gly Asp
 65                  70                  75                  80 aat gtc att ctg aga tgt cag ggg aaa gac aac aaa aac act cat caa     288
Asn Val Ile Leu Arg Cys Gln Gly Lys Asp Asn Lys Asn Thr His His
                 85                  90                  95 aag gtt tac tac aag gat gga aaa cag ctt cct aat agt tat aat tta     336
Lys Val Tyr Tyr Lys Asp Gly Lys Gln Leu Pro Asn Ser Tyr Asn Leu
            100                 105                 110 gag aag atc aca gtg aat tca gtc tcc agg gat aat agc aaa tat cat     384
Glu Lys Ile Thr Val Asn Ser Val Ser Arg Asp Asn Ser Lys Tyr His
        115                 120                 125 tgt act gct tat agg aag ttt tac ata ctt gac att gaa gta act tca     432
Cys Thr Ala Tyr Arg Lys Phe Tyr Ile Leu Asp Ile Glu Val Thr Ser
    130                 135                 140 aaa ccc cta aat atc caa gtt caa gag ctg ttt cta cat cct gtg ctg     480
Lys Pro Leu Asn Ile Gln Val Gln Glu Leu Phe Leu His Pro Val Leu
145                 150                 155                 160
```

| | | | | | | | | | | | | | | | |
|---|---|---|---|---|---|---|---|---|---|---|---|---|---|---|---|
| aga | gcc | agc | tct | tcc | acg | ccc | ata | gag | ggg | agt | ccc | atg | acc | ctg | acc | 528 |
| Arg | Ala | Ser | Ser | Ser | Thr | Pro | Ile | Glu | Gly | Ser | Pro | Met | Thr | Leu | Thr | |
| | | | 165 | | | | | 170 | | | | | 175 | | | |
| tgt | gag | acc | cag | ctc | tct | cca | cag | agg | cca | gat | gtc | cag | ctg | caa | ttc | 576 |
| Cys | Glu | Thr | Gln | Leu | Ser | Pro | Gln | Arg | Pro | Asp | Val | Gln | Leu | Gln | Phe | |
| | | 180 | | | | | 185 | | | | | 190 | | | | |
| tcc | ctc | ttc | aga | gat | agc | cag | acc | ctc | gga | ttg | ggc | tgg | agt | agg | tcc | 624 |
| Ser | Leu | Phe | Arg | Asp | Ser | Gln | Thr | Leu | Gly | Leu | Gly | Trp | Ser | Arg | Ser | |
| | | | 195 | | | | | 200 | | | | | 205 | | | |
| ccc | aga | ctc | cag | atc | cct | gcc | atg | tgg | act | gaa | gac | tca | ggg | tct | tac | 672 |
| Pro | Arg | Leu | Gln | Ile | Pro | Ala | Met | Trp | Thr | Glu | Asp | Ser | Gly | Ser | Tyr | |
| | 210 | | | | | 215 | | | | | 220 | | | | | |
| tgg | tgt | gag | gtg | gag | aca | gtg | act | cac | agc | atc | aaa | aaa | agg | agc | ctg | 720 |
| Trp | Cys | Glu | Val | Glu | Thr | Val | Thr | His | Ser | Ile | Lys | Lys | Arg | Ser | Leu | |
| 225 | | | | | 230 | | | | | 235 | | | | | 240 | |
| aga | tct | cag | ata | cgt | gta | cag | aga | gtc | cct | gtg | tct | aat | gtg | aat | cta | 768 |
| Arg | Ser | Gln | Ile | Arg | Val | Gln | Arg | Val | Pro | Val | Ser | Asn | Val | Asn | Leu | |
| | | | | 245 | | | | | 250 | | | | | 255 | | |
| gag | atc | cgg | ccc | acc | gga | ggg | cag | ctg | att | gaa | gga | gaa | aat | atg | gtc | 816 |
| Glu | Ile | Arg | Pro | Thr | Gly | Gly | Gln | Leu | Ile | Glu | Gly | Glu | Asn | Met | Val | |
| | | | 260 | | | | | 265 | | | | | 270 | | | |
| ctt | att | tgc | tca | gta | gcc | cag | ggt | tca | ggg | act | gtc | aca | ttc | tcc | tgg | 864 |
| Leu | Ile | Cys | Ser | Val | Ala | Gln | Gly | Ser | Gly | Thr | Val | Thr | Phe | Ser | Trp | |
| | | 275 | | | | | 280 | | | | | 285 | | | | |
| cac | aaa | gaa | gga | aga | gta | aga | agc | ctg | ggt | aga | aag | acc | cag | cgt | tcc | 912 |
| His | Lys | Glu | Gly | Arg | Val | Arg | Ser | Leu | Gly | Arg | Lys | Thr | Gln | Arg | Ser | |
| | | 290 | | | | | 295 | | | | | 300 | | | | |
| ctg | ttg | gca | gag | ctg | cat | gtt | ctc | acc | gtg | aag | gag | agt | gat | gca | ggg | 960 |
| Leu | Leu | Ala | Glu | Leu | His | Val | Leu | Thr | Val | Lys | Glu | Ser | Asp | Ala | Gly | |
| 305 | | | | | 310 | | | | | 315 | | | | | 320 | |
| aga | tac | tac | tgt | gca | gct | gat | aac | gtt | cac | agc | ccc | atc | ctc | agc | acg | 1008 |
| Arg | Tyr | Tyr | Cys | Ala | Ala | Asp | Asn | Val | His | Ser | Pro | Ile | Leu | Ser | Thr | |
| | | | 325 | | | | | 330 | | | | | 335 | | | |
| tgg | att | cga | gtc | acc | gtg | aga | att | ccg | gta | tct | cac | cct | gtc | ctc | acc | 1056 |
| Trp | Ile | Arg | Val | Thr | Val | Arg | Ile | Pro | Val | Ser | His | Pro | Val | Leu | Thr | |
| | | | 340 | | | | | 345 | | | | | 350 | | | |
| ttc | agg | gct | ccc | agg | gcc | cac | act | gtg | gtg | ggg | gac | ctg | ctg | gag | ctt | 1104 |
| Phe | Arg | Ala | Pro | Arg | Ala | His | Thr | Val | Val | Gly | Asp | Leu | Leu | Glu | Leu | |
| | | 355 | | | | | 360 | | | | | 365 | | | | |
| cac | tgt | gag | tcc | ctg | aga | ggc | tct | ccc | ccg | atc | ctg | tac | cga | ttt | tat | 1152 |
| His | Cys | Glu | Ser | Leu | Arg | Gly | Ser | Pro | Pro | Ile | Leu | Tyr | Arg | Phe | Tyr | |
| | 370 | | | | | 375 | | | | | 380 | | | | | |
| cat | gag | gat | gtc | acc | ctg | ggg | aac | agc | tca | gcc | ccc | tct | gga | gga | gga | 1200 |
| His | Glu | Asp | Val | Thr | Leu | Gly | Asn | Ser | Ser | Ala | Pro | Ser | Gly | Gly | Gly | |
| 385 | | | | | 390 | | | | | 395 | | | | | 400 | |
| gcc | tcc | ttc | aac | ctc | tct | ctg | act | gca | gaa | cat | tct | gga | aac | tac | tca | 1248 |
| Ala | Ser | Phe | Asn | Leu | Ser | Leu | Thr | Ala | Glu | His | Ser | Gly | Asn | Tyr | Ser | |
| | | | | 405 | | | | | 410 | | | | | 415 | | |
| tgt | gag | gct | ctc | gag | | | | | | | | | | | | 1263 |
| Cys | Glu | Ala | Leu | Glu | | | | | | | | | | | | |
| | | | 420 | | | | | | | | | | | | | |

```
<210> SEQ ID NO 96
<211> LENGTH: 421
<212> TYPE: PRT
<213> ORGANISM: Homo sapiens

<400> SEQUENCE: 96
```

| | | | | | | | | | | | | | | | |
|---|---|---|---|---|---|---|---|---|---|---|---|---|---|---|---|
| Lys | Leu | Gly | Glu | Lys | Val | Ala | Leu | Ile | Cys | Ser | Ser | Ile | Ser | His | Ser |
| 1 | | | | 5 | | | | | 10 | | | | | 15 | |

-continued

```
Leu Ala Gln Gly Asp Thr Tyr Trp Tyr His Asp Glu Lys Leu Leu Lys
             20                  25                  30
Ile Lys His Asp Lys Ile Gln Ile Thr Glu Pro Gly Asn Tyr Gln Cys
         35                  40                  45
Lys Thr Arg Gly Ser Ser Leu Ser Asp Ala Val His Val Glu Phe Ser
     50                  55                  60
Pro Asp Trp Leu Ile Leu Gln Ala Leu His Pro Val Phe Glu Gly Asp
 65                  70                  75                  80
Asn Val Ile Leu Arg Cys Gln Gly Lys Asp Asn Lys Asn Thr His Gln
                 85                  90                  95
Lys Val Tyr Tyr Lys Asp Gly Lys Gln Leu Pro Asn Ser Tyr Asn Leu
            100                 105                 110
Glu Lys Ile Thr Val Asn Ser Val Ser Arg Asp Asn Ser Lys Tyr His
        115                 120                 125
Cys Thr Ala Tyr Arg Lys Phe Tyr Ile Leu Asp Ile Glu Val Thr Ser
    130                 135                 140
Lys Pro Leu Asn Ile Gln Val Gln Glu Leu Phe Leu His Pro Val Leu
145                 150                 155                 160
Arg Ala Ser Ser Thr Pro Ile Glu Gly Ser Pro Met Thr Leu Thr
                165                 170                 175
Cys Glu Thr Gln Leu Ser Pro Gln Arg Pro Asp Val Gln Leu Gln Phe
            180                 185                 190
Ser Leu Phe Arg Asp Ser Gln Thr Leu Gly Leu Gly Trp Ser Arg Ser
        195                 200                 205
Pro Arg Leu Gln Ile Pro Ala Met Trp Thr Glu Asp Ser Gly Ser Tyr
    210                 215                 220
Trp Cys Glu Val Glu Thr Val Thr His Ser Ile Lys Lys Arg Ser Leu
225                 230                 235                 240
Arg Ser Gln Ile Arg Val Gln Arg Val Pro Val Ser Asn Val Asn Leu
                245                 250                 255
Glu Ile Arg Pro Thr Gly Gly Gln Leu Ile Glu Gly Glu Asn Met Val
            260                 265                 270
Leu Ile Cys Ser Val Ala Gln Gly Ser Gly Thr Val Thr Phe Ser Trp
        275                 280                 285
His Lys Glu Gly Arg Val Arg Ser Leu Gly Arg Lys Thr Gln Arg Ser
    290                 295                 300
Leu Leu Ala Glu Leu His Val Leu Thr Val Lys Glu Ser Asp Ala Gly
305                 310                 315                 320
Arg Tyr Tyr Cys Ala Ala Asp Asn Val His Ser Pro Ile Leu Ser Thr
                325                 330                 335
Trp Ile Arg Val Thr Val Arg Ile Pro Val Ser His Pro Val Leu Thr
            340                 345                 350
Phe Arg Ala Pro Arg Ala His Thr Val Val Gly Asp Leu Leu Glu Leu
        355                 360                 365
His Cys Glu Ser Leu Arg Gly Ser Pro Pro Ile Leu Tyr Arg Phe Tyr
    370                 375                 380
His Glu Asp Val Thr Leu Gly Asn Ser Ser Ala Pro Ser Gly Gly Gly
385                 390                 395                 400
Ala Ser Phe Asn Leu Ser Leu Thr Ala Glu His Ser Gly Asn Tyr Ser
                405                 410                 415
Cys Glu Ala Leu Glu
            420
```

<210> SEQ ID NO 97
<211> LENGTH: 1263
<212> TYPE: DNA
<213> ORGANISM: Homo sapiens
<220> FEATURE:
<221> NAME/KEY: CDS
<222> LOCATION: (1)..(1263)

<400> SEQUENCE: 97

| | | | | | | | | | | | | | | | | |
|---|---|---|---|---|---|---|---|---|---|---|---|---|---|---|---|---|
| aag | ctt | gga | gaa | aaa | gtg | gct | ctc | ata | tgc | agc | agc | ata | tca | cat | tcc | 48 |
| Lys | Leu | Gly | Glu | Lys | Val | Ala | Leu | Ile | Cys | Ser | Ser | Ile | Ser | His | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cta | gcc | cag | gga | gac | aca | tat | tgg | tat | cac | gat | gag | aag | ttg | ttg | aaa | 96 |
| Leu | Ala | Gln | Gly | Asp | Thr | Tyr | Trp | Tyr | His | Asp | Glu | Lys | Leu | Leu | Lys | |
| | | 20 | | | | | 25 | | | | | 30 | | | | |

| | | | | | | | | | | | | | | | | |
|---|---|---|---|---|---|---|---|---|---|---|---|---|---|---|---|---|
| ata | aaa | cat | gac | aag | atc | caa | att | aca | gag | cct | gga | aat | tac | caa | tgt | 144 |
| Ile | Lys | His | Asp | Lys | Ile | Gln | Ile | Thr | Glu | Pro | Gly | Asn | Tyr | Gln | Cys | |
| | | | 35 | | | | | 40 | | | | | 45 | | | |

| | | | | | | | | | | | | | | | | |
|---|---|---|---|---|---|---|---|---|---|---|---|---|---|---|---|---|
| aag | acc | cga | gga | tcc | tcc | ctc | agt | gat | gcc | gtg | cat | gtg | gaa | ttt | tca | 192 |
| Lys | Thr | Arg | Gly | Ser | Ser | Leu | Ser | Asp | Ala | Val | His | Val | Glu | Phe | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| cct | gac | tgg | ctg | atc | ctg | cag | gct | tta | cat | cct | gtc | ttt | gaa | gga | gac | 240 |
| Pro | Asp | Trp | Leu | Ile | Leu | Gln | Ala | Leu | His | Pro | Val | Phe | Glu | Gly | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aat | gtc | att | ctg | aga | tgt | cag | ggg | aaa | gac | aac | aaa | aac | act | cat | caa | 288 |
| Asn | Val | Ile | Leu | Arg | Cys | Gln | Gly | Lys | Asp | Asn | Lys | Asn | Thr | His | Gln | |
| | | | | 85 | | | | | 90 | | | | | 95 | | |

| | | | | | | | | | | | | | | | | |
|---|---|---|---|---|---|---|---|---|---|---|---|---|---|---|---|---|
| aag | gtt | tac | tac | aag | gat | gga | aaa | cag | ctt | cct | aat | agt | tat | aat | tta | 336 |
| Lys | Val | Tyr | Tyr | Lys | Asp | Gly | Lys | Gln | Leu | Pro | Asn | Ser | Tyr | Asn | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| gag | aag | atc | aca | gtg | aat | tca | gtc | tcc | agg | gat | aat | agc | aaa | tat | cat | 384 |
| Glu | Lys | Ile | Thr | Val | Asn | Ser | Val | Ser | Arg | Asp | Asn | Ser | Lys | Tyr | His | |
| | | 115 | | | | | 120 | | | | | 125 | | | | |

| | | | | | | | | | | | | | | | | |
|---|---|---|---|---|---|---|---|---|---|---|---|---|---|---|---|---|
| tgt | act | gct | tat | agg | aag | ttt | tac | ata | ctt | gac | att | gaa | gta | act | tca | 432 |
| Cys | Thr | Ala | Tyr | Arg | Lys | Phe | Tyr | Ile | Leu | Asp | Ile | Glu | Val | Thr | Ser | |
| | 130 | | | | | 135 | | | | | 140 | | | | | |

| | | | | | | | | | | | | | | | | |
|---|---|---|---|---|---|---|---|---|---|---|---|---|---|---|---|---|
| aaa | ccc | cta | aat | atc | caa | gtt | caa | gag | ctg | ttt | cta | cat | cct | gtg | ctg | 480 |
| Lys | Pro | Leu | Asn | Ile | Gln | Val | Gln | Glu | Leu | Phe | Leu | His | Pro | Val | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aga | gcc | agc | tct | tcc | acg | ccc | ata | gag | ggg | agt | ccc | atg | acc | ctg | acc | 528 |
| Arg | Ala | Ser | Ser | Ser | Thr | Pro | Ile | Glu | Gly | Ser | Pro | Met | Thr | Leu | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| tgt | gag | acc | cag | ctc | tct | cca | cag | agg | cca | gat | gtc | cag | ctg | caa | ttc | 576 |
| Cys | Glu | Thr | Gln | Leu | Ser | Pro | Gln | Arg | Pro | Asp | Val | Gln | Leu | Gln | Phe | |
| | | | 180 | | | | | 185 | | | | | 190 | | | |

| | | | | | | | | | | | | | | | | |
|---|---|---|---|---|---|---|---|---|---|---|---|---|---|---|---|---|
| tcc | ctc | ttc | aga | gat | agc | cag | acc | ctc | gga | ttg | ggc | tgg | agc | agg | tcc | 624 |
| Ser | Leu | Phe | Arg | Asp | Ser | Gln | Thr | Leu | Gly | Leu | Gly | Trp | Ser | Arg | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| ccc | aga | ctc | cag | atc | cct | gcc | atg | tgg | act | gaa | gac | tca | ggg | tct | tac | 672 |
| Pro | Arg | Leu | Gln | Ile | Pro | Ala | Met | Trp | Thr | Glu | Asp | Ser | Gly | Ser | Tyr | |
| | 210 | | | | | 215 | | | | | 220 | | | | | |

| | | | | | | | | | | | | | | | | |
|---|---|---|---|---|---|---|---|---|---|---|---|---|---|---|---|---|
| tgg | tgt | gag | gtg | gag | aca | gtg | act | cac | agc | atc | aaa | aaa | agg | agc | ctg | 720 |
| Trp | Cys | Glu | Val | Glu | Thr | Val | Thr | His | Ser | Ile | Lys | Lys | Arg | Ser | Leu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aga | tct | cag | ata | cgt | gta | cag | aga | gtc | cct | gtg | tct | aat | gtg | aat | cta | 768 |
| Arg | Ser | Gln | Ile | Arg | Val | Gln | Arg | Val | Pro | Val | Ser | Asn | Val | Asn | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| gag | atc | cgg | ccc | acc | gga | ggg | cag | ctg | att | gaa | gga | gaa | aat | atg | gtc | 816 |
| Glu | Ile | Arg | Pro | Thr | Gly | Gly | Gln | Leu | Ile | Glu | Gly | Glu | Asn | Met | Val | |
| | | | 260 | | | | | 265 | | | | | 270 | | | |

| | | | | | | | | | | | | | | | | |
|---|---|---|---|---|---|---|---|---|---|---|---|---|---|---|---|---|
| ctt | att | tgc | tca | gta | gcc | cag | ggt | tca | ggg | act | gtc | aca | ttc | tcc | tgg | 864 |

```

Leu Ile Cys Ser Val Ala Gln Gly Ser Gly Thr Val Thr Phe Ser Trp
        275                 280                 285 cac aaa gaa gga aga gta aga agc ctg ggt aga aag acc cag cgt tcc        912
His Lys Glu Gly Arg Val Arg Ser Leu Gly Arg Lys Thr Gln Arg Ser
290                 295                 300 ctg ttg gca gag ctg cat gtt ctc acc gtg aag gag agt gat gca ggg        960
Leu Leu Ala Glu Leu His Val Leu Thr Val Lys Glu Ser Asp Ala Gly
305                 310                 315                 320 aga tac tac tgt gca gct gat aac gtt cac agc ccc atc ctc agc acg       1008
Arg Tyr Tyr Cys Ala Ala Asp Asn Val His Ser Pro Ile Leu Ser Thr
            325                 330                 335 tgg att cga gtc acc gtg aga att ccg gta tct cac cct gtc ctc acc       1056
Trp Ile Arg Val Thr Val Arg Ile Pro Val Ser His Pro Val Leu Thr
        340                 345                 350 ttc agg gct ccc agg gcc cac act gtg gtg ggg gac ctg ctg gag ctt       1104
Phe Arg Ala Pro Arg Ala His Thr Val Val Gly Asp Leu Leu Glu Leu
    355                 360                 365 cac tgt gag tcc ctg aga ggc tct ccc ccg atc ctc tac cga ttt tat       1152
His Cys Glu Ser Leu Arg Gly Ser Pro Pro Ile Leu Tyr Arg Phe Tyr
370                 375                 380 cat gag gat gtc acc ctg ggg aac agc tca gcc ccc tct gga gga gga       1200
His Glu Asp Val Thr Leu Gly Asn Ser Ser Ala Pro Ser Gly Gly Gly
385                 390                 395                 400 gcc tcc ttc aac ctc tct ctg act gca gaa cat tct gga aac tac tca       1248
Ala Ser Phe Asn Leu Ser Leu Thr Ala Glu His Ser Gly Asn Tyr Ser
                405                 410                 415 tgt gag gct ctc gag                                                    1263
Cys Glu Ala Leu Glu
            420

<210> SEQ ID NO 98
<211> LENGTH: 421
<212> TYPE: PRT
<213> ORGANISM: Homo sapiens

<400> SEQUENCE: 98

Lys Leu Gly Glu Lys Val Ala Leu Ile Cys Ser Ser Ile Ser His Ser
1               5                   10                  15

Leu Ala Gln Gly Asp Thr Tyr Trp Tyr His Asp Glu Lys Leu Leu Lys
            20                  25                  30

Ile Lys His Asp Lys Ile Gln Ile Thr Glu Pro Gly Asn Tyr Gln Cys
        35                  40                  45

Lys Thr Arg Gly Ser Ser Leu Ser Asp Ala Val His Val Glu Phe Ser
    50                  55                  60

Pro Asp Trp Leu Ile Leu Gln Ala Leu His Pro Val Phe Glu Gly Asp
65                  70                  75                  80

Asn Val Ile Leu Arg Cys Gln Gly Lys Asp Asn Lys Asn Thr His Gln
                85                  90                  95

Lys Val Tyr Tyr Lys Asp Gly Lys Gln Leu Pro Asn Ser Tyr Asn Leu
            100                 105                 110

Glu Lys Ile Thr Val Asn Ser Val Ser Arg Asp Asn Ser Lys Tyr His
        115                 120                 125

Cys Thr Ala Tyr Arg Lys Phe Tyr Ile Leu Asp Ile Glu Val Thr Ser
    130                 135                 140

Lys Pro Leu Asn Ile Gln Val Gln Glu Leu Phe Leu His Pro Val Leu
145                 150                 155                 160

Arg Ala Ser Ser Ser Thr Pro Ile Glu Gly Ser Pro Met Thr Leu Thr
                165                 170                 175
```

```
Cys Glu Thr Gln Leu Ser Pro Gln Arg Pro Asp Val Gln Leu Gln Phe
            180                 185                 190

Ser Leu Phe Arg Asp Ser Gln Thr Leu Gly Leu Gly Trp Ser Arg Ser
        195                 200                 205

Pro Arg Leu Gln Ile Pro Ala Met Trp Thr Glu Asp Ser Gly Ser Tyr
        210                 215                 220

Trp Cys Glu Val Glu Thr Val Thr His Ser Ile Lys Lys Arg Ser Leu
225                 230                 235                 240

Arg Ser Gln Ile Arg Val Gln Arg Val Pro Val Ser Asn Val Asn Leu
                245                 250                 255

Glu Ile Arg Pro Thr Gly Gly Gln Leu Ile Glu Gly Glu Asn Met Val
                260                 265                 270

Leu Ile Cys Ser Val Ala Gln Gly Ser Gly Thr Val Thr Phe Ser Trp
                275                 280                 285

His Lys Glu Gly Arg Val Arg Ser Leu Gly Arg Lys Thr Gln Arg Ser
            290                 295                 300

Leu Leu Ala Glu Leu His Val Leu Thr Val Lys Glu Ser Asp Ala Gly
305                 310                 315                 320

Arg Tyr Tyr Cys Ala Ala Asp Asn Val His Ser Pro Ile Leu Ser Thr
                325                 330                 335

Trp Ile Arg Val Thr Val Arg Ile Pro Val Ser His Pro Val Leu Thr
                340                 345                 350

Phe Arg Ala Pro Arg Ala His Thr Val Val Gly Asp Leu Leu Glu Leu
            355                 360                 365

His Cys Glu Ser Leu Arg Gly Ser Pro Pro Ile Leu Tyr Arg Phe Tyr
        370                 375                 380

His Glu Asp Val Thr Leu Gly Asn Ser Ser Ala Pro Ser Gly Gly Gly
385                 390                 395                 400

Ala Ser Phe Asn Leu Ser Leu Thr Ala Glu His Ser Gly Asn Tyr Ser
                405                 410                 415

Cys Glu Ala Leu Glu
            420

<210> SEQ ID NO 99
<211> LENGTH: 1263
<212> TYPE: DNA
<213> ORGANISM: Homo sapiens
<220> FEATURE:
<221> NAME/KEY: CDS
<222> LOCATION: (1)..(1263)

<400> SEQUENCE: 99 aag ctt gga gaa aaa gtg gct ctc ata tgc agc agc ata tca cat tcc      48
Lys Leu Gly Glu Lys Val Ala Leu Ile Cys Ser Ser Ile Ser His Ser
  1               5                  10                  15 cta gcc cag gga gac aca tat tgg tat cac gat gag aag ttg ttg aaa      96
Leu Ala Gln Gly Asp Thr Tyr Trp Tyr His Asp Glu Lys Leu Leu Lys
             20                  25                  30 ata aaa cat gac aag atc caa att aca gag cct gga aat tac caa tgt     144
Ile Lys His Asp Lys Ile Gln Ile Thr Glu Pro Gly Asn Tyr Gln Cys
         35                  40                  45 aag acc cga gga tcc tcc ctc agt gat gcc gtg cat gtg gaa ttt tca     192
Lys Thr Arg Gly Ser Ser Leu Ser Asp Ala Val His Val Glu Phe Ser
     50                  55                  60 cct gac tgg ctg atc ctg cag gct tta cat cct gtc ttt gaa gga gac     240
Pro Asp Trp Leu Ile Leu Gln Ala Leu His Pro Val Phe Glu Gly Asp
 65                  70                  75                  80
```

|   |   |
|---|---|
| aat gtc att ctg aga tgt cag ggg aaa gac aac aaa aac act cat caa<br>Asn Val Ile Leu Arg Cys Gln Gly Lys Asp Asn Lys Asn Thr His Gln<br>               85                           90                     95 | 288 |
| aag gtt tac tac aag gat gga aaa cag ctt cct aat agt tat aat tta<br>Lys Val Tyr Tyr Lys Asp Gly Lys Gln Leu Pro Asn Ser Tyr Asn Leu<br>             100                      105                  110 | 336 |
| gag aag atc aca gtg aat tca gtc tcc agg gat aat agc aaa tat cat<br>Glu Lys Ile Thr Val Asn Ser Val Ser Arg Asp Asn Ser Lys Tyr His<br>        115                    120                    125 | 384 |
| tgt act gct tat agg aag ttt tac ata ctt gac att gaa gta act tca<br>Cys Thr Ala Tyr Arg Lys Phe Tyr Ile Leu Asp Ile Glu Val Thr Ser<br>130                         135                  140 | 432 |
| aaa ccc cta aat atc caa gtt cag gag ctg ttt cta cat cct gtg ctg<br>Lys Pro Leu Asn Ile Gln Val Gln Glu Leu Phe Leu His Pro Val Leu<br>145                      150                  155             160 | 480 |
| aga gcc agc tct tcc acg ccc ata gag ggg agt ccc atg acc ctg acc<br>Arg Ala Ser Ser Ser Thr Pro Ile Glu Gly Ser Pro Met Thr Leu Thr<br>                  165                    170                    175 | 528 |
| tgt gag acc cag ctc tct cca cag agg cca gat gtc cag ctg caa ttc<br>Cys Glu Thr Gln Leu Ser Pro Gln Arg Pro Asp Val Gln Leu Gln Phe<br>            180                       185                  190 | 576 |
| tcc ctc ttc aga gat agc cag acc ccc gga ttg ggc tgg agc agg tcc<br>Ser Leu Phe Arg Asp Ser Gln Thr Pro Gly Leu Gly Trp Ser Arg Ser<br>               195                    200                  205 | 624 |
| ccc aga ctc cag atc cct gcc atg tgg act gaa gac tca ggg tct tac<br>Pro Arg Leu Gln Ile Pro Ala Met Trp Thr Glu Asp Ser Gly Ser Tyr<br>210                      215                  220 | 672 |
| tgg tgt gag gtg gag aca gtg act cac agc atc aaa aaa agg agc ctg<br>Trp Cys Glu Val Glu Thr Val Thr His Ser Ile Lys Lys Arg Ser Leu<br>225                      230                  235             240 | 720 |
| aga tct cag ata cgt gta cag aga gtc cct gtg tct aat gtg aat cta<br>Arg Ser Gln Ile Arg Val Gln Arg Val Pro Val Ser Asn Val Asn Leu<br>                 245                  250                255 | 768 |
| gag atc cgg ccc acc gga ggg cag ctg att gaa gga gaa aat atg gtc<br>Glu Ile Arg Pro Thr Gly Gly Gln Leu Ile Glu Gly Glu Asn Met Val<br>            260                    265                  270 | 816 |
| ctt att tgc tca gta gcc cag ggt tca ggg act gtc aca ttc tcc tgg<br>Leu Ile Cys Ser Val Ala Gln Gly Ser Gly Thr Val Thr Phe Ser Trp<br>        275                    280                    285 | 864 |
| cac aaa gaa gga aga gta aga agc ctg ggt aga aag acc cag cgt tcc<br>His Lys Glu Gly Arg Val Arg Ser Leu Gly Arg Lys Thr Gln Arg Ser<br>290                      295                  300 | 912 |
| ctg ttg gca gag ctg cat gtt ctc acc gtg aag gag agt gat gca ggg<br>Leu Leu Ala Glu Leu His Val Leu Thr Val Lys Glu Ser Asp Ala Gly<br>305                      310                  315             320 | 960 |
| aga tac tac tgt gca gct gat aac gtt cac agc ccc atc ctc agc acg<br>Arg Tyr Tyr Cys Ala Ala Asp Asn Val His Ser Pro Ile Leu Ser Thr<br>                 325                  330                335 | 1008 |
| tgg att cga gtc acc gtg aga att ccg gta tct cac cct gtc ccc acc<br>Trp Ile Arg Val Thr Val Arg Ile Pro Val Ser His Pro Val Pro Thr<br>            340                       345                  350 | 1056 |
| ttc agg gct ccc agg gcc cac act gtg gtg ggg gac ctg ctg gag ctt<br>Phe Arg Ala Pro Arg Ala His Thr Val Val Gly Asp Leu Leu Glu Leu<br>        355                    360                  365 | 1104 |
| cac tgt gag tcc ctg aga ggc tct ccc ccg atc ctg tac cga ttt tat<br>His Cys Glu Ser Leu Arg Gly Ser Pro Pro Ile Leu Tyr Arg Phe Tyr<br>370                      375                  380 | 1152 |
| cat gag gat gtc acc ctg ggg aac agc tca gcc ccc tct gga gga gga<br>His Glu Asp Val Thr Leu Gly Asn Ser Ser Ala Pro Ser Gly Gly Gly | 1200 |

-continued

```
                385                 390                 395                 400
gac tcc ttc aac ctc tct ctg act gca gaa cat tct gga aac tac tca          1248
Asp Ser Phe Asn Leu Ser Leu Thr Ala Glu His Ser Gly Asn Tyr Ser
                405                 410                 415 tgt gag gct ctc gag                                                       1263
Cys Glu Ala Leu Glu
            420
```

<210> SEQ ID NO 100
<211> LENGTH: 421
<212> TYPE: PRT
<213> ORGANISM: Homo sapiens

<400> SEQUENCE: 100

```
Lys Leu Gly Glu Lys Val Ala Leu Ile Cys Ser Ser Ile Ser His Ser
 1               5                  10                  15

Leu Ala Gln Gly Asp Thr Tyr Trp Tyr His Asp Glu Lys Leu Leu Lys
            20                  25                  30

Ile Lys His Asp Lys Ile Gln Ile Thr Glu Pro Gly Asn Tyr Gln Cys
        35                  40                  45

Lys Thr Arg Gly Ser Ser Leu Ser Asp Ala Val His Val Glu Phe Ser
    50                  55                  60

Pro Asp Trp Leu Ile Leu Gln Ala Leu His Pro Val Phe Glu Gly Asp
65                  70                  75                  80

Asn Val Ile Leu Arg Cys Gln Gly Lys Asp Asn Lys Asn Thr His Gln
                85                  90                  95

Lys Val Tyr Tyr Lys Asp Gly Lys Gln Leu Pro Asn Ser Tyr Asn Leu
            100                 105                 110

Glu Lys Ile Thr Val Asn Ser Val Ser Arg Asp Asn Ser Lys Tyr His
        115                 120                 125

Cys Thr Ala Tyr Arg Lys Phe Tyr Ile Leu Asp Ile Glu Val Thr Ser
    130                 135                 140

Lys Pro Leu Asn Ile Gln Val Gln Glu Leu Phe Leu His Pro Val Leu
145                 150                 155                 160

Arg Ala Ser Ser Ser Thr Pro Ile Glu Gly Ser Pro Met Thr Leu Thr
                165                 170                 175

Cys Glu Thr Gln Leu Ser Pro Gln Arg Pro Asp Val Gln Leu Gln Phe
            180                 185                 190

Ser Leu Phe Arg Asp Ser Gln Thr Pro Gly Leu Gly Trp Ser Arg Ser
        195                 200                 205

Pro Arg Leu Gln Ile Pro Ala Met Trp Thr Glu Asp Ser Gly Ser Tyr
    210                 215                 220

Trp Cys Glu Val Glu Thr Val Thr His Ser Ile Lys Lys Arg Ser Leu
225                 230                 235                 240

Arg Ser Gln Ile Arg Val Gln Arg Val Pro Val Ser Asn Val Asn Leu
                245                 250                 255

Glu Ile Arg Pro Thr Gly Gly Gln Leu Ile Glu Gly Glu Asn Met Val
            260                 265                 270

Leu Ile Cys Ser Val Ala Gln Ser Gly Thr Val Thr Phe Ser Trp
        275                 280                 285

His Lys Glu Gly Arg Val Arg Ser Leu Gly Arg Lys Thr Gln Arg Ser
    290                 295                 300

Leu Leu Ala Glu Leu His Val Leu Thr Val Lys Glu Ser Asp Ala Gly
305                 310                 315                 320

Arg Tyr Tyr Cys Ala Ala Asp Asn Val His Ser Pro Ile Leu Ser Thr
```

```
                    325                 330                 335
Trp Ile Arg Val Thr Val Arg Ile Pro Val Ser His Pro Val Pro Thr
            340                 345                 350

Phe Arg Ala Pro Arg Ala His Thr Val Gly Asp Leu Leu Glu Leu
            355                 360                 365

His Cys Glu Ser Leu Arg Gly Ser Pro Pro Ile Leu Tyr Arg Phe Tyr
370                 375                 380

His Glu Asp Val Thr Leu Gly Asn Ser Ser Ala Pro Ser Gly Gly Gly
385                 390                 395                 400

Asp Ser Phe Asn Leu Ser Leu Thr Ala Glu His Ser Gly Asn Tyr Ser
            405                 410                 415

Cys Glu Ala Leu Glu
            420

<210> SEQ ID NO 101
<211> LENGTH: 360
<212> TYPE: DNA
<213> ORGANISM: Homo sapiens
<220> FEATURE:
<221> NAME/KEY: CDS
<222> LOCATION: (3)..(279)

<400> SEQUENCE: 101 cg ctg ctc ctg ctg ctg ctg gcg ctg tac acc gcg cgt gtg gac ggg      47
   Leu Leu Leu Leu Leu Leu Ala Leu Tyr Thr Ala Arg Val Asp Gly
    1               5                   10                  15 tcc aaa tgc aag tgc tcc cgg aag gga ccc aag atc cgc tac agc gac    95
Ser Lys Cys Lys Cys Ser Arg Lys Gly Pro Lys Ile Arg Tyr Ser Asp
                20                  25                  30 gtg aag aag ctg gaa atg aag cca aag tac ccg cac tgc gag gag aag   143
Val Lys Lys Leu Glu Met Lys Pro Lys Tyr Pro His Cys Glu Glu Lys
            35                  40                  45 atg gtt atc atc acc acc aag agc gtg tcc agg tac cga ggt cag gag   191
Met Val Ile Ile Thr Thr Lys Ser Val Ser Arg Tyr Arg Gly Gln Glu
        50                  55                  60 cac tgc ctg cac ccc aag ctg cag agc acc aag cgc ttc atc aag tgg   239
His Cys Leu His Pro Lys Leu Gln Ser Thr Lys Arg Phe Ile Lys Trp
    65                  70                  75 tac aac gcc tgg aac gag aag cgc agg gtc tac gaa gaa tagggtgaaa    288
Tyr Asn Ala Trp Asn Glu Lys Arg Arg Val Tyr Glu Glu
80                  85                  90 aacctcagaa gggaaaactc caaaccagtt gggagacttg tgcaaaggac              338
tttgcagatt aaaaaaaaaa aa                                            360

<210> SEQ ID NO 102
<211> LENGTH: 92
<212> TYPE: PRT
<213> ORGANISM: Homo sapiens

<400> SEQUENCE: 102

Leu Leu Leu Leu Leu Leu Ala Leu Tyr Thr Ala Arg Val Asp Gly Ser
 1               5                   10                  15

Lys Cys Lys Cys Ser Arg Lys Gly Pro Lys Ile Arg Tyr Ser Asp Val
            20                  25                  30

Lys Lys Leu Glu Met Lys Pro Lys Tyr Pro His Cys Glu Glu Lys Met
        35                  40                  45

Val Ile Ile Thr Thr Lys Ser Val Ser Arg Tyr Arg Gly Gln Glu His
    50                  55                  60
```

```
Cys Leu His Pro Lys Leu Gln Ser Thr Lys Arg Phe Ile Lys Trp Tyr
 65                  70                  75                  80

Asn Ala Trp Asn Glu Lys Arg Arg Val Tyr Glu Glu
                 85                  90

<210> SEQ ID NO 103
<211> LENGTH: 228
<212> TYPE: DNA
<213> ORGANISM: Homo sapiens
<220> FEATURE:
<221> NAME/KEY: CDS
<222> LOCATION: (1)..(228)

<400> SEQUENCE: 103 aaa tgc aag tgc tcc cgg aag gga ccc aag atc cgc tac agc gac gtg          48
Lys Cys Lys Cys Ser Arg Lys Gly Pro Lys Ile Arg Tyr Ser Asp Val
  1               5                  10                  15 aag aag ctg gaa atg aag cca aag tac ccg cac tgc gag gag aag atg          96
Lys Lys Leu Glu Met Lys Pro Lys Tyr Pro His Cys Glu Glu Lys Met
             20                  25                  30 gtt atc atc acc acc aag agc gtg tcc agg tac cga ggt cag gag cac         144
Val Ile Ile Thr Thr Lys Ser Val Ser Arg Tyr Arg Gly Gln Glu His
         35                  40                  45 tgc ctg cac ccc aag ctg cag agc acc aag cgc ttc atc aag tgg tac         192
Cys Leu His Pro Lys Leu Gln Ser Thr Lys Arg Phe Ile Lys Trp Tyr
     50                  55                  60 aac gcc tgg aac gag aag cgc agg gtc tac gaa gaa                         228
Asn Ala Trp Asn Glu Lys Arg Arg Val Tyr Glu Glu
 65                  70                  75

<210> SEQ ID NO 104
<211> LENGTH: 76
<212> TYPE: PRT
<213> ORGANISM: Homo sapiens

<400> SEQUENCE: 104

Lys Cys Lys Cys Ser Arg Lys Gly Pro Lys Ile Arg Tyr Ser Asp Val
  1               5                  10                  15

Lys Lys Leu Glu Met Lys Pro Lys Tyr Pro His Cys Glu Glu Lys Met
             20                  25                  30

Val Ile Ile Thr Thr Lys Ser Val Ser Arg Tyr Arg Gly Gln Glu His
         35                  40                  45

Cys Leu His Pro Lys Leu Gln Ser Thr Lys Arg Phe Ile Lys Trp Tyr
     50                  55                  60

Asn Ala Trp Asn Glu Lys Arg Arg Val Tyr Glu Glu
 65                  70                  75

<210> SEQ ID NO 105
<211> LENGTH: 228
<212> TYPE: DNA
<213> ORGANISM: Homo sapiens
<220> FEATURE:
<221> NAME/KEY: CDS
<222> LOCATION: (1)..(228)

<400> SEQUENCE: 105 aaa tgc aag tgc tcc cgg aag gga ccc aag atc cgc tac agc gac gtg          48
Lys Cys Lys Cys Ser Arg Lys Gly Pro Lys Ile Arg Tyr Ser Asp Val
  1               5                  10                  15 aag aag ctg gaa atg aag cca aag tac ccg cac tgc gag gag aag atg          96
Lys Lys Leu Glu Met Lys Pro Lys Tyr Pro His Cys Glu Glu Lys Met
             20                  25                  30
```

| | |
|---|---|
| gtt atc atc acc acc aag agc gtg tcc agg tac cga ggt cag gag cac<br>Val Ile Ile Thr Thr Lys Ser Val Ser Arg Tyr Arg Gly Gln Glu His<br>               35                    40                    45 | 144 |
| tgc ctg cac ccc aag ctg cag agc acc aag cgc ttc atc aag tgg tac<br>Cys Leu His Pro Lys Leu Gln Ser Thr Lys Arg Phe Ile Lys Trp Tyr<br> 50                    55                    60 | 192 |
| aac gcc tgg aac gag aag cgc agg gtc tac gaa gaa<br>Asn Ala Trp Asn Glu Lys Arg Arg Val Tyr Glu Glu<br>65                  70                    75 | 228 |

<210> SEQ ID NO 106
<211> LENGTH: 76
<212> TYPE: PRT
<213> ORGANISM: Homo sapiens

<400> SEQUENCE: 106

Lys Cys Lys Cys Ser Arg Lys Gly Pro Lys Ile Arg Tyr Ser Asp Val
1               5                   10                  15

Lys Lys Leu Glu Met Lys Pro Lys Tyr Pro His Cys Glu Glu Lys Met
            20                  25                  30

Val Ile Ile Thr Thr Lys Ser Val Ser Arg Tyr Arg Gly Gln Glu His
        35                  40                  45

Cys Leu His Pro Lys Leu Gln Ser Thr Lys Arg Phe Ile Lys Trp Tyr
    50                  55                  60

Asn Ala Trp Asn Glu Lys Arg Arg Val Tyr Glu Glu
65                  70                  75

<210> SEQ ID NO 107
<211> LENGTH: 619
<212> TYPE: DNA
<213> ORGANISM: Homo sapiens
<220> FEATURE:
<221> NAME/KEY: CDS
<222> LOCATION: (1)..(604)

<400> SEQUENCE: 107

| | |
|---|---|
| gct gcc tgc ctc ctc atg ttc ccc tcc acc aca gcg gac tgc ctg tcg<br>Ala Ala Cys Leu Leu Met Phe Pro Ser Thr Thr Ala Asp Cys Leu Ser<br>1               5                  10                15 | 48 |
| cgg tgc tcc ttg tgt gct gta aag acc cag gat ggt ccc aaa cct atc<br>Arg Cys Ser Leu Cys Ala Val Lys Thr Gln Asp Gly Pro Lys Pro Ile<br>             20                    25                30 | 96 |
| aat ccc ctg att tgc tcc ctg caa tgc agg ctg ccc tg ccc tct<br>Asn Pro Leu Ile Cys Ser Leu Gln Cys Gln Ala Ala Leu Leu Pro Ser<br>             35                    40                45 | 144 |
| gag gaa tgg gag aga tgc cag agc ttt ctg tct ttt ttc acc ccc tcc<br>Glu Glu Trp Glu Arg Cys Gln Ser Phe Leu Ser Phe Phe Thr Pro Ser<br> 50                    55                    60 | 192 |
| acc ctt ggg ctc aat gac aag gag gac ttg ggg agc aag tcg gtt ggg<br>Thr Leu Gly Leu Asn Asp Lys Glu Asp Leu Gly Ser Lys Ser Val Gly<br>65                  70                    75                80 | 240 |
| gaa ggg ccc tac agt gag ctg gcc aag ctc tct ggg tca ttc ctg aag<br>Glu Gly Pro Tyr Ser Glu Leu Ala Lys Leu Ser Gly Ser Phe Leu Lys<br>             85                    90                95 | 288 |
| gag ctg aac gat ggt gcc atg gag act ggc aca ctc tat ctc gct gag<br>Glu Leu Asn Asp Gly Ala Met Glu Thr Gly Thr Leu Tyr Leu Ala Glu<br>             100                 105              110 | 336 |
| gag gac ccc aag gag cag gtc aaa cgc tat ggg ggc ttt ttg cgc aaa<br>Glu Asp Pro Lys Glu Gln Val Lys Arg Tyr Gly Gly Phe Leu Arg Lys<br>             115                 120              125 | 384 |
| tac ccc aag agg agc tca gag gtg gct ggg gag ggg gac ggg gat agc | 432 |

```
Tyr Pro Lys Arg Ser Ser Glu Val Ala Gly Glu Gly Asp Gly Asp Ser
    130                 135                 140 atg ggc cat gag gac ctg tac aaa cgc tat ggg ggc ttc ttg cgg cgc         480
Met Gly His Glu Asp Leu Tyr Lys Arg Tyr Gly Gly Phe Leu Arg Arg
145                 150                 155                 160 att cgt ccc aag ctc aag tgg gac aac cag aag cgc tat ggc ggt ttt         528
Ile Arg Pro Lys Leu Lys Trp Asp Asn Gln Lys Arg Tyr Gly Gly Phe
                165                 170                 175 ctc cgg cgc cag ttc aag gtg gtg act cgg tct cag gaa gat ccg aat         576
Leu Arg Arg Gln Phe Lys Val Val Thr Arg Ser Gln Glu Asp Pro Asn
            180                 185                 190 gct tac tct gga gag ctt ttt gat gca taagcacttc ttttca                   619
Ala Tyr Ser Gly Glu Leu Phe Asp Ala
        195                 200

<210> SEQ ID NO 108
<211> LENGTH: 201
<212> TYPE: PRT
<213> ORGANISM: Homo sapiens

<400> SEQUENCE: 108

Ala Ala Cys Leu Leu Met Phe Pro Ser Thr Thr Ala Asp Cys Leu Ser
 1               5                  10                  15

Arg Cys Ser Leu Cys Ala Val Lys Thr Gln Asp Gly Pro Lys Pro Ile
            20                  25                  30

Asn Pro Leu Ile Cys Ser Leu Gln Cys Gln Ala Ala Leu Leu Pro Ser
        35                  40                  45

Glu Glu Trp Glu Arg Cys Gln Ser Phe Leu Ser Phe Phe Thr Pro Ser
    50                  55                  60

Thr Leu Gly Leu Asn Asp Lys Glu Asp Leu Gly Ser Lys Ser Val Gly
 65                 70                  75                  80

Glu Gly Pro Tyr Ser Glu Leu Ala Lys Leu Ser Gly Ser Phe Leu Lys
                85                  90                  95

Glu Leu Asn Asp Gly Ala Met Glu Thr Gly Thr Leu Tyr Leu Ala Glu
            100                 105                 110

Glu Asp Pro Lys Glu Gln Val Lys Arg Tyr Gly Phe Leu Arg Lys
        115                 120                 125

Tyr Pro Lys Arg Ser Ser Glu Val Ala Gly Glu Gly Asp Gly Asp Ser
    130                 135                 140

Met Gly His Glu Asp Leu Tyr Lys Arg Tyr Gly Gly Phe Leu Arg Arg
145                 150                 155                 160

Ile Arg Pro Lys Leu Lys Trp Asp Asn Gln Lys Arg Tyr Gly Gly Phe
                165                 170                 175

Leu Arg Arg Gln Phe Lys Val Val Thr Arg Ser Gln Glu Asp Pro Asn
            180                 185                 190

Ala Tyr Ser Gly Glu Leu Phe Asp Ala
        195                 200

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Forward Primer

<400> SEQUENCE: 109
tcttccagaa ggacatcaac tg                                                22
```

<210> SEQ ID NO 110
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 110
cagcttcatc cacttgagtt tccagg                                          26

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 111
cccctcgtcc aggatatagt ac                                              22

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Forward Primer

<400> SEQUENCE: 112
gtagtgaagc aggatagttc ataaatagaa                                      30

<210> SEQ ID NO 113
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 113
agtggaagcg ccttctcatc cttcat                                          26

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Reverse Primer

<400> SEQUENCE: 114
gcagtggtca cgtttgga                                                   18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Forward Primer

<400> SEQUENCE: 115
gtgaggcggc agatcttc                                                   18

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: probe

```
<400> SEQUENCE: 116
agctgaatca tctgcagcct gcatt                                          25

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Reverse Primer

<400> SEQUENCE: 117
attcccaggc atgatgct                                                  18

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Forward Primer

<400> SEQUENCE: 118
gtgaggcggc agatcttc                                                  18

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: probe

<400> SEQUENCE: 119
agctgaatca tctgcagcct gcatt                                          25

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Reverse Primer

<400> SEQUENCE: 120
attcccaggc atgatgct                                                  18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Forward Primer

<400> SEQUENCE: 121
gtgaggcggc agatcttc                                                  18

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: probe

<400> SEQUENCE: 122
agctgaatca tctgcagcct gcatt                                          25

<210> SEQ ID NO 123
<211> LENGTH: 18
```

```
<212> TYPE: DNA
<213> ORGANISM: Artificial Sequence
<220> FEATURE:
<223> OTHER INFORMATION: Description of Artificial Sequence: Reverse Primer

<400> SEQUENCE: 123
attcccaggc atgatgct                                                    18

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Forward Primer

<400> SEQUENCE: 124
acaacgagac caaacaggtg act                                              23

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: probe

<400> SEQUENCE: 125
tcaagctgcc caactgtgcc cc                                               22

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Reverse Primer

<400> SEQUENCE: 126
ggccacggga taggtgtaga                                                  20

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Forward Primer

<400> SEQUENCE: 127
acaacgagac caaacaggtg act                                              23

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: probe

<400> SEQUENCE: 128
caactgtgcc ccgggagtcg ac                                               22

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Reverse Primer

<400> SEQUENCE: 129
```

-continued ggccacggga taggtgtaga                          20

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Forward Primer

<400> SEQUENCE: 130
actctcggag gaggacattt t                        21

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: probe

<400> SEQUENCE: 131
cagtcccctg tgtccctctg ctg                      23

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 132
cactggagat agcagacaga ca                       22

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Forward Primer

<400> SEQUENCE: 133
actctcggag gaggacattt t                        21

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: probe

<400> SEQUENCE: 134
cagtcccctg tgtccctctg ctg                      23

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 135
cactggagat agcagacaga ca                       22

<210> SEQ ID NO 136
<211> LENGTH: 19
<212> TYPE: DNA
<213> ORGANISM: Artificial Sequence

```
<220> FEATURE:
<223> OTHER INFORMATION: Description of Artificial Sequence: Forward Primer

<400> SEQUENCE: 136
ccagccccaa gtcctggat                                                19

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: probe

<400> SEQUENCE: 137
aaccttggtg tccactgggc caca                                          24

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Reverse Primer

<400> SEQUENCE: 138
atcatggctg agccctgagt                                               20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Forward Primer

<400> SEQUENCE: 139
ggtcatggtc ctggagaagt                                               20

<210> SEQ ID NO 140
<211> LENGTH: 25
<212> TYPE: DNA
<213> ORGANISM: Artificial Sequence
<220> FEATURE:
<223> OTHER INFORMATION: Description of Artificial Sequence: probe

<400> SEQUENCE: 140
acctggcagc cctaccagtt ctacg                                         25

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Reverse Primer

<400> SEQUENCE: 141
acataccgaa ggcctccat                                                19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Forward Primer

<400> SEQUENCE: 142
ggcagggatg aaactgtca                                                19
```

<210> SEQ ID NO 143
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 143
ccttggcccc aatgtagaga acactg                                              26

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 144
ctcccgtgac atacactttg ac                                                  22

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Forward Primer

<400> SEQUENCE: 145
catggagact cccctttgac                                                     20

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 146
cctgaaggag gtcaccatct cattga                                              26

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Reverse Primer

<400> SEQUENCE: 147
cggatcttgg acttcaatct c                                                   21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Forward Primer

<400> SEQUENCE: 148
tgggacaaag aaagagacca a                                                   21

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: probe

```
<400> SEQUENCE: 149
ttgctgacgc ctgtgatcct cact                                          24

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Reverse Primer

<400> SEQUENCE: 150
caagggctga gtggagaag                                                19

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Forward Primer

<400> SEQUENCE: 151
cttcatccgc ttctccaaat                                               20

<210> SEQ ID NO 152
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 152
cctgaaaacc acatcgtctt ccctgt                                        26

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Reverse Primer

<400> SEQUENCE: 153
ctcatccaga ctggccatta c                                             21

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Forward Primer

<400> SEQUENCE: 154
ggagaacttc atccgcttct                                               20

<210> SEQ ID NO 155
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 155
cctgaaaacc acatcgtctt ccctgt                                        26

<210> SEQ ID NO 156
```

```
<211> LENGTH: 21
<212> TYPE: DNA
<213> ORGANISM: Artificial Sequence
<220> FEATURE:
<223> OTHER INFORMATION: Description of Artificial Sequence: Reverse Primer

<400> SEQUENCE: 156
ctcatccaga ctggccatta c                                              21

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Forward Primer

<400> SEQUENCE: 157
cctttgacgt tgaaaggtac ag                                             22

<210> SEQ ID NO 158
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 158
tcaagttgga cagcacttta cctttg                                         26

<210> SEQ ID NO 159
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 159
tctgcagaat ccaaatctct gt                                             22

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Forward Primer

<400> SEQUENCE: 160
gattgcaacg ctgaagttta tg                                             22

<210> SEQ ID NO 161
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 161
ctgtcaactg tcaaccactg ggaatg                                         26

<210> SEQ ID NO 162
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 162
```
gaggcctttt catcagtgag at       22

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Forward Primer

<400> SEQUENCE: 163
aatcttcact ccaggcacat ag       22

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: probe

<400> SEQUENCE: 164
acctctgcca gcaaccttga gagg       24

<210> SEQ ID NO 165
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 165
tcccatcttt cttcttgtcc tt       22

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Forward Primer

<400> SEQUENCE: 166
acgcagagcc caggtttt       18

<210> SEQ ID NO 167
<211> LENGTH: 27
<212> TYPE: DNA
<213> ORGANISM: Artificial Sequence
<220> FEATURE:
<223> OTHER INFORMATION: Description of Artificial Sequence: probe

<400> SEQUENCE: 167
tcacctttcc gatcatcacg aatagggg       27

<210> SEQ ID NO 168
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 168
cgcaggacct taggtgacta gt       22

<210> SEQ ID NO 169
<211> LENGTH: 22
<212> TYPE: DNA

```
<213> ORGANISM: Artificial Sequence
<220> FEATURE:
<223> OTHER INFORMATION: Description of Artificial Sequence: Forward Primer

<400> SEQUENCE: 169
gattgcaacg ctgaagttta tg                                              22

<210> SEQ ID NO 170
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 170
ctgtcaactg tcaaccactg ggaatg                                          26

<210> SEQ ID NO 171
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 171
gaggcctttt catcagtgag at                                              22

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Forward Primer

<400> SEQUENCE: 172
acagagcatt tggcaagct                                                  19

<210> SEQ ID NO 173
<211> LENGTH: 27
<212> TYPE: DNA
<213> ORGANISM: Artificial Sequence
<220> FEATURE:
<223> OTHER INFORMATION: Description of Artificial Sequence: probe

<400> SEQUENCE: 173
cagtactaca ccttctgcac agacaca                                         27

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Reverse Primer

<400> SEQUENCE: 174 gttggcccctt ctgtcttctc                                                20

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Forward Primer

<400> SEQUENCE: 175
cagccactgg agaatgca                                                   18
```

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: probe

<400> SEQUENCE: 176
agcagtacga aattctccgt ggctacc                                27

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Reverse Primer

<400> SEQUENCE: 177
gaatgggctc caggtctg                                          18

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Forward Primer

<400> SEQUENCE: 178
acgcagagcc caggtttt                                          18

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: probe

<400> SEQUENCE: 179
cacctttccg atcatcacga atagggg                                27

<210> SEQ ID NO 180
<211> LENGTH: 25
<212> TYPE: DNA
<213> ORGANISM: Artificial Sequence
<220> FEATURE:
<223> OTHER INFORMATION: Description of Artificial Sequence: Reverse Primer

<400> SEQUENCE: 180
gggtggactt acagttgttt cttct                                  25

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Forward Primer

<400> SEQUENCE: 181
ctttacttca tgcacttcaa cttg                                   24

<210> SEQ ID NO 182
<211> LENGTH: 30
<212> TYPE: DNA
<213> ORGANISM: Artificial Sequence
<220> FEATURE:

<223> OTHER INFORMATION: Description of Artificial Sequence: probe

<400> SEQUENCE: 182
cctcctacct tgtgaatat gactatgtga                                    30

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Reverse Primer

<400> SEQUENCE: 183
actctcgaag tgtcctcagt ttc                                          23

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Forward Primer

<400> SEQUENCE: 184
ttttaaaggg acccactact gg                                           22

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: probe

<400> SEQUENCE: 185
ctggcatagc tggcccattg ctcat                                        25

<210> SEQ ID NO 186
<211> LENGTH: 19
<212> TYPE: DNA
<213> ORGANISM: Artificial Sequence
<220> FEATURE:
<223> OTHER INFORMATION: Description of Artificial Sequence: Reverse Primer

<400> SEQUENCE: 186
gaaaaggcag catccactg                                               19

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: Forward Primer

<400> SEQUENCE: 187
agaccaaggc cactacaaat gt                                           22

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: probe

<400> SEQUENCE: 188
cacagatgcc actgtccagg gaa                                          23

<210> SEQ ID NO 189
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 189
acctgcactg tgtcctcata gt                                              22

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Forward Primer

<400> SEQUENCE: 190
tcacatgacc tttgactttg tg                                              22

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: probe

<400> SEQUENCE: 191
acctcggccc tctggggata aaa                                             23

<210> SEQ ID NO 192
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 192
gaaggaaagg tcagaagagc tt                                              22

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Forward Primer

<400> SEQUENCE: 193
cctcaaggtg accagtttgt c                                               21

<210> SEQ ID NO 194
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 194
cgcccttcag acactagagg aaacag                                          26

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Reverse Primer -continued

<400> SEQUENCE: 195
ctcctggatg tggcagataa                                                                                      20

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Forward Primer

<400> SEQUENCE: 196
agagcctgga aattaccaat gt                                                                                   22

<210> SEQ ID NO 197
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 197
agacccgagg atcctccctc agtgat                                                                               26

<210> SEQ ID NO 198
<211> LENGTH: 22
<212> TYPE: DNA
<213> ORGANISM: Artificial Sequence
<220> FEATURE:
<223> OTHER INFORMATION: Description of Artificial Sequence: Reverse Primer

<400> SEQUENCE: 198
cagtcaggtg aaaattccac at                                                                                   22

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Forward Primer

<400> SEQUENCE: 199
ccaagagcgt gtccaggta                                                                                       19

<210> SEQ ID NO 200
<211> LENGTH: 25
<212> TYPE: DNA
<213> ORGANISM: Artificial Sequence
<220> FEATURE:
<223> OTHER INFORMATION: Description of Artificial Sequence: probe

<400> SEQUENCE: 200
agagcaccaa gcgcttcatc aagtg                                                                                25

<210> SEQ ID NO 201
<211> LENGTH: 19
<212> TYPE: DNA
<213> ORGANISM: Artificial Sequence
<220> FEATURE:
<223> OTHER INFORMATION: Description of Artificial Sequence: Reverse Primer

<400> SEQUENCE: 201
ctcgttccag gcgttgtac                                                                                       19